US011369599B2

(12) United States Patent
Birtalan et al.

(10) Patent No.: US 11,369,599 B2
(45) Date of Patent: Jun. 28, 2022

(54) MELT-EXTRUDED SOLID DISPERSIONS CONTAINING AN APOPTOSIS-INDUCING AGENT

(71) Applicants: AbbVie Inc., North Chicago, IL (US); AbbVie Deutschland GMBH & Co KG, Wiesbaden (DE)

(72) Inventors: Esther Birtalan, Karlsruhe (DE); Peter Hoelig, Waechtersbach (DE); David J. Lindley, Antioch, IL (US); Yeshwant D. Sanzgiri, Gurnee, IL (US); Ping Tong, Libertyville, IL (US)

(73) Assignees: AbbVie Inc., North Chicago, IL (US); AbbVie Deutschland GMBH & Co KG, Wiesbaden (DE)

( * ) Notice: Subject to any disclaimer, the term of this patent is extended or adjusted under 35 U.S.C. 154(b) by 231 days.

(21) Appl. No.: 14/340,435

(22) Filed: Jul. 24, 2014

(65) Prior Publication Data
US 2015/0148331 A1 May 28, 2015

(51) Int. Cl.
A61K 31/496 (2006.01)
A61K 31/5377 (2006.01)
A61K 31/541 (2006.01)
A61K 47/02 (2006.01)
A61K 47/26 (2006.01)
A61K 47/32 (2006.01)
A61K 9/20 (2006.01)
A61K 9/16 (2006.01)
A61K 9/00 (2006.01)

(52) U.S. Cl.
CPC .......... *A61K 31/496* (2013.01); *A61K 9/0053* (2013.01); *A61K 9/1635* (2013.01); *A61K 9/1694* (2013.01); *A61K 9/2027* (2013.01); *A61K 9/2095* (2013.01); *A61K 31/5377* (2013.01); *A61K 31/541* (2013.01); *A61K 47/02* (2013.01); *A61K 47/26* (2013.01); *A61K 47/32* (2013.01)

(58) Field of Classification Search
CPC ................ A61K 31/496; A61K 9/0053; A61K 31/5377; A61K 31/541; A61K 47/02; A61K 47/26; A61K 47/32
See application file for complete search history.

(56) References Cited

U.S. PATENT DOCUMENTS

| | | |
|---|---|---|
| 5,536,729 A | 7/1996 | Waranis et al. |
| 5,538,737 A | 7/1996 | Leonard et al. |
| 5,559,121 A | 9/1996 | Harrison et al. |
| 5,635,187 A | 6/1997 | Bathurst et al. |
| 5,645,856 A | 7/1997 | Lacy et al. |
| 5,665,379 A | 9/1997 | Herslof et al. |
| 5,707,648 A | 1/1998 | Yiv |
| 5,891,469 A | 4/1999 | Amselem |
| 6,004,973 A | 12/1999 | Guitard et al. |
| 6,267,985 B1 | 7/2001 | Chen et al. |
| 6,309,663 B1 | 10/2001 | Patel et al. |
| 6,451,339 B2 | 9/2002 | Patel et al. |
| 6,464,987 B1 | 10/2002 | Fanara et al. |
| 6,599,528 B1 | 7/2003 | Rosenberg et al. |
| 6,720,338 B2 | 4/2004 | Augeri et al. |
| 6,787,534 B2 | 9/2004 | Haneda et al. |
| 6,858,638 B2 | 2/2005 | Damour et al. |
| 6,927,009 B2 | 8/2005 | Kodama et al. |
| 6,964,946 B1 | 11/2005 | Gutierrez-Rocca et al. |
| 7,151,188 B1 | 12/2006 | Simandan et al. |
| 7,390,799 B2 | 6/2008 | Bruncko et al. |
| 7,459,283 B2 | 12/2008 | Wertz et al. |
| 7,504,512 B2 | 3/2009 | Augeri et al. |
| 7,511,013 B2 | 3/2009 | Molino et al. |
| 7,514,068 B2 | 4/2009 | Tung |

(Continued)

FOREIGN PATENT DOCUMENTS

| | | |
|---|---|---|
| CN | 1561201 A | 1/2005 |
| CN | 1706371 A | 12/2005 |

(Continued)

OTHER PUBLICATIONS

Belikov, V.G., "General pharmaceutical chemistry", Pharmaceutical Chemistry, Second Edition, 1993, Part 1, pp. 43-47.
Kharkevich, D.A., "Dependence of the Pharmacotherapeutic Effect on Properties of Medicinal Drugs and Conditions of Their Administration", Pharmacology, Third Edition, 1987, Part 6, pp. 47-48.
Vasconcelos, T., et al., Solid dispersions as strategy to improve oral bioavailability of poor water soluble drugs, Drug Discovery Today, Oct. 2007, pp. 1-8, vol. 80, No. 00, Elsevier Ltd.
Non-Final Office Action dated Oct. 11, 2013, U.S. Appl. No. 13/282,773, 13 pages.
Final Office Action dated May 9, 2014, U.S. Appl. No. 13/282,773, 21 pages.
Breitenbach, Jörg, "Melt extrusion: from process to drug delivery technology", European Journal of Pharmaceutics and Biopharmaceutics, 2002, vol. 54, pp. 107-117.

(Continued)

*Primary Examiner* — Jared Barsky
(74) *Attorney, Agent, or Firm* — Foley Hoag LLP

(57) ABSTRACT

A pro-apoptotic solid dispersion comprises, in essentially non-crystalline form, a Bcl-2 family protein inhibitory compound of Formula I as defined herein, dispersed in a solid matrix that comprises (a) a pharmaceutically acceptable water-soluble polymeric carrier and (b) a pharmaceutically acceptable surfactant. A process for preparing such a solid dispersion comprises subjecting to elevated temperature the compound of Formula I, the water-soluble polymeric carrier and the surfactant, to provide an extrudable semi-solid mixture; extruding the semi-solid mixture; and cooling the resulting extrudate to provide a solid matrix comprising the polymeric carrier and the surfactant and having the compound dispersed in essentially non-crystalline form therein. The solid dispersion is suitable for oral administration to a subject in need thereof for treatment of a disease characterized by overexpression of one or more anti-apoptotic Bcl-2 family proteins, for example cancer or an immune or autoimmune disease.

54 Claims, 1 Drawing Sheet

(56) References Cited

U.S. PATENT DOCUMENTS

| | | |
|---|---|---|
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,642,260 B2 | 1/2010 | Bruncko et al. |
| 7,709,467 B2 | 5/2010 | Bruncko et al. |
| 7,754,886 B2 | 7/2010 | Augeri et al. |
| 7,767,684 B2 | 8/2010 | Bruncko et al. |
| 7,842,681 B2 | 11/2010 | Elmore et al. |
| 7,973,161 B2 | 7/2011 | Bruncko et al. |
| 8,084,607 B2 | 12/2011 | Bruncko et al. |
| 8,168,784 B2 | 5/2012 | Franczyk, II et al. |
| 8,173,811 B2 | 5/2012 | Bruncko et al. |
| 8,187,836 B2 | 5/2012 | Hsieh |
| 8,354,404 B2 | 1/2013 | Bruncko et al. |
| 8,546,399 B2 | 1/2013 | Bruncko et al. |
| 8,377,952 B2 | 2/2013 | Rosenberg et al. |
| 8,426,422 B2 | 4/2013 | Hexamer et al. |
| 8,563,735 B2 | 10/2013 | Bruncko et al. |
| 2002/0055631 A1 | 5/2002 | Augeri et al. |
| 2003/0144507 A1 | 7/2003 | Haneda et al. |
| 2003/0236236 A1 | 12/2003 | Chen et al. |
| 2005/0059722 A1 | 3/2005 | Damour et al. |
| 2005/0084529 A1 | 4/2005 | Rosenberg et al. |
| 2005/0101628 A1 | 5/2005 | Jiao et al. |
| 2005/0159427 A1 | 7/2005 | Bruncko et al. |
| 2005/0163835 A1 | 7/2005 | Gellert et al. |
| 2005/0208082 A1 | 9/2005 | Papas et al. |
| 2005/0236236 A1 | 10/2005 | Farooq |
| 2006/0128706 A1 | 6/2006 | Bruncko et al. |
| 2006/0177430 A1 | 8/2006 | Bhushan et al. |
| 2006/0183776 A9 | 8/2006 | Pratt |
| 2007/0015787 A1 | 1/2007 | Bruncko et al. |
| 2007/0027135 A1 | 2/2007 | Bruncko et al. |
| 2007/0072860 A1 | 3/2007 | Bruncko et al. |
| 2007/0104780 A1 | 5/2007 | Lipari et al. |
| 2007/0161681 A1 | 5/2007 | Lipari et al. |
| 2007/0237823 A1 | 10/2007 | Bock et al. |
| 2007/0243257 A1 | 10/2007 | Bedos et al. |
| 2008/0004286 A1 | 1/2008 | Wang et al. |
| 2008/0076779 A1 | 3/2008 | Elmore et al. |
| 2008/0085313 A1 | 4/2008 | Given et al. |
| 2008/0181948 A1 | 7/2008 | Berndl et al. |
| 2008/0182845 A1 | 7/2008 | Bardwell et al. |
| 2008/0280921 A1 | 11/2008 | Dreyer et al. |
| 2008/0300267 A1 | 12/2008 | Okram et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2009/0149461 A1 | 6/2009 | Krivoshik |
| 2009/0176785 A1 | 7/2009 | Bardwell et al. |
| 2010/0022773 A1 | 1/2010 | Bruncko et al. |
| 2010/0098763 A1 | 4/2010 | Bechtold et al. |
| 2010/0152183 A1 | 6/2010 | Bruncko et al. |
| 2010/0152186 A1 | 6/2010 | Charvat et al. |
| 2010/0160322 A1 | 6/2010 | Bruncko et al. |
| 2010/0184750 A1 | 7/2010 | Hexamer et al. |
| 2010/0184766 A1 | 7/2010 | Kunzer et al. |
| 2010/0227838 A1 | 9/2010 | Shah et al. |
| 2010/0233251 A1 | 9/2010 | Von Andrian et al. |
| 2010/0278905 A1 | 11/2010 | Catron et al. |
| 2010/0278921 A1 | 11/2010 | Fischer et al. |
| 2010/0280031 A1 | 11/2010 | David et al. |
| 2010/0297194 A1* | 11/2010 | Catron ................ A61P 35/00 424/400 |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2010/0305125 A1 | 12/2010 | Borchardt et al. |
| 2010/0310648 A1 | 12/2010 | Packhaeuser et al. |
| 2010/0311751 A1 | 12/2010 | Schmitt et al. |
| 2010/0323020 A1 | 12/2010 | Gokhale et al. |
| 2011/0071151 A1 | 3/2011 | Zhang et al. |
| 2011/0124628 A1* | 5/2011 | Bruncko ............... A61P 35/02 514/210.21 |
| 2012/0108590 A1 | 5/2012 | Birtalan et al. |
| 2012/0129853 A1 | 5/2012 | Elmore et al. |
| 2012/0157470 A1 | 6/2012 | Catron et al. |
| 2012/0190688 A1 | 7/2012 | Bruncko et al. |
| 2012/0277210 A1 | 11/2012 | Catron et al. |
| 2015/0021339 A1 | 1/2015 | Felts et al. |
| 2015/0148331 A1 | 5/2015 | Birtalan et al. |
| 2015/0157639 A1 | 6/2015 | Catron et al. |

FOREIGN PATENT DOCUMENTS

| | | |
|---|---|---|
| CN | 101175738 A | 5/2008 |
| CN | 101220008 A | 7/2008 |
| CN | 101325944 A | 12/2008 |
| CN | 101798292 A | 8/2010 |
| CN | 102131792 A | 7/2011 |
| CN | 101548960 B | 11/2012 |
| EA | 010832 B1 | 12/2008 |
| EP | 1796642 B1 | 6/2007 |
| EP | 1880715 A1 | 1/2008 |
| RU | 2159107 C2 | 11/2000 |
| RU | 2001103044 | 8/2003 |
| RU | 2239631 C2 | 11/2004 |
| RU | 2004130280 A | 6/2005 |
| RU | 2318518 C2 | 3/2008 |
| RU | 2008123798 A | 12/2009 |
| RU | 2387653 C2 | 4/2010 |
| WO | 199507271 A1 | 3/1995 |
| WO | 9703654 A2 | 2/1997 |
| WO | 199710223 A1 | 3/1997 |
| WO | 199729131 A1 | 8/1997 |
| WO | 200001389 A1 | 1/2000 |
| WO | 200057854 A2 | 10/2000 |
| WO | 200100175 A1 | 1/2001 |
| WO | 2002024636 A2 | 3/2002 |
| WO | 2002066470 A1 | 8/2002 |
| WO | 2002098848 A1 | 12/2002 |
| WO | 2003028705 A1 | 4/2003 |
| WO | 2003072108 A1 | 9/2003 |
| WO | 2005039551 A2 | 5/2005 |
| WO | 2005049593 A2 | 6/2005 |
| WO | 2005049594 A1 | 6/2005 |
| WO | 2005099353 A2 | 10/2005 |
| WO | 2006008754 A1 | 1/2006 |
| WO | 2006026500 A1 | 3/2006 |
| WO | 2006124863 A1 | 11/2006 |
| WO | 2007002325 A1 | 1/2007 |
| WO | 2007040650 A2 | 4/2007 |
| WO | 2007043057 A2 | 4/2007 |
| WO | 2008009689 A1 | 1/2008 |
| WO | 2008021347 A2 | 2/2008 |
| WO | 2008030836 A2 | 3/2008 |
| WO | 2008055966 A1 | 5/2008 |
| WO | 2008123798 A1 | 10/2008 |
| WO | 2008124878 A1 | 10/2008 |
| WO | 2009045464 A1 | 4/2009 |
| WO | 2009073835 A1 | 6/2009 |
| WO | 2009100176 A2 | 8/2009 |
| WO | 2009155386 A1 | 12/2009 |
| WO | 2010041051 A1 | 4/2010 |
| WO | 2010065824 A2 | 6/2010 |
| WO | 2010065865 A2 | 6/2010 |
| WO | 2010072734 A2 | 7/2010 |
| WO | 2010077740 A2 | 7/2010 |
| WO | 2010083441 A2 | 7/2010 |
| WO | 2010127190 A1 | 11/2010 |
| WO | 2010127193 A1 | 11/2010 |
| WO | 2010127198 A1 | 11/2010 |
| WO | 2010138588 A2 | 12/2010 |
| WO | 2010143074 A2 | 12/2010 |

(56) References Cited

FOREIGN PATENT DOCUMENTS

| | | |
|---|---|---|
| WO | 2010144646 A2 | 12/2010 |
| WO | 2011034934 A1 | 3/2011 |
| WO | 2011068560 A1 | 6/2011 |
| WO | 2011068561 A1 | 6/2011 |
| WO | 2011149492 A1 | 12/2011 |
| WO | 2011150016 A1 | 12/2011 |
| WO | 2012058392 A1 | 5/2012 |
| WO | 2012071336 A1 | 5/2012 |
| WO | 2012071374 A1 | 5/2012 |
| WO | 2012121758 A1 | 9/2012 |

OTHER PUBLICATIONS

Chapter 5, Recent Progress in Physicochemical Characterization and Formulation Technologies for Poorly Soluble Drugs, CMC Publishing Co., Ltd., Jan. 29, 2010, First copy, pp. 213-223.

Goddeeris et al., "Formulation of fast disintegrating tablets of Ternary solid dispersions consisting of TPGS 1000 and HPMC 2910 or PVPVA 64 to improve the dissolution of the anti-HIV drug UV 781", European Jounral of Pharmaceutical Sciences, 2008, vol. 34, pp. 293-302.

Repka et al, "Pharmaceutical applications of hot-melt extrusion: Part II", Drug Development and Industrial Pharmacy, vol. 33, No. 9, pp. 1043-1057.

Serajuddin, Abu T.M., "Solid Dispersion of Poorly Water-Soluble Durgs; Early Promises, Subsequent Problems, and Recent Breakthroughs", Journal of Pharmaceutical Sciences, 1999, vol. 88, No. 10, pp. 1058-1066.

Shanbhag et al., "Method for screening of solid dispersion formulations of low-solubility compounds-Miniaturization and automation of solvent casting and dissolution testing", 2008, vol. 351, pp. 209-218.

Droin et al., "Role of Bcl-2 family members in immunity and disease", Biochimica et Biophysica Acta, 2004, vol. 1644, pp. 179-188.

Ghebremeskel et al., "Use of Surfactants as Plasticizers in Preparing Solid Dispersions of Poorly Soluble API: Stability Testing of Selected Solid Dispersions", 2006, Pharmaceutical Research, vol. 23, No. 8, pp. 1928-1936.

Leverson et al., "Exploiting selective BCL-2 family inhibitors to dissect cell survival dependencies and define improved strategies for cancer therapy", Science Magazine, Mar. 18, 2015, vol. 7, Issue 279, pp. 1-12.

Montero et al. "Why do Bcl-2 inhibitors work and where should we use them in the clinic?", 2018, Cell Death and Differentiation, vol. 25, pp. 56-64.

Wermuth et al., Drug solubilization with organic solvents, surfactants and lipids, The Practice of Medicinal Chemistry, Elsevier, 2nd Ed., 2003, pp. 646-647.

Restriction Requirement dated May 2, 2016, U.S. Appl. No. 14/537,392, 12 pages.

Non-Final Office Action dated Nov. 3, 2016, U.S. Appl. No. 14/537,392, 27 pages.

Final Office Action dated May 19, 2017, U.S. Appl. No. 14/537,392, 29 pages.

Advisory Action dated Sep. 5, 2017, U.S. Appl. No. 14/537,392, 3 pages.

Non-Final Office Action dated Mar. 9, 2018, U.S. Appl. No. 14/537,392, 21 pages.

Albers, J., "Hot-melt extrusion with poorly soluble drugs", Inaugural-Dissertation, Jun. 2008, Heinrich-Heine-Universität Düsseldorf, 151 pages.

Sinha et al., "Solid Dispersion: An Alternative Technique for Bioavailability Enhancement of Poorly Soluble Drugs", Journal of Dispersion Science and Technology, 2009, vol. 30, pp. 1458-1473.

Cheung et al., "Pharmacokinetics of the BCL-2 Inhibitor Venetoclax in Healthy Chinese Subjects", Clinical Pharmacology in Drug Development, 2018, vol. 7, No. 4, pp. 435-440.

Coutant et al., "Understanding Disease—Drug Interactions in Cancer Patients: Implications for Dosing Within the Therapeutic Window", Clinical Pharmacology & Therapeutics, Jul. 2015, www.wileyonlinelibrary/cpt, vol. 98, No. 1, pp. 76-86.

Davids et al., "Phase I First-in-Human Study of Venetoclax in Patients With Relapsed or Refractory Non-Hodgkin Lymphoma", Journal of Clinical Oncology, 2017, vol. 35, No. 8, pp. 826-833.

Edlund et al., "Population Pharmacokinetics of the BTK Inhibitor Acalabrutinib and its Active Metabolite in Healthy Volunteers and Patients with B-Cell Malignancies", Clinical Pharmacokinetics, 2019, vol. 58, pp. 659-672.

Hughes et al., "Population pharmacokinetics of lenalidomide in patients with B-cell malignancies", British Journal of Clinical Pharmacology, 2019, vol. 85, pp. 924-934.

Jones et al., "Clinical Predictors of Venetoclax Pharmacokinetics in Chronic Lymphocytic Leukemia and Non-Hodgkin's Lymphoma Patients: a Pooled Population Pharmacokinetic Analysis", The AAPS Journal, Sep. 2016, vol. 18, No. 5, pp. 1192-1202.

Konopleva et al., "Efficacy and Biological Correlates of Response in a Phase II Study of Venetoclax Monotherapy in Patients with Acute Myelogenous Leukemia", Cancer Discovery, 2016, pp. 1107-1117.

Kumar et al., "Safety and Efficacy of Venetoclax (ABT-199/GDC-0199) Monotherapy for Relapsed/Refractory Multiple Myeloma: Phase 1 Preliminary Results", Presented at the 57th American Society of Hematology Annual Meeting and Exposition, Orlando, FL, Dec. 5-8, 2015, 2 pages.

Mistry et al., "Population pharmacokinetic modelling of decitabine in patients with myelodysplastic syndromes (MDS) and acute myeloid leukemia (AML)", Journal of Clinical Oncology, 2011, Suppl. 6551, Abstract only, 2 pages.

Moreau et al., "Promising efficacy and acceptable safety of venetoclax plus bortezomib and dexamethasone in relapsed/refractory MM", Blood, Nov. 30, 2017, vol. 130, No. 22, pp. 2392-2400.

Nader et al., "Pharmacokinetics of Upadacitinib in Healthy Subjects and Subjects With Rheumatoid Arthritis, Crohn's Disease, Ulcerative Colitis, or Atopic Dermatitis: Population Analyses of Phase 1 and 2 Clinical Trials", The Journal of Clinical Pharmacology, 2020, vol. 60, No. 4, pp. 528-539.

Nalpropion Pharmaceuticals, Inc. v. Actavis Laboratories FL, Inc., 934 F.3d 1344 (2019), 13 pages.

Ou et al., "Exposure-Response Relationship of the Bruton Tyrosine Kinase Inhibitor, Zanubrutinib (BGB-3111) in Patients with Hematologic Malignancies", Blood, 2019, vol. 134 (Supplement_1): 5063, 7 pages.

Pharmaceutical Technology, vol. I: Fundamental aspects of Pharmaceutical systems and basic operations, Chapter 3: Solutions, 3.6.3 Dispersions requested, 2001, Editor: Jose Luis Vila Jato, pp. 201-202; vol. II: Oral solid forms pp. 98-99.

Roberts et al., "Targeting BCL2 with venetoclax in relapsed chronic lymphocytic leukemia", NIHMS1562022—Supplementary Appendix, New England Journal of Medicine, 2016, vol. 374, No. 4, pp. 311-322.

Salem et al., "Effect of Low- and High-Fat Meals on the Pharmacokinetics of Venetoclax, a Selective First-in-Class BCL-2 Inhibitor", The Journal of Clinical Pharmacology, 2016, vol. 56, No. 11, pp. 1355-1361.

Salem et al., "Population Pharmacokinetic Modeling of Veliparib (ABT-888) in Patients with Non-Hematologic Malignancies", Clin Pharmacokinet, 2014, vol. 53, pp. 479-488.

Salem et al., "Pharmacokinetics of Venetoclax, a Novel BCL-2 Inhibitor, in Patients With Relapsed or Refractory Chronic Lymphocytic Leukemia or Non-Hodgkin Lymphoma", The Journal of Clinical Pharmacology, 2017, vol. 57, No. 4, pp. 484-492.

Winzenborg et al., "Population Pharmacokinetics of Elagolix in Healthy Women and Women with Endometriosis", Clin Pharmacokinet, 2018, vol. 57, pp. 1295-1306.

Bardwell P.D., et al., "The Bcl-2 Family Antagonist ABT-737 Significantly Inhibits Multiple Animal Models of Autoimmunity," Journal of Immunology, 2009, vol. 182 (12), pp. 7482-7489.

Becker D.P., et al., "Azaadamantane Benzamide 5-HT4 Agonists: Gastrointestinal Prokinetic SC-54750," Bioorganic and Medicinal Chemistry Letters, 2004, vol. 14 (22), pp. 5509-5512.

(56) References Cited

OTHER PUBLICATIONS

Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes & Metabolism, 1997, vol. 23 (3), pp. 251-257.
Blagojevic, N. et al., "Role of Heavy Water in Boron Neutron Capture Therapy," Topics in Dosimetry & Treatment Planning for Neutron Capture Therapy, 1994, pp. 125-134.
Blake, M.I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemishy, 1996, vol. 39 (3), pp. 673-679.
Bruncko, M., et al., "Studies Leading to Potent, Dual Inhibitors of Bcl-2 and Bcl-xL," Journal of Medicinal Chemistry, 2007, vol. 50 (4), pp. 641-662.
Caira, M.R., "Crystalline Polymorphism of Organic Compounds," 1998, vol. 198, pp. 163-208.
Cancer [online], [retrieved on Jul. 6, 2007]. Retrieved from the internet, <URL: http://www.nlm.nih.gov/medlineplus/cancer.html>, 8 pgs.
Cancer [online], [retrieved on Jul. 6, 2007]. Retrieved from the internet, <URL: http:// en.wikipedia.org/wiki/Cancer>, 34 pgs.
Certo, M., et al., "Mitochondria Primed by Death Signals Determine Cellular Addiction to Antiapoptotic BCL-2 Family Members," Cancer Cell, 2006, vol. 9 (5), pp. 351-365.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Crowley, M. M., et al., "Pharmaceutical Applications of Hot-Melt Extrusion: Part 1," Drug Development and Industrial Pharmacy, 2007, vol. 33 (9), pp. 909-926.
Czajka, D. M. et al., "Effect of Deuterium Oxide on the Reproductive Potential of Mice," Annals New York Academy of Sciences, 1960, vol. 84, pp. 770-779.
Czajka, D. M. et al., "Physiological Effects of Deuterium on Dogs," American Journal of Physiology, 1961, vol. 201 (2), pp. 357-362.
Del Gaizo Moore, V., et al., "BCL-2 Dependence and ABT-737 Sensitivity in Acute Lymphoblastic Leukemia," Blood, 2008, vol. 111 (4), pp. 2300-2309.
Durocher Y., et al., "High-Level and High-Throughput Recombinant Protein Production by Transient Transfection of Suspension-Growing Human 293-EBNA1 Cells," Nucleic Acids Research, 2002, vol. 30 (2), pp. e9.
Eliel, E. L. et al., "Stereochemistry of Organic Compounds," 1994, John Wiley & Sons, Inc., New York. Table of Contents. 6 pgs.
Fairhurst A.M., et al., "Systemic IFN-Alpha Drives Kidney Nephritis in B6.Sle123 Mice," European Journal of Immunology, 2008, vol. 38 (7), pp. 1948-1960.
Foster, A. B. et al., "Deuterium Isotope Effects in the Metabolism of Drugs and Xenobiotics: Implications for Drug Design," Advances in Drug Research, 1985, vol. 14, pp. 2-36.
Gelfand M.C., et al., "Therapeutic Studies in NZB/W Mice II. Relative Efficacy of Azathioprine, Cyclophosphamide and Methylprednisolone," Arthritis and Rheumatism,1972, vol. 15 (3), pp. 247-252.
Golub, T.R., et al., "Molecular Classification of Cancer: Class Discovery and Class Prediction by Gene Expression Monitoring", Science (1999), vol. 286, pp. 531-537.
Guo Z., et al., "Relationship between the Expression of bcl-2. Fas/FasL and the Apoptosis of Peripheral Lymphocytes in Patients with Systemic lupus Erythematosus," Chinese Journal of Dermatology, 2001, vol. 34 (1), pp. 25 and 27.
Gupta, P. K., "Solutions and Phase Equilibria", Remington, The Science and Practice of Pharmacy, 21st Edition, Chapter 16, (2005) pp. 211-230.

Hanahan, D., et al., "The Hallmarks of Cancer," Cell, 2000, vol. 100 (1 ), pp. 57-70.
Harada, H., et al., "Survival Factor-Induced Extracellular Signal-Regulated Kinase Phosphorylates BIM, Inhibiting its Association with BAX and Proapoptotic Activity," Proceedings of the National Academy of Sciences, 2004, vol. 101 (43), pp. 15313-15317.
Hoepfner, E.M., et al., eds., "Fiedler Encyclopedia of Excipients for Pharmaceuticals, Cosmetics and Related Areas," 5th Edition, Editio Cantor Verlag Aulendorf, 2002, Table of Contents, 6 pgs.
Holzelova, E. et al., "Autoimmune Lymphoproliferative Syndrome with Somatic Fas Mutations," New England Journal of Medicine, 2004, vol. 351 (14), pp. 1409-1418.
Hovorka, S. W. et al., "Oxidative Degradation of Pharmaceuticals: Theory, Mechanisms and Inhibition," J. Pharm. Sciences, 2001, vol. 90 (3), pp. 253-269.
Humerickhouse, R, "Clinical Activity of the Potent and Selective Bcl-2 Inhibitor ABT-199: Proving the Concept," Symposium presentation, Apr. 9, 2013, AACR Annual Meeting (Wash. DC), 31 pgs.
Janssens et al., "Formulation and characterization of ternary solid dispersions made up of Itraconazole and two excipients, TPGS 1000 and PVPVA 64, that were selected based on a supersaturation screening study," European Journal of Pharmaceutics and Biopharmaceutics 69, 2008, pp. 158-166.
Jones, C.D. et al., "Effects of Substituent Modification on Face Selection in Reduction," Journal of Organic Chemistry, 1998, vol. 63 (8), pp. 2758-2760.
Kato, S. et al., "Synthesis of Deuterated Mosapride Citrate," Journal of Labelled Compounds and Radiopharmaceuticals, 1995, vol. 36 (10), pp. 927-932.
Kayagaki N., et al., "BAFF/BLyS Receptor 3 Binds the B Cell Survival Factor BAFF Ligand Through a Discrete Surface Loop and Promotes Processing of NF-kB2," Immunity, 2002, vol. 10, pp. 515-524.
Kibbe, A.H., Handbook of Pharmaceutical Excipients, Third Edition, 2000, American Pharmaceutical Association, Table of Contents, 4 pgs.
Klein, C.E., et al., "The Tablet Formulation of Lopinavir/Ritonavir Provides Similar Bioavailability to the Soft-Gelatin Capsule Formulation With Less Pharmacokinetic Variability and Diminished Food Effect," Journal of Acquired Immune Deficiency Syndromes, 2007, vol. 44 (4), pp. 401-410.
Korolkovas A., "Development of Drugs" in: Essentials of Medicinal Chemistry, Second Edition, John Wiley and Sons, 1988, pp. 53-139.
Kushner, et al., "Pharmacological uses and perspectives of heavy water and deuterated compounds," Canadian Journal of Physiology and Pharmacology, 1999, vol. 77 (2), pp. 79-88.
Kwok S.K., et al., "Dysfunctional Interferon—a Production by Peripheral Plasmacytoid Dendritic Cells upon Toll-like Receptor-9 Stimulation in Patients with Systemic Lupus Erythematosus," Arthritis Research & Therapy, 2008, vol. 10 (2), 11 pgs.
Lala, P.K., et al., "Role of nitric oxide in tumor progression: Lessons from experimental tumors." Cancer and Metastasis Reviews, 1998, vol. 17(1 ), pp. 91-106.
Laurent, S.A., et al., "Synthesis of "Trioxaquantel" Derivatives as Potential New Antischistosomal Drugs," European Journal of Organic Chemistry, 2008, vol. 5, pp. 895-913.
Leuner, C., et al., "Improving Drug Solubility for Oral Delivery Using Solid Dispersions," European Journal of Pharmaceutics and Biopharmaceutics: Official Journal of Arbeitsgemeinschaft Fur Pharmazeutische Verfahrenstechnik E.V., 2000, vol. 50 (1), pp. 47-60.
Liao, G., "ABT-199 BH-3 Mimetic Enters Phase Ia Trial For Chronic Lymphocytic Leukemia", [Asian Scientist Magazine online], [retrieved on Aug. 12, 2011]. Retrieved from the Internet <URL: http://www.asianscientist.com/tech-pharma/abt-199-bh-3-mimetic-wehiphase-ia-trial-chronic-lymphocytic-leukemia>, 2 pgs.
Liu K., et al., "What do Mouse Models Teach us about Human SLE?," Clinical Immunology, 2006, vol. 119(2), pp. 123-130.
Lizondo, J. et al., "Linezolid: Oxazolidinone Antibacterial," Drugs of the Future, 1996, vol. 21 (11), pp. 1116-1123.

(56) References Cited

OTHER PUBLICATIONS

Mallesham, B. et al., "Highly Efficient CuI-Catalyzed Coupling of Aryl Bromides with Oxazolidinones Using Buchwald's Protocol: A Short Route to Linezolid and Toloxatone," Organic Letters, 2003, vol. 5 (7), pp. 963-965.
Marquina R., et al., "Inhibition of B Cell Death Causes the Development of an IgA Nephropathy in KNew Zealand White x C57BL/6) $F_1$-bcl-2 Transgenic Mice," Journal of Immunology, 2004, vol. 172 (11), pp. 7177-7185.
Mason K.D., et al., "Programmed Anuclear Cell Death Delimits Platelet Life Span," Cell, 2007, vol. 128 (6), pp. 1173-1186.
Mathian A., et al., "IFN-a induces Early Lethal Lupus in Preautoimmune (New Zealand Black x New Zealand White) $F_1$, but not in BALB/c Mice," Journal of Immunology, 2005, vol. 174 (5), pp. 2499-2506.
Mizushima S., et al., "pEF-BOS, a Powerful Mammalian Expression Vector," Nucleic Acids Research, 1990, vol. 18(17), pp. 5322.
Moschwitzer, J. et al., "Development of an Intravenously Injectable Chemically Stable Aqueous Omeprazole Formulation Using Nanosuspension Technology" Eur. J. Pharmaceutics and Biopharmaceutics, 58(3), 2004, pp. 615-619.
Oltersdorf, T., et al., "An inhibitor of Bcl-2 family proteins induces regression of solid tumours," Nature, 2005, vol. 435 (2), pp. 677-681.
Puck J.M., et al., "Immune Disorders Caused by Defects in the Caspase Cascade," Current Allergy and Asthma Reports, 2003, vol. 3, pp. 378-384.
Ramos M.A., et al., "Modulation of Autoantibody Production by Mycophenolate Mofetil: Effects on the Development of SLE in (NZB x NZW)$F_1$Mice," Nephrology Dialysis Transplantation, 2003, vol. 18 (5), pp. 878-883.
Rengan R., et al., "Actin Cytoskeletal Function is Spared, but Apoptosis is Increased, in WAS Patient Hematopoietic Cells," Blood, 2000, vol. 95 (4), pp. 1283-1292.
Roberti, M., et al., "Synthesis and Biological Evaluation of Resveratrol and Analogues as Apoptosis-Inducing Agents," J. Med. Chem. 2003, 46, 3546-3554.
Sharma, D.K, et al., "Solubility Enhancement Strategies for Poorly Water-Soluble Drugs in Solid Dispersions: A Review," Asian Journal of Pharmaceutics, 2007, vol. 1 (1), pp. 9-19.
Shimazaki K., et al., "Evaluation of Apoptosis as a Prognostic Factor in Myelodysplastic Svndromes," British Journal of Haematology, 2000, vol. 110 (3), pp. 584-590.
Skoug, J.W., et al., Enabling Discovery Through Formulation, American Association of Pharmaceutical Scientists (AAPS) Webinar [online]. Presented Mar. 18, 2010, 12:30 PM to 2:00PM EDT, 51 pgs.
Souers, Andrew J. et al., "ABT-199, a potent and selective BCL-2 inhibitor, achieves antitumor activity while sparing platelets," Nature Medicine, (2013), 9 pgs.
Sperling, L. H., "Introduction to Physical Polymer Science," Second Edition, John Wiley & Sons, Inc., 1992, Table of Contents, 18 pgs.
Sutton, V.R., et al., "Bcl-2 Prevents Apoptosis Induced by Perforin and Granzyme B, but Not That Mediated by Whole Cytotoxic Lymphocytes," Journal of Immunology, 1997, vol. 158 (12), pp. 5783-5790.
Thomson, J.F., "Physiological Effects of $D_2O$ in Mammals," Annals New York Academy of Sciences, 1960, vol. 84, pp. 736-744.
Tse, C., et al., "ABT-263: A Potent and Orally Bioavailable Bcl-2 Family Inhibitor," Cancer Research, 2008, vol. 68 (9), pp. 3421-3428—Including Supplementary Data.
U.S. Department of Health and Human Services Food and Drug Administration Center for Drug Evaluation and Research, Guidance for Industry, Aug. 2000, [retrieved on Jan.25, 2012], Retrieved from the internet <URL: http://www. f <la.gov I downloads/Drugs/GuidanceComplianceRegulatoryInformation/Guidances/ucm070246. pdf.>, 16 pgs.
Vandenberg, C.J. et al., "ABT-199, a new Bcl-2-specific BH3 mimetic, has in vivo efficacy against aggressive Myc-driven mouse lymphomas without provoking thrombocytopenia". Blood First Edition Paper, prepublished online Jan. 22, 2013; DOI 10.1182/blood-2013-01-475855, 12 pgs.
Vasanthavada, M. et al., "Development of Solid Dispersion of Poorly Water-Soluble Drugs", in Water-Insoluble Drug Formulation, Liu, R., ed., 2nd Edition, (2008), pp. 499-529.
Wang, Z.X., "An Exact Mathematical Expression for Describing Competitive Binding of Two Different Ligands to a Protein Molecule," FEBS Letters, 1995, vol. 360 (2), pp. 111-114.
Wendt, M.D., "Discovery of ABT-263, a Bcl-Family Protein Inhibitor: Observations on Targeting a Large Protein-Protein Interaction," Expert Opinion on Drug Discovery, 2008, vol. 3 (9), pp. 1123-1143.
Wilson L.E., et al., "Autoimmune Disease Complicating Antiviral Therapy for Hepatitis C Virus Infection," Seminars in Arthritis and Rheumatism, 2002, vol. 32 (3), pp. 163-173.
Xie M., et al., "Apoptosis and Fas/bcl-2 Expression in Peripheral Blood Lymphocytes of Patients with Systemic Lupus Erythematosus," Chinese Medical Journal, 1999, vol. 113, p. 1072.
Zhang R., et al., "Effect of Interferon-Alpha in Systemic Lupus Erthematosus (SLE) Serum on the Differentiation and Maturation of Dendritic Cells derived from CD34+Hematopoietic Precursor Cells," Journal of Nanjing Medical University, 2009, vol. 23 (6), pp. 380-385.
Zhang, H., et al., "Bcl-2 Family Proteins are Essential for Platelet Survival," Cell Death and Differentiation, 2007, vol. 14 (5), pp. 943-951.
International Searching Authority, Written Opinion dated Mar. 10, 2009 for Application No. PCT/US2007/077579, 9 pages.
International Searching Authority, International Search Report dated Jun. 17, 2010 for Application No. PCT/EP2009/067689, 5 pages.
International Searching Authority, International Search Report dated Jul. 28, 2010 for Application No. PCT/US2009/066790, 5 pages.
International Searching Authority, Supplementary International Search Report dated Mar. 24, 2011 for Application No. PCT/ US2009/066790, 2 pages.
International Searching Authority, International Search Report dated Jul. 28, 2010 for Application No. PCT/US2009/067335, 4 pages.
International Searching Authority, International Search Report dated Aug. 4, 2010 for Application No. PCT/US2009/066722, 4 pages.
International Searching Authority, Supplementary International Search Report dated Feb. 24, 2011 for Application No. PCT/US2009/066722, 2 pages.
International Searching Authority, Written Opinion dated Jun. 7, 2011 for Application No. PCT/US2009/066722, 7 pages.
International Searching Authority, International Search Report dated Aug. 16, 2010 for Application No. PCT/US2010/036844, 5 pages.
International Searching Authority, Written Opinion dated Jun. 5, 2012 for Application No. PCT/US2010/036844, 8 pages.
International Searching Authority, International Search Report dated Aug. 19, 2010 for Application No. for PCT/US2010/036919, 5 pages.
International Searching Authority, Written Opinion dated Jun. 5, 2012 for Application No. PCT/US2010/036919, 7 pages.
International Searching Authority, International Search Report dated Feb. 9, 2011 for Application No. PCT/US2010/036198, 3 pages.
International Searching Authority, Supplementary International Search Report dated Sep. 8, 2011 for PCT/US2010/036198, 2 pages.
International Searching Authority, Written Opinion dated Nov. 29, 2011 for Application No. PCT/US2010/036198, 7 pages.
International Searching Authority, International Search Report dated Apr. 28, 2011 for Application No. PCT/US2010/057587, 4 pages.
International Searching Authority, Supplementary International Search Report dated Jun. 28, 2012 for Application No. PCT/US2010/057587, 2 pages.
International Searching Authority, Supplementary International Search Report dated Sep. 29, 2011 for Application No. PCT/IB2010/001659, 3 pages.
International Searching Authority, International Search Report dated Dec. 16, 2011 for Application No. PCT/US2011/054959, 4 pages.
International Searching Authority, International Search Report dated Jan. 27, 2012 for Application No. PCT/US2011/058024, 4 pages.
International Searching Authority, International Search Report dated Feb. 3, 2012 for Application No. PCT/US2011/061678, 4 pages.

(56) References Cited

OTHER PUBLICATIONS

International Searching Authority, International Search Report dated Feb. 14, 2012 for Application No. PCT/US2011/061769, 4 pages.
(English Translation) Tecnologia Farmaceutica, vol. 1: Aspectos fundamentales de los sistemas farmaceuticos y operaciones basicas, Capitulo 3: Disoluciones, 3.6.3, Dispersiones solidas, pp. 201-202, vol. II: Formas solidas orales, pp. 98 to 100, Jose Luis Vila Jato (2001).
DiNunzio et al., "Fusion processing of itraconazole solid dispersions by kinetisol® dispersing: A comparative study to hot melt extrusion," Journal of Pharmaceutical Sciences, 99(3): 1239-1253 (2010).
Anonymous: "Phosal™ 53 MCT"[Online] Feb. 2007 (Feb. 2007), XP0026 0 1 344Phospholipid GmbH—American Lecithin Retrieved from the Internet:URL:h11n//www.americanlecithin.com/TDS/TDS 53MCT.PDF.
AusPAR Circadin, Australian Public Assessment Report for Melatonin, Commercial Eyes Pty Ltd, Dec. 2009, pp. 1-57.
Biopharmaceutical Classification System and Formulation Development Technical Brief 2011, Particle Sciences, Drug Development Services, vol. 9, 4 pages.
Brandrup et al., Polymer Handbook, 1975, 2 , John Wiley & Sons, Inc.
Brittain et al., Effects of pharmaceutical processing on drug polymorphs and solvates, Polymorphismin Pharmaceutical Solids, 1999, vol. 95, pp. 331-361.
Brittain et al., Polymorphism I Pharmaceutical Solids, 1 999, Chapter 1, pp. 1-10, and Chapter 5, pp. 183-226.
Buhler, (http://www.innovate-excipients.basf.com/Documents/ENP/Brochure/EN/GEMPMD256 Kollidon Polyvinylpyrrolidone excipients for_ the pharmaceutical_industry.pdf; Mar. 2008), 2 pages.
Byrn et al., Pharmaceutical Solids: A Strategic Approach to Regulatory Considerations, Pharmaceutical Research, 1995, vol. 12, No. 7, pp. 945-954.
Chawla et al., Polymorphism o f pharmaceuticals: Challenges and opportunities, Article, Oct. 23, 2003, www.ex2resspharmaonline.com/2003 I 023/edito2.shtml, 3 pages.
Dash et al., Role of Biopharmaceutical Classification System in Drug Development Program, Journal of Current Pharmaceutical Research, 2011, vol. 5. No. 1, pp. 28-31.
Design and Evaluation of Oral Administration Drugs, 1995, pp. 172-179.
Fiedler, H. B., Encyclopedia of Excipients: for Pharmaceuticals, Cosmetics and Related Areas (Der Pharmazeutische Betrieb), 5th Edition, Editio-Cantor 2002.
Formulations Platform Report 1; Intra-Agency Agreement Between the Eunice Kennedy ShriverNational Institute of Child Health and Human Development (NICHD) and the U.S. Food and DrugAdministration (FDA) Oral Formulations Platform—Report I;(http://www.acceessdata.fda.gov/scripts/cder/drugsatfda/index.cfm?fuseaction=Reports.ReportsMenu), 14 pages.
Gould, Salt selection for basic drags, International Journal of Pharmaceutics, Nov. 1986, 33(1-3), pp. 201-217.
Lessene et al., BLC-2 family antagonists for cancer therapy, Nature Reviews I Drug Discovery, Dec. 2008, vol. 7, Macmillan Publishers Limited, pp. 989-1000.
Paolini et al., Global mapping of pharamacological space, Jul. 2006, vol. 24, No. 24, Nature Biotechnology, Jul. 2006, vol. 24, No. 24, pp. 805-815.
Sachan, et al., Biopharmaceutical classification system: A strategic tool for oral drug delivery technology, Asian Journal of Pharmaceutics, 2009, vol. 3, Issue 2, pp. 76-81.
Shoemaker et al., Activity of the Bcl-2 Family Inhibitor ABT-263 in a Panel of Small Cell Lung Cancer Xenograft Models, Clinical Cancer Research, Jun. 1, 2008, vol. 14, No. 11, pp. 3268-3277.
SkypePharma, DissoCubes[online], 2010 [retrived on Nov. 17, 2012]. 1 page. Retrieved from the Internet:<URL: http//www.skyepharma.com/Technology/Oral_Technology_Particle_Engineering_Technologies/DisoCubes/Default.aspx?id=81.
Sophie et al., Synthesis of "Trioxaquantel" Derivatives as Potential New Antischistosomal Drags, European Journal of Organic Chemistry, 2008, pp. 895-913.
Trotta et al., Stability of drag-carrier emulsions containing phosphatidylcholine mixtures, European Journal of Pharmaceutics and Biopharmaceutics, Jun. 11, 2001, vol. 53, pp. 203-208.
Varma, European Journal of Pharmaceutical Sciences, vol. 25, 2005, pp. 445-453.
Wang et al., An Efficient Synthesis of ABT-263, A Novel inhibitor of Antiapoptotic Bcl-2 Proteins, Synthesis, Jun. 11, 2008, vol. 15 , pp. 2398-2404.
Wu et al., Predicting Drug Disposition via Application of BCS:Transport/Absorption/Elimination Interplay and Development of a Biopharmaceutics Drug DispositionClassification System; Pharmaceutical Research, vol. 22, No. 1, Jan. 2005; pp. 11-23.
Yasir et al., Biopharmaceutical Classification System: An Account, International Journal of Pharm Tech Research, Jul.-Sep. 2010, vol. 2, No. 3, pp. 1681-1690.
Yu et al., Vitamin E-TPGS Increases Absorption Flux of an HIV Protease Inhibitor by Enhancing Its Solubility and Permeability, Pharmaceutical Research, 1999, vol. 16, No. 12, pp. 1812-1817.

\* cited by examiner

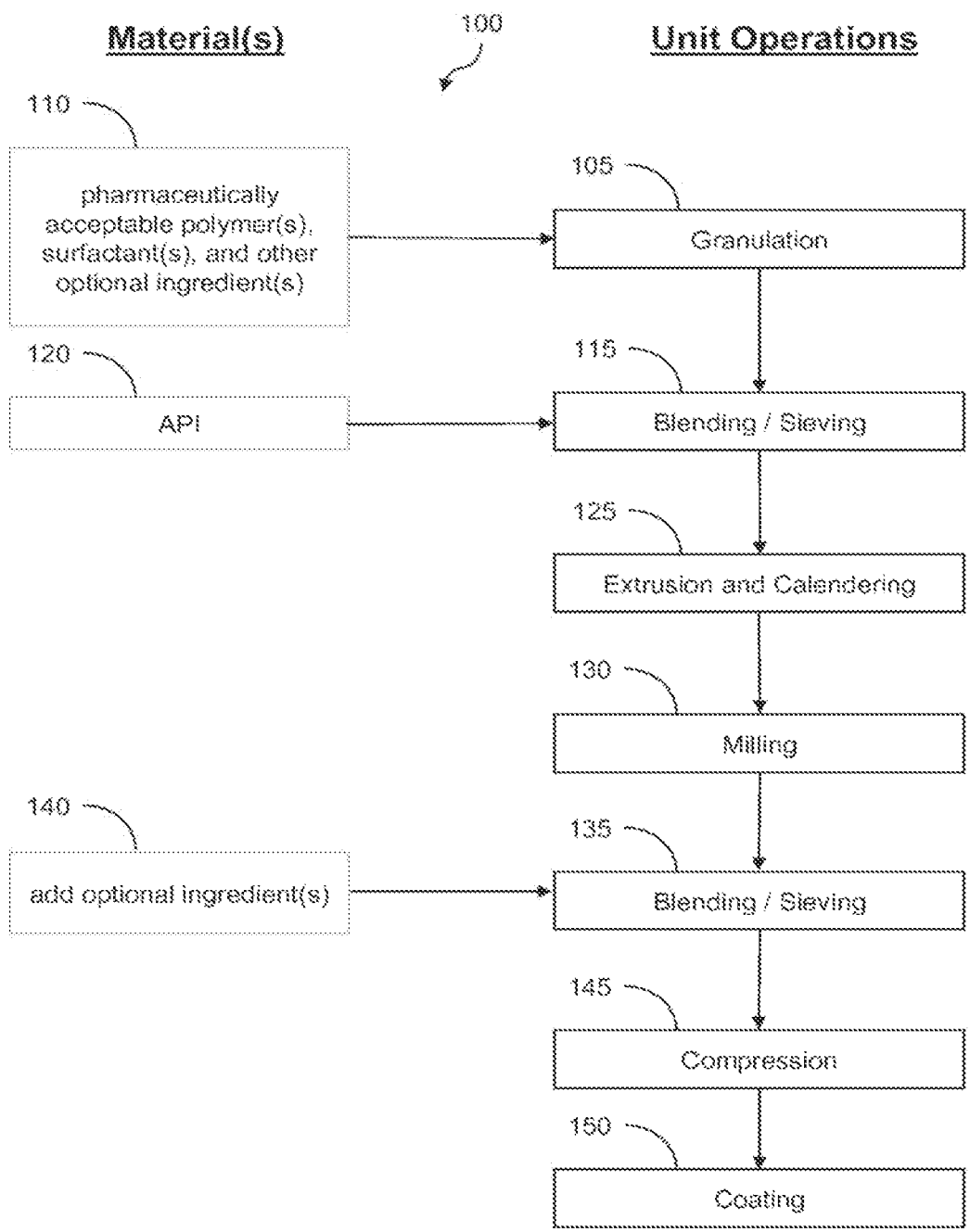

MELT-EXTRUDED SOLID DISPERSIONS CONTAINING AN APOPTOSIS-INDUCING AGENT

CROSS REFERENCE TO RELATED APPLICATIONS

This application is a continuation of U.S. application Ser. No. 13/253,727, filed Oct. 5, 2011, which claims the benefit of provisional application No. 61/408,527, filed Oct. 29, 2010, each of which is hereby incorporated by reference as if set forth in its entirety.

Cross-reference is also made, without claim to benefit of priority or admission as to prior art status, to the following U.S. application containing subject matter related to the present application Ser. No. 12/787,682 (U.S. 2010/0305122) titled "Apoptosis-inducing agents for the treatment of cancer and immune and autoimmune diseases," the entire disclosure of which is incorporated herein by reference.

FIELD OF THE INVENTION

The present invention relates to solid dispersions comprising an apoptosis-inducing agent, to pharmaceutical dosage forms comprising such dispersions, to processes for preparing such dispersions and dosage forms and to methods of use thereof for treating diseases characterized by overexpression of anti-apoptotic Bcl-2 family proteins.

BACKGROUND

Overexpression of Bcl-2 proteins correlates with resistance to chemotherapy, clinical outcome, disease progression, overall prognosis or a combination thereof in various cancers and disorders of the immune system.

Evasion of apoptosis is a hallmark of cancer (Hanahan & Weinberg (2000) Cell 100:57-70). Cancer cells must overcome a continual bombardment by cellular stresses such as DNA damage, oncogene activation, aberrant cell cycle progression and harsh microenvironments that would cause normal cells to undergo apoptosis. One of the primary means by which cancer cells evade apoptosis is by up-regulation of anti-apoptotic proteins of the Bcl-2 family.

A particular type of neoplastic disease for which improved therapies are needed is non-Hodgkin's lymphoma (NHL). NHL is the sixth most prevalent type of new cancer in the U.S. and occurs primarily in patients 60-70 years of age. NHL is not a single disease but a family of related diseases, which are classified on the basis of several characteristics including clinical attributes and histology.

One method of classification places different histological subtypes into two major categories based on natural history of the disease, i.e., whether the disease is indolent or aggressive. In general, indolent subtypes grow slowly and are generally incurable, whereas aggressive subtypes grow rapidly and are potentially curable. Follicular lymphomas are the most common indolent subtype, and diffuse large-cell lymphomas constitute the most common aggressive subtype. The oncoprotein Bcl-2 was originally described in non-Hodgkin's B-cell lymphoma.

Treatment of follicular lymphoma typically consists of biologically-based or combination chemotherapy. Combination therapy with rituximab, cyclophosphamide, doxorubicin, vincristine and prednisone (R-CHOP) is routinely used, as is combination therapy with rituximab, cyclophosphamide, vincristine and prednisone (RCVP). Single-agent therapy with rituximab (targeting CD20, a phosphoprotein uniformly expressed on the surface of B-cells) or fludarabine is also used. Addition of rituximab to chemotherapy regimens can provide improved response rate and increased progression-free survival.

Radioimmunotherapy agents, high-dose chemotherapy and stem cell transplants can be used to treat refractory or relapsed NHL. Currently, there is not an approved treatment regimen that produces a cure, and current guidelines recommend that patients be treated in the context of a clinical trial, even in a first-line setting.

First-line treatment of patients with aggressive large B-cell lymphoma typically consists of rituximab, cyclophosphamide, doxorubicin, vincristine and prednisone (R-CHOP), or dose-adjusted etoposide, prednisone, vincristine, cyclophosphamide, doxorubicin and rituximab (DA-EPOCH-R).

Most lymphomas respond initially to any one of these therapies, but tumors typically recur and eventually become refractory. As the number of regimens patients receive increases, the more chemotherapy-resistant the disease becomes. Average response to first-line therapy is approximately 75%, 60% to second-line, 50% to third-line, and about 35-40% to fourth-line therapy. Response rates approaching 20% with a single agent in a multiple relapsed setting are considered positive and warrant further study.

Other neoplastic diseases for which improved therapies are needed include leukemias such as chronic lymphocytic leukemia (like NHL, a B-cell lymphoma) and acute lymphocytic leukemia.

Chronic lymphoid leukemia (CLL) is the most common type of leukemia. CLL is primarily a disease of adults, more than 75% of people newly diagnosed being over the age of 50, but in rare cases it is also found in children. Combination chemotherapies are the prevalent treatment, for example fludarabine with cyclophosphamide and/or rituximab, or more complex combinations such as CHOP or R-CHOP.

Acute lymphocytic leukemia, also known as acute lymphoblastic leukemia (ALL), is primarily a childhood disease, once with essentially zero survival but now with up to 75% survival due to combination chemotherapies similar to those mentioned above. New therapies are still needed to provide further improvement in survival rates.

Current chemotherapeutic agents elicit their antitumor response by inducing apoptosis through a variety of mechanisms. However, many tumors ultimately become resistant to these agents. Bcl-2 and Bcl-$X_L$ have been shown to confer chemotherapy resistance in short-term survival assays in vitro and, more recently, in vivo. This suggests that if improved therapies aimed at suppressing the function of Bcl-2 and Bcl-$X_L$ can be developed, such chemotherapy-resistance could be successfully overcome.

Involvement of Bcl-2 proteins in bladder cancer, brain cancer, breast cancer, bone marrow cancer, cervical cancer, CLL, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer and the like is described in International Patent Publication Nos. WO 2005/024636 and WO 2005/049593.

Involvement of Bcl-2 proteins in immune and autoimmune diseases is described, for example, by Puck & Zhu (2003) Current Allergy and Asthma Reports 3:378-384; Shimazaki et al. (2000) British Journal of Haematology 110(3):584-590; Rengan et al. (2000) Blood 95(4):1283-

1292; and Holzelova et al. (2004) *New England Journal of Medicine* 351(14):1409-1418. Involvement of Bcl-2 proteins in bone marrow transplant rejection is disclosed in United States Patent Application Publication No. US 2008/0182845.

Compounds that occupy a binding site on Bcl-2 proteins are known. To be therapeutically useful by oral administration, such compounds must have high binding affinity, exhibiting for example $K_i<1$ nM, preferably <0.1 nM, more preferably <0.01 nM, to proteins of the Bcl-2 family, specifically Bcl-2, Bcl-$X_L$ and Bcl-w. They must also be formulated in a manner that provides high systemic exposure after oral administration. A typical measure of systemic exposure after oral administration of a compound is the area under the curve (AUC) resulting from graphing plasma concentration of the compound versus time from oral administration.

Where aqueous solubility of Bcl-2 binding compounds is very low, the formulator faces a significant challenge in assuring acceptable oral bioavailability, which is strongly dependent on solubility in the aqueous medium of the gastrointestinal tract. This is true even where binding affinity is very high. The challenge becomes even greater when considering the need to provide an adequate drug loading in the formulation, so that a therapeutically effective dose can be administered in an acceptably small volume of formulated product.

Liquid dosage forms (including encapsulated liquids) can be useful for some drugs of low aqueous solubility, provided a suitable pharmaceutically acceptable solvent system (generally lipid-based) can be found that provides adequate drug loading without posing solubility or storage-stability issues. Other approaches that have been proposed for such drugs include solid dispersions, which bring their own challenges.

For a variety of reasons, such as patient compliance and taste masking, a solid dosage form is usually preferred over a liquid dosage form. In most instances, however, oral solid dosage forms of a drug provide a lower bioavailability than oral solutions of the drug.

There have been attempts to improve the bioavailability provided by solid dosage forms by forming solid dispersions, or more particularly solid solutions, of drugs. Solid dispersions, or solutions, are preferred physical systems because the components therein readily form liquid solutions when contacted with a liquid medium, such as gastric juice. The ease of dissolution may be attributed at least in part to the fact that the energy required for dissolution of the components from a solid dispersion, or solid solution, is less than that required for the dissolution of the components from a crystalline or microcrystalline solid phase. It is, however, important that the drug released from the solid dispersion, or solid solution, remains water-solubilized in the aqueous fluids of the gastrointestinal tract; otherwise, the drug may precipitate in the gastrointestinal tract, resulting in low bioavailability.

International Patent Publication WO 01/00175 relates to mechanically stable pharmaceutical dosage forms which are solid solutions of active ingredients in an auxiliary agent matrix. The matrix contains a homopolymer or a copolymer of N-vinyl pyrrolidone and a liquid or semi-solid surfactant.

International Patent Publication WO 00/57854 relates to mechanically stable pharmaceutical dosage forms for oral administration, containing at least one active compound, at least one thermoplastically moldable, matrix-forming auxiliary and more than 10% and up to 40% by weight of a surface-active substance that has a hydrophilic-lipophilic balance (HLB) value of between 2 and 18 and is liquid at 20° C., or has a drop point between 20° C. and 50° C.

U.S. Patent Application Publication No. 2005/0208082 relates to a solubilizing composition comprising a mixture of TPGS (α-tocopheryl polyethylene glycol succinate or vitamin E polyethylene glycol succinate) and linoleic acid. The solubilizing composition is used to disperse a lipophile in an aqueous phase.

Hot melt-extrusion, an enabling technology in increasing use for enhancing bioavailability of poorly water-soluble drug compounds, is a solvent-free, non-ambient process that has been said to afford many advantages over conventional solid dosage forms in terms of robustness and versatility (Crowley et al. (2007) *Drug Development and Industrial Pharmacy* 33:908-926).

Proprietary melt-extrusion technology (Meltrex® of Abbott GmbH, Wiesbaden, Germany) has been shown to significantly improve the pharmacokinetic properties of certain drugs over alternative formulations. See, for example, Klein et al. (2007) *J. Acquir. Immune Defic. Syndr.* 44:401-410.

Apoptosis-inducing drugs that target Bcl-2 family proteins such as Bcl-2 and Bcl-$X_L$ are best administered according to a regimen that provides continual, for example daily, replenishment of the plasma concentration, to maintain the concentration in a therapeutically effective range. This can be achieved by daily parenteral, e.g., intravenous (i.v.) or intraperitoneal (i.p.) administration. However, daily parenteral administration is often not practical in a clinical setting, particularly for outpatients. To enhance clinical utility of an apoptosis-inducing agent, for example as a chemotherapeutic in cancer patients, a solid dosage form with acceptable oral bioavailability would be highly desirable. Such a dosage form, and a regimen for oral administration thereof, would represent an important advance in treatment of many types of cancer, including NHL, CLL and ALL, and would more readily enable combination therapies with other chemotherapeutics.

SUMMARY

There is now provided a solid dispersion comprising, in essentially non-crystalline, for example amorphous, form, a compound of Formula I:

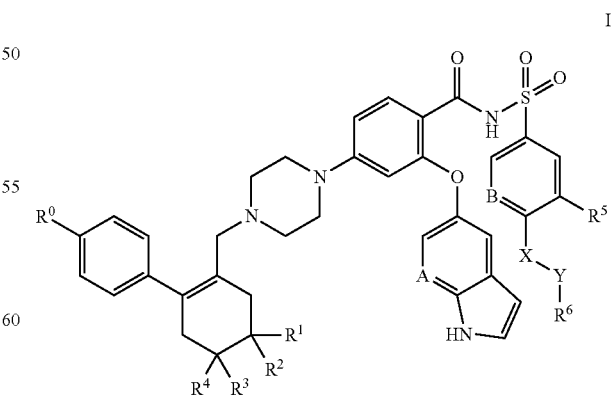

where:
 $R^0$ is halo;
 $R^1$ and $R^2$ are H or are independently methyl or methoxy;

$R^3$ and $R^4$ are independently methyl or methoxy if $R^1$ and $R^2$ are H, or are H if $R^1$ and $R^2$ are independently methyl or methoxy;

A and B are each independently CH or N;

$R^5$ is $C_{1-4}$ alkyl or haloalkyl, $C_{1-4}$ alkylsulfonyl or haloalkylsulfonyl, halo, nitro or cyano;

X is —O— or —NH—;

Y is —$(CH_2)_n$— where n is 0, 1, 2 or 3; and $R^6$ is an unsubstituted or substituted 3- to 7-membered carbocyclic or heterocyclic ring as defined herein, or is $NR^7R^8$;

wherein, if $R^6$ is $NR^7R^8$, $R^7$ and $R^8$ are each independently H or $R^9$—$(CH_2)_m$— groups, no more than one of $R^7$ and $R^8$ being H, where each $R^9$ is independently a 3- to 7-membered carbocyclic or heterocyclic ring, optionally substituted with no more than two $Z^1$ groups as defined below, and each m is independently 0 or 1; and wherein, if $R^6$ is a substituted carbocyclic or heterocyclic ring, substituents thereon are no more than two $Z^1$ groups and/or no more than one $Z^2$ group, $Z^1$ groups being independently selected from (a) $C_{1-4}$ alkyl, $C_{2-4}$ alkenyl, $C_{1-4}$ alkoxy, $C_{1-4}$ alkylthio, $C_{1-4}$ alkylamino, $C_{1-4}$ alkylsulfonyl, $C_{1-4}$ alkylsulfonylamino, $C_{1-4}$ alkylcarbonyl, $C_{1-4}$ alkylcarbonylamino and $C_{1-4}$ alkylcarboxy, each optionally substituted with one or more substituents independently selected from halo, hydroxy, $C_{1-4}$ alkoxy, amino, $C_{1-4}$ alkylamino, di-($C_{1-4}$ alkyl)amino and cyano, (b) halo, (e) hydroxy, (f) amino and (g) oxo groups, and $Z^2$ being (i) a further 3- to 6-membered carbocyclic or heterocyclic ring, optionally substituted with no more than two $Z^1$ groups as defined above, or (ii) $NR^7R^8$ where $R^7$ and $R^8$ are as defined above;

or a pharmaceutically acceptable salt of such compound. The compound or salt thereof is dispersed in a solid matrix that comprises (a) a pharmaceutically acceptable water-soluble polymeric carrier and (b) a pharmaceutically acceptable surfactant.

There is further provided a solid orally deliverable dosage form comprising such a solid dispersion, optionally together with one or more additional excipients.

There is still further provided a process for preparing a solid dispersion as described above. This process comprises:

(a) subjecting to elevated temperature (i) an active pharmaceutical ingredient (API) that comprises a compound of Formula I or a pharmaceutically acceptable salt thereof, (ii) a pharmaceutically acceptable water-soluble polymeric carrier and (iii) a pharmaceutically acceptable surfactant to provide an extrudable semi-solid mixture;

(b) extruding the semi-solid mixture, for example through a die; and (c) cooling the resulting extrudate to provide a solid matrix comprising the polymeric carrier and the surfactant and having the compound or salt thereof dispersed in an essentially non-crystalline form therein.

A "melt" herein is a liquid or semi-solid (e.g., rubbery) state induced by elevated temperature wherein it is possible for a first component to become homogeneously distributed in a matrix comprising a second component. Typically, the second (matrix) component, for example a polymeric carrier, is in such a state and other components, for example including a compound of Formula I or a salt thereof, dissolve in the melt, thus forming a solution.

By "elevated temperature" herein is meant a temperature above a softening point of the polymeric carrier, as affected by other components if present, such as plasticizers or surfactants.

Preparation of the melt can take place in a variety of ways. Mixing of the components can take place before, during or after formation of the melt. For example, the components can be mixed first and then subjected to elevated temperature to form the melt; alternatively mixing and melting can take place simultaneously. In one embodiment the polymeric carrier is first melted, optionally with the surfactant component, and the API is then added to the resulting melt. Usually, the melt is thoroughly mixed while at elevated temperature in order to ensure homogeneous dispersion of the API.

There is still further provided a solid dispersion prepared by the process described above.

There is still further provided a method for treating a neoplastic, immune or autoimmune disease, comprising orally administering to a subject having the disease a therapeutically effective amount of a solid dispersion as described above, or one or more solid dosage forms comprising such a dispersion. Examples of neoplastic diseases include cancers. A specific illustrative type of cancer that can be treated according to the present method is non-Hodgkin's lymphoma (NHL). Another specific illustrative type of cancer that can be treated according to the present method is chronic lymphocytic leukemia (CLL). Yet another specific illustrative type of cancer that can be treated according to the present method is acute lymphocytic leukemia (ALL), for example in a pediatric patient.

Additional embodiments of the invention, including more particular aspects of those provided above, will be found in, or will be evident from, the detailed description that follows.

DRAWINGS

Drawings herein are for illustrative purposes only of selected embodiments and not all possible implementations, and do not limit the scope of the present disclosure.

FIG. 1 is a flow-chart for a process including melt extrusion useful to form a solid dispersion product according to an embodiment of the present technology.

DETAILED DESCRIPTION

Attempts to formulate a compound of Formula I or a salt thereof as an orally deliverable dosage form have been frustrated by the very limited number of pharmaceutically acceptable liquid solvent systems providing acceptable solubility of the compound or salt, and by a tendency with all such solvent systems tested for precipitation of insoluble solids during storage. It has now been found that a more successful approach is to formulate the compound or salt as a solid dispersion. Details of that approach, by which a combination of satisfactory drug loading, acceptable stability and adequate bioavailability are all achievable with a very unpromising class of active ingredient, are disclosed herein.

A solid dispersion in accordance with the present disclosure comprises an active ingredient in an essentially non-crystalline or amorphous form, which is usually more soluble than the crystalline form. The term "solid dispersion" herein encompasses systems having small solid-state particles (e.g., essentially non-crystalline or amorphous particles) of one phase dispersed in another solid-state phase. More particularly, the present solid dispersions comprise particles of one or more active ingredients dispersed in an inert carrier or matrix in solid state, and can be prepared by melting or solvent methods or by a combination of melting and solvent methods. According to the present invention a melt-extrusion method as described herein is particularly favored.

An "amorphous form" refers to a particle without definite structure, i.e., lacking crystalline structure.

The term "essentially non-crystalline" herein means that no more than about 5%, for example no more than about 2% or no more than about 1% crystallinity, is observed by X-ray diffraction analysis. In a particular embodiment, no detectable crystallinity is observed by one or both of X-ray diffraction analysis or polarization microscopy. In this regard it is to be noted that, when no detectable crystallinity is observed, the solid dispersion referenced herein may additionally or alternatively be described as a solid solution.

A. Active Compound

Compounds of Formula I, including salts thereof, useful herein typically have very low solubility in water, being classed as essentially insoluble, i.e., having a solubility of less than about 10 µg/ml. Examples of such active ingredients are, for example, Biopharmaceutics Classification System (BCS) Class IV drug substances that are characterized by low solubility and low permeability (see "Waiver of in vivo bioavailability and bioequivalence studies for immediate-release solid oral dosage forms based on a biopharmaceutics classification system", U.S. Department of Health and Human Services, Food and Drug Administration, Center for Drug Evaluation and Research (CDER), August 2000). It will be recognized that aqueous solubility of many compounds is pH-dependent; in the case of such compounds the solubility of interest herein is at a physiologically relevant pH, for example a pH of about 1 to about 8. Thus, in various embodiments, the drug has a solubility in water, at least at one point in a pH range from about 1 to about 8, of less than about 10 µg/ml, in some cases less than about 1 µg/ml or even less than about 0.1 µg/ml. Illustratively, a particular compound useful herein has a solubility in water at pH 4 of <0.004 µg/ml.

Solid dispersions of the present invention comprise as active ingredient a compound of Formula I as defined above, or a pharmaceutically acceptable salt of such a compound. Optionally they may further comprise a second active ingredient, for example a therapeutic agent useful in combination therapy with the compound of Formula I as indicated hereinbelow.

In one embodiment, the compound has Formula I where $R^0$ is chloro.

In a further embodiment, the compound has Formula I where $R^1$ is methyl or methoxy, $R^2$ is methyl, and $R^3$ and $R^4$ are each H.

In a still further embodiment, the compound has Formula I where $R^5$ is trifluoromethyl, trifluoromethylsulfonyl, chloro, bromo or nitro. In a more particular embodiment, if $A^2$ is —CH— then $R^5$ is nitro; and if $A^2$ is —N— then $R^5$ is bromo.

In a more particular embodiment, the compound has Formula I where (a) $R^0$ is chloro, (b) $R^1$ is methyl or methoxy, $R^2$ is methyl, and $R^3$ and $R^4$ are each H, and (c) $R^5$ is trifluoromethyl, trifluoromethylsulfonyl, chloro, bromo or nitro.

Compounds useful herein vary considerably in the —X—Y—$R^6$ substituent, more particularly the $R^6$ group, of Formula I. In most embodiments, $R^6$ is a 3- to 7-membered carbocyclic or heterocyclic ring, optionally substituted as defined above.

The term "carbocyclic" herein embraces saturated and partly and fully unsaturated ring structures having 3 to 7 ring carbon atoms, including bicyclic structures. In one embodiment, $R^6$ is a saturated carbocyclic (i.e., cycloalkyl) ring, for example but not limited to cyclopropyl, cyclobutyl, cyclopentyl or cyclohexyl, in each case optionally substituted as more fully described below.

The term "heterocyclic" herein embraces saturated and partly and fully unsaturated ring structures having 4 to 7 ring atoms, one or more of which are heteroatoms independently selected from N, O and S. Typically the heterocyclic ring has no more than two such heteroatoms. In one embodiment, $R^6$ is a saturated heterocyclic ring, for example but not limited to azetidinyl, oxetanyl, thietanyl, pyrrolidinyl, imazolidinyl, pyrazolidinyl, tetrahydrofuranyl, oxazolidinyl, isoxazolidinyl, thiophanyl, thiazolidinyl, isothiazolidinyl, piperidinyl, piperazinyl, tetrahydropyranyl, 1,4-dioxanyl, morpholinyl or tetrahydrothiopyranyl, in each case optionally substituted as more fully described below.

Where $R^6$ is a carbocyclic or heterocyclic ring, for example a saturated ring as described immediately above, it can be unsubstituted or substituted at up to three positions on the ring. Substituents, if present, comprise no more than two $Z^1$ groups and/or no more than one $Z^2$ group.

$Z^1$ groups are independently selected from (a) $C_{1-4}$ alkyl, $C_{2-4}$ alkenyl, $C_{1-4}$ alkoxy, $C_{1-4}$ alkylthio, $C_{1-4}$ alkylamino, $C_{1-4}$ alkylsulfonyl, $C_{1-4}$ alkylsulfonylamino, $C_{1-4}$ alkylcarbonyl, $C_{1-4}$ alkylcarbonylamino and $C_{1-4}$ alkylcarboxy, each optionally substituted with one or more substituents independently selected from halo, hydroxy, $C_{1-4}$ alkoxy, amino, $C_{1-4}$ alkylamino, di-($C_{1-4}$ alkyl)amino and cyano, (b) halo, (e) hydroxy, (f) amino and (g) oxo groups. Illustrative examples of such $Z^1$ groups include without limitation methyl, cyanomethyl, methoxy, fluoro, hydroxy, amino and methylsulfonyl.

The $Z^2$ group, if present, is a further 3- to 7-membered carbocyclic or heterocyclic ring, optionally substituted with no more than two $Z^1$ groups as described above. Ring $Z^2$, if present, is typically but not necessarily saturated, and in most cases is not further substituted. In one embodiment $Z^2$ is a saturated carbocyclic ring, for example but not limited to cyclopropyl, cyclobutyl, cyclopentyl or cyclohexyl. In another embodiment $Z^2$ is a saturated heterocyclic ring, for example but not limited to azetidinyl, oxetanyl, thietanyl, pyrrolidinyl, imazolidinyl, pyrazolidinyl, tetrahydrofuranyl, oxazolidinyl, isoxazolidinyl, thiophanyl, thiazolidinyl, isothiazolidinyl, piperidinyl, piperazinyl, tetrahydropyranyl, 1,4-dioxanyl, morpholinyl or tetrahydrothiopyranyl.

In some embodiments, $R^6$ is a group $NR^7R^8$, where $R^7$ and $R^8$ are each independently H or $R^9$—$(CH_2)_m$— groups, no more than one of $R^7$ and $R^8$ being H, where each $R^9$ is independently a 3- to 7-membered carbocyclic or heterocyclic ring, optionally substituted with no more than two $Z^1$ groups as defined above, and each m is independently 0 or 1. Each of rings $R^9$ is typically but not necessarily saturated, and in most cases is unsubstituted. Illustrative carbocyclic rings at $R^7$ and/or $R^8$ include without limitation cyclopropyl, cyclobutyl, cyclopentyl or cyclohexyl. Illustrative heterocyclic rings at $R^7$ and/or $R^8$ include without limitation azetidinyl, oxetanyl, thietanyl, pyrrolidinyl, imazolidinyl, pyrazolidinyl, tetrahydrofuranyl, oxazolidinyl, isoxazolidinyl, thiophanyl, thiazolidinyl, isothiazolidinyl, piperidinyl, piperazinyl, tetrahydropyranyl, 1,4-dioxanyl, morpholinyl or tetrahydrothiopyranyl.

In particular embodiments, $R^6$ is selected from the group consisting of 4-methoxycyclohexyl, cis-4-hydroxy-4-methylcyclohexyl, trans-4-hydroxy-4-methylcyclohexyl, 4-morpholin-4-ylcyclohexyl, (3R)-1-(methylsulfonyl)pyrrolidin-3-yl, (3R)-1-tetrahydro-2H-pyran-4-ylpyrrolidin-3-yl, tetrahydro-2H-pyran-3-yl, (3S)-tetrahydro-2H-pyran-3-yl, 4-methoxytetrahydro-2H-pyran-4-yl, 4-fluorotetrahydro-2H-pyran-4-yl, 4-aminotetrahydro-2H-pyran-4-yl, 1-(cyanomethyl)piperidin-4-yl, 4-fluoro-1-oxetan-3-ylpiperidin-4-yl, 1-tetrahydro-2H-pyran-4-ylpiperidin-4-yl, 4-methylpiperazin-1-yl, 1,4-dioxan-2-yl, 4-methylmorpholin-2-yl and cyclopropyl(oxetan-3-yl)amino.

Compounds of Formula I may contain asymmetrically substituted carbon atoms in the R- or S-configuration; such compounds can be present as racemates or in an excess of one configuration over the other, for example in an enantiomeric ratio of at least about 85:15. The compound can be substantially enantiomerically pure, for example having an enantiomeric ratio of at least about 95:5, or in some cases at least about 98:2 or at least about 99:1.

Compounds of Formula I may alternatively or additionally contain carbon-carbon double bonds or carbon-nitrogen double bonds in the Z- or E-configuration, the term "Z" denoting a configuration wherein the larger substituents are on the same side of such a double bond and the term "E" denoting a configuration wherein the larger substituents are on opposite sides of the double bond. The compound can alternatively be present as a mixture of Z- and E-isomers.

Compounds of Formula I may alternatively or additionally exist as tautomers or equilibrium mixtures thereof wherein a proton shifts from one atom to another. Examples of tautomers illustratively include keto-enol, phenol-keto, oxime-nitroso, nitro-aci, imine-enamine and the like.

In one embodiment, the API present in the solid dispersion is selected from compounds specifically identified in above-referenced U.S. application Ser. No. 12/787,682 (U.S. 2010/0305122) in Examples 1-378 thereof, and pharmaceutically acceptable salts of such compounds, independently of whether these compounds are individually embraced by the present Formula I. Compounds 1-378 of these Examples, and illustrative procedures for their synthesis, are reproduced hereinbelow. In a further embodiment, the API present in the solid dispersion is selected from Compounds 1-378 and pharmaceutically acceptable salts thereof, but only to the extent that such Examples are individually embraced by the present Formula I. The entire disclosure of U.S. application Ser. No. 12/787,682 (U.S. 2010/0305122) is expressly incorporated herein by reference.

Description of the synthesis of representative compounds is given below. Other compounds of Formula I can be prepared by substantially analogous methods, as will be clear to one of skill in the art. The exemplified compounds have been named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Compound 1

4-{4-[(4'-chloro-1,1'-biphenyl-2-yl)methyl]piperazin-1-yl}-N-{3-nitro-4-[(tetrahydro-2H-pyran-4-ylmethyl)amino]phenyl}sulfonyl)-2-(1H-pyrrolo[2,3-b]pyridin-5-yloxy)benzamide Compound 1A tert-butyl 4-((4'-chlorobiphenyl-2-yl)methyl)piperazine-1-carboxylate 4'-Chlorobiphenyl-2-carboxaldehyde (4.1 g), tert-butyl piperazine-1-carboxylate (4.23 g), and sodium triacetoxyborohydride (5.61 g) in $CH_2Cl_2$ (60 ml) were stirred for 24 hours. The reaction was quenched with methanol and poured into ether. The solution was washed with water and brine, concentrated, and chromatographed on silica gel with 2-25% ethyl acetate/hexanes.

Compound 1B 1-((4'-chlorobiphenyl-2-yl)methyl)piperazine

Compound 1A (3.0 g) and triethylsilane (1 ml) were stirred in $CH_2Cl_2$ (30 ml) and trifluoroacetic acid (30 ml) for 2 hours, and the reaction was concentrated, and then taken up in ether and concentrated again. The material was taken up in dichloromethane (200 ml) and $NaHCO_3$ solution (100 ml), and partitioned. The organic layer was dried over $Na_2SO_4$, and condensed to give the title compound.

Compound 1C tert-butyl 4-(4-((4'-chlorobiphenyl-2-yl)methyl)piperazin-1-yl)-2-fluorobenzoate Tert-butyl 4-bromo-2-fluorobenzoate (14.0 g), Compound 1B (16.05 g), $Pd_2(dba)_3$ (tris(dibenzylideneacetone)dipalladium(0))(1.40 g), 2-(di-tert-butylphosphino)biphenyl (1.82 g), and $K_3PO_4$ (16.2 g) were stirred in 1,2-dimethoxyethane (300 ml) at 80° C. for 24 hours. The reaction was cooled and concentrated. The crude product was chromatographed on silica gel with 10-20% ethyl acetate/hexanes.

Compound 1D tert-butyl 2-(1H-pyrrolo[2,3-b]pyridin-5-yloxy)-4-(4-((4'-chlorobiphenyl-2-yl)methyl)piperazin-1-yl)benzoate 1H-Pyrrolo[2,3-B]pyridine-5-ol (167 mg), Compound 1C (500 mg), and $Cs_2CO_3$ (508 mg) were stirred in dimethylsulfoxide (5 ml) at 130° C. for 24 hours. The mixture was cooled, diluted with ethyl acetate, washed three times with water, and brine, and dried ($Na_2SO_4$), filtered and concentrated. The crude product was chromatographed on silica gel with 25% ethyl acetate/hexanes.

Compound 1E 2-(1H-pyrrolo[2,3-b]pyridin-5-yloxy)-4-(4-((4'-chlorobiphenyl-2-yl)methyl)piperazin-1-yl)benzoic Acid Compound 1D (200 mg) and triethylsilane (1 ml) were stirred in dichloromethane (15 ml) and trifluoroacetic acid (15 ml) for 1 hour. The mixture was concentrated, taken up in ethyl acetate, washed twice with $NaH_2PO_4$, and brine, and dried ($Na_2SO_4$), filtered and concentrated.

Compound 1F 3-nitro-4-((tetrahydro-2H-pyran-4-yl)methylamino)benzenesulfonamide

4-Fluoro-3-nitrobenzenesulfonamide (2.18 g), 1-(tetrahydropyran-4-yl)methylamine (1.14 g), and triethylamine (1 g) were stirred in tetrahydrofuran (30 ml) for 24 hours. The solution was diluted with ethyl acetate, washed with NaH$_2$PO$_4$ solution and brine, and dried (Na$_2$SO$_4$), filtered and concentrated. The product was triturated from ethyl acetate.

Compound 1G

4-{4-[(4'-chloro-1,1'-biphenyl-2-yl)methyl]piperazin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 1E (115 mg), Compound 1F (67 mg), 1-ethyl-3-[3-(dimethylamino)propyl]carbodiimide hydrochloride (82 mg), and 4-dimethylaminopyridine (26 mg) were stirred in CH$_2$Cl$_2$ (3 ml) for 24 hours. The reaction was cooled and chromatographed on silica gel with 0-5% methanol/ethyl acetate. $^1$H NMR (300 MHz, dimethylsulfoxide-d$_6$) δ 11.48 (brs, 1H), 8.34 (br s, 1H), 8.31 (m, 1H), 7.90 (d, 1H), 7.68 (m, 1H), 7.58 (m, 2H), 7.46 (m, 4H), 7.35 (m, 2H), 7.21 (dd, 1H), 6.76 (m, 4H), 6.28 (m, 2H), 3.02 (m, 2H), 2.89 (m, 4H), 2.80 (m, 4H), 2.40 (m, 3H), 1.59 (m, 2H), 1.25 (m, 4H), 0.87 (m, 2H).

Compound 2

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide Compound 2A 4-(3-morpholinopropylamino)-3-nitrobenzenesulfonamide This Compound was prepared by substituting 3-(N-morpholinyl)-propylamine for 1-(tetrahydropyran-4-yl)methylamine in the procedure for Compound 1F.

Compound 2B

4-{4-[(4'-chloro-1,1'-biphenyl-2-yl)methyl]piperazin-1-yl}-N-({4-[(3-morpholin-4-ylpropyl)amino]-3-nitrophenyl}sulfonyl)-2-(1H-pyrrolo[2,3-b]pyridin-5-yloxy)benzamide This Compound was prepared by substituting Compound 2A for Compound 1F in the procedure for Compound 1G. $^1$H NMR (300 MHz, dimethylsulfoxide-d$_6$) δ 11.60 (brs, 1H), 8.60 (m, 1H), 8.43 (d, 1H), 7.94 (d, 1H), 7.64 (m, 2H), 7.54 (d, 1H), 7.45 (m, 4H), 7.33 (m, 2H), 7.23 (dd, 1H), 6.96 (d, 1H), 6.85 (m, 2H), 6.32 (d, 1H), 6.26 (d, 1H), 3.60 (m, 4H), 3.10 (m, 4H), 3.05 (m, 10H), 2.40 (m, 2H), 2.33 (m, 2H), 1.77 (m, 2H).

Compound 3

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide Compound 3A methyl 4,4-dimethyl-2-(trifluoromethylsulfonyloxy)cyclohex-1-enecarboxylate To a suspension of hexane washed NaH (17 g) in dichloromethane (700 ml) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 ml) was added. The reaction mixture was warmed to room temperature and stirred for 24 hours. The organic layer was washed with brine, dried (Na$_2$SO$_4$), filtered, and concentrated to give the product.

Compound 3B methyl 2-(4-chlorophenyl)-4,4-dimethylcyclohex-1-enecarboxylate

Compound 3A (62.15 g), 4-chlorophenylboronic acid (32.24 g), CsF (64 g) and tetrakis(triphenylphosphine)palladium(0) (2 g) in 2:1 dimethoxyethane/methanol (600 ml) were heated to 70° C. for 24 hours. The mixture was concentrated. Ether (4×200 ml) was added and the mixture was filtered. The combined ether solution was concentrated to give the product.

Compound 3C (2-(4-chlorophenyl)-4,4-dimethylcyclohex-1-enyl)methanol

To a mixture of LiBH$_4$ (13 g), Compound 3B (53.8 g) and ether (400 ml), was added methanol (25 ml) slowly by syringe. The mixture was stirred at room temperature for 24 hours. The reaction was quenched with 1N HCl with ice-cooling. The mixture was diluted with water and extracted with ether (3×100 ml). The extracts were dried (Na$_2$SO$_4$), filtered, and concentrated. The crude product was chromatographed on silica gel with 0-30% ethyl acetate/hexanes.

Compound 3D tert-butyl 4-((2-(4-chlorophenyl)-4,4-dimethylcyclohex-1-enyl)methyl)piperazine-1-carboxylate Mesyl chloride (7.5 ml) was added via syringe to Compound 3C (29.3 g) and triethylamine (30 ml) in CH$_2$Cl$_2$ (500 ml) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The crude product was chromatographed on silica gel with 10-20% ethyl acetate/hexanes.

Compound 3E 1-((2-(4-chlorophenyl)-4,4-dimethylcyclohex-1-enyl)methyl)piperazine Compound 3D (1 g) was stirred in dichloromethane (10 ml), trifluoroacetic acid (10 ml), and triethylsilane (1 ml) for 1 hour. The mixture was concentrated, taken up in a mixture of dichloromethane (100 ml) and saturated aqueous Na$_2$CO$_3$ solution (20 ml) and stirred for 10 minutes. The layers were separated, and the organic layer was dried over Na$_2$SO$_4$, filtered, and concentrated to give the product.

Compound 3F 5-bromo-1-(triisopropylsilyl)-1H-pyrrolo[2,3-b]pyridine to a mixture of 5-bromo-1H-pyrrolo[2,3-b]pyridine (15.4 g) in tetrahydrofuran (250 ml) was added 1M lithium hexamethyldisilazide in tetrahydrofuran (86 ml), and after 10 minutes, TIPS-Cl (triisopropylchlorosilane) (18.2 ml) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Compound 3G 1-(triisopropylsilyl)-1H-pyrrolo[2,3-b]pyridin-5-ol

To a mixture of Compound 3F (24.3 g) in tetrahydrofuran (500 ml) at −78° C. was added 2.5M BuLi (30.3 ml). After 2 minutes, trimethylborate (11.5 ml) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 ml) at 0° C., and 1M NaOH (69 ml) was added, followed by 30% $H_2O_2$ (8.43 ml), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Compound 3H methyl 2-(1H-pyrrolo[2,3-b]pyridin-5-yloxy)-4-fluorobenzoate

A mixture of Compound 3G (8.5 g), methyl 2,4-difluorobenzoate (7.05 g), and $K_3PO_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 3I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound 3H (1.55 g), Compound 3E (2.42 g), and $HK_2PO_4$ (1.42 g) in dimethylsulfoxide (20 ml) at 135° C. was stirred for 24 hours. The reaction was cooled, diluted with ether (400 ml), and washed with 3×1M NaOH, and brine, and concentrated. The crude product was chromatographed on silica gel with 10-50% ethyl acetate/hexanes.

Compound 3J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic Acid Compound 3I (200 mg) in dioxane (10 ml) and 1M NaOH (6 ml) at 50° C. was stirred for 24 hours. The reaction was cooled, added to $NaH_2PO_4$ solution, and extracted three times with ethyl acetate. The combined extracts were washed with brine, and concentrated to give the pure product.

Compound 3K tert-butyl 1-(tetrahydro-2H-pyran-4-yl)piperidin-4-ylcarbamate

Tert-butyl piperidin-4-ylcarbamate (45.00 g, 225 mmol) and dihydro-2H-pyran-4(3H)-one (24.74 g, 247 mmol) were added to dichloromethane (1000 ml). Sodium triacetoxyborohydride (61.90 g, 292 mmol) was added, and the solution was stirred at room temperature for 16 hours. The solution was extracted with 1M sodium hydroxide and dried over anhydrous sodium sulfate. The solution was filtered and concentrated and purified by flash column chromatography on silica gel with 10% methanol (in dichloromethane) increasing to 20% methanol (in dichloromethane).

Compound 3L 1-(tetrahydro-2H-pyran-4-yl)piperidin-4-amine dihydrochloride

A solution of Compound 3K (52.57 g, 185 mmol) in dichloromethane (900 ml) was treated with 4M aqueous HCl (462 ml), and the solution was mixed vigorously at room temperature for 16 hours. Solvent was removed under vacuum to give crude product as the dihydrochloride salt, which was used without further purification.

Compound 3M 3-nitro-4-(1-(tetrahydro-2H-pyran-4-yl)piperidin-4-ylamino)benzenesulfonamide Compound 3L (22.12 g, 86 mmol) was added to 1,4-dioxane (300 ml) and water (43 ml). Triethylamine (43.6 ml, 31.6 g, 313 mmol) was added, and the mixture was stirred at room temperature until Compound 3L had completely dissolved. 4-Chloro-3-nitrobenzenesulfonamide was added and the mixture was heated at 90° C. for 16 hours. The mixture was cooled, and the solvents were removed under vacuum. 10% methanol (in dichloromethane) was added and the solution was stirred vigorously at room temperature until a fine suspension was obtained. The solid was isolated by vacuum filtration and washed with dichloromethane to give pure product.

Compound 3N 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-(1H-pyrrolo[2,3-b]pyridin-5-yloxy)benzamide This Compound was prepared by substituting Compound 3J for Compound 1E and Compound 3M for Compound 1F in the procedure for Compound 1G. $^1$H NMR (300 MHz, dimethylsulfoxide-$d_6$) δ 11.65 (brs, 1H), 8.53 (br s, 1H), 8.18 (m, 1H), 8.00 (br s, 1H), 7.63 (m, 1H), 7.49 (m, 3H), 7.34 (d, 2H), 7.12 (m, 1H), 7.04 (d, 2H), 6.67 (dd, 1H), 6.37 (d, 1H), 6.20 (d, 1H), 3.95 (m, 2H), 3.05 (m, 10H), 2.73 (m, 4H), 2.17 (m, 10H), 1.95 (m, 2H), 1.80 (m, 2H), 1.63 (m, 2H), 1.39 (t, 2H), 0.93 (s, 6H).

Compound 4

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide Compound 4A 4-(1-methylpiperidin-4-ylamino)-3-nitrobenzenesulfonamide This Compound was prepared by substituting 4-amino-N-methylpiperidine for 1-(tetrahydropyran-4-yl)methylamine in the procedure for Compound 1F.

Compound 4B 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-(1H-pyrrolo[2,3-b]pyridin-5-yloxy)benzamide This Compound was prepared by substituting Compound 3J for Compound 1E and Compound 4A for Compound 1F in the procedure for Compound 1G. $^1$H NMR (300 MHz, dimethylsulfoxide-$d_6$) δ 11.65 (brs, 1H), 8.55 (br s, 1H), 8.17 (m, 1H), 8.02 (d, 1H), 7.85 (dd, 1H), 7.51 (m, 3H), 7.35 (m, 2H), 7.18 (dd, 1H), 7.05 (d, 2H), 6.68 (dd, 1H), 6.38 (d, 1H), 6.20 (d, 1H), 3.90 (m, 1H), 3.09 (m, 8H), 2.77 (m, 2H), 2.05-2.30 (m, 10H), 1.95 (s, 3H), 1.39 (t, 2H), 1.24 (m, 2H), 0.93 (s, 6H).

Compound 5

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 5A 3-nitro-4-((tetrahydro-2H-pyran-4-yl)methylamino)benzenesulfonamide A mixture of 4-fluoro-3-nitrobenzenesulfonamide (2.18 g), 1-(tetrahydropyran-4-yl)methylamine (1.14 g), and triethylamine (1 g) in tetrahydrofuran (30 ml) were stirred overnight, neutralized with concentrated HCl and concentrated. The residue was suspended in ethyl acetate and the precipitates were collected, washed with water and dried to provide the title compound.

Compound 5B methyl 4,4-dimethyl-2-(trifluoromethylsulfonyloxy)cyclohex-1-enecarboxylate To a suspension of hexane washed NaH (17 g) in dichloromethane (700 ml) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 ml) was added. The reaction mixture was warmed to room temperature and stirred for 24 hours. The organic layer was washed with brine, dried ($Na_2SO_4$), filtered, and concentrated to give the product.

Compound 5C methyl 2-(4-chlorophenyl)-4,4-dimethylcyclohex-1-enecarboxylate

Compound 5B (62.15 g), 4-chlorophenylboronic acid (32.24 g), CsF (64 g) and tetrakis(triphenylphosphine)palladium(0) (2 g) in 2:1 dimethoxyethane/methanol (600 ml) were heated to 70° C. for 24 hours. The mixture was concentrated. Ether (4×200 ml) was added and the mixture was filtered. The combined ether solution was concentrated to give the product.

Compound 5D (2-(4-chlorophenyl)-4,4-dimethylcyclohex-1-enyl)methanol

To a mixture of $LiBH_4$ (13 g), Compound 5C (53.8 g) and ether (400 mil), was added methanol (25 ml) slowly by syringe. The mixture was stirred at room temperature for 24 hours. The reaction was quenched with 1N HCl with ice-cooling. The mixture was diluted with water and extracted with ether (3×100 ml). The extracts were dried ($Na_2SO_4$), filtered, and concentrated. The crude product was chromatographed on silica gel with 0-30% ethyl acetate/hexanes.

Compound 5E tert-butyl 4-((2-(4-chlorophenyl)-4,4-dimethylcyclohex-1-enyl)methyl)piperazine-1-carboxylate Mesyl chloride (7.5 ml) was added via syringe to Compound 5D (29.3 g) and triethylamine (30 ml) in $CH_2Cl_2$ (500 ml) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Compound 5F 1-((2-(4-chlorophenyl)-4,4-dimethylcyclohex-1-enyl)methyl)piperazine Compound 5E (200 mg) and triethylsilane (1 ml) were stirred in dichloromethane (15 ml) and trifluoroacetic acid (15 ml) for 1 hour. The mixture was concentrated, taken up in ethyl acetate, washed twice with $NaH_2PO_4$, and brine, and dried ($Na_2SO_4$), filtered and concentrated.

Compound 5G 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 ml) was added 1M lithium hexamethyldisilazide in tetrahydrofuran (86 ml), and after 10 minutes, TIPS-Cl (triisopropylchlorosilane) (18.2 ml) was added. The mixture was stirred at room temperature for

Compound 5H 1-(triisopropylsilyl)-1H-pyrrolo[2,3-b]pyridin-5-ol

To a mixture of Compound 5G (24.3 g) in tetrahydrofuran (500 mL) at −78° C. was added 2.5M BuLi (30.3 ml). After 2 minutes, trimethylborate (11.5 ml) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 ml) at 0° C., and 1M NaOH (69 mL) was added, followed by 30% $H_2O_2$ (8.43 ml), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Compound 5I methyl 2-(1H-pyrrolo[2,3-b]pyridin-5-yloxy)-4-fluorobenzoate

A mixture of Compound 5H (8.5 g), methyl 2,4-difluorobenzoate (7.05 g), and $K_3PO_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 5J methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound 5I (1.55 g), Compound 5F (2.42 g), and $HK_2PO_4$ (1.42 g) in dimethylsulfoxide (20 ml) at 135° C. was stirred for 24 hours. The reaction was cooled, diluted with ether (400 ml), and washed with 3×1M NaOH, and brine, and concentrated. The crude product was chromatographed on silica gel with 10-50% ethyl acetate/hexanes.

Compound 5K 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic Acid Compound 5J (200 mg) in dioxane (10 ml) and IM NaOH (6 ml) at 50° C. was stirred for 24 hours. The reaction was cooled, added to $NaH_2PO_4$ solution, and extracted three times with ethyl acetate. The combined extracts were washed with brine, and concentrated to give the pure product.

Compound 5L 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 5K (3.39 g), Compound 5A (1.87 g), 1-ethyl-3-[3-(dimethylamino)propyl]-carbodiimide hydrochloride (2.39 g), and 4-dimethylaminopyridine (1.09 g) were stirred in $CH_2Cl_2$ (40 ml) for 24 hours. The reaction was cooled and chromatographed on silica gel with 25-100% ethyl acetate/hexanes, then 10% methanol/ethyl acetate with 1% acetic acid, to give the product (1.62 g, 32%) as a white solid. $^1$H NMR (300 MHz, dimethylsulfoxide-$d_6$) 11.65 (br s, 1H), 8.55 (br s, 1H), 8.04 (d, 1H), 7.89 (dd, 1H), 7.51 (m, 3H), 7.33 (d, 2H), 7.08 (m, 1H), 7.04 (d, 2H), 6.68 (dd, 1H), 6.39 (d, 1H), 6.19 (d, 1H), 3.84 (m, 1H), 3.30 (m, 4H), 3.07 (m, 4H), 2.73 (m, 2H), 2.18 (m, 6H), 1.95 (m, 2H), 1.61 (dd, 2H), 1.38 (m, 2H), 1.24 (m, 4H), 0.92 (s, 6H).

Compound 6

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide

Compound 6A 4-(4-methylpiperazin-1-ylamino)-3-nitrobenzenesulfonamide

A 50 ml round-bottomed flask was charged with 4-chloro-3-nitrobenzenesulfonamide (1 g, 4.23 mmol), 4-methylpiperazin-1-amine dihydrochloride (1 g, 5.32 mmol), and $N^1,N^1,N^2,N^2$-tetramethylethane-1,2-diamine (3 ml, 20.01 mmol) in dioxane (10 ml). The reaction mixture was refluxed for 12 hours. After this time, the reaction mixture was cooled to room temperature, the salt filtered off via a Buchner funnel, and the solvent removed in vacuo. The crude product was added to a silica gel column (Analogix, SF65-200 g) and purified by eluting with 0-5% methanol in dichloromethane.

Compound 6B 4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide This Compound was prepared by substituting Compound 3J for Compound 1E and Compound 6A for Compound 1F in the procedure for Compound 1G. $^1$H NMR (300 MHz, dimethylsulfoxide-$d_6$) δ 11.65 (brs, 1H), 9.09 (br s, 1H), 8.47 (d, 1H), 8.24 (dd, 1H), 7.99 (d, 1H), 7.50 (m, 4H), 7.34 (d, 2H), 7.04 (d, 2H), 6.64 (dd, 1H), 6.35 (d, 1H), 6.20 (d, 1H), 3.04 (m, 4H), 2.89 (m, 4H), 2.73 (m, 2H), 2.34 (s, 3H), 2.17 (m, 6H), 1.95 (br s, 2H), 1.38 (t, 2H), 1.05 (m, 4H), 0.93 (s, 6H).

Compound 7

2-(9H-carbazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Compound 7A ethyl 2-(9H-carbazol-4-yloxy)-4-fluorobenzoate

This Compound was prepared by substituting ethyl 2,4-difluorobenzoate for methyl 2,4-difluorobenzoate and 4-hydroxycarbazole for Compound 3G in the procedure for Compound 3H.

Compound 7B ethyl 2-(9H-carbazol-4-yloxy)-4-(4-((2-(4-chlorophenyl)-4,4-dimethylcyclohex-1-enyl)methyl)piperazin-1-yl)benzoate This Compound was prepared by substituting Compound 7A for Compound 3H in the procedure for Compound 3I.

Compound 7C 2-(9H-carbazol-4-yloxy)-4-(4-((2-(4-chlorophenyl)-4,4-dimethylcyclohex-1-enyl)methyl)piperazin-1-yl) benzoic Acid This Compound was prepared by substituting Compound 7B for Compound 3I in the procedure for Compound 3J, except here upon completion of the reaction, water and 2N HCl were added to adjust the pH to 2, and the HCl salt of the product was extracted using $CHCl_3/CH_3OH$.

Compound 7D 2-(9H-carbazol-4-yloxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide This Compound was prepared by substituting Compound 7C for Compound 1E and Compound 4A for Compound 1F in the procedure for Compound 1G, except here the purification was done by preparative HPLC using a C18 column, 250×50 mm, 10 g, and eluting with a gradient of 20-100% $CH_3CN$ vs. 0.1% trifluoroacetic acid in water, giving the product as a bistrifluoroacetate salt. $^1$H NMR (300 MHz, dimethylsulfoxide-$d_6$) δ 11.82 (br s, 1H), 11.40 (s, 1H), 9.70, 9.40 (both v br s, total 2H), 8.40 (d, 1H), 8.10 (br d, 1H), 7.90 (br d, 1H), 7.72 (dd, 1H), 7.60 (d, 1H), 7.48 (d, 1H), 7.38 (m, 3H), 7.22 (m, 2H), 7.07 (m, 4H), 6.78 (dd, 1H), 6.43 (dd, 1H), 6.19 (s, 1H), 3.97 (m, 1H), 3.80 (m, 2H), 3.60, 3.30, 3.10, 2.80 (all br m, total 11H), 2.20, 2.10, 2.00 (all br m, total 8H), 1.78 (m, 2H), 1.42 (m, 2H), 1.25 (m, 2H), 0.92 (s, 6H).

Compound 8

2-(9H-carbazol-4-yloxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide

Compound 8A 3-nitro-4-(3-(pyrrolidin-1-yl)propylamino)benzenesulfonamide

This Compound was prepared by substituting 3-(pyrrolidin-1-yl)propan-1-amine for 1-(tetrahydropyran-4-yl)methylamine in the procedure for Compound 1F.

Compound 8B 2-(9H-carbazol-4-yloxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide This Compound was prepared by substituting Compound 7C for Compound 1E and Compound 8A for Compound 1F in the procedure for Compound 1G, except here the purification was done by preparative HPLC using a C18 column, 250×50 mm, 10μ, and eluting with a gradient of 20-100% $CH_3CN$ vs. 0.1% trifluoroacetic acid in water, giving the product as a bistrifluoroacetate salt. $^1$H NMR (300 MHz, dimethylsulfoxide-$d_6$) δ 11.80 (br s, 1H), 11.42 (s, 1H), 9.50, 9.25 (both v br s, total 2H), 8.58 (br t, 1H), 8.43 (d, 1H), 7.91 (d, 1H), 7.72 (dd, 1H), 7.60 (d, 1H), 7.50 (d, 1H), 7.38 (m, 3H), 7.23 (m, 2H), 7.07 (m, 3H), 6.93 (d, 1H), 6.78 (dd, 1H), 6.44 (dd, 1H), 6.18 (s, 1H), 3.70, 3.60, 3.20, 3.00 (all br m, total 18H), 2.18 (br m, 2H), 2.00-180 (envelope, 8H), 1.42 (m, 2H), 0.92 (s, 6H).

Compound 9 trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide

Compound 9A trans-tert-butyl 4-morpholinocyclohexylcarbamate

A solution of tert-butyl-4-aminocyclohexylcarbamate (20.32 g, 95 mmol), bis(2-bromoethyl) ether (14.30 ml, 114 mmol) and triethylamine (33.0 ml, 237 mmol) in N,N-dimethylformamide (200 ml) was stirred for 16 hours at 70° C. The reaction mixture was cooled down to room temperature, concentrated and the product was extracted with ethyl acetate. The organic layer was washed with sodium carbonate solution (15% aq.), dried and concentrated. The product was used in next step without purification.

Compound 9B trans-4-morpholinocyclohexanamine dihydrochloride

To a solution of trans-tert-butyl-4-morpholinocyclohexylcarbamate (19.2 g, 67.5 mmol) in dichloromethane (100 ml) was added HCl (100 ml, 400 mmol) (4M in dioxane) and the reaction mixture was stirred for 16 hours at room temperature. The reaction mixture was diluted with ether and solid salt was filtered off, and dried in an oven.

Compound 9C trans-4-(4-morpholinocyclohexylamino)-3-nitrobenzenesulfonamide

A solution of trans-4-morpholinocyclohexanamine dihydrochloride (5 g, 19.44 mmol), 4-fluoro-3-nitrobenzenesulfonamide (4.32 g, 19.63 mmol) and triethylamine (20 ml, 143 mmol) in tetrahydrofuran (60 ml) was stirred for 16 hours at room temperature. The solid product was filtered off, washed with tetrahydrofuran, ether, dichloromethane (3×) and dried under vacuum.

Compound 9D trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide This compound was prepared by substituting Compound 3J for Compound 1E and Compound 9C for Compound 1F in the procedure for Compound 1G. $^1$H NMR (300 MHz, dimethylsulfoxide-$d_6$) δ 11.61 (brs, 1H), 8.49 (br s, 1H), 8.12 (m, 1H), 7.99 (br s, 1H), 7.71 (m, 1H), 7.50 (m, 3H), 7.35 (d, 2H), 7.04 (d, 2H), 7.01 (m, 1H), 6.65 (dd, 1H), 6.36 (d, 1H), 6.21 (d, 1H), 3.60 (m, 4H), 3.04 (m, 4H), 2.73 (m, 2H), 2.57 (m, 2H), 2.42 (m, 1H), 2.18 (m, 6H), 2.05 (m, 2H), 1.95 (m, 2H), 1.90 (m, 2H), 1.38 (m, 6H), 1.15 (m, 3H), 0.92 (s, 6H).

Compound 10

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide Compound 10A 4-(2-methoxyethylamino)-3-nitrobenzenesulfonamide This compound was prepared by substituting 2-methoxyethylamine for 1-(tetrahydropyran-4-yl)methylamine in the procedure for Compound 1F.

Compound 10B 4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-(1H-pyrrolo[2,3-b]pyridin-5-yloxy)benzamide This compound was prepared by substituting Compound 3J for Compound 1E and Compound 10A for Compound 1F in the procedure for Compound 1G. $^1$H NMR (300 MHz, dimethylsulfoxide-$d_6$) δ 11.65 (brs, 1H), 8.58-8.49 (m, 1H), 8.55 (d, 1H), 8.03 (d, 1H), 7.79 (m, 1H), 7.49 (m, 3H), 7.34 (m, 2H), 7.06 (m, 1H), 7.04 (d, 2H), 6.68 (dd, 1H), 6.38 (m, 1H), 6.20 (d, 1H), 3.61-3.51 (m, 4H), 3.31 (s, 3H), 3.07 (m, 4H), 2.74 (m, 2H), 2.17 (m, 6H), 1.95 (br s, 2H), 1.38 (t, 2H), 0.92 (s, 6H).

Compound 11

4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide Compound 11A (S)-3-nitro-4-((tetrahydro-2H-pyran-3-yl)methylamino)benzenesulfonamide and (R)-3-nitro-4-((tetrahydro-2H-pyran-3-yl)methylamino)benzenesulfonamide This racemic mixture was prepared by substituting (tetrahydro-2H-pyran-3-yl)methanamine for 1-(tetrahydropyran-4-yl)methylamine in the procedure for Compound 1F.

Compound 11B (S)-3-nitro-4-((tetrahydro-2H-pyran-3-yl)methylamino)benzenesulfonamide The racemic mixture of Compound 11A was resolved by chiral SFC on an AD column (21 mm i.d.×250 mm in length) using a gradient of 10-30% 0.1% diethylamine methanol in $CO_2$ over 15 minutes (oven temperature: 40° C.; flow rate: 40 ml/minute) to provide the title compound.

Compound 11C (R)-3-nitro-4-((tetrahydro-2H-pyran-3-yl)methylamino)benzenesulfonamide The racemic mixture of Compound 11A was resolved by chiral SFC on an AD column (21 mm i.d.×250 mm in length) using a gradient of 10-30% 0.1% diethylamine methanol in $CO_2$ over 15 minutes (oven temperature: 40° C.; flow rate: 40 ml/minute) to provide the title compound.

Compound 11D 4-(4-{[2-(4-chlorophenyl)-4,4-dimethylcyclohex-1-en-1-yl]methyl}piperazin-1-yl)-N-[(3-nitro-4-{[(3S)-tetrahydro-2H-pyran-3-ylmethyl]amino}phenyl)sulfonyl]-2-(1H-pyrrolo[2,3-b]pyridin-5-yloxy)benzamide To a mixture of Compound 3J (59.8 mg, 0.105 mmol), Compound 11B (33 mg, 0.105 mmol) and N,N-dimethylpyridin-4-amine (38.4 mg, 0.314 mmol) in dichloromethane (5 ml) was added 1-ethyl-3-[3-(dimethylamino)propyl]-carbodiimide hydrochloride (24.07 mg, 0.13 mmol). The reaction mixture was stirred at room temperature overnight and concentrated. The residue was purified by reverse phase HPLC on a C18 column using a gradient of 40-60% acetonitrile/0.1% trifluoroacetic acid in water to give the title compound as the trifluoroacetate salt. The trifluoroacetic acid salt was dissolved in dichloromethane (6 ml) and washed with 50% aqueous $NaHCO_3$. The organic layer was dried over anhydrous $Na_2SO_4$ and concentrated to give the title compound. $^1$H NMR (500 MHz, dimethylsulfoxide-$d_6$)

δ 11.68 (s, 1H), 11.40 (s, br, 1H), 8.53-8.58 (m, 2H), 8.04 (d, 1H), 7.80 (dd, 1H), 7.47-7.54 (m, 3H), 7.34 (d, 2H), 7.02-7.09 (m, 3H), 6.67 (dd, 1H), 6.39 (dd, 1H), 6.19 (d, 1H), 3.79 (dd, 1H), 3.69-3.73 (m, 1H), 3.22-3.37 (m, 3H), 3.16-3.21 (m, 1H), 3.07 (s, 4H), 2.74 (s, 2H), 2.09-2.24 (m, 6H), 1.95 (s, 2H), 1.86-1.93 (m, 1H), 1.79-1.85 (m, 1H), 1.58-1.64 (m, 1H), 1.42-1.51 (m, 1H), 1.38 (t, 2H), 1.25-1.34 (m, 1H), 0.92 (s, 6H).

Compound 12

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide Compound 12A 4-((1,4-dioxan-2-yl)methoxy)-3-nitrobenzenesulfonamide (1,4-Dioxan-2-yl)methanol (380 mg, 3.22 mmol) in tetrahydrofuran (30 ml) was treated with sodium hydride (60%) (245 mg, 6.13 mmol) at room temperature for 30 minutes. The reaction mixture was cooled in an ice bath and 4-fluoro-3-nitrobenzenesulfonamide (675 mg, 3.06 mmol) was added. The resulting mixture was stirred at room temperature for 2 hours and another portion of sodium hydride (60%) (245 mg, 6.13 mmol) was added. The reaction mixture was stirred overnight and quenched with ice water (3 ml). The cloudy mixture was filtered and the filtrate was concentrated. The residue was triturated with methanol to give the title compound.

Compound 12B 4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide The title compound was prepared as described in the procedure for Compound 11D using Compound 12A in place of Compound 11B. $^1$H NMR (500 MHz, dimethylsulfoxide-$d_6$) δ 11.67 (s, 1H), 11.42 (s, br, 1H), 8.34 (s, 1H), 8.03 (d, 2H), 7.48-7.55 (m, 3H), 7.41 (d, 1H), 7.35 (d, 2H), 7.04 (d, 2H), 6.67 (dd, 1H), 6.39 (dd, 1H), 6.21 (d, 1H), 4.20-4.28 (m, 2H), 3.85-3.91 (m, 1H), 3.82 (dd, 1H), 3.74-3.78 (m, 1H), 3.59-3.69 (m, 2H), 3.41-3.51 (m, 2H), 3.05-3.17 (m, 4H), 2.83 (s, br, 2H), 2.27 (s, br, 4H), 2.15 (s, 2H), 1.96 (s, 2H), 1.39 (t, 2H), 0.93 (s, 6H).

Compound 13

4-(4-{[2-(4-chlorophenyl)-4,4-dimethylcyclohex-1-en-1-yl]methyl}piperazin-1-yl)-N-[(3-nitro-4-{[(3R)-tetrahydro-2H-pyran-3-ylmethyl]amino}phenyl)sulfonyl]-2-(1H-pyrrolo[2,3-b]pyridin-5-yloxy)benzamide The title compound was prepared as described in the procedure for Compound 11D using Compound 11C in place of Compound 11B. The proton NMR spectra of Compound 13 and Compound 11D are identical. $^1$H NMR (500 MHz, dimethylsulfoxide-$d_6$) δ 11.68 (s, 1H), 11.40 (s, br, 1H), 8.53-8.58 (m, 2H), 8.04 (d, 1H), 7.80 (dd, 1H), 7.47-7.54 (m, 3H), 7.34 (d, 2H), 7.02-7.09 (m, 3H), 6.67 (dd, 1H), 6.39 (dd, 1H), 6.19 (d, 1H), 3.79 (dd, 1H), 3.69-3.73 (m, 1H), 3.22-3.37 (m, 3H), 3.16-3.21 (m, 1H), 3.07 (s, 4H), 2.74 (s, 2H), 2.09-2.24 (m, 6H), 1.95 (s, 2H), 1.86-1.93 (m, 1H), 1.79-1.85 (m, 1H), 1.58-1.64 (m, 1H), 1.42-1.51 (m, 1H), 1.38 (t, 2H), 1.25-1.34 (m, 1H), 0.92 (s, 6H).

Compound 14

4-(4-{[2-(4-chlorophenyl)-4,4-dimethylcyclohex-1-en-1-yl]methyl}piperazin-1-yl)-N-(2-naphthylsulfonyl)-2-(1H-pyrrolo[2,3-b]pyridin-5-yloxy)benzamide The title compound was prepared as described in the procedure for Compound 11D using naphthalene-2-sulfonamide (47 mg, 0.227 mmol) in place of Compound 11B. $^1$H NMR (500 MHz, dimethylsulfoxide-$d_6$) δ 11.82 (s, 1H), 11.69 (s, 1H), 8.51 (s, 1H), 8.08 (d, 1H), 8.05 (d, 1H), 7.97 (dd, 2H), 7.82 (dd, 1H), 7.66-7.71 (m, 1H), 7.63 (t, 1H), 7.54 (d, 1H), 7.47-7.52 (m, 2H), 7.34 (d, 2H), 7.04 (d, 2H), 6.65 (dd, 1H), 6.39 (dd, 1H), 6.18 (s, 1H), 3.04 (s, 4H), 2.72 (s, 2H), 2.10-2.20 (m, 6H), 1.95 (s, 2H), 1.38 (t, 2H), 0.92 (s, 6H).

Compound 15

4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 15A methyl 6,6-dimethyl-4-oxotetrahydro-2H-pyran-3-carboxylate To a suspension of hexane-washed NaH (0.72 g, 60% in mineral oil) in tetrahydrofuran (30 mil) was added a solution of 2,2-dimethyldihydro-2H-pyran-4(3H)-one (2.0 g) in tetrahydrofuran (20 ml). The suspension was stirred at room temperature for 30 minutes. The dimethylcarbonate (6.31 ml) was added dropwise by syringe. The mixture was heated to reflux for 4 h. LC/MS showed the expected product as the major product. The mixture was acidified with 5% HCl and extracted with dichloromethane (100 mlx3) and washed with water, brine and dried over $Na_2SO_4$. After evaporation, the crude product was loaded on a column and eluted with 10% ethyl acetate in hexane to give the product.

Compound 15B methyl 6,6-dimethyl-4-(trifluoromethylsulfonyloxy)-5,6-dihydro-2H-pyran-3-carboxylate To a cooled (0° C.) stirring suspension of NaH (0.983 g, 60% in mineral oil) in ether (50 ml) was added Compound 15A (3.2 g). The mixture was stirred at 0° C. for 30 minutes before the addition of $Tf_2O$ (4.2 ml). The mixture was then stirred at room temperature overnight. The mixture was diluted with ether (200 ml) and washed with 5% HCl, water and brine. After drying over $Na_2SO_4$, evaporation of solvent gave the crude product which was used in the next step without further purification.

Compound 15C methyl 4-(4-chlorophenyl)-6,6-dimethyl-5,6-dihydro-2H-pyran-3-carboxylate To a solution of Compound 15B (2.88 g), 4-chlorophenylboronic acid (1.88 g) and Pd(Ph$_3$P)$_4$ (0.578 g) in toluene (40 ml) and ethanol (10 ml) was added 2N Na$_2$CO$_3$ (10 ml). The mixture was stirred at reflux overnight. The mixture was diluted ether (300 ml) and washed with water, brine and dried over Na$_2$SO$_4$. After evaporation of solvent, the residue was loaded on a column and eluted with 3% ethyl acetate in hexane to give the product.

Compound 15D (4-(4-chlorophenyl)-6,6-dimethyl-5,6-dihydro-2H-pyran-3-yl)methanol To a solution of Compound 15C (1.6 g) in ether (20 ml) was added LiAlH$_4$ (1.2 g). The mixture was stirred for 4 hours. The mixture was acidified carefully with 5% HCl and extracted with ethyl acetate (100 ml×3) and washed with water, brine and dried over Na$_2$SO$_4$. After concentration, the crude product was loaded on a column and eluted with 10% ethyl acetate in hexane to give the product.

Compound 15E 4-(4-chlorophenyl)-6,6-dimethyl-5,6-dihydro-2H-pyran-3-carbaldehyde To a solution of oxalyl chloride (1.1 g) in dichloromethane (30 ml) at −78° C. was added dimethylsulfoxide (6.12 mil). The mixture was stirred at the temperature for 30 minutes, and then a solution of Compound 15D (1.2 g) in dichloromethane (10 ml) was added. The mixture was stirred at −78° C. for 2 hours before the addition of triethylamine (10 ml). The mixture was stirred overnight and the temperature was allowed to rise to room temperature.

The mixture was diluted with ether (300 ml) and washed with water, brine and dried over Na$_2$SO$_4$. Concentration of the solvent and column purification (5% ethyl acetate in hexane) gave the product.

Compound 15F methyl 2-(1H-pyrrolo[2,3-b]pyridin-5-yloxy)-4-(piperazin-1-yl)benzoate A mixture of Compound 3H (20.5 g) and piperazine (37.0 g) in dimethylsulfoxide (200 ml) was heated to 110° C. for 24 hours, and the mixture was allowed to cool to room temperature. The mixture was poured into water (1 L), extracted three times with dichloromethane, and the combined extracts were washed with 2× water, and brine and filtered and concentrated to give the pure product.

Compound 15G methyl 2-(1H-pyrrolo[2,3-b]pyridin-5-yloxy)-4-(4-((4-(4-chlorophenyl)-6,6-dimethyl-5,6-dihydro-2H-pyran-3-yl)methyl)piperazin-1-yl)benzoate To a solution of Compound 15E (100 mg) and Compound 15F (177 mg) in dichloromethane (10 ml) was added sodium triacetoxyborohydride (154 mg). The mixture was stirred overnight. The mixture was diluted with ethyl acetate (200 ml) and washed with 2% NaOH, water and brine. After drying over Na$_2$SO$_4$, the mixture was filtered and the solvent was evaporated under vacuum. The residue was loaded on a column and eluted with 30% ethyl acetate in hexane to give the pure product.

Compound 15H 2-(1H-pyrrolo[2,3-b]pyridin-5-yloxy)-4-(4-((4-(4-chlorophenyl)-6,6-dimethyl-5,6-dihydro-2H-pyran-3-yl)methyl)piperazin-1-yl)benzoic Acid To a solution of Compound 15G (254 mg) in tetrahydrofuran (4 ml), methanol (2 ml) and water (2 ml) was added LiOH H$_2$O (126 mg). The mixture was stirred overnight. The mixture was then neutralized with 5% HCl and diluted with ethyl acetate (200 ml). After washing with brine, it was dried over Na$_2$SO$_4$. Filtration and evaporation of solvent gave the product.

Compound 15I 4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in the procedure for Compound 1G, substituting Compound 1E with Compound 15H. $^1$H NMR (300 MHz, dimethylsulfoxide-d$_6$) δ 11.68 (br s, 1H), 11.42 (s, 1H), 8.60 (m, 1H), 8.57 (d, 1H), 8.05 (d, 1H), 7.80 (dd, 1H), 7.48-7.54 (m, 3H), 7.38 (d, 2H), 7.12 (m, 3H), 6.68 (dd, 1H), 6.40 (dd, 1H), 6.20 (s, 1H), 4.11 (s, 2H), 3.85 (m, 2H), 3.27 (m, 6H), 3.07 (m, 2H), 2.84 (m, 2H), 2.14 (m, 5H), 1.92 (m, 1H), 1.42 (m, 2H), 1.24 (m, 2H), 1.10 (s, 6H).

Compound 16

4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide

Compound 16A 4-(2-methoxyethylamino)-3-(trifluoromethylsulfonyl)benzenesulfonamide 4-Fluoro-3-(trifluoromethylsulfonyl)benzenesulfonamide (1.536 g, 5 mmol), 2-methoxyethanamine (0.376 g, 5 mmol), and triethylamine (1.939 g, 15 mmol) in anhydrous tetrahydrofuran (30 ml) solution was heated at 55° C. for 3 hours. The solution was diluted with ethyl acetate, washed with water and brine, and dried (Na$_2$SO$_4$), filtered and the filtrate was concentrated. The crude material was used in the next step without further purification.

Compound 16B 4-(4-{[2-(4-chlorophenyl)-4,4-dimethylcyclohex-1-en-1-yl]methyl}piperazin-1-yl)-N-({4-[(2-methoxyethyl)amino]-3-[(trifluoromethyl)sulfonyl]phenyl}sulfonyl)-2-(1H-pyrrolo[2,3-b]pyridin-5-yloxy)benzamide This Compound was prepared by substituting Compound 3J for Compound 1E and Compound 16A for Compound 1F in the procedure for Compound 1G. $^1$H NMR (400 MHz, dimethylsulfoxide-d$_6$) δ 11.67 (brs, 1H), 8.14 (m 1H), 8.03 (d, 1H), 7.91 (d, 1H), 7.50 (m, 3H), 7.34 (d, 2H), 7.19 (s, 1H), 7.04 (m, 3H), 6.67 (dd, 1H), 6.39 (m, 1H), 6.19 (d, 1H), 3.51 (m, 4H), 3.28 (s, 3H), 3.06 (m, 4H), 2.75 (m, 2H), 2.17 (m, 6H), 1.95 (m, 2H), 1.39 (t, 2H), 0.93 (s, 6H).

Compound 17

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide Compound 17A 4-((tetrahydro-2H-pyran-4-yl)methylamino)-3-(trifluoromethylsulfonyl)benzenesulfonamide This Compound was prepared by substituting 1-(tetrahydropyran-4-yl)methylamine for 2-methoxyethanamine in the procedure for Compound 16A.

Compound 17B 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide This Compound was prepared by substituting Compound 3J for Compound 1E and Compound 17A for Compound 1F in the procedure for Compound 1G. $^1$H NMR (400 MHz, dimethylsulfoxide-d$_6$) δ 11.70 (brs, 1H), 8.15 (m 1H), 8.04 (d, 1H), 7.92 (d, 1H), 7.51 (m, 3H), 7.34 (d, 2H), 7.19 (s, 1H), 7.05 (m, 3H), 6.68 (dd, 1H), 6.40 (m, 1H), 6.18 (d, 1H), 3.85 (m, 2H), 3.25 (m, 4H), 3.07 (m, 4H), 2.77 (m, 2H), 2.17 (m, 6H), 1.95 (m, 2H), 1.84 (m, 1H), 1.54 (m, 2H), 1.39 (t, 2H), 1.24 (m, 2H), 0.93 (s, 6H).

Compound 18

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide Compound 18A methyl 2-(1H-indol-5-yloxy)-4-fluorobenzoate A mixture of 5-hydroxyindole (8.5 g), methyl 2,4-difluorobenzoate (7.05 g), and K$_3$PO$_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 18B methyl 2-(1H-indol-5-yloxy)-4-(4-((2-(4-chlorophenyl)-4,4-dimethylcyclohex-1-enyl)methyl)piperazin-1-yl)benzoate A mixture of Compound 18A (1.7 g), Compound 3E (1.8 g), and HK$_2$PO$_4$ (1.21 g) in dimethylsulfoxide (20 ml) at 135° C. was stirred for 24 hours. The reaction was cooled, diluted with ether (400 ml), and washed with 3×1M NaOH, and brine, and concentrated. The crude product was chromatographed on silica gel with 10-50% ethyl acetate/hexanes.

Compound 18C 2-(1H-indol-5-yloxy)-4-(4-((2-(4-chlorophenyl)-4,4-dimethylcyclohex-1-enyl)methyl)piperazin-1-yl) benzoic Acid Compound 18B (200 mg) in dioxane (10 ml) and 1M NaOH (6 ml) at 50° C. was stirred for 24 hours. The reaction was cooled, added to NaH$_2$PO$_4$ solution, and extracted three times with ethyl acetate. The combined extracts were washed with brine, and concentrated to give the pure product.

Compound 18D 4-(4-{[2-(4-chlorophenyl)-4,4-dimethylcyclohex-1-en-1-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as described in the procedure for Compound 11D by replacing Compound 3J with Compound 18C, and Compound 1F for Compound 11B. $^1$H NMR (300 MHz, dimethylsulfoxide-d$_6$) δ 11.18 (s, 2H), 8.59-8.64 (m, 2H), 7.80 (dd, 1H), 7.52 (d, 1H), 7.39-7.42 (m, 2H), 7.33 (d, 2H), 7.16 (d, 1H), 7.10 (d, 1H), 7.03 (d, 2H), 6.8 (dd, 1H), 6.65 (dd, 1H), 6.40)s, 1H), 6.14 (d, 1H), 3.85 (dd, 2H), 3.24-3.32 (m, 4H), 3.03 (s, 3H), 2.73 (s, 2H), 2.12-2.17 (m, 5H), 1.68-1.94 (m, 3H), 1.61 (d, 2H), 1.37 (t, 2H), 1.24-1.27 (m, 2H), 0.92 (s, 6H).

Compound 19 trans-4-(4-{[2-(4-chlorophenyl)-4,4-dimethylcyclohex-1-en-1-yl]methyl}piperazin-1-yl)-2-(1H-indol-5-yloxy)-N-({4-[(4-morpholin-4-ylcyclohexyl)amino]-3-nitrophenyl}sulfonyl)benzamide The title compound was prepared as described in the procedure for Compound 11D by replacing Compound 11B with Compound 9B and Compound 3J with Compound 18C. $^1$H NMR (500 MHz, pyridine-d$_5$) δ 12.29 (s, 1H), 9.29 (d, J=2.1 Hz, 1H), 8.37 (d, J=7.6 Hz, 1H), 8.32 (dd, J=9.3, 2.3 Hz, 1H), 8.18 (d, J=8.8 Hz, 1H), 7.52-7.57 (m, 2H), 7.39-7.47 (m, 3H), 7.10 (dd, J=8.7, 2.3 Hz, 1H), 7.05-7.08 (m, 2H), 6.90 (d, J=9.5 Hz, 1H), 6.74 (dd, J=9.0, 2.3 Hz, 1H), 6.59-6.63 (m, 1H), 6.55 (d, J=2.4 Hz, 1H), 3.72-3.78 (m, 4H), 3.33-3.43 (m, 1H), 2.99-3.09 (m, 4H), 2.76 (s, 2H), 2.46-2.54 (m, 4H), 2.16-2.29 (m, 3H), 2.09-2.14 (m, 4H), 2.05 (d, J=11.9 Hz, 2H), 1.97 (d, J=1.8 Hz, 2H), 1.87 (d, J=11.6 Hz, 2H), 1.19-1.42 (m, 6H), 0.93 (s, 6H).

Compound 20

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-nitrophenyl}sulfonyl)benzamide The title compound was prepared as described in the procedure for Compound 11D by replacing Compound 11B with Compound 10A and Compound 3J with Compound 18C. $^1$H NMR (400 MHz, dimethylsulfoxide-d$_6$) δ 11.20 (br. s, 1H) 11.15 (s, 1H) 8.59 (m, 2H) 7.81 (dd, 1H) 7.50 (d, 1H) 7.36 (m, 4H) 7.08 (m, 4H) 6.85 (dd, 1H) 6.65 (dd, 1H) 6.38 (m, 1H) 6.14 (m, 1H) 3.58 (m, 4H) 3.30 (s, 3H) 3.03 (m, 4H) 2.73 (s, 2H) 2.15 (m, 6H) 1.96 (s, 2H) 1.38 (t, 2H) 0.92 (s, 6H).

Compound 21

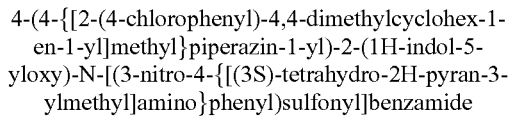
4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3S)-tetrahydro-2H-pyran-3-ylmethyl]amino}phenyl)sulfonyl]benzamide The title compound was prepared as described in the procedure for Compound 11D by replacing Compound 3J with Compound 18C. $^1$H NMR (400 MHz, dimethylsulfoxide-d$_6$) δ 11.17 (s, 2H), 8.53-8.65 (m, 2H), 7.80 (d, 1H), 7.51 (d, 1H), 7.38-7.44 (m, 2H), 7.33 (d, 2H), 7.15 (s, 1H), 7.02-7.09 (m, 3H), 6.82-6.92 (m, 1H), 6.65 (d, 1H), 6.39 (s, 1H), 6.14 (s, 1H), 3.68-3.82 (m, 2H), 3.22-3.32 (m, 2H), 3.13-3.22 (m, 1H), 3.03 (s, 4H), 2.72 (s, 2H), 2.09-2.23 (m, 6H), 1.78-1.98 (m, 4H), 1.56-1.66 (m, 1H), 1.43-1.51 (m, 1H), 1.37 (t, 2H), 1.22-1.33 (m, 1H), 0.92 (s, 6H).

Compound 22

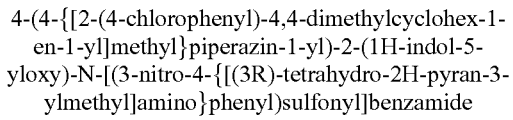
4-(4-{[2-(4-chlorophenyl)-4,4-dimethylcyclohex-1-en-1-yl]methyl}piperazin-1-yl)-2-(1H-indol-5-yloxy)-N-[(3-nitro-4-{[(3R)-tetrahydro-2H-pyran-3-ylmethyl]amino}phenyl)sulfonyl]benzamide The title compound was prepared as described in the procedure for Compound 11D using Compound 11C in place of Compound 11B, and Compound 18C in place of Compound 3J. $^1$H NMR (400 MHz, dimethylsulfoxide-d$_6$) δ 11.17 (s, 2H), 8.53-8.65 (m, 2H), 7.80 (d, 1H), 7.51 (d, 1H), 7.38-7.44 (m, 2H), 7.33 (d, 2H), 7.15 (s, 1H), 7.02-7.09 (m, 3H), 6.82-6.92 (m, 1H), 6.65 (d, 1H), 6.39 (s, 1H), 6.14 (s, 1H), 3.68-3.82 (m, 2H), 3.22-3.32 (m, 2H), 3.13-3.22 (m, 1H), 3.03 (s, 4H), 2.72 (s, 2H), 2.09-2.23 (m, 6H), 1.78-1.98 (m, 4H), 1.56-1.66 (m, 1H), 1.43-1.51 (m, 1H), 1.37 (t, 2H), 1.22-1.33 (m, 1H), 0.92 (s, 6H).

Compound 23

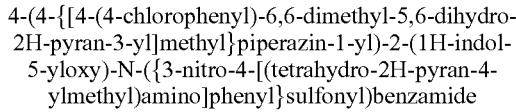
4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide Compound 23A

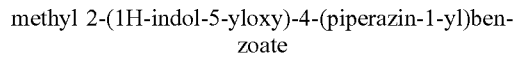
methyl 2-(1H-indol-5-yloxy)-4-(piperazin-1-yl)benzoate

The title compound was prepared as described in the procedure for Compound 15F by replacing Compound 3H with Compound 18A.

Compound 23B

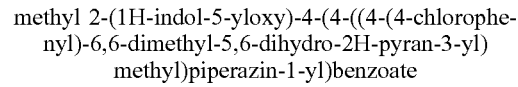
methyl 2-(1H-indol-5-yloxy)-4-(4-((4-(4-chlorophenyl)-6,6-dimethyl-5,6-dihydro-2H-pyran-3-yl)methyl)piperazin-1-yl)benzoate The title compound was prepared as described in the procedure for Compound 15G by replacing Compound 15F with Compound 23A.

Compound 23C

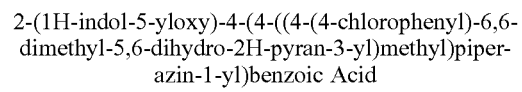
2-(1H-indol-5-yloxy)-4-(4-((4-(4-chlorophenyl)-6,6-dimethyl-5,6-dihydro-2H-pyran-3-yl)methyl)piperazin-1-yl)benzoic Acid The title compound was prepared as described in the procedure for Compound 15H by replacing Compound 15G with Compound 23B.

Compound 23D

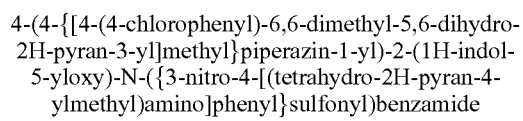
4-(4-{[4-(4-chlorophenyl)-6,6-dimethyl-5,6-dihydro-2H-pyran-3-yl]methyl}piperazin-1-yl)-2-(1H-indol-5-yloxy)-N-({3-nitro-4-[(tetrahydro-2H-pyran-4-ylmethyl)amino]phenyl}sulfonyl)benzamide The title compound was prepared as described in the procedure for Compound 11D by replacing Compound 11B with Compound 1F, and Compound 3J with Compound 23C. $^1$H NMR (400 MHz, dimethylsulfoxide-d$_6$) δ 11.20 (br s, 1H), 11.17 (s, 1H), 8.63 (t, 1H), 8.59 (d, 1H), 7.79 (dd, 1H), 7.51 (d, 1H), 7.36 (m, 3H), 7.13 (m, 2H), 6.86 (dd, 1H), 6.66 (dd, 1H), 6.39 (s, 1H), 6.15 (d, 1H), 4.10 (s, 2H), 3.85 (m, 3H), 3.50 (m, 2H), 3.42 (m, 2H), 3.24 (m, 4H), 3.02 (m, 4H), 2.82 (m, 2H), 2.16 (m, 2H), 1.61 (m, 3H), 1.25 (m, 4H), 1.17 (s, 6H).

Compound 24

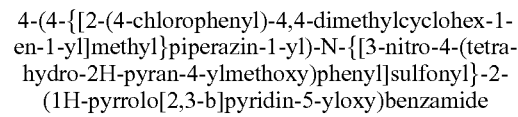
4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide Compound 24A

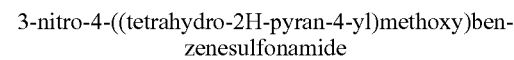
3-nitro-4-((tetrahydro-2H-pyran-4-yl)methoxy)benzenesulfonamide (Tetrahydro-2H-pyran-4-yl)methanol (2.0 g) in tetrahydrofuran (20 ml) was treated with 60% NaH (1.377 g). The solution was stirred for 20 minutes at the room temperature. To this solution was added 4-fluoro-3-nitrobenzenesulfonamide (2.84 g) portionwise. The reaction was stirred for another 2 hours. The mixture was poured into water, neutralized with 10% HCl, and extracted with ethyl acetate three times. The combined organic layers were washed with brine, dried over MgSO$_4$, filtered, and concentrated. The residue was purified with flash column chromatography on silica gel eluting with 20-60% ethyl acetate in hexanes.

Compound 24B 4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}-2-(1H-pyrrolo[2,3-b]pyridin-5-yloxy)benzamide The title compound was prepared by substituting Compound 24A for Compound 11B in the procedure for Compound 11D. $^1$H NMR (500 MHz, dimethylsulfoxide-d$_6$) δ 11.67 (s, 1H), 8.33 (s, 1H), 8.00-8.02 (m, 2H), 7.50-7.53 (m, 3H), 7.34-7.36 (m, 3H), 7.04 (d, 2H), 6.67 (dd, 1H), 6.38 (d, 1H), 6.21 (s, 1H), 4.06 (d, 2H), 3.88 (dd, 2H), 3.08 (s, 4H), 2.80 (s, 2H), 2.25 (s, 4H), 2.15 (s, 2H), 1.96 (s, 2H), 1.63-1.66 (m, 2H), 1.52-1.55 (m, 1H), 1.33-1.40 (m, 4H), 0.92 (s, 6H).

Compound 25

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide

Compound 25A 4-((1,4-dioxan-2-yl)methylamino)-3-nitrobenzenesulfonamide

The title compound was prepared as described in the procedure for Compound 1F using (1,4-dioxan-2-yl)methanamine in place of (tetrahydropyran-4-yl)methanamine.

Compound 25B 4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide The title compound was prepared as described in the procedure for Compound 11D using Compound 25A in place of Compound 11B. $^1$H NMR (500 MHz, dimethylsulfoxide-d$_6$) δ 11.66 (s, 1H), 11.38 (s, 1H), 8.53-8.59 (m, 2H), 8.03 (d, 1H), 7.81 (dd, 1H), 7.46-7.54 (m, 3H), 7.34 (d, 2H), 7.09 (d, 1H), 7.04 (d, 2H), 6.68 (dd, 1H), 6.38 (dd, 1H), 6.19 (d, 1H), 3.75-3.86 (m, 3H), 3.58-3.68 (m, 2H), 3.45-3.52 (m, 2H), 3.35-3.43 (m, 2H), 3.07 (s, 4H), 2.75 (s, 2H), 2.17 (d, 6H), 1.95 (s, 2H), 1.38 (t, 2H), 0.92 (s, 6H).

Compound 26

4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide

Compound 26A 3-nitro-4-(2,2,2-trifluoroethylamino)benzenesulfonamide

The title compound was prepared by substituting 2,2,2-trifluoroethanamine for (tetrahydropyran-4-yl)methylamine in the procedure for Compound 1F.

Compound 26B 4-(4-{[2-(4-chlorophenyl)-4,4-dimethylcyclohex-1-en-1-yl]methyl}piperazin-1-yl)-N-({3-nitro-4-[(2,2,2-trifluoroethyl)amino]phenyl}sulfonyl)-2-(1H-pyrrolo[2,3-b]pyridin-5-yloxy)benzamide The title compound was prepared by substituting Compound 26A for Compound 11B in the procedure for Compound 11D. $^1$H NMR (500 MHz, dimethylsulfoxide-d$_6$) δ 11.48 (s, 1H), 8.40 (m, 2H), 7.90 (d, 1H), 7.71 (dd, 1H), 7.59 (d, 1H), 7.40 (t, 1H), 7.34 (d, 2H), 7.25 (d, 1H), 7.06 (m, 3H), 6.61 (dd, 1H), 6.26 (m, 2H), 4.32 (m, 2H), 3.00 (m, 4H), 2.73 (s, 2H), 2.19 (m, 6H), 1.96 (s, 2H), 1.39 (t, 2H), 0.93 (s, 6H).

Compound 27

4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide

Compound 27A 3-nitro-4-(3,3,3-trifluoropropylamino)benzenesulfonamide

The title compound was prepared by substituting 3,3,3-trifluoropropan-1-amine for (tetrahydropyran-4-yl)methylamine in the procedure for Compound 1F.

Compound 27B 4-(4-{[2-(4-chlorophenyl)-4,4-dimethylcyclohex-1-en-1-yl]methyl}piperazin-1-yl)-N-({3-nitro-4-[(3,3,3-trifluoropropyl)amino]phenyl}sulfonyl)-2-(1H-pyrrolo[2,3-b]pyridin-5-yloxy)benzamide The title compound was prepared by substituting Compound 27A for Compound 11B in the procedure for Compound 11D. $^1$H NMR (500 MHz, dimethylsulfoxide-d$_6$) δ 11.47 (s, 1H), 8.37 (d, 1H), 8.29 (m, 1H), 7.89 (d, 1H), 7.61 (m, 2H), 7.39 (t, 1H), 7.35 (d, 2H), 7.22 (d, 1H), 7.05 (d, 2H), 6.75 (d, 1H), 6.62 (dd, 1H), 6.27 (m, 2H), 3.59 (q, 2H), 3.00 (m, 4H), 2.73 (s, 2H), 2.66 (m, 2H), 2.18 (m, 6H), 1.96 (s, 2H), 1.39 (t, 2H), 0.93 (m, 6H).

Compound 28

4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide

Compound 28A (S)-4-((1,4-dioxan-2-yl)methoxy)-3-nitrobenzenesulfonamide

The racemic mixture of Compound 12A was resolved on a SFC chiral AD column to provide the title compound.

Compound 28B 4-(4-{[2-(4-chlorophenyl)-4,4-dimethylcyclohex-1-en-1-yl]methyl}piperazin-1-yl)-N-({4-[(2S)-1,4-dioxan-2-ylmethoxy]-3-nitrophenyl}sulfonyl)-2-(1H-pyrrolo[2,3-b]pyridin-5-yloxy)benzamide The title compound was prepared as described in the procedure for Compound 11D using Compound 28A in place of Compound 11B. $^1$H NMR (500 MHz, dimethylsulfoxide-d$_6$) δ 11.67 (s, 2H), 8.35 (s, 1H), 8.03 (d, 2H), 7.48-7.57 (m, 3H), 7.42 (d, 1H), 7.35 (d, 2H), 7.05 (d, 2H), 6.68 (dd, 1H), 6.39 (dd, 1H), 6.21 (s, 1H), 4.19-4.30 (m, 2H), 3.85-3.92 (m, 1H), 3.73-3.85 (m, 2H), 3.58-3.70 (m, 2H), 3.40-3.52 (m, 2H), 3.10 (s, 4H), 2.85 (s, 2H), 2.18-2.39 (m, 3H), 2.15 (s, 2H), 1.96 (s, 2H), 1.39 (t, 2H), 0.93 (s, 6H).

Compound 29 cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide

Compound 29A

Cis-4-((4-methoxycyclohexyl)methylamino)-3-nitrobenzenesulfonamide

4-Fluoro-3-nitrobenzenesulfonamide (1.098 g) and Compound 34A (1 g) in tetrahydrofuran (20 ml) was treated with N,N-diisopropylethylamine (0.871 ml) overnight. The reaction mixture was concentrated and the residue was purified by reverse phase chromatography, eluted with 40-55% acetonitrile in 0.1% trifluoroacetic acid in water over 25 min to give the cis isomer Compound 29A and trans isomer Compound 34B.

Compound 29B cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 29A in place of Compound 11B. $^1$H NMR (500 MHz, dimethylsulfoxide-d$_6$) δ 11.69 (s, 1H), 11.36 (s, 1H), 8.53-8.63 (m, 2H), 8.04 (d, 1H), 7.79 (dd, 1H), 7.47-7.56 (m, 3H), 7.34 (d, 2H), 7.00-7.12 (m, 3H), 6.68 (dd, 1H), 6.39 (dd, 1H), 6.19 (d, 1H), 3.37 (s, 1H), 3.26 (t, 2H), 3.20 (s, 3H), 3.07 (s, 4H), 2.75 (s, 2H), 2.17 (d, 6H), 1.95 (s, 2H), 1.81 (dd, 2H), 1.64-1.74 (m, 1H), 1.48 (dd, 2H), 1.23-1.42 (m, 6H), 0.92 (s, 6H).

Compound 30

4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide

Compound 30A (R)-4-((1,4-dioxan-2-yl)methoxy)-3-nitrobenzenesulfonamide

The racemic mixture of Compound 12A was resolved on a SFC chiral AD column to provide the title compound.

Compound 30B 4-(4-{[2-(4-chlorophenyl)-4,4-dimethylcyclohex-1-en-1-yl]methyl}piperazin-1-yl)-N-({4-[(2R)-1,4-dioxan-2-ylmethoxy]-3-nitrophenyl}sulfonyl)-2-(1H-pyrrolo[2,3-b]pyridin-5-yloxy)benzamide The title compound was prepared as described in the procedure for Compound 11D using Compound 30A in place of Compound 11B. $^1$H NMR (500 MHz, dimethylsulfoxide-d$_6$) δ 11.67 (s, 2H), 8.35 (s, 1H), 8.03 (d, 2H), 7.48-7.57 (m, 3H), 7.42 (d, 1H), 7.35 (d, 2H), 7.05 (d, 2H), 6.68 (dd, 1H), 6.39 (dd, 1H), 6.21 (s, 1H), 4.19-4.30 (m, 2H), 3.85-3.92 (m, 1H), 3.73-3.85 (m, 2H), 3.58-3.70 (m, 2H), 3.40-3.52 (m, 2H), 3.10 (s, 4H), 2.85 (s, 2H), 2.18-2.39 (m, 3H), 2.15 (s, 2H), 1.96 (s, 2H), 1.39 (t, 2H), 0.93 (s, 6H).

Compound 31

4-(4-{[4-(4-chlorophenyl)-6,6-dimethyl-5,6-dihydro-2H-pyran-3-yl]methyl}piperazin-1-yl)-N-({4-[(1,4-dioxan-2-ylmethyl)amino]-3-nitrophenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 15H and Compound 25A, respectively. $^1$H NMR (300 MHz, dimethylsulfoxide-d$_6$) δ 11.66 (s, 1H), 11.46 (m, 1H), 8.54 (m, 2H), 8.45 (m, 1H), 8.03 (d, 1H), 7.83 (m, 2H), 7.50 (m, 3H), 7.34 (m, 3H), 7.12 (m, 2H), 6.68 (dd, 1H), 6.38 (dd, 1H), 6.20 (d, 1H), 4.11 (s, 2H), 3.79 (m, 4H), 3.51 (m, 6H), 3.05 (m, 4H), 2.17 (m, 3H), 1.17 (s, 6H).

Compound 32

4-(4-{[4-(4-chlorophenyl)-6,6-dimethyl-5,6-dihydro-2H-pyran-3-yl]methyl}piperazin-1-yl)-N-{[4-(1,4-dioxan-2-ylmethoxy)-3-nitrophenyl]sulfonyl}-2-(1H-pyrrolo[2,3-b]pyridin-5-yloxy)benzamide The title compound was prepared as described in the procedure for Compound 1G by replacing Compound 1E and Compound 1F with Compound 15H and Compound 12A, respectively. $^1$H NMR (300 MHz, dimethylsulfoxide-d$_6$) δ 11.67 (s, 1H), 8.37 (d, 1H), 8.03 (m, 2H), 7.50 (m, 3H), 7.37 (d, 2H), 7.13 (d, 2H), 6.68 (dd, 1H), 6.40 (dd, 1H), 6.20 (d, 1H), 4.25 (m, 2H), 4.12 (s, 2H), 3.84 (m, 3H), 3.63 (m, 2H), 3.45 (m, 2H), 3.06 (m, 4H), 2.86 (m, 2H), 2.24 (m, 6H), 1.20 (m, 6H).

Compound 33 trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 15H and Compound 9C, respectively. $^1$H NMR (300 MHz, dimethylsulfoxide-d$_6$) δ 11.63 (s, 1H), 8.51 (d, 1H), 8.15 (d, 1H), 8.01 (d, 1H), 7.76 (dd, 1H), 7.48 (m, 3H), 7.38 (d, 2H), 7.13 (d, 2H), 7.06 (d, 1H), 6.66 (dd, 1H), 6.36 (dd, 1H), 6.21 (d, 1H), 4.11 (s, 2H), 3.63 (m, 5H), 3.05 (m, 4H), 2.83 (s, 2H), 2.64 (m, 4H), 2.17 (m, 6H), 2.05 (m, 2H), 1.91 (s, 2H), 1.43 (m, 6H), 1.17 (m, 6H).

Compound 34 trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide

Compound 34A (4-methoxycyclohexyl) methanamine (4-Methoxyphenyl)methanamine (1 g, 1.29 mmol) in ethanol (10 ml) was treated with 5% Rh—Al$_2$O$_3$ (99.8 mg, 0.048 mmol) under H$_2$ atmosphere (500 psi) at 50° C. for 16 hours. Additional 5% Rh—Al$_2$O$_3$ (0.4 g) was added. The resulting mixture was stirred under H$_2$ atmosphere (500 psi) at 60° C. for 2 hours. The insoluble material was filtered off and the filtrate was concentrated to provide a mixture of cis and trans product as an oil, which was used in the next step without further purification.

Compound 34B trans-4-((4-methoxycyclohexyl)methylamino)-3-nitrobenzenesulfonamide 4-Fluoro-3-nitrobenzenesulfonamide (1.098 g) and Compound 34A (1 g) in tetrahydrofuran (20 ml) was treated with N,N-diisopropylethylamine (0.871 ml) overnight. The reaction mixture was concentrated and the residue was purified by reverse phase chromatography, and was eluted with 40-55% acetonitrile in 0.1% trifluoroacetic acid in water over 25 minutes.

Compound 34C trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 34B in place of Compound 11B. $^1$H NMR (500 MHz, dimethylsulfoxide-d$_6$) δ 11.69 (s, 1H), 11.37 (s, 1H), 8.52-8.62 (m, 2H), 8.04 (d, 1H), 7.79 (dd, 1H), 7.47-7.55 (m, 3H), 7.34 (d, 2H), 7.02-7.09 (m, 3H), 6.68 (dd, 1H), 6.39 (dd, 1H), 6.19 (d, 1H), 3.21-3.27 (m, 5H), 3.02-3.12 (m, 5H), 2.75 (s, 2H), 2.20 (s, 4H), 2.14 (s, 2H), 1.93-2.04 (m, 4H), 1.79 (d, 2H), 1.55-1.65 (m, 1H), 1.38 (t, 2H), 0.97-1.12 (m, 4H), 0.92 (s, 6H).

Compound 35

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide The title compound was prepared as described in the procedure for Compound 1G by replacing Compound 1E and Compound 1F with Compound 15H and Compound 36C, respectively. $^1$H NMR (300 MHz, dimethylsulfoxide-d$_6$) δ 11.65 (s, 1H), 8.78 (s, 1H), 8.58 (s, 1H), 8.00 (d, 1H), 7.51 (m, 3H), 7.38 (d, 2H), 7.14 (d, 2H), 6.68 (dd, 1H), 6.37 (dd, 1H), 6.23 (d, 1H), 4.31 (d, 2H), 4.13 (s, 2H), 3.88 (dd, 2H), 3.11 (m, 5H), 2.16 (m, 6H), 1.65 (m, 2H), 1.35 (m, 2H), 1.19 (s, 6H).

Compound 36

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide

Compound 36A 5-bromo-6-chloropyridine-3-sulfonamide

5-Bromo-6-chloropyridine-3-sulfonyl chloride (8.2 g) in methanol (20 ml) was cooled to 0° C. To this solution was added 7N NH$_3$ in methanol (80 ml). The reaction mixture was stirred overnight. The solvent was removed at low temperature, and the residue was partitioned between ethyl acetate and water. The aqueous layer was extracted with ethyl acetate three times. The combined organic layers were washed with brine, dried (MgSO$_4$), filtered, and concentrated. The solid was purified by flash column chromatography on silica gel using 20-100% ethyl acetate in hexanes to give the title compound.

Compound 36B 5-bromo-6-((tetrahydro-2H-pyran-4-yl)methoxy)pyridine-3-sulfonamide The title compound was prepared by substituting Compound 36A for 4-fluoro-3-nitrobenzenesulfonamide in the procedure for Compound 24A.

Compound 36C 5-cyano-6-((tetrahydro-2H-pyran-4-yl)methoxy)pyridine-3-sulfonamide A mixture of Compound 36B (0.702 g), dicyanozine (0.129 g), and tetrakis(triphenylphosphine)palladium(0) (0.231 g) in N,N-dimethylformamide (2 ml) was degassed via vacuum/nitrogen cycle three times. The reaction mixture was heated at 120° C. for 3 hours. After cooling, it was poured into water and extracted with ethyl acetate three times.

The combined organic layers were washed with brine, dried over MgSO$_4$, filtered, and concentrated. The residue was purified with flash column chromatography on silica gel eluting with 20%-60% ethyl acetate in hexanes to give the title compound.

Compound 36D 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy) benzamide The title compound was prepared by substituting Compound 36C for Compound 11B in the procedure for Compound 11D. $^1$H NMR (500 MHz, dimethylsulfoxide-d$_6$) δ 11.56 (s, 1H), 8.66 (s, 1H), 8.44 (s, 1H), 7.94 (d, 1H), 7.55 (d, 1H), 7.44 (t, 1H), 7.34-7.35 (m, 3H), 7.04 (d, 2H), 6.65 (dd, 1H), 6.32 (s, 1H), 6.24 (s, 1H), 4.26 (d, 2H), 3.86 (dd, 2H), 3.10 (s, 4H), 2.75 (s, 2H), 2.31-2.35 (m, 2H), 2.01-2.05 (m, 1H), 2.15 (s, 2H), 1.96 (s, 2H), 1.63-1.66 (m, 2H), 1.33-1.40 (m, 4H), 0.92 (s, 6H).

Compound 37

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide Compound 37A 1,6-dioxaspiro[2.5]octane-2-carbonitrile A mixture of tetrahydropyran-4-one (10 ml) and chloroacetonitrile (6.4 ml) in tert-butanol (10 ml) was stirred for 10 minutes. To this solution was added a solution of potassium tert-butoxide (12.11 g) in 200 ml of tert-butanol at room temperature over 40 minutes. The reaction mixture was stirred for 16 hours, diluted with water and quenched slowly with 1 N HCl. The solvent was partially removed by rotary evaporation. It was then extracted with ether (5×200 ml). The combined extracts was washed with brine, dried over MgSO$_4$, filtered, and the filtrate was concentrated and purified by flash chromatography on silica with 3:7 to 1:1 ethyl acetate:hexanes to provide the title compound.

Compound 37B 2-(4-fluorotetrahydro-2H-pyran-4-yl)-2-hydroxyacetonitrile

Compound 37A (11.5 g) in dichloromethane (40 ml) in a polypropylene bottle was treated with 70% hydrogen fluoride-pyridine (10.4 ml) dropwise at 0° C. The solution was allowed to warm to room temperature over 3 hours, and stirred for an additional 1.5 hours. The reaction mixture was diluted with ethyl acetate (200 ml) and poured into saturated aqueous NaHCO$_3$. Additional solid NaHCO$_3$ was used carefully until bubbling ceased. The organic layer was isolated, and the aqueous layer was extracted with additional ethyl acetate three times (150 ml each). The combined organic layers were washed with 5% HCl (50 ml each, twice), brine, dried over MgSO$_4$, filtered and concentrated to give the desired product which was used directly in the next step.

Compound 37C (4-fluorotetrahydro-2H-pyran-4-yl)methanol

Compound 37B (11.7 g, 74 mmol) in 2-propanol (150 ml) and water (37.5 ml) was cooled to 0° C. To this solution was added NaBH$_4$ (4.20 g, 111 mmol). The solution was stirred and allowed to warm to room temperature over 3 hours. It was quenched with acetone, and stirred for another 1 hour. The clear liquid was separated from solid by decanting. Additional ethyl acetate (2×100 ml) was used to wash the solid, and the mixture was decanted. The combined organic solutions were concentrated. The residue was purified by flash chromatography, eluting with 1:1 ethyl acetate:hexanes to provide the title compound.

Compound 37D 4-((4-fluorotetrahydro-2H-pyran-4-yl)methoxy)-3-nitrobenzenesulfonamide The title compound was prepared by substituting Compound 37C for (tetrahydro-2H-pyran-4-yl)methanol in the procedure for Compound 24A.

Compound 37E 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in the procedure for Compound 11D using Compound 37D in place of Compound 11B. $^1$H NMR (dimethylsulfoxide-d$_6$) δ 11.64 (s, 2H), 8.33 (s, 1H), 8.00-8.01 (m, 2H), 7.39-7.57 (m, 4H), 7.33 (d, J=8.24 Hz, 2H), 7.03 (d, J=8.54 Hz, 2H), 6.65 (dd, J=9, 1.98 Hz, 1H), 6.37-6.38 (m, 1H), 6.19 (d, J=1.53 Hz, 1H), 4.35 (d, J=20.75 Hz, 2H), 3.74-3.78 (m, 2H), 3.55-3.60 (m, 2H), 3.07 (br, 4H), 2.80 (br, 2H), 2.25 (br, 4H), 2.13 (br, 2H), 1.81-1.94 (m, 6H), 1.38 (t, J=6.26 Hz, 2H), 0.91 (s, 6H).

Compound 38

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide Compound 38A 3-cyano-4-((tetrahydro-2H-pyran-4-yl)methoxy) benzenesulfonamide The title compound was prepared by substituting 3-cyano-4-fluorobenzenesulfonamide for 4-fluoro-3-nitrobenzenesulfonamide in the procedure for Compound 24A.

Compound 38B 5-sulfamoyl-2-((tetrahydro-2H-pyran-4-yl)methoxy)
benzamide

To a solution of Compound 38A (0.455 g) in ethanol (3 ml) and tetrahydrofuran (1 ml) was added hydrogen peroxide (30% in water, 2 ml) followed by 1 N aqueous NaOH (1.024 ml) and heated to 35° C. for 3 hours. The reaction was poured into dichloromethane (50 ml) and 1N aqueous HCl (25 ml). The aqueous layer was extracted with dichloromethane (3×50 ml). The precipitate contained in the combined organic layers was collected by filtration to give the title compound.

Compound 38C

N-{[3-(aminocarbonyl)-4-(tetrahydro-2H-pyran-4-ylmethoxy)phenyl]sulfonyl}-4-(4-{[2-(4-chlorophenyl)-4,4-dimethylcyclohex-1-en-1-yl]
methyl}piperazin-1-yl)-2-(1H-pyrrolo[2,3-b]pyridin-5-yloxy)benzamide The title compound was prepared by substituting Compound 38B for Compound 1F and Compound 3J for Compound 1E in the procedure for Compound 1G. $^1$H NMR (300 MHz, dimethylsulfoxide-$d_6$) δ 11.79-11.70 (m, 1H), 11.66-11.54 (m, 1H), 9.29-9.08 (m, 1H), 8.27 (d, 1H), 8.08 (d, 1H), 7.97-7.90 (m, 1H), 7.76-7.72 (m, 1H), 7.62 (s, 1H), 7.54 (s, 1H), 7.50 (d, 1H), 7.39 (d, 1H), 7.23 (d, 1H), 7.08 (d, 1H), 6.74-6.67 (m, 1H), 6.44 (s, 1H), 6.22 (s, 1H), 4.03 (d, 6H), 3.74-3.52 (m, 4H), 3.33 (s, 4H), 3.11-2.90 (m, 2H), 2.01 (s, 4H), 1.79-1.58 (m, 2H), 1.24 (s, 5H), 0.94 (s, 6H).

Compound 39 cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide

Compound 39A cis-tert-butyl-4-morpholinocyclohexylcarbamate

To a solution of morpholine (4.08 g) and tert-butyl 4-oxocyclohexylcarbamate (10 g) stirred for 24 hours at room temperature in titanium (IV) isopropoxide (27.5 ml), methanol (10 ml) was added followed by careful addition of sodium borohydride (3.55 g). The reaction mixture was quenched with water/NaOH solution, extracted with ether, dried over magnesium sulfate, filtered, and concentrated. The product was separated from the trans isomer and purified by flash chromatography (silica gel, 50%-100% acetone in hexanes) to provide the title compound.

Compound 39B cis-4-morpholinocyclohexanamine
bis(2,2,2-trifluoroacetate)

To a solution of Compound 39A (2.43 g) in dichloromethane (15 ml) was added trifluoroacetic acid (5 ml) and the reaction mixture was stirred for 16 hours at room temperature. The reaction mixture was concentrated and the crude product was used without purification.

Compound 39C 4-(cis-4-morpholinocyclohexylamino)-3-nitrobenzenesulfonamide

A solution of Compound 39B (0.40 g), 4-fluoro-3-nitrobenzenesulfonamide (0.478 g) and triethylamine (2 ml) in tetrahydrofuran (10 ml) was stirred for 3 days at room temperature. The reaction mixture was concentrated and purified by flash chromatography (silica gel, 0-30% methanol/dichloromethane) providing the product.

Compound 39D cis-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared by substituting Compound 39C for Compound 11B in the procedure for Compound 11D. $^1$H NMR (500 MHz, pyridine-$d_5$) δ 13.07 (s, 1H), 9.30 (d, 1H), 8.64 (d, 1H), 8.43 (d, 1H), 8.38 (dd, 1H), 8.11 (d, 1H), 7.67 (t, 2H), 7.44 (d, 2H), 7.06 (d, 2H), 6.91 (d, 1H), 6.74 (dd, 1H), 6.48-6.55 (m, 2H), 3.65-3.73 (m, 5H), 3.02-3.09 (m, 4H), 2.76 (s, 2H), 2.41-2.48 (m, 4H), 2.25 (t, 2H), 2.09-2.16 (m, 5H), 1.97 (s, 2H), 1.77-1.86 (m, 2H), 1.55-1.63 (m, 6H), 1.39 (t, 2H), 0.93 (s, 6H).

Compound 40

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)
benzamide

Compound 40A 5,6-dichloropyridine-3-sulfonamide

The title compound was prepared by substituting 5,6-dichloropyridine-3-sulfonyl chloride for 5-bromo-6-chloropyridine-3-sulfonyl chloride in the procedure for Compound 36A.

Compound 40B 5-chloro-6-((tetrahydro-2H-pyran-4-yl)methoxy)
pyridine-3-sulfonamide The title compound was prepared by substituting Compound 40A for 4-fluoro-3-nitrobenzenesulfonamide in the procedure for Compound 24A.

Compound 40C 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)
benzamide The title compound was prepared by substituting Compound 40B for Compound 11B in the procedure for Compound 11D. $^1$H NMR (500 MHz, dimethylsulfoxide-$d_6$) δ 11.67 (s, 1H), 8.52 (s, 1H), 8.39 (d, 1H), 8.03 (d, 1H), 7.54

(d, 1H), 7.52 (d, 1H), 7.50 (dd, 1H), 7.35 (d, 2H), 7.04 (d, 2H), 6.67 (dd, 1H), 6.39 (m, 1H), 6.21 (d, 1H), 4.25 (d, 2H), 3.87 (dd, 2H), 3.30 (m, 2H), 3.10 (v br s, 4H), 2.90 (v br s, 2H), 2.35 (v br s, 4H), 2.17 (br m, 2H), 2.05 (m, 1H), 1.96 (s, 2H), 1.64 (d, 2H), 1.40 (t, 2H), 1.35 (ddd, 2H), 0.93 (s, 6H).

Compound 41

4-(4-{[4-(4-chlorophenyl)-6,6-dimethyl-5,6-dihydro-2H-pyran-3-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 15H for Compound 3J and Compound 40B for Compound 11B in the procedure for Compound 11D. $^1$H NMR (500 MHz, dimethylsulfoxide-$d_6$) δ 11.68 (s, 1H), 8.55 (d, 1H), 8.41 (d, 1H), 8.04 (d, 1H), 7.54 (m, 2H), 7.50 (dd, 1H), 7.38 (d, 2H), 7.14 (d, 2H), 6.68 (dd, 1H), 6.40 (m, 1H), 6.20 (d, 1H), 4.25 (d, 2H), 4.12 (s, 2H), 3.87 (dd, 2H), 3.30 (m, 2H), 3.10 (v br s, 4H), 2.90 (v br s, 2H), 2.27 (v br s, 4H), 2.17 (br m, 2H), 2.05 (m, 1H), 1.96 (s, 2H), 1.64 (d, 2H), 1.35 (ddd, 2H), 0.97 (s, 6H).

Compound 42

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide Compound 42A 4-((tetrahydro-2H-pyran-4-yl)methylamino)-3-(trifluoromethyl)benzenesulfonamide A mixture of 4-fluoro-3-(trifluoromethyl)benzenesulfonamide (1.056 g), (tetrahydro-2H-pyran-4-yl)methanamine (0.5 g) and N,N-diisopropylethylamine (1.68 g) in anhydrous dimethylsulfoxide (15 ml) solution was heated at 90° C. overnight. The reaction mixture was cooled to room temperature and diluted with ethyl acetate. The organic phase was washed with water, brine, dried over anhydrous sodium sulfate, filtered and concentrated to afford the title compound.

Compound 42B 4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-{[4-[(tetrahydro-2H-pyran-4-ylmethyl)amino]-3-(trifluoromethyl)phenyl]sulfonyl}benzamide The title compound was prepared as described in the procedure for Compound 1G by replacing Compound 1E and Compound 1F with Compound 15H and Compound 42A, respectively. $^1$H NMR (300 MHz, dimethylsulfoxide-$d_6$) δ 11.73 (s, 1H), 11.25 (s, 1H), 8.08 (d, 1H), 7.89 (d, 1H), 7.77 (m, 1H), 7.61 (d, 1H), 7.51 (m, 2H), 7.37 (d, 2H), 7.13 (d, 2H), 6.88 (d, 1H), 6.67 (dd, 1H), 6.53 (m, 1H), 6.43 (m, 1H), 6.15 (d, 1H), 4.11 (s, 2H), 3.82 (dd, 2H), 3.19 (m, 5H), 3.05 (m, 4H), 2.82 (s, 2H), 2.20 (m, 7H), 1.85 (m, 1H), 1.56 (m, 2H), 1.18 (s, 6H).

Compound 43

4-(4-{[4-(4-chlorophenyl)-6,6-dimethyl-5,6-dihydro-2H-pyran-3-yl]methyl}piperazin-1-yl)-2-(1H-pyrrolo[2,3-b]pyridin-5-yloxy)-N-({4-[(tetrahydro-2H-pyran-4-ylmethyl)amino]-3-[(trifluoromethyl)sulfonyl]phenyl}sulfonyl)benzamide The title compound was prepared as described in the procedure for Compound 1G by replacing Compound 1E and Compound 1F with Compound 15H and Compound 17A, respectively. $^1$H NMR (300 MHz, dimethylsulfoxide-$d_6$) δ 11.69 (s, 1H), 11.48 (m, 1H), 8.16 (d, 1H), 8.05 (d, 1H), 7.92 (dd, 1H), 7.52 (m, 3H), 7.37 (d, 2H), 7.27 (m, 1H), 7.11 (m, 3H), 6.68 (dd, 1H), 6.41 (dd, 1H), 6.18 (d, 1H), 4.11 (s, 2H), 3.84 (dd, 2H), 3.25 (m, 4H), 3.07 (m, 4H), 2.84 (m, 2H), 2.23 (m, 5H), 1.84 (m, 1H), 1.55 (m, 2H), 1.25 (m, 3H), 1.18 (s, 6H).

Compound 44 trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide Compound 44A trans-4-(4-morpholinocyclohexylamino)-3-(trifluoromethylsulfonyl)benzenesulfonamide The title compound was prepared as described in the procedure for Compound 16A by replacing 2-methoxyethanamine with Compound 9B.

Compound 44B trans-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-[(trifluoromethyl)sulfonyl]phenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 15H and Compound 44A, respectively. $^1$H NMR (300 MHz, dimethylsulfoxide-$d_6$) δ 11.62 (s, 1H), 8.08 (s, 1H), 8.00 (d, 1H), 7.85 (d, 1H), 7.47 (m, 3H), 7.38 (d, 2H), 7.14 (d, 2H), 6.98 (d, 1H), 6.65 (dd, 1H), 6.55 (m, 1H), 6.37 (m, 1H), 6.21 (d, 1H), 4.12 (s, 2H), 3.54 (m, 6H), 3.04 (m, 4H), 2.83 (s, 2H), 2.57 (m, 3H), 2.24 (m, 6H), 1.91 (m, 5H), 1.34 (m, 4H), 1.20 (s, 6H).

Compound 45

4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide

Compound 45A 4-(1-methylpiperidin-4-ylamino)-3-(trifluoromethylsulfonyl)benzenesulfonamide The title compound was prepared as described in the procedure for Compound 16A by replacing 2-methoxyethanamine with 1-methyl-4-aminopiperidine.

Compound 45B 4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-[(trifluoromethyl)sulfonyl]phenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 15H and Compound 45A, respectively. $^1$H NMR (300 MHz, dimethylsulfoxide-$d_6$) δ 11.59 (s, 1H), 8.10 (s, 1H), 7.98 (d, 1H), 7.90 (dd, 1H), 7.49 (m, 3H), 7.39 (m, 3H), 7.14 (d, 2H), 7.02 (d, 1H), 6.65 (dd, 2H), 6.36 (dd, 1H), 6.22 (d, 1H), 4.12 (s, 2H), 3.75 (m, 1H), 3.16 (m, 4H), 2.98 (m, 5H), 2.88 (m, 5H), 2.67 (s, 2H), 2.22 (m, 6H), 1.68 (m, 1H), 1.18 (s, 6H).

Compound 46

5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide

Compound 46A 5-sulfamoyl-2-((tetrahydro-2H-pyran-4-yl)methoxy)nicotinamide

To Compound 36C (0.025 g) in ethanol (1 ml) and tetrahydrofuran (1 ml) was added hydrogen peroxide (30% in water, 0.5 ml) followed by 1M aqueous sodium hydroxide (0.056 ml) then another 1 ml of tetrahydrofuran. The reaction was heated to 45° C. for 2 hours, cooled, quenched with 1N aqueous HCl (5 ml), and the product extracted into dichloromethane (10 ml). The organic layer was dried over magnesium sulfate, filtered and concentrated to give the title compound.

Compound 46B 5-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-(tetrahydro-2H-pyran-4-ylmethoxy)nicotinamide The title compound was prepared by substituting Compound 46A for Compound 1F and Compound 3J for Compound 1E in the procedure for Compound 1G. $^1$H NMR (300 MHz, CDCl$_3$) δ 10.31-10.09 (m, 1H), 9.09 (s, 2H), 8.93-8.81 (m, 1H), 8.28-8.18 (m, 1H), 8.03-7.87 (m, 1H), 7.77-7.68 (m, 1H), 7.59-7.51 (m, 1H), 7.48-7.41 (m, 1H), 6.91 (d, 2H), 6.59-6.48 (m, 2H), 5.97 (s, 2H), 4.50 (d, 2H), 4.08-3.98 (m, 2H), 3.45 (s, 4H), 3.13-2.99 (m, 4H), 2.82-2.68 (m, 2H), 2.19 (s, 4H), 1.86 (s, 5H), 1.61-1.35 (m, 4H), 0.94 (s, 6H).

Compound 47

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 47A 5-bromo-6-((1-methylpiperidin-4-yl)methoxy)pyridine-3-sulfonamide To (1-methylpiperidin-4-yl)methanol (0.109 g) in tetrahydrofuran (2 ml) was added sodium hydride (0.136 g). After 30 minutes, Compound 36A (0.230 g) was added as a solution in tetrahydrofuran (1 ml) and the reaction was heated to 50° C. After 4 hours, the reaction was cooled, poured into water (10 ml) and dichloromethane (50 ml), and the pH was adjusted to pH-8. The aqueous layer was extracted with dichloromethane (3×50 ml), and the organic layers were combined, washed with brine (30 ml), dried over magnesium sulfate, filtered, and concentrated to give the title compound.

Compound 47B

N-({5-bromo-6-[(1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 47A for Compound 1F and Compound 3J for Compound 1E in the procedure for Compound 1G. $^1$H NMR (300 MHz, dimethylsulfoxide-$d_6$) δ 11.51 (s, 1H), 8.35 (d, 1H), 8.17 (d, 1H), 7.93 (d, 1H), 7.60 (d, 1H), 7.44-7.40 (m, 1H), 7.33 (dd, 3H), 7.05 (d, 2H), 6.61 (d, 1H), 6.31 (dd, 1H), 6.24 (s, 1H), 4.25 (d, 2H), 3.40 (s, 4H), 3.01 (s, 4H), 2.73 (d, J=8.2, 5H), 2.20 (s, 6H), 1.93 (d, 4H), 1.54 (s, 1H), 1.39 (s, 2H), 1.24 (s, 2H), 0.93 (s, 6H).

Compound 48

4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide

Compound 48A 4-((1-methylpiperidin-4-yl)methoxy)-3-nitrobenzenesulfonamide

The title compound was prepared by substituting (1-methylpiperidin-4-yl)methanol for (tetrahydro-2H-pyran-4-yl)methanol in the procedure for Compound 24A.

Compound 48B 4-(4-{[2-(4-chlorophenyl)-4,4-dimethylcyclohex-1-en-1-yl]methyl}piperazin-1-yl)-N-({4-[(1-methylpiperidin-4-yl)methoxy]-3-nitrophenyl}sulfonyl)-2-(1H-pyrrolo[2,3-b]pyridin-5-yloxy)benzamide The title compound was prepared by substituting Compound 48A for Compound 1F and Compound 3J for Compound 1E in the procedure for Compound 1G. $^1$H NMR (300 MHz, dimethylsulfoxide-d$_6$) δ 11.54 (s, 1H), 8.17 (s, 1H), 7.92 (s, 1H), 7.87-7.77 (m, 1H), 7.58 (d, 1H), 7.43 (s, 1H), 7.40-7.00 (m, 7H), 6.70-6.56 (m, 1H), 6.31 (s, 1H), 6.24 (s, 1H), 4.05 (s, 2H), 3.46-3.33 (m, 2H), 3.02 (s, 6H), 2.72 (d, 5H), 2.21 (s, 6H), 1.96 (s, 5H), 1.70-1.48 (m, 2H), 1.39 (s, 2H), 0.93 (s, 6H).

Compound 49

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide

Compound 49A 6-((1,4-dioxan-2-yl)methoxy)-5-bromopyridine-3-sulfonamide

The title compound was prepared by substituting (1,4-dioxan-2-yl)methanol for (tetrahydro-2H-pyran-4-yl)methanol and Compound 36A for 4-fluoro-3-nitrobenzenesulfonamide in the procedure for Compound 24A.

Compound 49B 6-((1,4-dioxan-2-yl)methoxy)-5-cyanopyridine-3-sulfonamide

The title compound was prepared by substituting Compound 49A for Compound 36B in the procedure for Compound 36C.

Compound 49C 4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-(1H-pyrrolo[2,3-b]pyridin-5-yloxy)benzamide The title compound was prepared by substituting Compound 49B for Compound 11B in the procedure for Compound 11D. $^1$H NMR (400 MHz, dimethylsulfoxide-d$_6$) δ 11.50 (s, 1H), 8.60 (s, 1H), 8.40 (s, 1H), 7.91 (d, 1H), 7.58 (d, 1H), 7.42 (t, 1H), 7.35 (d, 2H), 7.28 (s, 1H), 7.06 (d, 2H), 6.64 (dd, 1H), 6.29 (m, 2H), 4.40 (d, 2H), 3.90 (m, 1H), 3.79 (m, 2H), 3.63 (m, 2H), 3.46 (m, 4H), 3.07 (s, 4H), 2.85 (m, 2H), 2.34 (m, 4H), 2.16 (m, 2H), 1.40 (t, 2H), 0.93 (s, 6H).

Compound 50

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 49A for Compound 11B in the procedure for Compound 11D. $^1$H NMR (400 MHz, dimethylsulfoxide-d$_6$) δ 11.60 (s, 1H), 8.46 (s, 1H), 8.27 (s, 1H), 7.99 (d, 1H), 7.56 (d, 1H), 7.46 (m, 2H), 7.35 (d, 2H), 7.05 (d, 2H), 6.65 (dd, 1H), 6.36 (dd, 1H), 6.22 (d, 1H), 4.34 (m, 2H), 3.88 (m, 1H), 3.79 (m, 2H), 3.63 (m, 2H), 3.46 (m, 2H), 3.06 (s, 4H), 2.81 (s, 2H), 2.26 (m, 4H), 2.15 (s, 2H), 1.96 (s, 2H), 1.38 (m, 2H), 0.93 (s, 6H).

Compound 51

4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide

Compound 51A 4-((2,2-dimethyltetrahydro-2H-pyran-4-yl)methoxy)-3-nitrobenzenesulfonamide The title compound was prepared as described in the procedure for Compound 12A by replacing (1,4-dioxan-2-yl)methanol with (2,2-dimethyltetrahydro-2H-pyran-4-yl)methanol.

Compound 51B 4-(4-{[2-(4-chlorophenyl)-4,4-dimethylcyclohex-1-en-1-yl]methyl}piperazin-1-yl)-N-({4-[(2,2-dimethyltetrahydro-2H-pyran-4-yl)methoxy]-3-nitrophenyl}sulfonyl)-2-(1H-pyrrolo[2,3-b]pyridin-5-yloxy)benzamide The title compound was prepared as described in the procedure for Compound 11D using Compound 51A in place of Compound 11B. $^1$H NMR (400 MHz, dimethylsulfoxide-d$_6$) δ 11.69 (s, 2H), 8.35 (s, 2H), 8.03 (d, 4H), 7.47-7.58 (m, 6H), 7.31-7.42 (m, 6H), 7.04 (d, 4H), 6.68 (dd, 2H), 6.40 (s, 2H), 6.20 (d, 2H), 3.96-4.09 (m, 2H), 3.54-3.68 (m, 2H), 3.09 (s, 4H), 2.83 (s, 2H), 2.09-2.37 (m, 7H), 1.96 (s, 2H), 1.55-1.69 (m, 2H), 1.39 (t, 2H), 1.19 (m, 8H), 0.92 (s, 6H).

Compound 52

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 52A 3-cyano-4-fluorobenzenesulfonamide

3-Cyano-4-fluorobenzene-1-sulfonyl chloride (1.1 g) in 1,4-dioxane (10 ml) at 0° C. was treated dropwise with a 7 M ammonia solution in methanol (3.57 ml) and stirred for 30 minutes. A small amount of solid was removed by filtration and discarded. The filtrate was concentrated, diluted with ethyl acetate, washed with water and brine, dried (MgSO$_4$), filtered, concentrated and triturated with diethyl ether to give the product.

Compound 52B 3-cyano-4-((tetrahydro-2H-pyran-4-yl)methylamino) benzenesulfonamide The title compound was prepared by substituting Compound 52A for 4-chloro-3-nitrobenzenesulfonamide and (tetrahydro-2H-pyran-4-yl)methanamine for 4-methylpiperazin-1-amine dihydrochloride in the procedure for Compound 6A.

Compound 52C 3-chloro-5-cyano-4-((tetrahydro-2H-pyran-4-yl) methylamino)benzenesulfonamide Compound 52B (0.148 g) in acetonitrile (5 ml) was treated with N-chlorosuccinimide (0.080 g), heated at 60° C. for 3 hours and filtered to remove a small amount of solid. The filtrate was concentrated and chromatographed on silica gel with 3-15% ethyl acetate in dichloromethane as eluent. The obtained solid was slurried in water, filtered, rinsed with additional water and dried under vacuum to give the product.

Compound 52D

N-({3-chloro-5-cyano-4-[(tetrahydro-2H-pyran-4-ylmethyl)amino]phenyl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting Compound 52C for Compound 11B in the procedure for Compound 11D. $^1$H NMR (300 MHz, dimethylsulfoxide-d$_6$) δ11.70 (s, 1H), 11.41 (br s, 1H), 8.07 (d, 1H), 7.89 (s, 2H), 7.61 (m, 1H), 7.53 (m, 2H), 7.35 (d, 2H), 7.18 (m, 1H), 7.05 (d, 2H), 6.69 (m, 1H), 6.42 (dd, 1H), 6.18 (dd, 1H), 3.83 (m, 2H), 3.55 (t, 2H), 3.23 (m, 3H), 3.06 (m, 4H), 2.15 (m, 4H), 1.92 (m, 4H), 1.60 (m, 2H), 1.40 (m, 2H), 1.19 (m, 4H), 0.93 (s, 6H).

Compound 53

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 53A N-[(4-chloro-3-nitrophenyl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting Compound 3J for Compound 1E and 4-chloro-3-nitrobenzenesulfonamide for Compound 1F in the procedure for Compound 1G.

Compound 53B

N-({4-[(1-acetylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide A 5 ml round-bottomed flask was charged with Compound 53A (120 mg), 1-acetylpiperidin-4-amine (28 mg), and triethylamine (0.064 ml) in dioxane (2 ml). The reaction mixture was heated to 90° C. for 24 hours. The reaction mixture was cooled to room temperature, and added to a silica gel column and purified by eluting with 0-5% methanol in dichloromethane. $^1$H NMR (300 MHz, dimethylsulfoxide-d$_6$) δ 11.66 (br s, 1H), 8.65 (d, 1H), 8.24 (d, 1H), 8.03 (d, 1H), 7.83 (dd, 1H), 7.54-7.46 (m, 3H), 7.35 (d, 2H), 7.19 (d, 1H), 7.04 (d, 2H), 6.68 (dd, 1H), 6.39 (m, 1H), 6.20 (d, 1H), 4.28 (d, 1H), 3.97-3.75 (m, 2H), 3.07 (br s, 4H), 2.87-2.70 (m, 4H), 2.29-2.10 (m, 6H), 2.02 (s, 3H), 2.00-1.89 (m, 4H), 1.66-1.54 (m, 2H), 1.39 (t, 2H), 0.92 (s, 6H).

Compound 54

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide Compound 54A 2-chloro-5-fluoro-4-((tetrahydro-2H-pyran-4-yl) methylamino)benzenesulfonamide The title compound was prepared by substituting 2-chloro-4,5-difluorobenzenesulfonamide for 4-chloro-3-nitrobenzenesulfonamide and (tetrahydro-2H-pyran-4-yl) methanamine for 4-methylpiperazin-1-amine dihydrochloride in the procedure for Compound 6A.

Compound 54

N-({2-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting Compound 54A for Compound 11B in the procedure for Compound 11D. $^1$H NMR (500 MHz, dimethylsulfoxide-d$_6$) δ 11.76 (s, 1H), 11.31 (s, 1H), 8.08 (d, 1H), 7.69 (d, 1H), 7.60 (d, 1H), 7.55 (m, 2H), 7.34 (d, 2H), 7.04 (d, 2H), 6.90 (s, 1H), 6.84 (d, 1H), 6.69 (dd, 1H), 6.45 (dd, 1H), 6.13 (d, 1H), 3.82 (dd, 2H), 3.24 (t, 2H), 3.05 (m, 6H), 2.73 (s, 2H), 2.14 (m, 6H), 1.95 (s, 2H), 1.81 (m, 1H), 1.61 (m, 2H), 1.38 (t, 2H), 1.17 (m, 2H), 0.92 (s, 6H).

Compound 55

4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)-2-(1H-pyrrolo[2,3-b]pyridin-5-yloxy)benzamide The title compound was prepared by substituting Compound 3J for Compound 1E and Compound 2A for Compound 1F in the procedure for Compound 1G. $^1$H NMR (300 MHz, dimethylsulfoxide-$d_6$) δ 11.66 (br s, 1H), 8.75 (t, 1H), 8.54 (d, 1H), 8.03 (d, 1H), 7.79 (dd, 1H), 7.54-7.48 (m, 3H), 7.35 (d, 2H), 7.08-7.02 (m, 3H), 6.67 (dd, 1H), 6.38 (m, 1H), 6.20 (d, 1H), 3.61 (t, 4H), 3.43 (q, 2H), 3.29 (m, 2H), 3.06 (br s, 4H), 2.73 (br s, 2H), 2.47 (br s, 4H), 2.18 (m, 6H), 1.95 (br s, 2H), 1.80 (m, 2H), 1.38 (t, 2H), 0.92 (s, 6H).

Compound 56

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide Compound 56A 5-bromo-6-((4-fluorotetrahydro-2H-pyran-4-yl)methoxy)pyridine-3-sulfonamide The title compound was prepared by substituting Compound 37C for tetrahydro-2H-pyran-4-yl)methanol and Compound 36A for 4-fluoro-3-nitrobenzenesulfonamide in the procedure for Compound 24A.

Compound 56B 5-cyano-6-((4-fluorotetrahydro-2H-pyran-4-yl)methoxy)pyridine-3-sulfonamide The title compound was prepared by substituting Compound 56A for Compound 36B in the procedure for Compound 36C.

Compound 56C 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting Compound 56B for Compound 11B in the procedure for Compound 11D. $^1$H NMR (500 MHz, dimethylsulfoxide-$d_6$) δ 11.58 (s, 1H), 8.70 (s, 1H), 8.51 (s, 1H), 7.96 (d, 1H), 7.57 (d, 1H), 7.45 (t, 1H), 7.35-7.37 (m, 3H), 7.06 (d, 2H), 6.67 (dd, 1H), 6.33 (d, 1H), 6.26 (s, 1H), 4.56 (d, 2H), 3.76-3.80 (s, 2H), 3.56-3.62 (m, 2H), 3.01-3.10 (m, 4H), 2.14-2.18 (m, 2H), 1.96 (s, 2H), 1.80-1.87 (m, 4H), 1.41 (t, 2H), 0.93 (s, 6H).

Compound 57

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide Compound 57A 5-bromo-6-(2-morpholinoethoxy)pyridine-3-sulfonamide The title compound was prepared by substituting 2-morpholinoethanol for tetrahydro-2H-pyran-4-yl)methanol and Compound 36A for 4-fluoro-3-nitrobenzenesulfonamide in the procedure for Compound 24A.

Compound 57B 5-cyano-6-(2-morpholinoethoxy)pyridine-3-sulfonamide

The title compound was prepared by substituting Compound 57A for Compound 36A in the procedure for Compound 36B.

Compound 57C 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-(1H-pyrrolo[2,3-b]pyridin-5-yloxy)benzamide The title compound was prepared by substituting Compound 57B for Compound 11B in the procedure for Compound 11D. $^1$H NMR (500 MHz, dimethylsulfoxide-$d_6$) δ 11.56 (s, 1H), 8.64 (s, 1H), 8.41 (s, 1H), 7.92 (d, 1H), 7.58 (d, 1H), 7.44 (t, 1H), 7.36 (d, 2H), 7.31 (s, 1H), 7.06 (d, 2H), 6.65 (dd, 1H), 6.31 (d, 1H), 6.27 (d, 1H), 4.59 (t, 2H), 3.59 (s, 4H), 3.08 (s, 4H), 2.89 (s, 2H), 2.65 (s, 4H), 2.16-2.18 (m, 2H), 1.97 (s, 2H), 1.41 (t, 2H), 0.93 (s, 6H).

Compound 58

N-[(3-chloro-4-{[2-(2-methoxyethoxy)ethyl]sulfonyl}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 58A 3-chloro-4-(2-(2-methoxyethoxy)ethylthio)benzenesulfonamide In a 25 ml microwave tube was added sodium hydride (0.6 g) in tetrahydrofuran (10 ml) to give a suspension. 2-(2-Methoxyethoxy)ethanethiol (1 g) was added slowly. After stirring for 30 minutes, 3-chloro-4-fluorobenzenesulfonamide (1.54 g) dissolved in 10 ml tetrahydrofuran was added slowly. The mixture was heated at 110° C. for 30 minutes in a Biotage Initiator microwave reactor. Water was added, the product was extracted with ether (20 ml×3), dried over $Na_2SO_4$, filtered, and the solvent was removed under reduced pressure. The crude product was purified by flash chromatography on silica eluting with 0-25% ethyl acetate in hexane.

Compound 58B 3-chloro-4-(2-(2-methoxyethoxy)ethylsulfonyl)benzenesulfonamide

Compound 58A (0.15 g) was suspended in acetic acid (3 ml). Peracetic acid (0.4 ml) was added slowly. The mixture was stirred at room temperature overnight, then poured into $Na_2S_2O_3$ solution, and the product precipitated. After filtration and washing with water, the product was dried under vacuum.

Compound 58C

N-[(3-chloro-4-{[2-(2-methoxyethoxy)ethyl]
sulfonyl}phenyl)sulfonyl]-4-(4-{[2-(4-chlorophe-
nyl)-4,4-dimethylcyclohex-1-en-1-yl]
methyl}piperazin-1-yl)-2-(1H-pyrrolo[2,3-b]pyridin-
5-yloxy)benzamide The title compound was prepared by substituting Compound 58B for Compound 11B in the procedure for Compound 11D. $^1$H NMR (500 MHz, dimethylsulfoxide-$d_6$) δ 11.52 (s, 1H), 7.92 (d, 1H), 7.84 (m, 2H), 7.68 (m, 1H), 7.62 (d, 1H), 7.42 (t, 1H), 7.35 (d, 2H), 7.29 (m, 1H), 7.05 (d, 2H), 6.62 (dd, 1H), 6.32 (m, 1H), 6.26 (d, 1H), 3.74 (t, 2H), 3.68 (t, 2H), 3.24 (m, 2H), 3.06 (m, 5H), 3.01 (m, 4H), 2.74 (s, 2H), 2.19 (m, 6H), 1.96 (s, 2H), 1.39 (t, 2H), 0.93 (s, 6H).

Compound 59

4-(4-{[2-(4-chlorophenyl)-4,4-dimethylcyclohex-1-
en-1-yl]methyl}piperazin-1-yl)-N-[(4-{[2-(2-
methoxyethoxy)ethyl]sulfonyl}-3-nitrophenyl)sulfo-
nyl]-2-(1H-pyrrolo[2,3-b]pyridin-5-yloxy)
benzamide

Compound 59A 4-(2-(2-methoxyethoxy)ethylthio)-3-nitrobenzene-
sulfonamide

The title compound was prepared by substituting 4-fluoro-3-nitrobenzenesulfonamide for 3-chloro-4-fluorobenzenesulfonamide in the procedure for Compound 58A.

Compound 59B 4-(2-(2-methoxyethoxy)ethylsulfonyl)-3-nitrobenze-
nesulfonamide The title compound was prepared by substituting Compound 59A for Compound 58A in the procedure for Compound 58B.

Compound 59C 4-(4-{[2-(4-chlorophenyl)-4,4-dimethylcyclohex-1-
en-1-yl]methyl}piperazin-1-yl)-N-[(4-{[2-(2-
methoxyethoxy)ethyl]sulfonyl}-3-nitrophenyl)sulfo-
nyl]-2-(1H-pyrrolo[2,3-b]pyridin-5-yloxy)
benzamide The title compound was prepared by substituting Compound 59B for Compound 11B in the procedure for Compound 11D. $^1$H NMR (500 MHz, dimethylsulfoxide-$d_6$) δ 11.51 (s, 1H), 8.17 (m, 1H), 7.94 (m, 3H), 7.64 (d, 1H), 7.42 (m, 1H), 7.35 (d, 2H), 7.28 (d, 1H), 7.05 (d, 2H), 6.62 (m, 1H), 6.28 (m, 2H), 3.83 (m, 4H), 3.16 (m, 2H), 3.08 (s, 3H), 3.01 (m, 4H), 2.73 (s, 2H), 2.18 (m, 6H), 1.96 (m, 4H), 1.39 (t, 2H), 0.93 (s, 6H)

Compound 60 trans-4-(4-{[2-(4-chlorophenyl)-4,4-dimethylcyclo-
hex-1-en-1-yl]methyl}piperazin-1-yl)-N-({4-[(4-
morpholin-4-ylcyclohexyl)oxy]-3-
nitrophenyl}sulfonyl)-2-(1H-pyrrolo[2,3-b]pyridin-
5-yloxy)benzamide

Compound 60A trans-4-(4-aminocyclohexyloxy)-3-nitrobenzene-
sulfonamide

To a solution of tert-butyl 4-hydroxycyclohexylcarbamate (0.250 g) in tetrahydrofuran (5 ml) was added sodium hydride (0.186 g). After stirring for 15 minutes, 4-fluoro-3-nitrobenzenesulfonamide (0.256 g) was added as a solution in tetrahydrofuran (1 ml). The reaction was heated to 60° C. for 1.5 hours, cooled, and poured into a mixture of dichloromethane (100 ml) and water (25 ml). The aqueous layer was adjusted to pH-4 with 1N aqueous HCl and the organic layer was separated, washed with brine (50 ml), dried over magnesium sulfate, filtered, and concentrated. The residue was loaded onto silica gel (GraceResolv 40 g) and eluted using a gradient of 0.5% to 7.5% methanol/dichloromethane over 30 minutes. This solid was treated with HCl (4.0M in dioxane, 5 ml) at room temperature for 1 hour and concentrated to give the title compound.

Compound 60B 4-(trans-4-morpholinocyclohexyloxy)-3-nitrobenze-
nesulfonamide To Compound 60A (0.220 g) and 1-bromo-2-(2-bromoethoxy)ethane (0.177 g) in N,N-dimethylformamide (3 ml) was added triethylamine (0.338 ml) and the reaction heated to 70° C. for 5 hours. The reaction was cooled and the resulting precipitate was removed by filtration. The reaction was concentrated and loaded onto silica gel and was eluted using a gradient of 0.5% to 7.5% methanol/dichloromethane to give the title compound.

Compound 60C trans-4-(4-{[2-(4-chlorophenyl)-4,4-dimethylcyclo-
hex-1-en-1-yl]methyl}piperazin-1-yl)-N-({4-[(4-
morpholin-4-ylcyclohexyl)oxy]-3-
nitrophenyl}sulfonyl)-2-(1H-pyrrolo[2,3-b]pyridin-
5-yloxy)benzamide The title compound was prepared by substituting Compound 60B for Compound 1F and Compound 3J for Compound 1E in the procedure for Compound 1G. $^1$H NMR (300 MHz, dimethylsulfoxide-$d_6$) δ 11.62 (s, 1H), 8.23 (s, 1H), 7.99 (s, 1H), 7.96-7.88 (m, 1H), 7.54 (d, 1H), 7.48 (s, 2H), 7.34 (d, 3H), 7.04 (d, 2H), 6.72-6.58 (m, 1H), 6.37 (s, 1H), 6.21 (s, 1H), 4.69-4.47 (m, 1H), 3.66 (s, 4H), 3.05 (s, 4H), 2.76 (s, 6H), 2.22 (s, 9H), 1.96 (s, 4H), 1.39 (s, 6H), 0.92 (s, 6H).

Compound 61

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 61A 5-bromo-6-(1-(tetrahydro-2H-pyran-4-yl)piperidin-4-ylamino)pyridine-3-sulfonamide A mixture of Compound 36A (1.0 g), Compound 3L (0.95 g) and triethylamine (3.08 ml) in anhydrous dioxane (20 ml) was heated at 110° C. overnight. The organic solvent was removed under vacuum. The residue was purified with flash column chromatography on silica gel eluting with 2%-8% methanol/dichloromethane to give the title compound.

Compound 61B

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 61A for Compound 11B in the procedure for Compound 11D. $^1$H NMR (400 MHz, dimethylsulfoxide-$d_6$) δ 11.59 (s, 1H), 8.35 (s, 1H), 8.00 (s, 2H), 7.55 (d, 1H), 7.46 (m, 2H), 7.34 (d, 2H), 7.04 (d, 2H), 6.63 (dd, 1H), 6.49 (m, 1H), 6.36 (s, 1H), 6.20 (s, 1H), 4.05 (m, 1H), 3.94 (d, 2H), 3.28 (m, 6H), 3.01 (s, 4H), 2.72 (s, 2H), 2.16 (m, 6H), 1.93 (m, 4H), 1.80 (m, 4H), 1.57 (m, 2H), 1.38 (t, 2H), 1.17 (t, 2H), 0.90 (s, 6H).

Compound 62

4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl-2-(1H-pyrrolo[2,3-b]pyridin-5-yloxy)benzamide

Compound 62A 4-(2-cyanoethylamino)-3-nitrobenzenesulfonamide

The title compound was prepared by substituting 3-aminopropanenitrile for Compound 39B in the procedure for Compound 39C.

Compound 62B 4-(4-{[2-(4-chlorophenyl)-4,4-dimethylcyclohex-1-en-1-yl]methyl}piperazin-1-yl)-N-({4-[(2-cyanoethyl)amino]-3-nitrophenyl}sulfonyl)-2-(1H-pyrrolo[2,3-b]pyridin-5-yloxy)benzamide The title compound was prepared by substituting Compound 62A for Compound 11B in the procedure for Compound 11D. $^1$H NMR (501 MHz, pyridine-$d_5$) δ 13.04 (s, 1H), 9.24 (d, 1H), 9.04 (t, 1H), 8.43 (d, 1H), 8.38 (dd, 1H), 8.13 (d, 1H), 7.64-7.68 (m, 2H), 7.44 (ddd, 2H), 7.07 (ddd, 2H), 7.02 (d, 1H), 6.76 (dd, 1H), 6.55 (d, 1H), 6.48 (dd, 1H), 3.83 (q, 2H), 3.07 (d, 4H), 2.98 (t, 2H), 2.77 (s, 2H), 2.26 (s, 2H), 2.11-2.17 (m, 4H), 1.97 (s, 2H), 1.39 (t, 2H), 0.93 (s, 6H).

Compound 63 cis-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared by substituting Compound 15H for Compound 3J and Compound 39C for Compound 11B in the procedure for Compound 11D. $^1$H NMR (501 MHz, pyridine-$d_5$) δ 13.09 (s, 1H), 9.30 (d, 1H), 8.64 (d, 1H), 8.43 (d, 1H), 8.38 (dd, 1H), 8.10 (d, 1H), 7.68 (dt, 2H), 7.46 (ddd, 2H), 7.12 (ddd, 2H), 6.91 (d, 1H), 6.72 (dd, 1H), 6.51 (dd, 1H), 6.49 (d, 1H), 5.69 (s, 2H), 4.40 (s, 2H), 3.69-3.73 (m, 4H), 3.68 (s, 1H), 2.95-3.02 (m, 4H), 2.84 (s, 2H), 2.40-2.46 (m, 4H), 2.21 (s, 2H), 2.08-2.15 (m, 5H), 1.76-1.84 (m, 2H), 1.55-1.63 (m, 6H), 1.29 (s, 6H).

Compound 64 trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 64A tert-butyl (trans)-4-(bis(cyclopropylmethyl)amino)cyclohexylcarbamate The title compound was prepared by substituting cyclopropanecarbaldehyde for 4'-chlorobiphenyl-2-carboxaldehyde and tert-butyl (trans)-4-aminocyclohexylcarbamate for tert-butyl piperazine-1-carboxylate in the procedure for Compound 1A.

Compound 64B (trans)-$N^1$,$N^1$-bis(cyclopropylmethyl)cyclohexane-1,4-diamine dihydrochloride To a solution of Compound 64A (1.4 g) in dichloromethane (10 ml) was added hydrogen chloride (10 ml, 4M in dioxane) and the reaction was stirred for 16 hours at room temperature. The reaction mixture was diluted with ether and pure product was filtered off.

Compound 64C trans-4-(4-(bis(cyclopropylmethyl)amino)cyclohexylamino)-3-nitrobenzenesulfonamide The title compound was prepared by substituting Compound 64B for Compound 39B in the procedure for Compound 39C.

Compound 64D trans-N-{[4-({4-[bis(cyclopropylmethyl)amino]cyclohexyl}amino)-3-nitrophenyl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 64C for Compound 11B in the procedure for Compound 11D. $^1$H NMR (500 MHz, pyridine-d$_5$) δ 13.06 (s, 1H), 9.30 (d, 1H), 8.44 (d, 1H), 8.41 (dd, 1H), 8.37 (d, 1H), 8.12 (d, 1H), 7.67 (d, 2H), 7.44 (d, 2H), 7.07 (d, 2H), 7.00 (d, 1H), 6.75 (dd, 1H), 6.53 (d, 1H), 6.49 (dd, 1H), 3.36-3.43 (m, 1H), 3.02-3.09 (m, 4H), 2.87-2.94 (m, 1H), 2.77 (s, 2H), 2.47 (d, 4H), 2.25 (t, 2H), 2.11-2.16 (m, 4H), 2.08 (d, 2H), 1.97 (s, 2H), 1.84 (d, 2H), 1.39 (t, 2H), 1.26-1.35 (m, 4H), 0.90-0.98 (m, 8H), 0.50-0.56 (m, 4H), 0.18-0.23 (m, 4H).

Compound 65

4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide

Compound 65A 4-((1-methylpiperidin-4-yl)methylamino)-3-nitrobenzenesulfonamide The title compound was prepared by substituting 4-aminomethyl-1-methyl piperidine for (tetrahydropyran-4-yl)methylamine in the procedure for Compound 1F.

Compound 65B 4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]-2-(1H-pyrrolo[2,3-b]pyridin-5-yloxy)benzamide The title compound was prepared by substituting Compound 65A for Compound 130C in the procedure for Compound 130D. $^1$H NMR (500 MHz, dichloromethane-d$_2$) δ 9.57 (bs, 1H), 8.78 (d, 1H), 8.41 (d, 1H), 8.14 (d, 1H), 7.90 (m, 2H), 7.64 (d, 1H), 7.45 (d, 1H), 7.23 (d, 2H), 6.95 (d, 2H), 6.76 (d, 1H), 6.59 (dd, 1H), 6.51 (d, 1H), 6.09 (d, 1H), 3.21 (m, 2H), 3.08 (m, 4H), 3.02 (m, 2H), 2.74 (s, 2H), 2.33 (s, 3H), 2.21-2.17 (m, 6H), 2.16-2.02 (m, 3H), 1.97 (br.s, 2H), 1.78 (m, 4H), 1.41 (t, 2H), 0.94 (s, 6H).

Compound 66

4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide

Compound 66A tert-butyl 3-((2-nitro-4-sulfamoylphenylamino)methyl)morpholine-4-carboxylate The title compound was prepared by substituting tert-butyl 3-(aminomethyl)morpholine-4-carboxylate for (tetrahydropyran-4-yl)methylamine in the procedure for Compound 1F.

Compound 66B tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared by substituting Compound 66A for Compound 1F and Compound 3J for Compound 1E in the procedure for Compound 1F, with the exception that the product was purified on a silica gel column eluted with 4% methanol in dichloromethane.

Compound 66C 4-(4-{[2-(4-chlorophenyl)-4,4-dimethylcyclohex-1-en-1-yl]methyl}piperazin-1-yl)-N-({4-[(morpholin-3-ylmethyl)amino]-3-nitrophenyl}sulfonyl)-2-(1H-pyrrolo[2,3-b]pyridin-5-yloxy)benzamide A solution of Compound 66B in 50% trifluoroacetic acid and dichloromethane mixture was stirred at ambient temperature for 2 hours. The solvents were evaporated and the residue was purified on a reverse phase HPLC using a gradient of 20-80% acetonitrile in water containing 10 mM ammonium acetate. $^1$H NMR (500 MHz, dimethylsulfoxide-d$_6$) δ 11.61 (s, 1H), 8.52 (bs, 1H), 8.49 (d, 1H), 7.98 (d, 1H), 7.78 (d, 1H), 7.54 (d, 1H), 7.46 (s, 1H), 7.42 (s, 1H), 7.34 (d, 2H), 7.04 (m, 3H), 6.65 (dd, 1H), 6.34 (s, 1H), 6.21 (d, 1H), 3.89 (d, 1H), 3.76 (d, 1H), 3.55-3.46 (m, 2H), 3.40-3.35 (m, 4H), 3.04 (m, 4H), 2.91 (t, 1H), 2.73 (s, 2H), 2.20-2.12 (m, 6H), 1.95 (s, 2H), 1.38 (t, 2H), 0.92 (s, 6H).

Compound 67

4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 15H and Compound 6A, respectively. $^1$H NMR (300 MHz, dimethylsulfoxide-d$_6$) δ 11.58 (s, 1H), 9.04 (s, 1H), 8.44 (d, 1H), 7.97 (d, 1H), 7.76 (dd, 1H), 7.49 (m, 4H), 7.38 (d, 2H), 7.14 (d, 2H), 6.64 (dd, 1H), 6.34 (d, 1H), 6.21 (d, 1H), 4.12 (s, 2H), 3.03 (m, 6H), 2.85 (m, 5H), 2.29 (m, 4H), 2.18 (m, 6H), 1.20 (s, 6H).

Compound 68

4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy-]-3-nitrophenyl}sulfonyl)-2-(1H-pyrrolo[2,3-b]pyridin-5-yloxy)benzamide

Compound 68A 4-morpholinobut-2-yn-1-ol

To a solution of morpholine (4.36 g) in toluene (15 ml) was added 4-chlorobut-2-yn-1-ol (2.09 g) in toluene (5 ml). The solution was stirred at 85° C. for 3 hours. After cooling, the solid was filtered off. The filtrate was subjected to vacuum distillation to give the pure title compound.

Compound 68B 4-(4-morpholinobut-2-ynyloxy)-3-nitrobenzene-sulfonamide

The title compound was prepared by substituting Compound 68A for (tetrahydro-2H-pyran-4-yl)methanol in the procedure for Compound 24A.

Compound 68C 4-(4-{[2-(4-chlorophenyl)-4,4-dimethylcyclohex-1-en-1-yl]methyl}piperazin-1-yl)-N-({4-[(4-morpholin-4-ylbut-2-ynyl)oxy]-3-nitrophenyl}sulfonyl)-2-(1H-pyrrolo[2,3-b]pyridin-5-yloxy)benzamide The title compound was prepared by substituting Compound 68B for Compound 11B in the procedure for Compound 11D. $^1$H NMR (500 MHz, dimethylsulfoxide-$d_6$) δ 11.68 (s, 1H), 8.36 (s, 1H), 8.08 (d, 1H), 8.03 (d, 1H), 7.47-7.53 (m, 4H), 7.35 (d, 2H), 7.04 (d, 2H), 6.67 (dd, 1H), 6.40 (dd, 1H), 6.20 (d, 1H), 5.15 (s, 2H), 3.52-3.55 (m, 4H), 3.09 (s, 4H), 2.84 (br s, 2H), 2.23-2.40 (m, 6H), 2.12-2.18 (m, 2H), 1.96 (s, 2H), 1.39 (t, 2H), 0.92 (s, 6H).

Compound 69

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide Compound 69A 6-((tetrahydro-2H-pyran-4-yl)methoxy)-5-((triisopropylsilyl)ethynyl)pyridine-3-sulfonamide Compound 36B (0.176 g), bis(triphenylphosphine)palladium(II) chloride (0.176 g), copper(I) iodide (0.010 g), N,N-dimethylacetamide (2.5 ml) and triethylamine (0.105 ml) were combined, flushed with nitrogen and stirred for 2 minutes. (Triisopropylsilyl)acetylene (0.135 ml) was added and the reaction mixture was flushed with nitrogen again, heated at 60° C. overnight, diluted with ethyl acetate, washed with water and brine, dried (MgSO$_4$), filtered, concentrated and chromatographed on silica gel with 10-30% ethyl acetate in hexanes as the eluent to give the product.

Compound 69B 5-ethynyl-6-((tetrahydro-2H-pyran-4-yl)methoxy)pyridine-3-sulfonamide Compound 69A (0.205 g) in tetrahydrofuran (3 ml) at ambient temperature was treated with tetrabutyl ammonium fluoride (1 M in tetrahydrofuran, 0.906 ml) and stirred at ambient temperature for 4 hours. Additional tetrabutyl ammonium fluoride (1 M in tetrahydrofuran, 1.8 ml) was added and the mixture was heated at 40° C. for 45 minutes. Solid tetrabutyl ammonium fluoride (0.253 g) was added and heating was continued for 30 minutes. The reaction mixture was concentrated and then chromatographed on silica gel using 0-2% methanol in dichloromethane as the eluent to give the product.

Compound 69C 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 69B for Compound 11B in the procedure for Compound 11D. $^1$H NMR (300 MHz, dimethylsulfoxide-$d_6$) δ 11.69 (s, 1H), 11.41 (s, 1H), 8.58 (d, 1H), 8.19 (d, 1H), 8.05 (d, 1H), 7.53 (m, 3H), 7.35 (d, 2H), 7.04 (d, 2H), 6.67 (dd, 1H), 6.41 (dd, 1H), 6.18 (d, 1H), 4.56 (s, 1H), 4.24 (d, 2H), 3.87 (dd, 2H), 3.38 (m, 3H), 3.07 (m, 4H), 2.86 (m, 2H), 2.29 (m, 5H), 2.04 (m, 3H), 1.64 (dd, 2H), 1.34 (m, 4H), 0.93 (s, 6H).

Compound 70

4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide Compound 70A 4-amino-3-cyanobenzenesulfonamide 3-Cyano-4-fluorobenzene-1-sulfonyl chloride (1.1 g) was dissolved in dioxane (4 ml). The solution was cooled to 0° C. and 7 ml of an ammonia (7N in methanol) solution was added. After the addition was complete, the ice bath was removed and the reaction was stirred at room temperature for 24 hours. After concentration of the reaction mixture, the crude material was purified by flash chromatography eluting with a gradient of 30-100% ethyl acetate/hexanes.

Compound 70B 2-(1H-pyrrolo[2,3-b]pyridin-5-yloxy)-N-(4-amino-3-cyanophenylsulfonyl)-4-(4-((2-(4-chlorophenyl)-4,4-dimethylcyclohex-1-enyl)methyl)piperazin-1-yl)benzamide The title compound was prepared by substituting Compound 70A for Compound 1F and Compound 3J for Compound 1E in the procedure for Compound 1G.

Compound 70C 2-(1H-pyrrolo[2,3-b]pyridin-5-yloxy)-N-(4-amino-3-carbamoylphenylsulfonyl)-4-(4-((2-(4-chlorophenyl)-4,4-dimethylcyclohex-1-enyl)methyl)piperazin-1-yl)benzamide To a solution of Compound 70B (90 mg) in ethanol (2 ml) was added tetrahydrofuran (2 ml), hydrogen peroxide (30%, 1 ml) and 1M sodium hydroxide solution (0.48 ml), followed by an additional 2 ml of tetrahydrofuran. The reaction was heated to 45° C. for 30 minutes, cooled, and then quenched with 5% HCl solution and extracted twice with dichloromethane. The extracts were combined and concentrated to obtain the product.

Compound 70D 4-(4-{[2-(4-chlorophenyl)-4,4-dimethylcyclohex-1-en-1-yl]methyl}piperazin-1-yl)-N-[(4-oxo-3,4-dihydroquinazolin-6-yl)sulfonyl]-2-(1H-pyrrolo[2,3-b]pyridin-5-yloxy)benzamide Compound 70C (80 mg) was combined with trimethyl orthoformate (2.3 ml) and trifluoroacetic acid (0.03 ml) and the resulting solution was stirred at room temperature for 4 hours. The mixture was purified by flash chromatography, eluting with a gradient of 3-10% methanol/dichloromethane. $^1$H NMR (300 MHz, dimethylsulfoxide-$d_6$) δ 12.61 (s, 1H), 11.71 (s, 1H), 8.65 (d, 1H), 8.24 (s, 1H), 8.17 (dd, 1H), 8.04 (m, 1H), 7.73 (d, 1H), 7.57 (d, 1H), 7.51 (m, 2H), 7.39 (d, 2H), 7.07 (d, 2H), 6.70 (dd, 1H), 6.40 (m, 1H), 6.24 (br s, 1H), 3.61 (m, 6H), 3.03 (m, 2H), 2.75 (m, 2H), 2.17 (m, 2H), 2.01 (m, 2H), 1.44 (m, 2H), 0.94 (s, 6H).

Compound 71 trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide

Compound 71A 8-chlorospiro[4.5]dec-7-ene-7-carbaldehyde

To a solution of N,N-dimethylformamide (2.81 ml) in dichloromethane (40 ml) was added dropwise POCl$_3$ (2.78 ml) at 0° C. The reaction mixture was warmed up to room temperature and spiro[4.5]decan-8-one (3.95 g) in dichloromethane (5 ml) was added dropwise. The mixture was stirred overnight. The reaction was quenched with cold aqueous sodium acetate and the resulting mixture was extracted with ether and the organic layer was dried over Na$_2$SO$_4$, filtered, and concentrated to provide the title compound.

Compound 71B 8-(4-chlorophenyl)spiro[4.5]dec-7-ene-7-carbaldehyde

To a suspension of Compound 71A (3 g) in water (50 ml) was added 4-chlorophenylboronic acid (2.83 g), tetrabutylammonium (4.87 g), potassium carbonate (6.26 g) and palladium(II) acetate (0.169 g). The reaction mixture was stirred at 45° C. for 5 hours and extracted with dichloromethane. The organic layer was concentrated and the residue was loaded onto a silica gel column, and eluted with 5-20% ethyl acetate in hexane to give the title compound.

Compound 71C methyl 2-(1H-pyrrolo[2,3-b]pyridin-5-yloxy)-4-(4-((8-(4-chlorophenyl)spiro[4.5]dec-7-en-7-yl)methyl)piperazin-1-yl)benzoate To a solution of Compound 71B (274 mg) in dichloroethane (3.5 ml) was added Compound 15F (387 mg) and sodium triacetoxyborohydride (317 mg). The reaction mixture was stirred overnight. Sodium cyanoborohydride (37.6 mg) was added and the resulting mixture stirred overnight. The reaction was quenched with water and diluted with dichloromethane. The mixture was washed with water extensively and the organic layer was dried over Na$_2$SO$_4$, filtered, and concentrated to provide the title compound.

Compound 71D 2-(1H-pyrrolo[2,3-b]pyridin-5-yloxy)-4-(4-((8-(4-chlorophenyl)spiro[4.5]dec-7-en-7-yl)methyl)piperazin-1-yl)benzoic Acid The title compound was prepared as described in the procedure for Compound 3J using Compound 71C in place of Compound 3I.

Compound 71E trans-4-(4-{[8-(4-chlorophenyl)spiro[4.5]dec-7-en-7-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide The title compound was prepared as described in the procedure for Compound 11D using Compound 71D and Compound 9C in place of Compound 3J and Compound 11B, respectively. $^1$H NMR (500 MHz, dimethylsulfoxide-$d_6$) δ 11.64 (s, 1H), 8.51 (s, 1H), 8.15 (d, 1H), 8.01 (d, 1H), 7.76 (d, 1H), 7.44-7.53 (m, 3H), 7.34 (d, 2H), 7.07 (d, 3H), 6.66 (dd, 1H), 6.37 (dd, 1H), 6.20 (d, 1H), 3.50-3.70 (m, 5H), 3.04 (s, 4H), 2.55-2.76 (m, 5H), 2.34-2.39 (m, 1H), 2.20 (d, 6H), 2.03 (s, 4H), 1.91 (s, 2H), 1.61 (q, 4H), 1.51 (t, 2H), 1.36-1.46 (m, 8H).

Compound 72 cis-4-(4-{[4-(4-chlorophenyl)-6,6-dimethyl-5,6-dihydro-2H-pyran-3-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 15H and 29A in place of Compound 3J and Compound 11B, respectively. $^1$H NMR (500 MHz, dimethylsulfoxide-$d_6$) δ 11.69 (s, 1H), 11.45 (s, 1H), 8.59 (t, 1H), 8.56 (d, 1H), 8.04 (d, 1H), 7.79 (dd, 1H), 7.54 (d, 1H), 7.47-7.52 (m, 2H), 7.37 (d, 2H), 7.13 (d, 2H), 7.08 (d, 1H), 6.68 (dd, 1H), 6.35-6.42 (m, 1H), 6.19 (d, 1H), 4.11 (s, 2H), 3.37 (s, 1H), 3.26 (t, 2H), 3.20 (s, 3H), 3.07 (s, 4H), 2.83 (s, 2H), 2.17 (d, 6H), 1.81 (dd, 2H), 1.64-1.73 (m, 1H), 1.48 (dd, 2H), 1.23-1.41 (m, 4H), 1.18 (s, 6H).

Compound 73

4-(4-{[8-(4-chlorophenyl)spiro[4.5]dec-7-en-7-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in the procedure for Compound 11D using Compound 71D and Compound 37D in place of Compound 3J and Compound 11B, respectively. $^1$H NMR (500 MHz, dimethylsulfoxide-d₆) δ 11.68 (s, 1H), 8.37 (s, 1H), 7.98-8.11 (m, 2H), 4.38 (d, 2H), 3.74-3.82 (m, 2H), 3.54-3.64 (m, 2H), 3.44 (s, 1H), 3.08 (s, 3H), 2.58-2.89 (m, 2H), 2.13-2.35 (m, 4H), 2.04 (s, 2H), 1.78-1.93 (m, 4H), 1.57-1.65 (m, 4H), 1.52 (t, 2H), 1.36-1.47 (m, 4H).

Compound 74 trans-4-(4-{[8-(4-chlorophenyl)spiro[4.5]dec-7-en-7-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 71D and Compound 34B in place of Compound 3J and Compound 11B, respectively. ¹H NMR (500 MHz, dimethylsulfoxide-d₆) δ 11.69 (s, 1H), 11.39 (s, 1H), 8.58 (t, 1H), 8.56 (d, 1H), 8.04 (d, 1H), 7.79 (dd, 1H), 7.47-7.55 (m, 3H), 7.34 (d, 2H), 7.07 (d, 3H), 6.68 (dd, 1H), 6.39 (dd, 1H), 6.19 (d, 1H), 3.25 (t, 2H), 3.22 (s, 3H), 3.06 (s, 5H), 2.71 (s, 2H), 2.21 (s, 6H), 1.94-2.06 (m, 4H), 1.79 (d, 2H), 1.57-1.65 (m, 5H), 1.51 (t, 2H), 1.39 (t, 4H), 0.95-1.11 (m, 4H).

Compound 75

4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 75A methyl 5,5-dimethyl-2-(trifluoromethylsulfonyloxy)cyclohex-1-enecarboxylate The title compound was prepared by substituting 4,4-dimethyl-2-methoxycarbonylcyclohexanone for 5,5-dimethyl-2-methoxycarbonylcyclohexanone in the procedure for Compound 3A.

Compound 75B methyl 2-(4-chlorophenyl)-5,5-dimethylcyclohex-1-enecarboxylate The title compound was prepared by substituting Compound 75A for Compound 3A in the procedure for Compound 3B.

Compound 75C (2-(4-chlorophenyl)-5,5-dimethylcyclohex-1-enyl)methanol

The title compound was prepared by substituting Compound 75B for Compound 3B in the procedure for Compound 3C.

Compound 75D 2-(4-chlorophenyl)-5,5-dimethylcyclohex-1-enecarbaldehyde

To a solution of Compound 75C (2.8 g) in dichloromethane (50 ml) was added Dess-Martin Periodinane (5.68 g). The reaction mixture was stirred at room temperature for 3 hours and diluted with ether and washed with 5% NaOH and brine. The organic layer was dried over Na₂SO₄, filtered, and concentrated. The residue was purified by flash chromatography using 20% ethyl acetate in hexanes to provide the title compound.

Compound 75E methyl 2-(1H-pyrrolo[2,3-b]pyridin-5-yloxy)-4-(4-((2-(4-chlorophenyl)-5,5-dimethylcyclohex-1-enyl)methyl)piperazin-1-yl)benzoate The title compound was prepared by replacing 4'-chlorobiphenyl-2-carboxaldehyde with Compound 75D and tert-butyl piperazine-1-carboxylate with Compound 15F in the procedure for Compound 1A.

Compound 75F 2-(1H-pyrrolo[2,3-b]pyridin-5-yloxy)-4-(4-((2-(4-chlorophenyl)-5,5-dimethylcyclohex-1-enyl)methyl)piperazin-1-yl)benzoic Acid The title compound was prepared as described in the procedure for Compound 15H by replacing Compound 15G with Compound 75E.

Compound 75G 4-(4-{[2-(4-chlorophenyl)-5,5-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in the procedure for Compound 11D using Compound 75F and Compound 1F in place of Compound 3J and Compound 11B, respectively. ¹H NMR (400 MHz, dimethylsulfoxide-d₆) δ 11.69 (s, 1H), 11.38 (s, 1H), 8.60 (t, 1H), 8.56 (d, 1H), 8.04 (d, 1H), 7.80 (dd, 1H), 7.47-7.55 (m, 3H), 7.31-7.36 (m, 2H), 7.05-7.13 (m, 3H), 6.68 (dd, 1H), 6.39 (dd, 1H), 6.18 (d, 1H), 3.85 (dd, 2H), 3.22-3.31 (m, 4H), 3.07 (s, 4H), 2.67-2.78 (m, 2H), 2.19 (s, 6H), 1.82-1.98 (m, 3H), 1.56-1.66 (m, 2H), 1.39 (t, 2H), 1.17-1.33 (m, 3H), 0.93 (s, 6H).

Compound 76

4-(4-{[2-(4-chlorophenyl)-5,5-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-(1H-pyrrolo[2,3-b]pyridin-5-yloxy)benzamide The title compound was prepared as described in the procedure for Compound 11D using Compound 75F and Compound 36C in place of Compound 3J and Compound 11B, respectively. ¹H NMR (400 MHz, dimethylsulfoxide-d₆) δ 11.62 (s, 1H), 8.73 (s, 1H), 8.52 (s, 1H), 7.98 (d, 1H), 7.56 (d, 1H), 7.45-7.51 (m, 1H), 7.43 (s, 1H), 7.37 (d, 2H), 7.10 (d, 2H), 6.68 (dd, 1H), 6.35 (dd, 1H), 6.25 (s, 1H), 4.29 (d, 2H), 3.88 (dd, 2H), 3.12 (d, 4H), 2.21 (s, 2H), 2.00-2.11 (m, 1H), 1.95 (s, 2H), 1.64 (dd, 2H), 1.27-1.46 (m, 4H), 0.95 (s, 6H)

Compound 77 tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate

Compound 77A tert-butyl 3-((2-nitro-4-sulfamoylphenoxy)methyl)morpholine-4-carboxylate The title compound was prepared as described in the procedure for Compound 12A by replacing (1,4-dioxan-2-yl)methanol with tert-butyl 3-(hydroxymethyl)morpholine-4-carboxylate.

Compound 77B tert-butyl 3-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}morpholine-4-carboxylate The title compound was prepared as described in the procedure for Compound 11D using Compound 77A in place of Compound 11B. $^1$H NMR (400 MHz, dimethylsulfoxide-$d_6$) δ 11.67 (s, 1H), 8.36 (s, 1H), 8.01-8.11 (m, 2H), 7.47-7.61 (m, 4H), 7.35 (d, 2H), 7.04 (d, 2H), 6.68 (dd, 1H), 6.39 (d, 1H), 6.20 (s, 1H), 4.41-4.52 (m, 2H), 4.15-4.28 (m, 1H), 3.59-3.95 (m, 3H), 3.51 (d, 1H), 3.34-3.43 (m, 1H), 3.10 (s, 5H), 2.84 (s, 2H), 2.28 (s, 4H), 2.15 (s, 2H), 1.96 (s, 2H), 1.20-1.45 (m, 12H), 0.92 (s, 6H).

Compound 78

4-(4-{[2-(4-chlorophenyl)-4,4-dimethylcyclohex-1-en-1-yl]methyl}piperazin-1-yl)-N-{[4-(morpholin-3-ylmethoxy)-3-nitrophenyl]sulfonyl}-2-(1H-pyrrolo[2,3-b]pyridin-5-yloxy)benzamide Compound 77B (100 mg) in dichloromethane (10 ml) at 0° C. was treated with trifluoroacetic acid (5 ml) for 20 minutes. The reaction mixture was concentrated. The residue was purified by reverse phase HPLC on a C18 column using a gradient of 35-60% acetonitrile in 0.1% trifluoroacetic acid water to give the title compound as a trifluoroacetate salt. The trifluoroacetic acid salt was dissolved in dichloromethane (10 mil) and washed with 50% aqueous NaHCO$_3$. The organic layer was dried over anhydrous Na$_2$SO$_4$ and concentrated to give the title compound. $^1$H NMR (400 MHz, dimethylsulfoxide-$d_6$) δ 11.56 (s, 1H), 8.23 (d, 1H), 7.94 (d, 1H), 7.90 (dd, 1H), 7.57 (d, 1H), 7.42-7.46 (m, 1H), 7.31-7.37 (m, 3H), 7.25 (d, 1H), 7.01-7.09 (m, 2H), 6.64 (dd, 1H), 6.29-6.37 (m, 1H), 6.24 (d, 1H), 4.17-4.31 (m, 2H), 3.90-4.05 (n, 1H), 3.77-3.85 (m, 1H), 3.45-3.59 (m, 4H), 2.94-3.13 (m, 6H), 2.76 (s, 2H), 2.18 (d, 6H), 1.96 (s, 2H), 1.39 (t, 2H), 0.93 (s, 6H).

Compound 79

4-(4-{[8-(4-chlorophenyl)spiro[4.5]dec-7-en-7-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared as described in the procedure for Compound 11D using Compound 71D and Compound 1F in place of Compound 3J and Compound 11B, respectively. $^1$H NMR (400 MHz, dimethylsulfoxide-$d_6$) δ 11.69 (s, 1H), 11.38 (s, 1H), 8.60 (t, 1H), 8.56 (d, 1H), 8.04 (d, 1H), 7.77-7.84 (m, 1H), 7.45-7.56 (m, 3H), 7.34 (d, 2H), 7.04-7.13 (m, 3H), 6.68 (dd, 1H), 6.39 (d, 1H), 6.19 (d, 1H), 3.85 (dd, 2H), 3.22-3.31 (m, 4H), 3.07 (s, 4H), 2.71 (s, 2H), 2.21 (s, 6H), 2.03 (s, 2H), 1.81-1.94 (m, 1H), 1.56-1.68 (m, 6H), 1.51 (t, 2H), 1.34-1.45 (m, 4H), 1.20-1.33 (m, 2H).

Compound 80

4-(4-{[2-(4-chlorophenyl)-4,4-dimethylcyclohex-1-en-1-yl]methyl}piperazin-1-yl)-N-[(4-{[1-(methylsulfonyl)piperidin-4-yl]amino}-3-nitrophenyl)sulfonyl]-2-(1H-pyrrolo[2,3-b]pyridin-5-yloxy)benzamide The title compound was prepared by substituting 1-(methylsulfonyl)piperidin-4-amine for 1-acetylpiperidin-4-amine in the procedure for Compound 53B. $^1$H NMR (300 MHz, dimethylsulfoxide-$d_6$) δ 11.67 (br s, 1H), 8.57 (d, 1H), 8.25 (d, 1H), 8.04 (d, 1H), 7.83 (dd, 1H), 7.54-7.46 (m, 3H), 7.35 (d, 2H), 7.17 (d, 1H), 7.04 (d, 2H), 6.68 (dd, 1H), 6.39 (m, 1H), 6.20 (d, 1H), 3.80 (m, 1H), 3.57 (m, 2H), 3.08 (br s, 4H), 2.95 (td, 2H), 2.92 (s, 3H), 2.85-2.72 (m, 2H), 2.30-2.10 (m, 6H), 2.07-1.93 (m, 4H), 1.70 (m, 2H), 1.39 (t, 2H), 0.93 (s, 6H).

Compound 81

4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide

Compound 81A 1,1-dioxotetrahydro-2H-thiopyran-4-amine

N-Benzyl-1,1-dioxotetrahydro-2H-thiopyran-4-amine (2.00 g) was added to ethanol (40 ml) in a pressure bottle. Palladium hydroxide on carbon (0.587 g) was added and the solution was stirred under 30 psi of hydrogen at room temperature for 2 hours. The mixture was filtered though a nylon membrane and the solvent was removed under vacuum.

Compound 81B 4-(4-{[2-(4-chlorophenyl)-4,4-dimethylcyclohex-1-en-1-yl]methyl}piperazin-1-yl)-N-({4-[(1,1-dioxidotetrahydro-2H-thiopyran-4-yl)amino]-3-nitrophenyl}sulfonyl)-2-(1H-pyrrolo[2,3-b]pyridin-5-yloxy)benzamide The title compound was prepared by substituting Compound 81A for 1-acetylpiperidin-4-amine in the procedure for Compound 53B. $^1$H NMR (300 MHz, dimethylsulfoxide-$d_6$) δ 11.65 (br s, 1H), 8.55 (d, 1H), 8.25 (d, 1H), 8.03 (d, 1H), 7.86 (dd, 1H), 7.52-7.47 (m, 3H), 7.35 (d, 2H), 7.17 (d, 1H), 7.04 (d, 2H), 6.68 (dd, 1H), 6.39 (m, 1H), 6.21 (d, 1H), 4.05 (m, 1H), 3.22-3.00 (m, 8H), 2.79 (br s, 2H), 2.31-2.11 (m, 10H), 1.96 (br s, 2H), 1.39 (t, 2H), 0.93 (s, 6H).

Compound 82

N-[(4-chloro-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and 4-chloro-3-nitrobenzenesulfonamide for Compound 1F in the procedure for Compound 1G. $^1$H NMR (300 MHz, dimethylsulfoxide-$d_6$) δ 11.60 (br s, 1H), 8.38 (br s, 1H), 7.96 (d, 1H), 7.91 (d, 1H), 7.68 (d, 1H), 7.58 (d, 1H), 7.46 (t, 1H), 7.39-7.35 (m, 3H), 7.07 (d, 2H), 6.67 (dd, 1H), 6.34 (m, 1H), 6.28 (d, 1H), 3.31 (br s, 2H), 3.17 (br s, 8H), 2.18 (m, 2H), 1.98 (br s, 2H), 1.42 (t, 2H), 0.94 (s, 6H).

Compound 83

4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide

Compound 83A

3-Nitro-4-[1-(2,2,2-trifluoro-ethyl)-piperidin-4-ylamino]-benzenesulfonamide

The title compound was prepared by substituting 1-(2,2,2-trifluoroethyl)piperidin-4-amine hydrochloride for (tetrahydropyran-4-yl)methylamine in the procedure for Compound 6A.

Compound 83B 4-(4-{[2-(4-chlorophenyl)-4,4-dimethylcyclohex-1-en-1-yl]methyl}piperazin-1-yl)-N-[(3-nitro-4-{[1-(2,2,2-trifluoroethyl)piperidin-4-yl]amino}phenyl)sulfonyl]-2-(1H-pyrrolo[2,3-b]pyridin-5-yloxy)benzamide The title compound was prepared by substituting Compound 3J for Compound 1E and Compound 82A for Compound 1F in the procedure for Compound 1G. $^1$H NMR (300 MHz, dimethylsulfoxide-$d_6$) δ 11.66 (br s, 1H), 8.56 (d, 1H), 8.24 (d, 1H), 8.04 (d, 1H), 7.81 (dd, 1H), 7.52 (d, 2H), 7.48 (d, 1H), 7.35 (d, 2H), 7.15 (d, 1H), 7.04 (d, 2H), 6.68 (dd, 1H), 6.38 (m, 1H), 6.20 (d, 1H), 3.68 (m, 1H), 3.22 (q, 2H), 3.07 (br s, 4H), 2.90 (m, 2H), 2.75 (br s, 2H), 2.29-2.12 (m, 8H), 1.97-1.86 (m, 4H), 1.63 (m, 2H), 1.38 (t, 2H), 0.92 (s, 6H).

Compound 84

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy)benzamide

Compound 84A 1-(tetrahydro-2H-pyran-4-yl)piperidin-4-ol

Piperidin-4-ol (7.8 g) and dihydro-2H-pyran-4(3H)-one (5.0 g) were dissolved in titanium(IV) isopropoxide (30 ml) and the reaction was stirred at room temperature overnight. Methanol (40 ml) was added and the reaction was cooled to 0° C. Then NaBH$_4$ (3.8 g) was added in portions over one hour. After 2 hours 1N aqueous NaOH was added, followed by ethyl acetate addition. After filtration though celite the layers were separated, the aqueous layer extracted with ethyl acetate, and the combined organic layers were dried over Na$_2$SO$_4$. The crude was purified by column chromatography using dichloromethane having 5-10% 7N NH$_3$ in methanol.

Compound 84B 5-bromo-6-(1-(tetrahydro-2H-pyran-4-yl)piperidin-4-yloxy)pyridine-3-sulfonamide The title compound was prepared by substituting Compound 84A for (tetrahydro-2H-pyran-4-yl)methanol and Compound 36A for 4-fluoro-3-nitrobenzenesulfonamide in the procedure for Compound 24A.

Compound 84C 5-cyano-6-(1-(tetrahydro-2H-pyran-4-yl)piperidin-4-yloxy)pyridine-3-sulfonamide The title compound was prepared by substituting Compound 84B for Compound 36B in the procedure for Compound 36C.

Compound 84D 4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-(1H-pyrrolo[2,3-b]pyridin-5-yloxy)benzamide The title compound was prepared by substituting Compound 84C for Compound 11B in the procedure for Compound 11D. $^1$H NMR (500 MHz, dimethylsulfoxide-$d_6$) δ 11.50 (s, 1H), 8.60 (d, 1H), 8.37 (d, 1H), 7.90 (d, 1H), 7.60 (d, 1H), 7.42 (dd, 1H), 7.35 (d, 2H), 7.25 (d, 1H), 7.04 (d, 2H), 6.63 (dd, 1H), 6.28 (m, 1H), 6.24 (d, 1H), 5.30 (br s, 1H), 4.50 (d, 2H), 3.95 (dd, 2H), 3.30 (m, 5H), 3.02 (br s, 4H), 2.95 (br s, 2H), 2.24 (br s, 4H), 2.17 (br m, 4H), 1.96 (s, 2H), 1.90 (br m, 4H), 1.60 (br m, 2H), 1.39 (t, 2H), 0.93 (s, 6H).

Compound 85

4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide

Compound 85A 5-isopropyl-6-((tetrahydro-2H-pyran-4-yl)methoxy)pyridine-3-sulfonamide Compound 36B (0.176 g), 2-dicyclohexylphosphino-2',6'-dimethoxybiphenyl (0.041 g), and palladium(II) acetate (0.011 g) were combined in a 10 ml oven-dried flask. Tetrahydrofuran (1 ml) was added and the mixture was flushed with nitrogen and stirred at ambient temperature for 5 minutes. 2-Propylzinc bromide solution (0.5 M in tetrahydrofuran) (1.5 ml) was added and stirring was continued under nitrogen overnight. Additional 2-2-dicyclohexylphosphino-2',6'-dimethoxybiphenyl (0.041 g) and palladium(II) acetate (0.011 g) were added. The mixture was flushed with nitrogen and stirred at ambient temperature for 5 minutes. 2-Propylzinc bromide solution (0.5 M in tetrahydrofuran) (1.5 ml) was added and stirring was continued under nitrogen for 2.5 days. The reaction mixture was diluted with ethyl acetate, washed with water and brine, dried (MgSO$_4$), filtered, concentrated, and chromatographed on silica gel with 0 to 3% methanol in CH$_2$Cl$_2$ as the eluent. The obtained material was chromatographed on silica gel a second time with 10-40% ethyl acetate in CH$_2$Cl$_2$ as the eluent, triturated with diethyl ether and dried under vacuum at 45° C. to give the product.

Compound 85B 4-(4-{[2-(4-chlorophenyl)-4,4-dimethylcyclohex-1-en-1-yl]methyl}piperazin-1-yl)-N-{[5-isopropyl-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 85A for Compound 11B in the procedure for Compound 11D. $^1$H NMR (500 MHz, dimethylsulfoxide-d$_6$) δ 11.70 (s, 1H), 8.49 (m, 1H), 8.04 (d, 1H), 7.90 (m, 1H), 7.57 (m, 1H), 7.52 (t, 1H), 7.48 (dd, 1H), 7.34 (d, 2H), 7.04 (d, 2H), 6.67 (dd, 1H), 6.41 (dd, 1H), 6.17 (s, 1H), 4.19 (m, 2H), 3.88 (m, 2H), 3.30 (m, 2H), 3.05 (m, 5H), 2.77 (s, 2H), 2.21 (s, 4H), 2.14 (s, 2H), 2.03 (m, 1H), 1.95 (s, 2H), 1.64 (m, 2H), 1.34 (m, 4H), 1.12 (d, 6H), 0.92 (s, 6H).

Compound 86

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 86A 3-fluoro-4-((tetrahydro-2H-pyran-4-yl)methylamino)benzenesulfonamide The title compound was prepared by substituting 3,4-difluorobenzenesulfonamide for 4-chloro-3-nitrobenzenesulfonamide and (tetrahydro-2H-pyran-4-yl)methanamine for 4-methylpiperazin-1-amine dihydrochloride in the procedure for Compound 6A.

Compound 86B 3-chloro-5-fluoro-4-((tetrahydro-2H-pyran-4-yl)methyl amino)benzenesulfonamide The title compound was prepared by substituting Compound 86A for Compound 52B in the procedure for Compound 52C.

Compound 86C

N-({3-chloro-5-fluoro-4-[(tetrahydro-2H-pyran-4-ylmethyl)amino]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 86B for Compound 11B in the procedure for Compound 11D. $^1$H NMR (500 MHz, dimethylsulfoxide-d$_6$) δ 11.72 (s, 1H), 11.20 (s, 1H), 8.08 (d, 1H), 7.61 (m, 2H), 7.50 (m, 3H), 7.34 (d, 2H), 7.04 (d, 2H), 6.68 (dd, 1H), 6.42 (dd, 1H), 6.16 (d, 1H), 6.09 (m, 1H), 3.81 (dd, 2H), 3.25 (m, 4H), 3.07 (m, 4H), 2.76 (s, 2H), 2.18 (m, 6H), 1.95 (s, 2H), 1.72 (m, 1H), 1.53 (d, 2H), 1.38 (t, 2H), 1.16 (m, 2H), 0.92 (s, 6H).

Compound 87

4-(4-[(4'-chloro-1,1'-biphenyl-2-yl)methyl]piperazin-1-yl)-2-(1H-indol-5-yloxy)-N-({3-nitro-4-[(tetrahydro-2H-pyran-4-ylmethyl)amino]phenyl}sulfonyl)benzamide Compound 87A methyl 2-(1H-indol-5-yloxy)-4-fluorobenzoate The title compound was prepared by substituting 5-hydroxyindole for Compound 3G in the procedure for Compound 3H.

Compound 87B methyl 2-(1H-indol-5-yloxy)-4-(4-((2-(4-chlorophenyl)-4,4-dimethylcyclohex-1-enyl)methyl)piperazin-1-yl)benzoate The title compound was prepared by substituting Compound 87A for Compound 3H in the procedure for Compound 3I.

Compound 87C 2-(1H-indol-5-yloxy)-4-(4-((2-(4-chlorophenyl)-4,4-dimethylcyclohex-1-enyl)methyl)piperazin-1-yl)benzoic Acid The title compound was prepared by substituting Compound 87B for Compound 3I in the procedure for Compound 3J.

Compound 87D

3-{4-[(4'-chloro-1,1'-biphenyl-2-yl)methyl]piperazin-1-yl}-2-(1H-indol-5-yloxy)-N-({3-nitro-4-[(tetrahydro-2H-pyran-4-ylmethyl)amino]phenyl}sulfonyl)benzamide The title compound was prepared by substituting Compound 87C for Compound 1E in the procedure for Compound 1G, except here the crude was purified by preparative HPLC using a 250×50 mm C18 column and eluting with 20-100% CH$_3$CN vs. 0.1% trifluoroacetic acid in water, giving the product as a trifluoroacetate salt. $^1$H NMR (300 MHz, dimethylsulfoxide-d$_6$) δ 11.40 (br s, 1H), 11.17 (s, 1H), 9.50 (v br s, 1H), 8.61 (t, 1H), 8.57 (d, 1H), 7.77 (dd, 1H), 7.70 (br s, 1H), 7.50 (m, 5H), 7.36 (m, 5H), 7.10 (d, 1H), 7.08 (d, 1H), 6.83 (dd, 1H), 6.69 (dd, 1H), 6.37 (m, 1H), 6.21 (d, 1H), 4.30 (br s, 1H), 3.84 (dd, 2H), 3.70 (br s, 1H), 3.30 (m, 6H), 3.20, 2.95, 2.80 (all br s, total 6H), 1.86 (m, 1H), 1.60 (m, 2H), 1.25 (m, 2H).

Compound 88

4-(4-[(4'-chloro-1,1'-biphenyl-2-yl)methyl]piperazin-1-yl)-2-(1H-indol-5-yloxy)-N-({4-[(3-morpholin-4-ylpropyl)amino]-3-nitrophenyl}sulfonyl)benzamide The title compound was prepared by substituting Compound 87C for Compound 1E and Compound 2A for Compound 1F in the procedure for Compound 1G, except here the crude was purified by preparative HPLC using a 250×50 mm C18 column and eluting with 20-100% $CH_3CN$ vs. 0.1% trifluoroacetic acid in water, giving the product as a trifluoroacetate salt. $^1$H NMR (300 MHz, dimethylsulfoxide-$d_6$) δ 11.40 (br s, 1H), 11.19 (s, 1H), 9.60 (v br s, 1H), 8.69 (t, 1H), 8.60 (d, 1H), 7.83 (dd, 1H), 7.65 (br s, 1H), 7.50 (m, 5H), 7.38 (m, 5H), 7.12 (m, 2H), 6.83 (dd, 1H), 6.69 (dd, 1H), 6.39 (m, 1H), 6.20 (d, 1H), 4.38 (br s, 1H), 4.00 (m, 2H), 3.80 (br s, 1H), 3.40 (m, 4H), 3.30-2.80 (envelope, 10H), 3.20 (m, 4H), 1.96 (m, 2H).

Compound 89

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}sulfonyl)benzamide This Compound was prepared by substituting Compound 87C for Compound 1E and Compound 3M for Compound 1F in the procedure for Compound 1G. $^1$H NMR (300 MHz, dimethylsulfoxide-$d_6$) δ 11.15 (s, 1H), 8.56 (d, 1H), 8.20 (d, 1H), 7.84 (dd, 1H), 7.52 (d, 1H), 7.39-7.31 (m, 4H), 7.12 (d, 2H), 7.04 (d, 2H), 6.84 (dd, 1H), 6.65 (dd, 1H), 6.38 (t, 1H), 6.14 (d, 1H), 3.94 (m, 2H), 3.84 (m, 1H), 3.02 (m, 8H), 2.79 (m, 3H), 2.72 (s, 2H), 2.20-2.02 (m, 8H), 1.85 (m, 6H), 1.60 (m, 2H), 1.38 (t, 2H), 0.92 (s, 6H).

Compound 90

4-(4-{[2-(4-chlorophenyl)-4,4-dimethylcyclohex-1-en-1-yl]methyl}piperazin-1-yl)-2-(1H-indol-5-yloxy)-N-({4-[(1-methylpiperidin-4-yl)amino]-3-nitrophenyl}sulfonyl)benzamide The title compound was prepared by substituting Compound 87C for Compound 1E and Compound 4A for Compound 1F in the procedure for Compound 1G. $^1$H NMR (300 MHz, dimethylsulfoxide-$d_6$) δ 11.08 (s, 1H), 8.51 (d, 1H), 8.13 (d, 1H), 7.78 (dd, 1H), 7.52 (d, 1H), 7.37-7.31 (m, 4H), 7.06-7.00 (m, 4H), 6.79 (dd, 1H), 6.59 (dd, 1H), 6.35 (t, 1H), 6.14 (d, 1H), 3.73 (m, 1H), 3.05-2.95 (m, 6H), 2.71 (s, 2H), 2.60 (m, 2H), 2.48 (s, 3H), 2.16 (m, 6H), 2.01 (m, 2H), 1.95 (s, 2H), 1.70 (m, 2H), 1.38 (t, 2H), 0.92 (s, 6H).

Compound 91

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)benzamide The title compound was prepared by substituting Compound 6A for Compound 11B and Compound 87C for Compound 3J in the procedure for Compound 11D. $^1$H NMR (500 MHz, dimethylsulfoxide-$d_6$) δ 11.14 (s, 1H), 9.18 (s, 1H), 8.53 (d, 1H), 7.84 (dd, 1H), 7.56 (d, 1H), 7.51 (d, 1H), 7.39 (m, 2H), 7.33 (d, 2H), 7.12 (d, 1H), 7.03 (d, 2H), 6.84 (dd, 1H), 6.62 (dd, 1H), 6.38 (m, 1H), 6.13 (d, 1H), 3.00 (m, 4H), 2.90 (m, 4H), 2.71 (s, 2H), 2.33 (s, 3H), 2.15 (m, 6H), 1.94 (s, 2H), 1.37 (t, 2H), 0.92 (s, 6H).

Compound 92

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-(1H-indol-5-yloxy)benzamide The title compound was prepared as described in the procedure for Compound 11D using Compound 87C and Compound 12A in place of Compound 3J and Compound 11B, respectively. $^1$H NMR (500 MHz, dimethylsulfoxide-$d_6$) δ 11.16 (s, 2H), 8.39 (d, 1H), 8.06 (dd, 1H), 7.51 (d, 1H), 7.38-7.43 (m, 3H), 7.34 (d, 2H), 7.15 (d, 1H), 7.04 (d, 2H), 6.85 (dd, 1H), 6.64 (dd, 1H), 6.39 (s, 1H), 6.15 (d, 1H), 4.20-4.28 (m, 2H), 3.85-3.91 (m, 1H), 3.82 (dd, 1H), 3.74-3.78 (m, 1H), 3.59-3.69 (m, 2H), 3.40-3.51 (m, 2H), 3.05 (s, 4H), 2.78 (s, 2H), 2.23 (s, 4H), 2.14 (s, 2H), 1.95 (s, 2H), 1.38 (t, 2H), 0.92 (s, 6H).

Compound 93

4-(4-{[2-(4-chlorophenyl)-4,4-dimethylcyclohex-1-en-1-yl]methyl}piperazin-1-yl)-2-(1H-indol-5-yloxy)-N-({4-[(2-methoxyethyl)amino]-3-[(trifluoromethyl)sulfonyl]phenyl}sulfonyl)benzamide The title compound was prepared by substituting Compound 87C for Compound 3J and Compound 16A for Compound 11B in the procedure for Compound 11D. $^1$H NMR (400 MHz, dimethylsulfoxide-$d_6$) δ 11.17 (s, 1H), 8.18 (d, 1H), 7.92 (dd, 1H), 7.49 (d, 1H), 7.40 (m, 2H), 7.33 (d, 2H), 7.26 (m, 1H), 7.17 (d, 1H), 7.04 (m, 3H), 6.86 (dd, 1H), 6.65 (dd, 1H), 6.40 (s, 1H), 6.14 (d, 1H), 3.51 (m, 4H), 3.28 (s, 3H), 3.03 (s, 4H), 2.74 (s, 2H), 2.16 (m, 6H), 1.95 (s, 2H), 1.38 (t, 2H), 0.92 (s, 6H).

Compound 94

4-(4-{[2-(4-chlorophenyl)-4,4-dimethylcyclohex-1-en-1-yl]methyl}piperazin-1-yl)-2-(1H-indol-5-yloxy)-N-({4-[(tetrahydro-2H-pyran-4-ylmethyl)amino]-3-[(trifluoromethyl)sulfonyl]phenyl}sulfonyl)benzamide The title compound was prepared by substituting Compound 87C for Compound 3J and Compound 17A for Compound 11B in the procedure for Compound 11D. $^1$H NMR (400 MHz, dimethylsulfoxide-$d_6$) δ 11.20 (s, 1H), 8.19 (d, 1H), 7.90 (dd, 1H), 7.53 (d, 1H), 7.40 (m, 4H), 7.33 (t, 1H), 7.17 (d, 1H), 7.07 (m, 3H), 6.86 (dd, 1H), 6.70 (dd, 1H), 6.41 (s, 1H), 6.21 (d, 1H), 3.84 (dd, 2H), 3.59 (m, 2H), 3.25 (m, 6H), 3.00 (m, 2H), 2.74 (s, 2H), 2.54 (m, 2H), 2.18 (s, 2H), 2.01 (s, 2H), 1.83 (m, 1H), 1.54 (m, 2H), 1.45 (t, 2H), 1.23 (m, 2H), 0.94 (s, 6H).

Compound 95

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide

Compound 95A 1-(1,3-difluoropropan-2-yl)piperidin-4-amine

Tert-butyl piperidin-4-ylcarbamate (0.212 g), 1,3-difluoropropan-2-one (0.149 g) and sodium triacetoxyborohydride (0.337 g) were stirred together in dichloroethane at room temperature. After stirring overnight the reaction was quenched with water (10 ml) and extracted into dichloromethane (2×20 ml). The organic layer was dried over magnesium sulfate, filtered, and concentrated. The residue was treated with hydrogen chloride (4.0M in dioxane, 1.323 ml) for 1 hour to give the title compound as the HCl salt after concentration.

Compound 95B 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}amino)-3-nitrophenyl]sulfonyl}-2-(1H-pyrrolo[2,3-b]pyridin-5-yloxy)benzamide Compound 95A (0.057 g) and Compound 53A (0.162 g) were suspended in dioxane (3 ml) and heated to 105° C. overnight. The reaction was concentrated, loaded onto silica gel (GraceResolv 12 g) and eluted with a gradient of 0.5% to 4% methanol/dichloromethane. The product containing fractions were concentrated and loaded onto C18 (SF25-75 g analogix column) and eluted using a gradient of 30% to 60% acetonitrile/water. The product was partitioned between dichloromethane (20 ml) and saturated aqueous NaHCO$_3$ solution (20 ml). The organic layer was dried over magnesium sulfate, filtered, and concentrated to give the title compound. $^1$H NMR (300 MHz, CDCl$_3$) δ 10.10 (s, 1H), 8.88 (d, 2H), 8.45 (d, 1H), 8.20 (s, 1H), 8.18-8.09 (m, 1H), 7.95 (d, 1H), 7.68 (d, 1H), 7.44 (s, 1H), 7.23-7.19 (m, 1H), 6.91 (d, 3H), 6.53 (d, 2H), 5.98 (d, 1H), 4.64 (dd, 4H), 3.68-3.50 (m, 1H), 3.01 (d, 6H), 2.72 (d, 4H), 2.19 (s, 11H), 1.69 (s, 2H), 1.41 (s, 2H), 0.94 (s, 6H).

Compound 96

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 96A 5-chloro-6-((4-fluorotetrahydro-2H-pyran-4-yl)methoxy)pyridine-3-sulfonamide The title compound was prepared by substituting Compound 40A for 4-fluoro-3-nitrobenzenesulfonamide and Compound 37C for (tetrahydro-2H-pyran-4-yl)methanol in the procedure for Compound 24A.

Compound 96B

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 96A for Compound 11B in the procedure for Compound 11D. $^1$H NMR (500 MHz, dimethylsulfoxide-d$_6$) δ 11.67 (s, 1H), 8.52 (s, 1H), 8.41 (s, 1H), 8.03 (d, 1H), 7.56 (d, 1H), 7.50 (m, 2H), 7.35 (d, 2H), 7.04 (d, 2H), 6.67 (dd, 1H), 6.39 (m, 1H), 6.22 (s, 1H), 4.50 (d, 2H), 3.78 (m, 2H), 3.60 (m, 2H), 3.12 (v br s, 4H), 2.93 (v br s, 2H), 2.38 (v br s, 4H), 2.17 (br m, 2H), 1.96 (s, 2H), 1.86 (m, 4H), 1.40 (t, 2H), 0.93 (s, 6H).

Compound 97

4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide

Compound 97A tert-butyl 4-(2-nitro-4-sulfamoylphenylamino)piperidine-1-carboxylate The title compound was prepared by substituting tert-butyl 4-aminopiperidine-1-carboxylate for 4-methylpiperazin-1-amine dihydrochloride in the procedure for Compound 6A.

Compound 97B 3-nitro-4-(piperidin-4-ylamino)benzenesulfonamide

Tert-butyl 4-(2-nitro-4-sulfamoylphenylamino)piperidine-1-carboxylate was dissolved in dichloromethane (3 ml) and treated with 1N HCl in ether (4 ml). The reaction was stirred overnight then concentrated to give the title compound.

Compound 97C 4-(1-(2,2-difluoroethyl)piperidin-4-ylamino)-3-nitrobenzenesulfonamide 3-nitro-4-(piperidin-4-ylamino)benzenesulfonamide hydrochloride (0.100 g), 1,1-difluoro-2-iodoethane (0.063 ml) and diisopropylamine (0.156 ml) were stirred together in N,N-dimethylformamide (3 ml) and heated to 85° C. The reaction was diluted with dichloromethane (50 ml) and washed with water (50 ml), brine (50 ml), dried over magnesium sulfate, filtered, and concentrated. The residue was loaded onto silica gel (GraceResolve 12 g) and eluted using a gradient of 0.5% methanol/dichloromethane to 3% methanol/dichloromethane over 30 minutes to give the title compound.

Compound 97D 4-(4-{[2-(4-chlorophenyl)-4,4-dimethylcyclohex-1-en-1-yl]methyl}piperazin-1-yl)-N-[(4-{[1-(2,2-difluoroethyl)piperidin-4-yl]amino}-3-nitrophenyl)sulfonyl]-2-(1H-pyrrolo[2,3-b]pyridin-5-yloxy)benzamide The title compound was prepared by substituting Compound 97B for Compound 1F and Compound 3J for Compound 1E in the procedure for Compound 1G. $^1$H NMR (300 MHz, dimethylsulfoxide-d$_6$) δ 11.67 (s, 1H), 11.54-11.27 (m, 1H), 8.55 (d, 1H), 8.24 (d, 1H), 8.03 (d, 1H), 7.81 (d, 1H), 7.50 (dd, 3H), 7.34 (d, 2H), 7.13 (d, 1H), 7.04 (d, 2H), 6.68 (d, 1H), 6.38 (dd, 1H), 6.15 (dt, 2H), 3.64 (s, 1H), 3.07 (s, 4H), 2.79 (ddd, 6H), 2.41 (t, 2H), 2.17 (d, 6H), 1.92 (d, 4H), 1.61 (d, 2H), 1.38 (s, 2H), 0.92 (s, 6H).

Compound 98

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(1H-pyrrolo[2,3-b]pyridin-5-yloxy)benzamide The title compound was prepared as described in the procedure for Compound 53B by replacing 1-acetylpiperidin-4-amine with 4-amino-1-cyclopropylpiperidine. $^1$H NMR (300 MHz, dimethylsulfoxide-d$_6$) δ 11.65 (s, 1H), 8.54 (d, 1H), 8.22 (d, 1H), 8.02 (d, 1H), 7.80 (dd, 1H), 7.49 (m, 3H), 7.34 (d, 2H), 7.11 (d, 1H), 7.04 (d, 2H), 6.67 (dd, 1H), 6.38 (dd, 1H), 6.19 (d, 1H), 3.69 (m, 1H), 3.06 (m, 4H), 2.92 (m, 2H), 2.74 (s, 2H), 2.23 (m, 7H), 1.93 (m, 5H), 1.77 (m, 1H), 1.55 (m, 3H), 1.38 (t, 2H), 0.92 (s, 6H), 0.43 (m, 4H).

Compound 99

4-(4-{[2-(4-chlorophenyl)-4,4-dimethylcyclohex-1-en-1-yl]methyl}piperazin-1-yl)-N-[(4-{[(1-morpholin-4-ylcyclohexyl)methyl]amino}-3-nitrophenyl)sulfonyl]-2-(1H-pyrrolo[2,3-b]pyridin-5-yloxy)benzamide The title compound was prepared as described in the procedure for Compound 53B by replacing 1-acetylpiperidin-4-amine with 1-(4-morpholino)cyclohexanemethylamine. $^1$H NMR (300 MHz, dimethylsulfoxide-d$_6$) δ 11.70 (s, 1H), 9.06 (s, 1H), 8.59 (d, 1H), 8.06 (d, 1H), 7.83 (dd, 1H), 7.57 (d, 1H), 7.50 (m, 2H), 7.34 (m, 3H), 7.19 (d, 1H), 7.04 (d, 2H), 6.67 (dd, 1H), 6.41 (dd, 1H), 6.17 (d, 1H), 3.56 (m, 6H), 3.44 (m, 2H), 3.07 (m, 5H), 2.57 (m, 5H), 2.24 (m, 6H), 1.95 (s, 3H), 1.45 (m, 6H), 1.23 (m, 3H), 0.92 (s, 6H).

Compound 100 trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide

Compound 100A trans-tert-butyl-4-(dicyclopropylamino)cyclohexylcarbamate

A suspension of trans-tert-butyl-4-aminocyclohexylcarbamate (1 g), molecular sieves 3A (1 g), acetic acid (2.67 ml), (1-ethoxycyclopropoxy)trimethysilane (3.74 ml) and sodium cyanoborohydride (0.880 g) in dry methanol (10 ml) was heated at reflux for 3 hours. The insolubles were filtered off, the resulting solution was basified with aqueous NaOH (6 M) to pH 14, and extracted with ether. The combined extracts were washed with brine, dried over Na$_2$SO$_4$, filtered, and concentrated. The residue was purified by flash chromatography (silica gel 80 g, 30-100% acetone/hexanes) to provide the title compound.

Compound 100B (trans)-N$^1$,N$^1$-dicyclopropylcyclohexane-1,4-diamine bis(2,2,2-trifluoroacetate)

The title compound was prepared by substituting Compound 100A for Compound 39A in the procedure for Compound 39B.

Compound 100C trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-(1H-pyrrolo[2,3-b]pyridin-5-yloxy)benzamide A suspension of Compound 53A (0.14 g), Compound 100B (0.112 g) and N,N-diisopropylethylamine (0.310 ml) in dioxane (10 ml) was stirred for 3 days at 100° C. The product was concentrated and purified by RP HPLC(C8, 30%-100% CH$_3$CN/water/0.1% trifluoroacetic acid). $^1$H NMR (500 MHz, pyridine-d$_5$) δ 13.07 (s, 1H), 9.28 (d, 1H), 8.41-8.45 (m, 2H), 8.37 (d, 1H), 8.12 (d, 1H), 7.67 (d, 2H), 7.44 (d, 2H), 7.07 (d, 2H), 7.01 (d, 1H), 6.75 (dd, 1H), 6.53 (d, 1H), 6.48-6.51 (m, 1H), 3.43 (ddd, 1H), 3.03-3.09 (m, 4H), 2.72-2.79 (m, 3H), 2.22-2.28 (m, 2H), 2.11-2.16 (m, 4H), 2.10 (s, 2H), 2.00-2.05 (m, 2H), 1.97 (s, 2H), 1.89 (s, 1H), 1.86 (s, 3H), 1.62-1.71 (m, 2H), 1.39 (t, 2H), 1.19-1.29 (m, 2H), 0.93 (s, 6H), 0.48 (d, 8H).

Compound 101

4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 101A ethyl 2-hydroxy-6,6-dimethylcyclohex-1-enecarboxylate

Into a 500 ml flame dried round-bottomed flask was added copper(1) iodide (18 g) in ether (200 ml) to give a suspension. After cooling to −5° C., methyllithium (120 ml, 1.6M in ether) was added dropwise. After stirring at −5° C. for 1 hour, 3-methylcyclohex-2-enone (5.15 ml) in 15 ml ether was added dropwise, and the mixture was stirred at −5° C. for 1 hour. After cooling to −78° C., hexamethylphosphoramide (60 ml) was added dropwise. Ethyl carbonocyanidate (23.74 ml) was added. After stirring at −78° C. for 20 minutes, the mixture was warmed up to room temperature, and stirred for 1 hour. The mixture was poured into cold water, and the layers were separated. The aqueous layer was extracted with ether (3×20 ml). The combined organic layers were washed with saturated aqueous NH$_4$Cl (3×20 ml), dried over Na$_2$SO$_4$, filtered, and dried under vacuum. The crude product was added to a silica gel column and purified by eluting with 0-10% ethyl acetate in hexane.

Compound 101B ethyl 6,6-dimethyl-2-(trifluoromethylsulfonyloxy) cyclohex-1-enecarboxylate Into a 500 ml round-bottomed flask was added hexane-washed sodium hydride (0.5 g) in dichloromethane (100 ml) to give a suspension. After cooling to −5° C., Compound 101A (2.0 g) was added. After stirring at −5° C. for 30 minutes, the mixture was cooled to −78° C. Trifluoromethanesulfonic anhydride (2.2 ml) was added. The mixture was warmed to room temperature and stirred overnight. Water was added slowly to the mixture, the aqueous layer was then extracted by dichloromethane (2×20 ml). The combined organic layers were washed with saturated NH$_4$Cl and brine, dried over Na$_2$SO$_4$, filtered, and concentrated.

Compound 101C ethyl 2-(4-chlorophenyl)-6,6-dimethylcyclohex-1-enecarboxylate

Into a 25 ml microwave tube was added Compound 101B (2.9 g), 4-chlorophenylboronic acid (2.2 g), and tetrakis(triphenylphosphine)palladium (0.05 g) in 1,2-dimethoxyethane/methanol (2:1, 10 ml) to give a solution. Cesium fluoride (4 g) was then added. The reaction mixture was stirred at 150° C. under (100 W) in a Biotage Initiator microwave reactor for 30 minutes. After removing the solvents, water was added, and the mixture was extracted with ethyl acetate (2×). The combined organic layers were dried by MgSO$_4$. After filtering, the crude product was purified by reverse phase chromatography eluting with 50-100% acetonitrile/water with 0.1% trifluoroacetic acid.

Compound 101D (2-(4-chlorophenyl)-6,6-dimethylcyclohex-1-enyl) methanol

In a 100 ml round-bottomed flask was placed lithium aluminum hydride (1 g) in ether (20 ml) to give a suspension. Compound 101C (1 g) dissolved in ether (5 ml) was added slowly by syringe. The mixture was stirred at room temperature overnight. After cooling to 0° C., the reaction was quenched by water. Ether (2×10 ml) was used to extract the product. The crude product was purified by flash chromatography on silica by eluting with 0-15% ethyl acetate in hexane.

Compound 101E methyl 2-(1H-pyrrolo[2,3-b]pyridin-5-yloxy)-4-(4-((2-(4-chlorophenyl)-6,6-dimethylcyclohex-1-enyl) methyl)piperazin-1-yl)benzoate To a 0° C. solution of Compound 101D (0.43 g) in dichloromethane (5 ml) was added triethylamine (1 ml). Methanesulfonyl chloride (0.134 ml) was then added slowly. After 5 minutes, Compound 15F (0.61 g) was added. The mixture was stirred at room temperature overnight. The crude product was purified by flash chromatography on silica with 0 to 25% ethyl acetate in hexanes to provide the title compound.

Compound 101F 2-(1H-pyrrolo[2,3-b]pyridin-5-yloxy)-4-(4-((2-(4-chlorophenyl)-6,6-dimethylcyclohex-1-enyl)methyl) piperazin-1-yl)benzoic acid In a 5 ml microwave tube was added lithium hydroxide hydrate (15 mg) and Compound 101E (45 mg) in dioxane/water (2:1) (2 ml) to give a suspension. The mixture was heated to 130° C. in a Biotage Initiator microwave reactor for 20 minutes. After cooling and neutralization by HCl, the crude product was added to a Prep HPLC column and was eluted with 20-80% acetonitrile/water with 0.1% trifluoroacetic acid.

Compound 101G 4-(4-{[2-(4-chlorophenyl)-6,6-dimethylcyclohex-1-en-1-yl]methyl}piperazin-1-yl)-N-({3-nitro-4-[(tetrahydro-2H-pyran-4-ylmethyl)amino] phenyl}sulfonyl)-2-(1H-pyrrolo[2,3-b]pyridin-5-yloxy)benzamide The title compound was prepared by substituting Compound 101F for Compound 3J and Compound 1F for Compound 11B in the procedure for Compound 11D. $^1$H NMR (500 MHz, dimethylsulfoxide-d$_6$) δ 11.68 (s, 1H), 11.47 (s, 1H), 8.58 (m, 2H), 8.03 (m, 1H), 7.79 (m, 1H), 7.51 (m, 3H), 7.31 (d, 2H), 7.10 (m, 1H), 7.02 (d, 2H), 6.65 (m, 1H), 6.39 (m, 1H), 6.15 (m, 1H), 3.85 (m, 2H), 3.27 (m, 4H), 2.97 (m, 4H), 2.76 (s, 2H), 2.14 (m, 6H), 1.70 (m, 2H), 1.61 (m, 2H), 1.44 (m, 2H), 1.26 (m, 3H), 1.16 (m, 6H)

Compound 102

N-({5-bromo-6-[(4-ethylmorpholin-3-yl)methoxy] pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 102A (4-ethylmorpholin-3-yl)methanol Morpholin-3-ylmethanol (500 mg) and iodoethane (666 mg) in N,N-dimethylformamide was treated with K$_2$CO$_3$ (1.1 g) overnight. The reaction mixture was diluted with water and extracted with ethyl acetate. The organic layer was dried over Na$_2$SO$_4$, filtered, and concentrated to provide the title compound.

Compound 102B 5-bromo-6-((4-ethylmorpholin-3-yl)methoxy)pyridine-3-sulfonamide

The title compound was prepared as described in the procedure for Compound 12A by replacing 4-fluoro-3-nitrobenzenesulfonamide and (1,4-dioxan-2-yl)methanol with 5-bromo-6-fluoropyridine-3-sulfonamide and Compound 102A, respectively.

Compound 102C

N-({5-bromo-6-[(4-ethylmorpholin-3-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in the procedure for Compound 11D using Compound 102B in place of Compound 11B. $^1$H NMR (500 MHz, dimethylsulfoxide-$d_6$) δ 11.62 (s, 1H), 8.51 (s, 1H), 8.30 (s, 1H), 8.00 (d, 1H), 7.55 (d, 1H), 7.45-7.50 (m, 2H), 7.35 (d, 2H), 7.05 (d, 2H), 6.66 (dd, 1H), 6.37 (s, 1H), 6.21 (d, 1H), 4.58 (dd, 1H), 4.39-4.50 (m, 1H), 3.78-3.90 (m, 1H), 3.67-3.77 (m, 1H), 3.50-3.65 (m, 2H), 3.08 (s, 4H), 2.59-3.00 (m, 4H), 2.20-2.39 (m, 2H), 2.15 (s, 2H), 1.96 (s, 2H), 1.39 (t, 2H), 0.99-1.11 (m, 3H), 0.93 (s, 6H)

Compound 103

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide

Compound 103A 4-((4-ethylmorpholin-3-yl)methoxy)-3-nitrobenzenesulfonamide

The title compound was prepared as described in the procedure for Compound 12A by replacing (1,4-dioxan-2-yl)methanol with Compound 102A.

Compound 103B 4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-(1H-pyrrolo[2,3-b]pyridin-5-yloxy)benzamide The title compound was prepared as described in the procedure for Compound 11D using Compound 103A in place of Compound 11B. $^1$H NMR (500 MHz, dimethylsulfoxide-$d_6$) δ 11.66 (s, 1H), 8.33 (s, 1H), 7.99-8.06 (m, 2H), 7.47-7.57 (m, 3H), 7.45 (d, 1H), 7.35 (d, 2H), 7.04 (d, 2H), 6.67 (dd, 1H), 6.38 (dd, 1H), 6.20 (d, 1H), 4.42 (dd, 1H), 4.23 (dd, 1H), 3.81 (d, 1H), 3.69 (d, 1H), 3.49-3.63 (m, 2H), 3.08 (s, 4H), 2.92 (s, 1H), 2.81 (s, 4H), 2.54 (s, 1H), 2.25 (s, 4H), 2.15 (s, 2H), 1.96 (s, 2H), 1.39 (t, 2H), 1.00 (t, 3H), 0.92 (s, 6H)

Compound 104

4-(4-{[2-(4-chlorophenyl)-4,4-dimethylcyclohex-1-en-1-yl]methyl}piperazin-1-yl)-N-({3-nitro-4-[(4-tetrahydro-2H-pyran-4-ylmorpholin-3-yl)methoxy]phenyl}sulfonyl)-2-(1H-pyrrolo[2,3-b]pyridin-5-yloxy)benzamide Compound 78 (20 mg) and dihydro-2H-pyran-4(3H)-one (10 mg) in dichloroethane (2 ml) was treated with NaCNBH$_3$ (9.74 mg) overnight. Additional dihydro-2H-pyran-4(3H)-one (20 mg) and titanium (IV) isopropoxide (0.05 ml) were added. The resulting mixture was stirred at room temperature overnight and concentrated. The residue was purified by reverse phase HPLC on a C18 column using a gradient of 35-60% acetonitrile in 0.1% trifluoroacetic acid water to give the title compound as a trifluoroacetate salt. The trifluoroacetic acid salt was dissolved in dichloromethane (6 ml) and washed with 50% aqueous NaHCO$_3$. The organic layer was dried over anhydrous Na$_2$SO$_4$ and concentrated to give the title compound. $^1$H NMR (500 MHz, dimethylsulfoxide-$d_6$) δ 11.68 (s, 1H), 8.35 (s, 1H), 8.04 (s, 2H), 7.44-7.58 (m, 4H), 7.35 (d, 2H), 7.04 (d, 2H), 6.67 (dd, 1H), 6.40 (s, 1H), 6.20 (s, 1H), 4.44 (s, 1H), 4.28 (s, 1H), 3.85 (d, 2H), 3.71 (d, 1H), 3.61 (s, 3H), 3.20-3.29 (m, 2H), 3.08 (s, 5H), 2.54-2.96 (m, 5H), 2.06-2.42 (m, 5H), 1.96 (s, 2H), 1.77 (d, 1H), 1.53-1.66 (m, 1H), 1.29-1.51 (m, 4H), 0.92 (s, 6H).

Compound 105

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide

Compound 105A (S)-tert-butyl 1-(tetrahydro-2H-pyran-4-yl)piperidin-3-ylcarbamate The title compound was prepared by substituting (S)-tert-butyl piperidin-3-ylcarbamate for tert-butyl piperazine-1-carboxylate and dihydro-2H-pyran-4(3H)-one for 4'-chlorobiphenyl-2-carboxaldehyde in the procedure for Compound 1A.

Compound 105B (S)-1-(tetrahydro-2H-pyran-4-yl)piperidin-3-amine

The title compound was prepared by substituting Compound 105A for Compound 1A in the procedure for Compound 1B.

Compound 105C 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpiperidin-3-yl]amino}phenyl)sulfonyl]-2-(1H-pyrrolo[2,3-b]pyridin-5-yloxy)benzamide The title compound was prepared by substituting Compound 105B for 1-acetylpiperidin-4-amine in the procedure for Compound 53B. $^1$H NMR (300 MHz, dimethylsulfoxide-$d_6$) δ 8.68 (br s, 1H), 8.54 (br s, 1H), 8.02 (d, 1H), 7.77 (m, 1H), 7.50 (m, 3H), 7.34 (d, 2H), 7.03 (m, 3H), 6.67 (dd, 1H), 6.38 (m, 1H), 6.19 (d, 1H), 3.98 (m, 2H), 3.90 (m, 2H), 3.52 (m, 2H), 3.09 (s, 2H), 3.05 (m, 4H), 2.77 (m, 2H), 2.60 (m, 2H), 2.16 (m, 6H), 1.95 (m, 2H), 1.65 (m, 5H), 1.50 (m, 3H), 1.38 (m, 2H), 0.94 (s, 6H).

Compound 106

4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide

Compound 106A 5-bromo-6-((tetrahydro-2H-pyran-4-yl)methylamino)pyridine-3-sulfonamide The title compound was prepared by substituting (tetrahydro-2H-pyran-4-yl)methanamine for Compound 3L in the procedure for Compound 61A.

Compound 106B 5-cyano-6-((tetrahydro-2H-pyran-4-yl)methylamino)pyridine-3-sulfonamide The title compound was prepared by substituting Compound 106A for Compound 36B in the procedure for Compound 36C.

Compound 106C 4-(4-{[2-(4-chlorophenyl)-4,4-dimethylcyclohex-1-en-1-yl]methyl}piperazin-1-yl)-N-({5-cyano-6-[(tetrahydro-2H-pyran-4-ylmethyl)amino]pyridin-3-yl}sulfonyl)-2-(1H-pyrrolo[2,3-b]pyridin-5-yloxy)benzamide The title compound was prepared by substituting Compound 106B for Compound 11B in the procedure for Compound 11D. $^1$H NMR (400 MHz, dimethylsulfoxide-$d_6$) δ 11.62 (s, 1H), 8.55 (s, 1H), 8.14 (s, 1H), 8.01 (d, 1H), 7.87 (s, 1H), 7.56 (d, 1H), 7.48 (d, 2H), 7.34 (d, 2H), 7.04 (d, 2H), 6.64 (m, 1H), 6.37 (s, 1H), 6.19 (d, 1H), 3.81 (dd, 2H), 3.25 (m, 4H), 3.04 (s, 4H), 2.74 (s, 2H), 2.17 (m, 6H), 1.95 (s, 2H), 1.87 (m, 1H), 1.53 (m, 2H), 1.37 (t, 2H), 1.18 (m, 2H), 0.91 (s, 6H).

Compound 107 trans-4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide

Compound 107A 3-nitro-4-(4-aminothiomorpholine-1,1-dioxide)benzenesulfonamide The title compound was prepared by substituting 4-aminothiomorpholine-1,1-dioxide for (tetrahydropyran-4-yl)methylamine in the procedure for Compound 1F.

Compound 107B trans-4-(4-{[2-(4-chlorophenyl)-4,4-dimethyl cyclohex-1-en-1-yl]methyl}piperazin-1-yl)-N-({4-[(1,1-dioxidothiomorpholin-4-yl)amino]-3-nitrophenyl}sulfonyl)-2-(1H-pyrrolo[2,3-b]pyridin-5-yloxy)benzamide The title compound was prepared by substituting Compound 107A for Compound 11B in the procedure for Compound 11D. $^1$H NMR (400 MHz, dimethylsulfoxide-$d_6$) δ 11.64 (s, 1H), 9.58 (s, 1H), 8.50 (s, 1H), 8.02 (d, 1H), 7.78 (m, 2H), 7.50 (m, 3H), 7.34 (d, 2H), 7.04 (d, 2H), 6.66 (dd, 1H), 6.38 (s, 1H), 6.19 (d, 1H), 3.48 (m, 4H), 3.23 (m, 4H), 3.05 (s, 4H), 2.73 (d, 2H), 2.16 (m, 6H), 1.95 (s, 2H), 1.38 (t, 2H), 0.92 (s, 6H).

Compound 108

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 108A 4-((4-aminotetrahydro-2H-pyran-4-yl)methylamino)-3-nitrobenzenesulfonamide The title compound was prepared by substituting 4-(aminomethyl)tetrahydro-2H-pyran-4-amine for (tetrahydro-2H-pyran-4-yl)methanamine in the procedure for Compound 1F.

Compound 108B

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 108A for Compound 11B in the procedure for Compound 11D. $^1$H NMR (500 MHz, dimethylsulfoxide-$d_6$) δ 11.55 (s, 1H), 8.45 (s, 2H), 7.95 (d, 1H), 7.75-7.77 (m, 1H), 7.57 (d, 2H), 7.44 (s, 1H), 7.34 (d, 2H), 7.09 (d, J=8.85 Hz, 1H), 7.05 (d, 2H), 6.69 (dd, 1H), 6.33 (d, 1H), 6.22 (d, 1H), 3.59-3.71 (m, 6H), 3.01 (s, 4H), 2.73 (s, 2H), 2.15-2.19 (m, 6H), 1.95 (s, 2H), 1.71-1.74 (m, 2H), 1.59-1.61 (m, 1H), 1.38 (t, 2H), 0.93 (s, 6H).

Compound 109 trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy)benzamide

Compound 109A trans-5-bromo-6-(4-morpholinocyclohexyloxy)pyridine-3-sulfonamide The title compound was prepared by substituting Compound 9B for Compound 3L in the procedure for Compound 61A.

Compound 109B trans-5-cyano-6-(4-morpholinocyclohexylamino) pyridine-3-sulfonamide The title compound was prepared by substituting Compound 109A for Compound 36B in the procedure for Compound 36C.

Compound 109C trans-4-(4-{[2-(4-chlorophenyl)-4,4-dimethylcyclohex-1-en-1-yl]methyl}piperazin-1-yl)-N-({5-cyano-6-[(4-morpholin-4-ylcyclohexyl)amino]pyridin-3-yl}sulfonyl)-2-(1H-pyrrolo[2,3-b]pyridin-5-yloxy) benzamide The title compound was prepared by substituting Compound 109B for Compound 11B in the procedure for Compound 11D. $^1$H NMR (400 MHz, dimethylsulfoxide-$d_6$) δ 11.59 (s, 1H), 8.56 (d, 1H), 8.13 (s, 1H), 8.00 (d, 1H), 7.55 (d, 1H), 7.47 (m, 2H), 7.34 (d, 2H), 7.04 (d, 2H), 6.64 (dd, 1H), 6.36 (d, 1H), 6.19 (d, 1H), 4.00 (m, 1H), 3.65 (m, 4H), 3.28 (m, 4H), 3.03 (m, 4H), 2.73 (m, 4H), 2.16 (m, 6H), 1.90 (m, 6H), 1.40 (m, 6H), 0.93 (s, 6H).

Compound 110

4-(4-{[2-(4-chlorophenyl)-4,4-dimethylcyclohex-1-en-1-yl]methyl}piperazin-1-yl)-N-({3-cyano-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 52B for Compound 11B in the procedure for Compound 11D. $^1$H NMR (300 MHz, dimethylsulfoxide-$d_6$) δ 11.71 (s, 1H), 11.23 (s, 1H), 8.08 (d, 1H), 7.91 (d, 1H), 7.74 (dd, 1H), 7.60 (d, 1H), 7.52 (m, 2H), 7.34 (m, 2H), 7.16 (s, 1H), 7.04 (m, 2H), 6.83 (d, 1H), 6.68 (dd, 1H), 6.43 (dd, 1H), 6.16 (d, 1H), 3.83 (dd, 2H), 3.23 (m, 2H), 3.12 (t, 2H), 3.06 (m, 4H), 2.73 (m, 2H), 2.15 (m, 6H), 1.95 (s, 2H), 1.82 (m, 1H), 1.58 (m, 2H), 1.38 (m, 2H), 1.18 (m, 2H), 0.92 (s, 6H).

Compound 111

4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy)benzamide

Compound 11A benzyl (1S,3R)-3-(tert-butoxycarbonylamino)cyclopentylcarbamate (1S,3R)-3-(tert-butoxycarbonylamino)cyclopentanecarboxylic acid (1.03 g), diphenylphosphoryl azide (DPPA, 1.00 ml), triethylamine (0.929 mil), and benzyl alcohol (0.931 ml) were combined in toluene (10 ml) and stirred at 100° C. for 24 hours. The solution was cooled and chromatographed on silica gel using 10% ethyl acetate/hexanes to give the pure product.

Compound 111B benzyl (1S,3R)-3-aminocyclopentylcarbamate

The title compound was prepared by substituting Compound 111A for Compound 1A in the procedure for Compound 1B.

Compound 111C benzyl (1S,3R)-3-morpholinocyclopentylcarbamate

A solution of Compound 111B (400 mg), 1-bromo-2-(2-bromoethoxy)ethane (0.246 ml), and triethylamine (0.595 ml) in N,N-dimethylformamide (6 ml) was stirred at 70° C. for 24 hours. The solution was cooled and poured into ethyl acetate (200 ml). The solution was extracted with 3× water, washed with brine, concentrated, and chromatographed on silica gel using 10% methanol/ethyl acetate to give the pure product.

Compound 111D (1S,3R)-3-morpholinocyclopentanamine

Compound 111C (300 mg) and ethanol (20 ml) were added to wet 20% Pd(OH)$_2$—C (60.0 mg) in a 50 ml pressure bottle and stirred for 8 hours at 30 psi. The mixture was filtered through a nylon membrane and condensed to give the product.

Compound 111E 4-(4-{[2-(4-chlorophenyl)-4,4-dimethylcyclohex-1-en-1-yl]methyl}piperazin-1-yl)-N-[(4-{[(1S,3R)-3-morpholin-4-ylcyclopentyl]amino}-3-nitrophenyl)sulfonyl]-2-(1H-pyrrolo[2,3-b]pyridin-5-yloxy) benzamide The title compound was prepared by substituting Compound 3J for Compound 1E and Compound 111D for Compound 1F in the procedure for Compound 1G. $^1$H NMR (dimethylsulfoxide-$d_6$) δ 11.65 (s, 1H), 8.45 (d, 1H), 8.28 (dd, 1H), 7.97 (d, 1H), 7.68 (d, 1H), 7.52 (d, 1H), 7.44 (d, 2H), 7.35 (d, 2H), 7.05 (d, 2H), 6.92 (dd, 1H), 6.85 (dd, 1H), 6.33 (s, 1H), 6.22 (s, 1H), 4.08 (m, 1H), 3.60 (br s, 4H), 3.06 (br s, 4H), 2.73 (br s, 3H), 2.48 (m, 4H), 2.28 (m, 1H), 2.18 (m, 6H), 2.07 (m, 1H), 1.95 (s, 2H), 1.79 (m, 2H), 1.63 (m, 2H), 1.38 (t, 2H), 0.93 (s, 6H).

Compound 112

4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide

Compound 112A tert-butyl (1R,3S)-3-aminocyclopentylcarbamate

The title compound was prepared by substituting Compound 111A for Compound 111C in the procedure for Compound 111D.

Compound 112B tert-butyl (1R,3S)-3-morpholinocyclopentylcarbamate

The title compound was prepared by substituting Compound 112A for Compound 111B in the procedure for Compound 111C.

Compound 112C (1R,3S)-3-morpholinocyclopentanamine

The title compound was prepared by substituting Compound 112B for Compound 1A in the procedure for Compound 1B.

Compound 112D 4-(4-{[2-(4-chlorophenyl)-4,4-dimethylcyclohex-1-en-1-yl]methyl}piperazin-1-yl)-N-[(4-{[(1R,3S)-3-morpholin-4-ylcyclopentyl]amino}-3-nitrophenyl)sulfonyl]-2-(1H-pyrrolo[2,3-b]pyridin-5-yloxy)benzamide The title compound was prepared by substituting Compound 3J for Compound 1E and Compound 112C for Compound 1F in the procedure for Compound 1G. $^1$H NMR (dimethylsulfoxide-d$_6$) δ 11.35 (s, 1H), 8.51 (d, 1H), 8.44 (dd, 1H), 8.00 (d, 1H), 7.77 (d, 1H), 7.50 (d, 1H), 7.48 (s, 2H), 7.34 (d, 2H), 7.04 (d, 2H), 7.02 (dd, 1H), 6.67 (dd, 1H), 6.37 (dd, 1H), 6.21 (d, 1H), 4.11 (m, 1H), 3.61 (br s, 4H), 3.06 (br s, 4H), 2.73 (br s, 3H), 2.50 (m, 4H), 2.28 (m, 1H), 2.18 (m, 6H), 2.06 (m, 1H), 1.95 (s, 2H), 1.77 (m, 2H), 1.66 (m, 2H), 1.38 (t, 2H), 0.92 (s, 6H).

Compound 113

4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide

Compound 113A tert-butyl 2-((2-nitro-4-sulfamoylphenylamino)methyl)morpholine-4-carboxylate The title compound was prepared by substituting tert-butyl 2-(aminomethyl)morpholine-4-carboxylate for (tetrahydropyran-4-yl)methylamine in the procedure for Compound 1F.

Compound 113B tert-butyl 2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared by substituting Compound 113A for Compound 1F and Compound 3J for Compound 1E in the procedure for Compound 1G, with the exception that the product was purified on a silica gel column eluted with 4% methanol in dichloromethane.

Compound 113C 4-(4-{[2-(4-chlorophenyl)-4,4-dimethylcyclohex-1-en-1-yl]methyl}piperazin-1-yl)-N-({4-[(morpholin-2-ylmethyl)amino]-3-nitrophenyl}sulfonyl)-2-(1H-pyrrolo[2,3-b]pyridin-5-yloxy)benzamide The title compound was prepared by substituting Compound 113B for Compound 66B in the procedure for Compound 66C. $^1$H NMR (500 MHz, dimethylsulfoxide-d$_6$) δ 11.60 (s, 1H), 8.55 (br, s, 1H), 8.51 (s, 1H), 8.00 (d, 1H), 7.80 (d, 1H), 7.52 (d, 1H), 7.49-7.46 (m, 2H), 7.34 (d, 2H), 7.07 (d, 1H), 7.04 (d, 2H), 6.66 (dd, 1H), 6.36 (s, 1H), 6.20 (d, 1H), 4.00 (dd, 1H), 3.91 (m, 1H), 3.70 (t, 1H), 3.60 (m, 1H), 3.58 (m, 1H), 3.32 (m, 1H), 3.16 (d, 1H), 3.05 (m, 4H), 2.98 (td, 1H), 2.86 (t, 1H), 2.73 (s, 2H), 2.20-2.12 (m, 6H), 1.95 (s, 2H), 1.38 (t, 2H), 0.92 (s, 6H).

Compound 114

4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide

Compound 114A 3-nitro-4-((tetrahydrofuran-3-yl)methylamino)benzenesulfonamide The title compound was prepared by substituting 3-aminomethyl-tetrahydrofuran for (tetrahydropyran-4-yl)methylamine in the procedure for Compound 1F.

Compound 114B 4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)-2-(1H-pyrrolo[2,3-b]pyridin-5-yloxy)benzamide The title compound was prepared by substituting Compound 114A for Compound 130C in the procedure for Compound 130D. $^1$H NMR (500 MHz, dimethylsulfoxide-d$_6$) δ 11.68 (s, 1H), 11.42 (bs, 1H), 8.63 (t, 1H), 8.56 (d, 1H), 8.04 (d, 1H), 7.80 (dd, 1H), 7.53-7.48 (m, 3H), 7.34 (d, 2H), 7.10 (d, 1H), 7.04 (d, 2H), 6.68 (dd, 1H), 6.39 (m, 1H), 6.19 (d, 1H), 3.82-3.79 (m, 1H), 3.71 (t, 1H), 3.62 (dd, 1H), 3.50 (dd, 1H), 3.38 (m, 1H), 3.32 (m, 1H), 3.07 (m, 4H), 2.76 (s, 2H), 2.58 (m, 1H), 2.25-2.00 (m, 6H), 1.98 (m, 1H), 1.95 (s, 2H), 1.65 (m, 1H), 1.38 (t, 2H), 0.92 (s, 6H).

Compound 115

4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide

Compound 115A cis-tert-butyl 1-(3-fluorotetrahydro-2H-pyran-4-yl)piperidin-4-ylcarbamate The title compound was prepared as a racemate of the cis diastereomer by substituting tert-butyl piperidin-4-ylcarbamate for piperidin-4-ol and 3-fluorodihydro-2H-pyran-4 (3H)-one (prepared by the method described in US 2005/0101628, incorporated herein by reference) for dihydro-2H-pyran-4(3H)-one) in the procedure for Compound 84A.

Compound 115B cis-1-(3-fluorotetrahydro-2H-pyran-4-yl)piperidin-4-amine

Compound 115A (0.29 g) was dissolved in $CH_2Cl_2$ (9 ml), then 4N HCl in dioxane (4 ml) was added and the reaction stirred at room temperature for 16 hours. The reaction was diluted with $CH_2Cl_2$ (30 ml), then 4N aqueous NaOH (5 ml) was added. After shaking and separating the layers the aqueous layer was saturated with solid NaCl and extracted with more $CH_2Cl_2$ (10 ml). The combined organic layers were dried over $Na_2SO_4$. After filtration and concentration the amine was used with no further purification.

Compound 115C 4-(4-{[2-(4-chlorophenyl)-4,4-dimethylcyclohex-1-en-1-yl]methyl}piperazin-1-yl)-N-{[4-({1-[cis-3-fluorotetrahydro-2H-pyran-4-yl]piperidin-4-yl}amino)-3-nitrophenyl]sulfonyl}-2-(1H-pyrrolo[2,3-b]pyridin-5-yloxy)benzamide The title compound was prepared by substituting Compound 115B for 1-acetylpiperidin-4-amine in the procedure for Compound 53B. $^1$H NMR (500 MHz, dimethylsulfoxide-$d_6$) δ 11.64 (s, 1H), 8.54 (d, 1H), 8.43 (br d, 1H), 8.03 (d, 1H), 7.80 (dd, 1H), 7.50 (m, 3H), 7.35 (d, 2H), 7.11 (d, 1H), 7.05 (d, 2H), 6.66 (dd, 1H), 6.38 (m, 1H), 6.20 (d, 1H), 4.92 (d, 1H), 3.95 (m, 2H), 3.70 (v br m, 1H), 3.50, 3.40, 3.30 (all m, total 5H), 3.05, 3.00 (both v br m, total 5H), 2.74 (s, 2H), 2.55 (v br m, 1H), 2.18 (br m, 6H), 1.95 (m, 4H), 1.88 (ddd, 1H), 1.63 (v br m, 3H), 1.38 (t, 2H), 0.92 (s, 6H).

Compound 116

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide Compound 116A 1-(tetrahydro-2H-pyran-4-yl)azetidin-3-amine Tert-butyl azetidin-3-ylcarbamate (0.46 g), dihydro-2H-pyran-4(3H)-one (0.29 g) and sodium triacetoxyborohydride (0.85 g) were stirred together in dichloromethane (5 ml) overnight. The reaction was poured into dichloromethane (50 ml) and saturated aqueous $NaHCO_3$ solution (25 ml). The organic layer was separated, washed with brine (25 ml), dried over $Na_2SO_4$, filtered, and concentrated. Silica gel chromatography (GraceResolv 12 g) eluting with a gradient of 0.75% to 7.5% methanol/dichloromethane over 20 minutes gave the Boc-protected intermediate. Treatment with HCl (4.0M in dioxane, 2 ml) and methanol (1 ml) for 1 hour gave the title compound after concentration as the di-HCl salt.

Compound 116B 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylazetidin-3-yl)amino]phenyl}sulfonyl)-2-(1H-pyrrolo[2,3-b]pyridin-5-yloxy)benzamide A suspension of 2-(1H-pyrrolo[2,3-b]pyridin-5-yloxy)-N-(4-chloro-3-nitrophenylsulfonyl)-4-(4-((2-(4-chlorophenyl)-4,4-dimethylcyclohex-1-enyl)methyl)piperazin-yl)benzamide (0.180 g), 1-(tetrahydro-2H-pyran-4-yl)azetidin-3-amine (0.078 g), and triethylamine (0.159 ml) in dioxane (2 ml) was degassed with nitrogen for 30 seconds then scaled. The reaction was heated to 110° C. After stirring for 16 hours, more triethylamine (10 equivalents total) and dimethylsulfoxide (1 mil) were added and the reaction stirred for an additional 18 hours at 110° C. The reaction was cooled, diluted with water (50 ml) and extracted with dichloromethane (2×150 ml). The organic layer was dried over magnesium sulfate, filtered and concentrated. Silica gel chromatography (GraceResolv 12 g) eluting with a gradient of 0.75% to 7.5% methanol/dichloromethane (flow=36 ml/minutes) gave the title compound. $^1$H NMR (300 MHz, dimethylsulfoxide-$d_6$) δ 11.59 (s, 1H), 8.49 (d, 1H), 8.40 (s, 1H), 7.97 (d, 1H), 7.77 (s, 1H), 7.47 (dd, 3H), 7.34 (d, 2H), 7.04 (d, 2H), 6.90-6.78 (m, 1H), 6.65 (d, 1H), 6.35 (s, 1H), 6.21 (s, 1H), 4.47-4.23 (m, 1H), 3.83 (s, 3H), 3.05 (s, 6H), 2.73 (s, 2H), 2.18 (s, 8H), 1.95 (s, 2H), 1.68 (s, 2H), 1.38 (s, 2H), 1.24 (s, 4H), 0.92 (s, 6H).

Compound 117

4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide Compound 117A 1-(tetrahydrofuran-3-yl)azetidin-3-amine Tert-butyl azetidin-3-ylcarbamate (0.550 g), dihydrofuran-3(2H)-one (0.412 g) and sodium triacetoxyborohydride (1.015 g) were stirred together in dichloromethane (5 ml). After stirring overnight, the reaction was poured into saturated aqueous $NaHCO_3$ solution (25 ml) and extracted with dichloromethane (50 ml). The organic layer was washed with brine (25 ml), dried over magnesium sulfate, filtered, and concentrated. Silica gel chromatography (GraceResolv 12 g) eluting with a gradient of 0.5% to 7.5% methanol/dichloromethane over 30 minutes gave tert-butyl 1-(tetrahydrofuran-3-yl)azetidin-3-ylcarbamate. The resulting material was treated with HCl/dioxane for 1 hour, and then concentrated to give the title compound.

Compound 117B 3-nitro-4-(1-(tetrahydrofuran-3-yl)azetidin-3-ylamino)benzenesulfonamide 4-Fluoro-3-nitrobenzenesulfonamide (0.084 g), 1-(tetrahydrofuran-3-yl)azetidin-3-amine (0.090 g) and triethylamine (0.266 ml) in tetrahydrofuran (3 ml) were heated to 60° C. After stirring for 4 hours, the reaction was cooled, the tetrahydrofuran was removed and the residue was partitioned between dichloromethane (200 ml) and water (20 ml). The organic layer was separated, washed with brine (25 ml), dried over magnesium sulfate, filtered, and concentrated to give the title compound.

Compound 117C 4-(4-{[2-(4-chlorophenyl)-4,4-dimethylcyclohex-1-en-1-yl]methyl}piperazin-1-yl)-N-({3-nitro-4-[(1-tetrahydrofuran-3-ylazetidin-3-yl)amino]phenyl}sulfonyl)-2-(1H-pyrrolo[2,3-b]pyridin-5-yloxy)benzamide The title compound was prepared by substituting Compound 117B for Compound 1F and Compound 3J for Compound 1E in the procedure for Compound 1G. $^1$H NMR (300 MHz, CDCl$_3$) δ 10.39-9.79 (m, 1H), 9.17 (s, 1H), 8.87 (d, 1H), 8.51 (d, 1H), 8.15 (dd, 2H), 7.94 (d, 1H), 7.68 (d, 1H), 7.48-7.42 (m, 1H), 7.23 (d, 2H), 6.91 (d, 2H), 6.69 (d, 1H), 6.54 (dd, 2H), 5.99 (d, 1H), 4.29 (d, 1H), 4.01-3.73 (m, 4H), 3.66 (d, 2H), 3.08 (s, 6H), 2.76 (s, 2H), 2.21 (s, 6H), 2.03-1.83 (m, 3H), 1.64 (s, 2H), 1.42 (d, 2H), 0.93 (s, 6H).

Compound 118

4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide Compound 118A (R)-tert-butyl (1-(tetrahydro-2H-pyran-4-yl)pyrrolidin-3-yl)methylcarbamate The title compound was prepared by substituting (S)-tert-butyl pyrrolidin-3-ylmethylcarbamate for tert-butyl piperazine-1-carboxylate and dihydro-2H-pyran-4(3H)-one for 4'-chlorobiphenyl-2-carboxaldehyde in the procedure for Compound 1A.

Compound 118B (R)-(1-(tetrahydro-2H-pyran-4-yl)pyrrolidin-3-yl)methanamine

The title compound was prepared by substituting Compound 118A for Compound 1A in the procedure for Compound 1B.

Compound 118C 4-(4-{[2-(4-chlorophenyl)-4,4-dimethylcyclohex-1-en-1-yl]methyl}piperazin-1-yl)-N-{[3-nitro-4-({[(3R)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide The title compound was prepared by substituting Compound 118B for 1-acetylpiperidin-4-amine in the procedure for Compound 53B. $^1$H NMR (500 MHz, dimethylsulfoxide-d$_6$) δ 11.57 (s, 1H), 8.59 (br s, 1H), 8.45 (br s, 1H), 8.02 (d, 1H), 7.95 (m, 1H), 7.71 (m, 1H), 7.56 (d, 1H), 7.45 (m, 1H), 7.35 (m, 3H), 7.05 (m, 2H), 6.90 (br s, 1H), 6.64 (d, 1H), 6.33 (m, 1H), 6.22 (m, 1H), 3.90 (m, 2H), 3.44 (m, 2H), 3.27 (m, 4H), 3.02 (m, 5H), 2.73 (m, 3H), 2.59 (m, 2H), 2.19 (m, 6H), 1.95 (m, 2H), 1.85 (m, 2H), 1.64 (m, 1H), 1.50 (m, 2H), 1.39 (m, 2H), 1.23 (m, 1H), 0.94 (s, 6H).

Compound 119

4-(4-{[2-(4-chlorophenyl)-5,5-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide The title compound was prepared as described in the procedure for Compound 11D using Compound 75F and Compound 37D in place of Compound 3J and Compound 11B, respectively. $^1$H NMR (500 MHz, dimethylsulfoxide-d$_6$) δ 11.69 (s, 1H), 8.39 (s, 1H), 8.08 (d, 1H), 8.04 (d, 1H), 7.41-7.59 (m, 4H), 7.35 (d, 2H), 7.08 (d, 2H), 6.68 (dd, 1H), 6.37-6.43 (m, 1H), 6.20 (s, 1H), 4.38 (d, 2H), 3.73-3.82 (m, 2H), 3.54-3.63 (m, 2H), 3.09 (s, 4H), 2.81 (s, 2H), 2.16-2.39 (m, 5H), 1.94 (s, 2H), 1.79-1.93 (m, 4H), 1.40 (t, 2H), 0.94 (s, 6H).

Compound 120

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide Compound 120A trans-4-(aminomethyl)cyclohexanol Tert-butyl ((1r,4r)-4-hydroxycyclohexyl)methylcarbamate (1 g) in dichloromethane (10 ml) was treated with trifluoroacetic acid (5 ml) at 0° C. for 10 minutes and at room temperature for 30 minutes. The reaction mixture was concentrated and dried in vacuo to provide the title compound as a trifluoroacetic acid salt.

Compound 120B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((trans-4-hydroxycyclohexyl)methoxy)-3-nitrophenylsulfonyl)benzamide A mixture of Compound 53A (211 mg), Compound 120A (104 mg) and N-ethyl-N-isopropylpropan-2-amine (0.3 ml) in dimethylsulfoxide (2 ml) was heated at 150° C. in a Biotage Initiator microwave synthesizer for 1.5 hours and concentrated. The residue was purified by reverse phase HPLC on a C18 column using a gradient of 40-60% acetonitrile in 0.1% trifluoroacetic acid water to give the title compound as a trifluoroacetate salt. The trifluoroacetic acid salt was dissolved in dichloromethane (30 ml) and washed with 50% aqueous NaHCO$_3$. The organic layer was dried over anhydrous Na$_2$SO$_4$, filtered, and concentrated to give the title compound. $^1$H NMR (500 MHz, dimethylsulfoxide-d$_6$) δ 11.69 (s, 1H), 11.41 (s, 1H), 8.61 (t, 1H), 8.53-8.58 (m, 1H), 8.04 (d, 1H), 7.76-7.83 (m, 1H), 7.47-7.56 (m, 3H), 7.34 (d, 2H), 7.07-7.11 (m, 1H), 7.04 (d, 2H), 6.68 (dd, 1H), 6.39 (dd, 1H), 6.19 (d, 1H), 4.82-4.99 (m, 1H), 4.50 (d, 1H), 3.26-3.31 (m, 2H), 3.23 (t, 1H), 3.07 (s, 4H), 2.76 (s, 2H), 2.10-2.28 (m, 6H), 2.05 (dd, 1H), 1.95 (s, 2H), 1.84 (t, 2H), 1.52-1.76 (m, 2H), 1.41-1.51 (m, 1H), 1.38 (t, 2H), 0.95-1.25 (m, 4H), 0.92 (s, 6H).

Compound 121

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide

Compound 121A (4-methoxycyclohexyl)methanol

4-Methoxycyclohexanecarboxylic acid (7 g) in tetrahydrofuran (20 ml) was treated with 1 M (in tetrahydrofuran) borane-tetrahydrofuran complex (100 ml) overnight. The mixture was concentrated and the residue was dissolved in methanol (100 ml) and concentrated HCl (10 ml). The resulting mixture was stirred for 1 hour and concentrated. The residue was dissolved in dichloromethane and washed with water. The organic layer was dried over $Na_2SO_4$, filtered, and concentrated to give the title compound.

Compound 121B 4-((4-methoxycyclohexyl)methoxy)-3-nitrobenzenesulfonamide

The title compound was prepared as described in the procedure for Compound 12A by replacing (1,4-dioxan-2-yl)methanol with Compound 121A.

Compound 121C 4-((cis-4-methoxycyclohexyl)methoxy)-3-nitrobenzenesulfonamide Separation of the cis and trans mixture of Compound 121B on a reverse phase HPLC (gradient: 40-55% acetonitrile in 0.1% TFA in water over 25 minutes) provided the title compound.

Compound 121D 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((cis-4-methoxycyclohexyl)methoxy)-3-nitrophenylsulfonyl)benzamide The title compound was prepared as described in the procedure for Compound 11D using Compound 121C in place of Compound 11B. $^1$H NMR (500 MHz, dimethylsulfoxide-$d_6$) δ 11.69 (s, 1H), 11.39 (s, 1H), 8.34 (s, 1H), 7.96-8.07 (m, 2H), 7.48-7.56 (m, 3H), 7.31-7.42 (m, 3H), 7.04 (d, 2H), 6.68 (dd, 1H), 6.40 (dd, 1H), 6.20 (d, 1H), 4.02 (d, 2H), 3.39 (s, 1H), 3.20 (s, 3H), 3.09 (s, 4H), 2.82 (s, 2H), 2.09-2.34 (m, 6H), 1.96 (s, 2H), 1.78-1.86 (m, 3H), 1.54 (dd, 2H), 1.28-1.46 (m, 6H), 0.92 (s, 6H).

Compound 122 cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide

Compound 122A cis-tert-butyl-4-(cyclopropylamino)cyclohexylcarbamate

The title compound was prepared by substituting tert-butyl 4-oxocyclohexylcarbamate for 4'-chlorobiphenyl-2-carboxaldehyde and cyclopropylamine for tert-butyl piperazine-1-carboxylate in the procedure for Compound 1A.

Compound 122B cis-$N^1$-cyclopropylcyclohexane-1,4-diamine bis(2,2,2-trifluoroacetate)

The title compound was prepared by substituting Compound 122A for Compound 39A in the procedure for Compound 39B.

Compound 122C cis-4-(4-{[2-(4-chlorophenyl)-4,4-dimethylcyclohex-1-en-1-yl]methyl}piperazin-1-yl)-N-[(4-{[4-(cyclopropylamino)cyclohexyl]amino}-3-nitrophenyl)sulfonyl]-2-(1H-pyrrolo[2,3-b]pyridin-5-yloxy)benzamide The title compound was prepared by substituting Compound 122B for Compound 100B in the procedure for Compound 100C. $^1$H NMR (500 MHz, pyridine-$d_5$) δ 13.06 (s, 1H), 9.28 (d, 1H), 8.59 (d, 1H), 8.44 (d, 1H), 8.37 (dd, 1H), 8.12 (d, 1H), 7.67 (t, 2H), 7.43 (t, 2H), 7.07 (d, 2H), 6.90 (d, 1H), 6.75 (dd, 1H), 6.53 (d, 1H), 6.50 (dd, 1H), 3.56-3.63 (m, 1H), 3.02-3.08 (m, 4H), 2.77 (s, 3H), 2.26 (t, 2H), 2.10-2.16 (m, 4H), 2.06 (ddd, 1H), 1.97 (s, 2H), 1.74-1.82 (m, 2H), 1.61-1.71 (m, 5H), 1.39 (t, 2H), 0.93 (s, 6H), 0.39-0.44 (m, 4H).

Compound 123 trans-4-(4-{[2-(4-chlorophenyl)-4,4-dimethylcyclohex-1-en-1-yl]methyl}piperazin-1-yl)-N-[(3-nitro-4-({[4-(tetrahydro-2H-pyran-4-ylamino)cyclohexyl]amino}phenyl)sulfonyl]-2-(1H-pyrrolo[2,3-b]pyridin-5-yloxy)benzamide

Compound 123A trans-tert-butyl-4-(tetrahydro-2H-pyran-4-ylamino)cyclohexylcarbamate The title compound was prepared by substituting trans-tert-butyl-4-aminocyclohexylcarbamate for tert-butyl piperazine-1-carboxylate and dihydro-2H-pyran-4(3H)-one for 4'-chlorobiphenyl-2-carboxaldehyde in the procedure for Compound 1A.

Compound 123B trans-N1-(tetrahydro-2H-pyran-4-yl)cyclohexane-1,4-diamine bis(2,2,2-trifluoroacetate)

The title compound was prepared by substituting Compound 123A for Compound 39A in the procedure for Compound 39B.

Compound 123C trans-4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-ylamino)cyclohexyl]amino}phenyl)sulfonyl]-2-(1H-pyrrolo[2,3-b]pyridin-5-yloxy)benzamide The title compound was prepared by substituting Compound 123B for Compound 100B in the procedure for Compound 100C. ¹H NMR (500 MHz, pyridine-d₅) δ 13.01 (s, 1H), 9.28 (d, 1H), 8.48 (d, 1H), 8.38 (dd, 1H), 8.32 (d, 1H), 8.24 (d, 1H), 7.67-7.69 (m, 2H), 7.44 (d, 2H), 7.08 (d, 2H), 6.91 (d, 1H), 6.78 (dd, 1H), 6.59 (d, 1H), 6.48 (dd, 1H), 4.01 (d, 2H), 3.44-3.49 (m, 1H), 3.37-3.43 (m, 2H), 3.01-3.09 (m, 5H), 2.85 (t, 1H), 2.78 (s, 2H), 2.27 (t, 2H), 2.13-2.18 (m, 4H), 2.05 (t, 4H), 1.97 (s, 2H), 1.93 (d, 2H), 1.52-1.60 (m, 2H), 1.44-1.50 (m, 2H), 1.39 (t, 2H), 1.25-1.34 (m, 2H), 0.94 (s, 6H).

Compound 124 trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 124A trans-4-morpholinocyclohexanol Trans-4-Aminocyclohexanol (0.5 g), 1-bromo-2-(2-bromoethoxy)ethane (1.07 g) and triethylamine (2.42 ml) were dissolved in anhydrous acetonitrile (20 ml). The reaction mixture was heated at 60° C. overnight. The organic solvent was removed under vacuum. The residue was purified with flash column chromatography on silica gel eluting with 7%-10% methanol in dichloromethane to give the title compound.

Compound 124B trans-5-bromo-6-(4-morpholinocyclohexyloxy)pyridine-3-sulfonamide

The title compound was prepared by substituting Compound 124A for (tetrahydro-2H-pyran-4-yl)methanol and Compound 36A for 4-fluoro-3-nitrobenzenesulfonamide in the procedure for Compound 24A.

Compound 124C trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 124B for Compound 11B in the procedure for Compound 11D. ¹H NMR (400 MHz, dimethylsulfoxide-d₆) δ 11.67 (s, 1H), 8.56 (m, 2H), 8.03 (d, 1H), 7.80 (m, 1H), 7.50 (m, 3H), 7.34 (d, 2H), 7.12 (m, 1H), 7.04 (d, 2H), 6.67 (dd, 1H), 6.39 (dd, 1H), 6.19 (d, 1H), 3.99 (m, 1H), 3.67 (m, 1H), 3.37 (m, 2H), 3.24 (m, 2H), 3.07 (m, 4H), 2.89 (m, 1H), 2.71 (m, 2H), 2.16 (m, 6H), 1.96 (s, 3H), 1.80 (m, 4H), 1.38 (t, 2H), 1.27 (m, 2H), 0.92 (s, 6H).

Compound 125 trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide Compound 125A 4-(((trans)-4-methoxycyclohexyl)methoxy)-3-nitrobenzenesulfonamide Separation of the cis and trans mixture of Compound 121B on a reverse phase HPLC provided the title compound.

Compound 125B trans-4-(4-{[2-(4-chlorophenyl)-4,4-dimethylcyclohex-1-en-1-yl]methyl}piperazin-1-yl)-N-({4-[(4-methoxycyclohexyl)methoxy]-3-nitrophenyl}sulfonyl)-2-(1H-pyrrolo[2,3-b]pyridin-5-yloxy)benzamide The title compound was prepared as described in the procedure for Compound 11D using Compound 125A in place of Compound 11B. ¹H NMR (500 MHz, dimethylsulfoxide-d₆) δ 11.68 (s, 1H), 8.34 (s, 1H), 7.96-8.09 (m, 2H), 7.51 (dd, 3H), 7.32-7.39 (m, 3H), 7.04 (d, 2H), 6.68 (dd, 1H), 6.39 (dd, 1H), 6.20 (d, 1H), 4.02 (d, 2H), 3.24 (s, 3H), 3.00-3.15 (m, 5H), 2.83 (s, 2H), 2.09-2.36 (m, 6H), 2.03 (d, 2H), 1.96 (s, 2H), 1.77-1.86 (m, 2H), 1.73 (s, 1H), 1.39 (t, 2H), 1.02-1.17 (m, 4H), 0.92 (s, 6H).

Compound 126 tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylate Compound 126A tert-butyl 4-fluoro-4-(hydroxymethyl)piperidine-1-carboxylate 1-Tert-butyl 4-ethyl 4-fluoropiperidine-1,4-dicarboxylate (1.0 g) in tetrahydrofuran (5 ml) was treated with 1.0 N LiAlH₄ in THF (2.54 ml) at 0° C. The reaction mixture was stirred at room temperature for 2 hours. Water (0.6 ml) was added to the reaction mixture drop-wise, followed by 2 N aqueous NaOH (0.2 ml). The reaction was stirred for another 1 hour. The solid was removed by filtration via a pack of Celite and washed with ethyl acetate. The filtrate was washed with brine, dried over MgSO₄, filtered, and concentrated to give the product.

Compound 126B tert-butyl 4-fluoro-4-((2-nitro-4-sulfamoylphenoxy)methyl)piperidine-1-carboxylate The title compound was prepared by substituting Compound 126A for (tetrahydro-2H-pyran-4-yl)methanol in the procedure for Compound 24A.

Compound 126C tert-butyl 4-{[4-({[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]amino}sulfonyl)-2-nitrophenoxy]methyl}-4-fluoropiperidine-1-carboxylatcyl)oxy]benzamide The title compound was prepared by substituting Compound 126B for Compound 11B in the procedure for Compound 11D. $^1$H NMR (500 MHz, dimethylsulfoxide-d$_6$) δ 11.67 (s, 1H), 8.36 (s, 2H), 8.02-8.06 (m, 2H), 7.49-7.53 (m, 3H), 7.40 (d, 1H), 7.35 (d, 2H), 7.04 (d, 1H), 6.67 (dd, 1H), 6.39 (dd, 1H), 6.21 (d, 1H), 4.36 (d, 2H), 3.83-3.85 (m, 2H), 3.09 (s, 4H), 2.33 (s, 2H), 2.27-2.32 (m, 4H), 2.13-2.16 (m, 2H), 1.96 (s, 2H), 1.83-1.92 (m, 2H), 1.67-1.75 (m, 2H), 1.38-1.41 (m, 11H), 0.92 (s, 6H).

Compound 127

4-(4-{[2-(4-chlorophenyl)-4,4-dimethylcyclohex-1-en-1-yl]methyl}piperazin-1-yl)-N-({4-[(4-fluoropiperidin-4-yl)methoxy]-3-nitrophenyl}sulfonyl)-2-(1H-pyrrolo[2,3-b]pyridin-5-yloxy)benzamide The title compound was prepared by substituting Compound 126C for Compound 1A in the procedure for Compound 1B. $^1$H NMR (500 MHz, dimethylsulfoxide-d$_6$) δ 11.50 (s, 1H), 8.14 (d, 1H), 7.90 (d, 2H), 7.80 (dd, 1H), 7.60 (d, 1H), 7.40 (t, 1H), 7.35 (d, 2H), 7.25 (t, 1H), 7.13 (d, 1H), 7.05 (d, 2H), 6.61 (dd, 1H), 6.30 (dd, 1H), 6.26 (d, 1H), 4.28 (d, 2H), 3.10-3.13 (m, 2H), 2.91-3.00 (m, 6H), 2.73 (s, 2H), 1.96-2.02 (m, 4H), 1.77-1.89 (m, 2H), 1.39 (t, 2H), 0.93 (s, 6H).

Compound 128 trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide

Compound 128A tert-butyl 4-(tetrahydro-2H-pyran-4-yl)piperazine-1-carboxylate The title compound was prepared by substituting tert-butyl piperazine-1-carboxylate for morpholine and dihydro-2H-pyran-4(3H)-one for tert-butyl 4-oxocyclohexylcarbamate in the procedure for Compound 39A.

Compound 128B 1-(tetrahydro-2H-pyran-4-yl)piperazine dihydrochloride

To a solution of Compound 128A (3.92 g) in ether was added HCl (25 ml, 2M in ether) and the reaction mixture was stirred for 16 hours at room temperature. The solid product was filtered off, dried and used in next step without further purification.

Compound 128C trans-tert-butyl-4-(4-(tetrahydro-2H-pyran-4-yl)piperazin-1-yl)cyclohexylcarbamate The title compound was prepared by substituting Compound 128B for morpholine in the procedure for Compound 39A.

Compound 128D trans-4-(4-(tetrahydro-2H-pyran-4-yl)piperazin-1-yl)cyclohexanamine tris(2,2,2-trifluoroacetate)

The title compound was prepared by substituting Compound 128C for Compound 39A in the procedure for Compound 39B.

Compound 128E trans-4-(4-{[2-(4-chlorophenyl)-4,4-dimethylcyclohex-1-en-1-yl]methyl}piperazin-1-yl)-N-[(3-nitro-4-{[4-(4-tetrahydro-2H-pyran-4-ylpiperazin-1-yl)cyclohexyl]amino}phenyl)sulfonyl]-2-(1H-pyrrolo[2,3-b]pyridin-5-yloxy)benzamide The title compound was prepared by substituting Compound 128D for Compound 100B in the procedure for Compound 100C. $^1$H NMR (500 MHz, pyridine-d$_5$) δ 13.07 (s, 1H), 9.28-9.32 (m, 1H), 8.44 (t, 1H), 8.34-8.39 (m, 2H), 8.10-8.14 (m, 1H), 7.66-7.69 (m, 2H), 7.44 (d, 2H), 7.07 (d, 2H), 6.92 (t, 1H), 6.73-6.77 (m, 1H), 6.52-6.55 (m, 1H), 6.49-6.52 (m, 1H), 3.99-4.06 (m, 2H), 3.29-3.36 (m, 2H), 3.03-3.09 (m, 4H), 2.77 (s, 2H), 2.62 (s, 8H), 2.24-2.29 (m, 3H), 2.10-2.16 (m, 5H), 2.05 (s, 2H), 1.97 (s, 2H), 1.92 (s, 2H), 1.70 (d, 2H), 1.57 (td, 2H), 1.34-1.43 (m, 4H), 1.20-1.30 (m, 2H), 0.93 (s, 6H).

Compound 129

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide

Compound 129A (1-(1,3-difluoropropan-2-yl)piperidin-4-yl)methanol

A suspension of piperidin-4-ylmethanol (0.250 g), sodium triacetoxyborohydride (0.690 g) and 1,3-difluoropropan-2-one (0.245 g) were stirred together in dichloromethane. After stirring overnight the reaction was poured into saturated aqueous NaHCO$_3$ solution (10 ml) and stirred for 15 minutes. The reaction was extracted with dichloromethane (3×25 ml), dried over magnesium sulfate, filtered, and concentrated. Silica gel chromatography (GraceResolv 12 g) eluting with a gradient of 0.75% to 3% methanol/dichloromethane gave the title compound.

Compound 129B 4-((1-(1,3-difluoropropan-2-yl)piperidin-4-yl)methoxy)-3-nitrobenzenesulfonamide To a solution of (1-(1,3-difluoropropan-2-yl)piperidin-4-yl)methanol (0.068 g) in tetrahydrofuran (1 ml) was added

Compound 129C 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]piperidin-4-yl}methoxy)-3-nitrophenyl]sulfonyl}-2-(1H-pyrrolo[2,3-b]pyridin-5-yloxy)benzamide The title compound was prepared by substituting Compound 129B for Compound 1F and Compound 3J for Compound 1E in the procedure for Compound 1G. $^1$H NMR (300 MHz, dimethylsulfoxide-$d_6$) δ 11.67 (s, 1H), 11.47-10.98 (m, 1H), 8.33 (d, 1H), 8.03 (d, 2H), 7.50 (dd, 3H), 7.36 (t, 3H), 7.04 (d, 2H), 6.67 (d, 1H), 6.39 (dd, 1H), 6.20 (s, 1H), 4.62 (dd, 4H), 4.06 (d, 2H), 3.18-2.71 (m, 11H), 2.20 (d, 6H), 1.96 (s, 2H), 1.73 (d, 3H), 1.35 (d, 4H), 0.92 (s, 6H).

Compound 130

4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide

Compound 130A (R)-tert-butyl 1-(tetrahydro-2H-pyran-4-yl)pyrrolidin-3-ylcarbamate The title compound was prepared by substituting dihydro-2H-pyran-4(3H)-one for 4'-chlorobiphenyl-2-carboxaldehyde and (R)-tert-butyl pyrrolidin-3-ylcarbamate for tert-butyl piperazine-1-carboxylate in the procedure for Compound 1A.

Compound 130B (R)-1-(tetrahydro-2H-pyran-4-yl)pyrrolidin-3-amino

A solution of Compound 130A (550 mg) in dichloromethane (25 ml) was cooled in an ice bath under nitrogen. 2,2,2-Trifluoroacetic acid (8.333 ml) was added and the reaction was stirred for 2 hours. The product was obtained by concentration and high vacuum drying.

Compound 130C (R)-3-nitro-4-(1-(tetrahydro-2H-pyran-4-yl)pyrrolidin-3-ylamino)benzenesulfonamide The title compound was prepared by substituting Compound 130B for (tetrahydropyran-4-yl)methylamine in the procedure for Compound 1F.

Compound 130D 4-(4-{[2-(4-chlorophenyl)-4,4-dimethylcyclohex-1-en-1-yl]methyl}piperazin-1-yl)-N-[(3-nitro-4-{[(3R)-1-tetrahydro-2H-pyran-4-ylpyrrolidin-3-yl]amino}phenyl)sulfonyl]-2-(1H-pyrrolo[2,3-b]pyridin-5-yloxy)benzamide To a solution of Compound 3J (90 mg), Compound 130C (64.2 mg), triethylamine (0.077 ml), N,N-dimethylpyridin-4-amine (38.5 mg) in a mixture of dichloromethane (5 ml) and N,N-dimethylformamide (0.5 ml) was added $N^1$-((ethylimino)methylene)-$N^3,N^3$-dimethylpropane-1,3-diamine, hydrochloric acid (60.4 mg) and the mixture was stirred 18 hours. This was concentrated on high vacuum and the crude was purified by reverse phase chromatography with ammonium acetate buffer/acetonitrile. 1H NMR (500 MHz, pyridine-$d_5$) δ 13.03 (s, 1H), 9.27 (d, 1H), 8.59 (d, 1H), 8.43 (d, 1H), 8.37 (dd, 1H), 8.11 (d, 1H), 7.65-7.67 (m, 2H), 7.44 (d, 2H), 7.07 (d, 2H), 6.88 (d, 1H), 6.76 (dd, 1H), 6.54 (d, 1H), 6.48 (m, 1H), 4.06 (m, 1H), 3.98 (d, 2H), 3.35 (t, 2H), 3.07 (m, 4H), 2.73-2.80 (m, 4H), 2.68-2.72 (m, 1H), 2.36 (q, 1H), 2.11-2.30 (m, 9H), 1.97 (m, 2H), 1.62-1.71 (m, 3H), 1.48-1.58 (m, 2H), 1.39 (t, 2H), 0.94 (s, 6H).

Compound 131

4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide

Compound 131A tert-butyl (3R)-1-(2,2-dimethyltetrahydro-2H-pyran-4-yl)pyrrolidin-3-ylcarbamate The title compound was prepared by substituting 2,2-dimethyldihydro-2H-pyran-4(3H)-one for 4'-chlorobiphenyl-2-carboxaldehyde and (R)-tert-butyl pyrrolidin-3-ylcarbamate for tert-butyl piperazine-1-carboxylate in the procedure for Compound 1A.

Compound 131B (3R)-1-(2,2-dimethyltetrahydro-2H-pyran-4-yl)pyrrolidin-3-amine The title compound was prepared by substituting Compound 131A for Compound 130A in the procedure for Compound 130B.

Compound 131C 4-((3R)-(1-(2,2-dimethyltetrahydro-2H-pyran-4-yl)pyrrolidin-3-ylamino)-3-nitrobenzenesulfonamide The title compound was prepared by substituting Compound 131B for (tetrahydropyran-4-yl)methylamine in the procedure for Compound 1F.

Compound 131D 4-(4-{[2-(4-chlorophenyl)-4,4-dimethylcyclohex-1-en-1-yl]methyl}piperazin-1-yl)-N-[(4-{[(3R)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide The title compound was prepared by substituting Compound 131C for Compound 130C in the procedure for Compound 130D. 1H NMR (500 MHz, pyridine-$d_5$) δ 13.03 (d, 1H), 9.28 (m, 1H), 8.61 (m, 1H), 8.44 (d, 1H), 8.38 (dd, 1H), 8.11 (d, 1H), 7.64-7.68 (m, 2H), 7.44 (d, 2H), 7.07 (d, 2H), 6.89 (m, 1H), 6.76 (dd, 1H), 6.54 (m, 1H), 6.49 (m, 1H), 4.08 (m, 1H), 3.78 (m, 1H), 3.61 (m, 1H), 3.07 (m, 4H), 2.71-2.82 (m, 5H), 2.37-2.44 (m, 2H), 2.19-2.29 (m, 3H), 2.14 (m, 5H), 1.97 (s, 2H), 1.76 (m, 1H), 1.66 (m, 2H), 1.32-1.49 (m, 4H), 1.28 (d, 3H), 1.20 (s, 3H), 0.94 (s, 6H).

Compound 132

4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide

Compound 132A (S)-tert-butyl 1-(tetrahydro-2H-pyran-4-yl)pyrrolidin-3-ylcarbamate The title compound was prepared by substituting dihydro-2H-pyran-4(3H)-one for 4'-chlorobiphenyl-2-carboxaldehyde and (S)-tert-butyl pyrrolidin-3-ylcarbamate for tert-butyl piperazine-1-carboxylate in the procedure for Compound 1A.

Compound 132B (S)-1-(tetrahydro-2H-pyran-4-yl)pyrrolidin-3-amine

The title compound was prepared by substituting Compound 132A for Compound 130A in the procedure for Compound 130B.

Compound 132C (S)-3-nitro-4-(1-(tetrahydro-2H-pyran-4-yl)pyrrolidin-3-ylamino)benzenesulfonamide The title compound was prepared by substituting Compound 132B for (tetrahydropyran-4-yl)methylamine in the procedure for Compound 1F.

Compound 132D 4-(4-{[2-(4-chlorophenyl)-4,4-dimethylcyclohex-1-en-1-yl]methyl}piperazin-1-yl)-N-[(3-nitro-4-{[(3S)-1-tetrahydro-2H-pyran-4-ylpyrrolidin-3-yl]amino}phenyl)sulfonyl]-2-(1H-pyrrolo[2,3-b]pyridin-5-yloxy)benzamide The title compound was prepared by substituting Compound 132C for Compound 130C in the procedure for Compound 130D. $^1$H NMR (500 MHz, pyridine-$d_5$) δ 13.04 (m, 1H), 9.27 (d, 1H), 8.58 (d, 1H), 8.43 (d, 1H), 8.37 (dd, 1H), 8.11 (d, 1H), 7.64-7.68 (m, 2H), 7.44 (d, 2H), 7.07 (d, 2H), 6.88 (d, 1H), 6.75 (dd, 1H), 6.54 (m, 1H), 6.49 (m, 1H), 4.06 (m, 1H), 3.98 (d, 2H), 3.36 (t, 2H), 3.07 (m, 4H), 2.68-2.80 (m, 5H), 2.36 (m, 1H), 2.09-2.29 (m, 9H), 1.97 (s, 2H), 1.62-1.72 (m, 3H), 1.48-1.60 (m, 2H), 1.39 (t, 2H), 0.94 (s, 6H).

Compound 133

4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide

Compound 133A tert-butyl (3S)-1-(2,2-dimethyltetrahydro-2H-pyran-4-yl)pyrrolidin-3-ylcarbamate The title compound was prepared by substituting 2,2-dimethyldihydro-2H-pyran-4(3H)-one for 4'-chlorobiphenyl-2-carboxaldehyde and (S)-tert-butyl pyrrolidin-3-ylcarbamate for tert-butyl piperazine-1-carboxylate in the procedure for Compound 1A.

Compound 133B (3S)-1-(2,2-dimethyltetrahydro-2H-pyran-4-yl)pyrrolidin-3-amine The title compound was prepared by substituting Compound 133A for Compound 130A in the procedure for Compound 130B.

Compound 133C 4-(3S)-(1-(2,2-dimethyltetrahydro-2H-pyran-4-yl)pyrrolidin-3-ylamino)-3-nitro benzenesulfonamide The title compound was prepared by substituting Compound 133B for (tetrahydropyran-4-yl)methylamine in the procedure for Compound 1F.

Compound 133D 4-(4-{[2-(4-chlorophenyl)-4,4-dimethylcyclohex-1-en-1-yl]methyl}piperazin-1-yl)-N-[(4-{[(3S)-1-(2,2-dimethyltetrahydro-2H-pyran-4-yl)pyrrolidin-3-yl]amino}-3-nitrophenyl)sulfonyl]-2-(1H-pyrrolo[2,3-b]pyridin-5-yloxy)benzamide The title compound was prepared by substituting Compound 133C for Compound 130C in the procedure for Compound 130D. $^1$H NMR (500 MHz, pyridine-$d_5$) δ 13.03 (d, 1H), 9.28 (m, 1H), 8.61 (m, 1H), 8.43 (d, 1H), 8.38 (dd, 1H), 8.11 (d, 1H), 7.64-7.68 (m, 2H), 7.44 (d, 2H), 7.07 (d, 2H), 6.89 (m, 1H), 6.76 (dd, 1H), 6.54 (m, 1H), 6.49 (m, 1H), 4.08 (m, 1H), 3.78 (m, 1H), 3.61 (m, 1H), 3.07 (m, 4H), 2.71-2.82 (m, 5H), 2.37-2.44 (m, 2H), 2.19-2.29 (m, 3H), 2.14 (m, 5H), 1.97 (s, 2H), 1.76 (m, 1H), 1.66 (m, 2H), 1.33-1.48 (m, 4H), 1.28 (d, 3H), 1.20 (s, 3H), 0.94 (s, 6H).

Compound 134

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide

Compound 134A 4-(morpholin-2-ylmethylamino)-3-nitrobenzenesulfonamide

A solution of Compound 113A (0.8 g) in dichloromethane (10 ml) and trifluoroacetic acid (10 ml) was stirred at room temperature for 2 hours. The solvents were evaporated and the residue triturated with diethyl ether. The resulting solid was dissolved in 5% aqueous sodium carbonate solution (20 ml). The solution was concentrated to dryness and the resulting solid was triturated with a solution of 10% methanol in dichloromethane several times. Evaporation of the organic solvents gave the title compound.

Compound 134B 4-((4-methylmorpholin-2-yl)methylamino)-3-nitrobenzenesulfonamide To a solution of Compound 134A (158 mg) in anhydrous N,N-dimethylformamide (4 ml) was added sodium carbonate (64 mg) and methyl iodide (78 mg). After stirring overnight at room temperature, the mixture was evaporated to dryness. The crude product was then absorbed on silica gel (6 g) and purified on a silica gel column eluting with 10% methanol in dichloromethane to give the title compound.

Compound 134C 4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide The title compound was prepared by substituting Compound 134B for Compound 130C in the procedure for Compound 130D. $^1$H NMR (500 MHz, pyridine-$d_5$) δ 13.00 (s, 1H), 9.27 (d, 1H), 8.87 (t, 1H), 8.43 (d, 1H), 8.32 (dd, 1H), 8.11 (d, 1H), 7.65 (m, 2H), 7.44 (d, 2H), 7.07 (d, 2H), 6.91 (d, 1H), 6.75 (dd, 1H), 6.54 (d, 1H), 6.48 (m, 1H), 3.92 (m, 1H), 3.86 (d, 1H), 3.67 (dt, 1H), 3.49-3.39 (m, 2H), 3.07 (m, 4H), 2.77 (s, 2H), 3.71 (m, 1H), 2.49 (d, 1H), 2.26 (m, 2H), 2.16 (s, 3H), 2.14 (m, 4H), 2.03 (dt, 1H), 1.97 (s, 2H), 1.90 (t, 1H), 1.39 (t, 2H), 0.94 (s, 6H).

Compound 135

4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide

Compound 135A 4-((4-(2-methoxyethyl)morpholin-2-yl)methylamino)-3-nitrobenzenesulfonamide The title compound was prepared by substituting 2-methoxyethyl bromide for methyl iodide in the procedure for Compound 134B.

Compound 135B 4-(4-{[2-(4-chlorophenyl)-4,4-dimethylcyclohex-1-en-1-yl]methyl}piperazin-1-yl)-N-{[4-({[4-(2-methoxyethyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 135A for Compound 130C in the procedure for Compound 130D. $^1$H NMR (500 MHz, pyridine-$d_5$) δ 12.98 (s, 1H), 9.26 (d, 1H), 8.88 (t, 1H), 8.43 (d, 1H), 8.32 (dd, 1H), 8.11 (d, 1H), 7.66 (m, 2H), 7.44 (d, 2H), 7.07 (d, 2H), 6.91 (d, 1H), 6.75 (dd, 1H), 6.54 (d, 1H), 6.48 (m, 1H), 3.93 (m, 1H), 3.87 (d, 1H), 3.70 (dt, 1H), 3.51 (t, 2H), 3.48-3.38 (m, 2H), 3.27 (s, 3H), 3.07 (m, 4H), 2.95 (d, 1H), 2.77 (s, 2H), 2.70 (m, 1H), 2.57 (t, 2H), 2.27-2.07 (m, 8H), 1.97 (s, 2H), 1.39 (t, 2H), 0.94 (s, 6H).

Compound 136

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 136A 4-((4-acetylmorpholin-2-yl)methylamino)-3-nitrobenzenesulfonamide The title compound was prepared by substituting acetic anhydride for methyl iodide in the procedure for Compound 134B.

Compound 136B

N-[(4-{[(4-acetylmorpholin-2-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 136A for Compound 130C in the procedure for Compound 130D. $^1$H NMR (500 MHz, pyridine-$d_5$) δ 13.00 (s, 1H), 9.26 (s, 1H), 8.85 (s, 1H), 8.43 (d, 1H), 8.32 (dd, 1H), 8.10 (d, 1H), 7.65 (m, 2H), 7.44 (d, 2H), 7.07 (d, 2H), 6.91 (dd, 1H), 6.75 (dd, 1H), 6.54 (s, 1H), 6.48 (s, 1H), 4.73 (dd, 1H), 3.93-3.65 (m, 2H), 3.60-3.40 (m, 4H), 3.12 (m, 1H), 3.07 (m, 4H), 2.77 (s, 2H), 2.70 (m, 1H), 2.57 (t, 2H), 2.14 (s, 3H), 2.27-2.07 (m, 4H), 1.97 (s, 2H), 1.39 (t, 2H), 0.93 (s, 6H).

Compound 137

4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide Compound 137A ethyl 4-fluorobut-2-enoate Ethyl 2-fluoroacetate (21.0 g) in $CH_2Cl_2$ (200 ml) at −78° C. was treated dropwise over 45 min with a 1.0 M solution of diisobutylaluminum hydride in $CH_2Cl_2$ (200 ml) maintaining the internal temperature below −70° C. Stirring was continued at −78° C. for 30 minutes and then (carbethoxymethylene)triphenylphosphorane (70.0 g) was added in one portion. The reaction mixture was allowed to slowly reach room temperature while stirring overnight. It was then quenched with methanol, filtered and concentrated to give the product as a mixture of isomers (E/Z=3:1).

Compound 137B trans-ethyl 1-benzyl-4-(fluoromethyl)pyrrolidine-3-carboxylate

A mixture of N-benzyl-1-methoxy-N-((trimethylsilyl)methyl)methanamine (4.5 g) and Compound 137A (2.5 g) in dichloromethane (50 ml) was cooled to 0° C., treated dropwise with trifluoroacetic acid (0.15 ml), stirred for 4 hours at 0° C. and neutralized with saturated aqueous $Na_2CO_3$ solution. The mixture was poured into a separatory funnel and the layers separated. The organic layer was washed with water and brine, dried ($MgSO_4$), filtered, concentrated and chromatographed on silica gel with 0-20% ethyl acetate in hexanes as eluent to give both the cis and trans isomers of the product. Only the trans diastereomers were carried on in the following steps.

Compound 137C trans-ethyl 4-(fluoromethyl)pyrrolidine-3-carboxylate

Compound 137B (0.83 g) in ethanol (9 ml) was treated with 10% Pd/C (0.208 g) and ammonium formate (1.97 g), refluxed for 1.5 hours, concentrated, dissolved in dichloromethane, filtered though a pad of celite rinsing with dichloromethane, and concentrated to give the product.

Compound 137D trans-1-benzyl 3-ethyl 4-(fluoromethyl)pyrrolidine-1,3-dicarboxylate Compound 137C (0.44 g) in dioxane (4 ml) and water (4 ml) at 0° C. was treated sequentially with $Na_2CO_3$ (0.89 g) and benzyl chloroformate (0.48 ml). The reaction mixture was stirred at 0° C. for 3 hours and was then allowed to slowly warm to room temperature over 1.5 hours. The reaction mixture was diluted with ethyl acetate, washed with water and brine, dried ($MgSO_4$), filtered, concentrated and chromatographed on silica gel with 10-25% ethyl acetate in hexanes as eluent to give the product.

Compound 137E trans-1-(benzyloxycarbonyl)-4-(fluoromethyl)pyrrolidine-3-carboxylic Acid The title compound was prepared by substituting Compound 137D for Compound 15G in the procedure for Compound 15H.

Compound 137F trans-benzyl 3-(fluoromethyl)-4-(hydroxymethyl)pyrrolidine-1-carboxylate Compound 137E (0.563 g) in tetrahydrofuran (10 ml) at 0° C. was treated dropwise with a 1 M solution of borane in tetrahydrofuran (4 ml), stirred for 3 hours and then slowly quenched with saturated aqueous $NH_4Cl$ solution. The reaction mixture was diluted with ethyl acetate, washed with water and brine, dried ($MgSO_4$), filtered and concentrated to give the product.

Compound 137G trans-benzyl 3-(fluoromethyl)-4-((2-nitro-4-sulfamoylphenoxy)methyl)pyrrolidine-1-carboxylate The title compound was prepared by substituting Compound 137F for (tetrahydro-2H-pyran-4-yl)methanol in the procedure for Compound 24A.

Compound 137H trans-4-((4-(fluoromethyl)pyrrolidin-3-yl)methoxy)-3-nitrobenzenesulfonamide Compound 137G (0.232 g) in acetic acid (2.5 ml) was treated with hydrobromic acid (33 wt % in acetic acid) (0.875 ml) at ambient temperature, stirred for 1 hour and concentrated. The product was free-based using a MEGA BE-SCX column with 1:1 $CH_2Cl_2$/methanol as eluent for the hydrobromic acid and acetic acid. The product was released from the column with 10% (7 M ammonia in methanol) in $CH_2Cl_2$ as eluent.

Compound 137I trans-4-((4-(fluoromethyl)-1-(oxetan-3-yl)pyrrolidin-3-yl)methoxy)-3-nitrobenzenesulfonamide The title compound was prepared by substituting Compound 137H for tert-butyl piperazine-1-carboxylate and 3-oxetanone for 4'-chlorobiphenyl-2-carboxaldehyde in the procedure for Compound 1A.

Compound 137J 4-(4-{[2-(4-chlorophenyl)-4,4-dimethylcyclohex-1-en-1-yl]methyl}piperazin-1-yl)-N-[(4-{[trans-4-(fluoromethyl)-1-oxetan-3-ylpyrrolidin-3-yl]methoxy}-3-nitrophenyl)sulfonyl]-2-(1H-pyrrolo[2,3-b]pyridin-5-yloxy)benzamide The title compound was prepared by substituting Compound 137I for Compound 11B in the procedure for Compound 11D. $^1$H NMR (300 MHz, dimethylsulfoxide-d$_6$) δ 11.67 (s, 1H), 8.35 (d, 1H), 8.03 (m, 2H), 7.51 (m, 3H), 7.37 (m, 3H), 7.04 (m, 2H), 6.67 (dd, 1H), 6.39 (dd, 1H), 6.21 (d, 1H), 4.45 (m, 6H), 4.21 (d, 2H), 3.62 (m, 1H), 3.08 (m, 4H), 2.72 (m, 5H), 2.31 (m, 9H), 1.96 (s, 2H), 1.39 (t, 2H), 0.93 (s, 6H).

Compound 138

4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide Compound 138A (4-fluorotetrahydro-2H-pyran-4-yl)methyl methanesulfonate A mixture of Compound 37C (1.4 g), methanesulfonyl chloride (1.054 ml), triethylamine (2.99 ml), and 4-dimethylaminopyridine (0.051 g) in CH$_2$Cl$_2$ (20 ml) was stirred at 0° C. for 2 hours, concentrated and chromatographed on silica gel eluting with 30% ethyl acetate in hexanes to give the product.

Compound 138B 2-((4-fluorotetrahydro-2H-pyran-4-yl)methyl)isoindoline-1,3-dione

A mixture of Compound 138A (1.8 g) and potassium phthalimide (2.356 g) in N,N-dimethylformamide (30 ml) was heated at 150° C. overnight, diluted with ethyl acetate, washed with water and brine, dried (MgSO$_4$), filtered, concentrated and chromatographed on silica gel eluting with 30% ethyl acetate in hexanes to give the product.

Compound 138C (4-fluorotetrahydro-2H-pyran-4-yl)methanamine

A mixture of Compound 138B (1.4 g) and hydrazine (1.548 ml) in ethanol (40 ml) was heated at 70° C. overnight, cooled to room temperature, slurried with CH$_2$Cl$_2$ (200 ml) and the solid removed by filtration. The filtrate was concentrated and chromatographed on silica gel eluting with 100:5:1 ethyl acetate/methanol/NH$_4$OH to give the product.

Compound 138D 4-((4-fluorotetrahydro-2H-pyran-4-yl)methylamino)-3-nitrobenzenesulfonamide A mixture of 4-fluoro-3-nitrobenzenesulfonamide (0.44 g), Compound 138C (0.266 g), and triethylamine (1.11 ml) in tetrahydrofuran (10 ml) was heated at 70° C. overnight, diluted with ethyl acetate, washed with water and brine, dried (MgSO$_4$), filtered, concentrated and chromatographed on silica gel eluting with 50% ethyl acetate in hexanes to give the product.

Compound 138E 4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]-2-(1H-pyrrolo[2,3-b]pyridin-5-yloxy)benzamide The title compound was prepared by substituting Compound 138D for Compound 11B in the procedure for Compound 11D. $^1$H NMR (500 MHz, dimethylsulfoxide-d$_6$) δ 11.68 (s, 1H), 8.62 (t, 1H), 8.56 (d, 1H), 8.04 (d, 1H), 7.82 (dd, 1H), 7.48-7.54 (m, 3H), 7.34 (d, 2H), 7.24 (d, 1H), 7.04 (d, 2H), 6.68 (dd, 1H), 6.39 (dd, 1H), 6.19 (d, 1H), 3.70-3.77 (m, 4H), 3.50-3.55 (m, 2H), 3.07 (s, 4H), 2.76 (s, 2H), 2.14-2.20 (m, 6H), 1.76-1.84 (m, 4H), 1.38 (t, 2H), 0.92 (s, 6H).

Compound 139

4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide Compound 139A tert-butyl 4-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate The title compound was prepared as described in the procedure for Compound 53B by replacing 1-acetylpiperidin-4-amine with 4-amino-piperidine-1-carboxylic acid tert-butyl ester.

Compound 139B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide To a cooled (0° C.) solution of Compound 139A (960 mg) in dichloromethane (10 ml) was added dropwise trifluoroacetic acid (5 ml). The mixture was stirred at the temperature for 3 hours. Then, the mixture was concentrated under vacuum and the residue was dissolved in dichloromethane (200 ml) and washed with aqueous NaHCO$_3$ and brine. After drying over Na$_2$SO$_4$, the mixture was filtered, and evaporation of the solvent from the filtrate gave the title compound.

Compound 139C 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)-2-(1H-pyrrolo[2,3-b]pyridin-5-yloxy)benzamide To a solution of Compound 139B (120 mg) in tetrahydrofuran (3 ml) and acetic acid (1 ml) was added oxetan-3-one (50.8 mg) and MP-cyanoborohydride (2.15 mmol/g, 150 mg). The mixture was stirred at room temperature overnight. The mixture was filtered. The filtrate was concentrated and the residue was loaded on a silica gel cartridge and eluted with 5-10% 7N NH₃ in methanol in dichloromethane to give the title compound. ¹H NMR (300 MHz, dimethylsulfoxide-d₆) δ 11.62 (s, 1H), 8.51 (d, 1H), 8.20 (d, 1H), 7.99 (d, 1H), 7.74 (m, 1H), 7.48 (m, 3H), 7.35 (d, 2H), 7.05 (d, 2H), 6.66 (dd, 1H), 6.36 (dd, 1H), 6.20 (d, 1H), 4.54 (t, 2H), 4.43 (t, 2H), 3.66 (m, 1H), 3.44 (m, 3H), 3.04 (m, 5H), 2.73 (s, 2H), 2.61 (m, 2H), 2.12 (m, 11H), 1.61 (m, 2H), 1.38 (t, 2H), 0.93 (m, 6H).

Compound 140

4-(4-{[2-(4-chlorophenyl)-4,4-dimethylcyclohex-1-en-1-yl]methyl}piperazin-1-yl)-N-({4-[(1-cyclobutylpiperidin-4-yl)amino]-3-nitrophenyl}sulfonyl)-2-(1H-pyrrolo[2,3-b]pyridin-5-yloxy)benzamide The title compound was prepared as described in the procedure for Compound 139C by replacing oxetan-3-one with cyclobutanone. ¹H NMR (300 MHz, dimethylsulfoxide-d₆) δ 11.58 (s, 1H), 8.47 (d, 1H), 8.12 (d, 1H), 7.97 (d, 1H), 7.74 (d, 1H), 7.53 (d, 1H), 7.45 (m, 1H), 7.36 (m, 3H), 7.02 (m, 3H), 6.64 (dd, 1H), 6.33 (m, 1H), 6.22 (d, 1H), 3.74 (m, 1H), 2.97 (m, 6H), 2.73 (s, 3H), 2.15 (m, 15H), 1.67 (m, 4H), 1.38 (t, 2H), 0.93 (s, 6H).

Compound 141

4-(4-{[2-(4-chlorophenyl)-4,4-dimethylcyclohex-1-en-1-yl]methyl}piperazin-1-yl)-N-[(4-{[1-(2,2-dimethyltetrahydro-2H-pyran-4-yl)piperidin-4-yl]amino}-3-nitrophenyl)sulfonyl]-2-(1H-pyrrolo[2,3-b]pyridin-5-yloxy)benzamide The title compound was prepared as described in the procedure for Compound 139C by replacing oxetan-3-one with 2,2-dimethyltetrahydropyran-4-one. ¹H NMR (300 MHz, dimethylsulfoxide-d₆) δ 11.60 (s, 1H), 8.50 (d, 1H), 8.15 (m, 1H), 7.99 (d, 1H), 7.78 (m, 1H), 7.62 (m, 1H), 7.47 (m, 3H), 7.34 (m, 3H), 7.05 (m, 3H), 6.65 (m, 2H), 6.35 (dd, 1H), 6.21 (d, 1H), 4.56 (d, 3H), 3.89 (m, 3H), 3.67 (m, 6H), 3.45 (m, 2H), 3.04 (m, 3H), 2.75 (m, 3H), 2.14 (m, 3H), 1.71 (m, 5H), 1.16 (s, 9H).

Compound 142

4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide Compound 142A (S)-tert-butyl 1-cyclopropylpyrrolidin-3-ylcarbamate (S)-tert-butyl pyrrolidin-3-ylcarbamate (415 mg), (1-ethoxycyclopropoxy)trimethylsilane (1.8 ml) and molecular sieves (500 mg) were combined in methanol (4.5 ml). Acetic acid (1.3 ml) was added, followed by sodium cyanoborohydride (420 mg). The resulting mixture was heated to reflux for 4 hours. Insoluble material was filtered off and reaction was made basic to pH 14 with addition of 6M aqueous NaOH solution. The solution was extracted three times with diethyl ether, and the combined extracts were dried over MgSO₄, filtered and concentrated to obtain an oil, which was purified by flash chromatography, eluting first with 100% dichloromethane, followed by 5% methanol/dichloromethane and 10% methanol/dichloromethane.

Compound 142B (S)-1-cyclopropylpyrrolidin-3-amine

The title compound was prepared by substituting Compound 142A for Compound 1A in the procedure for Compound 1B.

Compound 142C 4-(4-{[2-(4-chlorophenyl)-4,4-dimethylcyclohex-1-en-1-yl]methyl}piperazin-1-yl)-N-[(4-{[(3S)-1-cyclopropylpyrrolidin-3-yl]amino}-3-nitrophenyl)sulfonyl]-2-(1H-pyrrolo[2,3-b]pyridin-5-yloxy)benzamide The title compound was prepared by substituting Compound 142B for 1-acetylpiperidin-4-amine in the procedure for Compound 53B. ¹H NMR (500 MHz, dimethylsulfoxide-d₆) δ 11.64 (s, 1H), 8.51 (m, 2H), 8.30 (m, 1H), 8.00 (br s, 1H), 7.77 (m, 1H), 7.49 (m, 3H), 7.34 (d, 2H), 7.04 (d, 2H), 6.97 (br s, 1H), 6.67 (dd, 1H), 6.36 (m, 1H), 6.21 (m, 1H), 4.19 (m, 1H), 3.00 (m, 5H), 2.74 (m, 3H), 2.64 (m, 1H), 2.36 (m, 1H), 2.15 (m, 6H), 1.95 (s, 2H), 1.78 (br s, 1H), 1.68 (m, 1H), 1.38 (t, 2H), 1.23 (m, 1H), 0.92 (s, 6H), 0.39 (m, 4H).

Compound 143

4-(4-{[2-(4-chlorophenyl)-4,4-dimethylcyclohex-1-en-1-yl]methyl}piperazin-1-yl)-N-({3-nitro-4-[(1-tetrahydrofuran-3-ylpiperidin-4-yl)amino]phenyl}sulfonyl)-2-(1H-pyrrolo[2,3-b]pyridin-5-yloxy)benzamide The title compound was prepared as described in the procedure for Compound 139C by replacing oxetan-3-one with 3-oxotetrahydrofuran. ¹H NMR (300 MHz, dimethylsulfoxide-d₆) δ 11.65 (s, 1H), 8.53 (d, 1H), 8.21 (m, 1H), 8.02 (m, 1H), 7.80 (dd, 1H), 7.49 (m, 3H), 7.34 (m, 3H), 7.05 (m, 3H), 6.67 (dd, 1H), 6.37 (m, 1H), 6.19 (d, 1H), 4.29 (m, 3H), 3.73 (m, 6H), 3.09 (m, 4H), 2.76 (m, 2H), 2.05 (m, 8H), 1.68 (m, 2H), 1.37 (m, 2H), 0.94 (s, 6H).

Compound 144

4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide Compound 144A (R)-tert-butyl 1-cyclopropylpyrrolidin-3-ylcarbamate The title compound was prepared by substituting (R)-tert-butyl pyrrolidin-3-ylcarbamate for (S)-tert-butyl pyrrolidin-3-ylcarbamate in the procedure for Compound 142A.

Compound 144B (R)-1-cyclopropylpyrrolidin-3-amine

The title compound was prepared by substituting Compound 144A for Compound 1A in the procedure for Compound 1B.

Compound 144C 4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]-2-(1H-pyrrolo[2,3-b]pyridin-5-yloxy)benzamide The title compound was prepared by substituting Compound 144B for 1-acetylpiperidin-4-amine in the procedure for Compound 53B. $^1$H NMR (500 MHz, dimethylsulfoxide-$d_6$) δ 11.66 (s, 1H), 8.53 (d, 2H), 8.32 (d, 1H), 8.02 (d, 1H), 7.81 (m, 1H), 7.49 (m, 3H), 7.34 (d, 2H), 7.03 (m, 3H), 6.67 (dd, 1H), 6.37 (m, 1H), 6.20 (d, 1H), 4.21 (m, 1H), 3.00 (m, 5H), 2.74 (m, 3H), 2.64 (m, 1H), 2.36 (m, 1H), 2.15 (m, 6H), 1.95 (s, 2H), 1.74 (br s, 1H), 1.66 (m, 1H), 1.38 (t, 2H), 1.23 (m, 1H), 0.92 (s, 6H), 0.39 (m, 4H).

Compound 145

4-(4-{[2-(4-chlorophenyl)-4,4-dimethylcyclohex-1-en-1-yl]methyl}piperazin-1-yl)-N-{[3-nitro-4-({[(3S)-1-tetrahydro-2H-pyran-4-ylpyrrolidin-3-yl]methyl}amino)phenyl]sulfonyl}-2-(1H-pyrrolo[2,3-b]pyridin-5-yloxy)benzamide

Compound 145A (S)-tert-butyl (1-(tetrahydro-2H-pyran-4-yl)pyrrolidin-3-yl)methylcarbamate The title compound was prepared by substituting (R)-tert-butyl pyrrolidin-3-ylmethylcarbamate for tert-butyl piperazine-1-carboxylate and dihydro-2H-pyran-4(3H)-one for 4'-chlorobiphenyl-2-carboxaldehyde in the procedure for Compound 1A.

Compound 145B (S)-(1-(tetrahydro-2H-pyran-4-yl)pyrrolidin-3-yl)methanamine

The title compound was prepared by substituting Compound 145A for Compound 1A in the procedure for Compound 1B.

Compound 145C (S)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((1-(tetrahydro-2H-pyran-4-yl)pyrrolidin-3-yl)methylamino)phenylsulfonyl)benzamide The title compound was prepared by substituting Compound 145B for 1-acetylpiperidin-4-amine in the procedure for Compound 53B. $^1$H NMR (500 MHz, dimethylsulfoxide-$d_6$) δ 11.58 (s, 1H), 8.61 (br s, 1H), 8.46 (s, 1H), 7.96 (d, 1H), 7.72 (m, 1H), 7.54 (d, 1H), 7.45 (t, 1H), 7.37 (br s, 2H), 7.34 (d, 2H), 7.04 (m, 2H), 6.94 (m, 1H), 6.64 (dd, 1H), 6.34 (m, 1H), 6.22 (d, 1H), 3.89 (m, 2H), 3.38 (m, 4H), 3.27 (m, 4H), 3.02 (m, 5H), 2.73 (s, 2H), 2.61 (m, 1H), 2.18 (m, 6H), 2.05 (m, 1H), 1.95 (m, 2H), 1.85 (m, 2H), 1.64 (m, 1H), 1.50 (m, 2H), 1.38 (m, 2H), 0.94 (s, 6H).

Compound 146

4-(4-{[2-(4-chlorophenyl)-4,4-dimethylcyclohex-1-en-1-yl]methyl}piperazin-1-yl)-N-({4-[(3-hydroxy-2,2-dimethylpropyl)amino]-3-nitrophenyl}sulfonyl)-2-(1H-pyrrolo[2,3-b]pyridin-5-yloxy)benzamide The title compound was prepared as described in the procedure for Compound 120B using 3-amino-2,2-dimethylpropan-1-ol in place of Compound 120A. $^1$H NMR (500 MHz, dimethylsulfoxide-$d_6$) δ 11.68 (s, 1H), 11.35 (s, 1H), 8.96 (t, 1H), 8.56 (d, 1H), 8.05 (d, 1H), 7.79 (dd, 1H), 7.46-7.56 (m, 3H), 7.34 (d, 2H), 7.10 (d, 1H), 7.04 (d, 2H), 6.68 (dd, 1H), 6.39 (dd, 1H), 6.19 (d, 1H), 5.10 (t, 1H), 3.29 (d, 1H), 3.24 (d, 1H), 3.07 (s, 4H), 2.75 (s, 2H), 2.17 (d, 6H), 1.95 (s, 2H), 1.38 (t, 2H), 0.93 (d, 12H).

Compound 147

4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide

Compound 147A tert-butyl (1-(methylsulfonyl)piperidin-3-yl)methylcarbamate tert-Butyl piperidin-3-ylmethylcarbamate (500 mg) was dissolved in anhydrous dichloromethane (10 ml), and methanesulfonyl chloride (0.181 ml) was added followed by the addition of triethylamine (1.3 ml). The reaction mixture was stirred at room temperature overnight. The organic solvent was removed under vacuum. The residue was purified with flash column chromatography on silica gel eluting with 0-70% ethyl acetate in hexane to give the title compound.

Compound 147B (1-(methylsulfonyl)piperidin-3-yl)methanamine

Compound 147A (400 mg) was suspended in 4N HCl in dioxane (10 ml) followed by the addition of anhydrous methanol (1 ml). The clear solution was stirred at room temperature for 2 hours. The organic solvent was removed under vacuum. The solid residue was used in the next step without further purification.

Compound 147C 4-(4-{[2-(4-chlorophenyl)-4,4-dimethylcyclohex-1-en-1-yl]methyl}piperazin-1-yl)-N-{[4-({[1-(methylsulfonyl)piperidin-3-yl]methyl}amino)-3-nitrophenyl]sulfonyl}-2-(1H-pyrrolo[2,3-b]pyridin-5-yloxy)benzamide Compound 53A (50 mg), Compound 147B (26 mg) and triethylamine (0.088 ml) were dissolved in anhydrous dioxane (1 ml) and N,N-dimethylformamide (0.2 ml). The reaction vial was heated in a Biotage Initiator microwave reactor at 130° C. for 25 minutes. The solvent was removed under vacuum. The residue was purified by reverse phase HPLC on a C18 column using a gradient of 20-80% acetonitrile/0.1% trifluoroacetic acid in water to give the title compound as the trifluoroacetate salt. The trifluoroacetic acid salt was dissolved in dichloromethane (6 ml) and washed with 50% aqueous NaHCO$_3$. The organic layer was dried over anhydrous Na$_2$SO$_4$ and concentrated to give the title compound. $^1$H NMR (400 MHz, dimethylsulfoxide-d$_6$) δ 11.65 (s, 1H), 8.56 (m, 2H), 8.03 (d, 1H), 7.80 (m, 1H), 7.50 (m, 3H), 7.35 (d, 2H), 7.12 (m, 1H), 7.04 (d, 2H), 6.67 (dd, 1H), 6.38 (dd, 1H), 6.19 (d, 1H), 3.52 (m, 1H), 3.40 (m, 2H), 3.06 (m, 4H), 2.84 (s, 3H), 2.75 (m, 2H), 2.75 (m, 4H), 2.58 (m, 1H), 2.16 (m, 6H), 1.95 (s, 3H), 1.76 (m, 2H), 1.52 (m, 1H), 1.37 (m, 2H), 0.92 (s, 6H).

Compound 148

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 148A tert-butyl(1-acetylpiperidin-3-yl)methylcarbamate The title compound was prepared by substituting acetyl chloride for methanesulfonyl chloride in the procedure for Compound 147A.

Compound 148B 1-(3-(aminomethyl)piperidin-1-yl)ethanone

The title compound was prepared by substituting Compound 148A for Compound 147A in the procedure for Compound 147B.

Compound 148C

N-[(4-{[(1-acetylpiperidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 148B for Compound 147B in the procedure for Compound 147C. $^1$H NMR (400 MHz, dimethylsulfoxide-d$_6$) δ 11.67 (s, 1H), 8.56 (m, 2H), 8.03 (d, 1H), 7.80 (m, 1H), 7.50 (m, 3H), 7.34 (d, 2H), 7.12 (m, 1H), 7.04 (d, 2H), 6.67 (dd, 1H), 6.39 (dd, 1H), 6.19 (d, 1H), 3.99 (m, 1H), 3.67 (m, 1H), 3.37 (m, 2H), 3.24 (m, 2H), 3.07 (m, 4H), 2.89 (m, 1H), 2.71 (m, 2H), 2.16 (m, 6H), 1.96 (s, 3H), 1.80 (m, 4H), 1.38 (t, 2H), 1.27 (m, 2H), 0.92 (s, 6H).

Compound 149

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide Compound 149A (R)-tert-butyl 1-(methylsulfonyl)pyrrolidin-3-ylcarbamate The title compound was prepared by substituting (R)-tert-butyl pyrrolidin-3-ylcarbamate for tert-butyl piperidin-3-ylmethylcarbamate in the procedure for Compound 147A.

Compound 149B (R)-1-(methylsulfonyl)pyrrolidin-3-amine

The title compound was prepared by substituting Compound 149A for Compound 147A in the procedure for Compound 147B.

Compound 149C 4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide The title compound was prepared by substituting Compound 149B for Compound 147B in the procedure for Compound 147C. $^1$H NMR (400 MHz, dimethylsulfoxide-d$_6$) δ 11.65 (s, 1H), 8.55 (d, 1H), 8.29 (d, 1H), 8.02 (d, 1H), 7.86 (dd, 1H), 7.49 (m, 3H), 7.33 (d, 2H), 7.17 (d, 1H), 7.04 (d, 2H), 6.68 (dd, 1H), 6.38 (dd, 1H), 6.20 (d, 1H), 4.41 (m, 1H), 3.69 (m, 1H), 3.39 (m, 3H), 3.06 (m, 4H), 2.97 (s, 3H), 2.76 (m, 2H), 2.27 (m, 8H), 1.93 (m, 2H), 1.54 (m, 1H), 1.38 (t, 2H), 0.92 (s, 6H).

Compound 150

4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 150A ethyl 2-hydroxy-3,3-dimethylcyclohex-1-enecarboxylate Into a 500 ml round-bottomed flask was added diisopropylamine (3.5 ml) in ether (200 ml). After cooling to −30° C., butyllithium (16 ml) (1.6M in hexane) was added slowly. After stirring 30 minutes, the temperature was cooled to −5° C. 2,2-Dimethylcyclohexanone (3 g) was added slowly. The mixture was warmed up to 0° C. and stirred for 1 hour. After cooling to −5° C., hexamethylphosphoramide (8 ml) and ethyl carbonocyanidate (2.5 ml) were added. After stirring at −5° C. for 20 minutes, and warming to room temperature, the reaction was stirred for 1 hour. The mixture was poured into cold water, and the layers were separated. The aqueous layer was extracted with ether (3×20 ml). The combined the organic layers were washed with saturated aqueous NH$_4$Cl (3×20 ml). After drying over Na$_2$SO$_4$, the mixture was filtered and the filtrate was concentrated. The crude product was purified by flash chromatography on silica with 0-10% ethyl acetate in hexanes to provide the title compound.

Compound 150B ethyl 3,3-dimethyl-2-(trifluoromethylsulfonyloxy) cyclohex-1-enecarboxylate The title compound was prepared by substituting Compound 150A for Compound 101A in the procedure for Compound 101B.

Compound 150C ethyl 2-(4-chlorophenyl)-3,3-dimethylcyclohex-1-enecarboxylate

The title compound was prepared by substituting Compound 150B for Compound 101B in the procedure for Compound 101C.

Compound 150D (2-(4-chlorophenyl)-3,3-dimethylcyclohex-1-enyl) methanol

In a 200 ml round-bottomed flask was added Compound 150C (0.97 g) and lithium borohydride (0.47 g) in ether (20 ml) to give a suspension. Methanol (2.2 ml) was added slowly. The mixture was refluxed overnight. The reaction was then cooled, and methanol was added to quench the reaction. 1N aqueous HCl was then added until the pH<7, and ether (3×30 ml) was used to extract the product. The combined organic layers were dried over Na$_2$SO$_4$, filtered, and concentrated. The crude material was purified by flash chromatography on silica with 0-25% ethyl acetate in hexanes to provide the title compound.

Compound 150E 2-(4-chlorophenyl)-3,3-dimethylcyclohex-1-enecarbaldehyde

Into a 100 ml round-bottomed flask was added Compound 150D (0.3 g) and Dess-Martin Periodinane (0.6 g) in dichloromethane (10 ml) to give a suspension. The mixture was stirred at room temperature overnight. After filtration, the mixture was washed with saturated aqueous NaHCO$_3$ (2×20 ml), dried over Na$_2$SO$_4$, filtered, and concentrated. The crude product was purified by flash chromatography on silica with 0-25% ethyl acetate in hexanes to provide the title compound.

Compound 150F methyl 2-(1H-pyrrolo[2,3-b]pyridin-5-yloxy)-4-(4-((2-(4-chlorophenyl)-3,3-dimethylcyclohex-1-enyl) methyl)piperazin-1-yl)benzoate The title compound was prepared by substituting Compound 150E for 4'-chlorobiphenyl-2-carboxaldehyde and Compound 15F for tert-butyl piperazine-1-carboxylate in the procedure for Compound 1A.

Compound 150G 2-(1H-pyrrolo[2,3-b]pyridin-5-yloxy)-4-(4-((2-(4-chlorophenyl)-3,3-dimethylcyclohex-1-enyl)methyl) piperazin-1-yl)benzoic Acid The title compound was prepared by substituting Compound 150F for Compound 101E in the procedure for Compound 101F.

Compound 150H 4-(4-{[2-(4-chlorophenyl)-3,3-dimethylcyclohex-1-en-1-yl]methyl}piperazin-1-yl)-N-({3-nitro-4-[(tetrahydro-2H-pyran-4-ylmethyl)amino] phenyl}sulfonyl)-2-(1H-pyrrolo[2,3-b]pyridin-5-yloxy)benzamide The title compound was prepared by substituting Compound 150G for Compound 3J and Compound 1F for Compound 11B in the procedure for Compound 11D. $^1$H NMR (500 MHz, dimethyl sulfoxide-d$_6$) δ 11.50 (s, 1H), 8.36 (m, 1H), 8.32 (m, 1H), 7.91 (d, 1H), 7.59 (m, 2H), 7.40 (t, 1H), 7.35 (d, 2H), 7.25 (m, 1H), 6.94 (d, 2H), 6.79 (d, 1H), 6.60 (m, 1H), 6.29 (m, 1H), 6.24 (d, 1H), 3.83 (m, 2H), 3.25 (m, 4H), 2.98 (m, 4H), 2.42 (s, 2H), 2.14 (m, 6H), 1.60 (m, 6H), 1.25 (m, 3H), 0.86 (s, 6H).

Compound 151

4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide Compound 151A 1-(1,3-difluoropropan-2-yl)azetidin-3-amine To a solution of tert-butyl azetidin-3-ylcarbamate (0.256 g) and 1,3-difluoropropan-2-one (0.154 g) in dichloromethane (2 ml) was added sodium triacetoxyborohydride (0.473 g) and the reaction was allowed to stirred at room temperature. After 16 hours, the reaction was quenched with saturated NaHCO$_3$ solution (10 ml) and extracted into dichloromethane (25 ml). The organic layer was dried and concentrated. Silica gel chromatography (GraceResolv 12 g) eluting with a gradient of 0.5% to 3.5% methanol/dichloromethane followed by treatment with HCl (4.0M in dioxane, 3 ml) and methanol (0.5 ml) for 2 hours gave the title compound after concentration.

Compound 151B 4-(1-(1,3-difluoropropan-2-yl)azetidin-3-ylamino)-3-nitrobenzenesulfonamide To a suspension of 4-chloro-3-nitrobenzenesulfonamide (0.225 g) and 1-(1,3-difluoropropan-2-yl)azetidin-3-amine (0.193 g) in dioxane (5 ml) was added diisopropylamine (0.832 ml). The reaction was sonicated and then heated to 100° C. After stirring overnight, the reaction was concentrated and loaded onto silica gel (GraceResolv 12 g) and eluted with a gradient of 0.5% to 3.5% methanol/dichloromethane to give the title compound.

Compound 151C 4-(4-{[2-(4-chlorophenyl)-4,4-dimethylcyclohex-1-en-1-yl]methyl}piperazin-1-yl)-N-{[4-({1-[2-fluoro-1-(fluoromethyl)ethyl]azetidin-3-yl}amino)-3-nitrophenyl]sulfonyl}-2-(1H-pyrrolo[2,3-b]pyridin-5-yloxy)benzamide The title compound was prepared by substituting Compound 151B for Compound 1F and Compound 3J for Compound 1E in the procedure for Compound 1G. $^1$H NMR (300 MHz, dimethylsulfoxide-$d_6$) δ 11.66 (s, 1H), 11.54-11.28 (m, 1H), 8.54 (d, 1H), 8.45 (s, 1H), 8.01 (d, 1H), 7.82 (d, 1H), 7.48 (d, 3H), 7.34 (d, 2H), 7.04 (d, 2H), 6.90 (d, 1H), 6.67 (d, 1H), 6.37 (s, 1H), 6.20 (s, 1H), 4.64-4.23 (m, 6H), 3.81 (s, 2H), 3.08 (s, 4H), 2.75 (s, 3H), 2.15 (s, 7H), 1.95 (s, 2H), 1.38 (s, 2H), 0.92 (s, 6H).

Compound 152

4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide Compound 152A tert-butyl (1-(methylsulfonyl)pyrrolidin-3-yl)methylcarbamate The title compound was prepared by substituting tert-butyl pyrrolidin-3-ylmethylcarbamate for tert-butyl piperidin-3-ylmethylcarbamate in the procedure for Compound 147A.

Compound 152B (1-(methylsulfonyl)pyrrolidin-3-yl)methanamine

The title compound was prepared by substituting Compound 152A for Compound 147A in the procedure for Compound 147B.

Compound 152C 4-(4-{[2-(4-chlorophenyl)-4,4-dimethylcyclohex-1-en-1-yl]methyl}piperazin-1-yl)-N-{[4-({[1-(methylsulfonyl)pyrrolidin-3-yl]methyl}amino)-3-nitrophenyl]sulfonyl}-2-(1H-pyrrolo[2,3-b]pyridin-5-yloxy)benzamide The title compound was prepared by substituting Compound 152B for Compound 147B in the procedure for Compound 147C. $^1$H NMR (400 MHz, dimethylsulfoxide-$d_6$) δ 11.60 (s, 1H), 8.49 (m, 2H), 7.99 (s, 1H), 7.73 (m, 1H), 7.53 (d, 1H), 7.47 (s, 1H), 7.42 (m, 1H), 7.34 (d, 2H), 7.04 (m, 3H), 6.65 (m, 1H), 6.35 (s, 1H), 6.22 (s, 1H), 3.41 (m, 4H), 3.22 (m, 2H), 3.03 (m, 4H), 2.89 (s, 3H), 2.73 (m, 2H), 2.59 (m, 1H), 2.17 (m, 6H), 2.00 (m, 4H), 1.68 (m, 1H), 1.38 (t, 2H), 0.92 (s, 6H).

Compound 153

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 153A tert-butyl (1-acetylpyrrolidin-3-yl)methylcarbamate The title compound was prepared by substituting tert-butyl pyrrolidin-3-ylmethylcarbamate for tert-butyl piperidin-3-ylmethylcarbamate and acetyl chloride for methanesulfonyl chloride in the procedure for Compound 147A.

Compound 153B 1-(3-(aminomethyl)pyrrolidin-1-yl)ethanone

The title compound was prepared by substituting Compound 153A for Compound 147A in the procedure for Compound 147B.

Compound 153C

N-[(4-{[(1-acetylpyrrolidin-3-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 153B for Compound 147B in the procedure for Compound 147C. $^1$H NMR (400 MHz, dimethylsulfoxide-$d_6$) δ 11.66 (s, 1H), 8.62 (m, 1H), 8.54 (s, 1H), 8.03 (m, 1H), 7.78 (d, 1H), 7.50 (m, 3H), 7.35 (t, 2H), 7.09 (s, 1H), 7.04 (d, 2H), 6.67 (dd, 1H), 6.37 (d, 1H), 6.20 (s, 1H), 3.56 (m, 1H), 3.42 (m, 4H), 3.43 (m, 4H), 3.23 (m, 1H), 3.07 (m, 4H), 2.74 (m, 2H), 2.16 (m, 6H), 1.93 (m, 5H), 1.38 (t, 2H), 0.93 (s, 6H).

Compound 154

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 154A (R)-tert-butyl 1-acetylpyrrolidin-3-ylcarbamate The title compound was prepared by substituting (R)-tert-butyl pyrrolidin-3-ylcarbamate for tert-butyl piperidin-3-ylmethylcarbamate and acetyl chloride for methanesulfonyl chloride in the procedure for Compound 147A.

Compound 154B (R)-1-(3-aminopyrrolidin-1-yl)ethanone

The title compound was prepared by substituting Compound 154A for Compound 147A in the procedure for Compound 147B.

Compound 154C

N-[(4-{[(3R)-1-acetylpyrrolidin-3-yl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 154B for Compound 147B in the procedure for Compound 147. $^1$H NMR (400 MHz, dimethylsulfoxide-$d_6$) δ 11.61 (s, 1H), 8.50 (s, 1H), 8.17 (d, 1H), 7.98 (s, 1H), 7.78 (s, 1H), 7.49 (m, 3H), 7.34 (d, 2H), 7.10 (m, 1H), 7.04 (d, 2H), 6.66 (dd, 1H), 6.35 (s, 1H), 6.22 (s, 1H), 4.34 (m, 1H), 3.81 (m, 1H), 3.58 (m, 1H), 3.43 (m, 1H), 3.05 (m, 4H), 2.74 (s, 2H), 2.19 (m, 9H), 1.96 (m, 5H), 1.38 (t, 2H), 0.94 (s, 6H).

Compound 155

4-(4-{[2-(4-chlorophenyl)-4,4-dimethylcyclohex-1-en-1-yl]methyl}piperazin-1-yl)-N-({4-[(3-methoxy-2,2-dimethylpropyl)amino]-3-nitrophenyl}sulfonyl)-2-(1H-pyrrolo[2,3-b]pyridin-5-yloxy)benzamide The title compound was prepared as described in the procedure for Compound 120B using 3-methoxy-2,2-dimethylpropan-1-amine in place of Compound 120A. $^1$H NMR (500 MHz, dimethylsulfoxide-$d_6$) δ 11.69 (s, 1H), 11.32 (s, 1H), 8.92 (t, 1H), 8.57 (d, 1H), 8.04 (d, 1H), 7.80 (dd, 1H), 7.46-7.55 (m, 3H), 7.34 (d, 2H), 7.08 (d, 1H), 7.04 (d, 2H), 6.68 (dd, 1H), 6.36-6.42 (m, 1H), 6.19 (d, 1H), 3.25-3.30 (m, 5H), 3.19 (s, 2H), 3.07 (s, 4H), 2.76 (s, 2H), 2.17 (d, 6H), 1.95 (s, 2H), 1.38 (t, 2H), 0.96 (s, 6H), 0.92 (s, 6H).

Compound 156

4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide

Compound 156A 4-(((1R,3R)-3-hydroxycyclopentyl)methylamino)-3-nitrobenzenesulfonamide The title compound was prepared by substituting (1R,3R)-3-hydroxycyclopentyl)methylamine for (tetrahydropyran-4-yl)methylamine in the procedure for Compound 1F.

Compound 156B 4-(4-{[2-(4-chlorophenyl)-4,4-dimethylcyclohex-1-en-1-yl]methyl}piperazin-1-yl)-N-{[4-({[(1R,3R)-3-hydroxycyclopentyl]methyl}amino)-3-nitrophenyl]sulfonyl}-2-(1H-pyrrolo[2,3-b]pyridin-5-yloxy)benzamide The title compound was prepared by substituting Compound 156A for Compound 130C in the procedure for Compound 130D. $^1$H NMR (500 MHz, pyridine-$d_5$) δ 13.05 (s, 1H), 9.29 (s, 1H), 8.62 (t, 1H), 8.43 (d, 1H), 8.32 (dd, 1H), 8.10 (d, 1H), 7.66 (m, 2H), 7.44 (d, 2H), 7.07 (d, 2H), 6.85 (d, 1H), 6.74 (dd, 1H), 6.54 (s, 1H), 6.49 (m, 1H), 4.60 (m, 1H), 3.19 (dd, 2H), 3.06 (m, 4H), 2.77 (s, 2H), 2.70 (m, 1H), 2.26 (t, 2H), 2.20-2.07 (m, 6H), 2.00 (m, 1H), 1.97 (s, 2H), 1.90 (m, 1H), 1.56 (m, 1H), 1.39 (t, 2H), 1.34 (m, 1H), 0.93 (s, 6H).

Compound 157

4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide

Compound 157A 4-(((1S,3S)-3-hydroxycyclopentyl)methylamino)-3-nitrobenzenesulfonamide The title compound was prepared by substituting (1S,3S)-3-hydroxycyclopentyl)methylamine for (tetrahydropyran-4-yl)methylamine in the procedure for Compound 1F.

Compound 157B 4-(4-{[2-(4-chlorophenyl)-4,4-dimethylcyclohex-1-en-1-yl]methyl}piperazin-1-yl)-N-{[4-({[(1S,3S)-3-hydroxycyclopentyl]methyl}amino)-3-nitrophenyl]sulfonyl}-2-(1H-pyrrolo[2,3-b]pyridin-5-yloxy)benzamide The title compound was prepared by substituting Compound 157A for Compound 130C in the procedure for Compound 130D. $^1$H NMR (500 MHz, pyridine-$d_5$) δ 13.03 (s, 1H), 9.29 (s, 1H), 8.60 (t, 1H), 8.44 (d, 1H), 8.32 (dd, 1H), 8.14 (d, 1H), 7.66 (m, 2H), 7.44 (d, 2H), 7.07 (d, 2H), 6.83 (d, 1H), 6.75 (dd, 1H), 6.55 (s, 1H), 6.49 (m, 1H), 4.60 (m, 1H), 3.19 (dd, 2H), 3.06 (m, 4H), 2.77 (s, 2H), 2.70 (m, 1H), 2.26 (t, 2H), 2.20-2.07 (m, 6H), 2.00 (m, 1H), 1.97 (s, 2H), 1.90 (m, 1H), 1.56 (m, 1H), 1.39 (t, 2H), 1.34 (m, 1H), 0.93 (s, 6H).

Compound 158

4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide

Compound 158A 4-(((1S,3R)-3-hydroxycyclopentyl)methylamino)-3-nitrobenzenesulfonamide The title compound was prepared by substituting (1S,3R)-3-hydroxycyclopentyl)methylamine for (tetrahydropyran-4-yl)methylamine in the procedure for Compound 1F.

Compound 158B 4-(4-{[2-(4-chlorophenyl)-4,4-dimethylcyclohex-1-en-1-yl]methyl}piperazin-1-yl)-N-{[4-({[(1S,3R)-3-hydroxycyclopentyl]methyl}amino)-3-nitrophenyl]sulfonyl}-2-(1H-pyrrolo[2,3-b]pyridin-5-yloxy)benzamide The title compound was prepared by substituting Compound 158A for Compound 130C in the procedure for Compound 130D. $^1$H NMR (500 MHz, pyridine-$d_5$) δ 12.94 (s, 1H), 9.25 (d, 1H), 8.59 (t, 1H), 8.48 (d, 1H), 8.27 (m, 2H), 7.66 (m, 2H), 7.45 (d, 2H), 7.08 (d, 2H), 6.77 (dd, 1H), 6.72 (d, 1H), 6.60 (d, 1H), 6.47 (m, 1H), 4.53 (m, 1H), 3.30 (m, 2H), 3.06 (m, 4H), 2.78 (s, 2H), 2.27 (m, 3H), 2.19-2.10 (m, 5H), 1.98 (m, 3H), 1.85-1.66 (m, 4H), 1.39 (t, 2H), 0.94 (s, 6H).

Compound 159

4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide

Compound 159A 4-(((1R,3S)-3-hydroxycyclopentyl)methylamino)-3-nitrobenzenesulfonamide The title compound was prepared by substituting (1R,3S)-3-hydroxycyclopentyl)methylamine for (tetrahydropyran-4-yl)methylamine in the procedure for Compound 1F.

Compound 159B 4-(4-{[2-(4-chlorophenyl)-4,4-dimethylcyclohex-1-en-1-yl]methyl}piperazin-1-yl)-N-{[4-({[(1R,3S)-3-hydroxycyclopentyl]methyl}amino)-3-nitrophenyl]sulfonyl}-2-(1H-pyrrolo[2,3-b]pyridin-5-yloxy)benzamide The title compound was prepared by substituting Compound 158A for Compound 130C in the procedure for Compound 130D. $^1$H NMR (500 MHz, pyridine-$d_5$) δ 13.02 (s, 1H), 9.28 (d, 1H), 8.59 (t, 1H), 8.44 (d, 1H), 8.29 (d, 1H), 8.13 (d, 1H), 7.66 (m, 2H), 7.44 (d, 2H), 7.08 (d, 2H), 6.82 (dd, 1H), 6.74 (d, 1H), 6.55 (d, 1H), 6.48 (m, 1H), 4.53 (m, 1H), 3.34 (m, 2H), 3.06 (m, 4H), 2.77 (s, 2H), 2.27 (m, 3H), 2.19-2.10 (m, 5H), 1.97 (m, 3H), 1.85-1.66 (m, 4H), 1.39 (t, 2H), 0.93 (s, 6H).

Compound 160

4-(4-{[2-(4-chlorophenyl)-4,4-dimethylcyclohex-1-en-1-yl]methyl}piperazin-1-yl)-N-[(3-nitro-4-{[(3S)-2-oxopiperidin-3-yl]amino}phenyl)sulfonyl]-2-(1H-pyrrolo[2,3-b]pyridin-5-yloxy)benzamide The title compound was prepared by substituting (S)-3-aminopiperidin-2-one for 1-acetylpiperidin-4-amine in the procedure for Compound 53B. $^1$H NMR (300 MHz, dimethylsulfoxide-$d_6$) δ 11.68 (br s, 1H), 8.88 (d, 1H), 8.57 (d, 1H), 8.04 (d, 1H), 7.95 (br s, 1H), 7.83 (dd, 1H), 7.55-7.46 (m, 3H), 7.35 (d, 2H), 7.16 (d, 1H), 7.05 (d, 2H), 6.68 (dd, 1H), 6.38 (m, 1H), 6.21 (d, 1H), 4.41 (m, 1H), 3.22 (m, 2H), 3.09 (br s, 4H), 2.78 (br s, 2H), 2.35-2.09 (m, 8H), 1.96 (br s, 2H), 1.86 (m, 2H), 1.39 (t, 2H), 0.93 (s, 6H).

Compound 161

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide

Compound 161A tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)azetidine-1-carboxylate Compound 82 (305 mg). tert-butyl 3-(aminomethyl)azetidine-1-carboxylate (86 mg) and diisopropyl amine (0.202 ml) in dioxane (3 ml) were heated to 110° C. After stirring overnight, the reaction was concentrated. Silica gel chromatography (Reveleris, 12 g) eluting with a gradient of 0.5% to 3% methanol/dichloromethane (flow=36 ml/minute) gave the title compound.

Compound 161B 2-(1H-pyrrolo[2,3-b]pyridin-5-yloxy)-N-(4-(azetidin-3-ylmethylamino)-3-nitrophenylsulfonyl)-4-(4-((2-(4-chlorophenyl)-4,4-dimethylcyclohex-1-enyl)methyl)piperazin-1-yl)benzamide To a solution of Compound 161A (0.257 g) in dichloromethane (5 ml) was added trifluoroacetic acid (0.211 ml). After 30 minutes an additional 0.2 ml of trifluoroacetic acid was added. After 3 hours, the reaction was concentrated to give the title compound.

Compound 161C 4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]azetidin-3-yl}methyl)amino]-3-nitrophenyl}sulfonyl)-2-(1H-pyrrolo[2,3-b]pyridin-5-yloxy)benzamide A solution of Compound 161B (0.118 g), sodium triacetoxyborohydride (0.035 g) and 1,3-difluoropropan-2-one (0.012 g) were stirred together in dichloromethane (1 ml) overnight. The reaction was quenched with saturated aqueous NaHCO$_3$ solution (10 ml) and extracted into dichloromethane (30 ml). The organic layer was dried and concentrated. Silica gel chromatography (Reveleris 12 g) eluting with a gradient of 0.5% to 3.5% methanol/dichloromethane over 30 minutes (flow=36 ml/min) gave the title compound. $^1$H NMR (300 MHz, dimethylsulfoxide-$d_6$) δ 11.67 (s, 1H), 11.47-11.21 (m, 1H), 8.85 (s, 1H), 8.55 (d, 1H), 8.03 (d, 1H), 7.80 (dd, 1H), 7.54-7.45 (m, 3H), 7.33 (s, 2H), 7.04 (d, 3H), 6.67 (d, 1H), 6.38 (dd, 1H), 6.20 (d, 1H), 4.43 (dt, 4H), 3.56 (t, 2H), 3.46 (s, 2H), 3.12 (m, 6H), 2.74 (m, 3H), 2.17 (m, 7H), 1.95 (s, 2H), 1.39 (d, 2H), 0.92 (s, 6H).

Compound 162

4-(4-{[2-(4-chlorophenyl)-4,4-dimethylcyclohex-1-en-1-yl]methyl}piperazin-1-yl)-N-[(3-nitro-4-{[(1-oxetan-3-ylazetidin-3-yl)methyl]amino}phenyl)sulfonyl]-2-(1H-pyrrolo[2,3-b]pyridin-5-yloxy)benzamide The title compound was prepared by substituting oxetan-3-one for 1,3-difluoropropan-2-one in the procedure for Compound 161C. $^1$H NMR (300 MHz, dimethylsulfoxide-d$_6$) δ 11.66 (s, 1H), 11.51-11.03 (m, 1H), 8.81 (s, 1H), 8.54 (d, 1H), 8.02 (d, 1H), 7.79 (dd, 1H), 7.50 (dd, 3H), 7.34 (d, 2H), 7.04 (d, 3H), 6.67 (d, 1H), 6.38 (dd, 1H), 6.20 (d, 1H), 4.57 (s, 2H), 4.43-4.35 (m, 2H), 3.82 (s, 1H), 3.59 (t, 2H), 3.44 (t, 2H), 3.20 (s, 2H), 3.06 (s, 4H), 2.73 (s, 3H), 2.18 (s, 6H), 1.95 (s, 2H), 1.39 (d, 2H), 0.92 (s, 6H).

Compound 163

4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide

Compound 163A tert-butyl 4-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)piperidine-1-carboxylate The title compound was prepared by substituting tert-butyl 4-(aminomethyl)piperidine-1-carboxylate for 1-acetylpiperidin-4-amine in the procedure for Compound 53B.

Compound 163B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylmethylamino)phenylsulfonyl)benzamide The title compound was prepared by substituting Compound 163A for Compound 1A in the procedure for Compound 1B.

Compound 163C 4-(4-{[2-(4-chlorophenyl)-4,4-dimethylcyclohex-1-en-1-yl]methyl}piperazin-1-yl)-N-[(3-nitro-4-{[(1-oxetan-3-ylpiperidin-4-yl)methyl]amino}phenyl)sulfonyl]-2-(1H-pyrrolo[2,3-b]pyridin-5-yloxy)benzamide The title compound was prepared by substituting Compound 163B for Compound 161B and oxetan-3-one for 1,3-difluoropropan-2-one in the procedure for Compound 161C. $^1$H NMR (500 MHz, dimethylsulfoxide-d$_6$) δ 11.68 (s, 1H), 8.60 (t, 1H), 8.54 (d, 1H), 8.03 (d, 1H), 7.79 (d, 1H), 7.50 (m, 3H), 7.34 (d, 2H), 7.09 (d, 1H), 7.04 (d, 2H), 6.67 (dd, 1H), 6.39 (m, 1H), 6.19 (d, 1H), 4.55 (t, 2H), 4.46 (t, 2H), 3.52 (br s, 1H), 3.28 (m, 2H), 3.17 (d, 1H), 3.06 (m, 4H), 2.82 (m, 2H), 2.74 (m, 2H), 2.17 (m, 6H), 1.95 (m, 3H), 1.72 (m, 3H), 1.38 (t, 2H), 1.28 (m, 2H), 0.92 (s, 6H).

Compound 164

4-(4-{[2-(4-chlorophenyl)-4,4-dimethylcyclohex-1-en-1-yl]methyl}piperazin-1-yl)-N-[(4-{[(1-cyclopropylpiperidin-4-yl)methyl]amino}-3-nitrophenyl)sulfonyl]-2-(1H-pyrrolo[2,3-b]pyridin-5-yloxy)benzamide The title compound was prepared by substituting Compound 163B for (S)-tert-butyl pyrrolidin-3-ylcarbamate in the procedure for Compound 142A. $^1$H NMR (500 MHz, dimethylsulfoxide-d$_6$) δ 11.96 (br s, 1H), 11.62 (br s, 1H), 8.50 (m, 2H), 7.98 (d, 1H), 7.72 (m, 1H), 7.52 (d, 1H), 7.45 (m, 2H), 7.34 (d, 2H), 7.04 (m, 2H), 6.94 (m, 1H), 6.64 (dd, 1H), 6.34 (m, 1H), 6.22 (d, 1H), 3.28 (m, 3H), 3.04 (m, 5H), 2.72 (s, 2H), 2.64 (m, 1H), 2.64 (m, 1H), 2.36 (m, 1H), 2.16 (m, 7H), 1.95 (s, 2H), 1.68 (m, 3H), 1.38 (t, 2H), 1.18 (m, 3H), 0.94 (s, 6H), 0.35 (m, 3H).

Compound 165

4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide

Compound 165A 4-((4-(2-fluoroethyl)morpholin-2-yl)methylamino)-3-nitrobenzenesulfonamide The title compound was prepared by substituting 2-fluoro-ethyl bromide for methyl iodide in the procedure for Compound 134B.

Compound 165B 4-(4-{[2-(4-chlorophenyl)-4,4-dimethylcyclohex-1-en-1-yl]methyl}piperazin-1-yl)-N-{[4-({[4-(2-fluoroethyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 165A for Compound 130C in the procedure for Compound 130D. $^1$H NMR (500 MHz, pyridine-d$_5$) δ 13.00 (s, 1H), 9.26 (d, 1H), 8.87 (t, 1H), 8.43 (d, 1H), 8.32 (dd, 1H), 8.11 (d, 1H), 7.66 (m, 2H), 7.44 (d, 2H), 7.07 (d, 2H), 6.92 (d, 1H), 6.75 (dd, 1H), 6.54 (d, 1H), 6.48 (dd, 1H), 3.93 (m, 1H), 4.63, 4.51 (dt, 2H), 3.95-3.85 (m, 2H), 3.68 (dt, 1H), 3.43-3.37 (m, 2H), 3.07 (m, 4H), 2.92 (d, 1H), 2.77 (s, 2H), 2.65 (m, 2H), 2.59 (m, 1H), 2.26 (m, 2H), 2.17-2.08 (m, 5H), 1.97 (s, 2H), 1.39 (t, 2H), 0.93 (s, 6H).

Compound 166

4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide

Compound 166A 4-((4-(2,2-difluoroethyl)morpholin-2-yl)methylamino)-3-nitrobenzenesulfonamide The title compound was prepared by substituting 2,2-difluoro-ethyl bromide for methyl iodide in the procedure for Compound 134B.

Compound 166B 4-(4-{[2-(4-chlorophenyl)-4,4-dimethylcyclohex-1-en-1-yl]methyl}piperazin-1-yl)-N-{[4-({[4-(2,2-difluoroethyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 166A for Compound 130C in the procedure for Compound 130D. $^1$H NMR (500 MHz, pyridine-d$_5$) δ 13.01 (s, 1H), 9.26 (d, 1H), 8.86 (t, 1H), 8.43 (d, 1H), 8.34 (dd, 1H), 8.11 (d, 1H), 7.66 (m, 2H), 7.44 (d, 2H), 7.07 (d, 2H), 6.93 (d, 1H), 6.75 (dd, 1H), 6.54 (d, 1H), 6.48 (m, 1H), 6.31, 6.20, 6.09 (tt, 1H), 3.90 (m, 1H), 3.85 (d, 1H), 3.67 (dt, 1H), 3.49-3.30 (m, 2H), 3.07 (m, 4H), 2.84 (d, 1H), 2.82-2.75 (m, 4H), 2.69 (d, 1H), 2.33 (dt, 1H), 2.27-2.20 (m, 3H), 2.14 (m, 4H), 1.97 (s, 2H), 1.39 (t, 2H), 0.93 (s, 6H).

Compound 167

4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide

Compound 167A 4-((4-fluoro-1-(oxetan-3-yl)piperidin-4-yl)methoxy)-3-nitrobenzenesulfonamide The title compound was prepared by substituting Compound 173A for tert-butyl piperazine-1-carboxylate and 3-oxetanone for 4'-chlorobiphenyl-2-carboxaldehyde in the procedure for Compound 1A.

Compound 167B 4-(4-{[2-(4-chlorophenyl)-4,4-dimethylcyclohex-1-en-1-yl]methyl}piperazin-1-yl)-N-({4-[(4-fluoro-1-oxetan-3-ylpiperidin-4-yl)methoxy]-3-nitrophenyl}sulfonyl)-2-(1H-pyrrolo[2,3-b]pyridin-5-yloxy)benzamide The title compound was prepared by substituting Compound 167A for Compound 11B in the procedure for Compound 11D. $^1$H NMR (300 MHz, dimethylsulfoxide-d$_6$) 11.69 (s, 1H), 8.39 (s, 1H), 8.09 (d, 1H), 8.04 (d, 1H), 7.52 (m, 4H), 7.35 (d, 2H), 7.05 (m, 2H), 6.68 (dd, 1H), 6.40 (dd, 1H), 6.20 (s, 1H), 4.57 (t, 2H), 4.48 (m, 2H), 4.38 (d, 2H), 4.02 (m, 1H), 3.63 (m, 2H), 3.08 (m, 4H), 2.74 (m, 4H), 2.17 (m, 6H), 1.88 (m, 6H), 1.40 (t, 2H), 0.93 (s, 6H).

Compound 168

4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide

Compound 168A (S)-methyl 4,4-difluoropyrrolidine-2-carboxylate (S)-1-tert-butyl 2-methyl 4,4-difluoropyrrolidine-1,2-dicarboxylate (0.472 g) in CH$_2$Cl$_2$ (1 ml) was treated with trifluoroacetic acid (1.4 ml), stirred at ambient temperature for 4 hours, and concentrated. The product was free-based using a MEGA BE-SCX column with 1:1 CH$_2$Cl$_2$/methanol as eluent for the trifluoroacetic acid. The product was released from the column with 5% (7 M ammonia in methanol) in CH$_2$Cl$_2$ as eluent.

Compound 168B (S)-methyl 4,4-difluoro-1-(oxetan-3-yl)pyrrolidine-2-carboxylate The title compound was prepared by substituting Compound 168A for tert-butyl piperazine-1-carboxylate and 3-oxetanone for 4'-chlorobiphenyl-2-carboxaldehyde in the procedure for Compound 1A.

Compound 168C (S)-(4,4-difluoro-1-(oxetan-3-yl)pyrrolidin-2-yl)methanol

Compound 168B (0.180 g) in tetrahydrofuran (3 ml) was treated sequentially with a solution of calcium chloride (0.245 g) in ethanol (3 ml) and NaBH$_4$ (0.167 g) and then stirred at ambient temperature for 7 hours. The reaction was quenched with saturated aqueous NH$_4$Cl solution and extracted with ethyl acetate. The combined extracts were washed with brine, dried (MgSO$_4$), filtered, concentrated and chromatographed on silica gel with 50% ethyl acetate in hexanes as eluent to give the product.

Compound 168D (S)-4-((4,4-difluoro-1-(oxetan-3-yl)pyrrolidin-2-yl)methoxy)-3-nitrobenzenesulfonamide The title compound was prepared by substituting Compound 168C for (tetrahydro-2H-pyran-4-yl)methanol in the procedure for Compound 24A.

Compound 168E 4-(4-{[2-(4-chlorophenyl)-4,4-dimethylcyclohex-1-en-1-yl]methyl}piperazin-1-yl)-N-[(4-{[(2S)-4,4-difluoro-1-oxetan-3-ylpyrrolidin-2-yl]methoxy}-3-nitrophenyl)sulfonyl]-2-(1H-pyrrolo[2,3-b]pyridin-5-yloxy)benzamide The title compound was prepared by substituting Compound 168D for Compound 11B in the procedure for Compound 11D. ¹H NMR (300 MHz, dimethylsulfoxide-d₆) δ 11.69 (s, 1H), 8.38 (s, 1H), 8.06 (m, 2H), 7.49 (m, 4H), 7.35 (d, 2H), 7.05 (d, 2H), 6.68 (dd, 1H), 6.40 (m, 1H), 6.21 (s, 1H), 4.54 (m, 3H), 4.43 (t, 1H), 4.23 (m, 1H), 4.12 (m, 2H), 3.44 (m, 2H), 3.12 (m, 7H), 2.58 (m, 1H), 2.29 (m, 7H), 1.97 (s, 2H), 1.40 (t, 2H), 0.93 (s, 6H).

Compound 169

4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide Compound 169A tert-butyl 3-((4-(N-2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholine-4-carboxylate The title compound was prepared as described in the procedure for Compound 53B by replacing 1-acetylpiperidin-4-amine with tert-butyl 3-(aminomethyl)morpholine-4-carboxylate.

Compound 169B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-(morpholin-3-ylmethylamino)-3-nitrophenylsulfonyl)benzamide The title compound was prepared as described in the procedure for Compound 139B by replacing Compound 139A with Compound 169A.

Compound 169C 4-(4-{[2-(4-chlorophenyl)-4,4-dimethylcyclohex-1-en-1-yl]methyl}piperazin-1-yl)-N-[(3-nitro-4-{[(4-tetrahydro-2H-pyran-4-ylmorpholin-3-yl)methyl]amino}phenyl)sulfonyl]-2-(1H-pyrrolo[2,3-b]pyridin-5-yloxy)benzamide The title compound was prepared as described in the procedure for Compound 139C by replacing Compound 139B and oxetan-3-one with Compound 169B and tetrahydropyran-4-one, respectively. ¹H NMR (300 MHz, dimethylsulfoxide-d₆) δ 11.69 (s, 1H), 8.77 (m, 1H), 8.57 (d, 1H), 8.05 (d, 1H), 7.84 (dd, 1H), 7.52 (m, 3H), 7.34 (m, 2H), 7.03 (m, 3H), 6.68 (dd, 1H), 6.40 (dd, 1H), 6.18 (d, 1H), 3.86 (m, 2H), 3.72 (m, 2H), 3.11 (m, 6H), 2.74 (m, 4H), 2.20 (m, 6H), 1.95 (m, 3H), 1.51 (m, 7H), 0.92 (s, 6H).

Compound 170

4-(4-{[2-(4-chlorophenyl)-4,4-dimethylcyclohex-1-en-1-yl]methyl}piperazin-1-yl)-N-[(4-{[(4-cyclobutylmorpholin-3-yl)methyl]amino}-3-nitrophenyl)sulfonyl]-2-(1H-pyrrolo[2,3-b]pyridin-5-yloxy)benzamide The title compound was prepared as described in the procedure for Compound 139C by replacing Compound 139B and oxetan-3-one with Compound 169B and cyclobutanone. ¹H NMR (300 MHz, dimethylsulfoxide-d₆) δ 11.68 (s, 1H), 8.72 (s, 1H), 8.57 (d, 1H), 8.04 (d, 1H), 7.84 (dd, 1H), 7.52 (m, 3H), 7.34 (m, 3H), 7.03 (m, 4H), 6.67 (dd, 1H), 6.39 (dd, 1H), 6.18 (d, 1H), 3.47 (m, 3H), 3.10 (m, 6H), 2.72 (m, 6H), 2.25 (m, 8H), 1.95 (m, 4H), 1.56 (m, 3H), 1.38 (m, 2H), 0.92 (s, 6H).

Compound 171

4-(4-{[2-(4-chlorophenyl)-4,4-dimethylcyclohex-1-en-1-yl]methyl}piperazin-1-yl)-N-[(3-nitro-{[(4-tetrahydrofuran-3-ylmorpholin-3-yl)methyl]amino}phenyl)sulfonyl]-2-(1H-pyrrolo[2,3-b]pyridin-5-yloxy)benzamide The title compound was prepared as described in the procedure for Compound 139C by replacing Compound 139B and oxetan-3-one with Compound 169B and 3-oxotetrahydrofuran, respectively. ¹H NMR (300 MHz, dimethylsulfoxide-d₆) δ 11.64 (s, 1H), 8.66 (s, 1H), 8.53 (d, 1H), 8.01 (d, 1H), 7.80 (d, 1H), 7.50 (m, 3H), 7.35 (d, 2H), 7.05 (d, 2H), 6.98 (d, 1H), 6.66 (dd, 1H), 6.37 (d, 1H), 6.19 (d, 1H), 3.68 (m, 8H), 3.05 (m, 6H), 2.85 (m, 3H), 2.73 (s, 2H), 2.25 (m, 6H), 1.91 (m, 3H), 1.37 (m, 3H), 0.95 (m, 6H).

Compound 172

4-(4-{[2-(4-chlorophenyl)-4,4-dimethylcyclohex-1-en-1-yl]methyl}piperazin-1-yl)-N-({4-[({1-[2-fluoro-1-(fluoromethyl)ethyl]piperidin-4-yl}methyl)amino]-3-nitrophenyl}sulfonyl)-2-(1H-pyrrolo[2,3-b]pyridin-5-yloxy)benzamide The title compound was prepared by substituting Compound 163B for tert-butyl piperazine-1-carboxylate and 1,3-difluoropropan-2-one for 4'-chlorobiphenyl-2-carboxaldehyde in the procedure for Compound 1A. ¹H NMR (500 MHz, dimethylsulfoxide-d₆) δ 11.67 (s, 1H), 11.40 (br s, 1H), 8.57 (m, 2H), 8.03 (d, 1H), 7.78 (d, 1H), 7.50 (m, 3H), 7.34 (d, 2H), 7.07 (d, 1H), 7.04 (d, 2H), 6.67 (dd, 1H), 6.38 (m 1H), 6.19 (d, 1H), 4.63 (d, 2H), 4.53 (d, 2H), 3.28 (m, 2H), 3.07 (m, 4H), 2.89 (m, 2H), 2.74 (m, 2H), 2.40 (m, 2H), 2.16 (m, 6H), 1.95 (s, 2H), 1.67 (m, 3H), 1.38 (t, 2H), 1.23 (m, 3H), 0.94 (s, 6H).

Compound 173

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide Compound 173A 4-((4-fluoropiperidin-4-yl)methoxy)-3-nitrobenzenesulfonamide The title compound was prepared by substituting Compound 126B for Compound 1A in the procedure for Compound 1B.

Compound 173B 4-((1-cyclopropyl-4-fluoropiperidin-4-yl)methoxy)-3-nitrobenzenesulfonamide To Compound 173A (0.24 g) in methanol (3 ml) was added 3A molecular sieves (0.1 g), followed sequentially by acetic acid (0.31 ml), (1-ethoxycyclopropoxy)trimethylsilane (0.64 ml), and sodium cyanoborohydride (0.148 g). The reaction was heated under reflux overnight. After cooling, the reaction mixture was loaded onto a silica gel column. After drying, the column was eluted with 100:2:0.2 ethyl acetate/methanol/NH$_4$OH to give the title compound.

Compound 173C 4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-(1H-pyrrolo[2,3-b]pyridin-5-yloxy)benzamide The title compound was prepared by substituting Compound 173B for Compound 11B in the procedure for Compound 11D. $^1$H NMR (500 MHz, dimethylsulfoxide-d$_6$) δ 11.65 (s, 1H), 8.33 (s, 1H), 8.01 (m, 2H), 7.53 (d, 1H), 7.48-7.49 (m, 2H), 7.34-7.38 (m, 3H), 7.04 (d, 2H), 6.66 (dd, 1H), 6.38 (dd, 1H), 6.21 (d, 1H), 4.32 (d, 2H), 3.70-3.77 (m, 2H), 3.07 (s, 4H), 2.92 (s, 2H), 2.80 (s, 2H), 2.58 (s, 2H), 2.25 (s, 4H), 2.13-2.16 (m 2H), 1.38 (t, 2H), 0.92 (s, 6H), 0.40-0.49 (m, 4H).

Compound 174

4-(4-{[2-(4-chlorophenyl)-4,4-dimethylcyclohex-1-en-1-yl]methyl}piperazin-1-yl)-N-({4-[(4-methoxybenzyl)amino]-3-nitrophenyl}sulfonyl)-2-(1H-pyrrolo[2,3-b]pyridin-5-yloxy)benzamide A suspension of Compound 53A (120 mg), (4-methoxyphenyl)methanamine (31 mg) and Hunig's Base (0.159 ml) in dimethylsulfoxide (2 ml) was heated for 2 hours at 150° C. in a Biotage Initiator microwave reactor. The reaction mixture was diluted with methanol (2 ml) and purified by reverse phase HPLC (C8, 30%-100% CH$_3$CN/water/0.1% trifluoroacetic acid). $^1$H NMR (500 MHz, pyridine-d$_5$) δ 13.07 (s, 1H), 9.32 (d, 1H), 9.17 (t, 1H), 8.43 (d, 1H), 8.28 (dd, 1H), 8.08 (d, 1H), 7.64-7.68 (m, 2H), 7.44 (d, 2H), 7.38 (d, 2H), 7.07 (d, 2H), 6.97-7.02 (m, 2H), 6.90 (d, 1H), 6.74 (dd, 1H), 6.52 (d, 1H), 6.49 (dd, 1H), 4.55 (d, 2H), 3.68 (s, 3H), 3.03-3.09 (m, 4H), 2.77 (s, 2H), 2.26 (t, 2H), 2.10-2.17 (m, 4H), 1.97 (s, 2H), 1.39 (t, 2H), 0.93 (s, 6H).

Compound 175

4-(4-{[2-(4-chlorophenyl)-4,4-dimethylcyclohex-1-en-1-yl]methyl}piperazin-1-yl)-N-[(3-nitro-4-{[3-(trifluoromethoxy)benzyl]amino}phenyl)sulfonyl]-2-(1H-pyrrolo[2,3-b]pyridin-5-yloxy)benzamide The title compound was prepared by substituting (3-trifluoromethoxyphenyl)methanamine for (4-methoxyphenyl)methanamine in the procedure for Compound 174. $^1$H NMR (500 MHz, pyridine-d$_5$) δ 13.06 (s, 1H), 9.38 (t, 1H), 9.31 (d, 1H), 8.42 (d, 1H), 8.28 (dd, 1H), 8.08 (d, 1H), 7.65 (ddd, 2H), 7.41-7.46 (m, 3H), 7.36-7.40 (m, 2H), 7.07 (d, 2H), 6.88 (d, 1H), 6.74 (dd, 1H), 6.52 (d, 1H), 6.49 (d, 1H), 4.73 (d, 2H), 3.02-3.08 (m, 4H), 2.77 (s, 2H), 2.22-2.28 (m, 2H), 2.09-2.16 (m, 4H), 1.97 (s, 2H), 1.39 (t, 2H), 0.93 (s, 6H).

Compound 176

4-(4-{[2-(4-chlorophenyl)-4,4-dimethylcyclohex-1-en-1-yl]methyl}piperazin-1-yl)-N-({4-[(3-methoxybenzyl)amino]-3-nitrophenyl}sulfonyl)-2-(1H-pyrrolo[2,3-b]pyridin-5-yloxy)benzamide The title compound was prepared by substituting (3-methoxyphenyl)methanamine for (4-methoxyphenyl)methanamine in the procedure for Compound 174. $^1$H NMR (500 MHz, pyridine-d$_5$) δ 13.06 (s, 1H), 9.27-9.32 (m, 2H), 8.42 (d, 1H), 8.26 (dd, 1H), 8.08 (d, 1H), 7.64-7.67 (m, 2H), 7.44 (d, 2H), 7.32 (t, 1H), 7.14 (s, 1H), 7.04-7.09 (m, 3H), 6.88-6.94 (m, 2H), 6.74 (dd, 1H), 6.52 (d, 1H), 6.48-6.50 (m, 1H), 4.64 (d, 2H), 3.68 (s, 3H), 3.03-3.09 (m, 4H), 2.77 (s, 2H), 2.26 (t, 2H), 2.10-2.18 (m, 4H), 1.97 (s, 2H), 1.39 (t, 2H), 0.93 (s, 6H).

Compound 177

4-(4-{[2-(4-chlorophenyl)-4,4-dimethylcyclohex-1-en-1-yl]methyl}piperazin-1-yl)-N-[(4-{[4-(difluoromethoxy)benzyl]amino}-3-nitrophenyl)sulfonyl]-2-(1H-pyrrolo[2,3-b]pyridin-5-yloxy)benzamide The title compound was prepared by substituting (4-difluoromethoxyphenyl)methanamine for (4-methoxyphenyl)methanamine in the procedure for Compound 174. $^1$H NMR (500 MHz, pyridine-d$_5$) δ 13.06 (s, 1H), 9.32 (d, 1H), 9.28 (t, 1H), 8.42 (d, 1H), 8.28 (dd, 1H), 8.07 (d, 1H), 7.66 (t, 1H), 7.64 (d, 1H), 7.58 (s, 1H), 7.44 (s, 2H), 7.26 (s, 1H), 7.25 (d, 1H), 7.07 (d, 2H), 6.87 (d, 1H), 6.74 (dd, 1H), 6.52 (d, 1H), 6.49 (dd, 1H), 4.64 (d, 2H), 3.03-3.10 (m, 4H), 2.77 (s, 2H), 2.26 (t, 2H), 2.11-2.17 (m, 4H), 1.97 (s, 2H), 1.39 (t, 2H), 0.93 (s, 6H).

Compound 178

4-(4-{[2-(4-chlorophenyl)-4,4-dimethylcyclohex-1-en-1-yl]methyl}piperazin-1-yl)-N-{[4-(1,4-dioxaspiro[4.5]dec-8-ylamino)-3-nitrophenyl]sulfonyl}-2-(1H-pyrrolo[2,3-b]pyridin-5-yloxy)benzamide The title compound was prepared by substituting 1,4-dioxa-spiro[4.5]dec-8-ylamine for 1-acetylpiperidin-4-amine in the procedure for Compound 53B. $^1$H NMR (300 MHz, dimethylsulfoxide-d$_6$) δ 11.67 (br s, 1H), 8.55 (d, 1H), 8.26 (d, 1H), 8.04 (d, 1H), 7.81 (dd, 1H), 7.54-7.46 (m, 3H), 7.35 (d, 2H), 7.15 (d, 1H), 7.04 (d, 2H), 6.68 (dd, 1H), 6.38 (m, 1H), 6.19 (d, 1H), 3.89 (s, 4H), 3.78 (m, 1H), 3.07 (br s, 4H), 2.78 (br s, 2H), 2.28-2.11 (m, 6H), 2.00-1.88 (m, 4H), 1.75-1.57 (m, 4H), 1.54-1.35 (m, 4H), 0.92 (s, 6H).

Compound 179 trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 179A tert-butyl trans-4-acetamidocyclohexylcarbamate Tert-butyl (trans)-4-aminocyclohexylcarbamate (1.500 g) and triethylamine (2.93 ml, 2.125 g) were added to dichloromethane and stirred until the tert-butyl (trans)-4-aminocyclohexylcarbamate had dissolved completely. Acetyl chloride (0.577 g) was added slowly, and the solution was stirred at room temperature for 16 hours. The solvent was removed, and the residue taken up in ethyl acetate, washed with pH 4 buffer, washed with brine, dried with anhydrous sodium sulfate, and filtered. The filtrate was concentrated under vacuum.

Compound 179B

N-(trans-4-aminocyclohexyl)acetamide

The title compound was prepared by substituting Compound 179A for Compound 1A in the procedure for Compound 1B.

Compound 179C trans-N-[(4-{[4-(acetylamino)cyclohexyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 179B for 1-acetylpiperidin-4-amine in the procedure for Compound 53B. $^1$H NMR (300 MHz, dimethylsulfoxide-d$_6$) δ 11.67 (br s, 1H), 8.55 (d, 1H), 8.20 (d, 1H), 8.04 (d, 1H), 7.82-7.76 (m, 2H), 7.53-7.46 (m, 3H), 7.35 (d, 2H), 7.16 (d, 1H), 7.04 (d, 2H), 6.68 (dd, 1H), 6.39 (m, 1H), 6.19 (d, 1H), 3.57 (m, 2H), 3.07 (br s, 4H), 2.75 (br s, 2H), 2.28-2.10 (m, 6H), 2.03-1.94 (m, 4H), 1.83 (d, 2H), 1.80 (s, 3H), 1.55-1.24 (m, 6H), 0.92 (s, 6H).

Compound 180

4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide Compound 180A (R)-tert-butyl 1-(2,2-difluoroethyl)pyrrolidin-3-ylcarbamate To a solution of (R)-tert-butyl pyrrolidin-3-ylcarbamate (500 mg) and 1,1-difluoro-2-iodoethane (618 mg) in N,N-dimethylformamide (6 ml) was added N-ethyl-N-isopropylpropan-2-amine (1.403 ml) and the mixture was stirred at 70° C. for 72 hours. The reaction mixture was concentrated and the crude product was purified on silica gel with methanol/dichloromethane.

Compound 180B (R)-1-(2,2-difluoroethyl)pyrrolidin-3-amine

To a solution of Compound 180A (525 mg) in a mixture of dichloromethane (3 ml) and methanol (4.0 ml) was added hydrogen chloride, 4M in dioxane (5.24 ml) and the reaction was stirred for 1.5 hours. The reaction was concentrated and the crude material was taken up in dichloromethane and the solvent evaporated, then taken up in ether and the solvent evaporated, and then dried on high vacuum.

Compound 180C (R)-4-(1-(2,2-difluoroethyl)pyrrolidin-3-ylamino)-3-nitrobenzenesulfonamide The title compound was prepared by substituting Compound 180B for (tetrahydropyran-4-yl)methylamine in the procedure for Compound 1F.

Compound 180D 4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]-2-(1H-pyrrolo[2,3-b]pyridin-5-yloxy)benzamide The title compound was prepared by substituting Compound 180C for Compound 130C in the procedure for Compound 130D. $^1$H NMR (500 MHz, pyridine-d$_5$) δ 13.02 (m, 1H), 9.27 (d, 1H), 8.55 (d, 1H), 8.43 (d, 1H), 8.35 (dd, 1H), 8.10 (d, 1H), 7.64-7.68 (m, 2H), 7.44 (d, 2H), 7.07 (d, 2H), 6.83 (d, 1H), 6.75 (dd, 1H), 6.54 (m, 1H), 6.48 (m, 1H), 6.04-6.29 (m, 1H), 4.06 (m, 1H), 3.07 (m, 4H), 2.83-2.95 (m, 4H), 2.74-2.82 (m, 3H), 2.47 (m, 1H), 2.09-2.30 (m, 8H), 1.97 (s, 2H), 1.67 (m, 1H), 1.39 (t, 2H), 0.93 (s, 6H).

Compound 181

4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide Compound 181A (S)-tert-butyl 1-(2-fluoroethyl)pyrrolidin-3-ylcarbamate The title compound was prepared by substituting 1-fluoro-2-iodoethane for 1,1-difluoro-2-iodoethane and (S)-tert-butyl pyrrolidin-3-ylcarbamate for (R)-tert-butyl pyrrolidin-3-ylcarbamate in the procedure for Compound 180A.

Compound 181B (S)-1-(2-fluoroethyl)pyrrolidin-3-amine

The title compound was prepared by substituting Compound 181A for Compound 180A in the procedure for Compound 180B.

Compound 181C (S)-4-(1-(2-fluoroethyl)pyrrolidin-3-ylamino)-3-nitrobenzenesulfonamide The title compound was prepared by substituting Compound 181B for (tetrahydropyran-4-yl)methylamine in the procedure for Compound 1F.

Compound 181D 4-(4-{[2-(4-chlorophenyl)-4,4-dimethylcyclohex-1-en-1-yl]methyl}piperazin-1-yl)-N-[(4-{[(3S)-1-(2-fluoroethyl)pyrrolidin-3-yl]amino}-3-nitrophenyl)sulfonyl]-2-(1H-pyrrolo[2,3-b]pyridin-5-yloxy)benzamide The title compound was prepared by substituting Compound 181C for Compound 130C in the procedure for Compound 130D. $^1$H NMR (500 MHz, pyridine-$d_5$) δ 13.00 (m, 1H), 9.26 (d, 1H), 8.56 (d, 1H), 8.43 (d, 1H), 8.34 (dd, 1H), 8.10 (d, 1H), 7.63-7.66 (m, 2H), 7.44 (d, 2H), 7.07 (d, 2H), 6.82 (d, 1H), 6.75 (dd, 1H), 6.54 (d, 1H), 6.48 (m, 1H), 4.60 (t, 1H), 4.51 (t, 1H), 4.05 (m, 1H), 3.07 (m, 4H), 2.84 (m, 1H), 2.66-2.79 (m, 6H), 2.39 (q, 1H), 2.20-2.29 (m, 3H), 2.15 (m, 5H), 1.97 (s, 2H), 1.66 (m, 1H), 1.39 (t, 2H), 0.94 (s, 6H).

Compound 182

4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide

Compound 182A (S)-tert-butyl 1-(2,2-difluoroethyl)pyrrolidin-3-ylcarbamate

The title compound was prepared by substituting (S)-tert-butyl pyrrolidin-3-ylcarbamate for (R)-tert-butyl pyrrolidin-3-ylcarbamate in the procedure for Compound 180A.

Compound 182B (S)-1-(2,2-difluoroethyl)pyrrolidin-3-amine

The title compound was prepared by substituting Compound 182A for Compound 180A in the procedure for Compound 180B.

Compound 182C (S)-4-(1-(2,2-difluoroethyl)pyrrolidin-3-ylamino)-3-nitrobenzenesulfonamide The title compound was prepared by substituting Compound 182B for (tetrahydropyran-4-yl)methylamine in the procedure for Compound 1F.

Compound 182D 4-(4-{[2-(4-chlorophenyl)-4,4-dimethylcyclohex-1-en-1-yl]methyl}piperazin-1-yl)-N-[(4-{[(3S)-1-(2,2-difluoroethyl)pyrrolidin-3-yl]amino}-3-nitrophenyl)sulfonyl]-2-(1H-pyrrolo[2,3-b]pyridin-5-yloxy)benzamide The title compound was prepared by substituting Compound 182C for Compound 130C in the procedure for Compound 130D. $^1$H NMR (500 MHz, pyridine-$d_5$) δ 13.02 (m, 1H), 9.27 (d, 1H), 8.54 (d, 1H), 8.43 (d, 1H), 8.35 (dd, 1H), 8.11 (d, 1H), 7.64-7.68 (m, 2H), 7.44 (d, 2H), 7.07 (d, 2H), 6.82 (d, 1H), 6.75 (dd, 1H), 6.54 (m, 1H), 6.48 (m, 1H), 6.04-6.29 (m, 1H), 4.06 (m, 1H), 3.07 (m, 4H), 2.83-2.95 (m, 4H), 2.74-2.82 (m, 3H), 2.47 (m, 1H), 2.09-2.30 (m, 8H), 1.97 (s, 2H), 1.67 (m, 1H), 1.39 (t, 2H), 0.93 (s, 6H).

Compound 183

4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,b]pyridin-5-yloxy)benzamide

Compound 183A (R)-tert-butyl 1-(2-fluoroethyl)pyrrolidin-3-ylcarbamate

The title compound was prepared by substituting 1-fluoro-2-iodoethane for 1,1-difluoro-2-iodoethane in the procedure for Compound 180A.

Compound 183B (R)-1-(2-fluoroethyl)pyrrolidin-3-amine

The title compound was prepared by substituting Compound 183A for Compound 180A in the procedure for Compound 180B.

Compound 183C (R)-4-(1-(2-fluoroethyl)pyrrolidin-3-ylamino)-3-nitrobenzenesulfonamide The title compound was prepared by substituting Compound 183B for (tetrahydropyran-4-yl)methylamine in the procedure for Compound 1F.

Compound 183D 4-(4-{[2-(4-chlorophenyl)-4,4-dimethylcyclohex-1-en-1-yl]methyl}piperazin-1-yl)-N-[(4-{[(3R)-1-(2-fluoroethyl)pyrrolidin-3-yl]amino}-3-nitrophenyl)sulfonyl]-2-(1H-pyrrolo[2,3-b]pyridin-5-yloxy)benzamide The title compound was prepared by substituting Compound 183C for Compound 130C in the procedure for Compound 130D. $^1$H NMR (500 MHz, pyridine-$d_5$) δ 13.00 (m, 1H), 9.26 (d, 1H), 8.56 (d, 1H), 8.43 (d, 1H), 8.34 (dd, 1H), 8.10 (d, 1H), 7.63-7.66 (m, 2H), 7.44 (d, 2H), 7.07 (d, 2H), 6.83 (d, 1H), 6.75 (dd, 1H), 6.54 (d, 1H), 6.48 (m, 1H), 4.60 (t, 1H), 4.50 (t, 1H), 4.04 (m, 1H), 3.07 (m, 4H), 2.84 (m, 1H), 2.66-2.79 (m, 6H), 2.39 (q, 1H), 2.19-2.28 (m, 3H), 2.14 (m, 5H), 1.97 (s, 2H), 1.66 (m, 1H), 1.39 (t, 2H), 0.94 (s, 6H).

Compound 184

4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide

Compound 184A (S)-tert-butyl 3-((2-nitro-4-sulfamoylphenoxy)methyl)pyrrolidine-1-carboxylate To a solution of (S)-tert-butyl 3-(hydroxymethyl)pyrrolidine-1-carboxylate (0.300 g) in tetrahydrofuran (5 ml) was added sodium hydride (0.238 g). After stirring for 15 minutes, 4-fluoro-3-nitrobenzenesulfonamide (0.295 g) was added and reaction stirred at room temperature. After 1 hour, the reaction was partitioned between water (25 ml) and dichloromethane (50 ml) and the reaction quenched with 1N aqueous HCl (5.96 ml). The organic layer was separated, dried over magnesium sulfate, filtered, and concentrated. Silica gel chromatography (Reveleris 12 g) eluting with a gradient of 0.2% to 2% methanol/dichloromethane over 30 minutes (flow=36 m/minute) gave the title compound.

Compound 184B (S)-3-nitro-4-((1-(oxetan-3-yl)pyrrolidin-3-yl)methoxy)benzenesulfonamide To (S)-tert-butyl 3-((2-nitro-4-sulfamoylphenoxy)methyl)pyrrolidine-1-carboxylate (0.433 g) was added hydrogen chloride (4.0M in dioxane, 1.0 ml). After stirring for 1 hour, the reaction was concentrated and partitioned between dichloromethane (50 ml) and saturated aqueous $NaHCO_3$ solution (50 ml). The aqueous layer was separated and concentrated. The residue was triturated with methanol (100 ml), filtered and concentrated and treated with sodium cyanoborohyde (0.068 g) and cyclobutanone (0.078 g) and stirred overnight. The reaction was partitioned between dichloromethane (50 ml) and water (25 ml) and saturated aqueous $NaHCO_3$ (10 ml). The organic layer was dried over magnesium sulfate, filtered, and concentrated to give the title compound.

Compound 184C 4-(4-{[2-(4-chlorophenyl)-4,4-dimethylcyclohex-1-en-1-yl]methyl}piperazin-1-yl)-N-[(3-nitro-4-{[(3S)-1-oxetan-3-ylpyrrolidin-3-yl]methoxy}phenyl)sulfonyl]-2-(1H-pyrrolo[2,3-b]pyridin-5-yloxy)benzamide The title compound was prepared by substituting Compound 184B for Compound 1F and Compound 3J for Compound 1E in the procedure for Compound 1G. $^1$H NMR (300 MHz, dimethylsulfoxide-$d_6$) δ 11.64 (s, 1H), 11.45-11.01 (m, 1H), 8.30 (d, 1H), 7.98 (dd, 2H), 7.60-7.43 (m, 3H), 7.33 (t, 3H), 7.04 (d, 2H), 6.74-6.59 (m, 1H), 6.37 (dd, 1H), 6.21 (d, 1H), 4.49 (td, 2H), 4.33 (s, 1H), 4.13 (dd, 2H), 3.79 (s, 2H), 3.44 (dd, 2H), 3.07 (s, 4H), 2.74 (d, 6H), 2.19 (d, 6H), 1.98 (d, 2H), 1.74-1.52 (m, 1H), 1.39 (t, 2H), 0.92 (s, 6H).

Compound 185

4-(4-{[2-(4-chlorophenyl)-4,4-dimethylcyclohex-1-en-1-yl]methyl}piperazin-1-yl)-N-({4-[(4-hydroxybenzyl)amino]-3-nitrophenyl}sulfonyl)-2-(1H-pyrrolo[2,3-b]pyridin-5-yloxy)benzamide The title compound was prepared by substituting (4-hydroxyphenyl)methanamine for (4-methoxyphenyl)methanamine in the procedure for Compound 174. $^1$H NMR (500 MHz, pyridine-$d_5$) δ 13.06 (s, 1H), 11.67 (bs, 1H), 9.32 (d, 1H), 9.14 (s, 1H), 8.44 (d, 1H), 8.28 (dd, 1H), 8.09 (d, 1H), 7.65-7.68 (m, 2H), 7.44 (d, 2H), 7.37-7.41 (m, 2H), 7.19 (s, 2H), 7.07 (d, 2H), 6.93 (d, 1H), 6.75 (dd, 1H), 6.53 (d, 1H), 6.49 (dd, 1H), 4.54 (d, 2H), 3.02-3.09 (m, 4H), 2.77 (s, 2H), 2.22-2.29 (m, 2H), 2.10-2.17 (m, 4H), 1.97 (d, 2H), 1.39 (t, 2H), 0.94 (s, 6H).

Compound 186

4-(4-{[2-(4-chlorophenyl)-4,4-dimethylcyclohex-1-en-1-yl]methyl}piperazin-1-yl)-N-({4-[(3-hydroxybenzyl)amino]-3-nitrophenyl}sulfonyl)-2-(1H-pyrrolo[2,3-b]pyridin-5-yloxy)benzamide The title compound was prepared by substituting (3-hydroxyphenyl)methanamine for (4-methoxyphenyl)methanamine in the procedure for Compound 174. $^1$H NMR (500 MHz, pyridine-$d_5$) δ 13.06 (s, 1H), 11.67 (bs, 1H), 9.27-9.32 (m, 2H), 8.43 (d, 1H), 8.20 (dd, 1H), 8.08 (d, 1H), 7.66 (t, 2H), 7.44 (d, 2H), 7.33 (t, 1H), 7.25 (s, 1H), 7.13 (dd, 1H), 7.07 (d, 2H), 6.98 (d, 1H), 6.88 (d, 1H), 6.74 (dd, 1H), 6.52 (d, 1H), 6.49 (dd, 1H), 4.64 (d, 2H), 3.02-3.09 (m, 4H), 2.77 (s, 2H), 2.22-2.28 (m, 2H), 2.09-2.16 (m, 4H), 1.97 (s, 2H), 1.39 (t, 2H), 0.93 (s, 6H).

Compound 187

4-(4-{[2-(4-chlorophenyl)-4,4-dimethylcyclohex-1-en-1-yl]methyl}piperazin-1-yl)-N-[(4-{[3-(difluoromethoxy)benzyl]amino}-3-nitrophenyl)sulfonyl]-2-(1H-pyrrolo[2,3-b]pyridin-5-yloxy)benzamide The title compound was prepared by substituting (3-difluoromethoxyphenyl)methanamine for (4-methoxyphenyl)methanamine in the procedure for Compound 174. $^1$H NMR (500 MHz, pyridine-$d_5$) δ 13.06 (s, 1H), 9.34 (t, 1H), 9.30 (d, 1H), 8.42 (d, 1H), 8.26 (dd, 1H), 8.08 (d, 1H), 7.66 (ddd, 2H), 7.40-7.45 (m, 3H), 7.36 (t, 1H), 7.27-7.30 (m, 2H), 7.19 (d, 1H), 7.07 (d, 2H), 6.87 (d, 1H), 6.74 (dd, 1H), 6.52 (d, 1H), 6.49 (dd, 1H), 4.69 (d, 2H), 3.02-3.08 (m, 4H), 2.77 (s, 2H), 2.26 (t, 2H), 2.09-2.16 (m, 4H), 1.97 (s, 2H), 1.39 (t, 2H), 0.93 (s, 6H).

Compound 188

4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide Compound 188A cis-methyl 3-morpholinocyclopentanecarboxylate The title compound was prepared by substituting methyl 3-oxocyclopentanecarboxylate for 4'-chlorobiphenyl-2-carboxaldehyde and morpholine for tert-butyl piperazine-1-carboxylate in the procedure for Compound 1A.

Compound 188B cis-3-morpholinocyclopentyl)methanol

The title compound was prepared by substituting Compound 188A for Compound 101C in the procedure for Compound 101D.

Compound 188C 4-((cis-3-morpholinocyclopentyl)methoxy)-3-nitrobenzenesulfonamide The title compound was prepared by substituting Compound 188B for (1,4-dioxan-2-yl)methanol in the procedure for Compound 12A.

Compound 188D 4-(4-{[2-(4-chlorophenyl)-4,4-dimethylcyclohex-1-en-1-yl]methyl}piperazin-1-yl)-N-{[4-({[cis-3-morpholin-4-ylcyclopentyl]methyl}amino)-3-nitrophenyl]sulfonyl}-2-(1H-pyrrolo[2,3-b]pyridin-5-yloxy)benzamide The title compound was prepared by substituting Compound 188C for Compound 11B in the procedure for Compound 11D. $^1$H NMR (500 MHz, dimethylsulfoxide-$d_6$) δ 11.57 (s, 1H), 8.17 (m, 1H), 7.94 (m, 1H), 7.82 (m, 1H), 7.56 (d, 1H), 7.44 (t, 1H), 7.34 (m, 3H), 7.16 (m, 1H), 7.05 (d, 2H), 6.64 (dd, 1H), 6.33 (m, 1H), 6.24 (d, 1H), 4.06 (m, 2H), 3.62 (m, 4H), 3.03 (m, 4H), 2.75 (s, 2H), 2.35 (m, 2H), 2.19 (m, 6H), 2.03 (m, 2H), 1.96 (s, 2H), 1.78 (m, 2H), 1.51 (m, 4H), 1.39 (t, 2H), 0.93 (s, 6H)

Compound 189 trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide

Compound 189A trans-(4-methanesulfonylamino-cyclohexyl)-carbamic acid tert-butyl ester The title compound was prepared by substituting methanesulfonyl chloride for acetyl chloride in the procedure for Compound 179A.

Compound 189B trans-N-(4-aminocyclohexyl)-methanesulfonamide

The title compound was prepared by substituting Compound 189A for Compound 1A in the procedure for Compound 1B.

Compound 189C trans-4-(4-{[2-(4-chlorophenyl)-4,4-dimethylcyclohex-1-en-1-yl]methyl}piperazin-1-yl)-N-{[4-({4-[(methylsulfonyl)amino]cyclohexyl}amino)-3-nitrophenyl]sulfonyl}-2-(1H-pyrrolo[2,3-b]pyridin-5-yloxy)benzamide The title compound was prepared by substituting Compound 189B for 1-acetylpiperidin-4-amine in the procedure for Compound 53B. $^1$H NMR (300 MHz, dimethylsulfoxide-$d_6$) δ 11.68 (br s, 1H), 8.55 (d, 1H), 8.18 (d, 1H), 8.04 (d, 1H), 7.84 (d, 1H), 7.79 (dd, 1H), 7.56-7.47 (m, 3H), 7.34 (d, 2H), 7.16 (d, 1H), 7.04 (d, 2H), 6.68 (dd, 1H), 6.39 (m, 1H), 6.19 (d, 1H), 3.56 (m, 1H), 3.17 (m, 1H), 3.07 (br s, 4H), 2.93 (s, 3H), 2.75 (br s, 2H), 2.28-2.10 (m, 6H), 2.05-1.90 (m, 6H), 1.55-1.32 (m, 6H), 0.92 (s, 6H).

Compound 190

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide

Compound 190A 4-(1-cyclopropylpiperidin-4-ylamino)-3-(trifluoromethylsulfonyl)benzenesulfonamide The title compound was prepared as described in the procedure for Compound 17A by replacing (tetrahydropyran-4-yl)methylamine with 4-amino-1-cyclopropylpiperidine.

Compound 190B 4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-[(trifluoromethyl)sulfonyl]phenyl}sulfonyl)-2-(1H-pyrrolo[2,3-b]pyridin-5-yloxy)benzamide The title compound was prepared as described in the procedure for Compound 1G by replacing Compound 1E and Compound 1F with Compound 3J and Compound 190A, respectively. $^1$H NMR (300 MHz, dimethylsulfoxide-$d_6$) δ 11.66 (s, 1H), 8.13 (d, 1H), 8.02 (d, 1H), 7.91 (m, 1H), 7.48 (m, 3H), 7.34 (d, 2H), 7.04 (d, 2H), 6.67 (m, 2H), 6.38 (dd, 1H), 6.19 (d, 1H), 3.64 (m, 1H), 3.13 (m, 5H), 2.73 (m, 5H), 2.22 (m, 6H), 1.92 (m, 5H), 1.70 (m, 1H), 1.41 (m, 5H), 0.94 (s, 6H), 0.41 (m, 4H).

Compound 191

4-(4-{2-(4-chlorophenyl)-4,4-dimethylcyclohex-1-en-1-yl methyl}piperazin-1-yl)-N-({3-nitro-4-[(1-oxetan-3-ylpiperidin-4-yl)methoxy]phenyl}sulfonyl)-2-(1H-pyrrolo[2,3-b]pyridin-5-yloxy)benzamide

Compound 191A 3-nitro-4-(piperidin-4-ylmethoxy)benzenesulfonamide

To a solution of tert-butyl 4-(hydroxymethyl)piperidine-1-carboxylate (0.300 g) in tetrahydrofuran (5 ml) was added sodium hydride (0.223 g). After stirring for 15 minutes, 4-fluoro-3-nitrobenzenesulfonamide (0.276 g) was added and reaction stirred at room temperature. After 1 hour the reaction was partitioned between water (25 ml) and dichloromethane (50 ml) and the reaction quenched with 1N aqueous HCl (5.57 ml). The organic layer was separated, dried over magnesium sulfate, filtered, and concentrated. Treatment with HCl (4.0M in dioxane, 2 ml) and methanol (2 ml) for 1 hour, followed by concentration, trituration with dichloromethane and filtration gave the title compound.

Compound 191B 3-nitro-4-((1-(oxetan-3-yl)piperidin-4-yl)methoxy) benzenesulfonamide To a suspension of 3-nitro-4-(piperidin-4-ylmethoxy)benzenesulfonamide (0.100 g) and cyclobutanone (0.030 g) in methanol (1 ml) was added sodium cyanoborohydride (0.027 g). After stirring overnight, the reaction was quenched with saturated $NaHCO_3$ (5 ml) and extracted into dichloromethane (2×10 ml). The organic layer was dried over magnesium sulfate, filtered, and concentrated to give the title compound.

Compound 191C 4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)methoxy] phenyl}sulfonyl)-2-(1H-pyrrolo[2,3-b]pyridin-5-yloxy)benzamide The title compound was prepared by substituting Compound 191B for Compound 1F and Compound 3J for Compound 1E in the procedure for Compound 1G. $^1$H NMR (300 MHz, dimethylsulfoxide-$d_6$) δ 11.64 (s, 1H), 11.46-10.46 (m, 1H), 8.29 (s, 1H), 8.00 (d, 2H), 7.61-7.41 (m, 3H), 7.35 (d, 3H), 7.04 (d, 2H), 6.66 (d, 1H), 6.37 (s, 1H), 6.21 (s, 1H), 4.67-4.40 (m, 4H), 4.08 (d, 2H), 3.06 (s, 4H), 2.78 (s, 4H), 2.19 (m, 6H), 1.96 (s, 4H), 1.79 (m, 4H), 1.39 (s, 4H), 0.93 (s, 6H).

Compound 192

4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide Compound 192A 4-((4-fluoro-1-(tetrahydro-2H-pyran-4-yl)piperidin-4-yl)methoxy)-3-nitrobenzenesulfonamide A mixture of Compound 173A (0.4 g), dihydro-2H-pyran-4(3H)-one (0.179 g), sodium cyanoborohydride (0.112 g), and acetic acid (0.5 ml) in tetrahydrofuran (3 ml) was stirred overnight. The solvents were removed under reduced pressure. The residue was purified with flash column chromatography on silica gel eluting with 100:5:0.5 ethyl acetate/methanol/$NH_4OH$ to give the desired product.

Compound 192B 4-(4-{[2-(4-chlorophenyl)-4,4-dimethylcyclohex-1-en-1-yl]methyl}piperazin-1-yl)-N-({4-[(4-fluoro-1-tetrahydro-2H-pyran-4-ylpiperidin-4-yl)methoxy]-3-nitrophenyl}sulfonyl)-2-(1H-pyrrolo[2,3-b]pyridin-5-yloxy)benzamide The title compound was prepared by substituting Compound 192A for Compound 11B in the procedure for Compound 11D. $^1$H NMR (500 MHz, dimethylsulfoxide-$d_6$) δ 11.58 (s, 1H), 8.25 (s, 1H), 7.96 (d, 1H), 7.93 (d, 1H), 7.57 (d, 1H), 7.45 (t, 1H), 7.34-7.37 (m, 3H), 7.26 (d, 1H), 7.05 (d, 2H), 6.64 (dd, 1H), 6.34 (dd, 1H), 6.23 (d, 1H), 4.34 (d, 2H), 3.93 (dd, 2H), 3.03 (s, 6H), 2.76 (s, 4H), 2.09-2.22 (m, 6H), 1.96 (s, 2H), 1.52-1.27 (m, 2H), 1.39 (t, 2H), 0.93 (s, 6H).

Compound 193

4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide Compound 193A 4-((4-fluoro-1-(tetrahydrofuran-3-yl)piperidin-4-yl) methoxy)-3-nitrobenzenesulfonamide The title compound was prepared by substituting dihydrofuran-3(2H)-one for dihydro-2H-pyran-4(3H)-one in the procedure for Compound 192A.

Compound 193B 4-(4-{[2-(4-chlorophenyl)-4,4-dimethylcyclohex-1-en-1-yl]methyl}piperazin-1-yl)-N-({4-[(4-fluoro-1-tetrahydrofuran-3-ylpiperidin-4-yl)methoxy]-3-nitrophenyl}sulfonyl)-2-(1H-pyrrolo[2,3-b]pyridin-5-yloxy)benzamide The title compound was prepared by substituting Compound 193A for Compound 11B in the procedure for Compound 11D. $^1$H NMR (500 MHz, dimethylsulfoxide-$d_6$) δ 11.63 (s, 1H), 8.31 (s, 1H), 7.99-8.00 (m, 2H), 7.54 (d, 1H), 7.46-7.48 (m, 2H), 7.34-7.35 (m, 3H), 7.05 (d2H), 6.66 (dd, 1H), 6.37 (dd, 1H), 6.21 (d, 1H), 4.34 (d, 2H), 3.76-3.83 (m, 3H), 3.62-3.65 (m, 2H), 3.03 (s, 4H), 2.79 (s, 4H), 2.24 (s, 2H), 2.15 (s, 2H), 1.84-1.99 (m, 8H), 1.52-1.27 (m, 2H), 1.39 (t, 2H), 0.93 (s, 6H).

Compound 194

4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide Compound 194A 4-((4-fluoro-1-(methylsulfonyl)piperidin-4-yl) methoxy)-3-nitrobenzenesulfonamide A mixture of Compound 173A (0.4 g), methanesulfonyl chloride (0.113 g), and triethylamine (0.64 ml) in dichloromethane (5 ml) was stirred overnight. The reaction mixture was loaded onto a silica gel column and eluted with 100:1 ethyl acetate:methanol to give the clean product.

Compound 194B 4-(4-{[2-(4-chlorophenyl)-4,4-dimethylcyclohex-1-en-1-yl]methyl}piperazin-1-yl)-N-[(4-{[4-fluoro-1-(methylsulfonyl)piperidin-4-yl]methoxy}-3-nitrophenyl)sulfonyl]-2-(1H-pyrrolo[2,3-b]pyridin-5-yloxy)benzamide The title compound was prepared by substituting Compound 194A for Compound 11B in the procedure for Compound 11D. $^1$H NMR (500 MHz, dimethylsulfoxide-$d_6$) δ 11.66 (s, 1H), 8.37 (s, 1H), 8.06 (d, 1H), 8.02 (d, 1H), 7.49-7.53 (m, 3H), 7.42 (d, 1H), 7.35 (d, 2H), 7.05 (d, 2H), 6.67 (dd, 1H), 6.38-6.39 (m, 1H), 6.21 (d, 1H), 4.40 (d, 2H), 3.51-3.54 (m, 2H), 3.09 (s, 4H), 2.96-3.01 (m, 4H), 2.92 (s, 3H), 2.82 (s, 2H), 2.25-2.34 (m, 4H), 2.13-2.16 (m, 6H), 2.01-2.07 (m, 2H0, 1.99 (s, 2H), 1.39 (t, 2H), 0.93 (s, 6H).

Compound 195

4-(4-{[2-(4-chlorophenyl)-4,4-dimethylcyclohex-1-en-1-yl]methyl}piperazin-1-yl)-N-{[3-nitro-4-{[(3R)-1-oxetan-3-ylpyrrolidin-3-yl]methyl}amino)phenyl]sulfonyl}-2-(1H-pyrrolo[2,3-b]pyridin-5-yloxy)benzamide Compound 195A (R)-tert-butyl 3-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)pyrrolidine-1-carboxylate The title compound was prepared by substituting (R)-tert-butyl 3-(aminomethyl)pyrrolidine-1-carboxylate for 1-acetylpiperidin-4-amine in the procedure for Compound 53B.

Compound 195B (S)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(pyrrolidin-3-ylmethylamino)phenylsulfonyl)benzamide The title compound was prepared by substituting Compound 195A for Compound 1A in the procedure for Compound 1B.

Compound 195C (R)-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((1-(oxetan-3-yl)pyrrolidin-3-yl)methylamino)phenylsulfonyl)benzamide The title compound was prepared by substituting Compound 195B for tert-butyl piperazine-1-carboxylate and oxetan-3-one for 4'-chlorobiphenyl-2-carboxaldehyde in the procedure for Compound 1A. $^1$H NMR (500 MHz, dimethylsulfoxide-$d_6$) δ 11.67 (s, 1H), 8.81 (t, 1H), 8.55 (d, 1H), 8.02 (d, 1H), 7.79 (dd, 1H), 7.50 (m, 3H), 7.35 (m, 2H), 7.04 (m, 3H), 6.67 (dd, 1H), 6.39 (m, 1H), 6.19 (d, 1H), 4.57 (m, 2H), 4.48 (m, 2H), 3.68 (m, 2H), 3.30 (m, 2H), 3.06 (m, 4H), 2.74 (m, 3H), 2.56 (m, 3H), 2.44 (m, 1H), 2.18 (m, 5H), 1.95 (m, 3H), 1.58 (m, 1H), 1.36 (m, 2H), 0.94 (s, 6H).

Compound 196 trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide Compound 196A trans-4-(4-(tert-butyldimethylsilyloxy)cyclohexyl)methoxy)-3-nitrobenzenesulfonamide The title compound was prepared as described in the procedure for Compound 12A by replacing (1,4-dioxan-2-yl)methanol with trans-(4-(tert-butyldimethylsilyloxy)cyclohexyl)methanol (made according to the procedures in WO 2008/124878, incorporated herein by reference).

Compound 196B trans-2-(1H-pyrrolo[2,3-b]pyridin-5-yloxy)-N-(4-(((1r,4r)-4-(tert-butyldimethylsilyloxy)cyclohexyl)methoxy)-3-nitrophenylsulfonyl)-4-(4-((2-(4-chlorophenyl)-4,4-dimethylcyclohex-1-enyl)methyl)piperazin-1-yl)benzamide The title compound was prepared as described in the procedure for Compound 1G using Compound 196A in place of Compound 1F and Compound 3J in place of Compound 1E.

Compound 196C trans-4-(4-{[2-(4-chlorophenyl)-4,4-dimethylcyclohex-1-en-1-yl]methyl}piperazin-1-yl)-N-({4-[(4-hydroxycyclohexyl)methoxy]-3-nitrophenyl}sulfonyl)-2-(1H-pyrrolo[2,3-b]pyridin-5-yloxy)benzamide Compound 196B (150 mg) in dichloromethane (5 ml) and methanol (2 ml) was treated with 10% aqueous HCl (3 ml) for 1 hour and concentrated. The residue was purified by reverse phase HPLC on a C18 column using a gradient of 40-60% acetonitrile in 0.1% trifluoroacetic acid water to give the title compound as a trifluoroacetate salt. The trifluoroacetic acid salt was dissolved in dichloromethane (30 ml) and washed with 50% aqueous NaHCO$_3$. The organic layer was dried over anhydrous Na$_2$SO$_4$, filtered, and concentrated to give the title compound. $^1$H NMR (400 MHz, dimethylsulfoxide-$d_6$) δ 11.69 (s, 1H), 11.27 (s, 1H), 8.34 (d, 1H), 7.95-8.08 (m, 2H), 7.47-7.55 (m, 3H), 7.32-7.40 (m, 3H), 7.01-7.07 (m, 2H), 6.68 (dd, 1H), 6.39 (dd, 1H), 6.20 (d, 1H), 4.54 (d, 1H), 3.96-4.06 (m, 2H), 3.10 (s, 4H), 2.84 (s, 2H), 2.05-2.39 (m, 6H), 1.96 (s, 2H), 1.46-1.93 (m, 5H), 1.39 (t, 2H), 0.98-1.29 (m, 4H), 0.92 (s, 6H).

Compound 197

4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide Compound 197A 3-(4-(aminomethyl)phenoxy)-N,N-dimethylpropan-1-amine 4-(3-(Dimethylamino)propoxy)benzonitrile (300 mg) in methanol (20 ml) was treated with Raney nickel (wet, 1.5 g) under $H_2$ (30 psi) for 4 hour. The insoluble material was filtered off and the filtrate was concentrated to provide the title compound.

Compound 197B 4-(4-{[2-(4-chlorophenyl)-4,4-dimethylcyclohex-1-en-1-yl]methyl}piperazin-1-yl)-N-{[4-({4-[3-(dimethylamino)propoxy]benzyl}amino)-3-nitrophenyl]sulfonyl}-2-(1H-pyrrolo[2,3-b]pyridin-5-yloxy)benzamide The title compound was prepared as described in the procedure for Compound 120B using Compound 197A in place of Compound 120A. $^1$H NMR (400 MHz, dimethyl-sulfoxide-$d_6$) δ 11.56 (s, 1H), 8.80 (t, 1H), 8.42 (d, 1H), 7.93 (d, 1H), 7.52-7.61 (m, 2H), 7.41-7.47 (m, 1H), 7.26-7.36 (m, 5H), 7.03-7.08 (m, 2H), 6.89 (d, 2H), 6.73 (d, 1H), 6.61 (dd, 1H), 6.31 (dd, 1H), 6.22 (d, 1H), 4.52 (d, 2H), 3.99 (t, 2H), 2.90-3.05 (m, 7H), 2.72 (s, 2H), 2.61 (s, 6H), 2.09-2.24 (m, 6H), 1.89-2.04 (m, 5H), 1.38 (t, 2H), 0.92 (s, 6H).

Compound 198

4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide Compound 198A (4-(2-morpholinoethoxy)phenyl)methanamine The title compound was prepared as described in the procedure for Compound 197A using 4-(2-morpholinoethoxy)benzonitrile in place of 4-(3-(dimethylamino)propoxy)benzonitrile.

Compound 198B 4-(4-{[2-(4-chlorophenyl)-4,4-dimethylcyclohex-1-en-1-yl]methyl}piperazin-1-yl)-N-[(4-{[4-(2-morpholin-4-ylethoxy)benzyl]amino}-3-nitrophenyl)sulfonyl]-2-(1H-pyrrolo[2,3-b]pyridin-5-yloxy)benzamide The title compound was prepared as described in the procedure for Compound 120B using Compound 198A in place of Compound 120A. $^1$H NMR (400 MHz, dimethyl-sulfoxide-$d_6$) δ 11.69 (s, 1H), 9.00 (t, 1H), 8.56 (d, 1H), 8.02 (d, 1H), 7.72 (dd, 1H), 7.46-7.54 (m, 3H), 7.27-7.36 (m, 4H), 7.01-7.07 (m, 2H), 6.89-6.95 (m, 3H), 6.66 (dd, 1H), 6.38 (dd, 1H), 6.18 (d, 1H), 4.56 (d, 2H), 4.07 (t, 2H), 3.54-3.61 (m, 4H), 3.06 (s, 4H), 2.71-2.78 (m, 4H), 2.07-2.24 (m, 6H), 1.95 (s, 2H), 1.38 (t, 2H), 0.92 (s, 6H).

Compound 199

4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl)-2-(1H-pyrrolo[2,3-b]pyridin-5-yloxy)benzamide Compound 199A 4-[((E)-4-hydroxy-adamantan-1-ylmethyl)-amino]-3-nitro-benzenesulfonamide 4-Fluoro-3-nitrobenzenesulfonamide (0.5 g) and 5-(aminomethyl)adamantan-2-ol (0.6 g) in tetrahydrofuran (10 ml) were treated with triethylamine (1 ml) overnight. The reaction mixture was concentrated and the residue was purified by reverse phase HPLC, eluting 40-60% acetonitrile in 0.1 trifluoroacetic acid water to give two isomers, which were temporarily assigned as Compound 199A and Compound 199B, respectively.

Compound 199B

4-[((Z)-4-hydroxy-adamantan-1-ylmethyl)-amino]-3-nitro-benzenesulfonamide

4-Fluoro-3-nitrobenzenesulfonamide (0.5 g) and 5-(aminomethyl)adamantan-2-ol (0.6 g) in tetrahydrofuran (10 ml) were treated with triethylamine (1 ml) overnight. The reaction mixture was concentrated and the residue was purified by reverse phase HPLC, eluting 40-60% acetonitrile in 0.1 trifluoroacetic acid water to give two isomers, which were temporarily assigned as Compound 199A and Compound 199B, respectively.

Compound 199C 4-(4-{[2-(4-chlorophenyl)-4,4-dimethylcyclohex-1-en-1-yl]methyl}piperazin-1-yl)-N-{[4-({[(E)-4-hydroxy-1-adamantyl]methyl}amino)-3-nitrophenyl]sulfonyl}-2-(1H-pyrrolo[2,3-b]pyridin-5-yloxy)benzamide The title compound was prepared as described in the procedure for Compound 11D using Compound 199A in place of Compound 11B. $^1$H NMR (400 MHz, dimethyl-sulfoxide-$d_6$) δ 11.68 (s, 1H), 11.40 (s, 1H), 8.55 (d, 1H), 8.50 (t, 1H), 8.03 (d, 1H), 7.77 (dd, 1H), 7.46-7.54 (m, 3H), 7.31-7.38 (m, 2H), 7.14 (d, 1H), 7.01-7.06 (m, 2H), 6.68 (dd, 1H), 6.38 (dd, 1H), 6.19 (d, 1H), 4.61 (d, 1H), 3.63 (d, 1H), 3.02-3.16 (m, 6H), 2.75 (s, 2H), 2.17 (d, 6H), 2.04 (d, 2H), 1.95 (s, 2H), 1.76-1.88 (m, 3H), 1.49-1.61 (m, 6H), 1.38 (t, 2H), 1.29 (d, 2H), 0.92 (s, 6H).

Compound 200

4-(4-{[2-(4-chlorophenyl)-4,4-dimethylcyclohex-1-en-1-yl]methyl}piperazin-1-yl)-N-{[4-({[(Z)-4-hydroxy-1-adamantyl]methyl}amino)-3-nitrophenyl]sulfonyl}-2-(1H-pyrrolo[2,3-b]pyridin-5-yloxy)benzamide The title compound was prepared as described in the procedure for Compound 11D using Compound 199B in place of Compound 11B. $^1$H NMR (400 MHz, dimethylsulfoxide-d$_6$) δ 11.68 (s, 1H), 11.39 (s, 1H), 8.55 (d, 1H), 8.51 (t, 1H), 8.04 (d, 1H), 7.77 (dd, 1H), 7.46-7.55 (m, 3H), 7.31-7.37 (m, 2H), 7.14 (d, 1H), 7.01-7.06 (m, 2H), 6.68 (dd, 1H), 6.39 (dd, 1H), 6.19 (d, 1H), 4.61 (d, 1H), 3.61 (d, 1H), 3.08 (d, 6H), 2.75 (s, 2H), 2.17 (d, 6H), 1.79-1.99 (m, 7H), 1.55-1.69 (m, 4H), 1.49 (s, 2H), 1.38 (t, 2H), 1.22 (d, 2H), 0.92 (s, 6H).

Compound 201

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 201A 4-((1S,4S)-bicyclo[2.2.1]hept-5-en-2-ylmethoxy)-3-nitrobenzenesulfonamide The title compound was prepared as described in the procedure for Compound 12A by replacing (1,4-dioxan-2-yl)methanol with (1S,4S)-bicyclo[2.2.1]hept-5-en-2-ylmethanol.

Compound 201B

N-({4-[(1S,4S)-bicyclo[2.2.1]hept-5-en-2-ylmethoxy]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in the procedure for Compound 11D using Compound 201A in place of Compound 11B. $^1$H NMR (500 MHz, dimethylsulfoxide-d$_6$) δ 11.69 (s, 1H), 8.35 (d, 1H), 7.95-8.10 (m, 2H), 7.47-7.58 (m, 3H), 7.30-7.45 (m, 3H), 7.04 (d, 2H), 6.68 (dd, 1H), 6.40 (d, 1H), 5.92-6.23 (m, 3H), 3.65-4.39 (m, 3H), 3.00-3.22 (m, 4H), 2.76-2.98 (m, 4H), 2.28 (s, 4H), 2.15 (s, 2H), 1.96 (s, 2H), 1.71-1.91 (m, 1H), 1.33-1.47 (m, 3H), 1.20-1.32 (m, 2H), 0.92 (s, 6H), 0.50-0.66 (m, 1H).

Compound 202

4-(4-{[2-(4-chlorophenyl)-4,4-dimethylcyclohex-1-en-1-yl]methyl}piperazin-1-yl)-N-({4-[(1-methyl-5-oxopyrrolidin-3-yl)amino]-3-nitrophenyl}sulfonyl)-2-(1H-pyrrolo[2,3-b]pyridin-5-yloxy)benzamide Compound 82 (140 mg) was dissolved in dioxane (3.0 ml), and 4-amino-1-methylpyrrolidin-2-one hydrochloride (30 mg) and triethylamine (0.100 ml) were added. The reaction mixture was heated at 110° C. for 40 hours. The reaction was concentrated and the crude material was purified by preparative HPLC using a C18 column, 250×50 mm, 10µ, and eluting with a gradient of 20-100% CH$_3$CN vs. 0.1% trifluoroacetic acid in water, giving the product as a trifluoroacetate salt. The salt was dissolved in dichloromethane (6 ml) and washed with 50% aqueous NaHCO$_3$. The organic layer was dried over anhydrous Na$_2$SO$_4$ and concentrated to give the title compound. $^1$H NMR (400 MHz, dimethylsulfoxide-d$_6$) δ 11.65 (s, 1H), 8.74 (d, 1H), 8.37 (br d, 1H), 8.02 (d, 1H), 7.83 (dd, 1H), 7.49 (m, 3H), 7.34 (d, 2H), 7.07 (d, 1H), 7.04 (d, 2H), 6.68 (dd, 1H), 6.38 (m, 1H), 6.21 (d, 1H), 4.46 (m, 1H), 3.81 (dd, 1H), 3.38 (dd, 1H), 3.08 (br m, 4H), 2.82 (dd, 1H), 2.75 (s, 5H), 2.43 (dd, 1H), 2.21 (br m, 4H), 2.16 (br t, 2H), 1.95 (s, 2H), 1.39 (t, 2H), 0.94 (s, 6H).

Compound 203

4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide

Compound 203A 4-(((1R,4R,5R,6S)-5,6-dihydroxybicyclo[2.2.1]heptan-2-yl)methoxy)-3-nitrobenzenesulfonamide To a solution of Compound 201A (340 mg) in tetrahydrofuran (10 ml) and water (1 ml) was added N-methylmorpholine N-oxide (184 mg) and OsO$_4$ (2.5% in 2-methyl-2-propanol) (1.05 ml). The reaction mixture was stirred overnight and purified by reverse phase HPLC to provide two isomers, which were temporarily assigned as Compound 203A and Compound 203B, respectively.

Compound 203B 4-(((1R,4R,5S,6R)-5,6-dihydroxybicyclo[2.2.1]heptan-2-yl)methoxy)-3-nitrobenzenesulfonamide To a solution of Compound 201A (340 mg) in tetrahydrofuran (10 ml) and water (1 ml) was added N-methylmorpholine N-oxide (184 mg) and OsO$_4$ (2.5% in 2-methyl-2-propanol) (1.05 ml). The reaction mixture was stirred overnight and purified by reverse phase HPLC to provide two isomers, which were temporarily assigned as Compound 203A and Compound 203B, respectively.

Compound 203C 4-(4-{[2-(4-chlorophenyl)-4,4-dimethylcyclohex-1-en-1-yl]methyl}piperazin-1-yl)-N-[(4-{[(1R,4R,5R,6S)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide The title compound was prepared as described in the procedure for Compound 11D using Compound 203A in place of Compound 11B. $^1$H NMR (400 MHz, dimethylsulfoxide-d$_6$) δ 11.68 (s, 1H), 8.33 (s, 1H), 7.97-8.07 (m, 2H), 7.48-7.55 (m, 3H), 7.41 (d, 1H), 7.32-7.37 (m, 2H), 7.02-7.07 (m, 2H), 6.67 (dd, 1H), 6.40 (d, 1H), 6.20 (d, 1H), 4.58 (dd, 2H), 4.07-4.19 (m, 2H), 3.82 (t, 1H), 3.51 (t, 1H), 3.09 (s, 4H), 2.81 (s, 2H), 2.09-2.34 (m, 8H), 2.04-2.09

(m, 2H), 1.93-2.01 (m, 3H), 1.62-1.77 (m, 2H), 1.39 (t, 2H), 1.11 (d, 1H), 0.92 (s, 6H), 0.67-0.76 (m, 1H).

Compound 204

4-(4-{[2-(4-chlorophenyl)-4,4-dimethylcyclohex-1-en-1-yl]methyl}piperazin-1-yl)-N-[(4-{[(1R,4R,5S,6R)-5,6-dihydroxybicyclo[2.2.1]hept-2-yl]methoxy}-3-nitrophenyl)sulfonyl]-2-(1H-pyrrolo[2,3-b]pyridin-5-yloxy)benzamide The title compound was prepared as described in the procedure for Compound 11D using Compound 203B in place of Compound 11B. $^1$H NMR (400 MHz, dimethylsulfoxide-$d_6$) δ 11.68 (s, 1H), 8.33 (s, 1H), 7.98-8.07 (m, 2H), 7.49-7.54 (m, 3H), 7.41 (d, 1H), 7.32-7.36 (m, 2H), 7.02-7.07 (m, 2H), 6.67 (dd, 1H), 6.40 (dd, 1H), 6.20 (d, 1H), 4.58 (dd, 2H), 4.13 (dd, 2H), 3.82 (t, 1H), 3.51 (t, 1H), 3.09 (s, 4H), 2.81 (s, 2H), 2.09-2.35 (m, 8H), 2.07 (s, 2H), 1.93-2.02 (m, 3H), 1.61-1.80 (m, 2H), 1.39 (t, 2H), 1.11 (d, 1H), 0.92 (s, 6H), 0.66-0.78 (m, 1H).

Compound 205

4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide Compound 205A methyl 1,4-dioxaspiro[4.5]decane-7-carboxylate To a solution of trimethylsilyltrifluoromethanesulfonate (0.034 ml) in dry dichloromethane (5 ml) was added 1,2-bis(trimethylsiloxy)ethane (4.55 ml) followed by methyl 3-oxocyclohexanecarboxylate (2.9 g). The reaction mixture was stirred for 3 hours at −78° C. The reaction mixture was quenched with dry pyridine (0.5 ml), poured into saturated aqueous NaHCO$_3$, and extracted with ether. The ether layer was dried over Na$_2$CO$_3$/Na$_2$SO$_4$. The reaction mixture was concentrated and purified by flash chromatography on silica with 5 to 30% ethyl acetate in hexanes to provide the title compound.

Compound 205B 1,4-dioxaspiro[4.5]decan-7-ylmethanol

The title compound was prepared by substituting Compound 205A for Compound 101C in the procedure for Compound 101D.

Compound 205C 3-nitro-4-((3-oxocyclohexyl)methoxy)benzenesulfonamide

Into a 250 ml round-bottomed flask was added sodium hydride (0.5 g) in tetrahydrofuran (10 ml) and then 1,4-dioxaspiro[4.5]decan-7-ylmethanol (0.5 g) was added.
After the mixture stirred at room temperature for 20 minutes, 4-fluoro-3-nitrobenzenesulfonamide (0.65 g) was added. The mixture was stirred at room temperature for overnight. Water (20 ml) was added slowly. The aqueous layer was extracted by dichloromethane (3×20 ml). The combined organic layers were dried over Na$_2$SO$_4$. After filtration, and concentration of the filtrate, the residue was purified by reverse phase chromatography, eluting with 30-60% acetonitrile in water with 0.1% trifluoroacetic acid.

Compound 205D 4-(4-{[2-(4-chlorophenyl)-4,4-dimethylcyclohex-1-en-1-yl]methyl}piperazin-1-yl)-N-({3-nitro-4-[(3-oxocyclohexyl)methoxy]phenyl}sulfonyl)-2-(1H-pyrrolo[2,3-b]pyridin-5-yloxy)benzamide The title compound was prepared by substituting Compound 205C for Compound 11B in the procedure for Compound 11D. $^1$H NMR (400 MHz, dimethylsulfoxide-$d_6$) δ 11.59 (s, 1H), 8.22 (s, 1H), 7.96 (d, 1H), 7.87 (m, 1H), 7.55 (d, 1H), 7.45 (t, 1H), 7.35 (m, 3H), 7.20 (m, 1H), 7.04 (d, 2H), 6.64 (dd, 1H), 6.34 (m, 1H), 6.23 (d, 1H), 4.07 (d, 2H), 3.04 (m, 4H), 2.76 (s, 2H), 2.35 (m, 2H), 2.20 (m, 8H), 1.96 (m, 4H), 1.58 (m, 2H), 1.39 (t, 2H), 0.93 (s, 6H).

Compound 206

4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 206A 2-chloro-5,5-dimethylcyclohexa-1,3-dienecarbaldehyde In a 250 ml round-bottomed flask was added N,N-dimethylformamide (3.5 ml) in dichloromethane (30 ml), and the mixture was cooled to −10° C. Phosphoryl trichloride (4 ml) was added dropwise, and the solution was warmed up to room temperature. 4,4-Dimethylcyclohex-2-enone (5.5 ml) was then added slowly, and the mixture was heated to reflux overnight. The reaction mixture was cooled and quenched with a 0° C. solution of sodium acetate (25 g in 50 ml water). The aqueous layer was extracted with diethyl ether (200 ml×3). The combined organic layers were dried over Na$_2$SO$_4$, filtered, and concentrated to give the product.

Compound 206B 2-(4-chlorophenyl)-5,5-dimethylcyclohexa-1,3-dienecarbaldehyde

Into a 1 L round-bottomed flask was added Compound 206A (6.8 g), 4-chlorophenylboronic acid (6.5 g), and palladium (II) acetate (0.2 g) in water (100 ml) to give a suspension. Potassium carbonate (15 g) and tetrabutylammonium bromide (10 g) were added. After degassing, the mixture was stirred at 45° C. for 4 hours. After cooling and filtering though silica gel in a funnel, diethyl ether (4×200 ml) was used to extract the product. The combined organic layers were dried over Na$_2$SO$_4$, and filtered. The filtrate was concentrated and purified by flash chromatography on silica with 0-10% ethyl acetate in hexanes to provide the title compound.

Compound 206C

Methyl 2-(1H-pyrrolo[2,3-b]pyridin-5-yloxy)-4-(4-((2-(4-chlorophenyl)-5,5-dimethylcyclohexa-1,3-dienyl)methyl)piperazin-1-yl)benzoate The title compound was prepared by substituting Compound 206B for 4'-chlorobiphenyl-2-carboxaldehyde and Compound 15F for tert-butyl piperazine-1-carboxylate in the procedure for Compound 1A.

Compound 206D 2-(1H-pyrrolo[2,3-b]pyridin-5-yloxy)-4-(4-((2-(4-chlorophenyl)-5,5-dimethylcyclohexa-1,3-dienyl)methyl)piperazin-1-yl)benzoic Acid The title compound was prepared by substituting Compound 206C for Compound 101E in the procedure for Compound 101F.

Compound 206E 4-(4-{[2-(4-chlorophenyl)-5,5-dimethylcyclohexa-1,3-dien-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 206D for Compound 3J and Compound 1F for Compound 11B in the procedure for Compound 11D. $^1$H NMR (400 MHz, dimethylsulfoxide-$d_6$) δ 11.61 (s, 1H), 8.49 (m, 2H), 7.99 (m, 1H), 7.72 (m, 1H), 7.53 (d, 1H), 7.41 (m, 4H), 7.12 (d, 2H), 6.99 (m, 1H), 6.66 (dd, 1H), 6.35 (m, 1H), 6.23 (d, 1H), 5.74 (d, 1H), 5.58 (d, 1H), 3.84 (m, 2H), 3.26 (m, 4H), 3.06 (m, 4H), 2.88 (s, 2H), 2.24 (m, 6H), 1.61 (m, 2H), 1.26 (m, 3H), 1.00 (s, 6H).

Compound 207

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide

Compound 207A (R)-1-(1,3-difluoropropan-2-yl)pyrrolidin-3-amine

The title compound was prepared by substituting (R)-tert-butyl pyrrolidin-3-ylcarbamate for tert-butyl azetidin-3-ylcarbamate in the procedure for Compound 151A.

Compound 207B (R)-4-(1-(1,3-difluoropropan-2-yl)pyrrolidin-3-ylamino)-3-nitrobenzenesulfonamide The title compound was prepared by substituting Compound 207A for Compound 151A in the procedure for Compound 151B.

Compound 207C 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-(1H-pyrrolo[2,3-b]pyridin-5-yloxy)benzamide The title compound was prepared by substituting Compound 207B for Compound 1F and Compound 3J for Compound 1E in the procedure for Compound 1G. $^1$H NMR (300 MHz, dimethylsulfoxide-$d_6$) δ 11.67 (s, 1H), 11.52-11.24 (m, 1H), 8.55 (d, 1H), 8.37 (d, 1H), 8.03 (d, 1H), 7.83 (dd, 1H), 7.57-7.45 (m, 3H), 7.34 (d, 2H), 7.06 (t, 3H), 6.67 (d, 1H), 6.38 (dd, 1H), 6.20 (d, 1H), 4.70 (d, 2H), 4.54 (d, 2H), 4.23 (s, 1H), 3.11-2.87 (m, 7H), 2.74 (dd, 4H), 2.35-2.13 (m, 7H), 1.95 (s, 2H), 1.70 (s, 1H), 1.39 (d, 2H), 0.92 (s, 6H).

Compound 208

4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide

Compound 208A 2-((4-fluorotetrahydro-2H-pyran-4-yl)methoxy)-5-iodo-3-(trifluoromethyl)pyridine A mixture of Compound 37C (0.537 g), 5-iodo-3-(trifluoromethyl)pyridin-2-ol (1.156 g), and triphenylphosphine (1.574 g) in tetrahydrofuran (20 ml) was cooled to 0° C. To this solution was added (E)-di-tert-butyl diazene-1,2-dicarboxylate (0.921 g). The reaction mixture was stirred overnight. The solvent was removed, and the residue was purified with column flash chromatography on silica gel eluting with 4:1 hexanes/ethyl acetate to give the desired product.

Compound 208B 6-((4-fluorotetrahydro-2H-pyran-4-yl)methoxy)-5-(trifluoromethyl)pyridine-3-sulfonamide Compound 207A (1.3 g) in tetrahydrofuran (10 ml) was cooled to −42° C. with a cold bath of CH$_3$CN/dry ice. To this solution was added 2.0 M isopropylmagnesium chloride (1.6 ml) dropwise over 5 minutes. The reaction mixture was stirred for 30 minutes at −42° C., then allowed to warm to 0° C. over 10 minutes. The reaction mixture was cooled again to −42° C., and SO$_2$ was bubbled though it for 10 minutes. The reaction mixture was stirred for another 30 minutes. To this solution was sulfuryl dichloride (0.433 g). On warming to room temperature, concentrated NH$_4$OH (10 ml) was added and the reaction mixture was stirred for another 2 hours. The reaction mixture was partitioned between water and ethyl acetate. The aqueous layer was extracted with additional ethyl acetate three times. The combined organic layers were washed with brine, dried over MgSO$_4$, filtered, and concentrated. The residue was purified by flash column chromatography on silica gel eluting with 3:1 hexanes/ethyl acetate to give the title compound.

Compound 208C 4-(4-{[2-(4-chlorophenyl)-4,4-dimethylcyclohex-1-en-1-yl]methyl}piperazin-1-yl)-N-{[6-[(4-fluorotetrahydro-2H-pyran-4-yl)methoxy]-5-(trifluoromethyl)pyridin-3-yl]sulfonyl}-2-(1H-pyrrolo[2,3-b]pyridin-5-yloxy)benzamide The title compound was prepared by substituting Compound 208B for Compound 11B in the procedure for Compound 11D. $^1$H NMR (500 MHz, dimethylsulfoxide-d$_6$) δ 11.61 (s, 1H), 8.72 (s, 1H), 8.36 (s, 1H), 7.98 (d, 1H), 7.55 (d, 1H), 7.42-7.47 (m, 2H), 7.36 (d, 2H), 7.05 (d, 2H), 6.66 (dd, 1H), 6.35 (s, 1H), 6.23 (s, 1H), 4.56 (d, 2H), 3.75-3.79 (m, 2H), 3.56-3.61 (m, 2H), 3.09 (s, 4H), 2.32-2.37 (m, 2H), 2.16 (s, 2H), 1.97-1.99 (m, 2H), 1.79-1.86 (m, 4H), 1.40 (t, 2H), 0.93 (s, 6H).

Compound 209

4-(4-{[2-(4-chlorophenyl)-4,4-dimethylcyclohex-1-en-1-yl]methyl}piperazin-1-yl)-N-{[3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide

Compound 209A (S)-tert-butyl (1-(oxetan-3-yl)pyrrolidin-3-yl)methylcarbamate The title compound was prepared by substituting (R)-tert-butyl pyrrolidin-3-ylmethylcarbamate for tert-butyl piperazine-1-carboxylate and 3-oxetanone for 4'-chlorobiphenyl-2-carboxaldehyde in the procedure for Compound 1A.

Compound 209B (S)-(1-(oxetan-3-yl)pyrrolidin-3-yl)methanamine

The title compound was prepared by substituting Compound 209A for (S)-1-tert-butyl 2-methyl 4,4-difluoropyrrolidine-1,2-dicarboxylate in the procedure for Compound 168A.

Compound 209C (S)-3-nitro-4-((1-(oxetan-3-yl)pyrrolidin-3-yl)methylamino)benzenesulfonamide The title compound was prepared by substituting 4-fluoro-3-nitrobenzenesulfonamide for 4-chloro-3-nitrobenzenesulfonamide and Compound 209B for 4-methylpiperazin-1-amine dihydrochloride in the procedure for Compound 6A.

Compound 209D 4-(4-{[2-(4-chlorophenyl)-4,4-dimethylcyclohex-1-en-1-yl]methyl}piperazin-1-yl)-N-{3-nitro-4-({[(3S)-1-oxetan-3-ylpyrrolidin-3-yl]methyl}amino)phenyl]sulfonyl}-2-(1H-pyrrolo[2,3-b]pyridin-5-yloxy)benzamide The title compound was prepared by substituting Compound 209C for Compound 11B in the procedure for Compound 11D. $^1$H NMR (500 MHz, pyridine-d$_5$) δ 13.05 (s, 1H), 9.30 (d, 1H), 9.02 (t, 1H), 8.42 (d, 1H), 8.34 (dd, 1H), 8.10 (d, 1H), 7.67 (dd, 2H), 7.44 (d, 2H), 7.07 (d, 2H), 6.82 (d, 1H), 6.75 (m, 1H), 6.52 (m, 2H), 4.82 (t, 1H), 4.75 (t, 1H), 4.67 (t, 2H), 3.57 (m, 1H), 3.24 (t, 2H), 3.07 (m, 4H), 2.75 (m, 3H), 2.57 (dd, 1H), 2.45 (s, 1H), 2.36 (t, 1H), 2.26 (s, 2H), 2.18 (m, 5H), 1.93 (m, 3H), 1.56 (m, 1H), 1.39 (t, 2H), 0.93 (s, 6H).

Compound 210 trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 210A (4-methoxycyclohexyl)methanol

The title compound was prepared by substituting 4-methoxycyclohexanecarboxylic acid for 1-tert-butyl 4-ethyl 4-fluoropiperidine-1,4-dicarboxylate in the procedure for Compound 126A.

Compound 210B trans-5-chloro-6-((4-methoxycyclohexyl)methoxy)pyridine-3-sulfonamide The title compound was prepared by substituting Compound 210A for tetrahydro-2H-pyran-4-yl)methanol and Compound 40A for 4-fluoro-3-nitrobenzenesulfonamide in the procedure for Compound 24A.

Compound 210C trans-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 210C for Compound 11B in the procedure for Compound 11D. $^1$H NMR (500 MHz, dimethylsulfoxide-d$_6$) δ 11.67 (s, 1H), 8.50 (s, 1H), 8.17 (s, 1H), 8.02 (d, 1H), 7.49-7.54 (m, 3H), 7.35 (d, 2H), 7.05 (d, 2H), 6.67 (dd, J 1H), 6.39 (s, 1H), 6.21 (s, 1H), 4.20 (d, 2H), 3.23 (s, 3H), 3.06-3.09 (m, 4H), 2.15-2.37 (m, 4H), 1.96-2.03 (m, 4H), 1.74-1.84 (m, 2H), 1.40 (t, 2H), 1.04-1.13 (m, 4H), 0.93 (s, 6H).

Compound 211 cis-N-({5-chloro-6-[(4-methoxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 211A cis-5-chloro-6-((4-methoxycyclohexyl)methoxy)pyridine-3-sulfonamide The title compound was isolated as a by-product in the synthesis of Compound 210B.

Compound 211B cis-N-({5-chloro-6-[(4-methoxycyclohexyl)
methoxy]pyridin-3-yl}sulfonyl)-4-(4-{[2-(4-chloro-
phenyl)-4,4-dimethylcyclohex-1-en-1-yl]
methyl}piperazin-1-yl)-2-(1H-pyrrolo[2,3-b]pyridin-
5-yloxy)benzamide The title compound was prepared by substituting Compound 211A for Compound 11B in the procedure for Compound 11D. $^1$H NMR (500 MHz, dimethylsulfoxide-d$_6$) δ 11.67 (s, 1H), 8.51 (s, 1H), 8.17 (s, 1H), 8.03 (d, 1H), 7.49-7.54 (m, 3H), 7.35 (d, 2H), 7.05 (d, 2H), 6.68 (dd, 1H), 6.39 (s, 1H), 6.21 (s, 1H), 4.21 (d, 2H), 3.20 (s, 3H), 3.06 (s, 4H), 2.15-2.37 (m, 4H), 1.96 (s, 2H), 1.80-1.84 (m, 2H), 1.50-1.54 (m, 2H), 1.34-1.44 (m, 6H), 0.93 (s, 6H).

Compound 212

4-(4-{[2-(4-chlorophenyl)-4,4-dimethylcyclohex-1-
en-1-yl]methyl}piperazin-1-yl)-N-[(3-nitro-4-{[(3S)-
1-oxetan-3-ylpyrrolidin-3-yl]amino}phenyl)sulfo-
nyl]-2-(1H-pyrrolo[2,3-b]pyridin-5-yloxy)
benzamide

Compound 212A (S)-tert-butyl 1-(oxetan-3-yl)pyrrolidin-3-ylcarbamate

The title compound was prepared by substituting (S)-tert-butyl pyrrolidin-3-ylcarbamate for tert-butyl piperazine-1-carboxylate and 3-oxetanone for 4'-chlorobiphenyl-2-carboxaldehyde in the procedure for Compound 1A.

Compound 212B (S)-1-(oxetan-3-yl)pyrrolidin-3-amine

The title compound was prepared by substituting Compound 212A for (S)-1-tert-butyl 2-methyl 4,4-difluoropyrrolidine-1,2-dicarboxylate in the procedure for Compound 168A.

Compound 212C (S)-3-nitro-4-(1-(oxetan-3-yl)pyrrolidin-3-ylamino)
benzenesulfonamide The title compound was prepared by substituting 4-fluoro-3-nitrobenzenesulfonamide for 4-chloro-3-nitrobenzenesulfonamide and Compound 212B for 4-methylpiperazin-1-amine dihydrochloride in the procedure for Compound 6A.

Compound 212D 4-(4-{[2-(4-chlorophenyl)-4,4-dimethylcyclohex-1-
en-1-yl]methyl}piperazin-1-yl)-N-[(3-nitro-4-{[(3S)-
1-oxetan-3-ylpyrrolidin-3-yl]amino}phenyl)sulfo-
nyl]-2-(1H-pyrrolo[2,3-b]pyridin-5-yloxy)
benzamide The title compound was prepared by substituting Compound 212C for Compound 11B in the procedure for Compound 11D. $^1$H NMR (500 MHz, pyridine-d$_5$) δ 13.03 (s, 1H), 9.27 (d, 1H), 8.58 (d, 1H), 8.42 (d, 1H), 8.37 (dd, 1H), 8.09 (d, 1H), 7.67 (t, 1H), 7.64 (d, 1H), 7.44 (d, 2H), 7.07 (d, 2H), 6.86 (d, 1H), 6.75 (dd, 1H), 6.54 (d, 1H), 6.48 (dd, 1H), 4.67 (m, 4H), 4.09 (m, 1H), 3.59 (m, 1H), 3.07 (m, 4H), 2.77 (s, 2H), 2.69 (m, 2H), 2.62 (dd, 1H), 2.28 (m, 4H), 2.14 (m, 4H), 1.97 (s, 2H), 1.68 (m, 1H), 1.39 (t, 2H), 0.93 (s, 6H).

Compound 213

4-(4-{[2-(4-chlorophenyl)-4,4-dimethylcyclohex-1-
en-1-yl]methyl}piperazin-1-yl)-N-({4-[({4-[2-(2-
methoxyethoxy)ethyl]morpholin-2-yl}methyl)
amino]-3-nitrophenyl}sulfonyl)-2-(1H-pyrrolo[2,3-
b]pyridin-5-yloxy)benzamide

Compound 213A 4-((4-(2-(2-methoxyethoxy)ethyl)morpholin-2-yl)
methylamino)-3-nitrobenzenesulfonamide The title compound was prepared by substituting 2-(2'-methoxyethoxy)ethyl bromide for methyl iodide in the procedure for Compound 134B.

Compound 213B 4-(4-{[2-(4-chlorophenyl)-4,4-dimethylcyclohex-1-
en-1-yl]methyl}piperazin-1-yl)-N-({4-[({4-[2-(2-
methoxyethoxy)ethyl]morpholin-2-yl}methyl)
amino]-3-nitrophenyl}sulfonyl)-2-(1H-pyrrolo[2,3-
b]pyridin-5-yloxy)benzamide The title compound was prepared by substituting Compound 213A for Compound 130C in the procedure for Compound 130D. $^1$H NMR (500 MHz, pyridine-d$_5$) δ 12.98 (s, 1H), 9.26 (d, 1H), 8.87 (t, 1H), 8.43 (d, 1H), 8.32 (dd, 1H), 8.11 (d, 1H), 7.66 (m, 2H), 7.44 (d, 2H), 7.07 (d, 2H), 6.91 (d, 1H), 6.75 (dd, 1H), 6.54 (d, 1H), 6.48 (m, 1H), 3.96-3.86 (m, 2H), 3.72 (dd, 1H), 3.67-3.61 (m, 4H), 3.51 (t, 2H), 3.48-3.38 (m, 2H), 3.28 (s, 3H), 3.07 (m, 4H), 2.95 (d, 1H), 2.77 (s, 2H), 2.70 (m, 1H), 2.60 (t, 2H), 2.30-2.05 (m, 8H), 1.97 (s, 2H), 1.39 (t, 2H), 0.94 (s, 6H).

Compound 214

4-(4-{[2-(4-chlorophenyl)-4,4-dimethylcyclohex-1-
en-1-yl]methyl}piperazin-1-yl)-N-{[4-({[4-(cyanom-
ethyl)morpholin-2-yl]methyl}amino)-3-nitrophenyl]
sulfonyl}-2-(1H-pyrrolo[2,3-b]pyridin-5-yloxy)
benzamide

Compound 214A 4-((4-(cyanomethyl)morpholin-2-yl)methylamino)-
3-nitrobenzenesulfonamide The title compound was prepared by substituting 2-bromoacetonitrile for methyl iodide in the procedure for Compound 134B.

Compound 214B 4-(4-{[2-(4-chlorophenyl)-4,4-dimethylcyclohex-1-
en-1-yl]methyl}piperazin-1-yl)-N-{[4-({[4-(cyanom-
ethyl)morpholin-2-yl]methyl}amino)-3-nitrophenyl]
sulfonyl}-2-(1H-pyrrolo[2,3-b]pyridin-5-yloxy)
benzamide The title compound was prepared by substituting Compound 214A for Compound 130C in the procedure for Compound 130D. ¹H NMR (500 MHz, pyridine-$d_5$) δ 13.01 (s, 1H), 9.26 (d, 1H), 8.86 (t, 1H), 8.43 (d, 1H), 8.35 (dd, 1H), 8.11 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.93 (m, 1H), 3.87 (d, 1H), 3.77 (s, 2H), 3.65 (dt, 1H), 3.51-3.40 (m, 2H), 3.07 (m, 4H), 2.87 (d, 1H), 2.77 (s, 2H), 2.60 (d, 1H), 2.50 (m, 1H), 2.38 (t, 1H), 2.26 (m, 2H), 2.14 (m, 4H), 1.97 (s, 2H), 1.39 (t, 2H), 0.94 (s, 6H).

Compound 215

4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide Compound 215A 4-((4-(2-(dimethylamino)acetyl)morpholin-2-yl)methylamino)-3-nitrobenzenesulfonamide The title compound was prepared by substituting 2-dimethylaminoacetyl chloride hydrochloride for methyl iodide in the procedure for Compound 134B.

Compound 215B 4-(4-{[2-(4-chlorophenyl)-4,4-dimethylcyclohex-1-en-1-yl]methyl}piperazin-1-yl)-N-{[4-({[4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 215A for Compound 130C in the procedure for Compound 130D. ¹H NMR (500 MHz, pyridine-$d_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 2H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Compound 216

(2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid Compound 216A tert-butyl 2-(2-((2-nitro-4-sulfamoylphenylamino)methyl)morpholino)acetate The title compound was prepared by substituting tert-butyl 2-bromoacetate for methyl iodide in the procedure for Compound 134B.

Compound 216B tert-butyl 2-(2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)methyl)morpholino)acetate The title compound was prepared by substituting Compound 216A for Compound 130C in the procedure for Compound 130D.

Compound 216C (2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholin-4-yl)acetic acid The title compound was prepared by treating Compound 216B with 50% trifluoroacetic acid in dichloromethane. ¹H NMR (500 MHz, pyridine-$d_5$) δ 12.97 (s, 1H), 9.26 (d, 1H), 8.87 (t, 1H), 8.43 (d, 1H), 8.30 (dd, 1H), 8.12 (d, 1H), 7.69 (t, 1H), 7.64 (d, 1H), 7.43 (d, 2H), 7.08 (d, 2H), 6.88 (d, 1H), 6.76 (dd, 1H), 6.55 (d, 1H), 6.47 (m, 1H), 4.05-4.00 (m, 1H), 3.91 (d, 1H), 3.79 (dt, 1H), 3.50 (s, 2H), 3.45 (m, 2H), 3.13 (d, 1H), 3.07 (m, 4H), 2.88 (d, 1H), 2.78 (s, 2H), 2.57 (dt, 1H), 2.43 (t, 1H), 2.26 (m, 2H), 2.14 (m, 4H), 1.97 (s, 2H), 1.39 (t, 2H), 0.94 (s, 6H).

Compound 217

4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide Compound 217A 3-nitro-4-(((4-(oxetan-3-yl)morpholin-2-yl)methyl)amino)benzenesulfonamide The title compound was prepared by substituting Compound 134A for tert-butyl piperazine-1-carboxylate and 3-oxetanone for 4'-chlorobiphenyl-2-carboxaldehyde in the procedure for Compound 1A.

Compound 217B 4-(4-{[2-(4-chlorophenyl)-4,4-dimethylcyclohex-1-en-1-yl]methyl}piperazin-1-yl)-N-{[3-nitro-4-({[4-(oxetan-3-yl)morpholin-2-yl]methyl}amino)phenyl]sulfonyl}-2-(1H-pyrrolo[2,3-b]pyridin-5-yloxy)benzamide The title compound was prepared by substituting Compound 217A for Compound 130C in the procedure for Compound 130D. ¹H NMR (500 MHz, pyridine-$d_5$) δ 13.00 (s, 1H), 9.26 (d, 1H), 8.87 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 4.64 (m, 4H), 3.93 (m, 1H), 3.89 (d, 1H), 3.68 (dt, 1H), 3.53-3.35 (m, 3H), 3.07 (m, 4H), 2.77 (s, 2H), 2.72 (d, 1H), 2.44 (d, 1H), 2.26 (m, 2H), 2.14 (m, 4H), 1.97 (s, 2H), 1.85 (t, 1H), 1.39 (t, 2H), 0.94 (s, 6H).

Compound 218

4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide

Compound 218A 4-((4-cyclopropylmorpholin-2-yl)methylamino)-3-nitrobenzenesulfonamide The title compound was prepared by substituting Compound 134A for Compound 173A in the procedure for Compound 173B.

Compound 218B 4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide The title compound was prepared by substituting Compound 218A for Compound 130C in the procedure for Compound 130D. $^1$H NMR (500 MHz, pyridine-d$_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Compound 219

4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide

Compound 219A 5-(methylthio)-6-((tetrahydro-2H-pyran-4-yl)methoxy)pyridine-3-sulfonamide A mixture of Compound 36B (0.1 g) and sodium methanethiolate (0.04 g) in N,N-dimethylformamide (2 ml) was heated at 80° C. overnight. After cooling, the reaction mixture was partitioned between water and ethyl acetate. The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Compound 219B 5-(methylsulfonyl)-6-((tetrahydro-2H-pyran-4-yl)methoxy)pyridine-3-sulfonamide A mixture of Compound 219A (0.15 g) and 75% meta-chloroperoxybenzoic acid (0.217 g) in chloroform (4 ml) was stirred at room temperature. The reaction mixture was stirred overnight. The reaction mixture was then partitioned between ethyl acetate and water. The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Compound 219C 4-(4-{[2-(4-chlorophenyl)-4,4-dimethylcyclohex-1-en-1-yl]methyl}piperazin-1-yl)-N-{[5-(methylsulfonyl)-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 219B for Compound 11B in the procedure for Compound 11D. $^1$H NMR (500 MHz, dimethylsulfoxide-d$_6$) δ 11.65 (s, 1H), 8.81 (s, 1H), 8.55 (d, 1H), 8.01 (d, 1H), 7.55 (d, 1H), 7.49-7.50 (m, 2H), 7.37 (d, 2H), 7.05 (d, 2H), 6.67 (dd, 1H), 6.38 (dd, 1H), 6.21 (d, 1H), 4.36 (d, 2H), 3.88 (dd, 2H), 3.13 (s, 4H), 2.95 (s, 2H), 2.36-2.38 (m, 2H), 2.03-2.16 (m, 4H), 1.97 (s, 3H), 1.66-1.69 (m, 2H), 1.38-1.402 (m, 4H), 0.93 (s, 6H).

Compound 220

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide

Compound 220A 4-((4-fluorotetrahydro-2H-pyran-4-yl)methoxy)-3-(trifluoromethylsulfonyl)benzenesulfonamide To a solution of Compound 37C (0.500 g) in tetrahydrofuran (5 ml) was added sodium hydride (0.596 g). Additional tetrahydrofuran (25 ml) was added and the mixture stirred for 30 minutes, then 4-fluoro-3-(trifluoromethylsulfonyl)benzenesulfonamide (1.145 g) was added as a solution in tetrahydrofuran (5 ml). After stirring for 2 hours, the reaction mixture was partioned between 1N aqueous HCl (50 ml) and dichloromethane (200 ml). The organic layer was dried over magnesium sulfate, filtered, and concentrated. The resulting solid was chromatographed over silica gel (Reveleris 80 g) eluting with a gradient of 0.5% to 7.5% methanol/dichloromethane over 30 minutes (flow=40 ml/min) to provide the title compound.

Compound 220B 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)-2-(1H-pyrrolo[2,3-b]pyridin-5-yloxy)benzamide The title compound was prepared by substituting Compound 3J for Compound 1E and Compound 220A for Compound 1F in the procedure for Compound 1G. $^1$H NMR (300 MHz, dimethylsulfoxide-d$_6$) δ 11.66 (s, 1H), 8.42 (s, 1H), 8.35-8.22 (m, 1H), 8.01 (s, 1H), 7.49 (d, 4H), 7.35 (d, 2H), 7.05 (d, 2H), 6.68 (s, 1H), 6.38 (s, 1H), 6.21 (s, 1H), 4.42 (d, 2H), 3.76 (s, 2H), 3.59 (s, 2H), 3.10 (s, 6H), 2.15 (s, 6H), 2.02-1.74 (m, 6H), 1.40 (s, 2H), 0.93 (s, 6H).

Compound 221

4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide Compound 221A 4-((4-methyltetrahydro-2H-pyran-4-yl)methoxy)-3-nitrobenzenesulfonamide The title compound was prepared by substituting (4-methyltetrahydro-2H-pyran-4-yl)methanol for (tetrahydro-2H-pyran-4-yl)methanol in the procedure for Compound 24A.

Compound 221B 4-(4-{[2-(4-chlorophenyl)-4,4-dimethylcyclohex-1-en-1-yl]methyl}piperazin-1-yl)-N-({4-[(4-methyltetrahydro-2H-pyran-4-yl)methoxy]-3-nitrophenyl}sulfonyl)-2-(1H-pyrrolo[2,3-b]pyridin-5-yloxy)benzamide The title compound was prepared by substituting Compound 221A for Compound 11B in the procedure for Compound 11D. $^1$H NMR (500 MHz, dimethylsulfoxide-$d_6$) δ 11.69 (s, 1H), 8.36 (s, 1H), 8.04-8.06 (m, 2H), 7.50-7.53 (m, 3H), 7.41 (d, 1H), 7.35 (d, 2H), 7.04 (d, 2H), 6.67 (dd, 1H), 6.40 (dd, 1H), 6.20 (d, 1H), 4.00 (s, 2H), 3.63-3.67 (m, 2H), 3.53-3.58 (m, 2H), 3.09 (s, 4H), 2.82 (s, 2H), 2.27 (s, 2H), 2.15 (s, 2H), 1.58-1.63 (m, 2H), 1.39 (t, 2H), 1.30-1.34 (m, 2H), 1.09 (s, 3H), 0.92 (s, 6H).

Compound 222 ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate Compound 222A ethyl 4-(2-nitro-4-sulfamoylphenyl)piperazine-1-carboxylate The title compound was prepared by substituting ethyl piperazine-1-carboxylate for 1-(tetrahydropyran-4-yl)methylamine in the procedure for Compound 1F.

Compound 222B ethyl 4-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)piperazine-1-carboxylate The title compound was prepared by substituting Compound 3J for Compound 1E and Compound 222A for Compound 1F in the procedure for Compound 1G. $^1$H NMR (500 MHz, dimethylsulfoxide-$d_6$) δ 11.52 (br. s, 1H), 8.08 (d, 1H), 7.89 (d, 1H), 7.59 (m, 2H), 7.43 (t, 1H), 7.35 (d, 2H), 7.23 (d, 1H), 7.05 (d, 2H), 6.94 (d, 1H), 6.63 (dd, 1H), 6.29 (m, 2H), 4.07 (q, 2H), 3.47 (m, 4H), 3.17 (d, 2H), 3.00 (m, 8H), 2.73 (s, 2H), 2.18 (m, 6H), 1.96 (s, 2H), 1.39 (t, 2H), 1.20 (t, 3H), 0.93 (s, 6H).

Compound 223

4-(4-{[2-(4-chlorophenyl)-4,4-dimethylcyclohex-1-en-1-yl]methyl}piperazin-1-yl)-N-({4-[4-(morpholin-4-yl)piperidin-1-yl]-3-nitrophenyl}sulfonyl)-2-(1H-pyrrolo[2,3-b]pyridin-5-yloxy)benzamide Compound 223A 4-(4-morpholinopiperidin-1-yl)-3-nitrobenzenesulfonamide The title compound was prepared by substituting 4-(piperidin-4-yl)morpholine for 1-(tetrahydropyran-4-yl)methylamine in the procedure for Compound 1F.

Compound 223B 4-(4-{[2-(4-chlorophenyl)-4,4-dimethylcyclohex-1-en-1-yl]methyl}piperazin-1-yl)-N-({4-[4-(morpholin-4-yl)piperidin-1-yl]-3-nitrophenyl}sulfonyl)-2-(1H-pyrrolo[2,3-b]pyridin-5-yloxy)benzamide The title compound was prepared by substituting Compound 3J for Compound 1E and Compound 223A for Compound 1F in the procedure for Compound 1G. $^1$H NMR (500 MHz, dimethylsulfoxide-$d_6$) δ 11.53 (br. s, 1H), 8.05 (d, 1H), 7.91 (d, 1H), 7.58 (m, 2H), 7.43 (t, 1H), 7.35 (d, 2H), 7.26 (d, 1H), 7.05 (d, 2H), 6.91 (d, 1H), 6.62 (dd, 1H), 6.29 (m, 2H), 5.76 (s, 1H), 3.57 (m, 4H), 3.20 (m, 2H), 3.01 (m, 4H), 2.80 (t, 2H), 2.73 (s, 2H), 2.47 (m, 4H), 2.32 (m, 1H), 2.18 (m, 6H), 1.96 (m, 3H), 1.82 (m, 2H), 1.44 (m, 4H), 0.93 (s, 6H).

Compound 224

4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide Compound 224A (R)-tert-butyl 1-(oxetan-3-yl)pyrrolidin-3-ylcarbamate The title compound was prepared by substituting (R)-tert-butyl pyrrolidin-3-ylcarbamate for tert-butyl piperazine-1-carboxylate and 3-oxetanone for 4'-chlorobiphenyl-2-carboxaldehyde in the procedure for Compound 1A.

Compound 224B (R)-1-(oxetan-3-yl)pyrrolidin-3-amine

The title compound was prepared by substituting Compound 224A for (S)-1-tert-butyl 2-methyl 4,4-difluoropyrrolidine-1,2-dicarboxylate in the procedure for Compound 168A.

Compound 224C (R)-3-nitro-4-(1-(oxetan-3-yl)pyrrolidin-3-ylamino)benzenesulfonamide The title compound was prepared by substituting 4-fluoro-3-nitrobenzenesulfonamide for 4-chloro-3-nitrobenzenesulfonamide and Compound 224B for 4-methylpiperazin-1-amine dihydrochloride in the procedure for Compound 6A.

Compound 224D 4-(4-{[2-(4-chlorophenyl)-4,4-dimethylcyclohex-1-en-1-yl]methyl}piperazin-1-yl)-N-[(3-nitro-4-{[(3R)-1-(oxetan-3-yl)pyrrolidin-3-yl]amino}phenyl)sulfonyl]-2-(1H-pyrrolo[2,3-b]pyridin-5-yloxy)benzamide The title compound was prepared by substituting Compound 224C for Compound 11B in the procedure for Compound 11D. $^1$H NMR (400 MHz, pyridine-$d_5$) δ 13.03 (s, 1H), 9.26 (d, 1H), 8.57 (d, 1H), 8.42 (d, 1H), 8.36 (dd, 1H), 8.09 (d, 1H), 7.66 (m, 1H), 7.64 (d, 1H), 7.44 (m, 2H), 7.07 (m, 2H), 6.86 (d, 1H), 6.75 (dd, 1H), 6.54 (d, 1H), 6.48 (dd, 1H), 4.67 (m, 4H), 3.58 (m, 1H), 3.07 (m, 4H), 2.77 (m, 2H), 2.68 (m, 2H), 2.61 (m, 1H), 2.28 (m, 4H), 2.14 (m, 4H), 1.97 (m, 2H), 1.67 (m, 1H), 1.39 (t, 2H), 0.93 (s, 6H).

Compound 225

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide

Compound 225A (R)-4-(1-(1,3-difluoropropan-2-yl)pyrrolidin-3-ylamino)-3-(trifluoromethylsulfonyl)benzenesulfonamide To Compound 207A (0.217 g) and 4-fluoro-3-(trifluoromethylsulfonyl)benzenesulfonamide (0.281 g) in tetrahydrofuran (5 ml) was added diisopropylethylamine (0.559 ml) and the reaction was allowed to stir at room temperature for 1 hour and was then heated to 50° C. for 1 hour. The reaction was concentrated, the residue was loaded onto silica gel (Reveleris 40 g) and eluted with a gradient of 0.75% methanol/dichloromethane to 7.5% methanol/dichloromethane to provide the title compound.

Compound 225B 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]amino}-3-[(trifluoromethyl)sulfonyl]phenyl)sulfonyl]-2-(1H-pyrrolo[2,3-b]pyridin-5-yloxy)benzamide The title compound was prepared by substituting Compound 3J for Compound 1E and Compound 225A for Compound 1F in the procedure for Compound 1G. $^1$H NMR (300 MHz, dimethylsulfoxide-$d_6$) δ 11.69 (s, 1H), 11.52-11.23 (m, 1H), 8.17 (d, 1H), 8.04 (d, 1H), 7.95 (d, 1H), 7.54 (d, 1H), 7.53-7.50 (m, 1H), 7.48 (d, 1H), 7.34 (d, 2H), 7.10-6.97 (m, 4H), 6.67 (d, 1H), 6.40 (dd, 1H), 6.18 (d, 1H), 4.60 (dd, 4H), 4.20 (s, 1H), 3.11-2.63 (m, 12H), 2.19 (d, 6H), 1.95 (s, 2H), 1.58 (s, 1H), 1.40 (d, 2H), 0.92 (s, 6H).

Compound 226

4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide

Compound 226A tert-butyl 4-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate To a solution of Compound 82 (800 mg) and tert-butyl 4-aminopiperidine-1-carboxylate (203 mg) in dioxane (10 ml) was added Hunig's Base (1 ml). The mixture was stirred at 120° C. overnight. The mixture was diluted with ethyl acetate (200 ml) and washed with water, brine and dried over $Na_2SO_4$. After filtration and evaporation of solvent, the residue was loaded on a silica gel cartridge and eluted with 3% methanol in dichloromethane to give the title compound.

Compound 226B 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide To a solution of Compound 226A (902 mg) in dichloromethane (10 ml) was added trifluoroacetic acid (5 ml). The mixture was stirred at room temperature for 3 hours. The mixture was concentrated under vacuum and co-concentrated with dichloromethane twice to afford the crude product which was used in the next step without further purification.

Compound 226C 4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)-2-(1H-pyrrolo[2,3-b]pyridin-5-yloxy)benzamide To a solution of Compound 226B (79 mg) in tetrahydrofuran (3 ml) and acetic acid (1 ml) was added acetone (54 mg) and MP-cyanoborohydride (150 mg, 2.25 mmol/g). The mixture was stirred overnight. The mixture was filtered. The filtrate was concentrated and the residue was loaded on a silica gel cartridge and eluted with 5 to 10% 7N $NH_3$ in methanol in dichloromethane to provide the title compound. $^1$H NMR (300 MHz, dimethylsulfoxide-$d_6$) δ 12.09 (s, 1H), 8.34 (m, 1H), 7.93 (m, 2H), 7.66 (m, 4H), 7.35 (d, 2H), 7.06 (d, 2H), 6.89 (m, 1H), 6.74 (dd, 1H), 6.59 (dd, 1H), 6.50 (d, 1H), 3.11 (m, 6H), 2.73 (m, 4H), 2.26 (m, 9H), 1.97 (s, 3H), 1.40 (t, 2H), 1.23 (s, 8H), 0.94 (s, 6H).

Compound 227

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 227A 1-tert-butylpiperidin-4-amine To a solution of 1-tert-butylpiperidin-4-one (5.0 g) in methanol (100 ml) and water (10 ml) was added ammonium formate (20.3 g) and 0.5 g of Pd/C (10%). The mixture was stirred overnight. The mixture was filtered and the filtrate was concentrated under vacuum and the residue was diluted with ethyl acetate (500 ml) and washed with water and brine. After drying over $Na_2SO_4$ and filtration, the solvent was evaporated under vacuum to provide the title compound.

Compound 227B 4-(1-tert-butylpiperidin-4-ylamino)-3-nitrobenzenesulfonamide

To a mixture of 4-fluoro-3-nitrobenzenesulfonamide (2.2 g) and Compound 227A (1.56 g) in tetrahydrofuran (20 ml) was added Hunig's Base (6 ml). The mixture was stirred for 3 days. The mixture was diluted with ethyl acetate (300 ml) and water (100 ml) and stirred until the solid disappeared into the solution. The layers were separated and the organic phase was washed with water and brine, dried over $Na_2SO_4$, and filtered. The combined aqueous layers were extracted again with ethyl acetate and the combined organic phases were dried over $Na_2SO_4$. After filtration, the solvent was evaporated to provide the title compound.

Compound 227C

N-({4-[(1-tert-butylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 227B for Compound 1F in the procedure for Compound 1G. $^1$H NMR (300 MHz, dimethylsulfoxide-$d_6$) δ 11.51 (s, 1H), 8.43 (d, 1H), 8.04 (m, 1H), 7.93 (d, 1H), 7.72 (m, 1H), 7.56 (dd, 1H), 7.42 (m, 1H), 7.34 (m, 3H), 7.05 (d, 2H), 6.93 (dd, 1H), 6.62 (dd, 1H), 6.28 (m, 1H), 3.04 (m, 6H), 2.73 (s, 3H), 2.25 (m, 9H), 1.95 (s, 2H), 1.68 (m, 2H), 1.32 (m, 9H), 0.93 (s, 6H).

Compound 228

4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide Compound 228A tert-butyl 3-((2-nitro-4-sulfamoylphenylamino)methyl)piperidine-1-carboxylate The title compound was prepared by substituting tert-butyl 3-(aminomethyl)piperidine-1-carboxylate for (tetrahydropyran-4-yl)methylamine in the procedure for Compound 1F.

Compound 228B 3-nitro-4-(piperidin-3-ylmethylamino)benzenesulfonamide

The title compound was prepared by substituting Compound 228A for Compound 113A in the procedure for Compound 134A.

Compound 228C 4-((1-(2-methoxyethyl)piperidin-3-yl)methylamino)-3-nitrobenzenesulfonamide The title compound was prepared by substituting Compound 228B for Compound 134A and 2-methoxyethyl bromide for methyl iodide in the procedure for Compound 134B.

Compound 228D 4-(4-{[2-(4-chlorophenyl)-4,4-dimethylcyclohex-1-en-1-yl]methyl}piperazin-1-yl)-N-{[4-({[1-(2-methoxyethyl)piperidin-3-yl]methyl}amino)-3-nitrophenyl]sulfonyl}-2-(1H-pyrrolo[2,3-b]pyridin-5-yloxy)benzamide The title compound was prepared by substituting Compound 228C for Compound 130C in the procedure for Compound 130D. $^1$H NMR (500 MHz, pyridine-$d_5$, 90° C.) δ 12.40 (s, 1H), 8.52 (s, 1H), 8.43 (s, 1H), 8.20 (m, 2H), 7.95 (bs, 1H), 7.80 (s, 1H), 7.46 (d, 1H), 7.36 (d, 2H), 7.07 (d, 2H), 7.05 (s, 1H), 6.75 (d, 1H), 6.59 (s, 1H), 6.47 (s, 1H), 3.65-3.50 (m, 5H), 3.20 (s, 3H), 3.04 (m, 5H), 2.81 (s, 3H), 2.74 (m, 1H), 2.24 (m, 7H), 2.06 (s, 2H), 2.00 (s, 2H), 1.75 (m, 1H), 1.57 (m, 2H), 1.42 (t, 2H), 1.15 (m, 1H), 0.95 (s, 6H).

Compound 229

4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide

Compound 229A 4-((1-(cyanomethyl)piperidin-3-yl)methylamino)-3-nitrobenzenesulfonamide The title compound was prepared by substituting Compound 228B for Compound 134A and 2-bromoacetonitrile for methyl iodide in the procedure for Compound 134B.

Compound 229B 4-(4-{[2-(4-chlorophenyl)-4,4-dimethylcyclohex-1-en-1-yl]methyl}piperazin-1-yl)-N-{[4-({[1-(cyanomethyl)piperidin-3-yl]methyl}amino)-3-nitrophenyl]sulfonyl}-2-(1H-pyrrolo[2,3-b]pyridin-5-yloxy)benzamide The title compound was prepared by substituting Compound 229A for Compound 130C in the procedure for Compound 130D. $^1$H NMR (500 MHz, pyridine-$d_5$) δ 13.06 (s, 1H), 9.03 (s, 1H), 8.42 (s, 1H), 8.30 (d, 1H), 8.10 (d, 1H), 7.68 (m, 2H), 7.44 (d, 2H), 7.08 (m, 3H), 6.99 (d, 1H), 6.75 (d, 1H), 6.51 (m, 2H), 3.78 (m, 2H), 3.43 (d, 1H), 3.13 (m, 1H), 3.04 (m, 4H), 2.76 (s, 2H), 2.71-2.65 (m, 3H), 2.52 (m, 1H), 2.25 (m, 2H), 2.14 (m, 4H), 1.97 (s, 2H), 1.84 (m, 1H), 1.68 (m, 1H), 1.50 (m, 2H), 1.39 (t, 2H), 1.07-0.99 (m, 1H), 0.93 (s, 6H).

Compound 230

4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide

Compound 230A 4-((4-fluoro-1-methylpiperidin-4-yl)methoxy)-3-(trifluoromethylsulfonyl)benzenesulfonamide To a solution of (4-fluoro-1-methylpiperidin-4-yl)methanol (0.315 g) in tetrahydrofuran (5 ml) was added sodium hydride (0.342 g). After stirring for 15 minutes, 4-fluoro-3-(trifluoromethylsulfonyl)benzenesulfonamide (0.658 g) was added as a solution in tetrahydrofuran (2 ml) followed by additional tetrahydrofuran (5 ml). After stirring for 1 hour, the reaction was poured in dichloromethane (50 ml) and water (25 ml) and the pH of the water layer was adjusted to 8. The organic layer was dried over magnesium sulfate, filtered, and concentrated. The resulting oil was chromatographed over silica gel (Reveleris 40 g) eluting with a gradient of 1.0% to 10% 7N NH$_3$ in methanol/dichloromethane over 20 minutes then maintaining 10% 7N NH$_3$ in methanol/dichloromethane for 5 minutes (flow=30 ml/min) to provide the title compound.

Compound 230B 4-(4-{[2-(4-chlorophenyl)-4,4-dimethylcyclohex-1-en-1-yl]methyl}piperazin-1-yl)-N-({4-[(4-fluoro-1-methylpiperidin-4-yl)methoxy]-3-[(trifluoromethyl)sulfonyl]phenyl}sulfonyl)-2-(1H-pyrrolo[2,3-b]pyridin-5-yloxy)benzamide The title compound was prepared by substituting Compound 3J for Compound 1E and Compound 230A for Compound 1F in the procedure for Compound 1G. $^1$H NMR (300 MHz, dimethylsulfoxide-$d_6$) δ 11.63-11.57 (m, 1H), 8.40-8.36 (m, 1H), 8.28-8.17 (m, 1H), 7.97 (s, 1H), 7.53 (d, 1H), 7.50-7.32 (m, 5H), 7.05 (d, 1H), 7.05 (d, 1H), 6.68-6.61 (m, 1H), 6.35 (s, 1H), 6.22 (s, 1H), 4.55-4.40 (m, 2H), 3.06 (s, 8H), 2.79 (s, 4H), 2.06 (d, 13H), 1.39 (s, 2H), 0.93 (s, 6H).

Compound 231

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 231A (R)-5-chloro-6-(1-(1,3-difluoropropan-2-yl)pyrrolidin-3-ylamino)pyridine-3-sulfonamide To Compound 207A (0.051 g) and Compound 40A (0.049 g) in dioxane (5 ml) was added diisopropylethylamine (0.131 ml) and the reaction was heated to 75° C. for 1 hour then 85° C. for 2 days. The reaction was concentrated, loaded onto silica gel (Reveleris 12 g) and eluted with a gradient of 0.75% methanol/dichloromethane to 7.5% methanol/dichloromethane to provide the title compound.

Compound 231B

N-[(5-chloro-6-{[(3R)-1-(1,3-difluoropropan-2-yl)pyrrolidin-3-yl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 231A for Compound 1F in the procedure for Compound 1G. $^1$H NMR (300 MHz, dimethylsulfoxide-$d_6$) δ 11.71 (s, 1H), 11.44-11.11 (m, 1H), 8.44 (d, 1H), 8.07 (d, 1H), 7.90 (d, 1H), 7.61 (d, 1H), 7.52 (dd, 2H), 7.34 (d, 2H), 7.19 (s, 1H), 7.04 (d, 2H), 6.67 (d, 1H), 6.42 (dd, 1H), 6.16 (s, 1H), 4.77-4.39 (m, 5H), 3.19-2.63 (m, 11H), 2.19 (s, 7H), 1.91 (d, 3H), 1.38 (s, 2H), 0.92 (s, 6H).

Compound 232 tert-butyl 4-[(4-{[4-(4-({[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate

Compound 232A tert-butyl 4-nitrosopiperazine-1-carboxylate

In a 500 ml round-bottomed flask, 6N aqueous HCl (30 ml) was cooled to −10° C., and tert-butyl piperazine-1-carboxylate (10 g) was added. Sodium nitrite (4.5 g) dissolved in 35 ml water was added slowly. NaOH (10 g in 20 ml water) was used to neutralize the solution. Dichloromethane (3×50 ml) was used to extract the product. After drying over $Na_2SO_4$ and filtration, the solution was concentrated. The crude product was added to a silica gel column (Analogix, SF65-400 g) and purified by eluting with 0-30% ethyl acetate in hexane.

Compound 232B tert-butyl 4-aminopiperazine-1-carboxylate

In a 100 ml round-bottomed flask was added Compound 232A (0.15 g) and zinc (1 g) in water/methanol (1:1, 10 ml) to give a suspension. The mixture was cooled to 0° C. 12N Aqueous HCl (2 ml) was added slowly, and the mixture was stirred at 0° C. for 30 minutes. 2N Aqueous NaOH solution was used to adjust the mixture to basic pH. The mixture was filtered, and extracted with ether (3×30 ml). After drying over $Na_2SO_4$, filtration, and concentration, the crude product was added to a silica gel column (Analogix, SF15-12 g) and purified by eluting with 0-25% ethyl acetate in hexane.

Compound 232C tert-butyl 4-(2-nitro-4-sulfamoylphenylamino)piperazine-1-carboxylate The title compound was prepared by substituting Compound 232B for 1-(tetrahydropyran-4-yl)methylamine in the procedure for Compound 1F.

Compound 232D tert-butyl 4-[(4-{[4-(4-({[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]piperazine-1-carboxylate The title compound was prepared by substituting Compound 3J for Compound 1E and Compound 232C for Compound 1F in the procedure for Compound 1G. $^1H$ NMR (300 MHz, dimethylsulfoxide-$d_6$) δ 11.47 (br. s, 1H), 8.86 (s, 1H), 8.34 (d, 1H), 7.90 (d, 1H), 7.59 (m, 2H), 7.36 (m, 4H), 7.23 (m, 1H), 7.05 (d, 2H), 6.61 (dd, 1H), 6.27 (m, 2H), 2.99 (m, 5H), 2.76 (m, 6H), 2.19 (m, 6H), 1.96 (s, 2H), 1.41 (m, 11H), 1.24 (m, 4H), 0.93 (s, 6H).

Compound 233

4-(4-{[2-(4-chlorophenyl)-4,4-dimethylcyclohex-1-en-1-yl]methyl}piperazin-1-yl)-N-({3-(pentafluoro-lambda-6~-sulfanyl)-4-[(tetrahydro-2H-pyran-4-ylmethyl)amino]phenyl}sulfonyl)-2-(1H-pyrrolo[2,3-b]pyridin-5-yloxy)benzamide

Compound 233A 2-(5-bromo-2-nitrophenyl)sulfur pentafluoride

To a solution of 3-bromophenylsulfur pentafluoride (2.18 g) in concentrated $H_2SO_4$ (5 ml) was added $KNO_3$ (780 mg). The mixture was stirred overnight. The mixture was diluted with diethyl ether (100 ml) and washed with water and brine. After drying over $Na_2SO_4$ and filtration, the solvent was evaporated under vacuum to provide the title compound.

Compound 233B 2-(5-bromo-2-aminophenyl)sulfur pentafluoride

Compound 233A (6.4 g) and tetrahydrofuran (300 ml) were added to Ra—Ni, (12.80 g) in a 50 ml pressure bottle and the mixture stirred for 2 hours at 30 psi and room temperature. The mixture was filtered though a nylon membrane and the filtrate was concentrated under vacuum to provide the title compound.

Compound 233C 4-bromo-2-pentafluorosulfanyl-N-(tetrahydro-2H-pyran-4-ylmethyl)aniline To a solution of Compound 233B (4.4 g) in methanol (50 ml) was added tetrahydro-2H-pyran-4-carbaldehyde (1.68 g) and decaborane (1.1 g). The mixture was stirred and monitored by thin layer chromatography. More tetrahydro-2H-pyran-4-carbaldehyde (500 mg) was added to the stirring mixture to drive the reaction to completion. The reaction mixture was concentrated under vacuum and ethyl acetate (500 ml) and brine (200 ml) were added. The organic phase was dried over $Na_2SO_4$. Filtration and evaporation of the solvent and flash chromatography (20% ethyl acetate in hexane) gave the title compound.

Compound 233D 4-thioacetoxy-2-pentafluorosulfanyl-N-(tetrahydro-2H-pyran-4-ylmethyl)aniline To a solution of Compound 233C (456 mg) and potassium ethanethioate (197 mg) in dioxane (4 ml) was added tris(dibenzylideneacetone)dipalladium(0) (27 mg) and xantphos (33 mg) followed by N,N-diisopropylethylamine (0.5 ml). The mixture was purged with argon, sealed and stirred under microwave irradiation for 60 minutes at 120° C. The mixture was dissolved in ethyl acetate (300 ml) and water (100 ml). The organic phase was washed with brine and dried over $Na_2SO_4$. Filtration and evaporation of the solvent followed by flash chromatography (20% ethyl acetate in hexane) provided the title compound.

Compound 233E 3-pentafluorosulfanyl-4-[(tetrahydro-2H-pyran-4-ylmethyl)amino]phenylsulfonamide N-chlorosuccinimide (527 mg) was added to a mixture of 2N aqueous HCl (1.5 ml) and acetonitrile (12 ml) and then cooled to 0° C. A solution of Compound 233D (386 mg) in acetonitrile (3 ml) was added to the mixture which was then stirred at 0° C. for 2 hours, and then diluted with ethyl acetate (300 ml) and washed with brine and dried over $Na_2SO_4$. After filtration and evaporation of solvent, the residue was dissolved in isopropyl alcohol (20 ml) and cooled to 0° C. with stirring. Then, ammonium hydroxide (conc. 10 ml) was added to mixture. After stirring for 2 hours, the mixture was concentrated under vacuum and the residue was added to ethyl acetate (400 ml) and water (150 ml). The organic layer was washed with brine and dried over $Na_2SO_4$. After filtration and evaporation of solvent, the residue was purified by flash column (20% ethyl acetate in dichloromethane) to provide the title compound.

Compound 233F 4-(4-{[2-(4-chlorophenyl)-4,4-dimethylcyclohex-1-en-1-yl]methyl}piperazin-1-yl)-N-({3-(pentafluoro-lambda~1~-sulfanyl)-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 3J for Compound 1E and Compound 233E for Compound 1G in the procedure for Compound 1F. $^1$H NMR (300 MHz, dimethylsulfoxide-$d_6$) δ 11.71 (s, 1H), 11.33 (m, 1H), 8.12 (m, 2H), 7.72 (d, 1H), 7.54 (m, 3H), 7.33 (m, 2H), 7.02 (m, 3H), 6.67 (m, 2H), 6.42 (m, 1H), 6.16 (d, 1H), 3.82 (m, 2H), 3.21 (m, 4H), 3.05 (m, 4H), 2.73 (s, 2H), 2.21 (m, 8H), 1.97 (m, 3H), 1.29 (m, 4H), 0.92 (s, 6H).

Compound 234

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide

Compound 234A 4-vinyltetrahydro-2H-pyran-4-ol

Dihydro-2H-pyran-4(3H)-one (8.01 g) in anhydrous ethyl ether (50 ml) was treated with 1.0 M vinylmagnesium bromide (104 ml) over 20 minutes at 0° C. The reaction mixture was stirred at room temperature overnight. The reaction was quenched with saturated $NH_4Cl$, and the organic layer was separated. The aqueous layer was extracted with additional ethyl ether three times. The combined organic layers were washed with brine, dried, filtered, and concentrated. The residue was purified by flash column chromatography on silica gel using 20% ethyl acetate in hexanes to provide the title compound.

Compound 234B 4-methoxy-4-vinyltetrahydro-2H-pyran

To a solution of Compound 234A (9.4 g) in tetrahydrofuran (150 ml) was added 60% sodium hydride (5.28 g) at 0° C. portionwise. After the addition was complete, the solution was heated under reflux for three hours. After cooling, to this suspension was added dimethyl sulfate (8.41 ml) slowly. The solution was heated under reflux overnight, cooled to room temperature, and hydrolyzed with cool saturated aqueous $NH_4Cl$. After extraction with diethyl ether several times, the combined organic layers were washed with brine, dried over $MgSO_4$, filtered, and concentrated. The residue was purified by flash column chromatograph on silica gel using 1-10% ethyl acetate in hexanes to provide the title compound.

Compound 234C 4-methoxytetrahydro-2H-pyran-4-carbaldehyde

Compound 234B (4.3 g) in tetrahydrofuran (200 ml) and water (67 ml) was treated with 4% osmium tetroxide in water (9.24 ml). To this solution was added potassium periodate (13.91 g) portionwise over 2 hours. The solution was stirred overnight at room temperature. Water was added to the mixture followed by repeat extractions with diethyl ether. The combined organic layers were dried over $MgSO_4$, filtered, and concentrated. The residue was purified by flash column chromatography on silica gel using 5-20% ethyl acetate in hexanes to provide the title compound.

Compound 234D (4-methoxytetrahydro-2H-pyran-4-yl)methanol

Compound 234C (1.8 g) in 2-propanol (28 ml) and water (7 ml) was cooled to 0° C. To this solution was added sodium borohydride (0.709 g). The solution was stirred and allowed to warm to room temperature over 3 hours. The reaction was quenched with acetone, and stirred for another 1 hour. The clear liquid was separated from solid by decanting. Additional ethyl acetate was used to wash the solid, and was the mixture was decanted. The combined organic solutions were concentrated. The residue was purified by flash chromatography on silica gel eluting 1:1 ethyl acetate: hexane to provide the title compound.

Compound 234E 4-((4-methoxytetrahydro-2H-pyran-4-yl)methoxy)-3-nitrobenzenesulfonamide The title compound was prepared by substituting Compound 234D for (tetrahydro-2H-pyran-4-yl)methanol in the procedure for Compound 24A.

Compound 234F 4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide The title compound was prepared by substituting Compound 234E for Compound 11B in the procedure for Compound 11D. $^1$H NMR (500 MHz, dimethylsulfoxide-$d_6$) δ 11.68 (s, 1H), 8.36 (s, 1H), 8.04-8.07 (m, 2H), 7.50-7.53 (m, 3H), 7.45 (d, 1H), 7.35 (d, 2H), 7.05 (d, 2H), 6.68 (dd, 1H), 6.40 (dd, 1H), 6.20 (d, 1H), 4.21 (s, 2H), 3.65-3.67 (m, 2H), 3.53-3.56 (m, 2H), 3.19 (s, 3H), 3.10 (s, 4H), 2.86 (s, 2H), 2.30 (s, 4H), 2.15 (s, 2H), 1.96 (s, 2H), 1.61-1.74 (m, 4H), 1.39 (t, 2H), 0.93 (s, 6H).

Compound 235

4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide Compound 235A (R)-tert-butyl 3-(2-nitro-4-sulfamoylphenoxy)pyrrolidine-1-carboxylate The title compound was prepared by substituting (R)-tert-butyl 3-hydroxypyrrolidine-1-carboxylate for (tetrahydro-2H-pyran-4-yl)methanol in the procedure for Compound 24A.

Compound 235B (R)-tert-butyl 3-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenoxy)pyrrolidine-1-carboxylate The title compound was prepared by substituting Compound 3J for Compound 1E and Compound 235A for Compound 1F in the procedure for Compound 1G.

Compound 235C 4-(4-{[2-(4-chlorophenyl)-4,4-dimethylcyclohex-1-en-1-yl]methyl}piperazin-1-yl)-N-[(4-{[(3R)-1-(1,3-difluoropropan-2-yl)pyrrolidin-3-yl]oxy}-3-nitrophenyl)sulfonyl]-2-(1H-pyrrolo[2,3-b]pyridin-5-yloxy)benzamide To a solution of Compound 235B (0.230 g) in dichloromethane (3 ml) was added trifluoroacetic acid (0.377 ml). After stirring for 4 hours, the reaction was concentrated then dissolved in dichloromethane (3 ml) and treated with 1,3-difluoropropan-2-one (0.028 g) followed by sodium triacetoxyborohydride (0.078 g). After stirring for 4 hours, the reaction was quenched by the addition of saturated aqueous NaHCO$_3$ and dichloromethane (5 ml). The reaction was diluted with dichloromethane (250 ml) and saturated aqueous NaHCO$_3$ (100 ml) was added. The organic layer was separated, washed with brine (100 ml), dried over magnesium sulfate, filtered and concentrated. Trituration with acetonitrile gave the title compound. $^1$H NMR (300 MHz, dimethylsulfoxide-d$_6$) δ 11.67 (s, 1H), 8.34 (s, 1H), 8.03 (s, 2H), 7.52 (d, 3H), 7.35 (d, 3H), 7.04 (d, 2H), 6.75-6.60 (m, 1H), 6.40 (s, 1H), 6.20 (s, 1H), 5.17-5.06 (m, 1H), 4.60 (d, 4H), 2.98 (d, 12H), 2.37-2.02 (m, 6H), 1.96 (s, 3H), 1.39 (s, 2H), 0.93 (s, 6H).

Compound 236

4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide Compound 236A 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(piperazin-1-ylamino)phenylsulfonyl)benzamide The title compound was prepared by substituting Compound 232D for Compound 1A in the procedure for Compound 1B.

Compound 236B 4-(4-{[2-(4-chlorophenyl)-4,4-dimethylcyclohex-1-en-1-yl]methyl}piperazin-1-yl)-N-[(3-nitro-4-{[4-(oxetan-3-yl)piperazin-1-yl]amino}phenyl)sulfonyl]-2-(1H-pyrrolo[2,3-b]pyridin-5-yloxy)benzamide The title compound was prepared by substituting Compound 236A for tert-butyl piperazine-1-carboxylate and oxetan-3-one for 4'-chlorobiphenyl-2-carboxaldehyde in the procedure for Compound 1A. $^1$H NMR (400 MHz, dimethylsulfoxide-d$_6$) δ 11.67 (br. s, 1H), 9.20 (s, 1H), 8.53 (d, 1H), 8.04 (d, 1H), 7.83 (dd, 1H), 7.53 (m, 4H), 7.34 (d, 2H), 7.04 (d, 2H), 6.67 (dd, 1H), 6.39 (m, 1H), 6.18 (d, 1H), 4.55 (t, 2H), 4.44 (t, 2H), 3.47 (m, 1H), 3.06 (m, 4H), 2.88 (m, 4H), 2.74 (m, 4H), 2.09 (m, 11H), 1.38 (t, 2H), 0.91 (s, 6H).

Compound 237

4-(4-{[2-(4-chlorophenyl)-4,4-dimethylcyclohex-1-en-1-yl]methyl}piperazin-1-yl)-N-[(3-nitro-4-{[4-(tetrahydro-2H-pyran-4-yl)piperazin-1-yl]amino}phenyl)sulfonyl]-2-(1H-pyrrolo[2,3-b]pyridin-5-yloxy)benzamide The title compound was prepared by substituting Compound 236A for tert-butyl piperazine-1-carboxylate and dihydro-2H-pyran-4(3H)-one for 4'-chlorobiphenyl-2-carboxaldehyde in the procedure for Compound 1A. $^1$H NMR (400 MHz, pyridine-d$_5$) δ 13.05 (br. s, 1H), 9.27 (d, 1H), 9.23 (s, 1H), 8.44 (m, 2H), 8.12 (d, 1H), 7.68 (m, 3H), 7.44 (m, 2H), 7.06 (m, 2H), 6.75 (dd, 1H), 6.51 (m, 2H), 4.02 (m, 2H), 3.31 (m, 2H), 3.06 (m, 4H), 2.91 (m, 5H), 2.76 (s, 2H), 2.38 (m, 2H), 2.26 (m, 2H), 2.14 (m, 4H), 1.97 (s, 2H), 1.65 (m, 2H), 1.39 (m, 7H), 0.93 (s, 6H).

Compound 238

4-(4-{[2-(4-chlorophenyl)-4,4-dimethylcyclohex-1-en-1-yl]methyl}piperazin-1-yl)-N-({3-nitro-4-[(3R)-tetrahydrofuran-3-ylamino]phenyl}sulfonyl)-2-(1H-pyrrolo[2,3-b]pyridin-5-yloxy)benzamide

Compound 238A (R)-3-nitro-4-(tetrahydrofuran-3-ylamino)benzenesulfonamide

The title compound was prepared by substituting (R)-tetrahydrofuran-3-amine for 4-methylpiperazin-1-amine dihydrochloride in the procedure for Compound 6A.

Compound 238B 4-(4-{[2-(4-chlorophenyl)-4,4-dimethylcyclohex-1-en-1-yl]methyl}piperazin-1-yl)-N-({3-nitro-4-[(3R)-tetrahydrofuran-3-ylamino]phenyl}sulfonyl)-2-(1H-pyrrolo[2,3-b]pyridin-5-yloxy)benzamide The title compound was prepared by substituting Compound 238A for Compound 1F and Compound 3J for Compound 1E in the procedure for Compound 1G. $^1$H NMR (400 MHz, dimethylsulfoxide-$d_6$) δ 11.59 (s, 1H), 8.47 (d, 1H), 8.19 (m, 2H), 7.97 (d, 1H), 7.74 (m, 1H), 7.52 (d, 1H), 7.46 (t, 1H), 7.34 (m, 2H), 7.05 (m, 2H), 6.96 (d, 1H), 6.89 (d, 1H), 6.65 (dd, 1H), 6.33 (m, 1H), 6.22 (d, 1H), 4.31 (m, 1H), 3.92 (m, 1H), 3.87 (m, 1H), 3.76 (m, 1H), 3.69 (m, 1H), 3.04 (m, 4H), 2.73 (m, 2H), 2.33 (m, 1H), 2.18 (m, 6H), 1.95 (m, 2H), 1.88 (m, 1H), 1.39 (t, 2H), 0.92 (s, 6H).

Compound 239

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide

Compound 239A tert-butyl(4,4-difluorocyclohexyl)methylcarbamate

Tert-butyl(4-oxocyclohexyl)methylcarbamate (5 g) and diethylaminosulfur trifluoride (7.45 g) were stirred in dichloromethane (100 ml) for 24 hours. The mixture was quenched with pH 7 buffer (100 ml), and poured into ether (400 ml). The resulting solution was separated, and the organic layer was washed twice with water, and once with brine, and then concentrated to give the crude product and fluoroolefin by-product in a 3:2 ratio. The crude material was taken up in tetrahydrofuran (70 ml) and water (30 ml), and N-methylmorpholine-N-oxide (1.75 g), and OsO$_4$ (2.5 wt % solution in t-butanol) were added, and the mixture was stirred for 24 hours. Na$_2$S$_2$O$_3$ (10 g) was then added, and the mixture was stirred for 30 minutes. The mixture was then diluted with ether (300 ml), and the resulting solution was separated, and rinsed twice with water, and once with brine, and concentrated. The crude product was chromatographed on silica gel using 5-10% ethyl acetate in hexanes to provide the title compound.

Compound 239B (4,4-difluorocyclohexyl)methanamine

A solution of Compound 239A (3 g) in dichloromethane (35 ml), trifluoroacetic acid (15 ml), and triethylsilane (1 ml) was stirred for 2 hours. The solution was concentrated, then concentrated from toluene, and left on high vacuum for 24 hours. The semi-solid was taken up in ether/hexane and filtered to provide the title compound as its trifluoroacetic acid salt.

Compound 239C 4-((4,4-difluorocyclohexyl)methylamino)-3-nitrobenzenesulfonamide The title compound was prepared by substituting Compound 239B for (tetrahydropyran-4-yl)methylamine in the procedure for Compound 1F.

Compound 239D 4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-(1H-pyrrolo[2,3-b]pyridin-5-yloxy)benzamide The title compound was prepared by substituting Compound 3J for Compound 1E and Compound 239C for Compound 1F in the procedure for Compound 1G. $^1$H NMR (300 MHz, dimethylsulfoxide-$d_6$) δ 12.40 (s, 1H), 11.61 (br s, 1H), 8.53 (m, 1H), 8.50 (d, 1H), 7.99 (d, 1H), 7.73 (d, 1H), 7.49 (m, 2H), 7.32 (d, 2H), 7.04 (d, 2H), 7.00 (d, 1H), 6.65 (d, 1H), 6.32 (s, 1H), 6.21 (s, 1H), 3.37 (m, 4H), 3.06 (m, 4H), 2.73 (m, 2H), 2.18 (m, 4H), 1.97 (m, 4H), 1.81 (m, 4H), 1.38 (m, 2H), 1.20 (m, 4H), 0.92 (s, 6H).

Compound 240

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 240A 4-(1-tert-butylpiperidin-4-ylamino)-3-(trifluoromethylsulfonyl)benzenesulfonamide To a mixture of 4-fluoro-3-(trifluoromethylsulfonyl)benzenesulfonamide (307 mg) and Compound 227A (156 mg) in tetrahydrofuran (4 ml) was added Hunig's Base (1 ml). The mixture was stirred for 3 days. The mixture was diluted with ethyl acetate (300 ml) and water (100 ml) and stirred until the solid disappeared into the solution. The layers were separated and the organic phase was washed with water, brine and dried over Na$_2$SO$_4$. After filtration, the combined aqueous layers were extracted again with ethyl acetate and

Compound 240B

N-({4-[(1-tert-butylpiperidin-4-yl)amino]-3-[(trifluoromethyl)sulfonyl]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 240A for Compound 1F in the procedure for Compound 1 G. $^1$H NMR (300 MHz, dimethylsulfoxide-$d_6$) δ 11.53 (s, 1H), 8.04 (s, 1H), 7.94 (d, 1H), 7.86 (m, 1H), 7.55 (d, 2H), 7.44 (d, 1H), 7.33 (m, 3H), 7.05 (d, 2H), 6.92 (m, 1H), 6.62 (dd, 1H), 6.43 (m, 1H), 6.29 (d, 2H), 3.79 (m, 1H), 3.05 (m, 6H), 2.73 (s, 3H), 2.19 (m, 8H), 1.96 (s, 3H), 1.27 (m, 12H), 0.92 (s, 6H).

Compound 241

4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide

Compound 241A tert-butyl 2-((4-sulfamoyl-2-(trifluoromethylsulfonyl)phenylamino)methyl)morpholine-4-carboxylate The title compound was prepared by substituting tert-butyl 2-(aminomethyl)morpholine-4-carboxylate for (tetrahydropyran-4-yl)methylamine and 4-fluoro-3-(trifluoromethylsulfonyl)benzenesulfonamide for 4-fluoro-3-nitrobenzenesulfonamide in the procedure for Compound 1F.

Compound 241B tert-butyl 2-((4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-(trifluoromethylsulfonyl)phenylamino)methyl)morpholine-4-carboxylate The title compound was prepared by substituting Compound 241A for Compound 1F and Compound 3J for Compound 1E in the procedure for Compound 1G.

Compound 241C 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-(morpholin-2-ylmethylamino)-3-(trifluoromethylsulfonyl)phenylsulfonyl)benzamide The title compound was prepared by substituting Compound 241B for Compound 1A in the procedure for Compound 1B.

Compound 241D 4-(4-{[2-(4-chlorophenyl)-4,4-dimethylcyclohex-1-en-1-yl]methyl}piperazin-1-yl)-N-({4-({[4-(oxetan-3-yl)morpholin-2-yl]methyl}amino)-3-[(trifluoromethyl)sulfonyl]phenyl}sulfonyl)-2-(1H-pyrrolo[2,3-b]pyridin-5-yloxy)benzamide The title compound was prepared by substituting Compound 241C for tert-butyl piperazine-1-carboxylate and oxetan-3-one for 4'-chlorobiphenyl-2-carboxaldehyde in the procedure for Compound 1A. $^1$H NMR (300 MHz, dimethylsulfoxide-$d_6$) δ 11.69 (s, 1H), 8.15 (d, 1H), 8.04 (d, 1H), 7.92 (dd, 1H), 7.54 (d, 1H), 7.51 (t, 1H), 7.48 (d, 1H), 7.34 (d, 2H), 7.25 (m, 1H), 7.04 (m, 3H), 6.68 (dd, 1H), 6.41 (m, 1H), 6.19 (d, 1H), 4.54 (t, 2H), 4.43 (m, 2H), 3.85 (m, 1H), 3.69 (m, 1H), 3.52 (m, 1H), 3.48 (m, 1H), 3.39 (m, 2H), 3.07 (m, 4H), 2.77 (br s, 2H), 2.69 (d, 1H), 2.56 (d, 1H), 2.21 (br s, 4H), 2.15 (t, 2H), 1.94 (m, 3H), 1.76 (t, 1H), 1.38 (t, 2H), 0.92 (s, 6H).

Compound 242

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 242A 5-chloro-6-((4-fluorotetrahydro-2H-pyran-4-yl)methylamino)pyridine-3-sulfonamide The title compound was prepared by substituting Compound 40A for 4-fluoro-3-nitrobenzenesulfonamide in the procedure for Compound 138D.

Compound 242B

N-[(5-chloro-6-{[(4-fluorotetrahydro-2H-pyran-4-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 242A for Compound 11B in the procedure for Compound 11D. $^1$H NMR (500 MHz, dimethylsulfoxide-$d_6$) δ 11.71 (s, 1H), 8.41 (d, 1H), 8.07 (d, 1H), 7.93 (d, 1H), 7.60 (d, 1H), 7.51-7.53 (m, 2H), 7.40 (s, 1H), 7.33-7.35 (m, 2H), 7.03-7.05 (m, 2H), 6.68 (dd, 1H), 6.42 (dd, 1H), 6.16 (d, 1H), 3.77 (d, 1H), 3.69-3.71 (m, 3H), 3.48-3.53 (m, 2H), 3.07 (s, 4H), 2.76 (s, 2H), 2.14-2.20 (m, 6H), 1.96 (s, 2H), 1.65-1.76 (m, 4H), 1.38 (t, 2H), 0.93 (s, 6H).

Compound 243

N-({5-chloro-6-[(1-cyclopropylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 243A 5-chloro-6-(1-cyclopropylpiperidin-4-ylamino)pyridine-3-sulfonamide The title compound was prepared by substituting Compound 40A for 4-chloro-3-nitrobenzenesulfonamide, 1-cyclopropylpiperidin-4-amine for 4-methylpiperazin-1-amine dihydrochloride and Hunig's base for $N^1,N^1,N^2,N^2$-tetramethylethane-1,2-diamine in the procedure for Compound 6A.

Compound 243B

N-({5-chloro-6-[(1-cyclopropylpiperidin-4-yl) amino]pyridin-3-yl}sulfonyl)-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting Compound 243A for Compound 11B in the procedure for Compound 11D. $^1$H NMR (400 MHz, dimethylsulfoxide-$d_6$) δ 11.67 (s, 1H), 8.40 (d, 1H), 8.05 (d, 1H), 7.88 (d, 1H), 7.56 (d, 1H), 7.50 (m, 2H), 7.34 (d, 2H), 7.03 (d, 2H), 6.97 (br d, 1H), 6.66 (dd, 1H), 6.40 (m, 1H), 6.16 (d, 1H), 4.04 (m, 1H), 3.03 (br m, 6H), 2.73 (s, 2H), 2.42 (br m, 2H), 2.18 (br m, 6H), 1.95 (s, 2H), 1.80 (m, 3H), 1.62 (m, 2H), 1.38 (t, 2H), 0.91 (s, 6H), 0.47 (m, 2H), 0.40 (br m, 2H).

Compound 244

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide Compound 244A (S)-tert-butyl 2-((3-chloro-5-sulfamoylpyridin-2-yloxy)methyl)morpholine-4-carboxylate The title compound was prepared by substituting (S)-tert-butyl 2-(hydroxymethyl)-morpholine-4-carboxylate for tetrahydro-2H-pyran-4-yl-methanol and Compound 40A for 4-fluoro-3-nitrobenzenesulfonamide in the procedure for Compound 24A.

Compound 244B (S)-5-chloro-6-(morpholin-2-ylmethoxy)pyridine-3-sulfonamide

The title compound was prepared by substituting Compound 244A for Compound 113A in the procedure for Compound 134A.

Compound 244C (S)-5-chloro-6-((4-(cyanomethyl)morpholin-2-yl) methoxy)pyridine-3-sulfonamide The title compound was prepared by substituting Compound 244B for Compound 134A and 2-bromoacetonitrile for methyl iodide in the procedure for Compound 134B.

Compound 244D

N-[(5-chloro-6-{[(2S)-4-(cyanomethyl)morpholin-2-yl]methoxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide The title compound was prepared by substituting Compound 244C for Compound 130C in the procedure for Compound 130D. $^1$H NMR (500 MHz, pyridine-$d_5$) δ 12.99 (s, 1H), 9.09 (d, 1H), 8.70 (d, 1H), 8.42 (d, 1H), 8.12 (d, 1H), 7.66 (m, 2H), 7.44 (d, 2H), 7.07 (d, 2H), 6.75 (dd, 1H), 6.53 (d, 1H), 6.48 (m, 1H), 4.55 (dd, 1H), 4.43 (dd, 1H), 4.05 (m, 1H), 3.85 (d, 1H), 3.76 (s, 2H), 3.63 (dt, 1H), 3.06 (m, 4H), 2.91 (d, 1H), 2.77 (s, 2H), 2.58 (d, 1H), 2.51-2.44 (m, 2H), 2.26 (m, 2H), 2.14 (m, 4H), 1.97 (s, 2H), 1.39 (t, 2H), 0.94 (s, 6H).

Compound 245

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 245A (S)-5-chloro-6-((4-(2-(dimethylamino)acetyl)morpholin-2-yl)methoxy)pyridine-3-sulfonamide The title compound was prepared by substituting Compound 244B for Compound 134A and 2-(dimethylamino) acetyl chloride hydrochloride for methyl iodide in the procedure for Compound 134B.

Compound 245B

N-[(5-chloro-6-{[(2S)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 245A for Compound 130C in the procedure for Compound 130D. $^1$H NMR (500 MHz, pyridine-$d_5$) δ 13.00 (s, 1H), 9.09 (d, 1H), 8.69 (s, 1H), 8.42 (s, 1H), 8.11 (t, 1H), 7.66 (m, 2H), 7.44 (d, 2H), 7.07 (d, 2H), 6.76 (s, 1H), 6.54 (s, 1H), 6.49 (s, 1H), 4.85-4.46 (m, 3H), 4.45-3.87 (m, 3H), 3.50 (m, 1H), 3.37 (dd, 1H), 3.21 (m, 2H), 3.07 (m, 4H), 2.86 (t, 1H), 2.77 (s, 2H), 2.27 (m, 8H), 2.14 (m, 4H), 1.97 (s, 2H), 1.39 (t, 2H), 0.94 (s, 6H).

Compound 246

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide Compound 246A (R)-tert-butyl 2-((3-chloro-5-sulfamoylpyridin-2-yloxy)methyl)morpholine-4-carboxylate The title compound was prepared by substituting (R)-tert-butyl 2-(hydroxymethyl)-morpholine-4-carboxylate for tetrahydro-2H-pyran-4-yl-methanol and Compound 40A for 4-fluoro-3-nitrobenzenesulfonamide in the procedure for Compound 24A.

Compound 246B (R)-5-chloro-6-(morpholin-2-ylmethoxy)pyridine-3-sulfonamide

The title compound was prepared by substituting Compound 246A for Compound 113A in the procedure for Compound 134A.

Compound 246C (R)-5-chloro-6-((4-(cyanomethyl)morpholin-2-yl)methoxy)pyridine-3-sulfonamide The title compound was prepared by substituting Compound 246B for Compound 134A and 2-bromoacetonitrile for methyl iodide in the procedure for Compound 134B.

Compound 246D

N-[(5-chloro-6-{[(2R)-4-(cyanomethyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 246C for Compound 130C in the procedure for Compound 130D. $^1$H NMR (500 MHz, pyridine-$d_5$) δ 12.99 (s, 1H), 9.09 (d, 1H), 8.70 (d, 1H), 8.42 (d, 1H), 8.12 (d, 1H), 7.66 (m, 2H), 7.44 (d, 2H), 7.07 (d, 2H), 6.75 (dd, 1H), 6.53 (d, 1H), 6.48 (m, 1H), 4.55 (dd, 1H), 4.43 (dd, 1H), 4.05 (m, 1H), 3.85 (d, 1H), 3.76 (s, 2H), 3.63 (dt, 1H), 3.06 (m, 4H), 2.91 (d, 1H), 2.77 (s, 2H), 2.58 (d, 1H), 2.51-2.44 (m, 2H), 2.26 (m, 2H), 2.14 (m, 4H), 1.97 (s, 2H), 1.39 (t, 2H), 0.94 (s, 6H).

Compound 247

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 247A (R)-5-chloro-6-((4-(2-(dimethylamino)acetyl)morpholin-2-yl)methoxy)pyridine-3-sulfonamide The title compound was prepared by substituting Compound 246B for Compound 134A and 2-(dimethylamino)acetyl chloride hydrochloride for methyl iodide in the procedure for Compound 134B.

Compound 247B

N-[(5-chloro-6-{[(2R)-4-(N,N-dimethylglycyl)morpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 247A for Compound 130C in the procedure for Compound 130D. $^1$H NMR (500 MHz, pyridine-$d_5$) δ 13.00 (s, 1H), 9.09 (d, 1H), 8.69 (s, 1H), 8.42 (s, 1H), 8.11 (t, 1H), 7.66 (m, 2H), 7.44 (d, 2H), 7.07 (d, 2H), 6.76 (s, 1H), 6.54 (s, 1H), 6.49 (s, 1H), 4.85-4.46 (m, 3H), 4.45-3.87 (m, 3H), 3.50 (m, 1H), 3.37 (dd, 1H), 3.21 (m, 2H), 3.07 (m, 4H), 2.86 (t, 1H), 2.77 (s, 2H), 2.27 (m, 8H), 2.14 (m, 4H), 1.97 (s, 2H), 1.39 (t, 2H), 0.94 (s, 6H).

Compound 248

4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide

Compound 248A 5-bromo-3-fluoro-2-((4-fluorotetrahydro-2H-pyran-4-yl)methoxy)pyridine The title compound was prepared by substituting 5-bromo-2,3-difluoropyridine for 4-fluoro-3-nitrobenzenesulfonamide and Compound 37C for (tetrahydro-2H-pyran-4-yl)methanol in the procedure for Compound 24A.

Compound 248B tert-butyl 5-fluoro-6-((4-fluorotetrahydro-2H-pyran-4-yl)methoxy)pyridin-3-ylcarbamate Compound 248A (0.308 g), tert-butyl carbamate (0.141 g), palladium(II) acetate (0.011 g), Xantphos (0.043 g) and cesium carbonate (0.489 g) were combined with dioxane (5.0 ml) in a 20-ml vial equipped with a magnetic stir bar. The vial was flushed with nitrogen, capped and stirred at 100° C. overnight. Additional palladium(II) acetate (0.011 g), Xantphos (0.043 g) and tert-butyl carbamate (0.141 g) were added and heating was continued at 100° C. for 8 hours. The cooled reaction mixture was diluted with ethyl acetate, washed with water and brine, dried (MgSO$_4$), filtered and concentrated. The concentrate was chromatographed on silica gel with 7-25% ethyl acetate in hexanes as the eluent.

Compound 248C 5-fluoro-6-((4-fluorotetrahydro-2H-pyran-4-yl)methoxy)pyridine-3-sulfonyl chloride Under ice-cooling, thionyl chloride (1.563 ml) was added dropwise over 20 minutes to water (9 ml). The mixture was stirred for 12 hours to give a SO$_2$-containing solution. Separately, Compound 248B (0.295 g) was added to a mixture of 1,4-dioxane (3.2 ml) and concentrated HCl (8 ml) at 0° C. After stirring for 15 minutes, a solution of sodium nitrite (0.065 g) in water (2 ml) was added dropwise and stirring was continued at 0° C. for 3 hours. Copper(I) chloride (0.042 g) and then the freshly prepared solution of diazotized material were added sequentially to the previously prepared SO$_2$-containing solution. The resulting solution was stirred for 30 minutes and then extracted with ethyl acetate (2×125 ml). The combined extracts were dried (MgSO$_4$), filtered and concentrated. The concentrate was chromatographed on silica gel with 5% ethyl acetate in hexanes as the eluent.

Compound 248D 5-fluoro-6-((4-fluorotetrahydro-2H-pyran-4-yl)methoxy)pyridine-3-sulfonamide Compound 248C (0.08 g) in isopropanol (2 ml) at 0° C. was treated with ammonium hydroxide (1.697 ml), stirred overnight and then concentrated to dryness. The obtained solid was slurried in water, filtered, rinsed with water and dried under high vacuum to provide the title compound.

Compound 248E 4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting Compound 248D for Compound 11B in the procedure for Compound 11D. $^1$H NMR (500 MHz, pyridine-$d_5$) δ 13.05 (s, 1H), 9.03 (d, 1H), 8.44 (dd, 1H), 8.41 (d, 1H), 8.10 (d, 1H), 7.67 (m, 1H), 7.65 (d, 1H), 7.44 (m, 2H), 7.07 (m, 2H), 6.77 (dd, 1H), 6.53 (d, 1H), 6.49 (dd, 1H), 4.55 (d, 2H), 3.80 (m, 4H), 3.08 (m, 4H), 2.77 (s, 2H), 2.26 (t, 2H), 2.14 (m, 4H), 1.97 (s, 2H), 1.88 (m, 4H), 1.39 (t, 2H), 0.94 (s, 6H).

Compound 250

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 250A 5-chloro-6-((3-methyloxetan-3-yl)methoxy)pyridine-3-sulfonamide The title compound was prepared by substituting (3-methyloxetan-3-yl)methanol for (tetrahydro-2H-pyran-4-yl)methanol and Compound 40A for 4-fluoro-3-nitrobenzenesulfonamide in the procedure for Compound 24A.

Compound 250B

N-({5-chloro-6-[3-hydroxy-2-(hydroxymethyl)-2-methylpropoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 250A for Compound 11B in the procedure for Compound 11D. $^1$H NMR (500 MHz, pyridine-$d_5$) δ 13.05 (s, 1H), 9.22 (d, 1H), 8.51 (d, 1H), 8.42 (d, 1H), 8.09 (d, 1H), 7.66 (t, 2H), 7.43-7.46 (m, 2H), 7.04-7.09 (m, 2H), 6.75 (dd, 1H), 6.45-6.54 (m, 2H), 4.47 (s, 2H), 3.81-3.84 (m, 2H), 3.74 (d, 2H), 3.03-3.11 (m, 4H), 2.77 (s, 2H), 2.26 (t, 2H), 2.10-2.17 (m, 4H), 1.97 (s, 2H), 1.39 (t, 2H), 1.16 (s, 3H), 0.94 (s, 6H).

Compound 251

4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide

Compound 251A 5-bromo-6-((4-fluorotetrahydro-2H-pyran-4-yl)methoxy)pyridine-3-sulfonamide The title compound was prepared by substituting (4-fluorotetrahydro-2H-pyran-4-yl)methanol for (tetrahydro-2H-pyran-4-yl)methanol and 5-bromo-6-chloropyridine-3-sulfonamide for 4-fluoro-3-nitrobenzenesulfonamide in the procedure for Compound 24A.

Compound 251B 6-((4-fluorotetrahydro-2H-pyran-4-yl)methoxy)pyridine-3-sulfonamide To a suspension of 5-bromo-6-((4-fluorotetrahydro-2H-pyran-4-yl)methoxy)pyridine-3-sulfonamide (200 mg) and cyclohexene (0.549 ml) in ethyl acetate (10 ml) was added 10% palladium on carbon (57.6 mg). The suspension was stirred for 60 minutes at 120° C. The reaction mixture was filtered and concentrated. The product was purified by reverse-phase flash chromatography (C18, 150 g, 10%-1-100% acetonitrile/$H_2O$/trifluoroacetic acid 0.1%).

Compound 251C 4-(4-{[2-(4-chlorophenyl)-4,4-dimethylcyclohex-1-en-1-yl]methyl}piperazin-1-yl)-N-({6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting Compound 251B for Compound 11B in the procedure for Compound 11D. $^1$H NMR (500 MHz, pyridine-$d_5$) δ 13.06 (s, 1H), 9.29 (d, 1H), 8.50 (dd, 1H), 8.41 (d, 1H), 8.07 (d, 1H), 7.66-7.70 (m, 1H), 7.64 (d, 1H), 7.44 (d, 2H), 7.07 (d, 2H), 6.84 (d, 1H), 6.75 (dd, 1H), 6.52 (d, 1H), 6.49 (dd, 1H), 4.50 (d, 2H), 3.81-3.89 (m, 2H), 3.70-3.81 (m, 2H), 3.02-3.12 (m, 4H), 2.77 (s, 2H), 2.26 (t, 2H), 2.10-2.18 (m, 4H), 1.97 (s, 2H), 1.77-1.94 (m, 4H), 1.39 (t, 2H), 0.94 (s, 6H).

Compound 252

4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide

Compound 252A tert-butyl (4-(1,3-difluoropropan-2-yl)morpholin-2-yl)methylcarbamate The title compound was prepared by substituting 1,3-difluoropropan-2-one for 4'-chlorobiphenyl-2-carboxaldehyde and tert-butyl morpholin-2-ylmethylcarbamate for tert-butyl piperazine-1-carboxylate in the procedure for Compound 1A.

Compound 252B (4-(1,3-difluoropropan-2-yl)morpholin-2-yl)methanamine

A solution of Compound 252A (538 mg) in dioxane (4 ml) was treated with 4.0M HCl in dioxane solution (1.8 ml). The reaction was stirred at room temperature overnight. The reaction mixture was concentrated under vacuum and used without further purification.

Compound 252C 4-((4-(1,3-difluoropropan-2-yl)morpholin-2-yl)methylamino)-3-nitrobenzenesulfonamide The title compound was prepared by substituting Compound 252B for (tetrahydropyran-4-yl)methylamine in the procedure for Compound 1F.

Compound 252D 4-(4-{[2-(4-chlorophenyl)-4,4-dimethylcyclohex-1-en-1-yl]methyl}piperazin-1-yl)-N-{[4-({[4-(1,3-difluoropropan-2-yl)morpholin-2-yl]methyl}amino)-3-nitrophenyl]sulfonyl}-2-(1H-pyrrolo[2,3-b]pyridin-5-yloxy)benzamide The title compound was prepared by substituting Compound 252C for Compound 1F and Compound 3J for Compound 1E in the procedure for Compound 1G. $^1$H NMR (300 MHz, dimethylsulfoxide-$d_6$) δ 11.64 (s, 1H), 8.59 (t, 1H), 8.57 (d, 1H), 8.04 (d, 1H), 7.83 (dd, 1H), 7.51 (m, 3H), 7.33 (d, 2H), 7.07 (d, 1H), 7.03 (d, 2H), 6.66 (dd, 1H), 6.39 (m, 1H), 6.19 (d, 1H), 4.69 (t, 2H), 4.57 (t, 2H), 3.85 (m, 1H), 3.70 (m, 1H), 3.52 (m, 2H), 3.41 (m, 2H), 3.07 (br s, 4H), 2.91 (d, 1H), 2.74 (m, 3H), 2.59 (m, 1H), 2.43 (m, 1H), 2.20 (m, 4H), 2.15 (m, 2H), 1.95 (br s, 2H), 1.39 (t, 2H), 0.92 (s, 6H).

Compound 253

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 253A tert-butyl 4-((3-chloro-5-sulfamoylpyridin-2-yloxy)methyl)piperidine-1-carboxylate The title compound was prepared by substituting tert-butyl 4-(hydroxymethyl)piperidine-1-carboxylate for tetrahydro-2H-pyran-4-yl)methanol and Compound 40A for 4-fluoro-3-nitrobenzenesulfonamide in the procedure for Compound 24A.

Compound 253B 5-chloro-6-(piperidin-4-ylmethoxy)pyridine-3-sulfonamide ditrifluoroacetic Acid The title compound was prepared by substituting Compound 253A for Compound 39A in the procedure for Compound 39B.

Compound 253C 5-chloro-6-((1-(cyanomethyl)piperidin-4-yl)methoxy)pyridine-3-sulfonamide Compound 253B (0.061 g), 2-chloroacetonitrile (0.017 g), sodium carbonate (0.025 g) and N,N-dimethylformamide (1 ml) were combined in a 4-ml vial and heated at 60° C. overnight. The cooled reaction mixture was diluted with ethyl acetate, washed with water and brine, dried (MgSO$_4$), filtered and concentrated. The concentrate was chromatographed on silica gel with 2-10% methanol in CH$_2$Cl$_2$ as the eluent.

Compound 253D

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 253C for Compound 1F in the procedure for Compound 1G. $^1$H NMR (400 MHz, pyridine-$d_5$) δ 13.04 (s, 1H), 9.14 (d, 1H), 8.41 (d, 1H), 8.10 (d, 1H), 7.66 (t, 2H), 7.44 (m, 2H), 7.07 (m, 2H), 6.74 (dd, 1H), 6.50 (m, 2H), 4.18 (d, 2H), 3.64 (s, 2H), 3.05 (s, 4H), 2.77 (m, 4H), 2.24 (m, 4H), 2.13 (m, 4H), 1.97 (s, 2H), 1.69 (m, 3H), 1.41 (m, 4H), 0.93 (s, 6H).

Compound 254

4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yloxy)benzamide Compound 254A (R)-tert-butyl 3-(2-nitro-4-sulfamoylphenylamino)pyrrolidine-1-carboxylate The title compound was prepared by substituting (R)-tert-butyl 3-aminopyrrolidine-1-carboxylate for 1-(tetrahydropyran-4-yl)methylamine in the procedure for Compound 1F.

Compound 254B (R)-3-nitro-4-(pyrrolidin-3-ylamino)benzenesufonamide

The title compound was prepared by substituting Compound 254A for Compound 113A in the procedure for Compound 134A.

Compound 254C (R)-4-(1-(2-(2-methoxyethoxy)ethyl)pyrrolidin-3-ylamino)-3-nitrobenzenesufonamide To a solution of (R)-3-nitro-4-(pyrrolidin-3-ylamino)benzenesulfonamide (440 mg) in N,N-dimethylformamide (10 ml) was added sodium carbonate (132 mg) and 1-bromo-2-(2-methoxyethoxy)ethane (0.155 ml). The reaction mixture was heated at 60° C. for 18 hours and after an aqueous workup, the crude product was purified on silica gel with a 2.5-10% methanol in methylene chloride gradient to provide the title compound.

Compound 254D 4-(4-{[2-(4-chlorophenyl)-4,4-dimethylcyclohex-1-en-1-yl]methyl}piperazin-1-yl)-N-{[4-({(3R)-1-[2-(2-methoxyethoxy)ethyl]pyrrolidin-3-yl}amino)-3-nitrophenyl]sulfonyl}-2-(1H-pyrrolo[2,3-b]pyridin-5-yl-oxy)benzamide The title compound was prepared by substituting Compound 254C for Compound 130C in the procedure for Compound 130D. 1H NMR (500 MHz, pyridine-$d_5$) δ 12.96 (m, 1H), 9.25 (m, 1H), 8.57 (d, 1H), 8.43 (d, 1H), 8.34 (dd, 1H), 8.11 (d, 1H), 7.66 (t, 1H) 7.64 (d, 1H), 7.44 (d, 2H), 7.07 (d, 2H), 6.82 (d, 1H), 6.76 (dd, 1H), 6.55 (m, 1H), 6.47 (m, 1H), 5.26 (br s, 1H), 4.02 (m, 1H), 3.63 (m, 4H), 3.53 (m, 2H), 3.28 (s, 3H), 3.07 (m, 4H), 2.89-2.81 (m, 2H), 2.78 (s, 2H), 2.75-2.66 (m, 3H), 2.37 (m, 1H), 2.26 (m, 2H), 2.24-2.18 (m, 1H), 2.15 (m, 4H), 1.97 (s, 2H), 1.65 (m, 1H), 1.39 (t, 2H), 0.94 (s, 6H).

Compound 255

4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide

Compound 255A (R)-4-(1-(2-(dimethylamino)acetyl)pyrrolidin-3-ylamino)-3-nitrobenzenesufonamide The title compound was prepared by substituting 2-(dimethylamino)acetyl chloride, hydrochloric acid for 1-bromo-2-(2-methoxyethoxy)ethane in the procedure for Compound 254C except the reaction was stirred at ambient temperature for 18 hours.

Compound 255B 4-(4-{[2-(4-chlorophenyl)-4,4-dimethylcyclohex-1-en-1-yl]methyl}piperazin-1-yl)-N-[(4-{[(3R)-1-(N,N-dimethylglycyl)pyrrolidin-3-yl]amino}-3-nitrophenyl)sulfonyl]-2-(1H-pyrrolo[2,3-b]pyridin-5-yloxy)benzamide The title compound was prepared by substituting Compound 255A for Compound 130C in the procedure for Compound 130D. $^1$H NMR (500 MHz, pyridine-$d_5$) δ 13.01 (d, 1H), 9.26 (m, 1H), 8.46-8.33 (m, 3H), 8.14 (d, 1H), 7.66 (m, 2H), 7.44 (d, 2H), 7.07 (d, 2H), 7.01-6.89 (m, 1H), 6.76 (dd, 1H), 6.55 (m, 1H), 6.48 (m, 1H), 5.32 (br s, 1H), 4.27-4.14 (m, 1H), 4.05-3.95 (m, 1H), 3.82-3.62 (m, 3H), 3.27-3.15 (m, 2H), 3.07 (m, 4H), 2.77 (s, 2H), 2.34 (2, 3H), 2.32 (s, 3H), 2.30-2.20 (m, 3H), 2.15 (m, 4H), 1.97 (s, 2H), 1.87-1.81 (m, 1H), 1.39 (t, 2H), 0.94 (s, 6H).

Compound 256

4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide

Compound 256A tert-butyl 3-(2-nitro-4-sulfamoylphenylamino)azetidine-1-carboxylate The title compound was prepared by substituting tert-butyl 3-aminoazetidine-1-carboxylate for 4-methylpiperazin-1-amine dihydrochloride in the procedure for Compound 6A.

Compound 256B 4-(azetidin-3-ylamino)-3-nitrobenzenesulfonamide

The title compound was prepared by substituting Compound 256A for (S)-1-tert-butyl 2-methyl 4,4-difluoropyrrolidine-1,2-dicarboxylate in the procedure for Compound 168A.

Compound 256C 3-nitro-4-(1-(oxetan-3-yl)azetidin-3-ylamino)benzenesulfonamide The title compound was prepared by substituting Compound 256B for tert-butyl piperazine-1-carboxylate and 3-oxetanone for 4'-chlorobiphenyl-2-carboxaldehyde in the procedure for Compound 1A.

Compound 256D 4-(4-{[2-(4-chlorophenyl)-4,4-dimethylcyclohex-1-en-1-yl]methyl}piperazin-1-yl)-N-[(3-nitro-4-{[1-(oxetan-3-yl)azetidin-3-yl]amino}phenyl)sulfonyl]-2-(1H-pyrrolo[2,3-b]pyridin-5-yloxy)benzamide The title compound was prepared by substituting Compound 256C for Compound 11B in the procedure for Compound 1 JD. $^1$H NMR (500 MHz, pyridine-$d_5$) δ 13.04 (s, 1H), 9.27 (d, 1H), 8.62 (d, 1H), 8.42 (d, 1H), 8.35 (dd, 1H), 8.09 (d, 1H), 7.67 (m, 1H), 7.63 (d, 1H), 7.44 (m, 2H), 7.07 (m, 2H), 6.76 (dd, 1H), 6.67 (d, 1H), 6.55 (d, 1H), 6.48 (dd, 1H), 4.66 (t, 2H), 4.58 (m, 2H), 4.23 (m, 1H), 3.71 (m, 3H), 3.12 (dd, 2H), 3.07 (m, 4H), 2.77 (s, 2H), 2.26 (t, 2H), 2.14 (t, 4H), 1.97 (s, 2H), 1.39 (t, 2H), 0.94 (s, 6H).

Compound 257

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 257A tert-butyl 4-((3-chloro-5-sulfamoylpyridin-2-yloxy)methyl)-4-fluoropiperidine-1-carboxylate The title compound was prepared by substituting Compound 126A for (tetrahydro-2H-pyran-4-yl)methanol and Compound 40A for 4-fluoro-3-nitrobenzenesulfonamide in the procedure for Compound 24A.

Compound 257B 5-chloro-6-((4-fluoropiperidin-4-yl)methoxy)pyridine-3-sulfonamide ditrifluoroacetic Acid The title compound was prepared by substituting Compound 257A for Compound 39A in the procedure for Compound 39B.

Compound 257C 5-chloro-6-((1-(cyanomethyl)-4-fluoropiperidin-4-yl)methoxy)pyridine-3-sulfonamide Compound 257B (0.166 g) in acetonitrile (3 ml) was treated with 2-chloroacetonitrile (0.027 g) and sodium carbonate (0.064 g), heated at 60° C. overnight, cooled to room temperature and chromatographed on silica gel with 0 to 3% methanol in $CH_2Cl_2$ as the eluent. The obtained solid was slurried in water, filtered, rinsed with water and diethyl ether, and dried in a vacuum oven at 80° C.

Compound 257D

N-[(5-chloro-6-{[1-(cyanomethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 257C for Compound 1F in the procedure for Compound 1G. $^1$H NMR (400 MHz, pyridine-$d_5$) δ 13.05 (s, 1H), 9.12 (d, 1H), 8.72 (d, 1H), 8.41 (d, 1H), 8.10 (d, 1H), 7.66 (m, 2H), 7.44 (m, 2H), 7.07 (m, 2H), 6.75 (dd, 1H), 6.50 (m, 2H), 4.49 (d, 2H), 3.72 (s, 2H), 3.06 (m, 4H), 2.77 (s, 2H), 2.73 (m, 4H), 2.26 (t, 2H), 2.13 (m, 4H), 2.07 (m, 2H), 1.90 (m, 4H), 1.39 (t, 2H), 0.93 (s, 6H).

Compound 258

4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide Compound 258A (S)-tert-butyl 2-(tosyloxymethyl)morpholine-4-carboxylate To a solution of (S)-tert-butyl 2-(hydroxymethyl)morpholine-4-carboxylate (1 g) in dichloromethane (50 ml) was added triethylamine (1.604 ml) and 4-methylbenzene-1-sulfonyl chloride (1.097 g). The mixture was stirred at ambient temperature under nitrogen for 72 hours. The reaction was diluted with methylene chloride (50 ml) and brine (100 ml). The brine layer was extracted with methylene chloride (75 ml). The combined organics were dried over sodium sulfate, filtered and concentrated. The crude material was purified on a silica gel column eluting with a 15-65% ethyl acetate in hexane gradient to provide the title compound.

Compound 258B (S)-tert-butyl 2-(azidomethyl)morpholine-4-carboxylate

A solution of Compound 258A (1.66 g) and sodium azide (0.581 g) in anhydrous N,N-dimethylformamide (10 ml) was stirred at 90° C. for 4 hours. The mixture was cooled and concentrated to dryness. The residue was taken up in 5% aqueous sodium carbonate solution and extracted with methylene chloride. The organic solution was dried ($MgSO_4$), filtered and concentrated to give a solid.

Compound 258C (R)-tert-butyl 2-(aminomethyl)morpholine-4-carboxylate

This compound was obtained by hydrogenation of Compound 258B under 60 psi of hydrogen over 10% palladium on carbon in methanol for 24 hours, followed by filtration and evaporation of the solvent.

Compound 258D (R)-tert-butyl 2-((2-nitro-4-sulfamoylphenylamino)methyl)morpholine-4-carboxylate The title compound was prepared by substituting Compound 258C for (tetrahydropyran-4-yl)methylamine in the procedure for Compound 1F.

Compound 258E (S)-4-(morpholin-2-ylmethylamino)-3-nitrobenzenesulfonamide

The title compound was prepared by substituting Compound 258D for Compound 113A in the procedure for Compound 134A.

Compound 258F (R)-4-((4-(2-(dimethylamino)acetyl)morpholin-2-yl)methylamino)-3-nitrobenzenesulfonamide The title compound was prepared by substituting Compound 258E for Compound 134A and 2-(dimethylamino)acetyl chloride hydrochloride for methyl iodide in the procedure for Compound 134B.

Compound 258G 4-(4-{[2-(4-chlorophenyl)-4,4-dimethylcyclohex-1-en-1-yl]methyl}piperazin-1-yl)-N-{[4-({[(2R)-4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 258F for Compound 130C in the procedure for Compound 130D. $^1$H NMR (500 MHz, pyridine-$d_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 2H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Compound 259

4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide Compound 259A (R)-tert-butyl 2-(tosyloxymethyl)morpholine-4-carboxylate The title compound was prepared by substituting (R)-tert-butyl 2-(hydroxymethyl)morpholine-4-carboxylate for (S)-tert-butyl 2-(hydroxymethyl)morpholine-4-carboxylate in the procedure for Compound 258A.

Compound 259B (R)-tert-butyl 2-(azidomethyl)morpholine-4-carboxylate

The title compound was prepared by substituting Compound 259A for Compound 258A in the procedure for Compound 258B.

Compound 259C (S)-tert-butyl 2-(aminomethyl)morpholine-4-carboxylate

The title compound was prepared by substituting Compound 259B for Compound 258B in the procedure for Compound 258C.

Compound 259D (S)-tert-butyl 2-((2-nitro-4-sulfamoylphenylamino)methyl)morpholine-4-carboxylate The title compound was prepared by substituting Compound 259C for (tetrahydropyran-4-yl)methylamine in the procedure for Compound 1F.

Compound 259E (R)-4-(morpholin-2-ylmethylamino)-3-nitrobenzenesulfonamide

The title compound was prepared by substituting Compound 259D for Compound 113A in the procedure for Compound 134A.

Compound 259F (S)-4-((4-(2-(dimethylamino)acetyl)morpholin-2-yl)methylamino)-3-nitrobenzenesulfonamide The title compound was prepared by substituting Compound 259E for Compound 134A and 2-(dimethylamino)acetyl chloride hydrochloride for methyl iodide in the procedure for Compound 134B.

Compound 259G 4-(4-{[2-(4-chlorophenyl)-4,4-dimethylcyclohex-1-en-1-yl]methyl}piperazin-1-yl)-N-{[4-({[(2S)-4-(N,N-dimethylglycyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 259F for Compound 130C in the procedure for Compound 130D. $^1$H NMR (500 MHz, pyridine-$d_5$) δ 13.00 (s, 1H), 9.27 (d, 1H), 8.87 (bs, 1H), 8.43 (d, 1H), 8.34 (dd, 1H), 8.10 (dd, 1H), 7.66 (m, 2H), 7.44 (d, 2H), 7.07 (d, 2H), 6.94 (dd, 1H), 6.75 (d, 1H), 6.54 (s, 1H), 6.48 (s, 1H), 4.55 (dd, 1H), 4.20 (dd, 1H), 3.95-3.76 (m, 2H), 3.60-3.40 (m, 3H), 3.32 (dd, 1H), 3.25-3.12 (m, 2H), 3.07 (m, 4H), 2.80 (m, 1H), 2.77 (s, 2H), 2.26 (s, 6H), 2.23 (s, 2H), 2.14 (m, 4H), 1.97 (s, 2H), 1.39 (t, 2H), 0.94 (s, 6H).

Compound 260

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 260A 5-chloro-6-((1-(2-(dimethylamino)acetyl)piperidin-4-yl)methoxy)pyridine-3-sulfonamide Compound 253B (0.061 g), 2-(dimethylamino)acetyl chloride, hydrochloric acid (0.061 g), and sodium carbonate (0.032 g) were combined in a 4-ml vial with N,N-dimethylformamide (2 ml). The mixture was stirred at ambient temperature for 3 days. Additional 2-(dimethylamino)acetyl chloride, hydrochloric acid (0.037 g), sodium carbonate (0.032 g) and N,N-dimethylformamide (1 ml) were added and stirring was continued for 24 hours. The reaction mixture was diluted with ethyl acetate, washed with water and brine, dried (MgSO$_4$), filtered, concentrated and chromatographed on silica gel with 0 to 20% methanol in CH$_2$Cl$_2$ as the eluent.

Compound 260B

N-[(5-chloro-6-{[1-(N,N-dimethylglycyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 260A for Compound 11B in the procedure for Compound 11D. $^1$H NMR (400 MHz, pyridine-$d_5$) δ 12.91 (s, 1H), 9.16 (d, 1H), 8.75 (d, 1H), 8.51 (d, 1H), 8.33 (d, 1H), 7.70 (d, 1H), 7.62 (d, 1H), 7.45 (m, 2H), 7.09 (m, 2H), 6.77 (dd, 1H), 6.60 (d, 1H), 6.45 (d, 1H), 4.81 (d, 1H), 4.15 (m, 3H), 3.24 (m, 2H), 3.04 (m, 4H), 2.89 (m, 1H), 2.79 (s, 2H), 2.53 (m, 1H), 2.29 (m, 6H), 2.26 (m, 2H), 2.18 (m, 4H), 1.98 (m, 2H), 1.91 (m, 1H), 1.71 (m, 2H), 1.39 (t, 2H), 1.25 (m, 2H), 0.94 (s, 6H).

Compound 261

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 261A (R)-tert-Butyl 3-(3-chloro-5-sulfamoylpyridin-2-yloxy)pyrrolidine-1-carboxylate The title compound was prepared by substituting Compound 40A for 4-fluoro-3-nitrobenzenesulfonamide and (R)-tert-butyl 3-hydroxypyrrolidine-1-carboxylate for (tetrahydro-2H-pyran-4-yl)methanol in the procedure for Compound 24A.

Compound 261B (R)-5-Chloro-6-(pyrrolidin-3-yloxy)pyridine-3-sulfonamide

The title compound was prepared by substituting Compound 261A for tert-butyl (4-(1,3-difluoropropan-2-yl)morpholin-2-yl)methylcarbamate in the procedure for Compound 252B.

Compound 261C (R)-5-chloro-6-(1-(2,2-difluoroethyl)pyrrolidin-3-yloxy)pyridine-3-sulfonamide A mixture of Compound 261B (353 mg), 1,1-difluoro-2-iodoethane (268 mg), sodium carbonate (283 mg) in N,N-dimethylformamide (10 ml) was heated at 80° C. overnight. The reaction mixture was cooled to room temperature and diluted with ethyl acetate. The organic phase was washed with water, brine, dried over magnesium sulfate, filtered, and concentrated. The residue was loaded onto silica gel column and eluted using a gradient of 0.5 to 3% methanol in dichloromethane to provide the title compound.

Compound 261D

N-[(5-chloro-6-{[(3R)-1-(2,2-difluoroethyl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 261C for Compound 11B in the procedure for Compound 11D. $^1$H NMR (400 MHz, dimethylsulfoxide-$d_6$) δ 11.55 (s, 1H), 8.04 (s, 1H), 7.95 (d, 1H), 7.58 (d, 1H), 7.44 (t, 1H), 7.35 (m, 3H), 7.05 (d, 2H), 6.64 (dd, 1H), 6.33 (m, 1H), 6.24 (d, 1H), 6.25-5.97 (m, 1H), 5.39 (m, 1H), 2.98 (m, 6H), 2.86 (m, 6H), 2.55 (m, 2H), 2.24 (m, 7H), 1.96 (s, 2H), 1.83 (m, 1H), 1.39 (t, 2H), 0.93 (s, 6H)

Compound 262

4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide Compound 262A (R)-4-(1-(cyanomethyl)pyrrolidin-3-ylamino)-3-nitrobenzenesufonamide The title compound was prepared by substituting 2-bromoacetonitrile for 1-bromo-2-(2-methoxyethoxy)ethane in the procedure for Compound 254C.

Compound 262B 4-(4-{[2-(4-chlorophenyl)-4,4-dimethylcyclohex-1-en-1-yl]methyl}piperazin-1-yl)-N-[(4-{[(3R)-1-(cyanomethyl)pyrrolidin-3-yl]amino}-3-nitrophenyl)sulfonyl]-2-(1H-pyrrolo[2,3-b]pyridin-5-yloxy)benzamide The title compound was prepared by substituting Compound 262A for Compound 130C in the procedure for Compound 130D. 1H NMR (400 MHz, pyridine-$d_5$) δ 13.03 (s, 1H), 9.27 (d, 1H), 8.53 (d, 1H), 8.43 (d, 1H), 8.35 (dd, 1H), 8.10 (d, 1H), 7.67-7.64 (m, 2H), 7.44 (d, 2H), 7.07 (d, 2H), 6.81 (d, 1H), 6.76 (dd, 1H), 6.54 (m, 1H), 6.48 (m, 1H), 5.15 (br s, 1H), 4.10 (m, 1H), 3.89 (s, 2H), 3.07 (m, 4H), 2.93-2.86 (m, 2H), 2.80-2.77 (m, 3H), 2.61-2.53 (m, 1H), 2.31-2.21 (m, 3H), 2.14 (m, 4H), 1.97 (s, 2H), 1.75-1.68 (m, 1H), 1.39 (t, 2H), 0.94 (m, 6H).

Compound 263

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide Compound 263A tert-butyl 1-oxa-6-azaspiro[2.5]octane-6-carboxylate Sodium hydride (6.63 g, 60% in mineral oil) was added to trimethylsulfoxonium iodide (36.5 g) in dimethyl sulfoxide (150 ml) and tetrahydrofuran (150 ml), was and stirred for 30 minutes. tert-Butyl 4-oxopiperidine-1-carboxylate (25.4 g) was added and the reaction was stirred for 3 hours. The reaction was poured into water (800 ml) and extracted three times with ether. The combined extracts were washed three times with water, and brine, dried over Na$_2$SO$_4$, filtered, and concentrated to yield the crude product which was used without further purification.

Compound 263B tert-butyl 4-(2-(benzyloxy)benzyl)-4-hydroxypiperidine-1-carboxylate (2-(Benzyloxy)phenyl)magnesium bromide (33.8 ml, 1 M) was added to a solution of Compound 263A (6.0 g) and CuI (1.07 g) in tetrahydrofuran (220 ml) at 0° C. over 10 minutes. The reaction was quenched with pH 7 buffer (20 ml), extracted twice with ether, and the combined extracts were washed with brine, dried over $Na_2SO_4$, filtered, and concentrated. The crude product was chromatographed on silica gel using 2-20% ethyl acetate in hexanes to provide the title compound.

Compound 263C tert-butyl 4-hydroxy-4-(2-hydroxybenzyl)piperidine-1-carboxylate

Compound 263B (11.5 g) and methanol (120 ml) were added to Raney Nickel (1.150 g) in a 250 ml SS pressure bottle and stirred for 1 hour at 30 psi under hydrogen. The mixture was filtered through a nylon membrane and the solution was concentrated to yield the title compound.

Compound 263D tert-butyl 4-hydroxy-4-(2-(trifluoromethylsulfonyloxy)benzyl)piperidine-1-carboxylate A mixture of Compound 263C (4.6 g), N-phenylbis(trifluoromethanesulfonimide) (5.88 g), and Hunig's base (2.88 ml) in dichloromethane (100 ml) was stirred for 24 hours. The mixture was concentrated and chromatographed on silica gel using 5-50% ethyl acetate in hexanes to provide the title compound.

Compound 263E tert-butyl 4-((4'-chlorobiphenyl-2-yl)methyl)-4-hydroxypiperidine-1-carboxylate A mixture of Compound 263D (4.3 g), 4-chlorophenylboronic acid (1.84 g), $K_3PO_4$ (2.91 g), and [1,1'-bis(diphenylphosphino)ferrocene]dichloropalladium(II) (0.36 g) in 2-methyltetrahydrofuran (50 ml) was stirred at 70° C. for 24 hours. The reaction was cooled and quenched with water (50 ml), extracted twice with ether, and the combined extracts were washed with brine, dried over $Na_2SO_4$, filtered, and concentrated. The crude product was chromatographed on silica gel using 5-30% ethyl acetate in hexanes to provide the title compound.

Compound 263F tert-butyl 4-((4'-chlorobiphenyl-2-yl)methyl)-4-methoxypiperidine-1-carboxylate Sodium hydride (0.36 g, 60% in mineral oil) was added to Compound 263E (4.3 g), in tetrahydrofuran (40 ml) and the reaction was stirred for 10 minutes. Hexamethylphosphoramide (5 ml) and $CH_3I$ (2.34 ml) were added and the reaction was stirred at 50° C. for 18 hours. The reaction was cooled and quenched with water (50 ml), extracted twice with ether, and the combined extracts were washed with brine, dried over $Na_2SO_4$, filtered, and concentrated. The crude product was chromatographed on silica gel using 5-25% ethyl acetate in hexanes to provide the title compound.

Compound 263G 4-((4'-chlorobiphenyl-2-yl)methyl)-4-methoxypiperidine

The title compound was prepared by substituting Compound 263F for Compound 1A in the procedure for Compound 1B.

Compound 263H methyl 2-(1H-pyrrolo[2,3-b]pyridin-5-yloxy)-4-(4-((4'-chlorobiphenyl-2-yl)methyl)-4-methoxypiperidin-1-yl)benzoate A solution of Compound 263G (1.4 g), Compound 3H (1.06 g) and Hunig's base (0.75 ml) in dimethylsulfoxide (20 ml) was stirred at 120° C. for 18 hours. The reaction was cooled and quenched with water (200 ml), extracted three times with ether, and the combined extracts were washed three times with water, and brine, dried over $Na_2SO_4$, filtered, and concentrated. The crude product was chromatographed on silica gel using 5-50% ethyl acetate in hexanes to provide the title compound.

Compound 263I 2-(1H-pyrrolo[2,3-b]pyridin-5-yloxy)-4-(4-((4'-chlorobiphenyl-2-yl)methyl)-4-methoxypiperidin-1-yl) benzoic Acid The title compound was prepared by substituting Compound 263H for Compound 31 in the procedure for Compound 3J.

Compound 263J

4-{4-[(4'-chlorobiphenyl-2-yl)methyl]-4-methoxypiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting Compound 263I for Compound 1E and Compound 96A for Compound 1F in the procedure for Compound 1G. $^1$H NMR (300 MHz, dimethylsulfoxide-$d_6$) δ 11.71 (s, 1H), 11.58 (br s, 1H), 8.58 (d, 1H), 8.28 (d, 1H), 8.05 (d, 1H), 7.56 (d, 1H), 7.52 (m, 1H), 7.46 (d, 1H), 7.44 (d, 2H), 7.28 (m, 5H), 7.11 (dd, 1H), 6.62 (dd, 1H), 6.41 (dd, 1H), 6.11 (d, 1H), 4.54 (d, 2H), 3.75 (m, 2H), 3.59 (m, 2H), 3.20 (m, 2H), 2.97 (s, 3H), 2.81 (m, 2H), 2.74 (m, 2H), 1.89 (m, 2H), 1.83 (m, 2H), 1.36 (m, 2H), 1.09 (m, 2H).

Compound 264

4-{4-[(4'-chlorobiphenyl-2-yl)methyl]-4-methoxypiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 263I for Compound 1E in the procedure for Compound 1G. $^1$H NMR (300 MHz, dimethylsulfoxide-$d_6$) δ 11.71 (s, 1H), 11.40 (br s, 1H), 8.62 (t, 1H), 8.58 (d, 1H), 8.03 (d, 1H), 7.81 (dd, 1H), 7.54 (m, 2H), 7.44 (m, 3H), 7.28 (m, 5H), 7.13 (dd, 1H), 6.62 (dd, 1H), 6.41 (dd, 1H), 6.11 (d, 1H), 3.85 (dd, 2H), 3.31 (m, 4H), 3.20 (m, 2H), 2.97 (s, 3H), 2.81 (m, 2H), 2.73 (m, 2H), 1.89 (m, 1H), 1.62 (m, 2H), 1.38 (m, 2H), 1.25 (m, 2H), 1.09 (m, 2H).

Compound 265

4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 265A benzyl 4-(piperidin-1-ylmethylene)piperidine-1-carboxylate To a solution of benzyl 4-formylpiperidine-1-carboxylate (12.5 g) in toluene (120 ml) was added piperidine (6.46 g). The mixture was stirred at reflux under a Dean-Stark trap overnight. The mixture was then concentrated under vacuum and the residue was used directly in the next step.

Compound 265B benzyl 9-oxo-3-azaspiro[5.5]undec-7-ene-3-carboxylate

To a solution of Compound 265A (15.88 g) in ethanol (300 ml) was added but-3-enone (3.89 g). The mixture was stirred at reflux overnight. Then acetic acid (30 ml) was added to the mixture which was stirred at reflux again overnight. The mixture was then concentrated under vacuum and the residue was diluted with ethyl acetate (400 ml) and washed with water and brine and dried over Na$_2$SO$_4$. After filtration and evaporation of the solvent, column purification gave the title compound.

Compound 265C benzyl 9-hydroxy-3-azaspiro[5.5]undecane-3-carboxylate

Compound 265B (21 g) and tetrahydrofuran (160 ml) were added to 5% Pt—C wet (3.15 g) in a 250 ml pressure bottle and stirred for 1 hour at 30 psi and room temperature. The mixture was filtered though a nylon membrane and the filtrate was concentrated under vacuum to provide the title compound.

Compound 265D benzyl 9-oxo-3-azaspiro[5.5]undecane-3-carboxylate

To a solution of Compound 265C (8.0 g) in dichloromethane (200 ml) was added Dess-Martin Periodinane (11.2 g). The mixture was stirred overnight. The mixture was diluted with ethyl acetate (400 ml) and washed with 2N aqueous NaOH, water, and brine. After drying over Na$_2$SO$_4$ and filtration, concentration of the solvent gave the crude product which was used directly in the next reaction without further purification.

Compound 265E benzyl 9-chloro-8-formyl-3-azaspiro[5.5]undec-8-ene-3-carboxylate

Phosphorus oxychloride (2.33 ml) was added dropwise to a cooled (0° C.) solution of Compound 265D (7.5 g) in N,N-dimethylformamide (10 ml) and dichloromethane (30 ml). The mixture was then stirred overnight before it was diluted with ethyl acetate (300 ml) and washed with aqueous sodium acetate, water (3×), and brine and dried over Na$_2$SO$_4$. After filtration and concentration, the crude product was used directly in the next reaction without further purification.

Compound 265F benzyl 9-(4-chlorophenyl)-8-formyl-3-azaspiro[5.5]undec-8-ene-3-carboxylate To a mixture of 4-chlorophenylboronic acid (5.94 g), Compound 265E (11.01 g), palladium(II) acetate (142 mg), K$_2$CO$_3$ (13.2 g) and tetrabutylammonium bromide (10.2 g) was added water (120 ml). The mixture was stirred at 50° C. overnight. The mixture was diluted with ethyl acetate (400 ml) and washed with water (3×) and brine and dried over Na$_2$SO$_4$. After filtration and concentration, the residue was loaded on a column and eluted with 5 to 20% ethyl acetate in hexane to provide the title compound.

Compound 265G benzyl 8-((4-(3-(1H-pyrrolo[2,3-b]pyridin-5-yloxy)-4-(methoxycarbonyl)phenyl)piperazin-1-yl)methyl)-9-(4-chlorophenyl)-3-azaspiro[5.5]undec-8-ene-3-carboxylate To a solution of Compound 15F (1.37 g) and Compound 265F (1.65 g) in dichloromethane (20 ml) was added sodium triacetoxyborohydride (1.24 g). The mixture was stirred overnight. The mixture was diluted with ethyl acetate (200 ml) and washed with 2N aqueous NaOH, water and brine. After drying over Na$_2$SO$_4$, the mixture was filtered and the solvent was evaporated under vacuum to provide the title compound.

Compound 265H methyl 2-(1H-pyrrolo[2,3-b]pyridin-5-yloxy)-4-(4-((9-(4-chlorophenyl)-3-azaspiro[5.5]undec-8-en-8-yl)methyl)piperazin-1-yl)benzoate Compound 265G (2 g) and tetrahydrofuran (10 ml) were added to 20% Pd(OH)$_2$—C, wet (0.400 g) in a 50 ml pressure bottle and stirred for 16 hours at 30 psi and room temperature. The mixture was filtered though a nylon membrane and evaporation of the solvent gave the title compound.

Compound 265I methyl 2-(1H-pyrrolo[2,3-b]pyridin-5-yloxy)-4-(4-((9-(4-chlorophenyl)-3-(1,3-difluoropropan-2-yl)-3-azaspiro[5.5]undec-8-en-8-yl)methyl)piperazin-1-yl)benzoate To a solution of Compound 265H (320 mg) in dichloromethane (5 ml) was added 1,3-difluoroacetone (139 mg) and sodium triacetoxyborohydride (157 mg). The mixture was stirred overnight. The mixture was diluted with ethyl acetate (200 ml) and washed with 2N aqueous NaOH, water and brine. After drying over Na$_2$SO$_4$, the mixture was filtered and the solvent was evaporated under vacuum to provide the title compound.

Compound 265J 2-(1H-pyrrolo[2,3-b]pyridin-5-yloxy)-4-(4-((9-(4-chlorophenyl)-3-(1,3-difluoropropan-2-yl)-3-azaspiro[5.5]undec-8-en-8-yl)methyl)piperazin-1-yl) benzoic Acid To a solution of Compound 265I (320 mg) in tetrahydrofuran (4 ml) and methanol (2 ml) was added LiOH H$_2$O (120 mg) and the solution was stirred overnight. The reaction was cooled, carefully neutralized with 1N aqueous HCl and extracted with dichloromethane (3×50 ml). The combined organic layers were washed with brine (25 ml), dried over sodium sulfate, filtered and concentrated under vacuum to provide the title compound.

Compound 265K 4-(4-{[9-(4-chlorophenyl)-3-(1,3-difluoropropan-2-yl)-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 265J for Compound 1E in the procedure for Compound 1G. $^1$H NMR (300 MHz, dimethylsulfoxide-d$_6$) δ 11.61 (s, 1H), 8.49 (d, 2H), 7.72 (m, 1H), 7.49 (m, 2H), 7.32 (d, 2H), 7.07 (m, 3H), 6.65 (dd, 1H), 6.35 (d, 1H), 6.20 (m, 1H), 4.66 (m, 2H), 4.50 (m, 2H), 3.84 (m, 2H), 3.04 (m, 5H), 2.70 (m, 6H), 2.23 (m, 6H), 2.00 (m, 4H), 1.35 (m, 12H).

Compound 266

4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 266A methyl 2-(1H-pyrrolo[2,3-b]pyridin-5-yloxy)-4-(4-((9-(4-chlorophenyl)-3-isopropyl-3-azaspiro[5.5]undec-8-en-8-yl)methyl)piperazin-1-yl)benzoate To a solution of Compound 265H (320 mg) in dichloromethane (5 ml) was added acetone (143 mg) and sodium triacetoxyborohydride (157 mg). The mixture was stirred overnight. The mixture was diluted with ethyl acetate (200 ml) and washed with 2N aqueous NaOH, water and brine. After drying over Na$_2$SO$_4$, the mixture was filtered and the solvent was evaporated under vacuum to provide the title compound.

Compound 266B 2-(1H-pyrrolo[2,3-b]pyridin-5-yloxy)-4-(4-((9-(4-chlorophenyl)-3-isopropyl-3-azaspiro[5.5]undec-8-en-8-yl)methyl)piperazin-1-yl)benzoic Acid The title compound was prepared by substituting Compound 266A for Compound 265I in the procedure for Compound 265J.

Compound 266C 4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 266B for Compound 1E in the procedure for Compound 1G. $^1$H NMR (300 MHz, dimethylsulfoxide-d$_6$) δ 11.54 (s, 1H), 8.38 (m, 2H), 7.93 (d, 1H), 7.60 (m, 3H), 7.39 (m, 4H), 7.09 (d, 2H), 6.85 (d, 1H), 6.63 (dd, 1H), 6.27 (dd, 2H), 3.84 (m, 3H), 3.08 (m, 8H), 2.71 (s, 3H), 2.15 (m, 8H), 1.71 (m, 9H), 1.24 (m, 11H).

Compound 267

4-(4-{[9-(4-chlorophenyl)-3-(1,3-difluoropropan-2-yl)-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 265J for Compound 1E and Compound 40B for Compound 1F in the procedure for Compound 1G. $^1$H NMR (300 MHz, dimethylsulfoxide-d$_6$) δ 11.56 (s, 1H), 8.38 (s, 1H), 8.06 (m, 1H), 7.57 (d, 1H), 7.38 (m, 5H), 7.07 (m, 3H), 6.64 (dd, 1H), 6.33 (d, 1H), 6.23 (m, 1H), 4.68 (d, 2H), 4.52 (d, 2H), 4.21 (d, 2H), 3.86 (dd, 2H), 3.08 (m, 8H), 2.71 (m, 6H), 2.10 (m, 12H), 1.42 (m, 7H).

Compound 268

4-(4-{[9-(4-chlorophenyl)-3-isopropyl-3-azaspiro[5.5]undec-8-en-8-yl]methyl}piperazin-1-yl)-N-{[5-chloro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 266B for Compound 1E and Compound 40B for Compound 1F in the procedure for Compound 1G. $^1$H NMR (300 MHz, dimethylsulfoxide-d$_6$) δ 11.49 (s, 1H), 8.28 (d, 1H), 7.94 (dd, 2H), 7.60 (d, 1H), 7.35 (m, 4H), 7.08 (m, 2H), 6.61 (dd, 1H), 6.28 (dd, 2H), 4.18 (d, 2H), 3.85 (m, 2H), 3.05 (m, 7 H), 2.71 (s, 3H), 2.25 (m, 6H), 2.02 (m, 2H), 1.63 (m, 8H), 1.30 (m, 9H).

Compound 269

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 269A 5-chloro-6-((4-fluoro-1-methylpiperidin-4-yl)methoxy)pyridine-3-sulfonamide Compound 257B (0.131 g) in N,N-dimethylformamide (3.0 ml) was treated with iodomethane (0.043 g) and sodium carbonate (0.079 g) and stirred at ambient temperature for 3 days. The N,N-dimethylformamide was removed on high

Compound 269B

N-({5-chloro-6-[(4-fluoro-1-methylpiperidin-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 269A for Compound 11B in the procedure for Compound 11D. $^1$H NMR (400 MHz, pyridine-$d_5$) δ 13.01 (s, 1H), 9.11 (d, 1H), 8.71 (d, 1H), 8.44 (d, 1H), 8.16 (d, 1H), 7.66 (m, 2H), 7.44 (m, 2H), 7.07 (m, 2H), 6.76 (dd, 1H), 6.54 (d, 1H), 6.49 (dd, 1H), 4.49 (d, 2H), 3.06 (m, 4H), 2.77 (s, 2H), 2.68 (m, 2H), 2.38 (m, 2H), 2.26 (m, 5H), 2.14 (t, 4H), 1.97 (m, 6H), 1.39 (t, 2H), 0.94 (s, 6H).

Compound 270

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 270A 5-chloro-6-((1-(2-(dimethylamino)acetyl)-4-fluoropiperidin-4-yl)methoxy)pyridine-3-sulfonamide Compound 257B (0.131 g), 2-(dimethylamino)acetyl chloride, hydrochloric acid (0.139 g), and sodium carbonate (0.048 g) were combined in a 5-ml vial with N,N-dimethylformamide (3.0 ml) and stirred overnight at ambient temperature. Additional sodium carbonate (0.048 g) was added followed by 2-(dimethylamino)acetyl chloride, hydrochloric acid (0.139 g) and stirring was continued over a second night. The reaction mixture was concentrated under high vacuum, slurried in $CH_2Cl_2$, filtered, concentrated and chromatographed on amine functionalized silica gel with 0 to 4% methanol in $CH_2Cl_2$ as the eluent.

Compound 270B

N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 270A for Compound 11B in the procedure for Compound 11D. $^1$H NMR (500 MHz, pyridine-$d_5$) δ 13.04 (s, 1H), 9.12 (d, 1H), 8.73 (d, 1H), 8.42 (d, 1H), 8.11 (d, 1H), 7.66 (m, 2H), 7.44 (m, 2H), 7.07 (m, 2H), 6.76 (dd, 1H), 6.52 (d, 1H), 6.49 (dd, 1H), 4.66 (d, 1H), 4.52 (dd, 2H), 4.07 (d, 1H), 3.46 (m, 1H), 3.40 (m, 1H), 3.30 (m, 1H), 3.11 (m, 1H), 3.06 (m, 4H), 2.77 (s, 2H), 2.35 (s, 6H), 2.26 (t, 2H), 2.14 (m, 4H), 2.05 (m, 2H), 1.97 (s, 2H), 1.81 (m, 2H), 1.39 (t, 2H), 0.93 (s, 6H).

Compound 271

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 271A tert-butyl 4-((4'-chlorobiphenyl-2-yl)methyl)-4-fluoropiperidine-1-carboxylate A solution of Compound 263E (2.0 g) and diethylaminosulfur trifluoride (1.39 ml) in dichloromethane (40 ml) was stirred for 24 hours. The reaction was quenched with water (30 ml), extracted twice with ether, and the combined extracts were washed with water, and brine, dried over $Na_2SO_4$, filtered, and concentrated. The crude product was chromatographed on silica gel using 5% ethyl acetate in hexanes to provide the title compound.

Compound 271B 4-((4'-chlorobiphenyl-2-yl)methyl)-4-fluoropiperidine

The title compound was prepared by substituting Compound 271A for Compound 1A in the procedure for Compound 1B.

Compound 271C methyl 2-(1H-pyrrolo[2,3-b]pyridin-5-yloxy)-4-(4-((4'-chlorobiphenyl-2-yl)methyl)-4-fluoropiperidin-1-yl)benzoate The title compound was prepared by substituting Compound 271B for Compound 263G in the procedure for Compound 263H.

Compound 271D 2-(1H-pyrrolo[2,3-b]pyridin-5-yloxy)-4-(4-((4'-chlorobiphenyl-2-yl)methyl)-4-fluoropiperidin-1-yl)benzoic Acid The title compound was prepared by substituting Compound 271C for Compound 3I in the procedure for Compound 3J.

Compound 271E

4-{4-[(4'-chlorobiphenyl-2-yl)methyl]-4-fluoropiperidin-1-yl}-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 271D for Compound 1E Compound 1G. $^1$H NMR (300 MHz, dimethylsulfoxide-$d_6$) δ 11.66 (s, 1H), 11.46 (br s, 1H), 8.62 (t, 1H), 8.56 (d, 1H), 8.03 (d, 1H), 7.81 (dd, 1H), 7.52 (m, 3H), 7.44 (d, 2H), 7.28 (m, 5H), 7.14 (m, 1H), 6.68 (dd, 1H), 6.40 (dd, 1H), 6.19 (d, 1H), 3.84 (dd, 2H), 3.31 (m, 9H), 2.95 (d, 2H), 2.81 (m, 2H), 1.91 (m, 1H), 1.62 (m, 2H), 1.45 (m, 2H), 1.29 (m, 2H).

Compound 272

4-{4-[(4'-chlorobiphenyl-2-yl)methyl]-4-fluoropiperidin-1-yl}-N-({5-chloro-6-[(4-fluorotetrahydro-2H-pyran-4-yl)methoxy]pyridin-3-yl}sulfonyl)-2-(1H-pyrrolo[2,3-b]pyridin-5-yloxy)benzamide The title compound was prepared by substituting Compound 271D for Compound 1E and Compound 96A for Compound 1F in the procedure for Compound 1G. $^1$H NMR (300 MHz, dimethylsulfoxide-$d_6$) δ 11.68 (s, 1H), 11.64 (br s, 1H), 8.58 (m, 1H), 8.25 (m, 1H), 8.03 (d, 1H), 7.70 (dd, 1H), 7.50 (m, 4H), 7.43 (m, 3H), 7.28 (m, 4H), 7.15 (m, 1H), 6.68 (dd, 1H), 6.40 (dd, 1H), 6.19 (d, 1H), 4.54 (d, 2H), 4.04 (m, 1H), 3.75 (m, 2H), 3.58 (m, 2H), 2.95 (d, 2H), 2.80 (m, 2H), 1.88 (m, 2H), 1.82 (m, 2H), 1.48 (m, 2H), 1.28 (m, 2H), 0.85 (m, 2H).

Compound 273

4-(4-{[9-(4-chlorophenyl)-3-isopropyl-3-azaspiro[5.5]undec-8-en-8-yl]methyl}piperazin-1-yl)-2-(1H-pyrrolo[2,3-b]pyridin-5-yloxy)-N-({4-[(tetrahydro-2H-pyran-4-ylmethyl)amino]-3-(trifluoromethyl)phenyl}sulfonyl)benzamide The title compound was prepared by substituting Compound 266B for Compound 1E and Compound 42A for Compound 1F in the procedure for Compound 1G. $^1$H NMR (300 MHz, dimethylsulfoxide-$d_6$) δ 11.57 (s, 1H), 7.97 (d, 1H), 7.77 (s, 1H), 7.55 (m, 2H), 7.45 (m, 1H), 7.36 (m, 3H), 7.08 (d, 2H), 6.62 (dd, 2H), 6.35 (dd, 1H), 6.21 (d, 1H), 3.82 (m, 3H), 3.06 (m, 9H), 2.72 (m, 3H), 2.25 (m, 8H), 2.09 (m, 2H), 1.56 (m, 9H), 1.20 (m, 10H).

Compound 274

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 274A (R)-5-chloro-6-(1-(3-fluoro-2-(fluoromethyl)propyl)pyrrolidin-3-yloxy)pyridine-3-sulfonamide The title compound was prepared by substituting 1,3-difluoropropan-2-one for 4'-chlorobiphenyl-2-carboxaldehyde and Compound 261B for tert-butyl piperazine-1-carboxylate in the procedure for Compound 1A.

Compound 274B

N-[(5-chloro-6-{[(3R)-1-(1,3-difluoropropan-2-yl)pyrrolidin-3-yl]oxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 274A for Compound 11B in the procedure for Compound 11D. $^1$H NMR (400 MHz, dimethylsulfoxide-$d_6$) δ 11.52 (s, 1H), 8.32 (d, 1H), 8.01 (d, 1H), 7.93 (d, 1H), 7.59 (d, 1H), 7.42 (m, 1H), 7.33 (m, 3H), 7.05 (d, 2H), 6.63 (dd, 1H), 6.31 (dd, 1H), 6.25 (d, 1H), 5.38 (m, 1H), 4.65 (t, 2H), 4.53 (t, 2H), 3.02 (s, 4H), 2.94 (m, 5H), 2.75 (s, 2H), 2.66 (m, 1H), 2.23 (m, 7H), 1.96 (s, 2H), 1.82 (m, 1H), 1.39 (t, 2H), 0.93 (s, 6H).

Compound 275

4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide

Compound 275A 3-(2-(benzyloxy)ethoxy)tetrahydrofuran

Tetrahydrofuran-3-ol (0.881 g) in tetrahydrofuran (15 ml) was treated with 60% sodium hydride (0.8 g). After 10 minutes, ((2-bromoethoxy)methyl)benzene (3.23 g) was added. The solution was stirred for 16 hours. The reaction mixture was partitioned between water and ethyl acetate. The aqueous layer was separated, and was extracted with additional ethyl acetate twice. The combined organic layers were washed with brine, dried over MgSO$_4$, filtered, and concentrated. The residue was purified by flash chromatography on silica gel eluting with 1:1 ethyl acetate:hexane to provide the title compound.

Compound 275B 2-(tetrahydrofuran-3-yloxy)ethanol

Compound 275A (0.85 g) and 5% palladium on carbon (0.1 g) in ethanol (10 ml) was treated with a balloon of hydrogen. The reaction was stirred overnight. The solid was filtered off, and the filtrate was concentrated to give the title compound.

Compound 275C 3-nitro-4-(2-(tetrahydrofuran-3-yloxy)ethoxy)benzenesulfonamide The title compound was prepared by substituting Compound 275B for (tetrahydro-2H-pyran-4-yl)methanol in the procedure for Compound 24A.

Compound 275D 4-(4-{[2-(4-chlorophenyl)-4,4-dimethylcyclohex-1-en-1-yl]methyl}piperazin-1-yl)-N-({3-nitro-4-[2-(tetrahydrofuran-3-yloxy)ethoxy]phenyl}sulfonyl)-2-(1H-pyrrolo[2,3-b]pyridin-5-yloxy)benzamide The title compound was prepared by substituting Compound 275C for Compound 11B in the procedure for Compound 11D. $^1$H NMR (500 MHz, dimethylsulfoxide-$d_6$) δ 11.65 (s, 1H), 8.32 (s, 1H), 8.00-8.02 (m, 2H), 7.49-7.52 (m, 2H), 7.39-7.41 (m, 1H), 7.38 (d, 2H), 7.04 (d, 2H), 6.68 (dd, 1H), 6.39 (dd, 1H), 6.21 (d, 1H), 4.33-4.35 (m, 2H), 4.18-4.21 (m, 1H), 3.62-3.67 (m, 4H), 3.09 (s, 4H), 2.83 (s, 2H), 2.26 (s, 2H), 2.15 (s, 2H), 1.96 (s, 2H), 1.85-1.94 (m, 2H), 1.39 (t, 2H), 0.92 (s, 6H).

Compound 276

4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide

Compound 276A trans-4-(aminomethyl)cyclohexanecarbonitrile

To a solution of tert-butyl (trans-4-(cyanomethyl)cyclohexyl)methylcarbamate (500 mg) in dichloromethane (10 ml) was slowly added trifluoroacetic acid (2 ml) at 0° C. The reaction mixture was warmed to room temperature, stirred for 1 hour and concentrated to provide the title compound.

Compound 276B 4-((trans-4-cyanocyclohexyl)methylamino)-3-nitrobenzenesulfonamide A mixture of 4-fluoro-3-nitrobenzenesulfonamide (347 mg) and Compound 276A (300 mg) in tetrahydrofuran (20 ml) was treated with triethylamine (1.4 ml) overnight and concentrated. The residue was triturated with ethyl acetate to provide the title compound.

Compound 276C 4-(4-{[2-(4-chlorophenyl)-4,4-dimethylcyclohex-1-en-1-yl]methyl}piperazin-1-yl)-N-[(4-{[(trans-4-cyanocyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 276B in place of Compound 11B. $^1$H NMR (400 MHz, dimethylsulfoxide-$d_6$) δ 11.69 (s, 1H), 11.36 (s, 1H), 8.60 (t, 1H), 8.56 (d, 1H), 8.04 (d, 1H), 7.79 (dd, 1H), 7.47-7.54 (m, 3H), 7.34 (d, 2H), 7.01-7.09 (m, 3H), 6.68 (dd, 1H), 6.39 (dd, 1H), 6.19 (d, 1H), 3.25 (t, 2H), 3.07 (s, 4H), 2.76 (s, 2H), 2.57-2.68 (m, 1H), 2.17 (d, 6H), 1.92-2.06 (m, 4H), 1.78 (d, 2H), 1.66 (s, 1H), 1.35-1.53 (m, 4H), 0.96-1.10 (m, 2H), 0.92 (s, 6H).

Compound 277

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 277A methyl 4,4-dimethyl-2-(trifluoromethylsulfonyloxy)cyclohex-1-enecarboxylate To a suspension of hexane washed NaH (17 g) in dichloromethane (700 ml) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 ml) was added. The reaction mixture was warmed to room temperature and stirred for 24 hours. The organic layer was washed with brine, dried ($Na_2SO_4$), filtered, and concentrated to give the product.

Compound 277B methyl 2-(4-chlorophenyl)-4,4-dimethylcyclohex-1-enecarboxylate Compound 277A (62.15 g), 4-chlorophenylboronic acid (32.24 g), CsF (64 g) and tetrakis(triphenylphosphine)palladium(0) (2 g) in 2:1 dimethoxyethane/methanol (600 ml) were heated to 70° C. for 24 hours. The mixture was concentrated. Ether (4×200 ml) was added and the mixture was filtered. The combined ether solution was concentrated to give the product.

Compound 277C (2-(4-chlorophenyl)-4,4-dimethylcyclohex-1-enyl)methanol

To a mixture of $LiBH_4$ (13 g), Compound 277B (53.8 g) and ether (400 ml), was added methanol (25 ml) slowly by syringe. The mixture was stirred at room temperature for 24 hours. The reaction was quenched with 1N HCl with ice-cooling. The mixture was diluted with water and extracted with ether (3×100 ml). The extracts were dried ($Na_2SO_4$), filtered, and concentrated. The crude product was chromatographed on silica gel with 0-30% ethyl acetate/hexanes.

Compound 277D tert-butyl 4-((2-(4-chlorophenyl)-4,4-dimethylcyclohex-1-enyl)methyl)piperazine-1-carboxylate Mesyl Chloride (7.5 ml) was added via syringe to Compound 277C (29.3 g) and triethylamine (30 ml) in $CH_2Cl_2$ (500 ml) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Compound 277E 1-((2-(4-chlorophenyl)-4,4-dimethylcyclohex-1-enyl)methyl)piperazine Compound 277D (1 g) was stirred in dichloromethane (10 ml), trifluoroacetic acid (10 ml), and triethylsilane (1 ml) for 1 hour. The mixture was concentrated, taken up in a mixture of dichloromethane (100 ml) and saturated aqueous $Na_2CO_3$ solution (20 ml) and stirred for 10 minutes. The layers were separated, and the organic layer was dried over $Na_2SO_4$, filtered, and concentrated to give the product.

Compound 277F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 ml) was added 1M lithium hexamethyldisilazide in tetrahydrofuran (86 ml), and after 10 minutes, TIPS-Cl (triisopropylchlorosilane) (18.2 ml)

was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Compound 277G 1-(triisopropylsilyl)-1H-pyrrolo[2,3-b]pyridin-5-ol

To a mixture of Compound 277F (24.3 g) in tetrahydrofuran (500 ml) at −78° C. was added 2.5M BuLi (30.3 ml). After 2 minutes, trimethylborate (11.5 ml) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 ml) at 0° C., and 1M NaOH (69 ml) was added, followed by 30% $H_2O_2$ (8.43 ml), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Compound 277H methyl 2-(1H-pyrrolo[2,3-b]pyridin-5-yloxy)-4-fluorobenzoate

A mixture of Compound 277G (8.5 g), methyl 2,4-difluorobenzoate (7.05 g), and $K_3PO_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 277I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound 277H (1.55 g), Compound 277E (2.42 g), and $HK_2PO_4$ (1.42 g) in dimethylsulfoxide (20 ml) at 135° C. was stirred for 24 hours. The reaction was cooled, diluted with ether (400 ml), and washed three times with 1M NaOH, and brine, and concentrated. The crude product was chromatographed on silica gel with 10-50% ethyl acetate/hexanes.

Compound 277J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic Acid Compound 277I (200 mg) in dioxane (10 ml) and 1M NaOH (6 ml) at 50° C. was stirred for 24 hours. The reaction was cooled, added to $NaH_2PO_4$ solution, and extracted three times with ethyl acetate. The combined extracts were washed with brine, and concentrated to give the pure product.

Compound 277K 5,6-dichloropyridine-3-sulfonamide

To a solution of 5,6-dichloropyridine-3-sulfonyl chloride (32.16 g) in isopropyl alcohol (300 ml) at 0° C. was added a 30% aqueous solution of $NH_4OH$ (50.8 ml). After stirring overnight, the solvent was reduced to ⅓ of the original volume. It was then partitioned between water and ethyl acetate. The aqueous layer was extracted with additional ethyl acetate. The combined organic layers were washed with brine, dried over $MgSO_4$, filtered, and concentrated. The residue was chromatographed on silica gel. The material was then slurried in 1:9 ethyl acetate/hexanes, filtered and dried under vacuum to give the title compound.

Compound 277L tert-butyl 4-fluoro-4-(hydroxymethyl)piperidine-1-carboxylate

1-Tert-butyl 4-ethyl 4-fluoropiperidine-1,4-dicarboxylate (1.0 g) in tetrahydrofuran (5 ml) was treated with 1.0 N $LiAlH_4$ in tetrahydrofuran (2.54 ml) at 0° C. The reaction mixture was stirred at room temperature for 2 hours. Water (0.6 ml) was added to the reaction mixture drop-wise, followed by 2 N aqueous NaOH (0.2 ml). The reaction was stirred for another 1 hour. The solid was removed by filtration via a pack of diatomaceous earth and washed with ethyl acetate. The filtrate was washed with brine, dried over $MgSO_4$, filtered, and concentrated to give the product.

Compound 277M tert-butyl 4-((3-chloro-5-sulfamoylpyridin-2-yloxy)methyl)-4-fluoropiperidine-1-carboxylate To a solution of Compound 277L (1 g) in tetrahydrofuran (15 ml) was added NaH (60% dispersion in mineral oil, 685 mg), and the solution was stirred for 10 minutes. Compound 227K (1 g) was added and the reaction stirred for 24 hours. The mixture was poured into water, neutralized with 10% HCl, and extracted with ethyl acetate three times. The combined organic layers were washed with brine, dried over $MgSO_4$, filtered, and concentrated. The residue was purified with flash column chromatography on silica gel eluting with 30% ethyl acetate in hexanes.

Compound 277N 5-chloro-6-((4-fluoropiperidin-4-yl)methoxy)pyridine-3-sulfonamide ditrifluoroacetic Acid Compound 277M (13 ml) was treated with trifluoroacetic acid (2.363 ml), stirred at ambient temperature for 2 hours, concentrated and dried to give the title compound.

Compound 277O 5-chloro-6-((4-fluoro-1-(oxetan-3-yl)piperidin-4-yl)methoxy)pyridine-3-sulfonamide Compound 277N (0.088 g) and oxetan-3-one (0.014 g) were combined in dichloromethane (2.0 ml) and dimethylformamide (1.0 ml) and stirred at ambient temperature for 45 minutes. Sodium triacetoxyborohydride (0.064 g) was added in portions. Stirring was continued overnight at ambient temperature. Additional oxetan-3-one (0.014 g) was added and stirring was continued for 30 minutes at ambient temperature before more sodium triacetoxyborohydride (0.064 g) was added. The reaction mixture was stirred for 72 hours at ambient temperature, concentrated, chromatographed on silica gel with 0 to 5% methanol in dichloromethane as the eluent, and dried in a vacuum oven at 80° C. to give the title compound.

Compound 277P

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 277J (0.063 g), Compound 277O (0.042 g), 1-ethyl-3-[3-(dimethylamino)propyl]-carbodiimide hydrochloride (0.032 g), and 4-dimethylaminopyridine (0.027 g) were combined in a 4-ml vial with dichloromethane (1.0 ml) and stirred overnight at ambient temperature. The reaction mixture was chromatographed directly without aqueous workup on silica gel with 0-4% methanol in dichloromethane as the eluent. Fractions containing the desired product were concentrated, slurried in acetonitrile, concentrated and dried overnight in a vacuum oven at 80° C. to give the title compound. $^1$H NMR (500 MHz, pyridine-d$_5$) δ 13.05 (s, 1H), 9.13 (d, 1H), 8.72 (d, 1H), 8.41 (d, 1H), 8.10 (d, 1H), 7.67 (m, 1H), 7.66 (d, 1H), 7.44 (m, 2H), 7.07 (m, 2H), 6.76 (dd, 1H), 6.51 (m, 2H), 4.63 (m, 4H), 4.53 (d, 2H), 3.39 (m, 1H), 3.07 (m, 4H), 2.77 (s, 2H), 2.51 (m, 2H), 2.25 (m, 2H), 2.18 (m, 2H), 2.13 (m, 4H), 2.06 (t, 2H), 1.97 (s, 2H), 1.89 (m, 2H), 1.39 (t, 2H), 0.93 (s, 6H).

Compound 278

4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide Compound 278A 5-bromo-6-(2-(tetrahydro-2H-pyran-4-yl)ethoxy)pyridine-3-sulfonamide The title compound was prepared by substituting 2-(tetrahydro-2H-pyran-4-yl)ethanol for (tetrahydro-2H-pyran-4-yl)methanol in the procedure for Compound 36B.

Compound 278B 5-cyano-6-(2-(tetrahydro-2H-pyran-4-yl)ethoxy)pyridine-3-sulfonamide The title compound was prepared by substituting Compound 278A for Compound 36B in the procedure for Compound 36C.

Compound 278C 4-(4-{[2-(4-chlorophenyl)-4,4-dimethylcyclohex-1-en-1-yl]methyl}piperazin-1-yl)-N-({5-cyano-6-[2-(tetrahydro-2H-pyran-4-yl)ethoxy]pyridin-3-yl}sulfonyl)-2-(1H-pyrrolo[2,3-b]pyridin-5-yloxy)benzamide The title compound was prepared by substituting Compound 278B for Compound 11B in the procedure for Compound 11D. $^1$H NMR (500 MHz, dimethylsulfoxide-d$_6$) δ 11.60 (s, 1H), 8.70 (s, 1H), 8.48 (s, 1H), 7.96 (d, 1H), 7.56 (d, 1H), 7.45-7.47 (m, 1H), 7.40 (s, 1H), 7.36 (d, 2H), 7.06 (d, 2H), 6.67 (dd, 1H), 6.34 (dd, 1H), 6.25 (d, 1H), 4.47 (d, 2H), 3.80-3.84 (m, 2H), 3.24-3.28 (m, 2H), 3.12 (s, 2H), 2.16 (s, 2H), 1.97 (s, 2H), 1.61-1.71 (m, 4H), 1.40 (t, 2H), 1.21-1.25 (m, 2H), 0.93 (s, 6H).

Compound 279

4-(4-{[2-(4-chlorophenyl)-4,4-dimethylcyclohex-1-en-1-yl]methyl}piperazin-1-yl)-N-{[4-(3-furyl-methoxy)-3-nitrophenyl]sulfonyl}-2-(1H-pyrrolo[2,3-b]pyridin-5-yloxy)benzamide Compound 279A 4-(furan-3-ylmethoxy)-3-nitrobenzenesulfonamide The title compound was prepared by substituting furan-3-ylmethanol for (tetrahydro-2H-pyran-4-yl)methanol in the procedure for Compound 24A.

Compound 279B 4-(4-{[2-(4-chlorophenyl)-4,4-dimethylcyclohex-1-en-1-yl]methyl}piperazin-1-yl)-N-{[4-(3-furyl-methoxy)-3-nitrophenyl]sulfonyl}-2-(1H-pyrrolo[2,3-b]pyridin-5-yloxy)benzamide The title compound was prepared by substituting Compound 279A for Compound 11B in the procedure for Compound 11D. $^1$H NMR (500 MHz, dimethylsulfoxide-d$_6$) δ 11.69 (s, 1H), 8.34 (s, 1H), 8.03-8.06 (m, 2H), 7.83 (s, 1H), 7.69 (t, 1H), 7.51-7.53 (m, 4H), 7.34-7.36 (m, 2H), 7.04-7.06 (m, 2H), 6.68 (dd, 1H), 6.57 (s, 1H), 6.40 (dd, 1H), 6.20 (d, 1H), 5.23 (s, 2H), 3.10 (s, 4H), 2.83 (s, 2H), 2.15-2.32 (m, 6H), 1.39 (t, 2H), 0.92 (s, 6H).

Compound 280

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 280A (R)-tert-butyl 3-((3-chloro-5-sulfamoylpyridin-2-yloxy)methyl)pyrrolidine-1-carboxylate The title compound was prepared by substituting Compound 40A for 4-fluoro-3-nitrobenzenesulfonamide and (R)-tert-butyl 3-(hydroxymethyl)pyrrolidine-1-carboxylate for (tetrahydro-2H-pyran-4-yl)methanol in the procedure for Compound 24A.

Compound 280B (R)-5-chloro-6-(pyrrolidin-3-ylmethoxy)pyridine-3-sulfonamide

The title compound was prepared by substituting Compound 280A for tert-butyl (4-(1,3-difluoropropan-2-yl)morpholin-2-yl)methylcarbamate in the procedure for Compound 252B.

Compound 280C (R)-5-chloro-6-((1-(1,3-difluoropropan-2-yl)pyrrolidin-3-yl)methoxy)pyridine-3-sulfonamide The title compound was prepared by substituting 1,3-difluoropropan-2-one for 4'-chlorobiphenyl-2-carboxaldehyde and Compound 280B for tert-butyl piperazine-1-carboxylate in the procedure for Compound 1A.

Compound 280D

N-[(5-chloro-6-{[(3R)-1-(1,3-difluoropropan-2-yl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 280C for Compound 11B in the procedure for Compound 11D. $^1$H NMR (400 MHz, dimethylsulfoxide-d$_6$) δ 11.57 (s, 1H), 8.38 (d, 1H), 8.07 (d, 1H), 7.96 (d, 1H), 7.57 (d, 1H), 7.44 (m, 1H), 7.35 (m, 3H), 7.05 (d, 2H), 6.64 (dd, 1H), 6.33 (dd, 1H), 6.23 (d, 1H), 4.65 (d, 2H), 4.53 (dd, 2H), 2.92 (m, 8H), 2.75 (m, 4H), 2.58 (m, 2H), 2.20 (m, 6H), 1.96 (m, 4H), 1.53 (m, 1H), 1.39 (t, 2H), 0.89 (s, 6H).

Compound 281

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 281A (R)-5-chloro-6-((1-(2,2-difluoroethyl)pyrrolidin-3-yl)methoxy)pyridine-3-sulfonamide The title compound was prepared by substituting Compound 280B for Compound 261B in the procedure for Compound 261C.

Compound 281B

N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 281A for Compound 11B in the procedure for Compound 11D. $^1$H NMR (400 MHz, dimethylsulfoxide-d$_6$) δ 11.59 (s, 1H), 8.41 (d, 1H), 8.10 (d, 1H), 7.98 (d, 1H), 7.56 (d, 1H), 7.46 (m, 1H), 7.41 (d, 1H), 7.34 (d, 2H), 7.04 (d, 2H), 6.65 (dd, 1H), 6.35 (dd, 1H), 6.23 (m, 1H), 6.03 (m, 1H), 3.06 (s, 4H), 2.84 (m, 6H), 2.63 (m, 4H), 2.20 (m, 6H), 1.94 (m, 3H), 1.53 (m, 1H), 1.39 (t, 2H), 0.91 (s, 6H).

Compound 282

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 282A 5-chloro-6-((1-(1,3-difluoropropan-2-yl)-4-fluoropiperidin-4-yl)methoxy)pyridine-3-sulfonamide Compound 257B (0.088 g) and 1,3-difluoropropan-2-one (0.028 g) were combined in dichloromethane (2 ml) and N,N-dimethylformamide (0.500 ml) and stirred at ambient temperature for 45 minutes. Sodium triacetoxyborohydride (0.064 g) was added in portions and then the reaction mixture was stirred overnight at ambient temperature. Additional 1,3-difluoropropan-2-one (0.028 g) was added, followed 30 minutes later by the addition of more sodium triacetoxyborohydride (0.064 g). The reaction mixture was stirred at ambient temperature for 72 hours. Additional 1,3-difluoropropan-2-one (0.028 g) was again added, followed 30 minutes later by the addition of more sodium triacetoxyborohydride (0.064 g). The reaction mixture was stirred overnight at ambient temperature. Additional 1,3-difluoropropan-2-one (0.028 g) was again added, followed 30 minutes later by the addition of more sodium triacetoxyborohydride (0.064 g). The reaction mixture was stirred overnight at ambient temperature. The reaction mixture was concentrated under high vacuum to remove N,N-dimethylformamide and then chromatographed on silica gel with 0 to 4% methanol in CH$_2$Cl$_2$ as the eluent.

Compound 282B

N-[(5-chloro-6-{[1-(1,3-difluoropropan-2-yl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 282A for Compound 11B in the procedure for Compound 11D. $^1$H NMR (400 MHz, pyridine-d$_5$) δ 13.05 (s, 1H), 9.12 (t, 1H), 8.72 (d, 1H), 8.41 (d, 1H), 8.10 (d, 1H), 7.66 (m, 2H), 7.44 (m, 2H), 7.07 (m, 2H), 6.75 (dd, 1H), 6.50 (m, 2H), 4.77 (dd, 1H), 4.65 (dd, 1H), 4.52 (dd, 2H), 3.06 (m, 4H), 2.93 (t, 1H), 2.80 (m, 5H), 2.52 (m, 1H), 2.26 (t, 2H), 2.13 (m, 4H), 2.04 (m, 2H), 1.97 (s, 2H), 1.85 (m, 2H), 1.39 (t, 2H), 1.28 (m, 2H), 0.93 (s, 6H).

Compound 283

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 283A 3-chloro-4-((4-fluoro-1-methylpiperidin-4-yl)methoxy)benzenesulfonamide To a solution of (4-fluoro-1-methylpiperidin-4-yl)methanol (0.265 g) in tetrahydrofuran (2 ml) was added sodium hydride (0.288 g). After 15 minutes, 3-chloro-4-fluorobenzenesulfonamide (0.377 g) was added as a solution in tetrahydrofuran (1 ml). The reaction was stirred for 2 hours, quenched with water (5 ml), adjusted to pH-7 with 1N aqueous HCl, and extracted with dichloromethane (2×25 ml). The organic layer was washed with brine (25 ml), dried over magnesium sulfate, filtered and concentrated. Silica gel chromatography (Reveleris 40 g) eluting with a gradient of 0.1% to 10% methanol containing 2N $NH_3$/dichloromethane over 30 minutes gave the title compound.

Compound 283B

N-({3-chloro-4-[(4-fluoro-1-methylpiperidin-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 283A for Compound 1F in the procedure for Compound 1G. $^1$H NMR (300 MHz, dimethylsulfoxide-$d_6$) δ 11.60 (s, 1H), 10.68-9.84 (m, 1H), 7.99 (d, 1H), 7.79 (d, 1H), 7.63 (t, 1H), 7.54 (d, 1H), 7.50-7.38 (m, 2H), 7.34 (d, 2H), 7.04 (d, 3H), 6.64 (dd, 1H), 6.36 (dd, 1H), 6.22 (s, 1H), 4.23 (d, 2H), 3.03 (s, 6H), 2.71 (m, 4H), 2.07 (m, 12H), 1.38 (s, 3H), 1.24 (s, 2H), 0.92 (s, 6H).

Compound 284

4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide Compound 284A 3-cyano-4-((tetrahydro-2H-pyran-4-yl)methoxy)benzenesulfonamide To a solution of (tetrahydro-2H-pyran-4-yl)methanol (0.258 g) in tetrahydrofuran (5 ml) was added sodium hydride (0.355 g) and the reaction stirred at room temperature for 15 minutes. Compound 52A (0.400 g) was added and the reaction stirred for an additional 1 hour. The reaction was poured into ethyl acetate (50 ml) and 1N aqueous HCl (35 ml). The organic layer was washed with brine (35 ml) dried over magnesium sulfate, filtered, and concentrated. Silica gel chromatography (Reveleris 40 g) eluting with a gradient of 10% to 100% ethyl acetate/hexanes over 30 minutes gave the title compound.

Compound 284B 4-(4-{[2-(4-chlorophenyl)-4,4-dimethylcyclohex-1-en-1-yl]methyl}piperazin-1-yl)-N-{[3-cyano-4-(tetrahydro-2H-pyran-4-ylmethoxy)phenyl]sulfonyl}-2-(1H-pyrrolo[2,3-b]pyridin-5-yloxy)benzamide The title compound was prepared by substituting Compound 3J for Compound 1E and Compound 284A for Compound 1F in the procedure for Compound 1G. $^1$H NMR (300 MHz, dimethylsulfoxide-$d_6$) δ 11.69 (s, 1H), 11.60-11.16 (m, 1H), 8.15 (s, 1H), 8.08-8.01 (m, 2H), 7.58-7.46 (m, 3H), 7.35 (d, J=8.4, 2H), 7.29 (d, 1H), 7.04 (d, 2H), 6.68 (d, 1H), 6.40 (dd, 1H), 6.20 (s, 1H), 4.05 (d, 2H), 3.89 (d, 2H), 3.37 (d, 4H), 3.09 (s, 4H), 2.81 (s, 2H), 2.21 (d, 7H), 1.96 (s, 2H), 1.67 (d, 2H), 1.39 (s, 2H), 0.92 (s, 6H).

Compound 285

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 285A 5-chloro-6-((1-(2,2-difluoroethyl)-4-fluoropiperidin-4-yl)methoxy)pyridine-3-sulfonamide Compound 257B (0.263 g), 1,1-difluoro-2-iodoethane (0.23 g), and sodium carbonate (0.254 g) were combined in a 20-ml vial with N,N-dimethylformamide (6 ml) and stirred at 70° C. overnight. The reaction mixture was concentrated under high vacuum and then chromatographed on silica gel with 0 to 5% methanol in $CH_2Cl_2$ as the eluent.

Compound 285B

N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 285A for Compound 11B in the procedure for Compound 11D. $^1$H NMR (400 MHz, pyridine-$d_5$) δ 13.05 (s, 1H), 9.12 (d, 1H), 8.72 (d, 1H), 8.41 (d, 1H), 8.10 (d, 1H), 7.66 (m, 2H), 7.43 (m, 2H), 7.06 (m, 2H), 6.75 (dd, 1H), 6.50 (m, 2H), 6.18 (tt, 2H), 4.51 (d, 2H), 3.07 (m, 4H), 2.80 (m, 6H), 2.60 (td, 2H), 2.25 (t, 2H), 2.13 (m, 4H), 2.03 (t, 2H), 1.97 (s, 2H), 1.93 (m, 1H), 1.85 (m, 1H), 1.39 (t, 2H), 0.93 (s, 6H).

Compound 286

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 286A 3-chloro-4-((4-fluorotetrahydro-2H-pyran-4-yl)methoxy)benzenesulfonamide The title compound was prepared by substituting Compound 37C for (4-fluoro-1-methylpiperidin-4-yl)methanol in the procedure for Compound 283A.

Compound 286B

N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 286A for Compound 1F in the procedure for Compound 1G. $^1$H NMR (300 MHz, dimethylsulfoxide-$d_6$) δ 11.71 (s, 1H), 11.56-11.16 (m, 1H), 8.06 (d, 1H), 7.90 (d, 1H), 7.81 (d, 1H), 7.64-7.45 (m, 3H), 7.34 (d, 2H), 7.26 (d, 1H), 7.04 (d, 2H), 6.68 (d, 1H), 6.42 (dd, 1H), 6.18 (s, 1H), 4.28 (d, 2H), 3.78 (d, 2H), 3.61 (dd, 2H), 3.07 (s, 4H), 2.76 (s, 2H), 2.17 (d, 6H), 1.87 (dd, 6H), 1.38 (t, 2H), 0.92 (s, 6H).

Compound 287

N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 287A (4,4-difluorocyclohexyl)methanol Ethyl 4,4-difluorocyclohexanecarboxylate (1.0 g, 5.20 mmol) in diethyl ether (2 ml) was added dropwise to lithium aluminium hydride (0.24 g) in diethyl ether (15 ml), and heated under reflux for 4 hours. The reaction was then cooled to 0° C., and water was added (0.24 ml), followed by 5N aqueous NaOH (0.24 ml) and water (0.72 ml). Then $Na_2SO_4$ and more diethyl ether (40 ml) were added, and the mixture was stirred for 30 minutes, then filtered through celite. After concentration, the residue was diluted with $CH_2Cl_2$ and $Na_2SO_4$ was added, and the mixture was filtered and concentrated to provide the title compound.

Compound 287B 5-chloro-6-((4,4-difluorocyclohexyl)methoxy)pyridine-3-sulfonamide The title compound was prepared by substituting Compound 40A for 4-fluoro-3-nitrobenzenesulfonamide and Compound 287A for (tetrahydro-2H-pyran-4-yl)methanol in the procedure for Compound 24A.

Compound 287C

N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 287B for Compound 11B in the procedure for Compound 11D. $^1$H NMR (400 MHz, dimethylsulfoxide-$d_6$) δ 11.63 (s, 1H), 8.46 (d, 1H), 8.14 (d, 1H), 8.00 (d, 1H), 7.56 (d, 1H), 7.47 (m, 2H), 7.35 (d, 2H), 7.03 (d, 2H), 6.66 (dd, 1H), 6.37 (m, 1H), 6.21 (d, 1H), 4.25 (d, 2H), 3.07 (br m, 4H), 2.82 (br s, 2H), 2.30 (br m, 4H), 2.16 (br m, 2H), 2.00, 1.95, 1.85 (all m, total 9H), 1.40 (t, 2H), 1.37 (m, 2H), 0.92 (s, 6H).

Compound 288

4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide Compound 288A 5-nitro-3-(trifluoromethyl)pyridin-2-ol 3-(Trifluoromethyl)pyridin-2-ol (2.3 g) was added to concentrated sulfuric acid (15 ml) at 0° C. The mixture was stirred at 0° C. for 5 minutes. To this solution was added fuming nitric acid (6 ml) dropwise over 5 minutes. The reaction mixture was stirred at room temperature for 2 hours, and then heated at 50° C. for 3 hours. After cooling, the reaction mixture was poured onto ice (200 g), and the mixture was extracted with ethyl acetate three times. The combined organic layers were washed with brine, dried over $MgSO_4$, filtered, and concentrated under reduced pressure to provide the title compound.

Compound 288B 2-chloro-5-nitro-3-(trifluoromethyl)pyridine

A mixture of Compound 288A (1.69 g), phosphorus pentachloride (2.03 g), and phosphoryl trichloride (0.97 ml) was heated at 90° C. for 3 hours. After cooling, the reaction mixture was poured into ice, and extracted with ethyl acetate three times. The extract was washed with brine, dried over $MgSO_4$, filtered, and concentrated under reduced pressure. The residue was purified by flash column chromatography on silica gel eluting with 10% ethyl acetate in hexanes to provide the title compound.

Compound 288C 6-chloro-5-(trifluoromethyl)pyridin-3-amine

A mixture of iron (1.5 g) and ammonium chloride (2.38 g) in water (40 ml) was stirred at room temperature for 5 minutes. To this suspension was added Compound 288B in methanol (40 ml). The reaction mixture was stirred at room temperature for 1 hour. More iron (1.8 g) was added to the reaction mixture, and it was stirred for another 3 hours. The solid from the reaction mixture was filtered off, and the filtrate was partitioned between water and ethyl acetate. The combined organic layers were washed with brine, dried over $MgSO_4$, filtered, and concentrated under reduced pressure. The residue was purified by flash column chromatography on silica gel eluting with 20% ethyl acetate in hexanes to provide the title compound.

Compound 288D 6-chloro-5-(trifluoromethyl)pyridine-3-sulfonyl chloride

Under ice-cooling, thionyl chloride (4 ml) was added dropwise over 20 minutes to water (27 ml). The mixture was stirred overnight for 12 hours to give a $SO_2$ containing solution. Separately, Compound 288C (1.14 g) in dioxane (5 ml) was added to concentrated HCl (20 ml) at 0° C. The solution was stirred for 5 minutes. To this suspension/solution was added sodium nitrite (0.44 g) in water (6 ml) dropwise at 0° C. The solution was stirred at 0° C. for 3 hours. During this time, any solid formed was crushed with a glass rod to make sure that Compound 288C was completely reacted. To the $SO_2$ containing solution was added copper(I) chloride (0.115 g). Then, to this solution was added the diazotized Compound 288C at 0° C. The solution was stirred for 30 minutes. The reaction mixture was extracted with ethyl acetate. The combined organic layers were washed with brine, dried over $MgSO_4$, filtered, and concentrated under reduced pressure. The residue was purified by flash column chromatography on silica gel eluting with 5% ethyl acetate in hexanes to provide the title compound.

Compound 288E 6-chloro-5-(trifluoromethyl)pyridine-3-sulfonamide

Compound 288D (2.03 g) in dioxane (20 ml) solution was cooled to 0° C. Ammonium hydroxide solution was added dropwise. The reaction mixture was stirred at 0° C. for 2 hours followed by room temperature over night. The solvent was partially removed, and the residue was partitioned between water and ethyl acetate. The organic phase was washed with brine, dried over $MgSO_4$, filtered, and concentrated under reduced pressure. The residue was purified by flash column chromatography on silica gel eluting with 0-3% methanol in dichloromethane to afford the title compound.

Compound 288F tert-butyl 4-fluoro-4-((5-sulfamoyl-3-(trifluoromethyl)pyridin-2-yloxy)methyl)piperidine-1-carboxylate The title compound was prepared by substituting Compound 288E for 4-fluoro-3-nitrobenzenesulfonamide and Compound 322A for (tetrahydro-2H-pyran-4-yl)methanol in the procedure for Compound 24A.

Compound 288G 6-((4-fluoropiperidin-4-yl)methoxy)-5-(trifluoromethyl)pyridine-3-sulfonamide The title compound was prepared by substituting Compound 288F for tert-butyl (4-(1,3-difluoropropan-2-yl)morpholin-2-yl)methylcarbamate in the procedure for Compound 252B.

Compound 288H 6-((1-(1,3-difluoropropan-2-yl)-4-fluoropiperidin-4-yl)methoxy)-5-(trifluoromethyl)pyridine-3-sulfonamide The title compound was prepared by substituting 1,3-difluoropropan-2-one for 4'-chlorobiphenyl-2-carboxaldehyde and Compound 288G for tert-butyl piperazine-1-carboxylate in the procedure for Compound 1A.

Compound 288I 4-(4-{[2-(4-chlorophenyl)-4,4-dimethylcyclohex-1-en-1-yl]methyl}piperazin-1-yl)-N-{[6-{[1-(1,3-difluoropropan-2-yl)-4-fluoropiperidin-4-yl]methoxy}-5-(trifluoromethyl)pyridin-3-yl]sulfonyl}-2-(1H-pyrrolo[2,3-b]pyridin-5-yloxy)benzamide The title compound was prepared by substituting Compound 288H for Compound 11B in the procedure for Compound 11D. $^1$H NMR (400 MHz, dimethylsulfoxide-$d_6$) δ 11.50 (s, 1H), 8.57 (s, 1H), 8.27 (d, 1H), 7.91 (d, 1H), 7.58 (d, 1H), 7.40 (m, 1H), 7.35 (d, 2H), 7.28 (d, 1H), 7.05 (d, 2H), 6.61 (dd, 1H), 6.29 (dd, 1H), 6.24 (d, 1H), 4.67 (d, 2H), 4.55 (d, 2H), 4.50 (s, 1H), 4.44 (s, 1H), 3.06 (m, 5H), 2.73 (m, 6H), 2.19 (d, 6H), 1.90 (m, 7H), 1.39 (t, 2H), 0.93 (s, 6H).

Compound 289

4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide

Compound 289A 5-chloro-6-(2-(tetrahydrofuran-2-yl)ethoxy)pyridine-3-sulfonamide The title compound was prepared by substituting 2-(tetrahydro-2H-pyran-4-yl)ethanol for (tetrahydro-2H-pyran-4-yl)methanol and Compound 40A for Compound 36A in the procedure for Compound 36B.

Compound 289B 4-(4-{[2-(4-chlorophenyl)-4,4-dimethylcyclohex-1-en-1-yl]methyl}piperazin-1-yl)-N-({5-chloro-6-[2-(tetrahydrofuran-2-yl)ethoxy]pyridin-3-yl}sulfonyl)-2-(1H-pyrrolo[2,3-b]pyridin-5-yloxy)benzamide The title compound was prepared by substituting Compound 289A for Compound 11B in the procedure for Compound 11D. $^1$H NMR (500 MHz, dimethylsulfoxide-$d_6$) δ 11.66 (s, 1H), 8.52 (d, 1H), 8.18 (s, 1H), 8.02 (s, 1H), 7.50-7.55 (m, 3H), 7.35 (d, 2H), 7.05 (d, 2H), 6.68 (dd, 1H), 6.38 (dd, 1H), 6.21 (d, 1H), 4.39-4.51 (m, 4H), 3.87-3.94 (m, 1H), 3.73-3.78 (m, 1H), 3.57-3.62 (m, 1H), 3.11 (s, 4H), 2.89 (s, 2H), 2.33 (s, 4H), 2.15 (s, 2H), 1.77-2.01 (m, 7H), 1.45-1.54 (m, 1H), 1.40 (t, 2H), 0.93 (s, 6H).

Compound 290

4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 290A 2-chloro-4,4-dimethylcyclohex-1-enecarbaldehyde

Into a 250 ml round-bottomed flask was added N,N-dimethylformamide (3.5 ml) in dichloromethane (30 ml). The mixture was cooled to −10° C., and phosphoryl trichloride (4 ml) was added dropwise. The solution was warmed up to room temperature and 3,3-dimethylcyclohexanone (5.5 ml) was added slowly. The mixture was heated to reflux overnight. The reaction mixture was quenched by 0° C. solution of sodium acetate (25 g in 50 ml water). The aqueous layer was extracted with ether (3×200 ml). The organic layers were combined, dried over $Na_2SO_4$, filtered, and dried under vacuum.

Compound 290B 2-(4-chlorophenyl)-4,4-dimethylcyclohex-1-enecarbaldehyde

Into a 1 L round-bottomed flask was added Compound 290A (6.8 g), 4-chlorophenylboronic acid (6.5 g) and palladium(II) acetate (0.2 g) in water (100 ml) to give a suspension. Potassium carbonate (15 g) and tetrabutylam-

Compound 290C tert-butyl 4-((2-(4-chlorophenyl)-4,4-dimethylcyclohex-1-enyl)methyl)-3-methylpiperazine-1-carboxylate To a solution of tert-butyl 3-methylpiperazine-1-carboxylate (0.256 g) and Compound 290B (0.350 g) in dichloromethane (2 ml) was added sodium triacetoxyborohydride (0.406 g) and the reaction was stirred at room temperature overnight. The reaction was quenched with $NaHCO_3$ solution (50 ml) and extracted with dichloromethane (50 ml). The organic layer was dried over magnesium sulfate, filtered and concentrated. Silica gel chromatography (Reveleris 40 g) eluting with a gradient of 0.5% to 2.5% methanol/dichloromethane gave the title compound.

Compound 290D 1-((2-(4-chlorophenyl)-4,4-dimethylcyclohex-1-enyl)methyl)-2-methylpiperazine A solution of Compound 290C (0.298 g) and HCl (4.0M in dioxane, 2 ml) were stirred for 1 hour. The reaction was concentrated and partioned between dichloromethane (100 ml) and $NaHCO_3$ (100 ml). The organic layer was washed with brine (50 ml), dried over magnesium sulfate, filtered and concentrated to provide the title compound.

Compound 290E methyl 2-(1H-pyrrolo[2,3-b]pyridin-5-yloxy)-4-(4-((2-(4-chlorophenyl)-4,4-dimethylcyclohex-1-enyl)methyl)-3-methylpiperazin-1-yl)benzoate The title compound was prepared by substituting Compound 290D for Compound 3E in the procedure for Compound 31.

Compound 290F 2-(1H-pyrrolo[2,3-b]pyridin-5-yloxy)-4-(4-((2-(4-chlorophenyl)-4,4-dimethylcyclohex-1-enyl)methyl)-3-methylpiperazin-1-yl)benzoic Acid The title compound was prepared by substituting Compound 290E for Compound 15G in the procedure for Compound 15H.

Compound 290G 4-(4-{[2-(4-chlorophenyl)-4,4-dimethylcyclohex-1-en-1-yl]methyl}-3-methylpiperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 290F for Compound 1E in the procedure for Compound 1G. $^1$H NMR (300 MHz, dimethylsulfoxide-$d_6$) δ 11.66 (s, 1H), 11.54-11.30 (m, 1H), 8.62-8.53 (m, 2H), 8.03 (d, 1H), 7.78 (d, 1H), 7.48 (d, 3H), 7.34 (d, 2H), 7.06 (t, 3H), 6.68 (d, 1H), 6.38 (dd, 1H), 6.21 (s, 1H), 3.84 (d, 2H), 3.23 (s, 4H), 2.75 (s, 4H), 1.64 (s, 8H), 1.62 (d, 2H), 1.42-1.17 (m, 6H), 0.92 (s, 6H), 0.87 (s, 3H).

Compound 291

4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide

Compound 291A tert-butyl 2-cyanoethyl(cyclopropyl)carbamate

To a solution of 3-(cyclopropylamino)propanenitrile (5.0 g) in tetrahydrofuran (30 ml) was added di-tert-butyl dicarbonate (9.91 g) and a catalytic amount of 4-dimethylaminopyridine. The mixture was stirred overnight. The mixture was diluted with ethyl acetate (400 ml) and washed with 5% aqueous HCl, water and brine. After drying over $Na_2SO_4$, the mixture was filtered, and the solvent was evaporated under vacuum to provide the title compound.

Compound 291B tert-butyl 3-aminopropyl(cyclopropyl)carbamate

Compound 291A (9.75 g) and 7M $NH_3$-methanol (25 ml) were added to a Ra—Ni 2800, water slurry (19.50 g, 332 mmol) in a 250 ml pressure bottle and stirred for 2 hours at 30 psi and room temperature. The mixture was filtered though a nylon membrane and evaporation of the solvent gave the title compound.

Compound 291C tert-butyl cyclopropyl(3-(2-nitro-4-sulfamoylphenylamino)propyl)carbamate To a solution of 4-chloro-3-nitrobenzenesulfonamide (2.5 g), and Compound 291B (2.26 g) in dioxane (20 ml) was added N,N-diisopropylethylamine (5 ml). The mixture was stirred at reflux overnight. The mixture was diluted with ethyl acetate (400 ml) and washed with water and brine. After drying over $Na_2SO_4$, the mixture was filtered, and the solvent was evaporated under vacuum to provide the title compound.

Compound 291D tert-butyl 3-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenylamino)propyl(cyclopropyl)carbamate The title compound was prepared by substituting Compound 3J for Compound 1E and Compound 291C for Compound 1F in the procedure for Compound 1G.

Compound 291E 4-(4-{[2-(4-chlorophenyl)-4,4-dimethylcyclohex-1-en-1-yl]methyl}piperazin-1-yl)-N-[(4-{[3-(cyclopropylamino)propyl]amino}-3-nitrophenyl)sulfonyl]-2-(1H-pyrrolo[2,3-b]pyridin-5-yloxy)benzamide To a solution of Compound 291D (2.56 g) in dichloromethane (10 ml) was added trifluoroacetic acid (10 ml). The mixture was stirred for 2 hours. The mixture was concentrated under vacuum and the residue was dissolved in dichloromethane (300 ml) and washed with aqueous $NaHCO_3$, water, and brine and dried over $Na_2SO_4$. Filtration and evaporation of the solvent gave the crude product. The title compound was obtained by dissolving 200 mg of the crude material in dimethylsulfoxide/methanol (1:1, 10 ml) and loaded on Gilson, C18(100A) 250×121.2 mm (10 micron), eluting with 30% acetonitrile to 65% acetonitrile over 40 minutes. $^1H$ NMR (300 MHz, dimethylsulfoxide-$d_6$) δ 11.54 (s, 1H), 8.43 (m, 2H), 7.94 (d, 1H), 7.71 (dd, 1H), 7.57 (d, 1H), 7.43 (m, 1H), 7.34 (m, 3H), 7.05 (d, 2H), 6.90 (d, 1H), 6.63 (dd, 1H), 6.29 (d, 2H), 3.43 (m, 2H), 2.96 (m, 6H), 2.73 (m, 2H), 2.22 (m, 7H), 1.87 (m, 4H), 1.38 (m, 3H), 0.94 (m, 6H), 0.62 (m, 4H).

Compound 292

N-{[5-chloro-1-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 292A 5-chloro-6-(2-methoxyethoxy)pyridine-3-sulfonamide

The title compound was prepared by substituting Compound 40A for 4-fluoro-3-nitrobenzenesulfonamide and 2-methoxyethanol for (tetrahydro-2H-pyran-4-yl)methanol in the procedure for Compound 24A.

Compound 292B

N-{[5-chloro-6-(2-methoxyethoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 292A for Compound 11B in the procedure for Compound 11D. $^1H$ NMR (400 MHz, dimethylsulfoxide-$d_6$) δ 11.63 (s, 1H), 8.48 (d, 1H), 8.17 (d, 1H), 8.01 (d, 1H), 7.56 (d, 1H), 7.49 (m, 2H), 7.35 (d, 2H), 7.04 (d, 2H), 6.66 (dd, 1H), 6.37 (m, 1H), 6.21 (d, 1H), 4.52 (m, 2H), 3.70 (m, 2H), 3.28 (s, 3H), 3.13 (br m, 4H), 2.88 (br s, 2H), 2.34 (br m, 4H), 2.16 (br m, 2H), 1.97 (s, 2H), 1.40 (t, 2H), 0.92 (s, 6H).

Compound 293

4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide

Compound 293A 5-bromo-3-fluoro-2-((tetrahydro-2H-pyran-4-yl)methoxy)pyridine The title compound was prepared by substituting 5-bromo-2,3-difluoropyridine for 4-fluoro-3-nitrobenzenesulfonamide in the procedure for Compound 24A.

Compound 293B tert-butyl 5-fluoro-6-((tetrahydro-2H-pyran-4-yl)methoxy)pyridin-3-ylcarbamate The title compound was prepared by substituting Compound 293A for Compound 248A in the procedure for Compound 248B.

Compound 293C 5-fluoro-6-((tetrahydro-2H-pyran-4-yl)methoxy)pyridine-3-sulfonyl chloride The title compound was prepared by substituting Compound 293B for Compound 248B in the procedure for Compound 248C.

Compound 293D 5-fluoro-6-((tetrahydro-2H-pyran-4-yl)methoxy)pyridine-3-sulfonamide The title compound was prepared by substituting Compound 293C for Compound 248C in the procedure for Compound 248D.

Compound 293E 4-(4-{[2-(4-chlorophenyl)-4,4-dimethylcyclohex-1-en-1-yl]methyl}piperazin-1-yl)-N-{[5-fluoro-6-(tetrahydro-2H-pyran-4-ylmethoxy)pyridin-3-yl]sulfonyl}-2-(1H-pyrrolo[2,3-b]pyridin-5-yloxy)benzamide The title compound was prepared by substituting Compound 293D for Compound 11B in the procedure for Compound 11D. $^1H$ NMR (400 MHz, pyridine-$d_5$) δ 13.07 (s, 1H), 9.05 (d, 1H), 8.44 (dd, 1H), 8.41 (d, 1H), 8.09 (d, 1H), 7.67 (t, 1H), 7.65 (d, 1H), 7.44 (m, 2H), 7.07 (m, 2H), 6.76 (dd, 1H), 6.53 (d, 1H), 6.49 (dd, 1H), 4.21 (d, 2H), 3.96 (dd, 2H), 3.31 (td, 2H), 3.07 (m, 4H), 2.77 (s, 2H), 2.26 (t, 2H), 2.14 (m, 4H), 1.97 (m, 3H), 1.58 (dd, 2H), 1.38 (m, 4H), 0.94 (s, 6H).

Compound 294

N-[(3-chloro-4-{[1-(methoxyacetyl)piperidin-4-yl]
methoxy}phenyl)sulfonyl]-4-(4-{[2-(4-chlorophe-
nyl)-4,4-dimethylcyclohex-1-en-1-yl]
methyl}piperazin-1-yl)-2-(1H-pyrrolo[2,3-b]pyridin-
5-yloxy)benzamide

Compound 294A tert-butyl 4-((2-chloro-4-sulfamoylphenoxy)methyl)
piperidine-1-carboxylate The title compound was prepared by substituting tert-butyl-4-(hydroxymethyl)piperidine-1-carboxylate for (4-fluoro-1-methylpiperidin-4-yl)methanol in the procedure for Compound 283A.

Compound 294B tert-butyl 4-((4-(N-(2-(1H-pyrrolo[2,3-b]pyridin-5-
yloxy)-4-(4-((2-(4-chlorophenyl)-4,4-dimethylcyclo-
hex-1-enyl)methyl)piperazin-1-yl)benzoyl)sulfa-
moyl)-2-chlorophenoxy)methyl)piperidine-1-
carboxylate The title compound was prepared by substituting Compound 3J for Compound 1E and Compound 294A for Compound 1F in the procedure for Compound 1G.

Compound 294C 2-(1H-pyrrolo[2,3-b]pyridin-5-yloxy)-N-(3-chloro-
4-(piperidin-4-ylmethoxy)phenylsulfonyl)-4-(4-((2-
(4-chlorophenyl)-4,4-dimethylcyclohex-1-enyl)
methyl)piperazin-1-yl)benzamide To Compound 294B (0.286 g) in dichloromethane (3 ml) was added trifluoroacetic acid (1 ml) and the reaction stirred at room temperature. After 3 hours the reaction was concentrated to provide the title compound.

Compound 294D

N-[(3-chloro-4-{[1-(methoxyacetyl)piperidin-4-yl]
methoxy}phenyl)sulfonyl]-4-(4-{[2-(4-chlorophe-
nyl)-4,4-dimethylcyclohex-1-en-1-yl]
methyl}piperazin-1-yl)-2-(1H-pyrrolo[2,3-b]pyridin-
5-yloxy)benzamide To Compound 294C (0.75 g) as a solution in dichloromethane (1 ml) was added N,N-diisopropylethylamine (0.055 ml) followed by 2-methoxyacetyl chloride (6 µl). After stirring for 10 minutes the reaction was loaded onto silica gel (Reveleris 40 g) and eluted using a gradient of 0.5% to 3.5% methanol/dichloromethane over 30 minutes (flow=40 ml/minutes) to provide the title compound. $^1$H NMR (300 MHz, dimethylsulfoxide-d$_6$) δ 11.71 (s, 1H), 11.55-11.24 (m, 1H), 8.06 (d, 1H), 7.88 (d, 1H), 7.78 (d, 1H), 7.57 (s, 1H), 7.51 (s, 1H), 7.48 (d, 1H), 7.34 (d, 2H), 7.21 (d, 1H), 7.04 (d, 2H), 6.67 (d, 1H), 6.42 (dd, 1H), 6.18 (s, 1H), 4.42-4.32 (m, 1H), 4.03 (dd, 4H), 3.86-3.74 (m, 1H), 3.28 (s, 3H), 3.07 (s, 5H), 2.77 (s, 3H), 2.30-1.92 (m, 9H), 1.77 (s, 2H), 1.31 (d, 4H), 0.92 (s, 6H).

Compound 295

N-[(3-chloro-4-{[1-(N,N-dimethylglycyl)piperidin-
4-yl]methoxy}phenyl)sulfonyl]-4-(4-{[2-(4-chloro-
phenyl)-4,4-dimethylcyclohex-1-en-1-yl]
methyl}piperazin-1-yl)-2-(1H-pyrrolo[2,3-b]pyridin-
5-yloxy)benzamide The title compound was prepared by substituting 2-(dimethylamino)acetyl chloride for 2-methoxyacetyl chloride in the procedure for Compound 294D. $^1$H NMR (300 MHz, dimethylsulfoxide-d$_6$) δ 11.58 (s, 1H), 10.35-9.94 (m, 1H), 7.96 (d, 1H), 7.74 (d, 1H), 7.55 (d, 2H), 7.45 (s, 1H), 7.41-7.29 (m, 3H), 7.05 (d, 3H), 6.63 (d, 1H), 6.37-6.32 (m, 1H), 6.22 (d, 1H), 4.39 (d, 1H), 3.94 (s, 6H), 3.01 (s, 6H), 2.73 (m, 4H), 2.55 (m, 5H), 2.19 (s, 6H), 1.95 (m, 2H), 1.82 (m, 2H), 1.38 (s, 4H), 0.93 (s, 6H).

Compound 296

4-(4-{[2-(4-chlorophenyl)-4,4-dimethylcyclohexyl]
methyl}piperidin-1-yl)-N-({3-nitro-4-[(tetrahydro-
2H-pyran-4-ylmethyl)amino]phenyl}sulfonyl)-2-
(1H-pyrrolo[2,3-b]pyridin-5-yloxy)benzamide

Compound 296A tert-butyl 4-((4,4-dimethyl-2-oxocyclohexyl)methyl)
piperidine-1-carboxylate 3,3-Dimethylcyclohexanone (5.60 ml) was added to sodium bis(trimethylsilyl)amide (45.3 ml, 1M in tetrahydrofuran), and the reaction was stirred for 1 hour. tert-Butyl 4-(bromomethyl)piperidine-1-carboxylate (11.1 g) in dimethylsulfoxide (30 ml) was added, and the reaction was stirred at 50° C. for 24 hours. The reaction was cooled, poured into water (300 ml), extracted three times with ether, and the combined extracts were washed three times with water, and brine, dried over Na$_2$SO$_4$, filtered, and concentrated. The crude product was chromatographed on silica gel using 5-20% ethyl acetate in hexanes to provide the title compound.

Compound 296B tert-butyl 4-((2-(4-chlorophenyl)-2-hydroxy-4,4-
dimethylcyclohexyl)methyl)piperidine-1-carboxylate (4-Chlorophenyl)magnesium bromide (14.1 ml, 1M in ether) was added to Compound 296A (3.25 g) in tetrahydrofuran (40 ml) at −78° C., and the reaction was stirred for 20 minutes, and then allowed to warm to room temperature overnight. The reaction was quenched with pH 7 buffer (20 ml), extracted with 2× ether, and the combined extracts were washed with brine, dried over Na$_2$SO$_4$, filtered, and concentrated. The crude product was chromatographed on silica gel using 1-20% ethyl acetate in hexanes to provide the title compound.

Compound 296C trans-4-((2-(4-chlorophenyl)-4,4-dimethylcyclohexyl)methyl)piperidine The title compound was prepared by substituting Compound 296B for Compound 1A in the procedure for Compound 1B.

Compound 296D trans-methyl 2-(1H-pyrrolo[2,3-b]pyridin-5-yloxy)-4-(4-((2-(4-chlorophenyl)-4,4-dimethylcyclohexyl)methyl)piperidin-1-yl)benzoate The title compound was prepared by substituting Compound 296C for Compound 263G in the procedure for Compound 263H.

Compound 296E trans-2-(1H-pyrrolo[2,3-b]pyridin-5-yloxy)-4-(4-((2-(4-chlorophenyl)-4,4-dimethylcyclohexyl)methyl)piperidin-1-yl)benzoic Acid The title compound was prepared by substituting Compound 296D for Compound 31 in the procedure for Compound 3J.

Compound 296F trans-4-(4-{[2-(4-chlorophenyl)-4,4-dimethylcyclohexyl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 296E for Compound 1E in the procedure for Compound 1G. $^1$H NMR (300 MHz, dimethylsulfoxide-$d_6$) δ 11.69 (s, 1H), 11.36 (br s, 1H), 8.60 (t, 1H), 8.55 (d, 1H), 8.03 (d, 1H), 7.78 (dd, 1H), 7.52 (m, 3H), 7.27 (d, 2H), 7.16 (d, 2H), 7.09 (m, 1H), 6.63 (dd, 1H), 6.38 (dd, 1H), 6.11 (d, 1H), 3.83 (dd, 2H), 3.52 (m, 2H), 3.26 (m, 4H), 2.61 (m, 2H), 2.35 (m, 1H), 1.89 (m, 2H), 1.76 (m, 1H), 1.62 (m, 2H), 1.38 (m, 4H), 1.25 (m, 6H), 1.12 (m, 2H), 0.95 (m, 2H), 0.94 (s, 3H), 0.88 (s, 3H).

Compound 297

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide

Compound 297A 6-((tetrahydro-2H-pyran-4-yl)methoxy)-5-(trifluoromethyl)pyridine-3-sulfonamide The title compound was prepared by substituting Compound 288E for 4-fluoro-3-nitrobenzenesulfonamide in the procedure for Compound 24A.

Compound 297B 4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[6-(tetrahydro-2H-pyran-4-ylmethoxy)-5-(trifluoromethyl)pyridin-3-yl]sulfonyl}benzamide The title compound was prepared by substituting Compound 297A for Compound 11B in the procedure for Compound 11D. $^1$H NMR (400 MHz, dimethylsulfoxide-$d_6$) δ 11.49 (s, 1H), 8.56 (d, 1H), 8.23 (d, 1H), 7.90 (d, 1H), 7.58 (d, 1H), 7.40 (m, 1H), 7.34 (m, 2H), 7.26 (d, 1H), 7.05 (d, 2H), 6.61 (dd, 1H), 6.28 (dd, 1H), 6.24 (d, 1H), 4.24 (d, 2H), 3.86 (dd, 2H), 3.30 (m, 4H), 3.00 (s, 4H), 2.73 (s, 2H), 2.16 (m, 6H), 1.97 (m, 2H), 1.61 (dd, 2H), 1.33 (m, 4H), 0.93 (s, 6H).

Compound 298

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 298A 6-((trans-4-(tert-butyldimethylsilyloxy)cyclohexyl)methoxy)-5-chloropyridine-3-sulfonamide The title compound was prepared by substituting (trans-4-(tert-butyldimethylsilyloxy)cyclohexyl)methanol for (tetrahydro-2H-pyran-4-yl)methanol and Compound 40A for Compound 36A in the procedure for Compound 36B.

Compound 298B

N-({5-chloro-6-[(trans-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 298A for Compound 11B in the procedure for Compound 11D. After the reaction was over, the solvent was removed, and the residue was treated with 1:1 trifluoroacetic acid/dichloromethane for two hours. The solvents were removed, and the residue was purified by reverse phase Gilson Prep HPLC system with a Phenomenex prep column (Luna, 5μ, C18(2), 250×21.20 mm, 5 Å) eluting with 20-80% acetonitrile in water with 0.1% trifluoroacetic acid to provide the title compound. $^1$H NMR (500 MHz, dimethylsulfoxide-$d_6$) δ 11.65 (s, 1H), 8.47 (s, 1H), 8.15 (s, 1H), 8.01 (d, 1H), 7.54 (d, 1H), 7.48-7.49 (m, 1H), 7.35 (d, 2H), 7.05 (d, 2H), 6.67 (dd, 1H), 6.37 (d, 1H), 6.21 (s, 1H), 4.53 (t, 1H), 4.18 (d, 2H), 3.08 (s, 4H), 2.84 (s, 2H), 2.29 (s, 4H), 2.15 (s, 2H), 1.96 (s, 2H), 1.79-1.83 (m, 5H), 1.39 (t, 2H), 1.08-1.13 (m, 5H), 0.93 (s, 6H).

Compound 299

4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide

Compound 299A 3-cyano-4-((4-fluorotetrahydro-2H-pyran-4-yl)methoxy)benzenesulfonamide The title compound was prepared by substituting Compound 37C for (tetrahydro-2H-pyran-4-yl)methanol in the procedure for Compound 284A.

Compound 299B 4-(4-{[2-(4-chlorophenyl)-4,4-dimethylcyclohex-1-en-1-yl]methyl}piperazin-1-yl)-N-({3-cyano-4-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting Compound 3J for Compound 1E and Compound 299A for Compound 1F in the procedure for Compound 1G. $^1$H NMR (300 MHz, dimethylsulfoxide-$d_6$) δ 11.72 (s, 1H), 10.24-9.27 (m, 1H), 8.21 (d, 1H), 8.12 (dd, 1H), 8.05 (d, 1H), 7.63-7.46 (m, 3H), 7.45-7.31 (m, 3H), 7.07 (d, 2H), 6.70 (dd, 1H), 6.42 (s, 1H), 6.23 (s, 1H), 4.38 (d, 2H), 3.91-3.73 (m, 2H), 3.68-3.51 (m, 2H), 3.22-2.96 (m, 10H), 2.31-2.12 (m, 2H), 1.99 (s, 6H), 1.43 (t, 2H), 0.93 (s, 6H).

Compound 300

4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide

Compound 300A 6-((trans-4-methoxycyclohexyl)methoxy)-5-(trifluoromethyl)pyridine-3-sulfonamide The title compound was prepared by substituting Compound 288E for 4-fluoro-3-nitrobenzenesulfonamide and Compound 121A for (tetrahydro-2H-pyran-4-yl)methanol in the procedure for Compound 24A.

Compound 300B 4-(4-{[2-(4-chlorophenyl)-4,4-dimethylcyclohex-1-en-1-yl]methyl}piperazin-1-yl)-N-({6-[(trans-4-methoxycyclohexyl)methoxy]-5-(trifluoromethyl)pyridin-3-yl}sulfonyl)-2-(1H-pyrrolo[2,3-b]pyridin-5-yloxy)benzamide The title compound was prepared by substituting Compound 300A for Compound 11B in the procedure for Compound 11D. $^1$H NMR (400 MHz, dimethylsulfoxide-$d_6$) δ 11.50 (s, 1H), 8.56 (d, 1H), 8.23 (d, 1H), 7.90 (d, 1H), 7.58 (d, 1H), 7.40 (m, 1H), 7.35 (d, 2H), 7.27 (d, 1H), 7.05 (d, 2H), 6.61 (dd, 1H), 6.28 (dd, 1H), 6.24 (d, 1H), 4.20 (d, 2H), 3.23 (s, 3H), 3.03 (m, 5H), 2.73 (s, 2H), 2.18 (m, 6H), 1.98 (m, 5H), 1.80 (m, 3H), 1.39 (t, 2H), 1.09 (m, 4H), 0.93 (s, 6H).

Compound 301

4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3-b]pyridin-5-yloxy)benzamide

Compound 301A 6-((cis-4-methoxycyclohexyl)methoxy)-5-(trifluoromethyl)pyridine-3-sulfonamide The title compound was prepared by substituting Compound 288E for 4-fluoro-3-nitrobenzenesulfonamide and Compound 121A for (tetrahydro-2H-pyran-4-yl)methanol in the procedure for Compound 24A.

Compound 301B 4-(4-{[2-(4-chlorophenyl)-4,4-dimethylcyclohex-1-en-1-yl]methyl}piperazin-1-yl)-N-({6-[(cis-4-methoxycyclohexyl)methoxy]-5-(trifluoromethyl)pyridin-3-yl}sulfonyl)-2-(1H-pyrrolo[2,3b]pyridin-5-yloxy)benzamide The title compound was prepared by substituting Compound 301A for Compound 11B in the procedure for Compound 11D. $^1$H NMR (400 MHz, dimethylsulfoxide-$d_6$) δ 11.49 (m, 1H), 8.54 (m, 1H), 8.23 (d, 1H), 7.91 (d, 1H), 7.59 (d, 1H), 7.40 (m, 1H), 7.34 (m, 2H), 7.27 (d, 1H), 7.04 (d, 2H), 6.61 (dd, 1H), 6.29 (dd, 1H), 6.24 (d, 1H), 4.20 (d, 2H), 3.37 (m, 2H), 3.19 (s, 3H), 3.00 (s, 4H), 2.73 (s, 2H), 2.18 (m, 6H), 1.96 (s, 2H), 1.80 (m, 3H), 1.50 (dd, 2H), 1.37 (m, 6H), 0.93 (s, 6H).

Compound 302

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide

Compound 302A 4-((2-(4-chlorophenyl)-4,4-dimethylcyclohex-1-enyl)methyl)piperidine Compound 296B (1.0 g) was stirred in dichloromethane (15 ml) and trifluoroacetic acid (15 ml) at 35° C. for 48 hours. The mixture was concentrated, taken up in dichloromethane (100 ml), and stirred, and saturated $Na_2CO_3$ solution (20 ml) was added slowly. The solution was separated and the organic layer was dried over Na$_2$SO$_4$, filtered, and concentrated to provide the title compound.

Compound 302B methyl 2-(1H-pyrrolo[2,3-b]pyridin-5-yloxy)-4-(4-((2-(4-chlorophenyl)-4,4-dimethylcyclohex-1-enyl)methyl)piperidin-1-yl)benzoate The title compound was prepared by substituting Compound 302A for Compound 263G in the procedure for Compound 263H.

Compound 302C 2-(1H-pyrrolo[2,3-b]pyridin-5-yloxy)-4-(4-((2-(4-chlorophenyl)-4,4-dimethylcyclohex-1-enyl)methyl)piperidin-1-yl)benzoic Acid The title compound was prepared by substituting Compound 302B for Compound 31 in the procedure for Compound 3J.

Compound 302D 1,1-difluoro4-methylenecyclohexane

Butyllithium (12.32 ml, 2.5 M solution in hexanes) was added to a solution of methyltriphenylphosphonium chloride (9.63 g) in tetrahydrofuran (50 ml) at 0° C., and the reaction was stirred for 5 minutes. 4,4-Difluorocycleohexanone (3.76 g) in dioxane (150 ml) was then added, and the reaction was stirred for 30 minutes. Water (3 ml) was added, and then hexane (150 ml) was slowly added, the reaction was filtered, and the solution carried on.

Compound 302E 4,4-difluoro-1-(hydroxymethyl)cyclohexanol

To the solution from Compound 302D was added water (75 ml), then N-methylmorpholine-N-oxide (6.4 ml, 50% solution in water) and OsO$_4$ (14.2 g, 2.5 wt % solution in tert-butanol) were added, and the reaction was stirred for 96 hours at 50° C. The solution was cooled to room temperature, treated with saturated aqueous Na$_2$S$_2$O$_3$ solution (100 ml) for 30 minutes, and then acidified with concentrated aqueous HCl. The solution was then extracted three times with ethyl acetate, and the organic layers were combined, washed with 1M HCl, and brine, and concentrated. The crude mixture was chromatographed on silica gel using 10-100% ethyl acetate in hexanes, and then 5% methanol in ethyl acetate to give the product.

Compound 302F 5-chloro-6-((4,4-difluoro-1-hydroxycyclohexyl)methoxy)pyridine-3-sulfonamide This compound was prepared by substituting Compound 302E for tetrahydro-2H-pyran-4-yl)methanol and Compound 40A for 4-fluoro-3-nitrobenzenesulfonamide in the procedure for Compound 24A.

Compound 302G

N-({5-chloro-6-[(4,4-difluoro-1-hydroxycyclohexyl)methoxy]pyridin-3-yl}sulfonyl)-4-(4-{[2-(4-chlorophenyl)-4,4-dimethylcyclohex-1-en-1-yl]methyl}piperidin-1-yl)-2-(1H-pyrrolo[2,3-b]pyridin-5-yloxy)benzamide The title compound was prepared by substituting Compound 302C for Compound 1E and Compound 302F for Compound 1F in the procedure for Compound 1G. $^1$H NMR (300 MHz, dimethylsulfoxide-d$_6$) δ 11.65 (br s, 2H), 8.51 (s, 1H), 8.18 (s, 1H), 8.02 (d, 1H), 7.53 (m, 3H), 7.35 (d, 2H), 7.04 (d, 2H), 6.69 (dd, 1H), 6.39 (dd, 1H), 6.21 (d, 1H), 4.88 (s, 1H), 4.27 (s, 2H), 3.10 (m, 4H), 2.88 (m, 1H), 2.33 (m, 2H), 2.15 (m, 4H), 1.97 (s, 2H), 1.91 (m, 2H), 1.73 (m, 4H), 1.52 (m, 1H), 1.40 (m, 2H), 1.31 (m, 1H), 0.93 (s, 3H), 0.91 (m, 2H).

Compound 303

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 303A trans-4-morpholinocyclohexyl)methano 1

To tert-butyl trans-4-(hydroxymethyl)cyclohexylcarbamate (0.500 g) was added hydrogen chloride (4.0M in dioxane, 2.2 ml) and the reaction was stirred for 1 hour and concentrated. The resulting solid was dissolved in acetonitrile (4 ml) and treated with N,N-diisopropylethylamine (1.523 ml) followed by 1-bromo-2-(2-bromoethoxy)ethane (0.556 g) and heated to 60° C. After stirring overnight the reaction was concentrated, loaded onto silica gel (Reveleris 40 g) and eluted using a gradient of 1% to 10% methanol/dichloromethane over 30 minutes (flow=40 ml/min) to provide the title compound.

Compound 303B 3-chloro-4-(((1r,4r)-4-morpholinocyclohexyl)methoxy)benzenesulfonamide The title compound was prepared by substituting Compound 303A for (4-fluoro-1-methylpiperidin-4-yl)methanol in the procedure for Compound 283A.

Compound 303C

N-[(3-chloro-4-{[trans-4-(morpholin-4-yl)cyclohexyl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 303B for Compound 1F in the procedure for Compound 1G. $^1$H NMR (300 MHz, dimethylsulfoxide-d$_6$) δ 11.65 (s, 1H), 10.96-

10.59 (m, 1H), 8.02 (d, 1H), 7.82 (d, 1H), 7.69 (s, 1H), 7.50 (dd, 3H), 7.38-7.30 (m, 2H), 7.15-6.99 (m, 3H), 6.65 (dd, 1H), 6.39 (dd, 1H), 6.20 (d, 1H), 3.91 (d, 2H), 3.64 (s, 4H), 3.04 (s, 4H), 2.73 (s, 7H), 2.18 (s, 6H), 1.93 (m, 6H), 1.80-1.65 (m, 1H), 1.32 (m, 6H), 0.92 (s, 6H).

Compound 304

4-(4-{[2-(4-chlorophenyl)-4,4-dimethylcyclohex-1-en-1-yl]methyl}piperazin-1-yl)-N-{[4-({3-[cyclopropyl(1,3-thiazol-5-ylmethyl)amino]propyl}amino)-3-nitrophenyl]sulfonyl}-2-(1H-pyrrolo[2,3-b]pyridin-5-yloxy)benzamide To a solution of Compound 291E (95 mg) in dichloromethane (2 ml) and acetic acid (0.5 ml) was added thiazole-5-carbaldehyde (13 mg) followed by sodium triacetoxyborohydride (35 mg). The mixture was stirred overnight. The mixture was diluted with dichloromethane (300 ml) and washed with aqueous $NaHCO_3$, water, and brine and dried over $Na_2SO_4$. Filtration and evaporation of the solvent gave crude product which was dissolved in dimethylsulfoxide/methanol (6 ml, 1:1) and loaded on Gilson, C18(100A) 250×121.2 mm (10 micron), with 30% acetonitrile to 65% acetonitrile over 40 minutes. $^1$H NMR (300 MHz, dimethylsulfoxide-$d_6$) δ 11.67 (s, 1H), 8.95 (s, 1H), 8.57 (m, 2H), 8.03 (d, 1H), 7.78 (m, 2H), 7.49 (m, 3H), 7.35 (m, 2H), 7.02 (m, 3H), 6.67 (dd, 1H), 6.38 (dd, 1H), 6.19 (d, 1H), 4.00 (s, 2H), 3.05 (d, 4H), 2.73 (m, 2H), 2.60 (m, 2H), 2.18 (m, 7H), 1.95 (s, 2H), 1.79 (m, 3H), 1.37 (m, 3H), 0.92 (s, 6H), 0.45 (m, 4H).

Compound 305

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 305A 3-chloro-4-((trans-4-hydroxycyclohexyl)methoxy)benzenesulfonamide (Trans-4-(tert-butyldimethylsilyloxy)cyclohexyl)methanol (275 mg, prepared according to a procedures in WO 2008/124878) and 3-chloro-4-fluorobenzenesulfonamide (259 mg) in tetrahydrofuran (15 ml) were treated with sodium hydride (180 mg, 60%) overnight. The reaction was quenched with water (1 ml) and trifluoroacetic acid (4 ml) was added. The resulting mixture was stirred for 1 hour and concentrated. The residue was triturated with water and methanol to provide the title compound.

Compound 305B

N-({3-chloro-4-[(trans-4-hydroxycyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in the procedure for Compound 11D using Compound 305A in place of Compound 11B. $^1$H NMR (500 MHz, dimethylsulfoxide-$d_6$) δ 11.71 (s, 1H), 11.38 (s, 1H), 8.06 (d, 1H), 7.87 (d, 1H), 7.76 (dd, 1H), 7.57 (d, 1H), 7.51-7.55 (m, 1H), 7.49 (d, 1H), 7.34 (d, 2H), 7.18 (d, 1H), 7.04 (d, 2H), 6.67 (dd, 1H), 6.42 (dd, 1H), 6.18 (d, 1H), 4.54 (d, 1H), 3.91 (d, 2H), 3.07 (s, 4H), 2.75 (s, 2H), 2.17 (d, 6H), 1.95 (s, 2H), 1.78-1.90 (m, 4H), 1.63-1.75 (m, 1H), 1.38 (t, 2H), 1.00-1.25 (m, 4H), 0.92 (s, 6H).

Compound 306

4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide Compound 306A 3-chloro-4-((tetrahydro-2H-pyran-4-yl)methylamino)benzenesulfonamide The title compound was prepared by substituting 4-fluoro-3-chlorobenzenesulfonamide for 4-chloro-3-nitrobenzenesulfonamide, (tetrahydro-2H-pyran-4-yl)methanamine for 4-methylpiperazin-1-amine dihydrochloride and Hunig's base for $N^1,N^1,N^2,N^2$-tetramethylethane-1,2-diamine in the procedure for Compound 6A.

Compound 306B 4-(4-{[2-(4-chlorophenyl)-4,4-dimethylcyclohex-1-en-1-yl]methyl}piperazin-1-yl)-N-({3-chloro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 306A for Compound 11B in the procedure for Compound 11D. $^1$H NMR (400 MHz, dimethylsulfoxide-$d_6$) δ 11.80 (s, 1H), 11.17 (br s, 1H), 8.09 (d, 1H), 7.71 (d, 1H), 7.63 (d, 1H), 7.58 (dd, 1H), 7.53 (dd, 1H), 7.50 (d, 1H), 7.34 (d, 2H), 7.03 (d, 2H), 6.74 (d, 1H), 6.66 (dd, 1H), 6.42 (m, 1H), 6.40 (t, 1H), 6.16 (d, 1H), 3.83 (m, 2H), 3.24 (m, 2H), 3.10 (m, 2H), 3.06 (br m, 4H), 2.72 (s, 2H), 2.17 (br m, 6H), 1.95 (s, 2H), 1.83 (m, 1H), 1.59 (br m, 2H), 1.38 (t, 2H), 1.20 (ddd, 2H), 0.92 (s, 6H).

Compound 307

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide Compound 307A 4-((4-fluorotetrahydro-2H-pyran-4-yl)methoxy)-3-(trifluoromethyl)benzenesulfonamide The title compound was prepared by substituting 4-fluoro-3-(trifluoromethyl)benzenesulfonamide for 4-fluoro-3-nitrobenzenesulfonamide and Compound 37C for (tetrahydro-2H-pyran-4-yl)methanol in the procedure for Compound 24A.

Compound 307B 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-(trifluoromethyl)phenyl}sulfonyl)-2-(1H-pyrrolo[2,3-b]pyridin-5-yloxy)benzamide The title compound was prepared by substituting Compound 3J for Compound 1E and Compound 307A for Compound 1F in the procedure for Compound 1G. $^1$H NMR (400 MHz, pyridine-d$_5$) δ 13.07 (s, 1H), 8.78 (d, 1H), 8.58 (dd, 1H), 8.42 (d, 1H), 8.09 (d, 1H), 7.67 (t, 1H), 7.65 (d, 1H), 7.43 (m, 2H), 7.16 (d, 1H), 7.06 (m, 2H), 6.74 (dd, 1H), 6.51 (m, 2H), 4.21 (d, 2H), 3.87 (m, 2H), 3.78 (td, 2H), 3.06 (m, 4H), 2.76 (s, 2H), 2.25 (t, 2H), 2.13 (m, 4H), 1.95 (m, 6H), 1.39 (t, 2H), 0.93 (s, 6H).

Compound 308

4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide Compound 308A 4-(3-(cyclopropylamino)propylamino)-3-nitrobenzenesulfonamide To a solution of Compound 291C (4.14 g) in dichloromethane (10 ml) was added trifluoroacetic acid (10 ml). The mixture was stirred for 2 hours. The mixture was concentrated under vacuum and the residue was dissolved in dichloromethane (300 ml) and washed with aqueous NaHCO$_3$, water, and brine and dried over Na$_2$SO$_4$. Filtration and evaporation of solvent gave the title compound.

Compound 308B 4-(3-(cyclopropyl(2,2,2-trifluoroethyl)amino)propylamino)-3-nitrobenzenesulfonamide To a solution of Compound 308A (314 mg) in dichloromethane (6 ml) was added 2,2,2-trifluoroethyl trifluoromethanesulfonate (255 mg) and N,N-diisopropylethylamine (258 mg). The mixture was stirred overnight. The mixture was diluted with dichloromethane (300 ml) and washed with aqueous NaHCO$_3$, water, brine and dried over Na$_2$SO$_4$. Filtration and evaporation of solvent gave the title compound.

Compound 308C 4-(4-{[2-(4-chlorophenyl)-4,4-dimethylcyclohex-1-en-1-yl]methyl}piperazin-1-yl)-N-{[4-({3-[cyclopropyl(2,2,2-trifluoroethyl)amino]propyl}amino)-3-nitrophenyl]sulfonyl}-2-(1H-pyrrolo[2,3-b]pyridin-5-yloxy)benzamide The title compound was prepared by substituting Compound 3J for Compound 1E and Compound 308B for Compound 1F in the procedure for Compound 1G. $^1$H NMR (300 MHz, dimethylsulfoxide-d$_6$) δ 11.67 (s, 1H), 11.38 (m, 1H), 8.55 (d, 2H), 8.03 (d, 1H), 7.81 (dd, 1H), 7.50 (m, 3H), 7.34 (d, 2H), 7.05 (m, 3H), 6.67 (dd, 1H), 6.38 (dd, 1H), 6.19 (d, 1H), 3.07 (m, 4H), 2.82 (m, 4H), 2.18 (m, 7H), 1.38 (m, 2H), 0.92 (s, 6H), 0.44 (m, 4H).

Compound 309

N-[(3-chloro-4-{[1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide To a solution of Compound 294B (0.150 g) in dichloromethane (2 ml) was added trifluoroacetic acid (1 ml). After stirring for 1 hour the reaction was concentrated and dried under high vacuum. The residue was dissolved in dichloromethane (2 ml) and treated with sodium triacetoxyborohydride (0.050 g) and oxetan-3-one (0.017 g) and stirred overnight at room temperature. The reaction was quenched with saturated aqueous NaHCO$_3$ (20 ml) and extracted into dichloromethane (50 ml). The organic layer was separated, washed with brine (25 ml), dried over Na$_2$SO$_4$, filtered, and concentrated. Silica gel chromatography (Reveleris 40 g) eluting with a gradient of 0.5% to 5% methanol/dichloromethane over 30 minutes (flow=40 ml/min) provided the title compound. $^1$H NMR (300 MHz, dimethylsulfoxide-d$_6$) δ 11.70 (s, 1H), 11.21 (s, 1H), 8.05 (d, 1H), 7.87 (d1H), 7.75 (dd, 1H), 7.61-7.42 (m, 3H), 7.42-7.26 (m, 2H), 7.18 (d, 1H), 7.14-6.97 (m, 2H), 6.67 (dd, 1H), 6.41 (dd, 1H), 6.18 (d, 1H), 4.51 (dt, 4H), 3.99 (d, 2H), 3.56-3.32 (m, 1H), 3.06 (s, 4H), 2.89-2.68 (m, 4H), 2.16 (d, 6H), 2.01-1.69 (m, 7H), 1.50-1.07 (m, 4H), 0.92 (s, 6H).

Compound 310

4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide Compound 310A 3,5-difluoro-4-((4-fluorotetrahydro-2H-pyran-4-yl)methoxy)benzenesulfonamide Compound 37C (0.423 g) in tetrahydrofuran (30 ml) was treated with NaH (60% oil dispersion) (0.480 g), stirred 20 minutes at ambient temperature, treated with 3,4,5-trifluorobenzenesulfonamide (0.633 g) and stirred 30 minutes. N,N-Dimethylacetamide (15 ml) was added to increase solubility of the reactants and stirring was continued overnight at ambient temperature. Additional NaH (60% oil dispersion) (0.480 g) and N,N-dimethylacetamide (15 ml) were added and the mixture was heated overnight at 50° C. The reaction was quenched with saturated aqueous NH$_4$Cl solution and then partitioned between saturated aqueous NH$_4$Cl solution and ethyl acetate. The organic layer was washed with water and brine, dried (MgSO$_4$), filtered and concentrated. The concentrate was chromatographed on amine functionalized silica gel with 0 to 2% methanol in CH$_2$Cl$_2$ as the eluent. The residue was further purified by reverse phase HPLC on a C18 column using a gradient of 10-70% acetonitrile/0.1% trifluoroacetic acid in water to provide the title compound.

Compound 310B 4-(4-{[2-(4-chlorophenyl)-4,4-dimethylcyclohex-1-en-1-yl]methyl}piperazin-1-yl)-N-({3,5-difluoro-4-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting Compound 3J for Compound 1E and Compound 310A for Compound 1F in the procedure for Compound 1G. $^1$H NMR (500 MHz, pyridine-$d_5$) δ 13.06 (s, 1H), 8.41 (d, 1H), 8.11 (m, 2H), 8.08 (d, 1H), 7.66 (m, 2H), 7.44 (m, 2H), 7.07 (m, 2H), 6.75 (dd, 1H), 6.52 (d, 1H), 6.50 (dd, 1H), 4.26 (d, 2H), 3.85 (dd, 1H), 3.83 (dd, 1H), 3.74 (m, 2H), 3.07 (m, 4H), 2.77 (s, 2H), 2.26 (t, 2H), 2.14 (m, 4H), 1.97 (s, 2H), 1.87 (m, 4H), 1.39 (t, 2H), 0.94 (s, 6H).

Compound 311

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide Compound 311A 4-(3-(cyclopropyl(oxetan-3-yl)amino)propylamino)-3-nitrobenzenesulfonamide To a solution of Compound 308A (314 mg) in dichloromethane (5 ml) was added oxetan-3-one (72 mg) followed by sodium triacetoxyborohydride (318 mg). The mixture was stirred overnight. The mixture was diluted with dichloromethane (300 ml) and washed with aqueous NaHCO$_3$, water and brine and dried over Na$_2$SO$_4$. After filtration, evaporation of the solvent gave the crude title compound.

Compound 311B 4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide The title compound was prepared by substituting Compound 3J for Compound 1E and Compound 311A for Compound 1F in the procedure for Compound 1G. $^1$H NMR (300 MHz, dimethylsulfoxide-$d_6$) δ 11.65 (s, 1H), 11.37 (s, 1H), 8.68 (s, 1H), 8.54 (d, 1H), 8.02 (d, 1H), 7.79 (d, 1H), 7.49 (m, 3H), 7.34 (d, 2H), 7.03 (m, 3H), 6.67 (dd, 1H), 6.38 (dd, 1H), 6.19 (d, 1H), 4.62 (m, 2H), 4.48 (t, 2H), 3.98 (m, 1H), 3.37 (m, 2H), 3.06 (m, 4H), 2.73 (d, 2H), 2.59 (m, 2H), 2.23 (m, 6H), 1.95 (s, 2H), 1.74 (m, 3H), 1.38 (t, 2H), 0.92 (s, 6H), 0.41 (m, 4H).

Compound 312

N-[(3-chloro-4-{[1-(1-methyl-L-prolyl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide To Compound 294B (0.065 g) was added hydrogen chloride (4.0M in dioxane, 0.339 ml) and a few drops of methanol. After 30 minutes, the reaction was concentrated, and (S)-1-methylpyrrolidine-2-carboxylic acid (0.013 g), N$^1$-((ethylimino)methylene)-N$^3$,N$^3$-dimethylpropane-1,3-diamine hydrochloride (0.026 g), suspended in dichloromethane (0.5 ml) were added followed by diisopropylethylamine (0.036 ml). The mixture stirred at room temperature. After stirring overnight, the reaction mixture was loaded onto silica gel (Reveleris 40 g) and eluted using a gradient of 1% to 10% methanol (containing 1N NH$_3$)/dichloromethane over 30 minutes (flow=40 ml/minutes) to provide the title compound. $^1$H NMR (300 MHz, dimethylsulfoxide-$d_6$) δ 11.51 (s, 1H), 10.00-9.22 (m, 1H), 7.92 (d, 1H), 7.68 (d, 1H), 7.57 (d, 1H), 7.47 (dd, 1H), 7.44-7.38 (m, 1H), 7.38-7.31 (m, 2H), 7.29 (d, 1H), 7.12-7.01 (m, 2H), 6.90 (d, 1H), 6.61 (dd, 1H), 6.31 (dd, 1H), 6.25 (d, 1H), 5.85 (d, 1H), 4.40 (s, 1H), 3.92 (s, 4H), 3.17-2.89 (m, 8H), 2.73 (s, 4H), 2.38 (s, 3H), 2.18 (m, 6H), 1.96 (s, 2H), 1.80 (m, 2H), 1.57 (s, 2H), 1.39 (s, 2H), 1.22 (m, 2H), 0.96 (m, 6H).

Compound 313

4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide Compound 313A 3,4-difluoro-5-((4-fluorotetrahydro-2H-pyran-4-yl)methoxy)benzenesulfonamide The title compound was obtained as a side product in the procedure for Compound 310A.

Compound 313B 4-(4-{[2-(4-chlorophenyl)-4,4-dimethylcyclohex-1-en-1-yl]methyl}piperazin-1-yl)-N-({3,4-difluoro-5-[(4-fluorotetrahydro-2H-pyran-4-yl)methoxy]phenyl}sulfonyl)-2-(1H-pyrrolo[2,3-b]pyridin-5-yloxy)benzamide The title compound was prepared by substituting Compound 3J for Compound 1E and Compound 313A for Compound 1F in the procedure for Compound 1G. $^1$H NMR (400 MHz, pyridine-$d_5$) δ 13.05 (s, 1H), 8.41 (d, 1H), 8.10 (d, 1H), 7.98 (m, 2H), 7.66 (m, 1H), 7.63 (d, 1H), 7.44 (m, 2H), 7.07 (m, 2H), 6.77 (dd, 1H), 6.54 (d, 1H), 6.48 (dd, 1H), 4.12 (d, 2H), 3.83 (m, 2H), 3.75 (m, 2H), 3.08 (m, 4H), 2.77 (s, 2H), 2.26 (t, 2H), 2.15 (m, 4H), 1.97 (s, 2H), 1.82 (m, 4H), 1.39 (t, 2H), 0.94 (s, 6H).

Compound 314

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 314A (S)-5-chloro-6-((4-cyclopropylmorpholin-2-yl)methoxy)pyridine-3-sulfonamide A solution of Compound 244B (250 mg), anhydrous methanol (6 ml), (1-ethoxycyclopropoxy)trimethylsilane (0.474 ml), and acetic acid (0.509 ml) was heated at 70° C. for 30 minutes. After cooling to ambient temperature, sodium cyanoborohydride (112 mg) was added and the mixture was stirred for 18 hours. Additional sodium cyanoborohydride (75 mg) was added and stirring was continued 18 hours. The reaction was concentrated and the residue was partitioned between methylene chloride and saturated sodium bicarbonate solution. The crude product was isolated from the dried methylene chloride layer and was purified on silica gel and was eluted with a 1, 2.5, 5, 10% methanol in methylene chloride step gradient to provide the title compound.

Compound 314B

N-[(5-chloro-6-{[(2S)-4-cyclopropylmorpholin-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 314A for Compound 130C in the procedure for Compound 130D. $^1$H NMR (400 MHz, pyridine-$d_5$) δ 12.98 (s, 1H), 9.09 (d, 1H), 8.69 (d, 1H), 8.41 (d, 1H), 8.11 (d, 1H), 7.66-7.64 (m, 2H), 7.44 (d, 2H), 7.07 (d, 2H), 6.75 (dd, 1H), 6.53 (m, 1H), 6.48 (m, 1H), 5.72 (br s, 1H), 4.62-4.57 (m, 1H), 4.51-4.47 (m, 1H), 3.99 (m, 1H), 3.85 (m, 1H), 3.57 (m, 1H), 3.08-3.01 (m, 5H), 2.77 (s, 2H), 2.69 (m, 1H), 2.39-2.24 (m, 4H), 2.14 (m, 4H), 1.97 (s, 2H), 1.57 (m, 1H), 1.39 (t, 2H), 0.94 (m, 6H), 0.48-0.3 (m, 4H).

Compound 315

4-(4-{[2-(4-chlorophenyl)-4,4-dimethylcyclohex-1-en-1-yl]methyl}piperidin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 302C for Compound 1E and Compound 3J for Compound 1E in the procedure for Compound 1G. $^1$H NMR (300 MHz, dimethylsulfoxide-$d_6$) δ 11.70 (s, 1H), 11.35 (br s, 1H), 8.61 (m, 1H), 8.57 (d, 1H), 8.04 (d, 1H), 7.82 (d, 1H), 7.45-7.57 (m, 3H), 7.33 (d, 2H), 7.15 (d, 1H), 7.01 (d, 2H), 6.65 (dd, 1H), 6.40 (dd, 1H), 6.11 (d, 1H), 3.85 (dd, 2H), 3.53 (m, 2H), 3.27 (m, 4H), 2.63 (m, 2H), 2.04 (m, 2H), 1.91 (s, 2H), 1.77 (m, 2H), 1.62 (m, 4H), 1.45 (m, 2H), 1.38 (m, 2H), 1.27 (m, 1H), 1.23 (m, 4H), 0.92 (s, 6H).

Compound 316

4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide Compound 316A 3-chloro-4-((tetrahydro-2H-pyran-4-yl)methoxy)benzenesulfonamide The title compound was prepared by substituting (tetrahydro-2H-pyran-4-yl)methanol for (4-fluoro-1-methylpiperidin-4-yl)methanol in the procedure for Compound 283A.

Compound 316B 4-(4-{[2-(4-chlorophenyl)-4,4-dimethylcyclohex-1-en-1-yl]methyl}piperidin-1-yl)-N-{[3-chloro-4-(tetrahydro-2H-pyran-4-ylmethoxy)phenyl]sulfonyl}-2-(1H-pyrrolo[2,3-b]pyridin-5-yloxy)benzamide The title compound was prepared by substituting Compound 302C for Compound 1E and Compound 316A for Compound 1F in the procedure for Compound 1G. $^1$H NMR (300 MHz, dimethylsulfoxide-$d_6$) δ 11.77 (s, 1H), 11.35 (br s, 1H), 8.06 (m, 1H), 7.88 (d, 1H), 7.79 (dd, 1H), 7.58 (s, 1H), 7.53 (t, 1H), 7.46 (d, 1H), 7.34 (d, 2H), 7.22 (d, 1H), 7.01 (d, 2H), 6.66 (dd, 1H), 6.42 (dd, 1H), 6.11 (d, 1H), 3.99 (d, 2H), 3.88 (dd, 2H), 3.52 (m, 2H), 3.34 (m, 4H), 2.62 (m, 2H), 2.04 (m, 4H), 1.76 (m, 2H), 1.68 (m, 2H), 1.46 (m, 2H), 1.38 (m, 4H), 0.92 (s, 6H), 0.75 (m, 2H).

Compound 317 methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate Compound 317A methyl 2-((2-nitro-4-sulfamoylphenylamino)methyl)morpholine-4-carboxylate The title compound was prepared by substituting methyl chloroformate for methyl iodide in the procedure for Compound 134B.

Compound 317B methyl 2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}morpholine-4-carboxylate The title compound was prepared by substituting Compound 317A for Compound 130C in the procedure for Compound 130D. $^1$H NMR (500 MHz, pyridine-$d_5$) δ 13.00 (s, 1H), 9.26 (d, 1H), 8.84 (t, 1H), 8.43 (d, 1H), 8.35 (d, 1H), 8.12 (d, 1H), 7.66 (m, 2H), 7.44 (d, 2H), 7.07 (d, 2H), 6.91 (bs, 1H), 6.75 (dd, 1H), 6.54 (d, 1H), 6.48 (m, 1H), 4.29-4.03 (m, 1H), 3.89-3.70 (m, 3H), 3.71 (s, 3H), 3.55-3.38 (m, 3H), 3.07 (m, 4H), 2.96 (dt, 1H), 2.86 (dd, 1H), 2.77 (s, 2H), 2.26 (m, 2H), 2.14 (m, 4H), 1.97 (s, 2H), 1.39 (t, 2H), 0.94 (s, 6H).

Compound 318

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methylmorpholine-4-carboxamide

Compound 318A

N-ethyl-N-methyl-2-((2-nitro-4-sulfamoylphenylamino)methyl)morpholine-4-carboxamide The title compound was prepared by substituting N-methyl-N-ethyl carbamyl chloride for methyl iodide in the procedure for Compound 134B.

Compound 318B

2-{[(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)amino]methyl}-N-ethyl-N-methyl morpholine-4-carboxamide The title compound was prepared by substituting Compound 318A for Compound 130C in the procedure for Compound 130D. $^1$H NMR (500 MHz, pyridine-$d_5$) δ 13.00 (s, 1H), 9.26 (d, 1H), 8.86 (t, 1H), 8.44 (d, 1H), 8.33 (dd, 1H), 8.12 (d, 1H), 7.67 (t, 1H), 7.64 (d, 1H), 7.44 (d, 2H), 7.07 (d, 2H), 6.91 (d, 1H), 6.75 (dd, 1H), 6.54 (d, 1H), 6.48 (m, 1H), 3.92-3.85 (m, 2H), 3.75 (d, 1H), 3.62 (dt, 1H), 3.55-3.48 (m, 1H), 3.45-3.39 (m, 2H), 3.21 (q, 2H), 3.07 (m, 4H), 2.99 (dt, 1H), 2.90 (dd, 1H), 2.77 (s, 2H), 2.76 (s, 3H), 2.26 (m, 2H), 2.14 (m, 4H), 1.97 (s, 2H), 1.39 (t, 2H), 1.06 (t, 3H), 0.93 (s, 6H).

Compound 319

4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide

Compound 319A 4-((4-(methylsulfonyl)morpholin-2-yl)methylamino)-3-nitrobenzenesulfonamide The title compound was prepared by substituting methanesulfonyl chloride for methyl iodide in the procedure for Compound 134B.

Compound 319B 4-(4-{[2-(4-chlorophenyl)-4,4-dimethylcyclohex-1-en-1-yl]methyl}piperazin-1-yl)-N-{[4-({[4-(methylsulfonyl)morpholin-2-yl]methyl}amino)-3-nitrophenyl]sulfonyl}-2-(1H-pyrrolo[2,3-b]pyridin-5-yloxy)benzamide The title compound was prepared by substituting Compound 319A for Compound 130C in the procedure for Compound 130D. $^1$H NMR (500 MHz, pyridine-$d_5$) δ 13.00 (s, 1H), 9.25 (d, 1H), 8.84 (t, 1H), 8.43 (d, 1H), 8.32 (dd, 1H), 8.13 (d, 1H), 7.67 (t, 1H), 7.65 (d, 1H), 7.44 (d, 2H), 7.07 (d, 2H), 6.92 (d, 1H), 6.75 (dd, 1H), 6.54 (d, 1H), 6.48 (m, 1H), 3.99 (m, 1H), 3.92-3.88 (m, 2H), 3.64 (m, 2H), 3.56 (m, 1H), 3.50 (m, 1H), 3.07 (m, 4H), 3.04 (s, 3H), 2.95-2.88 (m, 2H), 2.77 (s, 2H), 2.26 (m, 2H), 2.14 (m, 4H), 1.97 (s, 2H), 1.39 (t, 2H), 0.94 (s, 6H).

Compound 320

4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide

Compound 320A 4-(3-(cyclobutyl(cyclopropyl)amino)propylamino)-3-nitrobenzenesulfonamide To a solution of Compound 308A (314 mg) in dichloromethane (5 ml) was added cyclobutanone (70 mg) followed by sodium triacetoxyborohydride (318 mg). The mixture was stirred overnight. The mixture was diluted with dichloromethane (300 ml) and washed with aqueous NaHCO$_3$, water and brine and dried over Na$_2$SO$_4$. After filtration, evaporation of solvent gave the title compound.

Compound 320B 4-(4-{[2-(4-chlorophenyl)-4,4-dimethylcyclohex-1-en-1-yl]methyl}piperazin-1-yl)-N-{[4-({3-[cyclobutyl(cyclopropyl)amino]propyl}amino)-3-nitrophenyl]sulfonyl}-2-(1H-pyrrolo[2,3-b]pyridin-5-yloxy)benzamide The title compound was prepared by substituting Compound 3J for Compound 1E and Compound 320A for Compound 1F in the procedure for Compound 1G. $^1$H NMR (300 MHz, dimethylsulfoxide-d6) δ 11.65 (s, 1H), 8.70 (m, 1H), 8.54 (d, 1H), 8.02 (d, 1H), 7.79 (dd, 1H), 7.49 (m, 3H), 7.34 (d, 2H), 7.03 (m, 3H), 6.66 (dd, 1H), 6.38 (dd, 1H), 6.19 (d, 1H), 3.37 (q, 2H), 3.06 (m, 4H), 2.73 (s, 2H), 2.63 (m, 2H), 2.21 (m, 8H), 1.82 (m, 3H), 1.53 (m, 2H), 1.38 (t, 2H), 0.94 (m, 6H), 0.41 (m, 4H).

Compound 321

4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 321A ethyl 5,5-difluoro-2-oxocyclohexanecarboxylate

To a solution of diethyl 4,4-difluoroheptanedioate (4.3 g) in toluene (50 ml) was added potassium 2-methylpropan-2-olate (2.87 g) and the reaction stirred overnight at room temperature. The reaction was quenched with 1N aqueous HCl (100 ml) and extracted with diethyl ether (150 ml). The ether layer was washed with brine (50 ml), dried over magnesium sulfate, filtered, and concentrated. Silica gel chromatography (Reveleris 40 g) eluting with a gradient of 1% to 5% ethyl acetate/hexanes gave the title compound.

Compound 321B ethyl 5,5-difluoro-2-(trifluoromethylsulfonyloxy) cyclohex-1-enecarboxylate To a solution of Compound 321A (2.37 g) in dichloromethane (40 ml) at 0° C. was added N,N-diisopropylethylamine (5.02 ml) followed by trifluoromethanesulfonic anhydride (2.33 ml) and the reaction was allowed to slowly warm to room temperature. After stirring overnight the reaction was quenched with 10 ml of water then 1N aqueous HCl (100 ml). The reaction was extracted with dichloromethane (3×75 ml), and the combined organics were washed with brine (50 ml) and concentrated. Silica gel chromatography (Reveleris 40 g) eluting with a gradient of 1% to 25% ethyl acetate/hexanes gave the title compound.

Compound 321C ethyl 2-(4-chlorophenyl)-5,5-difluorocyclohex-1-enecarboxylate A solution of Compound 321B (3.47 g), 4-chlorophenylboronic acid (1.925 g) and cesium fluoride (3.43 g) in 30 ml of 1,2-dimethoxyethane and 15 ml of ethanol was degassed with nitrogen for 5 minutes. Tetrakis(triphenylphosphine) palladium(0) (0.237 g) was added and the reaction was heated to 70° C. The reaction was diluted with ether (200 ml) and washed with 1N aqueous HCl (100 ml) and brine (100 ml), dried over magnesium sulfate, filtered, and concentrated. Silica gel chromatography (Reveleris 40 g) eluting with a gradient of 1% to 8% ethyl acetate/hexanes over 40 minutes gave the title compound.

Compound 321D (2-(4-chlorophenyl)-5,5-difluorocyclohex-1-enyl) methanol

To a solution of Compound 321C (1.84 g) in diethyl ether (25 ml) at 0° C. was added lithium aluminum hydride (1.0M, 4.28 ml). The reaction was quenched with the dropwise addition of water, then 1N aqueous HCl (50 ml) was added and the reaction diluted with diethyl ether (100 ml). The organic layer was separated, washed with brine (50 ml) dried over magnesium sulfate, filtered and concentrated to provide the title compound.

Compound 321E 2-(4-chlorophenyl)-5,5-difluorocyclohex-1-enecarbaldehyde

To a solution of Compound 321D (1.38 g) in dichloromethane (25 ml) was added Dess-Martin periodinane (2.489 g) and the reaction stirred for 1 hour at room temperature. The reaction was quenched with 1N aqueous NaOH solution (75 ml) and the product was extracted into dichloromethane (2×100 ml). The combined organics were washed with brine (75 ml), dried over magnesium sulfate, filtered, and concentrated. Silica gel chromatography (Reveris 80 g) eluting with a gradient of 1% to 10% ethyl acetate/hexanes over 40 minutes gave the title compound.

Compound 321F methyl 2-(1H-pyrrolo[2,3-b]pyridin-5-yloxy)-4-(4-((2-(4-chlorophenyl)-5,5-difluorocyclohex-1-enyl) methyl)piperazin-1-yl)benzoate The title compound was prepared by substituting Compound 321E for Compound 15E in the procedure for Compound 15G.

Compound 321G 2-(1H-pyrrolo[2,3-b]pyridin-5-yloxy)-4-(4-((2-(4-chlorophenyl)-5,5-difluorocyclohex-1-enyl)methyl) piperazin-1-yl)benzoic Acid The title compound was prepared by substituting Compound 321F for Compound 15G in the procedure for Compound 15H.

Compound 321H 4-(4-{[2-(4-chlorophenyl)-5,5-difluorocyclohex-1-en-1-yl]methyl}piperazin-1-yl)-N-({3-nitro-4-[(tetrahydro-2H-pyran-4-ylmethyl)amino] phenyl}sulfonyl)-2-(1H-pyrrolo[2,3-b]pyridin-5-yloxy)benzamide The title compound was prepared by substituting Compound 321G for Compound 1E and Compound 3J for Compound 1E in the procedure for Compound 1G. $^1$H NMR (300 MHz, dimethylsulfoxide-$d_6$) δ 11.74-11.63 (m, 1H), 11.53-11.29 (m, 1H), 8.57 (d, 2H), 8.05 (d, 1H), 7.85-7.77 (m, 1H), 7.49 (d, 3H), 7.38 (d, 2H), 7.16-7.06 (m, 3H), 6.73-6.64 (m, 1H), 6.43-6.36 (m, 1H), 6.21-6.14 (m, 1H), 3.93-3.77 (m, 2H), 3.29 (d, 4H), 3.07 (s, 4H), 2.79-2.57 (m, 4H), 2.45 (dd, 2H), 2.19 (s, 6H), 1.99-1.80 (m, 1H), 1.70-1.54 (m, 2H), 1.38-1.13 (n, 2H).

Compound 322

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl] methyl}piperazin-1-yl)-2-(1H-pyrrolo[2,3-b]pyridin-5-yloxy)benzamide

Compound 322A tert-butyl 4-fluoro-4-(hydroxymethyl)piperidine-1-carboxylate

1-Tert-butyl 4-ethyl 4-fluoropiperidine-1,4-dicarboxylate (2 g) was taken up in tetrahydrofuran (20 ml) and cooled in an ice bath. Lithium aluminum hydride (1.0M in dioxane, 5.09 ml) was added dropwise. The reaction was stirred at room temperature for 2 hours. The reaction was quenched with water and with 1M aqueous NaOH solution and then stirred another 1 hour at room temperature. The mixture was extracted with ethyl acetate, and the extracts were combined and washed with water and with brine, dried over $MgSO_4$, filtered and concentrated under vacuum. The crude product was used without further purification.

Compound 322B tert-butyl 4-((2-chloro-4-sulfamoylphenoxy)methyl)-4-fluoropiperidine-1-carboxylate The title compound was prepared by substituting Compound 322A for (tetrahydro-2H-pyran-4-yl)methanol and 3-chloro-4-fluorobenzenesulfonamide for 4-fluoro-3-nitrobenzenesulfonamide in the procedure for Compound 24A.

Compound 322C 3-chloro-4-((4-fluoropiperidin-4-yl)methoxy)benzenesulfonamide

The title compound was prepared by substituting Compound 322B for Compound 1A in the procedure for Compound 1B.

Compound 322D 3-chloro-4-((4-fluoro-1-(oxetan-3-yl)piperidin-4-yl)methoxy)benzenesulfonamide To a solution of Compound 322C (830 mg) in tetrahydrofuran (15 ml) and acetic acid (5 ml) was added oxetan-3-one (163 mg) and MP-cyanoborohydride (2.38 mmol/g, 1.9 g). The mixture was stirred at room temperature overnight. The reaction was then filtered and the filtrate was concentrated under vacuum. The residue was slurried in ether and the solid product was collected by filtration.

Compound 322E

N-[(3-chloro-4-{[4-fluoro-1-(oxetan-3-yl)piperidin-4-yl]methoxy}phenyl)sulfonyl]-4-(4-{[2-(4-chlorophenyl)-4,4-dimethylcyclohex-1-en-1-yl]methyl}piperazin-1-yl)-2-(1 1H-pyrrolo[2,3-b]pyridin-5-yloxy)benzamide The title compound was prepared by substituting Compound 322D for Compound 1F and Compound 3J for Compound 1E in the procedure for Compound 1G. $^1$H NMR (400 MHz, dimethylsulfoxide-d$_6$) δ 11.71 (s, 1H), 8.06 (d, 1H), 7.89 (d, 1H), 7.79 (m, 1H), 7.58 (d, 1H), 7.52 (t, 1H), 7.49 (d, 1H), 7.34 (d, 2H), 7.25 (d, 1H), 7.04 (d, 2H), 6.67 (dd, 1H), 6.42 (m, 1H), 6.18 (d, 1H), 4.55 (t, 2H), 4.44 (t, 2H), 4.24 (d, 2H), 3.44 (m, 2H), 3.07 (br s, 4H), 2.74 (m, 2H), 2.59 (m, 2H), 2.14 (m, 7H), 1.95 (m, 4H), 1.78 (m, 2H), 1.38 (t, 2H), 0.92 (s, 6H).

Compound 323

4-(4-{[2-(4-chlorophenyl)-4,4-dimethylcyclohex-1-en-1-yl]methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide Compound 323A 3-chloro-4-((tetrahydrofuran-3-yl)methoxy)benzenesulfonamide The title compound was prepared by substituting 4-fluoro-3-chlorobenzenesulfonamide for 4-fluoro-3-nitrobenzenesulfonamide and (tetrahydrofuran-3-yl)methanol for (tetrahydro-2H-pyran-4-yl)methanol in the procedure for Compound 24A, except here, dimethylformamide was used in place of tetrahydrofuran and the reaction was heated at 70° C. for two days.

Compound 323B 4-(4-{[2-(4-chlorophenyl)-4,4-dimethylcyclohex-1-en-1-yl]methyl}piperazin-1-yl)-N-{[3-chloro-4-(tetrahydrofuran-3-ylmethoxy)phenyl]sulfonyl}-2-(1H-pyrrolo[2,3-b]pyridin-5-yloxy)benzamide The title compound was prepared by substituting Compound 323A for Compound 11B in the procedure for Compound 11D. $^1$H NMR (500 MHz, dimethylsulfoxide-d$_6$) δ 11.73 (s, 1H), 8.07 (d, 1H), 7.89 (d, 1H), 7.80 (dd, 1H), 7.59 (d, 1H), 7.51 (dd, 1H), 7.49 (d, 1H), 7.34 (d, 2H), 7.23 (d, 1H), 7.03 (d, 2H), 6.66 (dd, 1H), 6.42 (m, 1H), 6.19 (d, 1H), 4.07 (m, 2H), 3.80 (m, 2H), 3.68 (m, 1H) 3.56 (m, 1H), 3.10 (br m, 4H), 2.85 (br s, 2H), 2.69 (m, 1H), 2.32 (br m, 4H), 2.17 (br m, 2H), 2.02 (m, 1H), 1.96 (s, 2H), 1.69 (m, 1H), 1.40 (t, 2H), 0.92 (s, 6H).

Compound 324

4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide Compound 324A 4-((trans-4-hydroxycyclohexyl)methylamino)-3-nitrobenzenesulfonamide The title compound was prepared by substituting Compound 120A for Compound 39B in the procedure for Compound 39C.

Compound 324B 4-(4-{[2-(4-chlorophenyl)-5,5-difluorocyclohex-1-en-1-yl]methyl}piperazin-1-yl)-N-[(4-{[(trans-4-hydroxycyclohexyl)methyl]amino}-3-nitrophenyl)sulfonyl]-2-(1H-pyrrolo[2,3-b]pyridin-5-yloxy)benzamide The title compound was prepared by substituting Compound 321G for Compound 1E and Compound 324A for Compound 1F in the procedure for Compound 1G. $^1$H NMR (300 MHz, dimethylsulfoxide-d$_6$) δ 11.69 (s, 1H), 11.41 (s, 1H), 8.65-8.50 (m, 2H), 8.05 (d, 1H), 7.80 (dd, 1H), 7.60-7.44 (m, 3H), 7.41-7.34 (m, 2H), 7.14-7.02 (m, 3H), 6.68 (dd, 1H), 6.39 (dd, 1H), 6.17 (d, 1H), 4.50 (d, 1H), 3.23 (t, 2H), 3.06 (s, 4H), 2.70 (d4H), 2.44 (s, 2H), 2.33-1.94 (m, 6H), 1.78 (dd, 4H), 1.51 (d, 2H), 1.23 (s, 2H), 1.16-0.92 (m, 2H).

Compound 325

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide

Compound 325A methyl 2-(1H-pyrrolo[2,3-b]pyridin-5-yloxy)-4-(4-((9-(4-chlorophenyl)-3-(oxetan-3-yl)-3-azaspiro[5.5]undec-8-en-8-yl)methyl)piperazin-1-yl)benzoate The title compound was prepared by substituting oxetan-3-one for 1,3-difluoropropan-2-one in the procedure for Compound 265G.

Compound 325B 2-(1H-pyrrolo[2,3-b]pyridin-5-yloxy)-4-(4-((9-(4-chlorophenyl)-3-(oxetan-3-yl)-3-azaspiro[5.5]undec-8-en-8-yl)methyl)piperazin-1-yl)benzoic Acid The title compound was prepared by substituting Compound 325A for Compound 15G in the procedure for Compound 15H.

Compound 325C

N-({3-chloro-4-[(4-fluorotetrahydro-2H-pyran-4-yl)methoxy]phenyl}sulfonyl)-4-(4-{[9-(4-chlorophenyl)-3-(oxetan-3-yl)-3-azaspiro[5.5]undec-8-en-8-yl]methyl}piperazin-1-yl)-2-(1H-pyrrolo[2,3-b]pyridin-5-yloxy)benzamide The title compound was prepared by substituting Compound 325B for Compound 1E and Compound 286A for Compound 1F in the procedure for Compound 1G. $^1$H NMR (300 MHz, dimethylsulfoxide-$d_6$) δ 11.67 (s, 1H), 11.13 (s, 1H), 8.05 (d, 1H), 7.87 (d, 1H), 7.80-7.70 (m, 1H), 7.59-7.46 (m, 3H), 7.34 (d, 2H), 7.21 (d, 1H), 7.11-7.03 (m, 2H), 6.66 (d, 1H), 6.41 (dd, 1H), 6.18 (d, 1H), 4.50 (dd, 4H), 4.26 (d, 2H), 3.85-3.69 (m, 2H), 3.61 (d, 3H), 3.05 (s, 4H), 2.69 (s, 2H), 2.37 (s, 4H), 2.17 (s, 6H), 2.04 (s, 2H), 1.87 (d, 4H), 1.49 (d, 6H).

Compound 326

4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide

Compound 326A (R)-4-((4-cyclopropylmorpholin-2-yl)methylamino)-3-nitrobenzenesulfonamide The title compound was prepared by substituting Compound 258E for Compound 173A in the procedure for Compound 173B.

Compound 326B 4-(4-{[2-(4-chlorophenyl)-4,4-dimethylcyclohex-1-en-1-yl]methyl}piperazin-1-yl)-N-{[4-({[(2R)-4-cyclopropylmorpholin-2-yl]methyl}amino)-3-nitrophenyl]sulfonyl}-2-(1H-pyrrolo[2,3-b]pyridin-5-yloxy)benzamide The title compound was prepared by substituting Compound 326A for Compound 130C in the procedure for Compound 130D. $^1$H NMR (500 MHz, pyridine-$d_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Compound 327

4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide

Compound 327A (S)-4-((4-cyclopropylmorpholin-2-yl)methylamino)-3-nitrobenzenesulfonamide The title compound was prepared by substituting Compound 259E for Compound 173A in the procedure for Compound 173B.

Compound 327B 4-(4-{[2-(4-chlorophenyl)-4,4-dimethylcyclohex-1-en-1-yl]methyl}piperazin-1-yl)-N-{[4-({[(2S)-4-cyclopropylmorpholin-2-yl]methyl}amino)-3-nitrophenyl]sulfonyl}-2-(1H-pyrrolo[2,3-b]pyridin-5-yloxy)benzamide The title compound was prepared by substituting Compound 327A for Compound 130C in the procedure for Compound 130D. $^1$H NMR (500 MHz, pyridine-$d_5$) δ 13.00 (s, 1H), 9.26 (d, 1H), 8.88 (t, 1H), 8.44 (d, 1H), 8.34 (dd, 1H), 8.12 (d, 1H), 7.66 (m, 2H), 7.44 (d, 2H), 7.07 (d, 2H), 6.94 (d, 1H), 6.75 (dd, 1H), 6.54 (d, 1H), 6.48 (m, 1H), 3.88 (d, 1H), 3.84-3.81 (m, 1H), 3.59 (dt, 1H), 3.50-3.40 (m, 2H), 3.07 (m, 4H), 2.93 (d, 1H), 2.77 (s, 2H), 2.69 (d, 1H), 2.34 (dt, 1H), 2.26 (m, 2H), 2.21 (t, 1H), 2.14 (m, 4H), 1.97 (s, 2H), 1.58 (m, 1H), 1.39 (t, 2H), 0.94 (s, 6H), 0.45-0.39 (m, 4H).

Compound 328

4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 328A spiro[2.5]octan-5-one

To a solution of 3-ethoxycyclohex-2-enone (48.1 ml) in ether (1000 ml) was added titanium(IV) isopropoxide (110 ml) followed by addition of ethylmagnesium bromide (357 ml) at ambient temperature. The reaction mixture was stirred for 2 hours at ambient temperature and was then quenched with water (500 ml). The organic layer was separated (decanted) and the water layer was extracted with ether (3×300 ml). The combined extracts were partially concentrated to approximately 300 ml. p-Toluenesulfonic acid monohydrate (3.0 g) was added and the reaction mixture was stirred overnight at ambient temperature. The reaction mixture was then washed with saturated aqueous NaHCO$_3$ solution., dried (MgSO$_4$), filtered and concentrated. The concentrate was purified by fractional distillation (1st fraction b.p. 27° C. at 23 torr (not product), 2nd fraction (product) b.p. 75° C. at 8 torr).

Compound 328B 5-chlorospiro[2.5]oct-5-ene-6-carbaldehyde

N,N-dimethylformamide (2.1 ml) in dichloromethane (3.2 ml) at −5° C. was treated slowly with POCl$_3$ (2.33 ml) keeping the bath temperature less than 0° C. The cooling bath was removed and the mixture was stirred at ambient temperature for 30 minutes. The reaction mixture was returned to the cooling bath and Compound 328A (2.484 g) in dichloromethane (4 ml) was added slowly to the reaction mixture. The reaction mixture was heated at 45° C. for 15 hours, cooled to room temperature and then poured into a mixture of ice and saturated aqueous sodium acetate solution. After the ice melted, the mixture was extracted with diethyl ether. The combined extracts were washed with saturated aqueous NaHCO$_3$ solution and brine, dried (MgSO$_4$), filtered and concentrated. The concentrate was chromatographed with 0 to 10% CH$_2$Cl$_2$ in hexanes, then 25% CH$_2$Cl$_2$ in hexanes and then 100% CH$_2$Cl$_2$ as the eluents.

Compound 328C 5-(4-chlorophenyl)spiro[2.5]oct-5-ene-6-carbaldehyde

Compound 328B (2.9 g), 4-chlorophenylboronic acid (2.87 g), palladium(II) acetate (0.103 g), K$_2$CO (5.28 g) and tetrabutylammonium bromide (4.93 g) were combined in a 100-ml round bottomed flask with water (17.0 ml). The flask was flushed with nitrogen and stirred at 45° C. for 14 hours. The reaction mixture was partitioned between brine and diethyl ether. The organic layer was washed with brine, dried (MgSO$_4$), filtered through a plug of celite, concentrated and chromatographed on silica gel with 0 to 2% ethyl acetate in hexanes as the eluent.

Compound 328D methyl 2-(1H-pyrrolo[2,3-b]pyridin-5-yloxy)-4-(4-((5-(4-chlorophenyl)spiro[2.5]oct-5-en-6-yl)methyl)piperazin-1-yl)benzoate The title compound was prepared by substituting Compound 15F for tert-butyl piperazine carboxylate and Compound 328C for 4-chlorobiphenyl-2-carboxaldehyde in the procedure for Compound 1A.

Compound 328E 2-(1H-pyrrolo[2,3-b]pyridin-5-yloxy)-4-(4-((5-(4-chlorophenyl)spiro[2.5]oct-5-en-6-yl)methyl)piperazin-1-yl)benzoic acid hydrochloride Compound 328D (0.85 g) in a mixture of tetrahydrofuran (4.8 ml), methanol (2.4 ml) and water (2.4 ml) was treated with LiOH.H$_2$O (0.184 g) and heated overnight at 50° C.
The reaction mixture was cooled to room temperature, concentrated to remove tetrahydrofuran and methanol and acidified with 1 N aqueous HCl causing precipitation of the product. The solid was collected by filtration, rinsed with water and dried overnight in a vacuum oven at 80° C. to provide the title compound.

Compound 328F 4-(4-{[5-(4-chlorophenyl)spiro[2.5]oct-5-en-6-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide The title compound was prepared by substituting Compound 328E for Compound 1E in the procedure for Compound 1G. $^1$H NMR (500 MHz, pyridine-d$_5$) 13.07 (s, 1H), 9.32 (d, 1H), 8.68 (t, 1H), 8.44 (d, 1H), 8.38 (dd, 1H), 8.10 (d, 1H), 7.68 (m, 1H), 7.66 (d, 1H), 7.43 (m, 2H), 7.10 (m, 2H), 6.91 (d, 1H), 6.75 (dd, 1H), 6.51 (m, 2H), 3.97 (dd, 2H), 3.30 (td, 2H), 3.16 (t, 2H), 3.06 (m, 4H), 2.81 (s, 2H), 2.37 (t, 2H), 2.16 (m, 4H), 2.11 (s, 2H), 1.81 (m, 1H), 1.58 (dd, 2H), 1.45 (t, 2H), 1.32 (qd, 2H), 0.38 (s, 4H).

Compound 329

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 329A ethyl 4-(cyclopropylamino)cyclohexanecarboxylate To a solution of ethyl 4-oxocyclohexanecarboxylate (3.4 g) in dichloromethane (30 ml) was added cyclopropanamine (1.14 g) followed by sodium triacetoxyborohydride (4.24 g). The mixture was stirred overnight. The mixture was diluted with dichloromethane (300 ml) and washed with 2N NaOH, water, brine and dried over Na$_2$SO$_4$. Filtration and evaporation of the solvent gave the title compound.

Compound 329B ethyl 4-(cyclopropyl(oxetan-3-yl)amino)cyclohexanecarboxylate

To a solution of Compound 329A (1.05 g) in dichloromethane (10 ml) was added oxetan-3-one (0.358 g) followed by sodium triacetoxyborohydride (1.05 g). The mixture was stirred overnight. The mixture was diluted with dichloromethane (300 ml) and washed with 2N aqueous NaOH, water, brine and dried over Na$_2$SO$_4$. Filtration and evaporation of the solvent gave the title compound.

Compound 329C (4-(cyclopropyl(oxetan-3-yl)amino)cyclohexyl)methanol

To a solution of Compound 329B (1.2 g) in tetrahydrofuran (20 ml) was added lithium aluminum hydride (0.681 g). The mixture was stirred overnight. 2N aqueous NaOH solution was added dropwise to the reaction mixture. The mixture was then diluted with ethyl acetate (300 ml) and washed with water, brine and dried over $Na_2SO_4$. Filtration and evaporation of the solvent gave the title compound.

Compound 329D 5-chloro-6-((4-(cyclopropyl(oxetan-3-yl)amino)cyclohexyl)methoxy)pyridine-3-sulfonamide To a solution of Compound 329C (706 mg) in N,N-dimethylformamide (6 ml) was added NaH (60% in mineral oil, 300 mg). The mixture was stirred for 30 minutes, and then 5,6-dichloropyridine-3-sulfonamide (706 mg) was added. The mixture was stirred overnight. The mixture was poured over aqueous $NH_4Cl$ and extracted with ethyl acetate (3×200 ml). The combined organic layers were washed with water, brine and dried over $Na_2SO_4$. After filtration and evaporation of the solvent the residue was loaded on a silica gel cartridge and eluted with 5 to 10% 7N $NH_3$ in methanol in dichloromethane to provide the title compound.

Compound 329E

N-{[5-chloro-6-({4-[cyclopropyl(oxetan-3-yl)amino]cyclohexyl}methoxy)pyridin-3-yl]sulfonyl}-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 329D for Compound 1F in the procedure for Compound 1G. $^1$H NMR (300 MHz, dimethylsulfoxide-$d_6$) δ 11.64 (s, 1H), 8.50 (m, 1H), 8.16 (s, 1H), 8.02 (d, 1H), 7.51 (m, 3H), 7.35 (d, 2H), 7.04 (d, 2H), 6.67 (dd, 1H), 6.38 (m, 1H), 6.21 (s, 1H), 4.70 (m, 2 H), 4.43 (t, 3H), 4.19 (m, 2H), 3.12 (m, 4H), 2.84 (m, 2H), 2.19 (m, 6H), 1.96 (s, 3H), 1.77 (m, 3H), 1.38 (m, 7H), 0.93 (s, 6H), 0.44 (m, 4H).

Compound 330

4-(4-{[5-(4-chlorophenyl)spiro[2.5]oct-5-en-6-yl]methyl}piperazin-1-yl)-N-[(4-{[(4-cyclopropylmorpholin-2-yl)methyl]amino}-3-nitrophenyl)sulfonyl]-2-(1H-pyrrolo[2,3-b]pyridin-5-yloxy)benzamide The title compound was prepared by substituting Compound 328E for Compound 3J and Compound 218A for Compound 11B in the procedure for Compound 11D. $^1$H NMR (400 MHz, pyridine-$d_5$) δ 13.01 (s, 1H), 9.26 (d, 1H), 8.88 (t, 1H), 8.43 (d, 1H), 8.34 (dd, 1H), 8.11 (d, 1H), 7.66 (m, 2H), 7.42 (m, 2H), 7.09 (m, 2H), 6.95 (d, 1H), 6.75 (dd, 1H), 6.53 (d, 1H), 6.49 (dd, 1H), 3.84 (m, 2H), 3.58 (td, 1H), 3.45 (m, 2H), 3.06 (m, 4H), 2.93 (d, 1H), 2.81 (s, 2H), 2.69 (d, 1H), 2.35 (m, 3H), 2.19 (m, 5H), 2.11 (s, 2H), 1.58 (m, 1H), 1.45 (t, 2H), 0.42 (m, 8H).

Compound 331

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 331A tert-butyl 2-((2-chloro-4-sulfamoylphenoxy)methyl)morpholine-4-carboxylate To a solution of tert-butyl 2-(hydroxymethyl)morpholine-4-carboxylate (0.478 g) in anhydrous N,N-dimethylformamide (5 ml) was added sodium hydride (0.280 g). The mixture was stirred at room temperature for 30 minutes, followed by addition of 3-chloro-4-fluorobenzenesulfonamide (0.419 g). The mixture was stirred at 40° C. overnight. The reaction was quenched with water (10 ml), and the mixture was adjusted to ~pH 7 and extracted with ethyl acetate. The crude product was purified on a silica gel column eluting with 60% ethyl acetate in hexane to provide the title compound.

Compound 331B 3-chloro-4-(morpholin-2-ylmethoxy)benzenesulfonamide

The title compound was prepared by substituting Compound 331A for Compound 113A in the procedure for Compound 134A.

Compound 331C 3-chloro-4-((4-cyclopropylmorpholin-2-yl)methoxy)benzenesulfonamide The title compound was prepared by substituting Compound 331B for Compound 173A in the procedure for Compound 173B.

Compound 331D

N-({3-chloro-4-[(4-cyclopropylmorpholin-2-yl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 331C for Compound 130C in the procedure for Compound 130D. $^1$H NMR (500 MHz, pyridine-$d_5$) δ 13.04 (s, 1H), 8.54 (d, 1H), 8.43 (d, 1H), 8.27 (dd, 1H), 8.09 (d, 1H), 7.66 (m, 2H), 7.44 (d, 2H), 7.07 (d, 2H), 7.05 (d, 1H), 6.75 (dd, 1H), 6.52 (d, 1H), 6.50 (m, 1H), 4.20 (dd, 1H), 4.10 (dd, 1H), 3.94 (m, 1H), 3.86 (d, 1H), 3.58 (dt, 1H), 3.06 (m, 5H), 2.77 (s, 2H), 2.69 (d, 1H), 2.40-2.20 (m, 4H), 2.14 (m, 4H), 1.97 (s, 2H), 1.60 (m, 1H), 1.39 (t, 2H), 0.94 (s, 6H), 0.41 (m, 4H).

Compound 332

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 332A tert-butyl 2-((2-chloro-4-sulfamoylphenylamino)methyl)morpholine-4-carboxylate A solution of 3-chloro-4-fluorobenzenesulfonamide (1.0 g), tert-butyl 2-(aminomethyl)morpholine-4-carboxylate (1.135 g) and N-ethyl-N-isopropylpropan-2-amine (1.246 ml) in dimethylsulfoxide (15 ml) was stirred at 115° C. for 72 hours. The mixture was concentrated, and the residue was purified on a silica gel column eluting with 60% ethyl acetate to provide the title compound.

Compound 332B 3-chloro-4-(morpholin-2-ylmethylamino)benzenesulfonamide

The title compound was prepared by substituting Compound 332A for Compound 113A in the procedure for Compound 134A.

Compound 332C 3-chloro-4-(((4-cyclopropylmorpholin-2-yl)methyl)amino)benzenesulfonamide The title compound was prepared by substituting Compound 332B for Compound 173A in the procedure for Compound 173B.

Compound 332D

N-[(3-chloro-4-{[(4-cyclopropylmorpholin-2-yl)methyl]amino}phenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 332C for Compound 130C in the procedure for Compound 130D. $^1$H NMR (500 MHz, pyridine-$d_5$) δ 13.05 (s, 1H), 8.45 (m, 2H), 8.21 (dd, 1H), 8.12 (d, 1H), 7.69 (d, 1H), 7.67 (t, 1H), 7.44 (d, 2H), 7.07 (d, 2H), 6.78 (d, 1H), 6.74 (dd, 1H), 6.52 (d, 1H), 6.50 (m, 1H), 6.37 (m, 1H), 3.84 (d, 1H), 3.77 (m, 1H), 3.54 (dt, 1H), 3.35 (m, 2H), 3.05 (m, 4H), 2.94 (d, 1H), 2.77 (s, 2H), 2.68 (d, 1H), 2.32 (dt, 1H), 2.26 (m, 2H), 2.18-2.12 (m, 5H), 1.97 (s, 2H), 1.55 (m, 1H), 1.39 (t, 2H), 0.94 (s, 6H), 0.41 (m, 4H).

Compound 333

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide

Compound 333A 2-((2-chloro-4-sulfamoylphenylamino)methyl)-N-ethyl-N-methylmorpholine-4-carboxamide The title compound was prepared by substituting Compound 332B for Compound 134A and N-methyl-N-ethyl carbamyl chloride for methyl iodide in the procedure for Compound 134B.

Compound 333B

2-{[(2-chloro-4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}phenyl)amino]methyl}-N-ethyl-N-methylmorpholine-4-carboxamide The title compound was prepared by substituting Compound 333A for Compound 130C in the procedure for Compound 130D. $^1$H NMR (500 MHz, pyridine-$d_5$) δ 13.05 (s, 1H), 8.46 (s, 1H), 8.45 (s, 1H), 8.20 (dd, 1H), 8.10 (d, 1H), 7.69 (d, 1H), 7.67 (t, 1H), 7.44 (d, 2H), 7.07 (d, 2H), 6.79 (d, 1H), 6.73 (dd, 1H), 6.52 (dd, 1H), 6.49 (d, 1H), 6.43 (m, 1H), 3.83 (d, 2H), 3.73 (d, 1H), 3.59 (dt, 1H), 3.41-3.35 (m, 3H), 3.20 (q, 2H), 3.05 (m, 4H), 2.95 (t, 1H), 2.84 (dd, 1H), 2.76 (s, 2H), 2.73 (s, 3H), 2.25 (m, 2H), 2.14 (m, 4H), 1.97 (s, 2H), 1.39 (t, 2H), 1.04 (t, 3H), 0.94 (s, 6H).

Compound 334

(2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide

Compound 334A (S)-2-((3-chloro-5-sulfamoylpyridin-2-yloxy)methyl)-N-ethyl-N-methylmorpholine-4-carboxamide The title compound was prepared by substituting Compound 244B for Compound 134A and N-methyl-N-ethyl carbamyl chloride for methyl iodide in the procedure for Compound 134B.

Compound 334B (2S)-2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)oxy]methyl}-N-ethyl-N-methylmorpholine-4-carboxamide The title compound was prepared by substituting Compound 334A for Compound 130C in the procedure for Compound 130D. $^1$H NMR (500 MHz, pyridine-$d_5$) δ 12.98

(s, 1H), 9.08 (d, 1H), 8.70 (d, 1H), 8.42 (d, 1H), 8.11 (d, 1H), 7.67 (t, 1H), 7.64 (d, 1H), 7.44 (d, 2H), 7.07 (d, 2H), 6.75 (dd, 1H), 6.53 (d, 1H), 6.48 (m, 1H), 4.58 (dd, 1H), 4.47 (dd, 1H), 4.03 (m, 1H), 3.84 (m, 2H), 3.63 (dt, 1H), 3.45 (d, 1H), 3.22 (q, 2H), 3.07 (m, 4H), 3.05-2.95 (m, 2H), 2.78 (s, 3H), 2.77 (s, 2H), 2.26 (m, 2H), 2.14 (m, 4H), 1.97 (s, 2H), 1.39 (t, 2H), 1.07 (t, 3H), 0.94 (s, 6H).

Compound 335

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 335A tert-butyl 2-((3-chloro-5-sulfamoylpyridin-2-ylamino)methyl)morpholine-4-carboxylate The title compound was prepared by substituting Compound 40A for 4-fluoro-3-nitrobenzenesulfonamide and tert-butyl 2-(aminomethyl)morpholine-4-carboxylate for (tetrahydropyran-4-yl)methylamine in the procedure for Compound 1F.

Compound 335B 5-chloro-6-(morpholin-2-ylmethylamino)pyridine-3-sulfonamide

The title compound was prepared by substituting Compound 335A for Compound 113A in the procedure for Compound 134A.

Compound 335C 5-chloro-6-((4-cyclopropylmorpholin-2-yl)methylamino)pyridine-3-sulfonamide The title compound was prepared by substituting Compound 335B for Compound 173A in the procedure for Compound 173B.

Compound 335D

N-[(5-chloro-6-{[(4-cyclopropylmorpholin-2-yl)methyl]amino}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 335C for Compound 130C in the procedure for Compound 130D. $^1$H NMR (500 MHz, pyridine-$d_5$) δ 13.02 (s, 1H), 9.15 (d, 1H), 8.49 (d, 1H), 8.43 (d, 1H), 8.11 (d, 1H), 7.80 (t, 1H), 7.69 (d, 1H), 7.65 (t, 1H), 7.44 (d, 2H), 7.07 (d, 2H), 6.73 (dd, 1H), 6.52 (m, 1H), 6.49 (d, 1H), 3.92 (m, 1H), 3.84 (m, 2H), 3.70 (m, 1H), 3.54 (dt, 1H), 3.05 (m, 4H), 2.99 (d, 1H), 2.76 (s, 2H), 2.68 (d, 1H), 2.32 (dt, 1H), 2.25 (m, 2H), 2.12 (m, 5H), 1.97 (s, 2H), 1.53 (m, 1H), 1.39 (t, 2H), 0.93 (s, 6H), 0.40 (m, 4H).

Compound 336

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide Compound 336A 2-((3-chloro-5-sulfamoylpyridin-2-ylamino)methyl)-N-ethyl-N-methylmorpholine-4-carboxamide The title compound was prepared by substituting Compound 335B for Compound 134A and N-methyl-N-ethyl carbamyl chloride for methyl iodide in the procedure for Compound 134B.

Compound 336B

2-{[(3-chloro-5-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}pyridin-2-yl)amino]methyl}-N-ethyl-N-methylmorpholine-4-carboxamide The title compound was prepared by substituting Compound 336A for Compound 130C in the procedure for Compound 130D. $^1$H NMR (500 MHz, pyridine-$d_5$) δ 13.03 (s, 1H), 9.14 (d, 1H), 8.51 (d, 1H), 8.43 (d, 1H), 8.11 (d, 1H), 7.89 (m, 1H), 7.69 (d, 1H), 7.66 (t, 1H), 7.44 (d, 2H), 7.07 (d, 2H), 6.74 (dd, 1H), 6.51 (m, 1H), 6.48 (d, 1H), 3.96 (m, 1H), 3.90-3.70 (m, 4H), 3.59 (dt, 1H), 3.43 (d, 1H), 3.17 (q, 2H), 3.05 (m, 4H), 2.95 (dt, 1H), 2.81 (dd, 1H), 2.76 (s, 2H), 2.72 (s, 3H), 2.25 (m, 2H), 2.13 (m, 4H), 1.97 (s, 2H), 1.39 (t, 2H), 1.03 (t, 3H), 0.93 (s, 6H).

Compound 337

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide Compound 337A methyl 4,4-dimethyl-2-(trifluoromethylsulfonyloxy)cyclohex-1-enecarboxylate To a suspension of hexane washed NaH (17 g) in dichloromethane (700 ml) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried ($Na_2SO_4$), filtered, and concentrated to give the product.

Compound 337B methyl 2-(4-chlorophenyl)-4,4-dimethylcyclohex-1-enecarboxylate

Compound 337A (62.15 g), 4-chlorophenylboronic acid (32.24 g), CsF (64 g) and tetrakis(triphenylphosphine)palladium(0) (2 g) in 2:1 dimethoxyethane/methanol (600 ml) were heated to 70° C. for 24 hours. The mixture was concentrated. Ether (4×200 ml) was added and the mixture was filtered. The combined ether solution was concentrated to give the product.

Compound 337C (2-(4-chlorophenyl)-4,4-dimethylcyclohex-1-enyl) methanol

To a mixture of $LiBH_4$ (13 g), Compound 337B (53.8 g) and ether (400 ml), was added methanol (25 ml) slowly by syringe. The mixture was stirred at room temperature for 24 hours. The reaction was quenched with 1N HCl with ice-cooling. The mixture was diluted with water and extracted with ether (3×100 ml). The extracts were dried ($Na_2SO_4$), filtered, and concentrated. The crude product was chromatographed on silica gel with 0-30% ethyl acetate/hexanes.

Compound 337D tert-butyl 4-((2-(4-chlorophenyl)-4,4-dimethylcyclohex-1-enyl)methyl)piperazine-1-carboxylate Mesyl Chloride (7.5 mil) was added via syringe to Compound 337C (29.3 g) and triethylamine (30 ml) in $CH_2Cl_2$ (500 ml) at 0° C., and the mixture was stirred for 1 minute. N-t-butoxycarbonylpiperazine (25 g) was added and the mixture was stirred at room temperature for 24 hours. The suspension was washed with brine, dried, ($Na_2SO_4$), filtered, and concentrated. The crude product was chromatographed on silica gel with 10-20% ethyl acetate/hexanes.

Compound 337E 1-((2-(4-chlorophenyl)-4,4-dimethylcyclohex-1-enyl)methyl)piperazine Compound 337D (1 g) was stirred in dichloromethane (10 ml), trifluoroacetic acid (10 ml), and triethylsilane (1 ml) for 1 hour. The mixture was concentrated, taken up in a mixture of dichloromethane (100 ml) and saturated aqueous $Na_2CO_3$ solution (20 ml) and stirred for 10 minutes. The layers were separated, and the organic layer was dried over $Na_2SO_4$, and concentrated to give the product.

Compound 337F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 ml) was added 1M lithium hexamethyldisilazide in tetrahydrofuran (86 ml), and after 10 minutes, TIPS-Cl (triisopropylchlorosilane) (18.2 ml) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Compound 337G 1-(triisopropylsilyl)-1H-pyrrolo[2,3-b]pyridin-5-ol

To a mixture of Compound 337F (24.3 g) in tetrahydrofuran (500 ml) at −78° C. was added 2.5M BuLi (30.3 ml). After 2 minutes, trimethylborate (11.5 ml) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 ml) at 0° C., and 1M aqueous NaOH (69 ml) was added, followed by 30% aqueous $H_2O_2$ (8.43 ml), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Compound 337H methyl 2-(1H-pyrrolo[2,3-b]pyridin-5-yloxy)-4-fluorobenzoate

A mixture of Compound 337G (8.5 g), methyl 2,4-difluorobenzoate (7.05 g), and $K_3PO_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 337I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound 337H (1.55 g), Compound 337E (2.42 g), and $HK_2PO_4$ (1.42 g) in dimethylsulfoxide (20 ml) at 135° C. was stirred for 24 hours. The reaction was cooled, diluted with ether (400 ml), and washed three times with 1M aqueous NaOH, and brine, and concentrated. The crude product was chromatographed on silica gel with 10-50% ethyl acetate/hexanes.

Compound 337J 2-(1H-pyrrolo[2,3-b]pyridin-5-yloxy)-4-(4-((2-(4-chlorophenyl)-4,4-dimethylcyclohex-1-enyl)methyl) piperazin-1-yl)benzoic Acid Compound 337I (200 mg) in dioxane (10 ml) and 1M aqueous NaOH (6 ml) at 50° C. was stirred for 24 hours. The reaction was cooled, added to $NaH_2PO_4$ solution, and extracted three times with ethyl acetate. The combined extracts were washed with brine, and concentrated to give the pure product.

Compound 337K tert-butyl (4-hydroxy-4-methylcyclohexyl)methylcarbamate

To a vigorous stirring solution of tert-butyl(4-oxocyclohexyl)methylcarbamate (1.7 g) in tetrahydrofuran (40 ml) at −78° C. was dropwise added 1.6 M methyllithium (14.02 ml) in ether. After completion of the addition, the mixture was stirred at −78° C. for 1.2 hours and poured into a cold $NH_4Cl$ aqueous solution. The resulting mixture was extracted with dichloromethane (100 ml, three times) and the organic layer was dried over Na$_2$SO$_4$, filtered, and concentrated. The residue was dissolved in dichloromethane and loaded onto an Analogix purification system, and it was eluted with 0-50% ethyl acetate in dichloromethane to provide the title compound.

Compound 337L 4-(aminomethyl)-1-methylcyclohexanol

Compound 337K (1.3 g) in dichloromethane (5 ml) at 0° C. was treated with trifluoroacetic acid (2.1 ml) and a few drops of water for 1 hour. The reaction mixture was concentrated and the residue was directly used for next step.

Compound 337M 4-((trans-4-hydroxy-4-methylcyclohexyl)methylamino)-3-nitrobenzenesulfonamide Compound 337L (732 mg) and 4-fluoro-3-nitrobenzenesulfonamide (1.1 g) in tetrahydrofuran (15 ml) was treated with triethylamine overnight. The reaction mixture, was concentrated and the residue was purified by a reverse phase chromatography, eluting with 30%-50% acetonitrile in 0.1% trifluoroacetic acid water solution to isolate the title compound.

Compound 337N 4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide A mixture of Compound 337J (3.0 g), Compound 337M (1.98 g), N, N-dimethylpyridin-4-amine (1.93 g) and N$^1$-((ethylimino)methylene)-N$^3$,N$^3$-dimethylpropane-1,3-diamine hydrochloride (1.31 g) in dichloromethane (50 ml) was stirred overnight and concentrated. The residue was purified by reverse chromatography, eluted with 40%-70% acetonitrile in 0.1% TFA water. The desired fractions were concentrated to remove acetonitrile, neutralized with NaHCO$_3$ and extracted with dichloromethane. The organic layer was dried over Na$_2$SO$_4$, concentrated and dried to provide the title compound. $^1$H NMR (400 MHz, dimethylsulfoxide-d$_6$) δ 11.68 (s, 1H), 8.52-8.58 (m, 2H), 8.04 (d, 1H), 7.79 (dd, 1H), 7.53 (d, 1H), 7.47-7.52 (m, 2H), 7.30-7.37 (m, 2H), 7.07 (d, 1H), 7.01-7.06 (m, 2H), 6.68 (dd, 1H), 6.39 (dd, 1H), 6.19 (d, 1H), 4.25 (s, 1H), 3.25-3.32 (m, 4H), 3.07 (s, 4H), 2.75 (s, 2H), 2.09-2.24 (m, 6H), 1.95 (s, 2H), 1.50-1.73 (m, 5H), 1.28-1.43 (m, 4H), 1.06-1.18 (m, 5H), 0.92 (s, 6H).

Compound 338

4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide Compound 338A methyl 4,4-dimethyl-2-(trifluoromethylsulfonyloxy)cyclohex-1-enecarboxylate To a suspension of hexane washed NaH (17 g) in dichloromethane (700 ml) was added 5,5-dimethyl-2-methoxycarbonylcyclohexanone (38.5 g) dropwise at 0° C. After stirring for 30 minutes, the mixture was cooled to −78° C. and trifluoromethanesulfonic anhydride (40 mL) was added. The reaction mixture was warmed to room temperature and stirred for 24 hours. The organic layer was washed with brine, dried (Na$_2$SO$_4$), filtered, and concentrated to give the product.

Compound 338B methyl 2-(4-chlorophenyl)-4,4-dimethylcyclohex-1-enecarboxylate

Compound 338A (62.15 g), 4-chlorophenylboronic acid (32.24 g), CsF (64 g) and tetrakis(triphenylphosphine)palladium(0) (2 g) in 2:1 dimethoxyethane/methanol (600 ml) were heated to 70° C. for 24 hours. The mixture was concentrated. Ether (4×200 ml) was added and the mixture was filtered. The combined ether solution was concentrated to give the product.

Compound 338C (2-(4-chlorophenyl)-4,4-dimethylcyclohex-1-enyl)methanol

To a mixture of LiBH$_4$ (13 g), Compound 338B (53.8 g) and ether (400 ml), was added methanol (25 ml) slowly by syringe. The mixture was stirred at room temperature for 24 hours. The reaction was quenched with 1N aqueous HCl with ice-cooling. The mixture was diluted with water and extracted with ether (3×100 ml). The extracts were dried (Na$_2$SO$_4$), filtered, and concentrated. The crude product was chromatographed on silica gel with 0-30% ethyl acetate/hexanes.

Compound 338D tert-butyl 4-((2-(4-chlorophenyl)-4,4-dimethylcyclohex-1-enyl)methyl)piperazine-1-carboxylate Mesyl Chloride (7.5 ml) was added via syringe to Compound 338C (29.3 g) and triethylamine (30 ml) in CH$_2$Cl$_2$ (500 ml) at 0° C., and the mixture was stirred for 1 minute. N-t-butoxycarbonylpiperazine (25 g) was added and the mixture was stirred at room temperature for 24 hours. The suspension was washed with brine, dried, (Na$_2$SO$_4$), filtered, and concentrated. The crude product was chromatographed on silica gel with 10-20% ethyl acetate/hexanes.

Compound 338E 1-((2-(4-chlorophenyl)-4,4-dimethylcyclohex-1-enyl)methyl)piperazine Compound 338D (1 g) was stirred in dichloromethane (10 ml), trifluoroacetic acid (10 ml), and triethylsilane (1 ml) for 1 hour. The mixture was concentrated, taken up in a mixture of dichloromethane (100 ml) and saturated aqueous Na$_2$CO$_3$ solution (20 ml) and stirred for 10 minutes. The layers were separated, and the organic layer was dried over Na$_2$SO$_4$, filtered, and concentrated to give the product.

Compound 338F 5-bromo-1-(triisopropylsilyl)-1H-pyrrolo[2,3-b]pyridine

To a mixture of 5-bromo-1H-pyrrolo[2,3-b]pyridine (15.4 g) in tetrahydrofuran (250 ml) was added 1M lithium hexamethyldisilazide in tetrahydrofuran (86 ml), and after 10 minutes, TIPS-Cl (triisopropylchlorosilane) (18.2 ml) was added. The mixture was stirred at room temperature for 24 hours. The reaction was diluted with ether, and the resulting solution was washed twice with water. The extracts were dried ($Na_2SO_4$), filtered, and concentrated. The crude product was chromatographed on silica gel with 10% ethyl acetate/hexanes.

Compound 338G 1-(triisopropylsilyl)-1H-pyrrolo[2,3-b]pyridin-5-ol

To a mixture of Compound 338F (24.3 g) in tetrahydrofuran (500 ml) at −78° C. was added 2.5M BuLi (30.3 ml). After 2 minutes, trimethylborate (11.5 ml) was added, and the mixture was allowed to warm to room temperature over 1 hour. The reaction was poured into water, extracted three times with ethyl acetate, and the combined extracts were washed with brine and concentrated. The crude product was taken up in tetrahydrofuran (200 ml) at 0° C., and 1M aqueous NaOH (69 ml) was added, followed by 30% aqueous $H_2O_2$ (8.43 ml), and the solution was stirred for 1 hour. $Na_2S_2O_3$ (10 g) was added, and the pH was adjusted to 4-5 with concentrated HCl and solid $NaH_2PO_4$. The solution was extracted twice with ethyl acetate, and the combined extracts were washed with brine, dried ($Na_2SO_4$), filtered, and concentrated. The crude product was chromatographed on silica gel with 5-25% ethyl acetate/hexanes.

Compound 338H methyl 2-(1H-pyrrolo[2,3-b]pyridin-5-yloxy)-4-fluorobenzoate

A mixture of Compound 338G (8.5 g), methyl 2,4-difluorobenzoate (7.05 g), and $K_3PO_4$ (9.32 g) in diglyme (40 ml) at 115° C. was stirred for 24 hours. The reaction was cooled, diluted with ether (600 ml), and washed twice with water, and brine, and concentrated. The crude product was chromatographed on silica gel with 2-50% ethyl acetate/hexanes.

Compound 338I methyl 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoate A mixture of Compound 338H (1.55 g), Compound 338E (2.42 g), and $HK_2PO_4$ (1.42 g) in dimethylsulfoxide (20 ml) at 135° C. was stirred for 24 hours. The reaction was cooled, diluted with ether (400 ml), and washed three times with 1M aqueous NaOH, and brine, and concentrated. The crude product was chromatographed on silica gel with 10-50% ethyl acetate/hexanes.

Compound 338J 2-(1H-pyrrolo[2,3-b]pyridin-5-yloxy)-4-(4-((2-(4-chlorophenyl)-4,4-dimethylcyclohex-1-enyl)methyl)piperazin-1-yl)benzoic Acid Compound 338I (200 mg) in dioxane (10 ml) and 1M NaOH (6 ml) at 50° C. was stirred for 24 hours. The reaction was cooled, added to $NaH_2PO_4$ solution, and extracted three times with ethyl acetate. The combined extracts were washed with brine, and concentrated to give the pure product.

Compound 338K tert-butyl (4-hydroxy-4-methylcyclohexyl)methylcarbamate

To a vigorous stirring solution of tert-butyl(4-oxocyclohexyl)methylcarbamate (1.7 g) in tetrahydrofuran (40 ml) at −78° C. was dropwise added 1.6 M methyllithium (14.02 ml) in ether. After completion of the addition, the mixture was stirred at −78° C. for 1.2 hours and poured into a cold $NH_4Cl$ aqueous solution. The resulting mixture was extracted with dichloromethane (100 ml, three times) and the organic layer was dried over $Na_2SO_4$, filtered, and concentrated. The residue was dissolved in dichloromethane and loaded onto an Analogix purification system, and it was eluted with 0-50% ethyl acetate in dichloromethane to provide the title compound.

Compound 338L 4-(aminomethyl)-1-methylcyclohexanol

Compound 338K (1.3 g) in dichloromethane (5 ml) at 0° C. was treated with trifluoroacetic acid (2.1 ml) and a few drops of water for 1 hour. The reaction mixture was concentrated and the residue was directly used for next step.

Compound 338M 4-((cis-4-hydroxy-4-methylcyclohexyl)methylamino)-3-nitrobenzenesulfonamide Compound 338L (732 mg) and 4-fluoro-3-nitrobenzenesulfonamide (1.1 g) in tetrahydrofuran (15 ml) was treated with triethylamine overnight. The reaction mixture, was concentrated and the residue was purified by a reverse phase chromatography, eluting with 30%-50% acetonitrile in 0.1% trifluoroacetic acid water solution to isolate the title compound.

Compound 338N 4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide A mixture of Compound 338J (144 mg), Compound 338M (95 mg), N,N-dimethylpyridin-4-amine (123 mg) and $N^1$-((ethylimino)methylene)-$N^3$,$N^3$-dimethylpropane-1,3-diamine hydrochloride (62.7 mg) in dichloromethane (7 ml) was stirred overnight and concentrated. The residue was purified by reverse chromatography, eluted with 40%-70% acetonitrile in 0.1% TFA water. The desired fractions were concentrated, neutralized with $NaHCO_3$ and extracted with dichloromethane. The organic layer was dried over $Na_2SO_4$, filtered, concentrated and dried to provide the title compound. $^1$H NMR (400 MHz, dimethylsulfoxide-$d_6$) δ 11.69 (s, 1H), 11.38 (s, 1H), 8.59 (t, 1H), 8.55 (d, 1H), 8.04 (d, 1H), 7.79 (dd, 1H), 7.54 (d, 1H), 7.46-7.52 (m, 2H), 7.30-7.38 (m, 2H), 7.00-7.10 (m, 3H), 6.68 (dd, 1H), 6.39 (dd, 1H), 6.19 (d, 1H), 3.95 (s, 1H), 3.25 (t, 4H), 3.07 (s, 4H), 2.75 (s, 2H), 2.10-2.26 (m, 6H), 1.95 (s, 2H), 1.29-1.62 (m, 8H), 1.16-1.30 (m, 2H), 1.08 (s, 3H), 0.92 (s, 6H).

Compound 339

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 339A (1R,4S)-methyl spiro[bicyclo[2.2.1]heptane-2,2'-[1,3]dioxolane]-5-carboxylate A reaction mixture of 1,4-dioxaspiro[4.4]non-6-ene (5 g), methyl acrylate (10.24 g), and hydroquinone (0.13 g) was heated at 100° C. in acetonitrile (12 ml) for three days. After cooling, the solvent was removed, and residue was purified by flash chromatography on silica gel eluting with 4:1 hexane/ethyl acetate to provide the title compound as a mixture of two isomers.

Compound 339B (1R,4S)-spiro[bicyclo[2.2.1]heptane-2,2'-[1,3]dioxolane]-5-ylmethanol Compound 339A (1.0 g) in tetrahydrofuran was cooled to 0° C. To this solution was added 1.0 N lithium aluminum hydride (2.8 ml) dropwise. The reaction mixture was stirred for 2 hours. Water (0.4 ml) was added followed by 2 N aqueous NaOH (0.2 ml). The solid was filtered off, and the filtrate was concentrated. Toluene was added, and it was then distilled to remove any trace amount of water. The title compound was used for the next reaction without further purification.

Compound 339C 5-chloro-6-(((1S,2R,4R)-5-oxobicyclo[2.2.1]heptan-2-yl)methoxy)pyridine-3-sulfonamide The title compound was prepared by substituting Compound 339B for (tetrahydro-2H-pyran-4-yl)methanol and Compound 40A for Compound 36A in the procedure for Compound 36B. The two stereoisomers at the 5 position were isolated by reverse phase Gilson Prep HPLC system with a Phenomenex prep column (Luna, 5μ, C18(2), 250× 21.20 mm, 5 Å) eluting with 20-80% acetonitrile in water with 0.1% trifluoroacetic acid. The desired fractions were collected, and the solvents were removed under reduced vacuum at 60° C. During this process, a lot of solid formed. It was then partitioned between water and ethyl acetate. The organic layer was separated, and the aqueous layer was extracted with additional ethyl acetate. The combined organic layers were washed with brine, dried over MgSO$_4$, filtered and concentrated to give the title compound.

Compound 339D 5-chloro-6-(((1S,2R,4R,5R)-5-hydroxy-5-methylbicyclo[2.2.1]hept-2-yl)methoxy)pyridine-3-sulfonamide Compound 339C (0.44 g) in tetrahydrofuran (15 ml) was treated with 3.0 M methylmagnesium bromide (5.3 ml) at 0° C. The solution was stirred for 16 hours. The reaction mixture was then partitioned between ethyl acetate and 0.05 N aqueous HCl (20 ml). The organic layer was separated, and the aqueous layer was extracted with additional ethyl acetate three times. The combined organic layers were washed with brine, dried over MgSO$_4$, filtered, and concentrated. The residue was purified by flash column chromatography on silica gel using 10-50% ethyl acetate in hexanes to provide the title compound.

Compound 339E

N-[(5-chloro-6-{[(1R,2R,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 339D for Compound 11B in the procedure for Compound 11D. $^1$H NMR (500 MHz, dimethylsulfoxide-d$_6$) δ 11.66 (s, 1H), 8.50 (s, 1H), 8.16 (s, 1H), 8.02 (d, 1H), 7.49-7.55 (m, 3H), 7.35 (d, 2H), 7.05 (d, 2H), 6.67 (dd, 1H), 6.38 (dd, 1H), 6.20 (s, 1H), 4.40-4.48 (m, 2H), 4.31 (s, 1H), 3.09 (s, 4H), 2.83 (s, 2H), 2.15-2.33 (m, 7H), 1.96 (s, 2H), 1.87 (d, 1H), 1.65-1.69 (m, 1H), 1.54-1.56 (m, 2H), 1.36-1.47 (m, 6H), 1.26-1.30 (m, 1H), 1.19 (s, 3H), 0.93 (s, 6H).

Compound 340

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide Compound 340A 4-(1,4-dioxaspiro[4.5]decan-8-ylamino)-3-nitrobenzenesulfonamide To a solution of 4-fluoro-3-nitrobenzenesulfonamide (1.4 g) in tetrahydrofuran (30 ml) was added 1,4-dioxaspiro[4.5]decan-8-amine (1.0 g) and diisopropylethylamine (5 ml). The mixture was stirred overnight. The mixture was diluted with ethyl acetate (300 ml) and washed with water, brine and dried over Na$_2$SO$_4$. Filtration and evaporation of the solvent gave the title compound.

Compound 340B

N-(4-(1,4-dioxaspiro[4.5]decan-8-ylamino)-3-nitrophenylsulfonyl)-2-(1H-pyrrolo[2,3-b]pyridin-5-yloxy)-4-(4-((2-(4-chlorophenyl)-4,4-dimethylcyclohex-1-enyl)methyl)piperazin-1-yl)benzamide To a solution of Compound 3J (617 mg) and Compound 340A (386 mg) in dichloromethane (10 ml) was added 1-ethyl-3-[3-(dimethylamino)propyl]carbodiimide hydrochloride (288 mg) and 4-(dimethylamino)pyridine (183 mg). The mixture was stirred overnight. The mixture was diluted with dichloromethane (300 ml) and washed with aqueous NaHCO₃, water, brine and dried over Na₂SO₄. Filtration and evaporation of the solvent gave the title compound.

Compound 340C 2-(1H-pyrrolo[2,3-b]pyridin-5-yloxy)-4-(4-((2-(4-chlorophenyl)-4,4-dimethylcyclohex 1-enyl)methyl)piperazin-1-yl)-N-(3-nitro-4-(4-oxocyclohexylamino)phenylsulfonyl)benzamide To a solution of Compound 340B (386 mg) in acetone (10 ml) and water (5 ml) was added para-toluenesulfonic acid monohydrate (50 mg). The mixture was stirred at 120° C. in a Biotage Initiator microwave reactor for 30 minutes. The mixture was diluted with dichloromethane (300 ml) and washed with aqueous NaHCO₃, water, brine and dried over Na₂SO₄. Filtration and evaporation of the solvent gave the title compound.

Compound 340D 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]cyclohexyl}amino)-3-nitrophenyl]sulfonyl}-2-(1H-pyrrolo[2,3-b]pyridin-5-yloxy)benzamide To a solution of Compound 340C (240 mg) and 3-(cyclopropylamino)propanenitrile (62 mg) in tetrahydrofuran (10 ml) was added acetic acid (2 ml) and MP-cyanoborohydride (300 mg, 2.15 mmol/g). The mixture was stirred overnight. The mixture was filtered and concentrated under vacuum and the residue was dissolved in dimethylsulfoxide/methanol (1:1, 10 ml) and loaded on Gilson, C18(100A) 250×121.2 mm (10 micron), with 30% acetonitrile to 65% acetonitrile over 40 minutes. ¹H NMR (300 MHz, dimethylsulfoxide-d₆) δ 11.66 (s, 1H), 8.55 (dd, 1H), 8.17 (d, 1H), 8.03 (d, 1H), 7.79 (d, 1H), 7.49 (m, 3H), 7.34 (d, 2H), 7.11 (m, 1H), 7.04 (d, 2H), 6.67 (dd, 1H), 6.38 (d, 1H), 6.19 (d, 1H), 4.01 (m, 1H), 3.56 (m, 1H), 3.06 (m, 4H), 2.88 (t, 2H), 2.65 (m, 6H), 2.19 (m, 6H), 2.00 (m, 7H), 1.51 (m, 6H), 0.92 (s, 6H), 0.42 (m, 4H).

Compound 341

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide Compound 341A ethyl 1,4-dioxaspiro[4.5]decane-8-carboxylate To a solution of ethyl 4-oxocyclohexanecarboxylate (31.8 g) in toluene (100 ml) was added ethylene glycol (36.5 ml) and p-toluenesulfonic acid monohydrate (0.426 g). The two phase mixture was stirred rapidly at ambient temperature for 72 hours. The reaction was diluted with water (900 ml) and extracted with ether (900 ml). The organic layer was washed with saturated sodium bicarbonate solution and brine, and then dried over anhydrous sodium sulfate. After filtration, the title compound was obtained by concentration under high vacuum.

Compound 341B 1,4-dioxaspiro[4.5]decan-8-ylmethanol

To a suspension of lithium aluminum hydride (8.19 g) in tetrahydrofuran (400 ml) was added dropwise a solution of Compound 341A (37.8 g) in tetrahydrofuran (75 ml). The mixture was then heated at reflux for 2 hours. The reaction mixture was cooled in an ice bath and quenched very slowly with water (8 ml). Then added sequentially were 4N sodium hydroxide (8 ml), ether (200 ml), water (24 ml), ether (500 ml) and anhydrous sodium sulfate (250 g). The resulting mixture was stirred rapidly for 2 hours and was filtered. The title compound was isolated by concentration of the filtrate.

Compound 341C 8-(benzyloxymethyl)-1,4-dioxaspiro[4.5]decane

To a suspension of sodium hydride (60% oil dispersion, 8.86 g) in tetrahydrofuran (170 ml) was added a solution of Compound 341B (30.52 g) in tetrahydrofuran (100 ml). This mixture was stirred for 30 minutes and benzyl bromide (24 ml) was added. After stirring for 72 hours, the reaction was quenched with saturated ammonium chloride solution (400 ml) and diluted with ether (500 ml). The layers were separated and the aqueous layer was extracted with ether (2×150 ml). The combined organics were dried over sodium sulfate, filtered and concentrated. The crude product was purified on silica gel eluting with a 0, 10, 15, 75% ethyl acetate in hexanes step gradient to provide the title compound.

Compound 341D 4-(benzyloxymethyl)cyclohexanone

To a solution of Compound 341C (43.02 g) in dioxane (500 ml) was added water (125 ml) and 2M hydrochloric acid (90 ml). The mixture was heated at 85° C. for 18 hours. Upon cooling, the reaction mixture was diluted with brine (1500 ml), saturated sodium bicarbonate solution (300 ml) and ether (1000 ml). The organic layer was dried over sodium sulfate, filtered and concentrated. The crude product was purified on silica gel eluting with a 5-50% ethyl acetate in hexanes step gradient to provide the title compound.

Compound 341E trans-4-(benzyloxymethyl)-1-methylcyclohexanol

To 2,6-di-t-butyl-4-methylphenol (83.4 g) in toluene (1100 ml) was added 2.0M (in hexanes) trimethylaluminum (95 ml) somewhat carefully to control methane evolution and a small exotherm. The reaction mixture was stirred at ambient temperature under N₂ for 75 minutes and was then cooled to −77° C. A solution of Compound 341D (14 g) in toluene (15 ml) was added dropwise, keeping the temperature below −74° C. Methyllithium (1.6M in diethyl ether, 120 ml) was then added dropwise, keeping the temperature below −65° C. The resulting mixture was stirred at −77° C. under N₂ for 2 hours. The reaction mixture was then poured into 1N aqueous HCl (1600 ml), rinsing the flask with toluene. The organic layer was washed with brine and the combined aqueous layers were extracted with diethyl ether. The combined organic layers were dried (Na₂SO₄), filtered and concentrated. The concentrate was chromatographed on 650 g of spherical silica gel using 2.5 L of 80/20 hexanes/ethyl acetate, then 3.0 L of 75/25 hexanes/ethyl acetate, and finally 4.0 L of 70/30 hexanes/ethyl acetate as the eluents to provide the title compound.

Compound 341F trans-4-(hydroxymethyl)-1-methylcyclohexanol

Compound 341E (12.6 g) and ethanol (120 ml) were added to 20% Pd(OH)$_2$/C, wet (1.260 g) in a 500 ml SS pressure bottle. The reaction mixture was stirred at ambient temperature under 30 psi hydrogen gas. Hydrogen uptake eased at 5 minutes. The mixture was filtered through a nylon membrane rinsing with ethanol. The filtrate was concentrated and then azeotroped with toluene (100 ml) to remove any remaining ethanol. The concentrate was dried under high vacuum for 40 minutes to provide the title compound.

Compound 341G 5-chloro-6-((trans-4-hydroxy-4-methylcyclohexyl)methoxy)pyridine-3-sulfonamide The title compound was prepared by substituting Compound 40A for 4-fluoro-3-nitrobenzenesulfonamide and Compound 341F for (tetrahydro-2H-pyran-4-yl)methanol in the procedure for Compound 24A.

Compound 341H

N-({5-chloro-6-[(trans-4-hydroxy-4-methylcyclohexyl)methoxy]pyridin-3-yl}sulfonyl)-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide The title compound was prepared by substituting Compound 328E for Compound 3J and Compound 341G for Compound 11B in the procedure for Compound 11D. $^1$H NMR (500 MHz, pyridine-d$_5$) δ 13.09 (s, 1H), 9.18 (d, 1H), 8.74 (d, 1H), 8.41 (d, 1H), 8.09 (d, 1H), 7.67 (m, 2H), 7.42 (m, 2H), 7.09 (m, 2H), 6.74 (dd, 1H), 6.52 (dd, 1H), 6.49 (d, 1H), 4.29 (d, 2H), 3.05 (m, 4H), 2.80 (s, 2H), 2.37 (t, 2H), 2.15 (m, 4H), 2.11 (s, 2H), 1.89 (m, 6H), 1.75 (m, 2H), 1.45 (t, 2H), 1.41 (s, 3H), 1.32 (m, 2H), 0.37 (m, 4H).

Compound 342

4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide Compound 342A methyl 5,6,7,8-tetrahydroimidazo[1,2-a]pyridine-6-carboxylate To a 50 ml pressure bottle were placed methyl imidazo[1,2-a]pyridine-6-carboxylate (0.26 g), acetic acid (10 ml), and wet 5% palladium on carbon (0.052 g). The reaction mixture was stirred for 16 hours at 30 psi and 50° C. The solid was filtered off, and the filtrate was concentrated. The residue was taken up in ethyl acetate. It was then washed with saturated sodium bicarbonate, brine, dried over MgSO$_4$, filtered, and concentrated. The residue was purified by flash column chromatography on silica gel using 10-100% ethyl acetate in hexanes to provide the title compound.

Compound 342B (5,6,7,8-tetrahydroimidazo[1,2-a]pyridin-6-yl)methanol

The title compound was prepared by substituting Compound 342A for Compound 339A in the procedure for Compound 339B.

Compound 342C 5-chloro-6-((5,6,7,8-tetrahydroimidazo[1,2-a]pyridin-6-yl)methoxy)pyridine-3-sulfonamide The title compound was prepared by substituting Compound 342B for (tetrahydro-2H-pyran-4-yl)methanol and Compound 40A for Compound 36A in the procedure for Compound 36B.

Compound 342D 4-(4-{[2-(4-chlorophenyl)-4,4-dimethylcyclohex-1-en-1-yl]methyl}piperazin-1-yl)-N-{[5-chloro-6-(5,6,7,8-tetrahydroimidazo[1,2-a]pyridin-6-ylmethoxy)pyridin-3-yl]sulfonyl}-2-(1H-pyrrolo[2,3-b]pyridin-5-yloxy)benzamide The title compound was prepared by substituting Compound 342C for Compound 11B in the procedure for Compound 11D. $^1$H NMR (500 MHz, dimethylsulfoxide-d$_6$) δ 11.54 (s, 1H), 8.36 (s, 1H), 8.06 (s, 1H), 7.93 (s, 1H), 7.58 (d, 1H), 7.41-7.44 (m, 2H), 7.2-7.36 (m, 4H), 7.05 (d, 2H), 6.63 (dd, 1H), 6.32 (dd, 1H), 6.24 (d, 1H), 4.42-4.51 (m, 1H), 4.37-4.40 (m, 1H), 4.29 (dd, 1H), 3.91 (dd, 1H), 3.03 (s, 4H), 2.90-2.95 (m, 2H), 2.77 (s, 2H), 2.51-2.52 (m, 1H), 2.07-2.23 (m, 7H), 1.96 (s, 2H), 1.76-1.82 (m, 1H), 1.65-1.69 (m, 2H), 1.54-1.56 (m, 2H), 1.39 (t, 2H), 0.93 (s, 6H).

Compound 343

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 343A 5-chloro-6-(((1S,2S,4R)-5-oxobicyclo[2.2.1]heptan-2-yl)methoxy)pyridine-3-sulfonamide The title compound was isolated as another isomer in the procedure for Compound 339C.

Compound 343B 5-chloro-6-(((1S,2S,4R,5R)-5-hydroxy-5-methylbicyclo[2.2.1]heptan-2-yl)methoxy)pyridine-3-sulfonamide The title compound was prepared by substituting Compound 343A for Compound 339B in the procedure for Compound 339C.

Compound 343C

N-[(5-chloro-6-{[(1R,2S,4R,5R)-5-hydroxy-5-methylbicyclo[2.2.1]hept-2-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 343B for Compound 11B in the procedure for Compound 11D. $^1$H NMR (500 MHz, dimethylsulfoxide-$d_6$) δ 11.67 (s, 1H), 8.51 (s, 1H), 8.17 (s, 1H), 8.03 (s, 1H), 7.49-7.55 (m, 3H), 7.35 (d, 2H), 7.05 (d, 2H), 6.67 (dd, 1H), 6.39 (dd, 1H), 6.20 (d, 1H), 4.27 (s, 1H), 4.11-4.19 (m, 2H), 3.11 (s, 4H), 2.87 (s, 2H), 1.96-2.23 (m, 10H), 1.88 (d, 1H), 1.50 (dd, 1H), 1.33-1.44 (m, 2H), 1.13-1.19 (m, 4H), 0.88-0.93 (m, 8H).

Compound 344

4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide

Compound 344A 4-((cis-4-hydroxy-4-methylcyclohexyl)methoxy)-3-nitrobenzenesulfonamide Compound 347A (732 mg) and 4-fluoro-3-nitrobenzenesulfonamide (1.2 g) in tetrahydrofuran (40 ml) were treated with 60% sodium hydride (1.6 g) for 3 days. The reaction was quenched with water. The resulting mixture was neutralized with diluted aqueous HCl, and extracted with ethyl acetate. The organic layer was dried over $Na_2SO_4$, filtered, and concentrated. The residue was purified by a reverse phase chromatography, eluting with 30-50% $CH_3CN$ in 0.1% trifluoroacetic acid water to provide the title compound as a single enantiomer.

Compound 344B 4-(4-{[2-(4-chlorophenyl)-4,4-dimethylcyclohex-1-en-1-yl]methyl}piperazin-1-yl)-N-({4-[(cis-4-hydroxy-4-methylcyclohexyl)methoxy]-3-nitrophenyl}sulfonyl)-2-(1H-pyrrolo[2,3-b]pyridin-5-yloxy)benzamide The title compound was prepared by substituting Compound 344A for Compound 1F and Compound 3J for Compound 1E in the procedure for Compound 1G. $^1$H NMR (400 MHz, dimethylsulfoxide-$d_6$) δ 11.69 (s, 1H), 8.34 (d, 1H), 8.04 (m, 2H), 7.52 (m, 3H), 7.40 (d, 1H), 7.35 (d, 2H), 7.04 (d, 2H), 6.68 (dd, 1H), 6.40 (m, 1H), 6.20 (d, 1H), 4.02 (d, 2H), 3.96 (s, 1H), 3.10 (br s, 4H), 2.85 (m, 2H), 2.29 (m, 3H), 2.15 (t, 2H), 1.96 (br s, 2H), 1.68 (m, 1H), 1.55 (m, 4H), 1.42 (m, 2H), 1.27 (m, 2H), 1.10 (s, 3H), 0.92 (s, 6H).

Compound 345

N-[(5-chloro-6-{[4-fluoro-1-(oxetan-3-yl)piperidin-4-yl]methoxy}pyridin-3-yl)sulfonyl]-4-(4-{[5-(4-chlorophenyl)spiro[2.5]oct-5-en-6-yl]methyl}piperazin-1-yl)-2-(1H-pyrrolo[2,3-b]pyridin-5-yloxy)benzamide The title compound was prepared by substituting Compound 328E for Compound 3J and Compound 277O for Compound 11B in the procedure for Compound 11D. $^1$H NMR (500 MHz, pyridine-$d_5$) δ 13.07 (s, 1H), 9.13 (d, 1H), 8.41 (d, 1H), 8.09 (d, 1H), 7.68 (t, 1H), 7.66 (d, 1H), 7.42 (m, 2H), 7.09 (m, 2H), 6.75 (dd, 1H), 6.51 (m, 2H), 4.64 (d, 4H), 4.53 (d, 2H), 3.39 (m, 1H), 3.06 (m, 4H), 2.81 (s, 2H), 2.51 (m, 2H), 2.37 (m, 2H), 2.12 (m, 10H), 1.90 (m, 2H), 1.45 (t, 2H), 0.38 (s, 4H).

Compound 346

4-(4-{[2-(4-chlorophenyl)-4,4-dimethylcyclohex-1-en-1-yl]methyl}piperazin-1-yl)-N-[(4-{[4-(3,3-difluoropyrrolidin-1-yl)cyclohexyl]amino}-3-nitrophenyl)sulfonyl]-2-(1H-pyrrolo[2,3-b]pyridin-5-yloxy)benzamide The title compound was prepared by substituting 3,3-difluoropyrrolidine hydrochloride for 3-(cyclopropylamino)propanenitrile in the procedure for Compound 340D. $^1$H NMR (300 MHz, dimethylsulfoxide-$d_6$) δ 11.68 (s, 1H), 11.38 (m, 1H), 8.55 (m, 1H), 8.36 (d, 1H), 8.03 (d, 1H), 7.80 (m, 1H), 7.50 (m, 3H), 7.34 (d, 2H), 7.13 (d, 1H), 7.04 (d, 2H), 6.83 (m, 1H), 6.68 (m, 1H), 6.38 (d, 1H), 6.19 (s, 1H), 4.02 (s, 1H), 3.83 (m, 1H), 3.06 (m, 4H), 2.96 (m, 2H), 2.73 (m, 4H), 2.26 (m, 8H), 1.97 (m, 4H), 1.68 (m, 4H), 1.37 (m, 2H), 0.92 (s, 6H).

Compound 347

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 347A 4-(hydroxymethyl)-1-methylcyclohexanol 4-(Hydroxymethyl)cyclohexanone (800 mg) in tetrahydrofuran (15 ml) was treated with 3 M methylmagnesium chloride in tetrahydrofuran (6.24 ml) at 0° C. The reaction was warmed to room temperature over 2 hours and quenched with methanol and water. The resulting mixture was concentrated and the residue was suspended in ethyl acetate. The precipitates were filtered off and the filtrate was concentrated. The residue was purified by chromatography, eluting with 0-100% ethyl acetate in hexane to provide the title compound.

Compound 347B 5-chloro-6-((trans-4-hydroxy-4-methylcyclohexyl)methoxy)pyridine-3-sulfonamide Compound 347A (970 mg) and Compound 40A (1.6 g) in N,N-dimethylformamide (8 ml) were treated with sodium hydride (1.8 g, 60%) at room temperature for 2 days. The reaction was quenched with water. The resulting mixture was neutralized with diluted aqueous HCl, and extracted with ethyl acetate. The organic layer was dried over $Na_2SO_4$, filtered, and concentrated. The residue was purified by a reverse phase chromatography, eluting with 30-45% acetonitrile in 0.1% trifluoroacetic acid water to isolate the title compound.

263

Compound 347C 5-chloro-6-((cis-4-hydroxy-4-methylcyclohexyl)methoxy)pyridine-3-sulfonamide The title compound was prepared and isolated as described in the procedure for Compound 347B.

Compound 347D

N-({5-chloro-6-[(trans-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in the procedure for Compound 11D using Compound 347B in place of Compound 11B. $^1$H NMR (400 MHz, dimethylsulfoxide-$d_6$) δ 11.67 (s, 1H), 8.51 (d, 1H), 8.18 (d, 1H), 8.03 (d, 1H), 7.48-7.56 (m, 3H), 7.35 (d, 2H), 7.05 (d, 2H), 6.68 (dd, 1H), 6.39 (dd, 1H), 6.21 (d, 1H), 4.17-4.34 (m, 3H), 3.11 (s, 4H), 2.89 (s, 2H), 2.24-2.42 (m, 4H), 2.15 (s, 2H), 1.96 (s, 2H), 1.66-1.82 (m, 3H), 1.55 (d, 2H), 1.31-1.44 (m, 4H), 1.12-1.27 (m, 2H), 1.10 (s, 3H), 0.93 (s, 6H).

Compound 348

N-({5-chloro-6-[(cis-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared as described in the procedure for Compound 1D using Compound 347C in place of Compound 1B. $^1$H NMR (400 MHz, dimethylsulfoxide-$d_6$) δ 11.67 (s, 1H), 8.51 (d, 1H), 8.18 (d, 1H), 8.03 (d, 1H), 7.47-7.58 (m, 3H), 7.35 (d, 2H), 7.05 (d, 2H), 6.68 (dd, 1H), 6.39 (dd, 1H), 6.21 (d, 1H), 4.21 (d, 2H), 3.95 (s, 1H), 3.11 (s, 4H), 2.89 (s, 2H), 2.33 (d, 4H), 2.15 (s, 2H), 1.96 (s, 2H), 1.63-1.77 (m, 1H), 1.48-1.60 (m, 4H), 1.35-1.48 (m, 4H), 1.20-1.33 (m, 2H), 1.09 (s, 3H), 0.93 (s, 6H).

Compound 349

4-(4-{[2-(4-chlorophenyl)-4,4-dimethylcyclohex-1-en-1-yl]methyl}piperazin-1-yl)-N-{[4-({4-[(2,2-difluorocyclopropyl)amino]cyclohexyl}amino)-3-nitrophenyl]sulfonyl}-2-(1H-pyrrolo[2,3-b]pyridin-5-yloxy)benzamide The title compound was prepared by substituting 2,2-difluorocyclopropanamine hydrochloride for 3-(cyclopropylamino)propanenitrile in the procedure for Compound 340D. $^1$H NMR (300 MHz, dimethylsulfoxide-$d_6$) δ 11.60 (s, 1H), 8.47 (m, 2H), 8.12 (m, 1H), 7.98 (m, 1H), 7.72 (m, 2H), 7.47 (m, 3H), 7.34 (m, 3H), 7.05 (m, 2H), 6.65 (dd, 1H), 6.35 (m, 1H), 6.22 (d, 1H), 3.54 (m, 2H), 3.08 (m, 4H), 2.74 (m, 4H), 2.25 (m, 4H), 2.01 (m, 4H), 1.38 (m, 4H), 0.92 (s, 6H).

264

Compound 350

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 350A ethyl spiro[benzo[d][1,3]dioxole-2,1'-cyclohexane]-4'-carboxylate To a solution of ethyl 4-oxocyclohexanecarboxylate (22.75 g) and pyrocatechol (14.75 g) in toluene (200 ml) was added catalytic amount of para-toluenesulfonic acid monohydrate and the mixture was stirred under reflux and a Dean-Stark trap overnight. The mixture was diluted with diethyl ether (600 ml) and washed with aqueous NaHCO$_3$, water and brine. After drying over Na$_2$SO$_4$, the mixture was filtered and the solvent was evaporated under vacuum to provide the title compound.

Compound 350B ethyl 4'-fluorospiro[benzo[d][1,3]dioxole-2,1'-cyclohexane]-4'-carboxylate A solution of Compound 350A (5.25 g) in tetrahydrofuran (40 ml) was added dropwise to a solution of lithium diisopropylamide (12 ml, 2.0M in tetrahydrofuran/heptane/ethylbenzene) at 0° C. The solution was stirred at 0° C. for 30 minutes, and then was transferred by cannula to a pre-cooled (0° C.) stirring solution of N-fluorobenzenesulfonimide (7.89 g) in dry tetrahydrofuran (20 ml). The reaction mixture was stirred at 0° C. for 30 minutes, and then at 20° C. for 18 hours. The reaction mixture was poured over aqueous NH$_4$CL and extracted with diethyl ether (3×200 ml). The combined organic layers were washed with water, brine and dried over Na$_2$SO$_4$. Filtration and evaporation of the solvent gave the crude product.

Compound 350C (4'-fluorospiro[benzo[d][1,3]dioxole-2,1'-cyclohexane]-4'-yl)methanol To a solution of Compound 350B (23 g) in tetrahydrofuran (150 ml) was added lithium aluminum hydride (3.11 g). The mixture was stirred overnight. Aqueous 2N NaOH solution was added dropwise to the reaction mixture. The mixture was then diluted with ethyl acetate (600 ml) and washed with water, brine and dried over Na$_2$SO$_4$. Filtration and evaporation of the solvent gave the crude product which was loaded on a 600 g analogics column and eluted with 10% to 20% ethyl acetate in hexane to provide the title compound.

Compound 350D 5-chloro-6-((4'-fluorospiro[benzo[d][1,3]dioxole-2,1'-cyclohexane]-4'-yl)methoxy)pyridine-3-sulfonamide To a solution of Compound 350C (89 mg) in N,N-dimethylformamide (3 ml) was added NaH (65% in mineral oil, 36 mg). The mixture was stirred for 30 minutes, and then 5,6-dichloropyridine-3-sulfonamide (85 mg) was added. The mixture was stirred overnight. The mixture was poured over aqueous NH₄Cl and extracted with ethyl acetate (100 ml). The combined organic layers were washed with water, brine and dried over Na₂SO₄. After filtration and evaporation of the solvent, the residue was loaded on a silica gel cartridge and eluted with 30% ethyl acetate in hexane to provide the title compound.

Compound 350E 5-chloro-6-((1-fluoro-4-oxocyclohexyl)methoxy)pyridine-3-sulfonamide To a solution of Compound 350D (1.6 g) and pyridinium p-toluenesulfonate (1.2 g) in acetone (10 ml) was added water (2 ml) and the mixture was stirred under microwave irradiation at 100° C. for 10 minutes. The mixture was diluted with dichloromethane (300 ml) and washed with aqueous NaHCO₃, water, brine and dried over Na₂SO₄. Filtration and evaporation of the solvent gave the title compound.

Compound 350F 5-chloro-6-((cis-1-fluoro-4-hydroxycyclohexyl)methoxy)pyridine-3-sulfonamide To a solution of Compound 350E (336 mg) in tetrahydrofuran (10 ml) was added NaBH₄ (75 mg). The mixture was stirred for 45 minutes. The mixture was diluted with ethyl acetate (300 ml) and washed with 2N aqueous NaOH, water, and brine. After drying over Na₂SO₄, the mixture was filtered and the solvent was evaporated to give the crude product.

Compound 350G

N-({5-chloro-6-[(cis-1-fluoro-4-hydroxycyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1 1H-pyrrolo[2,3-b]pyridin-5-yloxy)benzamide The title compound was prepared by substituting Compound 3J for Compound 1E and Compound 350F for Compound 1F in the procedure for Compound 1G. ¹H NMR (300 MHz, dimethylsulfoxide-d₆) δ 11.63 (s, 1H), 8.48 (s, 1H), 8.18 (s, 1H), 8.01 (d, 1H), 7.50 (m, 3H), 7.35 (d, 2H), 7.05 (d, 2H), 6.67 (dd, 1H), 6.37 (dd, 1H), 6.21 (d, 1H), 4.62 (d, 1H), 4.47 (s, 1H), 4.40 (s, 1H), 3.46 (m, 1H), 3.06 (m, 4H), 2.88 (m, 1H), 2.25 (m, 6H), 1.99 (m, 4H), 1.58 (m, 8H), 0.93 (s, 6H).

Compound 351

4-(4-{[2-(4-chlorophenyl)-4,4-dimethylcyclohex-1-en-1-yl]methyl}piperazin-1-yl)-N-{[3-nitro-4-(2-oxaspiro[3.5]non-7-ylmethoxy)phenyl]sulfonyl}-2-(1H-pyrrolo[2,3-b]pyridin-5-yloxy)benzamide Compound 351A diethyl 1,4-dioxaspiro[4.5]decane-8,8-dicarboxylate A 500 ml round-bottomed flask was charged with diisopropylamine (16 ml) and tetrahydrofuran (311 ml). The solution was cooled to −78° C. under N₂ and n-BuLi (2.5 M in hexanes, 44.8 ml)) was added. The reaction was stirred for 30 minutes at −78° C. and ethyl 1,4-dioxaspiro[4.5]decane-8-carboxylate (20 g) was added as a tetrahydrofuran solution (ca. 10 ml). The solution was stirred at −78° C. for 1 hour and ethyl chloroformate (9 ml) was added neat. After stirring at −78° C. for 10 minutes, the reaction was warmed to room temperature over 2 hours. The reaction was quenched with saturated aqueous NH₄Cl and was diluted with diethyl ether. The layers were separated, the aqueous layer was extracted with diethyl ether and the combined organics were dried (Na₂SO₄), filtered and concentrated by rotary evaporation. The residue was purified by regular phase flash column chromatography (Analogix, 0-65% hexanes/ethyl acetate).

Compound 351B 1,4-dioxaspiro[4.5]decane-8,8-diyldimethanol

To a 1 L round-bottomed flask was added Compound 351A (26.6 g) and tetrahydrofuran (310 ml) to give a colorless solution. The solution was cooled to 0° C. and lithium aluminum hydride (2M in tetrahydrofuran, 62 ml) was added via syringe. The reaction was allowed to warm to room temperature and stirred overnight. The mixture was cooled back down to 0° C. and quenched slowly with 4.7 ml water, 4.7 ml 10% aqueous NaOH and 14 ml water. The mixture was allowed to stir until salts were formed and was then filtered through a Supelco 90 mm silica gel Buchner funnel. The filtrate was concentrated by rotary evaporation and the residue was purified by regular phase flash column chromatography (Analogix, 0-80% hexanes/ethyl acetate).

Compound 351C 2,8,11-trioxa-dispiro[3.2.4]tridecane

To a 1 L round-bottomed flask was added Compound 351B (13 g) in tetrahydrofuran (321 ml). The solution was cooled to −78° C. under N₂ and n-BuLi (25.7 ml) was added dropwise via syringe. After addition was complete, the mixture stirred for 30 minutes and a tetrahydrofuran solution of 4-toluenesulfonyl chloride (12.25 g) was added via addition funnel. The reaction was allowed to stir overnight, and gradually warm to room temperature. The reaction mixture was cooled to −78° C. and n-BuLi (25.7 ml) was added. The mixture was warmed to room temperature and stirred for 3 hours. The reaction was quenched with sat aqueous NH₄Cl and diluted with diethyl ether. The layers were separated, the aqueous layers extracted with diethyl ether and the combined organics were dried (Na₂SO₄), filtered and concentrated by rotary evaporation. The residue was purified by regular phase flash column chromatography (Analogix, 0-20% acetone/hexanes).

Compound 351D 2-oxaspiro[3.5]nonan-7-one

To a 500 ml round-bottomed flask was added Compound 351C (11 g) in 80% aqueous acetic acid (200 ml). The reaction was heated to 65° C. and stirred for about 4 hours. Most of the acetic acid and water were removed by rotary evaporation and the residue was purified by regular phase flash column chromatography (Analogix, 0-65% hexanes/ethyl acetate).

Compound 351E

7-methylene-2-oxaspiro[3.5]nonane

To a 250 ml round-bottomed flask was added methyltriphenylphosphonium iodide (4.33 g) in tetrahydrofuran (35.7 ml) to give a suspension. The suspension was cooled to −15° C. n-BuLi (2.5 M in hexanes, 4.28 ml) was added dropwise and the mixture was stirred at −15° C. for 40 minutes and Compound 351D (1 g) was added as a tetrahydrofuran (ca. 5 ml) solution. The mixture was stirred at −15° C. for about 15 minutes and warmed to room temperature. After 1.5 hours, the reaction was complete and was quenched with saturated aqueous $NH_4Cl$ and diluted with diethyl ether. The layers were separated and the aqueous layer was extracted (2×) with diethyl ether. The combined organics were washed with brine, dried ($Na_2SO_4$), filtered and concentrated by rotary evaporation. The residue was purified by regular phase chromatography (Analogix, 80 g Grace silica gel column, 0-50% hexanes/ethyl acetate).

Compound 351F

2-oxaspiro[3.5]nonan-7-ylmethanol

To a 25 ml round-bottomed flask was added Compound 351E (568 mg) and Compound 351F tetrahydrofuran (4.11 ml) to give a colorless solution. 9-Borabicyclo[3.3.1]nonane (0.5 M in tetrahydrofuran, 24.7 ml) was added and the reaction was allowed to stir for 2 hours at room temperature. Ethanol (11 ml) was added followed by aqueous NaOH (5M, 4.11 ml) and then hydrogen peroxide (2.1 ml) was added. The reaction was heated at 50° C. for 2 hours. The mixture was concentrated by rotary evaporation, and diluted with water and ethyl acetate. The aqueous layer was extracted with ethyl acetate (3×) and the combined organics were dried ($Na_2SO_4$), filtered and concentrated by rotary evaporation. The residue was purified by regular phase flash column chromatography (Analogix, 80 g Grace, 0-70% hexanes/ethyl acetate).

Compound 351G

4-(2-oxaspiro[3.5]nonan-7-ylmethoxy)-3-nitrobenzenesulfonamide

Compound 351G was prepared substituting Compound 351F for (tetrahydro-2H-pyran-4-yl)methanol in the procedure for Compound 24A.

Compound 351H

2-(1H-pyrrolo[2,3-b]pyridin-5-yloxy)-N-(4-(2-oxaspiro[3.5]nonan-7-ylmethoxy)-3-nitrophenylsulfonyl)-4-(4-((2-(4-chlorophenyl)-4,4-dimethylcyclohex-1-enyl)methyl)piperazin-1-yl)benzamide The title compound was prepared by substituting Compound 3J for Compound 1E and Compound 351G for Compound 1F in the procedure for Compound 1G. $^1H$ NMR (300 MHz, dimethylsulfoxide-$d_6$) δ 11.67 (s, 1H) 8.34 (s, 1H) 8.03 (d, 2H) 7.45-7.57 (m, 3H) 7.30-7.40 (m, 3H) 7.04 (d, 2H) 6.67 (dd, 1H) 6.39 (dd, 1H) 6.17-6.23 (m, 1H) 4.29 (s, 2H) 4.20 (s, 2H) 4.00 (d, 2H) 3.08 (s, 4H) 2.73-2.90 (m, 2H) 2.72 (s, 1H) 2.01-2.32 (m, 6H) 1.96 (s, 2H) 1.64-1.78 (m, 4H) 1.33-1.50 (m, 6H) 0.96-1.15 (m, 2H) 0.92 (s, 6H).

Compound 352

4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide

Compound 352A

4-((trans-4-hydroxy-4-methylcyclohexyl)methoxy)-3-nitrobenzenesulfonamide

The title compound was prepared by substituting Compound 341F for (tetrahydro-2H-pyran-4-yl)methanol in the procedure for Compound 24A.

Compound 352B

4-(4-{[2-(4-chlorophenyl)-4,4-dimethylcyclohex-1-en-1-yl]methyl}piperazin-1-yl)-N-({4-[(trans-4-hydroxy-4-methylcyclohexyl)methoxy]-3-nitrophenyl}sulfonyl)-2-(1H-pyrrolo[2,3-b]pyridin-5-yloxy)benzamide The title compound was prepared by substituting Compound 352A for Compound 1F and Compound 3J for Compound 1E in the procedure for Compound 1G. $^1H$ NMR (400 MHz, dimethylsulfoxide-$d_6$) δ 11.66 (s, 1H), 8.31 (br s, 1H), 8.01 (m, 2H), 7.49 (m, 3H), 7.33 (m, 3H), 7.03 (m, 2H), 6.66 (dd, 1H), 6.37 (m, 1H), 6.19 (d, 1H), 4.27 (s, 1H), 4.05 (d, 2H), 3.40 (m, 2H), 3.17 (s, 1H), 3.07 (m, 3H), 2.79 (m, 1H), 2.24 (m, 3H), 2.14 (m, 2H), 1.94 (m, 2H), 1.71 (m, 3H), 1.52 (m, 2H), 1.38 (m, 4H), 1.22 (m, 2H), 1.09 (s, 3H), 0.91 (s, 6H).

Compound 353

4-(4-{[2-(4-chlorophenyl)-5,5-bis(fluoromethyl)cyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 353A

1,4-dioxaspiro[4.5]decane-8,8-diylbis(methylene)bis(4-methylbenzenesulfonate)

To a 500 ml round-bottomed flask was added Compound 351B (10 g) and dichloromethane (165 ml) to give a colorless solution. Triethylamine (24.1 ml) and toluene-2-sulfonyl chloride (19.8 g) were added followed by 4-dimethylaminopyridine (0.604 g). The reaction was refluxed overnight. Saturated aqueous $NH_4Cl$ was added followed by dilution with water and additional dichloromethane. The aqueous layer was extracted with dichloromethane (2×) and the combined organics were dried ($MgSO_4$), filtered and concentrated by rotary evaporation. The residue was purified by regular phase flash column chromatography (Analogix, 0-55% hexanes/ethyl acetate).

Compound 353B

8,8-bis(fluoromethyl)-1,4-dioxaspiro[4.5]decane

To a 500 ml round-bottomed flask was added Compound 353A (20 g). tetra-n-Butylammonium fluoride (1M in tetrahydrofuran, 200 ml) was added and the resulting solution was refluxed for 6 days. The reaction was cooled, diluted with diethyl ether and washed with water (3x). The organics were dried (Na$_2$SO$_4$), filtered and concentrated by rotary evaporation. The residue was purified by regular phase flash column chromatography (Analogix, 0-30% hexanes/ethyl acetate).

Compound 353C 4,4-bis(fluoromethyl)cyclohexanone

To a 250 ml round bottom flask was added Compound 353B (1.1 g) and 80% aqueous acetic acid (50 ml). The reaction was heated at 65° C. for 3 hours, cooled and concentrated by rotary evaporation to remove most of the acetic acid and water. The residue was purified by regular phase flash column chromatography (Analogix, 0-50% hexanes/ethyl acetate).

Compound 353D 2-chloro-5,5-bis(fluoromethyl)cyclohex-1-enecarbaldehyde

To a 100 ml pear flask was added N,N-dimethylformamide (498 l) and dichloromethane (8.9 ml) to give a colorless solution. The solution was cooled to 0° C. and POCl$_3$ (550 µl) was added dropwise and then the mixture was warmed to room temperature for 30 minutes. In the meantime, to a 100 ml pear shaped flask was added Compound 353C (870 mg, 5.36 mmol) in dichloromethane (8941 µl) to give a colorless solution. The Vilsmeier reagent was then taken up in a syringe and added dropwise to the 4,4-bis(fluoromethyl)cyclohexanone (870 mg) solution at room temperature. The resulting solution was stirred overnight. The reaction was poured into saturated aqueous NaHCO$_3$ and ice, warmed to room temperature and extracted with dichloromethane (3×30 ml). The organics were combined, dried over MgSO$_4$, filtered and concentrated by rotary evaporation. The residue was purified by regular phase flash column chromatography (Analogix (0-60% hexanes/ethyl acetate).

Compound 353E 2-(4-chlorophenyl)-5,5-bis(fluoromethyl)cyclohex-1-enecarbaldehyde To a 20 ml vial was added Compound 353D (460 mg), 4-chlorophenylboronic acid (414 mg), potassium carbonate (762 mg), tetrabutylammonium bromide (711 mg), palladium (II) acetate (14.85 mg) and water (2450 µl) to give a suspension which was degassed with N$_2$ for 2 minutes. The reaction was stirred at 45° C. overnight, cooled, and poured over a Supelco silica gel Buchner funnel, washing with ethyl acetate several times. The filtrate was concentrated by rotary evaporation and the residue was purified by regular phase flash column chromatography (Analogix, 0-60% hexanes/ethyl acetate).

Compound 353F methyl 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)benzoate To a 20 mil vial was added Compound 353E (240 mg), Compound 15F (297 mg) and dichloromethane (4.2 ml).

Sodium triacetoxyborohydride (268 mg) was added and the reaction was stirred overnight at room temperature. The reaction was loaded directly onto silica gel and purified by regular phase flash column chromatography (Analogix, 0-80% hexanes/ethyl acetate).

Compound 353G 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)benzoic Acid The title compound was prepared by substituting Compound 353F for Compound 15G in the procedure for Compound 15H.

Compound 353H 2-(1H-pyrrolo[2,3-b]pyridin-5-yloxy)-4-(4-((2-(4-chlorophenyl)-5,5-bis(fluoromethyl)cyclohex-1-enyl)methyl)piperazin-1-yl)-N-(3-nitro-4-((tetrahydro-2H-pyran-4-yl)methylamino)phenylsulfonyl)benzamide Compound 353H was prepared by replacing Compound 3J with Compound 353G and Compound 11B with Compound 1F in the procedure for Compound 11D. $^1$H NMR (300 MHz, dimethylsulfoxide-d$_6$) δ 11.69 (s, 1H) 11.44 (s, 1H) 8.48-8.70 (m, 1H) 8.05 (d, 2H) 7.81 (dd, 1H) 7.46-7.59 (m, 3H) 7.35 (d, 2H) 7.12 (d, 2H) 6.68 (dd, 1H) 6.40 (dd, 1H) 6.16 (d, 1H) 4.39-4.49 (m, 2H) 4.23-4.35 (m, 2H) 3.85 (dd, J=−11.87, 2.71 Hz, 2H) 3.20-3.30 (m, 4H) 2.98-3.10 (m, 4H) 2.66-2.77 (m, 2H) 2.11-2.30 (m, 6H) 2.02-2.12 (m, 3H) 1.99 (s, 1H) 1.82-1.97 (m, 1H) 1.54-1.67 (m, 4H) 1.20-1.34 (m, 2H).

Compound 354

4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide Compound 354A tert-butyl 2-((2-nitro-4-sulfamoylphenoxy)methyl)morpholine-4-carboxylate The title compound was prepared by substituting tert-butyl 2-(hydroxymethyl)-morpholine-4-carboxylate for tetrahydro-2H-pyran-4-yl-methanol Compound 24A.

Compound 354B 4-(morpholin-2-ylmethoxy)-3-nitrobenzenesulfonamide

The title compound was prepared by substituting Compound 354A for Compound 113A in the procedure for Compound 134A.

Compound 354C

4-((4-cyclopropylmorpholin-2-yl)methoxy)-3-nitrobenzenesulfonamide

The title compound was prepared by substituting Compound 354B for Compound 173A in the procedure for Compound 173B.

Compound 354D

4-(4-{[2-(4-chlorophenyl)-4,4-dimethylcyclohex-1-en-1-yl]methyl}piperazin-1-yl)-N-({4-[(4-cyclopropylmorpholin-2-yl)methoxy]-3-nitrophenyl}sulfonyl)-2-(1H-pyrrolo[2,3-b]pyridin-5-yloxy)benzamide The title compound was prepared by substituting Compound 354C for Compound 130C in the procedure for Compound 130D. $^1$H NMR (500 MHz, pyridine-d$_5$) δ 12.98 (s, 1H), 9.06 (d, 1H), 8.50 (dd, 1H), 8.41 (d, 1H), 8.09 (d, 1H), 7.66 (t, 1H), 7.62 (d, 1H), 7.44 (d, 2H), 7.26 (d, 1H), 7.07 (d, 2H), 6.75 (dd, 1H), 6.54 (d, 1H), 6.48 (m, 1H), 4.31 (dd, 1H), 4.22 (dd, 1H), 3.92 (m, 1H), 3.83 (d, 1H), 3.56 (dt, 1H), 3.07 (m, 5H), 2.77 (s, 2H), 2.68 (d, 1H), 2.35 (m, 2H), 2.26 (m, 2H), 2.14 (m, 4H), 1.97 (s, 2H), 1.59 (m, 1H), 1.39 (t, 2H), 0.94 (s, 6H), 0.40 (m, 4H).

Compound 355

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 355A

5-chloro-6-((trans-1-fluoro-4-hydroxy-4-methylcyclohexyl)methoxy)pyridine-3-sulfonamide To a cooled (0° C.) solution of Compound 350E (1.2 g) in tetrahydrofuran (30 ml) was added dropwise a solution of methylmagnesium bromide (5 ml, 3.0M in ether). Upon addition, the reaction mixture solidified. More tetrahydrofuran (10 ml) was added to the mixture and stirring was continued for 1 hour. The mixture was poured over aqueous NH$_4$Cl and extracted with ethyl acetate (3×150 ml). The combined organic layers were washed with water, brine and dried over Na$_2$SO$_4$. The mixture was filtered and concentrated. The residue was dissolved in dimethylsulfoxide/methanol (20 ml, 1:1) and loaded on loaded on Gilson, C18(100A) 250×121.2 mm (10 micron), with 30% acetonitrile to 65% acetonitrile over 40 minutes to separate the two isomers and isolate the title compound.

Compound 355B

N-({5-chloro-6-[(trans-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 355A for Compound 1F in the procedure for Compound 1G. $^1$H NMR (300 MHz, dimethylsulfoxide-d$_6$) δ 11.63 (s, 1H), 8.47 (s, 1H), 8.17 (s, 1H), 7.54 (d, 1H), 7.48 (m, 2H), 7.35 (d, 2H), 7.05 (d, 2H), 6.67 (dd, 1H), 6.37 (d, 1H), 6.22 (d, 1H), 4.49 (s, 1H), 4.42 (s, 1H), 4.15 (s, 1H), 3.06 (m, 4H), 2.84 (m, 1H), 2.25 (m, 6H), 1.96 (s, 3H), 1.83 (m, 4H), 1.44 (m, 6H), 1.14 (s, 3H), 0.93 (s, 6H).

Compound 356

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide

Compound 356A

5-chloro-6-((cis-1-fluoro-4-hydroxy-4-methylcyclohexyl)methoxy)pyridine-3-sulfonamide The title compound was prepared as described for Compound 355A.

Compound 356B

N-({5-chloro-6-[(cis-1-fluoro-4-hydroxy-4-methylcyclohexyl)methoxy]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 3J for Compound 1E and Compound 356A for Compound 1F in the procedure for Compound 1G. $^1$H NMR (300 MHz, dimethylsulfoxide-d$_6$) δ 11.65 (s, 1H), 8.52 (s, 1H), 8.20 (s, 1H), 8.03 (d, 1H), 7.51 (m, 3H), 7.35 (d, 2H), 7.05 (d, 2H), 6.67 (dd, 1H), 6.39 (dd, 1H), 6.21 (d, 1H), 4.55 (s, 1H), 4.48 (s, 1H), 4.34 (s, 1H), 3.08 (m, 4H), 2.89 (d, 2H), 2.27 (m, 5H), 1.93 (m, 4H), 1.66 (m, 4H), 1.43 (m, 4H), 1.11 (s, 3H), 0.93 (s, 6H).

Compound 357

4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide

Compound 357A ethyl 4-fluoro-1-(oxetan-3-yl)piperidine-4-carboxylate

To 1-tert-butyl 4-ethyl 4-fluoropiperidine-1,4-dicarboxylate (1.000 g) was added HCl (4.0M in dioxane, 4.54 ml). After 1 hour the reaction was concentrated and dried under high vacuum. The resulting solid was dissolved in dichloromethane (5 ml) and treated with sodium triacetoxyborohydride (1.155 g) and oxetan-3-one (0.262 g) and stirred overnight. The reaction was quenched with saturated NaHCO$_3$ solution (20 ml) and extracted into dichloromethane (2×25 ml). The organic layer was dried over magnesium sulfate, filtered, and concentrated. Silica gel chromatography (Reveleris 80 g) eluting with a gradient of 0.5% to

Compound 357B (4-fluoro-1-(oxetan-3-yl)piperidin-4-yl)methanol

To a solution of Compound 357A (0.59 g) in tetrahydrofuran (5 ml) was added lithium aluminum hydride (1.80 ml) at 0° C. The reaction was removed from the ice bath and allowed to warm to room temperature. The reaction was quenched by the dropwise addition of 0.6 ml of water followed by 0.2 ml of 2N aqueous NaOH. The reaction was filtered through celite and rinsed with ethyl acetate (50 ml). The mixture and the residue was loaded onto silica gel (Reveleris 40 g) and eluted using a gradient of 0.75% to 7.5% methanol/dichloromethane over 30 minutes (flow=40 ml/min) to provide the title compound.

Compound 357C 3-cyano-4-((4-fluoro-1-(oxetan-3-yl)piperidin-4-yl) methoxy)benzenesulfonamide The title compound was prepared by substituting Compound 357B for (tetrahydro-2H-pyran-4-yl)methanol in the procedure for Compound 284A.

Compound 357D 4-(4-{[2-(4-chlorophenyl)-4,4-dimethylcyclohex-1-en-1-yl]methyl}piperazin-1-yl)-N-[(3-cyano-4-{[4-fluoro-1-(oxetan-3-yl)piperidin-4-yl]methoxy}phenyl)sulfonyl]-2-(1H-pyrrolo[2,3-b]pyridin-5-yloxy)benzamide The title compound was prepared by substituting Compound 3J for Compound 1E and Compound 357C for Compound 1F in the procedure for Compound 1G. $^1$H NMR (300 MHz, dimethylsulfoxide-d$_6$) δ 11.67 (s, 1H), 11.49-11.14 (m, 1H), 8.17 (d, 1H), 8.03 (d, 2H), 7.51 (dd, 3H), 7.43-7.26 (m, 3H), 7.12-6.96 (m, 2H), 6.67 (dd, 1H), 6.40 (dd, 1H), 6.20 (d, 1H), 4.55 (t, 2H), 4.45 (t, 2H), 4.34 (d, 2H), 3.49 (s, 1H), 3.09 (s, 8H), 2.39-1.66 (m, 14H), 1.39 (s, 2H), 0.92 (s, 6H).

Compound 358

4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide

Compound 358A benzyl (4-ethyl-4-hydroxycyclohexyl)methylcarbamate

To a vigorous stirring solution of benzyl (4-oxocyclohexyl)methylcarbamate (1 g) in tetrahydrofuran (20 ml) at −78° C. was slowly added 1 M ethylmagnesium bromide (11.48 ml, 11.48 mmol) in ether. After completion of the addition, the mixture was stirred at −78° C. for 2 hours and was warmed to 0° C., and stirred in an ice bath for 30 minutes. The reaction was quenched with a cold NH$_4$Cl aqueous solution. The precipitates were filtered off and washed with ethyl acetate. The filtrate was concentrated. The residue was dissolved in dichloromethane and loaded onto Analogix purification system, and was eluted with 0-50% ethyl acetate in dichloromethane to provide the title compound.

Compound 358B 4-(aminomethyl)-1-ethylcyclohexanol

A mixture of Compound 358A (500 mg) and 10% Pd/C (100 mg) in tetrahydrofuran (15 ml) was stirred under H$_2$ for 3 hours. The insoluble material was removed by filtration, and the filtrate was concentrated to provide the title compound.

Compound 358C 4-((trans-4-ethyl-4-hydroxycyclohexyl)methylamino)-3-nitrobenzenesulfonamide Compound 358B (270 mg) and 4-fluoro-3-nitrobenzenesulfonamide (417 mg) in tetrahydrofuran were treated with triethylamine (0.8 ml) overnight. The reaction was quenched with water. The resulting mixture was neutralized with diluted aqueous HCl, and extracted with ethyl acetate. The organic layer was dried over Na$_2$SO$_4$, filtered and concentrated. The residue was purified by a reverse phase chromatography, eluting with 40-55% acetonitrile in 0.1% trifluoroacetic acid water to isolate the title compound.

Compound 358D 4-((cis-4-ethyl-4-hydroxycyclohexyl)methylamino)-3-nitro benzenesulfonamide The title compound was prepared and isolated as described for Compound 358C.

Compound 358E 4-(4-{[2-(4-chlorophenyl)-4,4-dimethylcyclohex-1-en-1-yl]methyl}piperazin-1-yl)-N-[(4-{[(trans-4-ethyl-4-hydroxycyclohexyl)methyl]amino}-3-nitrophenyl)sulfonyl]-2-(1H-pyrrolo[2,3-b]pyridin-5-yloxy)benzamide The title compound was prepared as described in the procedure for Compound 11D using Compound 358C in place of Compound 111B. $^1$H NMR (400 MHz, dimethylsulfoxide-d$_6$) δ 11.69 (s, 1H), 11.35 (s, 1H), 8.56 (d, 2H), 8.05 (d, 1H), 7.80 (dd, 1H), 7.45-7.57 (m, 3H), 7.34 (d, 2H), 7.00-7.10 (m, 3H), 6.68 (dd, 1H), 6.39 (dd, 1H), 6.19 (d, 1H), 3.98 (s, 1H), 3.24-3.31 (m, 4H), 3.07 (s, 4H), 2.75 (s, 2H), 2.17 (d, 6H), 1.95 (s, 2H), 1.54-1.73 (m, 5H), 1.35-1.47 (m, 4H), 1.20-1.32 (m, 2H), 1.03-1.18 (m, 2H), 0.92 (s, 6H), 0.81 (t, 3H).

Compound 359

4-(4-{[2-(4-chlorophenyl)-4,4-dimethylcyclohex-1-en-1-yl]methyl}piperazin-1-yl)-N-[(4-{[(cis-4-ethyl-4-hydroxycyclohexyl)methyl]amino}-3-nitrophenyl) sulfonyl]-2-(1H-pyrrolo[2,3-b]pyridin-5-yloxy) benzamide The title compound was prepared as described in the procedure for Compound 11D using Compound 358D in place of Compound 11B. ¹H NMR (400 MHz, dimethylsulfoxide-$d_6$) δ 11.69 (s, 1H), 11.34 (s, 1H), 8.60 (t, 1H), 8.56 (d, 1H), 8.05 (d, 1H), 7.80 (dd, 1H), 7.54 (d, 1H), 7.47-7.52 (m, 2H), 7.34 (d, 2H), 7.01-7.10 (m, 3H), 6.68 (dd, 1H), 6.39 (dd, 1H), 6.19 (d, 1H), 3.77 (s, 1H), 3.26 (t, 2H), 3.07 (s, 4H), 2.76 (s, 2H), 2.10-2.26 (m, 6H), 1.95 (s, 2H), 1.46-1.61 (m, 5H), 1.28-1.46 (m, 6H), 1.12-1.24 (m, 2H), 0.92 (s, 6H), 0.82 (t, 3H).

Compound 360

4-(4-{[2-(4-chlorophenyl)-5-(methoxymethyl)-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide Compound 360A ethyl 8-methyl-1,4-dioxaspiro[4.5]decane-8-carboxylate Into a 500 ml round-bottomed flask was added diisopropylamine (7.98 ml) in tetrahydrofuran (233 ml) to give a colorless solution. The mixture was cooled to −78° C. under $N_2$ and n-BuLi (2.5 M in hexanes, 22.40 ml) was added. The reaction was stirred for 30 minutes and ethyl 1,4-dioxaspiro[4.5]decane-8-carboxylate (10 g) was added. The reaction was allowed to stir for 1.5 hours upon which time $CH_3I$ (4.38 ml) was added. The reaction was allowed to warm to room temperature overnight with stirring. Water was added and the aqueous layer was extracted with ethyl acetate. The combined organics were dried ($Na_2SO_4$), filtered and concentrated by rotary evaporation. The residue was purified by normal phase flash column chromatography (Analogix, 0-50% hexanes/ethyl acetate).

Compound 360B (8-methyl-1,4-dioxaspiro[4.5]decan-8-yl)methanol

In a 500 ml round-bottomed flask was lithium aluminum hydride (1.772 g) in tetrahydrofuran (234 ml) to give a suspension. This suspension was cooled to 0° C. and ethyl 8-methyl-1,4-dioxaspiro[4.5]decane-8-carboxylate (10.66 g) was added via addition funnel. The reaction was stirred overnight at room temperature and then cooled back down to 0° C. The excess lithium aluminum hydride was slowly quenched with 1.8 ml water, 1.8 ml aqueous NaOH (5N) and 5.6 ml water. The suspension was stirred until the salts turned white and was then filtered through a plug of silica gel. The filtrate was concentrated by rotary evaporation and the residue was purified by regular phase flash column chromatography (Analogix, 0-75% hexanes/ethyl acetate).

Compound 360C 8-(methoxymethyl)-8-methyl-1,4-dioxaspiro[4.5]decane

To a 250 ml round-bottomed flask was added NaH (0.902 g) and tetrahydrofuran (37.6 ml) to give a suspension. Compound 360B was added as a tetrahydrofuran solution at room temperature. The suspension was stirred for 30 minutes and then $CH_3I$ (0.611 ml) was added. The reaction was stirred under $N_2$ overnight, carefully quenched with brine and diluted with water and ether. The aqueous layer was extracted with ether (2×) and the combined organics were dried ($Na_2SO_4$), filtered and concentrated by rotary evaporation. The residue was purified by flash column chromatography (Analogix, 0-60% hexanes/ethyl acetate).

Compound 360D 4-(methoxymethyl)-4-methylcyclohexanone

The title compound was prepared by substituting Compound 360C for Compound 353B in the procedure for Compound 353C.

Compound 360E 2-chloro-5-(methoxymethyl)-5-methylcyclohex-1-enecarbaldehyde

The title compound was prepared by substituting Compound 360D for Compound 353C in the procedure for Compound 353D.

Compound 360F 2-(4-chlorophenyl)-5-(methoxymethyl)-5-methylcyclohex-1-enecarbaldehyde The title compound was prepared by substituting Compound 360E for Compound 353D in the procedure for Compound 353E.

Compound 360G methyl 2-(1H-pyrrolo[2,3-b]pyridin-5-yloxy)-4-(4-((2-(4-chlorophenyl)-5-(methoxymethyl)-5-methylcyclohex-1-enyl)methyl)piperazin-1-yl)benzoate The title compound was prepared by substituting Compound 360F for Compound 353E in the procedure for Compound 353F.

Compound 360H 2-(1H-pyrrolo[2,3-b]pyridin-5-yloxy)-4-(4-((2-(4-chlorophenyl)-5-(methoxymethyl)-5-methylcyclohex-1-enyl)methyl)piperazin-1-yl)benzoic Acid The title compound was prepared by substituting Compound 360G for Compound 15G in the procedure for Compound 15H.

Compound 360I 2-(1H-pyrrolo[2,3-b]pyridin-5-yloxy)-4-(4-((2-(4-chlorophenyl)-5-(methoxymethyl)-5-methylcyclohex-1-enyl)methyl)piperazin-1-yl)-N-(3-nitro-4-((tetrahydro-2H-pyran-4-yl)methylamino)phenylsulfonyl)benzamide The title compound was prepared by replacing Compound 3J with Compound 360H and Compound 11B with Compound 1F in the procedure for Compound 1 D. ¹H NMR (300 MHz, dimethylsulfoxide-$d_6$) δ 11.68 (s, 1H) 11.43 (s, 1H) 8.45-8.72 (m, 2H) 8.04 (d, 1H) 7.80 (dd, 1H) 7.44-7.61 (m, 3H) 7.34 (d, 2H) 6.99-7.20 (m, 3H) 6.68 (dd, 1H) 6.39 (dd, 1H) 6.18 (d, 1H) 3.85 (dd, 2H) 3.25-3.30 (m, 4H) 3.24 (s, 3H) 3.02-3.17 (m, 6H) 2.72 (dd, 2H) 2.18 (s, 5H)

2.03-2.13 (m, 2H) 1.81-1.93 (m, 2H) 1.57-1.67 (m, 2H) 1.47-1.56 (m, 1H) 1.17-1.41 (m, 3H) 0.91 (s, 3H).

Compound 361

4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide Compound 361A (S)-3-nitro-4-((4-(oxetan-3-yl)morpholin-2-yl)methylamino)benzenesulfonamide The title compound was prepared by substituting Compound 259E for tert-butyl piperazine-1-carboxylate and 3-oxetanone for 4'-chlorobiphenyl-2-carboxaldehyde in the procedure for Compound 1A.

Compound 361B 4-(4-{[2-(4-chlorophenyl)-4,4-dimethylcyclohex-1-en-1-yl]methyl}piperazin-1-yl)-N-{[3-nitro-4-({[(2S)-4-(oxetan-3-yl)morpholin-2-yl]methyl}amino)phenyl]sulfonyl}-2-(1H-pyrrolo[2,3-b]pyridin-5-yloxy)benzamide The title compound was prepared by substituting Compound 361A for Compound 130C in the procedure for Compound 130D. $^1$H NMR (500 MHz, pyridine-d$_5$) δ 13.00 (s, 1H), 9.26 (d, 1H), 8.87 (t, 1H), 8.43 (d, 1H), 8.35 (dd, 1H), 8.11 (d, 1H), 7.66 (m, 2H), 7.44 (d, 2H), 7.07 (d, 2H), 6.96 (d, 1H), 6.75 (dd, 1H), 6.54 (d, 1H), 6.48 (m, 1H), 4.64 (m, 4H), 3.93 (m, 1H), 3.89 (d, 1H), 3.68 (dt, 1H), 3.53-3.35 (m, 3H), 3.07 (m, 4H), 2.77 (s, 2H), 2.72 (d, 1H), 2.44 (d, 1H), 2.26 (m, 2H), 2.14 (m, 4H), 1.97 (s, 2H), 1.85 (t, 1H), 1.39 (t, 2H), 0.94 (s, 6H).

Compound 362

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide Compound 362A 3-chloro-4-(((1 r, 4r)-4-hydroxy-4-methylcyclohexyl)methoxy)benzenesulfonamide To a solution of Compound 341F (300 mg) in N,N-dimethylformamide (10 ml) was added sodium hydride (416 mg) portionwise. The resulting suspension was stirred for 15 minutes. 3-Chloro-4-fluorobenzenesulfonamide (425 mg) was added and stirring was continued for 72 hours. The reaction was quenched with water and the pH was adjusted to ca. 7. The mixture was diluted with brine (75 ml) and extracted with methylene chloride. The crude product was isolated from the dried methylene chloride layer by concentration and was purified on silica gel eluted with a 10, 25, 50% ethyl acetate in methylene chloride step gradient to provide the title compound.

Compound 362B

N-({3-chloro-4-[(trans-4-hydroxy-4-methylcyclohexyl)methoxy]phenyl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide The title compound was prepared by substituting Compound 362A for Compound 130C in the procedure for Compound 130D. $^1$H NMR (400 MHz, pyridine-d$_5$) δ 13.07 (m, 1H), 8.58 (d, 1H), 8.45 (d, 1H), 8.31 (dd, 1H), 8.11 (d, 1H), 7.69-7.67 (m, 2H), 7.44 (d, 2H), 7.07 (d, 2H), 6.97 (d, 1H), 6.74 (dd, 1H), 6.52 (m, 2H), 5.34 (br s, 2H), 3.82 (d, 2H), 3.06 (m, 4H), 2.77 (s, 2H), 2.25 (m, 2H), 2.13 (m, 4H), 1.97-1.85 (m, 7H), 1.82-1.73 (m, 2H), 1.44-1.32 (m, 7H), 0.94 (m, 6H).

Compound 363

4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide Compound 363A 4-((4'-fluorospiro[benzo[d][1,3]dioxole-2,1'-cyclohexane]-4'-yl)methoxy)-3-nitrobenzenesulfonamide To a solution of Compound 350C (495 mg) in N,N-dimethylformamide (6 ml) was added NaH (65% in mineral oil, 320 mg). The mixture was stirred for 30 minutes, and then 4-fluoro-3-nitrobenzenesulfonamide (457 mg) was added. The mixture was stirred overnight. The mixture was poured over aqueous NH$_4$Cl and extracted with ethyl acetate (300 ml). The combined organic layers were washed with water, brine and dried over Na$_2$SO$_4$. After filtration and evaporation of the solvent, the residue was loaded on a silica gel cartridge and was eluted with 30% ethyl acetate in hexane to provide the title compound.

Compound 363B 4-((1-fluoro-4-oxocyclohexyl)methoxy)-3-nitrobenzenesulfonamide

To a solution of Compound 363A (860 mg) in ethanol (30 ml) was added concentrated HCl (10 ml) and the mixture was stirred at 100° C. for 3 hours. The mixture was neutralized with solid Na$_2$CO$_3$ and extracted with dichloromethane (300 ml) and washed with aqueous NaHCO$_3$, water, brine and dried over Na$_2$SO$_4$. Filtration and evaporation of the solvent gave the title compound.

Compound 363C 4-((4-((2-cyanoethyl)cyclopropyl)amino)-1-fluorocyclohexyl)methoxy)-3-nitrobenzenesulfonamide To a solution of Compound 363B (200 mg) in dichloromethane (6 ml) was added 3-(cyclopropylamino)propanenitrile (64 mg) followed by sodium triacetoxyborohydride (184 mg). The mixture was stirred overnight. The reaction mixture was diluted with dichloromethane (400 ml) and washed with 2N aqueous NaOH, water, and brine. After drying over Na$_2$SO$_4$, the mixture was filtered and evaporation of the solvent gave the title compound.

Compound 363D 4-(4-{[2-(4-chlorophenyl)-4,4-dimethylcyclohex-1-en-1-yl]methyl}piperazin-1-yl)-N-{[4-({4-[(2-cyanoethyl)(cyclopropyl)amino]-1-fluorocyclohexyl}methoxy)-3-nitrophenyl]sulfonyl}-2-(1H-pyrrolo[2,3-b]pyridin-5-yloxy)benzamide The title compound was prepared by substituting Compound 3J for Compound 1E and Compound 363C for Compound 1F in the procedure for Compound 1G. $^1$H NMR (300 MHz, dimethylsulfoxide-d$_6$) δ 11.66 (s, 1H), 8.35 (s, 1H), 8.02 (d, 2H), 7.51 (m, 3H), 7.40 (m, 1H), 7.35 (d, 2H), 7.04 (d, 2H), 6.67 (dd, 1H), 6.39 (d, 1H), 6.20 (s, 1H), 4.27 (d, 2H), 3.13 (m, 4H), 2.88 (m, 3H), 2.67 (m, 4H), 2.09 (m, 10H), 1.49 (m, 9H), 0.93 (s, 6H), 0.45 (m, 4H).

Compound 364

4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide Compound 364A 6-amino-5-nitropyridine-3-sulfonic Acid 6-Aminopyridine-3-sulfonic acid (20 g) in concentrated H$_2$SO$_4$ (80 ml) was heated at 50° C. until it was completely dissolved. To this solution was added fuming HNO$_3$ slowly over 20 minutes, so the internal temperature did not exceed 55° C. After the addition was complete, the reaction mixture was heated at 50° C. for 1 hour. After it was cooled to room temperature, it was poured into 150 g of ice. The mixture was stirred for another hour. The flask was cooled to 0° C., and was kept at 0° C. for another 2 hours. The solid was collected by filtration, and washed with cold 1:1 water/ethanol (20 ml), followed by diethyl ether (10 ml). The solid was dried in a vacuum oven overnight to provide the title compound.

Compound 364B 6-hydroxy-5-nitropyridine-3-sulfonic Acid

Compound 364A (4.0 g) in aqueous HCl (37%, 12 ml) and water (50 ml) was treated with sodium nitrite (1.19 g) in water (8 ml) dropwise at 0° C. After the addition was complete, the reaction mixture was stirred at 0° C. for 1 hour. The mixture was heated at reflux for 2 hours. Water was distilled off to give a dry residue. After the residue was cooled to room temperature, a solution of 1:1 ethano/water (20 ml) was added. The resulting suspension was cooled to 0'C, and kept at 0° C. for 1 hour. The solid was collected by filtration to provide the title compound.

Compound 364C 6-chloro-5-nitropyridine-3-sulfonyl chloride

A mixture of Compound 364B (2.6 g), PCl$_5$ (5.91 g), and POCl$_3$ (10 ml) was heated at 120° C. for 4 hours. The initial suspension became a clear solution. The excess of POCl$_3$ was distilled off. After it was cooled to room temperature, the residue was poured into 50 g of crushed ice. The solid was extracted into ethyl acetate. The aqueous layer was extracted with additional ethyl acetate. The combined organic layers were washed with brine, dried over MgSO$_4$, filtered, and concentrated to give crude product that was used in the next step without further purification.

Compound 364D 6-chloro-5-nitropyridine-3-sulfonamide

Compound 364C in tetrahydrofuran (10 ml) was cooled to −10° C. To this solution was added concentrated ammonium hydroxide (0.82 ml) dropwise. The solution was stirred at −10° C. for 10 minutes. The solvent was removed under pressure at room temperature. The residue was partitioned between water and ethyl acetate. The aqueous layer was extracted with additional ethyl acetate. The combined organic layers were washed with brine, dried over MgSO$_4$, filtered, and concentrated. The residue was purified by flash column chromatography on silica gel using 5-50% ethyl acetate in hexanes to provide the title compound.

Compound 364E 5-nitro-6-((tetrahydro-2H-pyran-4-yl)methylamino)pyridine-3-sulfonamide The title compound was prepared by substituting Compound 364D for 4-fluoro-3-nitrobenzenesulfonamide and (tetrahydro-2H-pyran-4-yl)methanamine for (4-fluorotetrahydro-2H-pyran-4-yl)methanamine in the procedure for Compound 138D.

Compound 364F 4-(4-{[2-(4-chlorophenyl)-4,4-dimethylcyclohex-1-en-1-yl]methyl}piperazin-1-yl)-N-({5-nitro-6-[(tetrahydro-2H-pyran-4-ylmethyl)amino]pyridin-3-yl}sulfonyl)-2-(1H-pyrrolo[2,3-b]pyridin-5-yloxy)benzamide The title compound was prepared by substituting Compound 364E for Compound 11B in the procedure for Compound 11D. $^1$H NMR (500 MHz, dimethylsulfoxide-d$_6$) δ 11.63 (s, 1H), 8.93 (s, 1H), 8.73 (d, 1H), 8.69 (d, 1H), 8.00 (d, 1H), 7.54 (d, 1H), 7.47-7.48 (m, 2H), 7.35 (d, 2H), 7.05 (d, 2H), 6.68 (dd, 1H), 6.35 (dd, 1H), 6.22 (d, 1H), 3.83 (dd, 2H), 3.51 (t, 2H), 3.21-3.27 (m, 2H), 3.10 (s, 4H), 2.83 (s, 2H), 1.90-2.27 (m, 12H), 1.58 (dd, 2H), 1.39 (t, 2H), 1.18-1.28 (m, 2H), 0.88-0.93 (m, 8H).

Compound 365

4-(4-{[2-(4-chlorophenyl)-4,4-dimethylcyclohex-1-en-1-yl]methyl}piperazin-1-yl)-N-({3-nitro-4-[(2-oxaspiro[3.5]non-7-ylmethyl)amino]phenyl}sulfonyl)-2-(1H-pyrrolo[2,3-b]pyridin-5-yloxy)benzamide Compound 365A 7-(azidomethyl)-2-oxaspiro[3.5]nonane To a 250 ml round-bottomed flask was Compound 351F (350 mg) in tetrahydrofuran (75.0 ml) to give a colorless solution. The solution was cooled to 0° C., triphenylphosphine (2.94 g), diisopropyl azodicarboxylate (2.18 ml) and diphenyl phosphorazidate (2.32 ml) were added and the reaction was stirred for 30 minutes at room temperature. The mixture was concentrated and purified the residue by regular phase flash column chromatography (Analogix, 0-20% hexanes/ethyl acetate).

Compound 365B 2-oxaspiro[3.5]nonan-7-ylmethanamine

To a 50 ml round-bottomed flask was added 10% palladium on carbon (58.7 mg). The flask was flushed with $N_2$ and Compound 365A (400 mg) was added as a methanol solution (10.5 ml). The flask was then flushed several times with $H_2$ (via balloon) and heated to 45° C. for 2 hours. The reaction was cooled to room temperature, filtered through celite and the filtrate was concentrated by rotary evaporation. The residue was used in the next step without further purification.

Compound 365C 4-(2-oxaspiro[3.5]nonan-7-ylmethylamino)-3-nitrobenzenesulfonamide The title compound was prepared by substituting Compound 365B for 1-(tetrahydropyran-4-yl)methylamine in the procedure for Compound 1F.

Compound 365D 2-(1H-pyrrolo[2,3-b]pyridin-5-yloxy)-N-(4-(2-oxaspiro[3.5]nonan-7-ylmethylamino)-3-nitrophenylsulfonyl)-4-(4-((2-(4-chlorophenyl)-4,4-dimethylcyclohex-1-enyl)methyl)piperazin-1-yl)benzamide The title compound was prepared by substituting Compound 3J for Compound 1E and Compound 365C for Compound 1F in the procedure for Compound 1G. $^1$H NMR (300 MHz, dimethylsulfoxide-$d_6$) δ 11.67 (s, 1H) 11.25-11.49 (m, 1H) 8.48-8.66 (m, 2H) 8.03 (d, 1H) 7.79 (dd, 1H) 7.41-7.61 (m, 3H) 7.27-7.40 (m, 2H) 7.05 (t, 3H) 6.67 (dd, 1H) 6.39 (dd, 1H) 6.18 (d, 1H) 4.29 (s, 2H) 4.19 (s, 2H) 3.17-3.27 (m, 2H) 2.99-3.14 (m, 4H) 2.69-2.79 (m, 2H) 2.09-2.28 (m, 6H) 2.04 (d, 2H) 1.95 (s, 2H) 1.66 (d, 2H) 1.49-1.61 (m, 1H) 1.29-1.45 (m, 4H) 0.93-1.05 (m, 2H) 0.92 (s, 6H).

Compound 366

4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide Compound 366A tert-butyl (4-cyano-4-methylcyclohexyl)methylcarbamate To a cooled (−78° C.) solution of tert-butyl(4-cyanocyclohexyl)methylcarbamate (500 mg) in tetrahydrofuran (10 ml) was added lithium diisopropylamide (2.0 ml, 2M in heptane). The mixture was stirred at −78° C. for 30 minutes before the addition of $CH_3I$ (1 ml). The mixture was then stirred and the temperature was allowed to warm to room temperature. The reaction was quenched with aqueous $NH_4Cl$ and the mixture was extracted with ethyl acetate (300 ml) and washed with water, brine and dried over $Na_2SO_4$. Filtration and evaporation of the solvent and silica gel chromatography (40% ethyl acetate in hexane) of the crude material gave the title compound.

Compound 366B 4-(aminomethyl)-1-methylcyclohexanecarbonitrile

To a solution of Compound 366A (480 mg) in dichloromethane (10 ml) was added trifluoroacetic acid (10 ml). The mixture was stirred for 3 hours. The mixture was then concentrated under vacuum and was used directly in the next reaction without further purification.

Compound 366C 4-((4-cyano-4-methylcyclohexyl)methylamino)-3-nitrobenzenesulfonamide To a solution of 4-fluoro-3-nitrobenzenesulfonamide (362 mg) in tetrahydrofuran (10 ml) was added Compound 366B (250 mg) and N,N-diisopropylethylamine (2 ml). The mixture was stirred overnight. The mixture was diluted with ethyl acetate (300 ml) and washed with water, brine and dried over $Na_2SO_4$. Filtration and evaporation of the solvent gave the title compound.

Compound 366D 4-(4-{[2-(4-chlorophenyl)-4,4-dimethylcyclohex-1-en-1-yl]methyl}piperazin-1-yl)-N-[(4-{[(4-cyano-4-methylcyclohexyl)methyl]amino}-3-nitrophenyl)sulfonyl]-2-(1H-pyrrolo[2,3-b]pyridin-5-yloxy)benzamide The title compound was prepared by substituting Compound 3J for Compound 1E and Compound 366C for Compound 1F in the procedure for Compound 1G. $^1$H NMR (300 MHz, dimethylsulfoxide-$d_6$) δ 11.67 (s, 1H), 11.37 (m, 1H), 8.59 (m, 2H), 8.04 (d, 1H), 7.80 (d, 1H), 7.51 (m, 3H), 7.34 (d, 2H), 7.10 (d, 1H), 7.04 (d, 2H), 6.68 (dd, 1H), 6.39 (m, 1H), 6.19 (s, 1H), 3.07 (m, 4H), 2.75 (m, 2H), 2.17 (m, 7H), 1.76 (m, 9H), 1.32 (m, 9H), 0.92 (s, 6H).

Compound 367

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl pivalate This compound was prepared by substituting chloromethyl pivalate for chloromethyl butyrate in the procedure for Compound 368. $^1$H NMR (400 MHz, dimethylsulfoxide-$d_6$) δ11.72 (s, 1H), 8.43 (d, 1H), 8.22 (dd, 1H), 8.01 (d, 1H), 7.55 (m, 3H), 7.36 (m, 3H), 7.03 (d, 2H), 6.68 (dd, 1H), 6.41 (m, 1H), 6.17 (d, 1H), 5.83 (s, 2H), 4.40 (d, 2H), 3.78 (m, 2H), 3.59 (m, 2H), 3.08 (br m, 4H), 2.73 (br s, 2H), 2.18 (br m, 6H), 1.96 (s, 2H), 1.84 (m, 4H), 1.39 (m, 2H), 1.00 (s, 9H), 0.92 (s, 6H).

Compound 368

{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]({4-[(4-fluorotetrahydro-2H-pyran-4-yl)methoxy]-3-nitrophenyl}sulfonyl)amino}methyl butyrate Compound 37E (500 mg) was dissolved in acetonitrile (3.7 ml) and chloromethyl butyrate (77 mg) and Hunig's base (73 mg) were added. The reaction was heated under reflux for one day. After cooling and dilution with dimethylsulfoxide (4 ml) the reaction was purified by preparative HPLC using a 250×50 mm C18 column and eluting with 20-100% CH$_3$CN vs. 0.1% trifluoroacetic acid in water, giving the product as a trifluoroacetate salt. The trifluoroacetic acid salt was dissolved in dichloromethane (6 ml) and washed with 50% aqueous NaHCO$_3$. The organic layer was dried over anhydrous Na$_2$SO$_4$, filtered, and concentrated to provide the title compound. $^1$H NMR (400 MHz, dimethylsulfoxide-d$_6$) δ 11.72 (s, 1H), 8.43 (d, 1H), 8.22 (dd, 1H), 8.01 (d, 1H), 7.55 (m, 3H), 7.36 (m, 3H), 7.03 (d, 2H), 6.68 (dd, 1H), 6.41 (m, 1H), 6.17 (d, 1H), 5.83 (s, 2H), 4.40 (d, 2H), 3.78 (m, 2H), 3.59 (m, 2H), 3.08 (br m, 4H), 2.73 (br s, 2H), 2.18 (m, 8H), 1.96 (s, 2H), 1.84 (m, 4H), 1.39 (m, 4H), 0.92 (s, 6H), 0.75 (t, 3H).

Compound 369

4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 369A methyl 4-[(2,2,3,3,5,5,6,6-$^2$H$_8$)piperazin-1-yl]-2-(1H-pyrrolo[2,3-b]pyridin-5-yloxy)benzoate Into a 40 ml vial were added Compound 3H (1.55 g) and piperazine-d$_8$ (2.040 g) in dimethylsulfoxide (13 ml). The solution was heated to 85° C. for 2.5 hours, and was then allowed to cool to room temperature overnight. The mixture was transferred to a 120 ml flask and was cooled to 5-10° C. Dichloromethane (30 ml) was added, then water (10 ml) was added via syringe over 5 minutes maintaining temp at no more than 15° C. The layers were separated and the organic layer was washed with water (4×10-15 ml) until pH of aqueous layer was 8-9. The organic layer was filtered through Na$_2$SO$_4$ and rinsed with dichloromethane (5 ml), and concentrated to provide the title compound.

Compound 369B methyl 4-[4-{[2-(4-chlorophenyl)-4,4-dimethylcyclohex-1-en-1-yl]methyl}($^2$H$_8$)piperazin-1-yl]-2-(1H-pyrrolo[2,3-b]pyridin-5-yloxy)benzoate In a 100 ml round-bottomed flask, Compound 369A (3.4 g), Compound 290B (1.321 g) and dichloromethane (3 ml) were added to a 100 ml round bottom flask at room temperature. To a separate 50 ml 3 neck round bottom flask, sodium triacetoxyborohydride (1.330 g) and dichloromethane (12 ml) were added to give a slurry. After cooling the 50 ml round bottom flask to 18-20° C., the piperazine adduct/aldehyde solution was added via syringe over 5 minutes. The triacetoxyborohydride gradually dissolved to give a clear solution after ~5 minutes. After an additional 10 minutes, the solution became hazy. After 16 hours, the reaction was cooled to 5-10° C. Saturated aqueous NaHCO$_3$ (12 ml) was added over 5 minutes maintaining the temperature at no more than 10° C. The layers were separated and the organic layer was washed with saturated aqueous NaHCO$_3$, and 10% NaCl (12 ml), and then filtered through Na$_2$SO$_4$ and rinsed with dichloromethane (4 ml). The solution was concentrated on a rotovap, and chase concentrated with methanol (40 ml). The resulting solution was cooled to 5-10° C., and the product precipitated. The solution was mixed at room temperature for 30 minutes, then filtered and rinsed with methanol (5 ml), and the product was air dried.

Compound 369C

4-[4-{[2-(4-chlorophenyl)-4,4-dimethylcyclohex-1-en-1-yl]methyl}($^2$H$_8$)piperazin-1-yl]-2-(1H-pyrrolo[2,3-b]pyridin-5-yloxy)benzoic Acid The title compound was prepared by substituting Compound 369B for Compound 15G in the procedure for Compound 15H.

Compound 369D

4-[4-{[2-(4-chlorophenyl)-4,4-dimethylcyclohex-1-en-1-yl]methyl}($^2$H$_8$)piperazin-1-yl]-N-({3-nitro-4-[(tetrahydro-2H-pyran-4-ylmethyl)amino]phenyl}sulfonyl)-2-(1H-pyrrolo[2,3-b]pyridin-5-yloxy)benzamide To a mixture of Compound 369C (2.0 g), Compound 1F (1.1 g) and N,N-dimethylpyridin-4-amine (0.7 g) in dichloromethane (20 ml) was added 1-ethyl-3-[3-(dimethylamino)propyl]-carbodiimide hydrochloride (0.8 g). The reaction mixture was stirred at room temperature overnight. The reaction was quenched with N,N-dimethylethane-1,2-diamine (0.6 g) and stirred at room temperature for 3 hours. The mixture was extracted with 20% aqueous acetic acid and washed with 5% aqueous NaCl. Methanol (2 ml) and ethyl acetate (18 ml) were added and the precipitate was collected by filtration to provide the title compound. $^1$H NMR (400 MHz, dimethylsulfoxide-d$_6$) 11.71 (s, 1H), 11.37 (s, br, 1H), 8.60 (t, 1H), 8.55 (d, 1H), 8.04 (d, 1H), 7.80 (dd, 1H), 7.47-7.54 (m, 3H), 7.31-7.34 (m, 2H), 7.09 (d, 1H), 7.01-7.03 (m, 2H), 6.67 (dd, 1H), 6.39 (dd, 1H), 6.19 (d, 1H), 3.83 (dd, 2H), 3.21-3.30 (m, 4H), 3.00-3.10 (s, 4H), 2.75 (s, 2H), 2.05-2.24 (m, 6H), 1.95 (s, 2H), 1.80-1.93 (m, 1H), 1.55-1.64 (m, 2H), 1.37 (t, 2H), 1.18-1.31 (m, 2H), 0.90 (s, 6H).

Compound 370

4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)-N-{[3-(tetrahydro-2H-pyran-4-ylmethyl)-3H-[1,2,3]triazolo[4,5-b]pyridin-6-yl]sulfonyl}benzamide

Compound 370A 5-amino-6-((tetrahydro-2H-pyran-4-yl)methylamino)pyridine-3-sulfonamide A mixture of Compound 364E (0.16 g) and 5% palladium on carbon (0.025 g) in ethanol (5 ml) was treated with a balloon of hydrogen. The reaction mixture was stirred overnight. The solid was filtered off. The filtrate was concentrated. The residue was purified by flash chromatography on silica gel to give the title compound.

Compound 370B 3-((tetrahydro-2H-pyran-4-yl)methyl)-3H-[1,2,3]
triazolo[4,5-b]pyridine-6-sulfonamide Compound 370A (0.085 g) in water (10 ml) was treated with concentrated $H_2SO_4$ (0.5 ml). The solution was cooled to 0° C. To this solution was added $NaNO_2$ (0.023 g) in water (1 ml) dropwise. The solution was stirred for 1 hour at 0° C. The reaction mixture was poured into saturated $NaHCO_3$ solution, and extracted with ethyl acetate three times. The combined organic layers were washed with brine, dried over $MgSO_4$, filtered, and concentrated to give the title compound.

Compound 370C 2-(1H-pyrrolo[2,3-b]pyridin-5-yloxy)-4-(4-((2-(4-chlorophenyl)-4,4-dimethylcyclohex-1-enyl)methyl)
piperazin-1-yl)-N-(3-((tetrahydro-2H-pyran-4-yl)
methyl)-3H-[1,2,3]triazolo[4,5-b]pyridin-6-ylsulfonyl)benzamide This compound was prepared by substituting Compound 370B for Compound 11B in the procedure for Compound 11D. $^1$H NMR (500 MHz, dimethylsulfoxide-$d_6$) δ 11.60 (s, 1H), 9.11 (s, 1H), 8.92 (d, 1H), 7.96 (d, 1H), 7.55 (d, 1H), 7.45-7.46 (m, 1H), 7.42 (s, 1H), 7.36 (d, 2H), 7.05 (d, 2H), 6.66 (dd, 1H), 6.32 (s, 1H), 6.22 (s, 1H), 4.63 (d, 2H), 3.80 (dd, 2H), 3.21-3.30 (m, 2H), 3.16 (s, 4H), 2.83 (s, 2H), 2.19-2.29 (m, 6H), 1.97 (s, 2H), 1.33-1.41 (m, 6H), 0.93 (s, 2H).

Compound 371

4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]
pyridin-5-yloxy)benzamide Compound 371A 6-((trans-4-hydroxy-4-methylcyclohexyl)methylamino)-5-nitropyridine-3-sulfonamide This compound was prepared by substituting Compound 364D for 4-fluoro-3-nitrobenzenesulfonamide and Compound 376B for Compound 138C in the procedure for Compound 138D. The title compound was isolated by reverse phase Gilson Prep HPLC system with a Phenomenex prep column (Luna, 5μ, C18(2), 250×21.20 mm, 5 Å) eluting with 20-80% acetonitrile in water with 0.1% TFA.

Compound 371B 4-(4-{[2-(4-chlorophenyl)-4,4-dimethylcyclohex-1-en-1-yl]methyl}piperazin-1-yl)-N-[(6-{[(trans-4-hydroxy-4-methylcyclohexyl)methyl]amino}-5-nitropyridin-3-yl)sulfonyl]-2-(1H-pyrrolo[2,3-b]
pyridin-5-yloxy)benzamide The title compound was prepared by substituting Compound 371A for Compound 11B in the procedure for Compound 11D. $^1$H NMR (300 MHz, dimethylsulfoxide-$d_6$) δ 11.63 (s, 1H), 11.53-10.99 (m, 1H), 8.91 (s, 1H), 8.71 (dd, 2H), 8.01 (d, 1H), 7.61-7.44 (m, 3H), 7.44-7.28 (m, 2H), 7.12-6.97 (m, 2H), 6.76-6.61 (m, 1H), 6.36 (dd, 1H), 6.21 (d, 1H), 3.92 (s, 1H), 3.48 (t, 2H), 3.10 (s, 4H), 2.83 (s, 2H), 2.24 (dd, 6H), 1.96 (s, 2H), 1.37 (ddd, 11H), 1.07 (s, 3H), 0.93 (s, 6H).

Compound 372

4-(4-{[2-(4-chlorophenyl)-4,4-dimethylcyclohex-1-en-1-yl]methyl}piperazin-1-yl)-N-[(5-cyano-6-{[4-fluoro-1-(oxetan-3-yl)piperidin-4-yl]
methoxy}pyridin-3-yl)sulfonyl]-2-(1H-pyrrolo[2,3-b]pyridin-5-yloxy)benzamide Compound 372A ethyl
4-fluoro-1-(oxetan-3-yl)piperidine-4-carboxylate To 1-tert-butyl 4-ethyl 4-fluoropiperidine-1,4-dicarboxylate (1.00 g) was added HCl (4.0M in dioxane, 4.54 ml). After 1 hour the reaction was concentrated and dried under high vacuum. The resulting solid was dissolved in dichloromethane (5 ml) and treated with sodium triacetoxyborohydride (1.155 g) and oxetan-3-one (0.262 g) and stirred overnight. The reaction was quenched with saturated NaHCO3 solution (20 ml) and extracted into dichloromethane (2×25 ml). The organic layer was dried over magnesium sulfate, filtered, and concentrated. Silica gel chromatography (Reveleris 80 g) eluting with a gradient of 0.5% to 3.75% methanol/dichloromethane over 40 minutes (flow=30 ml/minute) gave the title compound.

Compound 372B (4-fluoro-1-(oxetan-3-yl)piperidin-4-yl)methanol

To a solution of Compound 372A (0.59 g) in tetrahydrofuran (5 ml) was added lithium aluminum hydride (1.80 ml) at 0° C. The reaction was removed from the ice bath and allowed to warm to room temperature. The reaction was quenched by the dropwise addition of 0.6 ml of water followed by 0.2 ml of 2N aqueous NaOH. The reaction was filtered through diatomaceous earth and rinsed with ethyl acetate (50 ml). The organics were concentrated and loaded onto silica gel (Reveleris 40 g) and eluted using a gradient of 0.75% to 7.5% methanol/dichloromethane over 30 minute (flow=40 ml/minutes) to give the title compound.

Compound 372C 5-bromo-6-((4-fluoro-1-(oxetan-3-yl)piperidin-4-yl)
methoxy)pyridine-3-sulfonamide This compound was prepared by substituting Compound 372B for (tetrahydro-2H-pyran-4-yl)methanol and Compound 36A for 4-fluoro-3-nitrobenzenesulfonamide in the procedure for Compound 24A.

Compound 372D 5-cyano-6-((4-fluoro-1-(oxetan-3-yl)piperidin-4-yl)
methoxy)pyridine-3-sulfonamide This compound was prepared by substituting Compound 372C for Compound 36B in the procedure for Compound 36C.

Compound 372E 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(5-cyano-6-((4-fluoro-1-(oxetan-3-yl)piperidin-4-yl)methoxy)pyridin-3-ylsulfonyl)benzamide The title compound was prepared by substituting Compound 372D for Compound 11B in the procedure for Compound 11D. $^1$H NMR (300 MHz, dimethylsulfoxide-d$_6$) δ 11.58 (s, 1H), 8.71 (s, 1H), 8.52 (s, 1H), 7.96 (d, 1H), 7.57 (d, 1H), 7.48-7.30 (m, 4H), 7.06 (d, 2H), 6.68 (d, 1H), 6.37-6.22 (m, 2H), 4.65-4.40 (m, 6H), 3.58 (s, 1H), 3.12 (s, 6H), 2.84-2.59 (m, 4H), 2.17 (s, 6H), 1.96 (d, 6H), 1.41 (s, 2H), 0.93 (s, 6H).

Compound 373

N-(4-{[4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzoyl]sulfamoyl}-2-nitrophenyl)morpholine-4-carboxamide

Compound 373A morpholine-4-carboxamide

A solution of morpholine-4-carbonyl chloride (2.0 g) in methanol (10 ml) and 7 N NH$_3$ in methanol (5 ml) was stirred at 45° C. overnight. The mixture was concentrated to give a solid, which was dried under vacuum.

Compound 373B

N-(2-nitro-4-sulfamoylphenyl)morpholine-4-carboxamide

This compound was prepared by substituting Compound 373A for (tetrahydro-2H-pyran-4-yl)methanol in the procedure for Compound 24A.

Compound 373C

N-(4-(N-(2-(1H-pyrrolo[2,3-b]pyridin-5-yloxy)-4-(4-((2-(4-chlorophenyl)-4,4-dimethylcyclohex-1-enyl)methyl)piperazin-1-yl)benzoyl)sulfamoyl)-2-nitrophenyl)morpholine-4-carboxamide This compound was prepared by substituting Compound 373B for Compound 130C in the procedure for Compound 130D. $^1$H NMR (500 MHz, pyridine-d$_5$) δ 13.02 (s, 1H), 10.41 (s, 1H), 9.27 (d, 1H), 8.81 (d, 1H), 8.50 (dd, 1H), 8.40 (d, 1H), 8.09 (d, 1H), 7.65 (m, 2H), 7.44 (d, 2H), 7.07 (d, 2H), 6.76 (dd, 1H), 6.54 (d, 1H), 6.48 (m, 1H), 3.67 (m, 4H), 3.58 (m, 4H), 3.07 (m, 4H), 2.77 (s, 2H), 2.26 (t, 2H), 2.14 (m, 4H), 1.97 (s, 2H), 1.39 (t, 2H), 0.94 (s, 6H).

Compound 374

4-(4-{[2-(4-chlorophenyl)-4,4-dimethylcyclohex-1-en-1-yl]methyl}piperazin-1-yl)-N-{[4-({[4-(methoxymethyl)cyclohexyl]methyl}amino)-3-nitrophenyl]sulfonyl}-2-(1H-pyrrolo[2,3-b]pyridin-5-yloxy)benzamide

Compound 374A (4,4-diethoxycyclohexyl)methanol

Ethyl 4,4-diethoxycyclohexanecarboxylate (6.67 g) synthesized according to a literature procedure (*European Journal of Organic Chemistry* (2008) 5:895) in tetrahydrofuran (60 ml) was treated with 2 M lithium aluminum hydride in tetrahydrofuran (14.5 ml) at 0° C. for 1 hour. Water (3 ml) was slowly added to quench the reaction. The precipitates were filtered off and washed with ethyl acetate. The filtrate was dried over Na$_2$SO$_4$, filtered, and concentrated to provide the title compound.

Compound 374B 1,1-diethoxy-4-(methoxymethyl)cyclohexane

Compound 374A (665 mg) in tetrahydrofuran (20 ml) was treated with NaH (394 mg) for 30 minutes and then CH$_3$I (0.267 ml) was slowly added. The resulting mixture was stirred overnight and the reaction was quenched with a few drops of water. The mixture was concentrated and the residue was suspended in water and extracted with dichloromethane. The organic layer was dried over Na$_2$SO$_4$, filtered and concentrated. The residue was purified by flash chromatography, and was eluted with 0-15% ethyl acetate in dichloromethane to provide the title compound.

Compound 374C 4-(methoxymethyl)cyclohexanone

Compound 374B (2.2 g) in a mixture of water (3 ml) and acetic acid (12 ml) was heated at 65° C. for 2 hours. The reaction mixture was concentrated. The residue was mixed with water and saturated aqueous NaHCO$_3$ and extracted with dichloromethane. The dichloromethane layer was dried over Na$_2$SO$_4$, filtered, and concentrated to provide the title compound.

Compound 374D 4-(methoxymethyl)cyclohexanecarbonitrile

To a cold (−10° C.) solution of Compound 374C (1.18 g) and toluenesulfonylmethyl isocyanide (2.268 g) in dimethoxyethane (3 ml) and absolute ethanol (0.1 ml) was added (in small portions) potassium tert-butoxide (2.235 g). The reaction mixture was continued to stir at <5° C. for 30 minutes, warmed to room temperature, heated at 35° C. for 30 minutes and then at room temperature for 2 hours. The reaction mixture was concentrated and the residue was dissolved in water-brine, and extracted with dichloromethane. The dichloromethane layer was purified by flash chromatography, and was eluted with 5% ethyl acetate in dichloromethane to provide the title compound.

Compound 374E (4-(methoxymethyl)cyclohexyl)methanamine

To a solution of Compound 374D (460 mg) in tetrahydrofuran (15 ml) was added 2M lithium aluminum hydride in tetrahydrofuran (2.252 ml) slowly. The reaction mixture was stirred at room temperature for 1 hour, refluxed for 1 hour and cooled. 2 ml of 2M aqueous NaOH and water (5 ml) was added. The solid was filtered off and washed with ether.

The filtrate was concentrated. The residue was mixed with dichloromethane (50 ml) and the resulting mixture was dried over Na$_2$SO$_4$ and concentrated to provide the title compound.

Compound 374F

4-((4-(methoxymethyl)cyclohexyl)methylamino)-3-nitrobenzenesulfonamide

Compound 374E (450 mg) and 4-fluoro-3-nitrobenzenesulfonamide (693 mg) in tetrahydrofuran (10 ml) were stirred overnight. The reaction mixture was concentrated and the residue was suspended in a mixture of $CH_3CN$, methanol and water. The precipitates were collected, washed with water and dried to give the title compound.

Compound 374G

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-((4-(methoxymethyl)cyclohexyl)methylamino)-3-nitrophenylsulfonyl)benzamide The title compound was prepared as described in the procedure for Compound 11D using Compound 374F in place of Compound 11B. $^1$H NMR (400 MHz, dimethylsulfoxide-$d_6$) δ 11.69 (s, 1H), 11.40 (s, 1H), 8.53-8.61 (m, 2H), 8.04 (d, 1H), 7.77-7.82 (m, 1H), 7.47-7.55 (m, 3H), 7.34 (d, 2H), 7.02-7.09 (m, 3H), 6.68 (dd, 1H), 6.39 (dd, 1H), 6.19 (d, 1H), 3.18-3.27 (m, 5H), 3.04-3.14 (m, 5H), 2.75 (s, 2H), 2.11-2.24 (m, 6H), 1.95 (s, 2H), 1.69-1.84 (m, 3H), 1.33-1.63 (m, 7H), 0.84-1.05 (m, 9H).

Compound 375

4-(4-{[2-(4-chlorophenyl)-4,4-dimethylcyclohex-1-en-1-yl]methyl}piperazin-1-yl)-N-[(5-chloro-6-{[1-(1,3-thiazol-2-yl)piperidin-4-yl]methoxy}pyridin-3-yl)sulfonyl]-2-(1H-pyrrolo[2,3-b]pyridin-5-yloxy)benzamide

Compound 375A methyl 1-(thiazol-2-yl)piperidine-4-carboxylate

A mixture of methyl piperidine-4-carboxylate (2.045 g), 2-bromothiazole (1.64 g), and $Cs_2CO_3$ (5.86 g) in dimethylformamide (15 ml) was heated at 100° C. overnight. After it cooled to room temperature, the reaction mixture was partitioned between water and ethyl acetate. The organic layer was separated, and the aqueous layer was extracted with additional ethyl acetate three times. The combined organic layers were washed with brine, dried over $MgSO_4$, filtered, and concentrated. The residue was purified by flash chromatography on silica gel to give the title compound.

Compound 375B

(1-(thiazol-2-yl)piperidin-4-yl)methanol

This compound was prepared by substituting Compound 375A for Compound 339A in the procedure for Compound 339B.

Compound 375C

5-chloro-6-((1-(thiazol-2-yl)piperidin-4-yl)methoxy)pyridine-3-sulfonamide

This compound was prepared by substituting Compound 375B for (tetrahydro-2H-pyran-4-yl)methanol and Compound 40A for Compound 36A in the procedure for Compound 36B.

Compound 375D

2-(1H-pyrrolo[2,3-b]pyridin-5-yloxy)-N-(5-chloro-6-((1-(thiazol-2-yl)piperidin-4-yl)methoxy)pyridin-3-ylsulfonyl)-4-(4-((2-(4-chlorophenyl)-4,4-dimethylcyclohex-1-enyl)methyl)piperazin-1-yl)benzamide This compound was prepared by substituting Compound 375C for Compound 11B in the procedure for Compound 11D. $^1$H NMR (500 MHz, dimethylsulfoxide-$d_6$) δ 11.65 (s, 1H), 8.49 (s, 1H), 8.17 (s, 1H), 8.01 (d, 1H), 7.54 (d, 1H), 7.48-7.49 (m, 2H), 7.35 (d, 2H), 7.14 (d, 1H), 7.05 (d, 2H), 6.80 (d, 1H), 6.67 (dd, 1H), 6.38 (dd, 1H), 6.21 (d, 1H), 4.28 (d, 2H), 3.92 (d, 2H), 2.98-3.10 (m, 6H), 2.86 (s, 2H), 2.30 (m, 4H), 2.03-2.15 (m, 3H), 1.96 (s, 2H), 1.96 (s, 2H), 1.82-1.86 (m, 2H), 1.33-1.44 (m, 4H), 0.93 (s, 6H).

Compound 376

4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide

Compound 376A tert-butyl (4-hydroxy-4-methylcyclohexyl)methylcarbamate

A solution of tert-butyl(4-oxocyclohexyl)methylcarbamate (1.00 g) was dissolved in tetrahydrofuran (20 ml) and cooled to –78° C. Methylmagnesium bromide (4.40 ml) was added dropwise. The reaction was stirred for 2 hours at –78° C. then allowed to warm to 0° C. and stirred for 30 minutes. The resulting suspension was quenched with water (10 ml), diluted with ether (50 ml), washed with ammonium chloride (25 ml), washed with brine (25 ml), dried over magnesium sulfate, filtered, and concentrated. Silica gel chromatography (Reveleris 80 g) eluting using a gradient of 5% to 50% ethyl acetate/dichloromethane over 30 minutes (flow=60 ml/min) gave the title compound as a ~2:1 mixture of cis and trans isomers.

Compound 376B

4-(aminomethyl)-1-methylcyclohexanol

To a solution of Compound 376A (0.75 g) in dichloromethane (3 ml) was added a few drops of water followed by trifluoroacetic acid (1.19 ml) and the reaction stirred at room temperature. After stirring for 2 h added additional trifluoroacetic acid (0.5 ml). After an additional 4 h the reaction was concentrated and dried under high vacuum. The resulting oily solid was triturated with diethyl ether with sonication. Filtration and washing with diethyl ether gave the title compound as a trifluoroacetic acid salt and a mixture of cis and trans isomers.

Compound 376C 6-((cis-4-hydroxy-4-methylcyclohexyl)methyl-amino)-5-nitropyridine-3-sulfonamide This compound was prepared by substituting Compound 364D for 4-fluoro-3-nitrobenzenesulfonamide and Compound 376B for (4-fluorotetrahydro-2H-pyran-4-yl)methanamine in the procedure for Compound 138D. The title compound was isolated by reverse phase Gilson Prep HPLC system with a Phenomenex prep column (Luna, 5μ, C18(2), 250×21.20 mm, 5 Å) eluting with 20-80% acetonitrile in water with 0.1% TFA.

Compound 376D 4-(4-{[2-(4-chlorophenyl)-4,4-dimethylcyclohex-1-en-1-yl]methyl}piperazin-1-yl)-N-[(6-{[(cis-4-hydroxy-4-methylcyclohexyl)methyl]amino}-5-nitropyridin-3-yl)sulfonyl]-2-(1H-pyrrolo[2,3-b]pyridin-5-yloxy)benzamide This compound was prepared by substituting Compound 376C for Compound 11B in the procedure for Compound 11D. $^1$H NMR (500 MHz, dimethylsulfoxide-d$_6$) δ 11.64 (s, 1H), 8.91 (s, 1H), 8.72 (d, 1H), 8.70 (d, 1H), 8.01 (d, 1H), 7.47-7.54 (m, 3H), 7.35 (d, 2H), 7.04 (d, 2H), 6.68 (dd, 1H), 6.36 (dd, 1H), 6.21 (d, 1H), 3.93 (s, 1H), 3.48 (t, 2H), 3.10 (s, 4H), 2.83 (s, 2H), 2.15-2.33 (m, 6H), 1.96 (s, 1H), 1.34-1.59 (m, 9H), 1.17-1.24 (m, 2H), 1.07 (s, 2H), 0.92 (s, 6H).

Compound 377

4-(4-{[2-(4-chlorophenyl)-5-methoxy-5-methylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide The title compound was prepared by substituting Compound 378D for Compound 1E and Compound 337M for Compound 1F in the procedure for Compound 1G. $^1$H NMR (500 MHz, pyridine-d$_5$) δ 13.07 (s, 1H), 9.31 (d, 1H), 8.68 (t, 1H), 8.44 (d, 1H), 8.37 (dd, 1H), 8.10 (d, 1H), 7.68 (m, 1H), 7.66 (d, 1H), 7.41 (m, 2H), 7.09 (m, 2H), 6.92 (d, 1H), 6.74 (dd, 1H), 6.52 (d, 1H), 6.50 (dd, 1H), 3.20 (m, 5H), 3.06 (t, 4H), 2.77 (m, 2H), 2.57 (d, 1H), 2.49 (m, 1H), 2.17 (m, 6H), 1.86 (m, 5H), 1.69 (m, 4H), 1.40 (s, 3H), 1.23 (m, 5H).

Compound 378

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide

Compound 378A 2-chloro-5-methoxy-5-methylcyclohex-1-enecarbaldehyde

Dimethylformamide (1.298 ml) in dichloromethane (2.0 ml) at −10° C. was treated dropwise with POCl$_3$ (1.426 ml) to give a colorless solution. The mixture was stirred 5 minutes and then warmed to room temperature and stirred 30 minutes. The solution was cooled to −10° C., treated dropwise with a solution of 4-methoxy-4-methylcyclohexanone (1.74 g) in dichloromethane (2.5 ml), and stirred for 4 hours at ambient temperature. The reaction mixture was poured over a mixture of ice and 25% aqueous sodium acetate solution. After the ice melted, the reaction mixture was poured into a separatory funnel and extracted with diethyl ether (4×125 ml). The diethyl ether extracts were washed with NaHCO$_3$ solution and brine, dried (MgSO$_4$), filtered and concentrated. The concentrate was chromatographed on silica gel with 0 to 5% ethyl acetate in hexanes as the eluent.

Compound 378B 2-(4-chlorophenyl)-5-methoxy-5-methylcyclohex-1-enecarbaldehyde Compound 378A (1.55 g), 4-chlorophenylboronic acid (1.542 g), PdOAc$_2$ (0.055 g), K$_2$CO$_3$ (2.84 g) and tetrabutylammonium bromide (2.65 g) were combined in a 50-ml round-bottomed flask equipped with a magnetic stir bar. Water (9.13 ml) was added. The vial was flushed with nitrogen, capped and stirred at 45° C. for 14 hours. The reaction mixture was cooled to room temperature and partitioned between brine and diethyl ether. The organic layer was washed with brine, dried (MgSO$_4$), filtered through a plug of celite, concentrated and chromatographed on silica gel with 5 to 20% ethyl acetate in hexanes as the eluent.

Compound 378C methyl 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)benzoate The title compound was prepared by substituting Compound 378B for 4'-chlorobiphenyl-2-carboxaldehyde and Compound 15F for tert-butyl piperazine-1-carboxylate in the procedure for Compound 1A except that a small amount of DMSO was added to the reaction mixture.

Compound 378D 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)benzoic Acid The title compound was prepared by substituting Compound 378C for Compound 15G in the procedure for Compound 15H.

Compound 378E 2-(1H-pyrrolo[2,3-b]pyridin-5-yloxy)-4-(4-((2-(4-chlorophenyl)-5-methoxy-5-methylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting Compound 378D for Compound 1E in the procedure for Compound 1G. $^1$H NMR (500 MHz, pyridine-d$_5$) δ 13.07 (s, 1H), 9.31 (d, 1H), 8.68 (t, 1H), 8.43 (d, 1H), 8.37 (dd, 1H), 8.09 (d, 1H), 7.68 (m, 1H), 7.66 (d, 1H), 7.41 (m, 2H), 7.09 (m, 2H), 6.90 (d, 1H), 6.74 (dd, 1H), 6.52 (d, 1H), 6.50 (dd, 1H), 3.97 (dd, 2H), 3.30 (td, 2H), 3.21 (s, 3H), 3.15 (m, 2H), 3.06 (t, 4H), 2.77 (m, 2H), 2.57 (d, 1H), 2.50 (m, 1H), 2.16 (m, 6H), 1.81 (m, 2H), 1.63 (m, 1H), 1.57 (dd, 2H), 1.32 (m, 2H), 1.21 (s, 3H).

Table 1 below presents the inhibition constant ($K_i$) for binding of representative compounds to Bcl-2 protein, as determined by a TR-FRET (Time-Resolved Fluorescence-Resonance-Energy-Transfer) assay. The smaller the $K_i$ value, the greater is the binding affinity. It will be noted that the overwhelming majority of the compounds have $K_i < 0.0001$ μM (<0.1 nM), and very many have $K_i < 0.00001$ μM (<0.01 nM).

TABLE 1

| Bcl-2 binding $K_i$ (μM) | | | |
| --- | --- | --- | --- |
| Compound | $K_i$ | Compound | $K_i$ |
| 1 | 0.000225 | 190 | 0.000026 |
| 2 | <0.000010 | 191 | <0.000010 |
| 3 | 0.000013 | 192 | <0.000010 |
| 4 | <0.000010 | 193 | <0.000010 |
| 5 | <0.000010 | 194 | <0.000010 |
| 6 | 0.000018 | 195 | <0.000010 |
| 7 | 0.00492 | 196 | <0.000010 |
| 8 | 0.000153 | 197 | <0.000010 |
| 9 | <0.000010 | 198 | <0.000010 |
| 10 | <0.000010 | 199 | <0.000010 |
| 11 | 0.000016 | 200 | <0.000010 |
| 12 | <0.000010 | 201 | 0.000014 |
| 13 | <0.000010 | 202 | <0.000010 |
| 14 | 0.002798 | 203 | <0.000010 |
| 15 | <0.000010 | 204 | <0.000010 |
| 16 | 0.000219 | 205 | <0.000010 |
| 17 | 0.00009 | 206 | 0.000036 |
| 18 | 0.000017 | 207 | 0.00003 |
| 19 | 0.000226 | 208 | 0.000104 |
| 20 | 0.000181 | 209 | <0.000010 |
| 21 | 0.000912 | 210 | 0.000011 |
| 22 | 0.000291 | 211 | 0.000058 |
| 23 | 0.000083 | 212 | 0.0001330 |
| 24 | <0.000010 | 213 | <0.000010 |
| 25 | <0.000010 | 214 | <0.000010 |
| 26 | 0.000011 | 215 | <0.000010 |
| 27 | 0.000134 | 216 | <0.000010 |
| 28 | <0.000010 | 217 | <0.000010 |
| 29 | <0.000010 | 218 | 0.000013 |
| 30 | <0.000010 | 219 | 0.001192 |
| 31 | <0.000010 | 220 | 0.000988 |
| 32 | <0.000010 | 221 | 0.000049 |
| 33 | <0.000010 | 222 | 0.000938 |
| 34 | 0.00001 | 223 | 0.000053 |
| 35 | <0.000010 | 224 | <0.000010 |
| 36 | 0.000017 | 225 | 0.000196 |
| 37 | <0.000010 | 226 | 0.000139 |
| 38 | 0.0003 | 227 | <0.000010 |
| 39 | 0.000012 | 228 | 0.026761 |
| 40 | <0.000010 | 229 | 0.002109 |
| 41 | <0.000010 | 230 | 0.000031 |
| 42 | 0.000439 | 231 | 0.000770 |
| 43 | 0.000012 | 232 | 0.001631 |
| 44 | <0.000010 | 233 | 0.001654 |
| 45 | <0.000010 | 234 | 0.000115 |
| 46 | 0.000935 | 235 | 0.000023 |
| 47 | <0.000010 | 236 | 0.000033 |
| 48 | <0.000010 | 237 | 0.000024 |
| 49 | 0.000074 | 238 | <0.000010 |
| 50 | 0.000021 | 239 | 0.000026 |
| 51 | <0.000010 | 240 | <0.000010 |
| 52 | 0.000114 | 241 | <0.000010 |
| 53 | <0.000010 | 242 | 0.000057 |
| 54 | 0.002071 | 243 | 0.000546 |
| 55 | <0.000010 | 244 | 0.000281 |
| 56 | 0.000037 | 245 | 0.000015 |
| 57 | 0.000063 | 246 | 0.000144 |
| 58 | <0.000010 | 247 | 0.000019 |

TABLE 1-continued

| Bcl-2 binding $K_i$ (μM) | | | |
| --- | --- | --- | --- |
| Compound | $K_i$ | Compound | $K_i$ |
| 59 | 0.000203 | 248 | 0.000029 |
| 60 | <0.000010 | 250 | 0.000412 |
| 61 | 0.000091 | 251 | 0.000571 |
| 62 | <0.000010 | 252 | <0.000010 |
| 63 | <0.000010 | 253 | 0.000052 |
| 64 | <0.000010 | 254 | <0.000010 |
| 65 | <0.000010 | 255 | <0.000010 |
| 66 | <0.000010 | 256 | <0.000010 |
| 67 | <0.000010 | 257 | 0.000052 |
| 68 | 0.000012 | 258 | <0.000010 |
| 69 | 0.001157 | 259 | <0.000010 |
| 70 | 0.003964 | 260 | 0.000016 |
| 71 | 0.00001 | 261 | 0.000134 |
| 72 | <0.000010 | 262 | <0.000010 |
| 73 | <0.000010 | 263 | 0.000156 |
| 74 | 0.000029 | 264 | 0.000036 |
| 75 | <0.000010 | 265 | <0.000010 |
| 76 | 0.000196 | 266 | <0.000010 |
| 77 | 0.000213 | 267 | 0.000035 |
| 78 | <0.000010 | 268 | <0.000010 |
| 79 | <0.000010 | 269 | 0.000016 |
| 80 | <0.000010 | 270 | <0.000010 |
| 81 | <0.000010 | 271 | 0.000039 |
| 82 | 0.000328 | 272 | 0.000031 |
| 83 | 0.000071 | 273 | 0.000035 |
| 84 | 0.000123 | 274 | 0.000040 |
| 85 | 0.000391 | 275 | <0.000010 |
| 86 | 0.000498 | 276 | <0.000010 |
| 87 | 0.000618 | 277 | <0.000010 |
| 88 | 0.000672 | 278 | 0.000252 |
| 89 | 0.000073 | 279 | 0.000035 |
| 90 | 0.000013 | 280 | 0.000071 |
| 91 | 0.000487 | 281 | 0.000145 |
| 92 | 0.000128 | 282 | <0.000010 |
| 93 | 0.003461 | 283 | <0.000010 |
| 94 | 0.000678 | 284 | 0.000024 |
| 95 | 0.000014 | 285 | <0.000010 |
| 96 | 0.000014 | 286 | <0.000010 |
| 97 | 0.000017 | 287 | 0.000081 |
| 98 | <0.000010 | 288 | 0.000251 |
| 99 | 0.000233 | 289 | 0.000090 |
| 100 | <0.000010 | 290 | <0.000010 |
| 101 | 0.000021 | 291 | <0.000010 |
| 102 | 0.000094 | 292 | 0.000190 |
| 103 | <0.000010 | 293 | 0.000093 |
| 104 | 0.000016 | 294 | 0.000046 |
| 105 | <0.000010 | 295 | <0.000010 |
| 106 | 0.000895 | 296 | 0.000512 |
| 107 | 0.000035 | 297 | 0.000174 |
| 108 | <0.000010 | 298 | <0.000010 |
| 109 | 0.000127 | 299 | 0.000039 |
| 110 | 0.000557 | 300 | 0.001627 |
| 111 | <0.000010 | 301 | 0.002065 |
| 112 | <0.000010 | 302 | 0.000332 |
| 113 | <0.000010 | 303 | 0.000044 |
| 114 | <0.000010 | 304 | nd |
| 115 | <0.000010 | 305 | 0.000033 |
| 116 | <0.000010 | 306 | 0.002067 |
| 117 | <0.000010 | 307 | 0.000130 |
| 118 | <0.000010 | 308 | 0.000141 |
| 119 | <0.000010 | 309 | 0.000023 |
| 120 | <0.000010 | 310 | 0.000165 |
| 121 | <0.000010 | 311 | <0.000010 |
| 122 | <0.000010 | 312 | <0.000010 |
| 123 | <0.000010 | 313 | 0.001102 |
| 124 | <0.000010 | 314 | 0.000042 |
| 125 | <0.000010 | 315 | 0.000052 |
| 126 | <0.000010 | 316 | 0.000601 |
| 127 | <0.000010 | 317 | <0.000010 |
| 128 | <0.000010 | 318 | <0.000010 |
| 129 | 0.000002 | 319 | <0.000010 |
| 130 | <0.000010 | 320 | <0.000010 |
| 131 | <0.000010 | 321 | <0.000010 |
| 132 | <0.000010 | 322 | <0.000010 |
| 133 | <0.000010 | 323 | 0.000104 |
| 134 | <0.000010 | 324 | <0.000010 |

TABLE 1-continued

Bcl-2 binding $K_i$ (μM)

| Compound | $K_i$ | Compound | $K_i$ |
|---|---|---|---|
| 135 | <0.000010 | 325 | <0.000010 |
| 136 | <0.000010 | 326 | <0.000010 |
| 137 | <0.000010 | 327 | <0.000010 |
| 138 | <0.000010 | 328 | <0.000010 |
| 139 | <0.000010 | 329 | 0.000030 |
| 140 | <0.000010 | 330 | <0.000010 |
| 141 | <0.000010 | 331 | 0.001086 |
| 142 | 0.00013 | 332 | 0.000621 |
| 143 | <0.000010 | 333 | 0.000511 |
| 144 | <0.000010 | 334 | 0.000572 |
| 145 | <0.000010 | 335 | 0.000150 |
| 146 | <0.000010 | 336 | 0.000198 |
| 147 | <0.000010 | 337 | <0.000010 |
| 148 | <0.000010 | 338 | 0.000013 |
| 149 | <0.000010 | 339 | 0.000036 |
| 150 | <0.000010 | 340 | <0.000010 |
| 151 | 0.000017 | 341 | <0.000010 |
| 152 | <0.000010 | 342 | <0.000010 |
| 153 | <0.000010 | 343 | <0.000010 |
| 154 | <0.000010 | 344 | <0.000010 |
| 155 | 0.000059 | 345 | <0.000010 |
| 156 | <0.000010 | 346 | 0.000042 |
| 157 | <0.000010 | 347 | 0.000013 |
| 158 | <0.000010 | 348 | 0.000034 |
| 159 | <0.000010 | 349 | 0.000023 |
| 160 | <0.000010 | 350 | <0.000010 |
| 161 | <0.000010 | 351 | <0.000010 |
| 162 | <0.000010 | 352 | 0.000014 |
| 163 | <0.000010 | 353 | <0.000010 |
| 164 | <0.000010 | 354 | 0.000010 |
| 165 | <0.000010 | 355 | 0.000014 |
| 166 | <0.000010 | 356 | 0.000039 |
| 167 | <0.000010 | 357 | <0.000010 |
| 168 | <0.000010 | 358 | <0.000010 |
| 169 | 0.000021 | 359 | <0.000010 |
| 170 | 0.000022 | 360 | <0.000010 |
| 171 | <0.000010 | 361 | <0.000010 |
| 172 | <0.000010 | 362 | 0.000016 |
| 173 | <0.000010 | 363 | 0.000017 |
| 174 | <0.000010 | 364 | <0.000010 |
| 175 | 0.000119 | 365 | <0.000010 |
| 176 | 0.000023 | 366 | 0.000024 |
| 177 | 0.000111 | 367 | nd |
| 178 | 0.000076 | 368 | nd |
| 179 | <0.000010 | 369 | <0.000010 |
| 180 | <0.000010 | 370 | 0.000285 |
| 181 | 0.000017 | 371 | <0.0000010 |
| 182 | 0.000068 | 372 | nd |
| 183 | <0.000010 | 373 | <0.0000010 |
| 184 | <0.000010 | 374 | <0.0000010 |
| 185 | 0.000022 | 375 | 0.00010999 |
| 186 | 0.000047 | 376 | <0.0000010 |
| 187 | 0.00008 | 377 | <0.0000010 |
| 188 | <0.000010 | 378 | <0.0000010 |
| 189 | 0.000018 | | | nd = not determined

Table 2 below presents data for log D (a parameter related to lipophilicity) at pH 7.4, as determined by an HPLC method, for representative compounds. It will be noted that all compounds have high log D values (most in excess of 5.3), indicating a high degree of lipophilicity and very poor solubility in water at pH 7.4.

TABLE 2 log D at pH 7.4

| Compound | log D |
|---|---|
| 5 | 5.37 |
| 6 | 5.74 |
| 9 | 5.71 |
| 12 | 5.17 |
| 18 | 6.35 |
| 20 | 6.24 |
| 24 | 5.72 |
| 37 | 5.27 |
| 87 | 5.86 |
| 89 | 6.21 |
| 90 | 6.69 |
| 91 | 6.59 |
| 92 | 5.60 |
| 120 | 5.40 |
| 208 | 5.57 |
| 239 | 5.92 |
| 242 | 5.51 |
| 276 | 5.59 |
| 277 | 5.26 |
| 286 | 5.66 |
| 303 | 6.24 |
| 311 | 5.60 |
| 312 | 6.47 |
| 322 | 5.48 |
| 337 | 5.48 |
| 338 | 5.67 |

B. Exemplary Compounds

Compounds believed to be particularly useful in preparation of solid dispersions of the invention include without limitation:

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}-sulfonyl)benzamide—Compound 89;

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)-benzamide—Compound 91;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide—Compound 5;

trans-4-(4-({[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide—Compound 9;

cis-4-(4-{[2-(4-chlorophenyl)-4,4-dimethylcyclohex-1-en-1-yl]methyl}piperazin-1-yl)-N-[(4-f{[(4-methoxycyclohexyl)methyl]amino}-3-nitrophenyl)sulfonyl]-2-(1H-pyrrolo[2,3-b]pyridin-5-yloxy)benzamide—Compound 29;

trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide—Compound 34;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide—Compound 37;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 277;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 61;

4-(4-{4 [2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide—Compound 378;

4-(4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide—Compound 149;

4-(4-{[2-(4-chlorophenyl)-4,4-dimethylcyclohex-1-en-1-yl]methyl}piperazin-1-yl)-N-[(4-{[(trans-4-hydroxy-4-methylcyclohexyl)methyl]amino}-3-nitrophenyl)sulfonyl]-2-(1H-pyrrolo[2,3-b]pyridin-5-yloxy)benzamide—Compound 337;

4-(4-{[2-(4-chlorophenyl)-4,4-dimethylcyclohex-1-en-1-yl]methyl}piperazin-1-yl)-N-[(4-{[(cis-4-hydroxy-4-methylcyclohexyl)methyl]amino}-3-nitrophenyl)sulfonyl]-2-(1H-pyrrolo[2,3-b]pyridin-5-yloxy)benzamide—Compound 338;

4-(4-{[2-(4-chlorophenyl)-4,4-dimethylcyclohex-1-en-1-yl]methyl}piperazin-1-yl)-N-{[4-({3-[cyclopropyl(oxetan-3-yl)amino]propyl}amino)-3-nitrophenyl]sulfonyl}-2-(1H-pyrrolo[2,3-b]pyridin-5-yloxy)benzamide—Compound 311;

4-(4-{[2-(4-chlorophenyl)-4,4-dimethylcyclohex-1-en-1-yl]methyl}piperazin-1-yl)-N-{3-nitro-4-({[(3R)-1-tetrahydro-2H-pyran-4-ylpyrrolidin-3-yl]methyl}amino)phenyl]-sulfonyl}-2-(1H-pyrrolo[2,3-b]pyridin-5-yloxy)benzamide—Compound 118;

4-(4-{[2-(4-chlorophenyl)-4,4-dimethylcyclohex-1-en-1-yl]methyl}piperazin-1-yl)-N-[(4-{[(4-methylmorpholin-2-yl)methyl]amino}-3-nitrophenyl)sulfonyl]-2-(1H-pyrrolo[2,3-b]pyridin-5-yloxy)benzamide—Compound 134;

N-[(5-chloro-6-{[1-(cyanomethyl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 253;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 108;

4-(4-{[2-(4-chlorophenyl)-4,4-dimethylcyclohex-1-en-1-yl]methyl}piperazin-1-yl)-N-({4-[(4-methoxytetrahydro-2H-pyran-4-yl)methoxy]-3-nitrophenyl}sulfonyl)-2-(1H-pyrrolo[2,3-b]pyridin-5-yloxy)benzamide—Compound 234;

and pharmaceutically acceptable salts thereof.

C. Compound Forms

In some embodiments, a compound of Formula I is present in the solid dispersion in its parent-compound form, alone or together with a salt form of the compound.

Compounds of Formula I may form acid addition salts, basic addition salts or zwitterions. Salts of compounds of Formula I can be prepared during isolation or following purification of the compounds.

Acid addition salts are those derived from reaction of a compound of Formula I with an acid. For example, salts including the acetate, adipate, alginate, ascorbate, bicarbonate, citrate, aspartate, benzoate, benzenesulfonate (besylate), bisulfate, butyrate, camphorate, camphorsulfonate, digluconate, ethanedisulfonate, formate, fumarate, glycerophosphate, glutamate, hemisulfate, heptanoate, hexanoate, hydrobromide, hydrochloride, hydroiodide, 1-hydroxy-2-naphthoate, lactate, lactobionate, malate, maleate, malonate, mesitylenesulfonate, methanesulfonate, naphthalenesulfonate, nicotinate, oxalate, pamoate, pectinate, persulfate, phosphate, picrate, propionate, succinate, sulfate, tartrate, thiocyanate, trichloroacetate, trifluoroacetate, para-toluenesulfonate and undecanoate salts of a compound of Formula I can be used in a composition of the invention.

Basic addition salts, including those derived from reaction of a compound with the bicarbonate, carbonate, hydroxide or phosphate of cations such as lithium, sodium, potassium, calcium and magnesium, can likewise be used.

A compound of Formula I typically has more than one protonatable nitrogen atom and is consequently capable of forming acid addition salts with more than one, for example about 1.2 to about 2, about 1.5 to about 2 or about 1.8 to about 2, equivalents of acid per equivalent of the compound.

Without being bound by theory, it is believed that the therapeutic efficacy of compounds of Formula I is due at least in part to their ability to bind to a Bcl-2 family protein such as Bcl-2, Bcl-$X_L$ or Bcl-w in a way that inhibits the anti-apoptotic action of the protein, for example by occupying the BH3 binding groove of the protein. It will generally be found desirable to select a compound having high binding affinity for a Bcl-2 family protein, for example a $K_i$<1 nM, preferably <0.1 nM, more preferably <0.01 nM.

A compound of Formula I or a salt thereof is present in a solid dispersion of the invention in an amount that can be therapeutically effective when the composition is administered to a subject in need thereof according to an appropriate regimen. Dosage amounts are expressed herein as parent-compound-equivalent amounts unless the context requires otherwise. Typically, a unit dose (the amount administered at a single time), which can be administered at an appropriate frequency, e.g., twice daily to once weekly, is about 10 to about 1,000 mg, depending on the compound in question. Where frequency of administration is once daily (q.d.), unit dose and daily dose are the same. Illustratively, the unit dose is typically about 25 to about 1,000 mg, more typically about 50 to about 500 mg, for example about 50, about 100, about 150, about 200, about 250, about 300, about 350, about 400, about 450 or about 500 mg. Where the dosage form comprises a capsule shell enclosing the solid dispersion, or a tablet wherein the solid dispersion is formulated with other ingredients, a unit dose can be deliverable in a single dosage form or a plurality of dosage forms, most typically 1 to about 10 dosage forms.

D. Formulations

The higher the unit dose, the more desirable it becomes to prepare a solid dispersion having a relatively high concentration of the drug therein. Typically, the concentration of drug in the solid dispersion is at least about 1%, e.g., about 1% to about 50%, by parent-compound-equivalent weight, but lower and higher concentrations can be acceptable or achievable in specific cases. Illustratively, the drug concentration in various embodiments is at least about 2%, e.g., about 2% to about 50%, or at least about 5%, e.g., about 5% to about 40%, for example about 5%, about 10%, about 15%, about 20%, about 25%, about 30%, about 35% or about 40%, by parent-compound-equivalent weight. In some embodiments, the drug concentration may be between about 5% and about 15%, such as between about 5% and about 12%, such as about 5%, about 6%, about 7%, about 8%, about 9%, about 10%, about 11%, or about 12%.

The major component of the matrix of a solid dispersion product is a polymer that is hydrophilic or water-soluble at least in a part of the pH scale, more particularly at a pH occurring in the gastrointestinal (GI) tract, or a combination of such polymers. A polymer or polymer mixture useful herein is solid at ambient temperature and, in the interests of good storage stability at a range of temperatures, should remain solid even at the highest temperatures typically experienced during storage, transport and handling of the product. A useful property of a polymer determining its usefulness herein is therefore its glass transition temperature ($T_g$). Suitable water-soluble polymers include, but are not limited to, those having a $T_g$ of at least about 40° C., at least about 50° C., at least about 60° C., or more, and more particularly about 80° C. to about 180° C. Methods for determining $T_g$ values of organic polymers are described for example in Sperling, ed. (1992) *Introduction To Physical Polymer Science*, 2nd edition, John Wiley & Sons, Inc.

Polymers are considered water-soluble if they form a clear homogeneous solution in water (e.g., a solution that is essentially uniform throughout, and that appears clear under visual inspection or alternatively using an instrument such as a turbidimeter, the solution for example exhibiting little or no scattering of a light beam going therethrough). When dissolved at 20° C. in an aqueous solution at 2% (w/v), a suitable water-soluble polymer illustratively has an apparent viscosity of about 1 to about 5000 mPa·s, for example about 1 to about 700 mPa·s, or about 5 to about 100 mPa·s. Water-dispersable or water-swellable polymers can also be used.

Non-limiting examples of polymeric carriers useful herein include:

- homopolymers and copolymers of N-vinyl lactams, especially homopolymers and copolymers of N-vinyl pyrrolidone, e.g., the homopolymer polyvinylpyrrolidone (PVP or povidone) and copolymers such as those comprising monomers of N-vinyl pyrrolidone and vinyl acetate (copovidone) or N-vinyl pyrrolidone and vinyl propionate;
- cellulose esters and cellulose ethers, in particular methylcellulose, ethylcellulose, (hydroxyalkyl) celluloses such as hydroxypropylcellulose, (hydroxyalkyl)alkylcelluloses such as hydroxypropylmethylcellulose (HPMC or hypromellose), cellulose phthalates and succinates such as cellulose acetate phthalate, hydroxypropylmethylcellulose phthalate (HPMC-P), hydroxypropylmethylcellulose succinate (HPMC-S) and hydroxypropylmethylcellulose acetate succinate (HPMC-AS);
- high molecular weight polyalkylene oxides such as polyethylene oxides (PEGs or PEOs) and copolymers of ethylene oxide and propylene oxide (poloxamers);
- polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly (hydroxyalkyl acrylates) and poly(hydroxyalkyl methacrylates);
- polyacrylamides;
- vinyl acetate polymers such as copolymers of vinyl acetate and crotonic acid, polyvinyl acetate, polyvinyl alcohol and partially hydrolyzed polyvinyl acetate (also referred to as partially saponified polyvinyl alcohol);
- graft copolymers of polyethylene glycol, polyvinyl caprolactam and polyvinyl acetate (e.g., Soluplus™ of BASF or equivalent product);
- oligo- and polysaccharides such as carrageenans, galactomannans and xanthan gum;

and mixtures of two or more thereof.

Suitable povidones include, without limitation, those having a K-value (a measure of viscosity of an aqueous solution of the povidone) of about 12, about 15, about 17, about 25, about 30 or about 90, and mixtures thereof. A particular example of a useful povidone is povidone (or PVP) K30.

Another suitable polymer is a mixture of PVP and polyvinyl acetate such as that sold under the name Kollidon™ SR by BASF AG. In some embodiments, a vinylpyrrolidone-vinyl acetate copolymer commercially available as Kollidon VA 64, which is soluble both in water and in alcohol, is suitable in the formulations of the present invention.

A particular example of a useful copovidone is one consisting of about 60% N-vinyl pyrrolidone and about 40% vinyl acetate monomers, referred to herein as "copovidone 60/40".

Suitable HPMCs and derivatives thereof include, without limitation, HPMC E3, HPMC E5, HPMC E6, HPMC E15, HPMC K3, HPMC A4, HPMC A15, HPMC-AS LF, HPMC-AS MF, HPMC-AS HF, HPMC-AS LG, HPMC-AS MG, HPMC-AS HG, HPMC-P 50, HPMC-P 55 and mixtures thereof.

Suitable ethylcelluloses include, without limitation, those sold under the Ethocel™ trademark of Dow Chemical Company as Ethocel™ 4, Ethocel™ 7, Ethocel™ 10, Ethocel™ 14 and Ethocel™ 20, products of other manufacturers equivalent thereto, and mixtures thereof.

Suitable methacrylic acid/methyl methacrylate copolymers include, without limitation, those sold under the Eudragit™ trademark of Rohm GmbH as Eudragit™ L100, Eudragit™ L100-55 and Eudragit™ S100, products of other manufacturers equivalent thereto, and mixtures thereof.

Suitable PEGs include, without limitation, PEG 400, PEG 600, PEG 1450, PEG 3350, PEG 4000, PEG 6000, PEG 8000, PEG 20000 and mixtures thereof. Lower molecular-weight PEGs such as PEG 400 and PEG 600 may be unsuitable as the sole polymeric carrier but can be useful in combination with other polymers.

Suitable poloxamers include, without limitation, poloxamer 124, poloxamer 188, poloxamer 237, poloxamer 338, poloxamer 407 and mixtures thereof. It will be noted that poloxamers have surfactant properties and can be included primarily for these properties as well as their polymeric nature.

In one embodiment, the solid dispersion matrix comprises one or more polymeric carriers selected from the group consisting of povidones, copovidones, HPMCs, polyethylene glycol/polyvinyl caprolactam/polyvinyl acetate graft copolymers and mixtures thereof. In a more particular embodiment, the solid dispersion matrix comprises one or more polymeric carriers selected from the group consisting of povidone K30, copovidone 60/40, HPMC E5, Soluplus™ polyethylene glycol/polyvinyl caprolactam/polyvinyl acetate graft copolymer and products equivalent to Soluplus™.

One or more polymeric carriers typically constitute in total about 20% to about 95%, such as about 20% to about 90%, for example about 40% to about 85%, or about 60% to about 85%, or about 70% to about 85%, or even about 75% to about 85%, by weight of the solid dispersion.

Upon oral administration and exposure to GI fluid, it is believed without being bound by theory that, through interplay between the polymeric carrier and a surfactant component of the solid dispersion, a suitable release rate and inhibition of crystallization or recrystallization of the active ingredient are provided, thereby permitting bioabsorption.

The surfactant component can be anionic, non-ionic or can comprise a combination of anionic and non-ionic surfactants. Useful pharmaceutically acceptable anionic surfactants include alkyl sulfates (e.g., sodium lauryl sulfate), alkylcarboxylates, alkylbenzole sulfates and secondary alkane sulfonates.

Particularly useful as surfactants herein are pharmaceutically acceptable non-ionic surfactants, especially those having a hydrophilic-lipophilic balance (HLB) value of about 12 to about 18, for example about 13 to about 17, or about 14 to about 16. The HLB system (see Fiedler (2002) *Encyclopedia of Excipients*, 5th edition, Aulendorf: ECV-Editio-Cantor-Verlag) assigns numeric values to surfactants, with lipophilic substances receiving lower HLB values and hydrophilic substances receiving higher HLB values.

Non-limiting examples of non-ionic surfactants useful herein include:

polyoxyethylene castor oil derivatives such as PEG-35 castor oil (e.g., Cremophor EL™ of BASF or equivalent product), PEG-40 hydrogenated castor oil (e.g., Cremophor RH™ 40 or equivalent product) and PEG-60 hydrogenated castor oil (e.g., Cremophor RH™ 60 or equivalent product);

other polyoxyethylene glycerides such as PEG-32 glyceryl laurate (e.g., Gelucire™ 44/14 of Gattefossé or equivalent product) and PEG-32 glyceryl palmitostearate (e.g., Gelucire™ 50/13 or equivalent product), and Labrafil M1944 CS (oleoyl macrogol 6 glycerides prepared by transesterification of apricot kernel oil with PEG 300);

fatty acid monoesters of sorbitan, for example sorbitan monooleate (e.g., Span™ 80 or equivalent product), sorbitan monostearate (e.g., Span™ 60 or equivalent product), sorbitan monopalmitate (e.g., Span™ 40 or equivalent product) and sorbitan monolaurate (e.g., Span™ 20 or equivalent product);

other fatty acid esters of sorbitan, for example, sorbitan tristearate and sorbitan trioleate;

fatty acid monoesters of polyoxyethylene sorbitan (polysorbates) such as PEG-20 sorbitan monooleate (polysorbate 80, e.g., Tween™ 80 or equivalent product) PEG-20 sorbitan monostearate (polysorbate 60, e.g., Tween™ 60 or equivalent product), PEG-20 sorbitan monopalmitate (polysorbate 40, e.g., Tween™ 40 or equivalent product), or PEG-20 sorbitan monolaurate (polysorbate 20, e.g., Tween™ 20 or equivalent product);

other fatty acid esters of polyoxyethylene sorbitan, for example, polyoxyethylene (20) sorbitan tristearate (Tween 65), polyoxyethylene (20) sorbitan trioleate (Tween 85);

fatty acid ester of polyalkylene glycols such as, for example, PEG 660 hydroxystearic acid (polyglycol ester of 12-hydroxystearic acid (70 mol %) with 30 mol % ethylene glycol);

polyalkoxylated ethers of fatty alcohols such as, for example, PEG (2) stearyl ether (Brij 72), macrogol 6 cetylstearyl ether or macrogol 25 cetylstearyl ether;

A tocopheryl compound corresponding to the structure below:

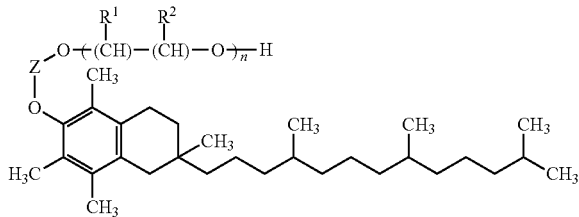

wherein Z is a linking group, $R^1$ and $R^2$ are, independently of one another, hydrogen or $C_1$-$C_4$ alkyl and n is an integer from 5 to 100, preferably 10 to 50. Typically, Z is the residue of an aliphatic dibasic acid such as glutaric, succinic, or adipic acid. Preferably, both $R^1$ and $R^2$ are hydrogen. The preferred tocopheryl compound is α-tocopheryl polyethylene glycol succinate, which is commonly abbreviated as vitamin E-TPGS. Vitamin E-TPGS is a water-soluble form of natural-source vitamin E prepared by esterifying d-alpha-tocopheryl acid succinate with polyethylene glycol 1000;

and mixtures of two or more thereof.

In one embodiment, the solid dispersion comprises one or more surfactants selected from the group consisting of polyoxyethylene glycerides (including polyoxyethylene castor oil derivatives), polysorbates, TPGS and mixtures thereof. In a more particular embodiment, the solid dispersion matrix comprises one or more polymeric carriers selected from the group consisting of PEG-40 hydrogenated castor oil, polysorbate 80, polysorbate 20 and TPGS.

One or more surfactants typically constitute in total about 2% to about 25%, for example about 5% to about 20%, such as between about 5% and about 15%, or between about 5% and about 10% by weight of the solid dispersion.

Other, optional, components of the solid dispersion include, without limitation, one or more lubricants, glidants or flow regulators. Such a material, for example colloidal silicon dioxide or fumed silica (e.g., Aerosil), can reduce adhesion of the extrudable mixture to the screw and wall of the extruder and can facilitate the smooth passage of extrudate through the die. Illustratively, colloidal silicon dioxide can constitute zero to about 5%, for example about 0.1% to about 2%, by weight of the solid dispersion. The solid dispersion can also optionally contain one or more bulking agents (fillers), disintegrants, cosolvents such as propylene glycol esters of fatty acids (e.g., propylene glycol laurate), plasticizers and/or stabilizers such as antioxidants, light stabilizers, free radical scavengers or antimicrobial agents.

A dosage form of the invention can consist of, or consist essentially of, a solid dispersion as described above. However, in some embodiments a dosage form contains additional excipients and requires additional processing of the solid dispersion. For example, the solid dispersion can be ground to a powder and filled into a capsule shell or molded or compressed to form a tablet, with additional excipients as may be conventionally used in such dosage forms.

Thus orally deliverable solid dosage forms of the invention include but are not limited to capsules, dragees, granules, pills, powders and tablets. Excipients commonly used to formulate such dosage forms include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, preservatives, propellants, releasing agents, sterilizing agents, sweeteners, solubilizers and mixtures thereof. Many excipients have two or more functions in a pharmaceutical composition. Characterization herein of a particular excipient as having a certain function, e.g., diluent, disintegrant, binding agent, etc., should not be read as limiting to that function. Further information on excipients can be found in standard reference works such as *Handbook of Pharmaceutical Excipients,* 3rd ed. (Kibbe, ed. (2000), Washington: American Pharmaceutical Association).

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dicalcium phosphate (e.g., dibasic calcium phosphate dihydrate), monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 1% to about 95%, for example about 5% to about 50%, or about 10% to about 30%, by weight of the composition. The diluent or diluents selected preferably exhibit suitable flow properties and, where tablets are desired, compressibility.

Microcrystalline cellulose and silicified microcrystalline cellulose are particularly useful diluents, and are optionally used in combination with a water-soluble diluent such as mannitol. Illustratively, a suitable weight ratio of microcrystalline cellulose or silicified microcrystalline cellulose to mannitol is about 10:1 to about 1:1, but ratios outside this range can be useful in particular circumstances.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

Sodium starch glycolate is a particularly useful disintegrant, and typically constitutes in total about 1% to about 20%, for example about 2% to about 15%, or about 5% to about 10%, by weight of the composition.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

Povidone and hydroxypropylcellulose, either individually or in combination, are particularly useful binding agents for tablet formulations, and, if present, typically constitute about 0.5% to about 15%, for example about 1% to about 10%, or about 2% to about 8%, by weight of the composition.

Wetting agents can be added to the formulation if desired, in addition to the surfactant component of the solid dispersion. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; α-tocopherol polyethylene glycol (1000) succinate (TPGS); tyloxapol; and the like. One or more wetting agents, if present, typically constitute in total about 0.1% to about 15%, for example about 0.2% to about 10%, or about 0.5% to about 7%, by weight of the composition, excluding surfactant present in the solid dispersion.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition, excluding surfactant present in the solid dispersion.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate;

talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition, excluding glidant present in the solid dispersion. Colloidal silicon dioxide is a particularly useful glidant.

Other excipients such as buffering agents, stabilizers, antioxidants, antimicrobials, colorants, flavors and sweeteners are known in the pharmaceutical art and can be used in compositions of the present invention. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

E. Method of Preparation

As indicated above, the solid dispersion of the present invention can be prepared by a process comprising melt-extrusion. Accordingly, the solid dispersion product is a melt-processed, solidified mixture. The melt-extrusion process comprises the steps of preparing a homogeneous melt of the active ingredient or the combination of active ingredients, the pharmaceutically acceptable polymer and the solubilizers, and cooling the melt until it solidifies. "Melting" refers to a transition from a solid to a liquid (or alternatively from a solid to a softened or rubbery state), such that it is possible for one component to become homogeneously mixed with or embedded in the other. Typically, one component will melt and the other components will dissolve in the melt, thus forming a solution. In accordance with the present disclosure, melting generally involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient first to melt the pharmaceutically acceptable polymer and then to admix and homogenize the active ingredients.

In a first step of this process, at least three components are subjected to elevated temperature to provide an extrudable mixture: a compound of Formula I or a pharmaceutically acceptable salt thereof; at least one pharmaceutically acceptable water-soluble polymeric carrier; and at least one pharmaceutically acceptable surfactant. Other components can optionally be included at this stage, for example one or more additional active ingredients and/or one or more additional excipients, for example a glidant.

The components can be mixed together before, during or after melting or softening of the polymeric carrier. In one embodiment, the components are mixed first and then subjected to elevated temperature to form the extrudable mixture. In another embodiment, the components are mixed while at elevated temperature to form the extrudable mixture. In yet another embodiment the polymeric carrier is first melted or softened, optionally with the surfactant component, and the compound of Formula I or salt thereof is then added to the resulting melt. In yet another embodiment, the surfactant is added to the polymer/API melt. According to all these embodiments, it will be found preferable to thoroughly mix the melt while at elevated temperature in order to ensure homogeneous dispersion or dissolution of the active ingredient in the partially or completely molten matrix. In one embodiment, the polymeric carrier, the surfactant, and optionally the glidant are mixed first into a pre-blend. The API is then added and the mixture is blended, in order to achieve a sufficiently homogeneous blend.

The melting and mixing takes place in an apparatus customary for this purpose. Particularly suitable are extruders or kneaders. Suitable extruders include single-screw extruders, intermeshing screw extruders and multiscrew extruders, for example twin-screw extruders, which can be co-rotating or counter-rotating and, optionally, equipped with kneading disks or other screw elements for mixing or dispersing the components of the melt. In some preferred embodiments, a single screw extruder may be used for small (e.g., benchtop) and large scale (commercial) production of extrudates.

The elevated temperature attained during this part of the process can suitably be about 70° C. to about 250° C., preferably 80° C. to about 250° C., such as for example about 80° C. to about 180° C., about 100° C. to about 180° C., or about 90° C. to about 160° C., or 120° C. to about 160° C. Illustratively the temperature at the feeding end of the extruder is maintained at a relatively moderate temperature, for example about 80° C. to about 120° C., about 80° C. to about 110° C., or about 90° C. to about 100° C.; in the middle portion of the extruder at a higher temperature, for example about 130° C. to about 180° C., or about 140° C. to about 160° C.; and near the extrusion die at a somewhat lower temperature, for example about 110° C. to about 160° C., or about 120° C. to about 150° C. It will be appreciated that appropriate working temperatures are determined in part by the kind of extruder and the configuration of elements within the extruder used. Part of the energy needed to melt, mix and dissolve the components in the extruder can be provided by heating elements. However, friction and shearing of the material in the extruder can also impart a substantial amount of thermal energy to the mixture and aid in the formation of a homogeneous melt of the components.

Other process parameters such as screw speed and feed rate will depend on the particular composition and equipment used and can readily be optimized by one of ordinary skill in the art without undue experimentation.

An API such as a compound of Formula I or a salt thereof can be added as a solid powder or in solution or dispersion in a suitable liquid solvent such as an alcohol or aliphatic hydrocarbon or ester, or liquid carbon dioxide. Such solvent is removed, e.g., evaporated, in preparation of the melt.

The extrudate emerging from the extruder die is semi-solid, for example pasty or viscous in texture. Before cooling to ambient temperature, the extrudate can, if desired, be shaped into any desired shape, for example by use of a calender with two counter-rotating rollers having mutually matching depressions on their surface. Typically such a procedure results in "lentils" (small lenticular tablets). If the rollers do not have depressions on their surfaces, films can be obtained. In one embodiment, extrudate is fed directly from the extrusion equipment to the calender. Alternatively, the extrudate can molded into a desired shape by injection-molding, or simply cut into pieces, either before solidification (hot-cut) or after solidification (cold-cut).

In a variant of the above process, a foam can be formed if the extrudate contains a propellant such as a gas, e.g., carbon dioxide, or volatile compound, e.g., a low molecular-weight hydrocarbon, or a compound that is thermally decomposable to a gas. The propellant is dissolved in the extrudate under the relatively high pressure conditions within the extruder and, when the extrudate emerges from the die, the sudden release of pressure causes the propellant to come out of solution and vaporize, resulting in formation of a foam.

According to empirical results to-date, it has been observed that the manufacturability and quality of the extrudates may be affected and improved by the selection of matrix polymer and surfactant, as well as the percentage of API (i.e. drug load) in the extrusion blend. In general, the maximum drug load in a desirably clear, homogenous extrudate may be improved via the selection of polymer and surfactant in the extrusion blend and selection of the concentrations of the API, the polymer, and the surfactant in the extrusion blend. In some embodiments of the invention, copovidone (Kollidon VA64) or Soluplus is used as polymer carrier, at a concentration of for example about 70% to about 90%, about 75% to about 84%, or about 78% to 82%. In these or other embodiments of the invention, the surfactant (e.g., Vitamin E TPGS, Tween20, Tween80, poloxamer F68NF, Span 20, Sucroester WP15, Lauroglycol FCC, SDS, or PEG 400) may be employed at about 2% to about 15%, preferably about 5% to about 12%, most preferably about 6% to about 9% level. In these or still other preferred embodiments, the API content in the extrusion blend may range from about 1% to about 25%, preferably about 5% to 20%, most preferably about 10% to about 15%. Optionally, glidant (e.g., Aerosil) can also be included in the extrusion blend at about 0% to about 3%, preferably about 0.5% to about 1.5% level.

In this regard, it is to be noted that, in one or more embodiments, it may be desirable to control the weight % ratio of two or more of the components (e.g., the API and the surfactant) of the extrusion blend, in order for example to optimize the processability of the blend (e.g., to optimize the physical properties of the blend for manufacturing purposes, such as degradation, glass transition temperature (Tg), release time, etc.). Thus, these ratios may vary as a function of, for example, the process conditions and/or components utilized in the extrusion blend. However, in various exemplary embodiments, the weight % ratio of, for example, the API to surfactant may range from about 15:1 to about 1:15, from about 10:1 to about 1:10, from about 5:1 to about 1:5, from about 4:1 to about 1:4, or from about 2:1 to about 1:2 (e.g., about 2:1, about 1.5:1, about 1:1, about :1.5 or about 1:2). In this regard it is to be further noted that, in these or yet additional embodiments, two or more APIs (e.g., two or more compounds falling within the scope of Formula I, or alternatively a compound falling within the scope of Formula I and another compound or active, such as another chemotherapeutic compound disclosed elsewhere herein) may be utilized in the extrusion blend (provided, for example, the compounds are suitable stable under the processing conditions and there is little or no interaction between the compounds that would lead to chemical instability of the compounds).

In this regard it is to be still further noted that selection or choice of the polymer carrier may impact various performance properties of the resulting extrudate (or composition). For example, in some instances, it has been observed that as the drug load increases relative to the amount of polymer carrier, the release rate is slower. However, it has also been observed that the release rate may vary, in at least some instances, from one polymer carrier to the other; for example, it has been observed that the release rate using Soluplus was slower than when comparable copovidone polymer carriers were used. Empirical results to-date also suggest that the release rate, as well as the variations therein, are in at least some instances independent of the surfactant (e.g., poloxamer, Tween80, solutol, cremophor, etc.) that is used; for example, it has been observed that the amount of surfactant (e.g., poloxamer) has little if any impact on the release rate when used with Soluplus (alone or in combination with a copovidone polymer carrier). Without being held to any particular theory, it is generally believed that this may be due, at least in part, to Soluplus acting as a surfactant, as well.

Empirical results to-date still further suggest that differences in release rate occur when mixtures of polymer carriers are used, as well; for example, it has been observed that an equal parts mixture of Soluplus and a copovidone polymer carrier results in a release rate that is slower than the release rate observed when only Soluplus is used. In addition, it has been observed that as the amount of the copovidone polymer carrier increases in this mixture, the more the release rate decreases.

Bioavailability of the solid dispersion produced by melt extrusion may be assessed by dispersibility studies. The release rate of API from the extrudates may measured in samples after dispensing the extrudates in acidic environment (e.g., 0.1N HCl) at about physiological temperature (e.g., 37° C.) to simulate drug release in the gastrointestinal tract in human. Generally, current empirical results to-date have shown that the formulations with higher drug load have slower API release rate. It is also observed that although higher surfactant level leads to faster API release rate, excessive surfactant may affect the manufacturability of the extrudates.

Once cooled to ambient temperature, the melt-extruded solid dispersion can be stored until ready for use or further processing. It has been determined, e.g., by differential scanning calorimetry (DSC), that extrudates manufactured by the process of the present invention generally are monophasic systems in which the risk of phase separation is negligible even for extended storage durations. If desired, the solid dispersion can be milled or ground to form granules suitable for filling into capsules or for molding or compression to form a tablet, with additional excipients as may be conventionally used in such dosage forms, for example those listed hereinabove.

In one embodiment, a milling apparatus (e.g., a Quadro U5 Comil) equipped with screens having various aperture sizes (in the range of 100 to 1000 μm) may be used for milling the extrudates. The distribution of the sizes of the particles produced by the milling is substantially consistent throughout the milling process and is not significantly affected by the batch size (e.g., from about 100 g to about 45 kg) of the extrudates. The milled extrudate can be further blended with filler (e.g., dicalcium phosphate (DCP) or crosarmellose sodium), or lubricant (e.g., sodium stearyl fumarate). Tabletability, characterized by the tensile strength as a function of compaction pressure, can be assessed on a tablet press simulator (e.g., Presster, Metropolitan Computing Corporation). In general, formulations made from clear extrudates typically show better tabletability than those made from cloudy extrudates. Further, the addition of DCP or other fillers and reduction of particle size (as determined by the screen aperture sizes of Comil), as well as an increase in moisture content in the milled extrudate, all improve tabletability.

Bioavailability of the tablets produced from the milled extrudates may be assessed by in vitro dissolution studies using, for example, USP apparatus Type 2 method. It has been observed in preferred embodiments that about 90% to about 100% of the API may be released from 50 mg tablets within 6 to 8 hours. Similar results may be obtained using either phosphate buffer or 0.01 N HCl. Based on empirical results to-date, the dissolution rate appears to be independent of the particle size of the milled extrudates before compression and the moisture content in the tablets, and is only slightly decreased by the addition of DCP. This appears to support an erosion-based drug release mechanism in the tablets, with the dissolution rate apparently being a function of the tablet composition.

F. Dosage Forms and Regimen

The terms "orally deliverable", "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

The active ingredient form (e.g., parent compound or salt), the polymeric carrier(s), surfactant(s) and other optional ingredients should be selected, and relative amounts of these components should be used, to provide a solid dispersion or dosage form having acceptable bioabsorption when administered orally. Such bioabsorption can be evidenced, for example, by the pharmacokinetic (PK) profile of the solid dispersion or dosage form, more particularly by the $C_{max}$ or AUC, for example $AUC_{0-24}$ or $AUC_{0-\infty}$ at a particular dose or over a range of doses. Illustratively, bioavailability can be expressed as a percentage, for example using the parameter F, which computes AUC for oral delivery of a test composition as a percentage of AUC for intravenous (i.v.) delivery of the drug in a suitable solvent, taking into account any difference between oral and i.v. doses.

Bioavailability can be determined by PK studies in humans or in any suitable model species. For present purposes, a dog model is generally suitable. In various illustrative embodiments, compositions of the invention exhibit oral bioavailability of at least about 15%, at least about 20%, at least about 25% or at least about 30%, up to or exceeding about 50%, in a dog model, when administered as a single dose of about 2.5 to about 10 mg/kg to fasting or non-fasting animals.

Compositions embraced herein, including compositions described generally or with specificity herein, are useful for orally delivering a drug that is a compound of Formula I or a pharmaceutically acceptable salt thereof to a subject. Accordingly, a method of the invention for delivering such a drug to a subject comprises orally administering a composition as described above.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or overexpression of an anti-apoptotic Bcl-2 family protein. A human subject can be male or female and of any age. The patient is typically an adult, but a method of the invention can be useful to treat a childhood cancer such as leukemia, for example acute lymphocytic leukemia, in a pediatric patient.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the particular compound, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein docs not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of a compound of Formula I are generally about 25 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

Where the composition is in the form of a capsule, one to a small plurality of capsules can be swallowed whole, typically with the aid of water or other imbibable liquid to help the swallowing process. Suitable capsule shell materials include, without limitation, gelatin (in the form of hard gelatin capsules or soft elastic gelatin capsules), starch, carrageenan and HPMC.

Administration can be with or without food, i.e., in a non-fasting or fasting condition. It is generally preferred to administer the present compositions to a non-fasting patient.

G. Montherapies and Combination Therapies

Compositions of the invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

Combination therapies illustratively include administration of a composition of the present invention concomitantly with one or more of bortezomib, carboplatin, cisplatin, cyclophosphamide, dacarbazine, dexamethasone, docetaxel, doxorubicin, etoposide, fludarabine, irinotecan, paclitaxel, rapamycin, rituximab, vincristine and the like, for example with a polytherapy such as CHOP (cyclophosphamide+doxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

A composition of the invention can be administered in combination therapy with one or more therapeutic agents that include, but are not limited to, alkylating agents, angiogenesis inhibitors, antibodies, antimetabolites, antimitotics, antiproliferatives, antivirals, aurora kinase inhibitors, other apoptosis inducing agents (for example, Bcl-xL, Bcl-w and Bfl-1 inhibitors), activators of a death receptor pathway, Bcr-Abl kinase inhibitors, BiTE (bi-specific T-cell engager) antibodies, antibody-drug conjugates, biological response modifiers, cyclin-dependent kinase (CDK) inhibitors, cell cycle inhibitors, cyclooxygenase-2 (COX-2) inhibitors, dual variable domain binding proteins (DVDs), human epidermal growth factor receptor 2 (ErbB2 or HER/2neu) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs), intercalating antibiotics, kinase inhibitors, kinesin inhibitors, JAK2 inhibitors, mammalian target of rapamycin (mTOR) inhibitors, microRNAs, mitogen-activated extracellular signal-regulated kinase (MEK) inhibitors, multivalent binding proteins, non-steroidal anti-inflammatory drugs (NSAIDs), poly-ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids, deltoids, plant alkaloids, small inhibitory ribonucleic acids (siRNAs), topoisomerase inhibitors, ubiquitin ligase inhibitors, and the like.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

siRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 or ABT-737 in various tumor cell lines (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, Cloretazine™ (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include epidermal growth factor receptor (EGFR) inhibitors, endothelial-specific receptor tyrosine kinase (Tie-2) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include Alimta™ (pemetrexed disodium, LY231514, MTA), 5-azacitidine, Xeloda™ (capecitabine), carmofur, Leustat™ (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethenylcytidine, fludarabine, 5-fluorouracil (5-FU) alone or in combination with leucovorin, Gemzar™ (gemcitabine), hydroxyurea, Alkeran™ (melphalan), mercaptopurine, 6-mercaptopurine riboside, methotrexate, mycophenolic acid, nelarabine, nolatrexed, ocfosfate, pelitrexol, pentostatin, raltitrexed, ribavirin, S-1, triapine, trimetrexate, TS-1, tiazofurin, tegafur, vidarabine, UFT and the like.

Antivirals include ritonavir, hydroxychloroquine and the like.

Aurora kinase inhibitors include ABT-348, AZD-1152, MLN-8054, VX-680, aurora A-specific kinase inhibitors, aurora B-specific kinase inhibitors, pan-aurora kinase inhibitors and the like.

Bcl-2 family protein inhibitors other than compounds of Formula I herein include AT-101 ((−)gossypol), Genasense™ Bcl-2-targeting antisense oligonucleotide (G3139 or oblimersen), IPI-194, IPI-565, ABT-737, ABT-263, GX-070 (obatoclax) and the like.

Bcr-Abl kinase inhibitors include dasatinib (BMS-354825), Gleevec™ (imatinib) and the like.

CDK inhibitors include AZD-5438, BMI-1040, BMS-387032, CVT-2584, flavopyridol, GPC-286199, MCS-5A, PD0332991, PHA-690509, seliciclib (CYC-202 or R-roscovitine), ZK-304709 and the like.

COX-2 inhibitors include ABT-963, Arcoxia™ (etoricoxib), Bextra™ (valdecoxib), BMS-347070, Celebrex™ (celecoxib), COX-189 (lumiracoxib), CT-3, Deramaxx™ (deracoxib), JTE-522, 4-methyl-2-(3,4-dimethylphenyl)-1-(4-sulfamoylphenyl)-1H-pyrrole, MK-663 (etoricoxib), NS-398, parecoxib, RS-57067, SC-58125, SD-8381, SVT-2016, S-2474, T-614, Vioxx™ (rofecoxib) and the like.

EGFR inhibitors include ABX-EGF, anti-EGFR immunoliposomes, EGF-vaccine, EMD-7200, Erbitux™ (cetuximab), HR3, IgA antibodies, Iressa™ (gefitinib), Tarceva™ (erlotinib or OSI-774), TP-38, EGFR fusion protein, Tykerb™ (lapatinib) and the like.

ErbB2 receptor inhibitors include CP-724714, CI-1033 (canertinib), Herceptin™ (trastuzumab), Tykerb™ (lapatinib), Omnitarg™ (2C4, petuzumab), TAK-165, GW-572016 (ionafamib), GW-282974, EKB-569, PI-166, dHER2 (HER2 vaccine), APC-8024 (HER2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17AAG, CNF-101, CNF-1010, CNF-2024, 17-DMAG, geldanamycin, IPI-504, KOS-953, Mycograb™ (human recombinant antibody to HSP-90), nab-17AAG, NCS-683664, PU24FCl, PU-3, radicicol, SNX-2112, STA-9090, VER-49009 and the like.

Inhibitors of apoptosis proteins include HGS-1029, GDC-0145, GDC-0152, LCL-161, LBW-242 and the like.

Antibody-drug conjugates include anti-CD22-MC-MMAF, anti-CD22-MC-MMAE, anti-CD22-MCC-DM1, CR-011-vcMMAE, PSMA-ADC, MEDI-547, SGN-19A, SGN-35, SGN-75 and the like.

Activators of death receptor pathway include TRAIL and antibodies or other agents that target TRAIL or death receptors (e.g., DR4 and DR5) such as apomab, conatumumab, ETR2-ST01, GDC0145 (lexatumumab), HGS-1029, LBY-135, PRO-1762, trastuzumab and the like.

Kinesin inhibitors include Eg5 inhibitors such as AZD-4877 and ARRY-520, CENPE inhibitors such as GSK-923295A, and the like.

JAK2 inhibitors include CEP-701 (lesaurtinib), XL019, INCB-018424 and the like.

MEK inhibitors include ARRY-142886, ARRY-438162, PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30 and Torin 1, and the like.

Non-steroidal anti-inflammatory drugs include Amigesic™ (salsalate), Dolobid™ (diflunisal), Motrin™ (ibuprofen), Orudis™ (ketoprofen), Relafen™ (nabumetone), Feldene™ (piroxicam), ibuprofen cream, Aleve™ and Naprosyn™ (naproxen), Voltaren™ (diclofenac), Indocin™ (indomethacin), Clinoril™ (sulindac), Tolectin™ (tolmetin), Lodine™ (etodolac), Toradol™ (ketorolac), Daypro™ (oxaprozin) and the like.

PDGFR inhibitors include CP-673451, CP-868596 and the like.

Platinum chemotherapeutics include cisplatin, Eloxatin™ (oxaliplatin), eptaplatin, lobaplatin, nedaplatin, Paraplatin™ (carboplatin), picoplatin, satraplatin and the like.

Polo-like kinase inhibitors include BI-2536 and the like.

Phosphoinositide-3 kinase inhibitors include wortmannin, LY-294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include Avastin™ (bevacizumab), ABT-869, AEE-788, Angiozyme™ (a ribozyme that inhibits angiogenesis (Ribozyme Pharmaceuticals (Boulder, Colo.) and Chiron (Emeryville, Calif.)), axitinib (AG-13736), AZD-2171, CP-547632, IM-862, Macugen™ (pegaptanib), Nexavar™ (sorafenib, BAY43-9006), pazopanib (GW-786034), vatalanib (PTK-787 or ZK-222584), Sutent™ (sunitinib or SU-11248). VEGF trap, Zactima™ (vandetanib or ZD-6474) and the like.

Antibiotics include intercalating antibiotics such as aclarubicin, actinomycin D, amrubicin, annamycin, Adriamycin™ (doxorubicin), Blenoxane™ (bleomycin), daunorubicin, Caelyx™ and Myocet™ (liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, Valstar™ (valrubicin), zinostatin and the like.

Topoisomerase inhibitors include aclarubicin, 9-aminocamptothecin, amonafide, amsacrine, becatecarin, belotecan, BN-80915, Camptosar™ (irinotecan hydrochloride), camptothecin, Cardioxane™ (dexrazoxane), diflomotecan, edotecarin, Ellence™ and Pharmorubicin™ (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include Avastin™ (bevacizumab), CD40-specific antibodies, chTNT-1/B, denosumab, Erbitux™ (cetuximab), Humax-CD4T™ (zanolimumab), IGF1R-specific antibodies, lintuzumab, Panorex™ (edrecolomab), Rencarex™ (WX G250), Rituxan™ (rituximab), ticilimumab, trastuzumab, CD20 antibodies types I and II and the like.

Hormonal therapies include Arimidex™ (anastrozole), Aromasin™ (exemestane), arzoxifene, Casodex™ (bicalutamide), Cetrotide™ (cetrorelix), degarelix, deslorelin, Desopan™ (trilostane), dexamethasone, Drogenil™ (flutamide), Evista™ (raloxifene), Afema™ (fadrozole), Fareston™ (toremifene), Faslodex™ (fulvestrant), Femara™ (letrozole), formestane, glucocorticoids, Hectorol™ (doxercalciferol), Renagel™ (sevelamer carbonate), lasofoxifene, leuprolide acetate, Megace™ (megestrol), Mifeprex™ (mifepristone), Nilandron™ (nilutamide), tamoxifen including Nolvadex™ (tamoxifen citrate), Plenaxis™ (abarclix), prednisone, Propecia™ (finasteride), rilostane, Suprefact™ (buserelin), luteinizing hormone releasing hormone (LHRH) including Trelstar™ (triptorelin), histrelin including Vantas™ (histrelin implant), Modrastane™ (trilostane), Zoladex™ (goserelin) and the like.

Deltoids and retinoids include seocalcitol (EB1089 or CB1093), lexacalcitol (KH1060), fenretinide, Panretin™ (alitretinoin), tretinoin including Atragen™ (liposomal tretinoin), Targretin™ (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include vincristine, vinblastine, vindesine, vinorelbine and the like.

Proteasome inhibitors include Velcade™ (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, Actimmune™ (interferon gamma-1b), interferon gamma-n1, combinations thereof and the like. Other agents include Alfaferone (IFN-α), BAM-002 (oxidized glutathione), Beromun™ (tasonermin), Bexxar™ (tositumomab), Campath™ (alemtuzumab), CTLA4 (cytotoxic lymphocyte antigen 4), dacarbazine, denileukin, epratuzumab, Granocyte™ (lenograstim), lentinan, leukocyte alpha interferon, imiquimod, MDX-010 (anti-CTLA-4), melanoma vaccine, mitumomab, molgramostim, Mylotarg™ (gemtuzumab ozogamicin), Neupogen™ (filgrastim), OncoVAC-CL, Ovarex™ (oregovomab), pemtumomab (Y-muHMFG1), Provenge™ (sipuleucel-T), sargaramostim, sizofiran, teceleukin, Theracys™ (BCG or Bacillus Calmette-Guerin), ubenimex, Virulizin™ (immunotherapeutic, Lorus Pharmaceuticals), Z-100 (Specific Substance of Maruyama or SSM), WF-10 (tetrachlorodecaoxide or TCDO), Proleukin™ (aldesleukin), Zadaxin™ (thymalfasin), Zenapax™ (daclizumab), Zevalin™ (90Y-ibritumomab tiuxetan) and the like.

Biological response modifiers are agents that modify defense mechanisms of living organisms or biological responses, such as survival, growth or differentiation of tissue cells to direct them to have anti-tumor activity, and include krestin, lentinan, sizofiran, picibanil, PF-3512676 (CpG-8954), ubenimex and the like.

Pyrimidine analogs include cytarabine (cytosine arabinoside, ara C or arabinoside C), doxifluridine, Fludara™ (fludarabine), 5-FU (5-fluorouracil), floxuridine, Gemzar™ (gemcitabine), Tomudex™ (raltitrexed), triacetyluridine, Troxatyl™ (troxacitabine) and the like.

Purine analogs include Lanvis™ (thioguanine), Purinethol™ (mercaptopurine) and the like.

Antimitotic agents include batabulin, epothilone D (KOS-862), N-(2-((4-hydroxy-phenyl)amino)pyridin-3-yl)-4-methoxybenzenesulfonamide, ixabepilone (BMS-247550), paclitaxel, Taxotere™ (docetaxel), larotaxel (PNU-100940, RPR-109881 or XRP-9881), patupilone, vinflunine, ZK-EPO (synthetic epothilone) and the like.

Ubiquitin ligase inhibitors include MDM2 inhibitors such as nutlins, NEDD8 inhibitors such as MLN4924, and the like.

Compositions of this invention can also be used as radiosensitizers that enhance the efficacy of radiotherapy. Examples of radiotherapy include, but are not limited to, external beam radiotherapy (XBRT), teletherapy, brachytherapy, sealed-source radiotherapy, unsealed-source radiotherapy and the like.

Additionally or alternatively, a composition of the present invention can be administered in combination therapy with one or more antitumor or chemotherapeutic agents selected from Abraxane™ (ABI-007), ABT-100 (farnesyl transferase inhibitor), Advexin™ (Ad5CMV-p53 vaccine or contusugene ladenovec), Altocor™ or Mevacor™ (lovastatin), Ampligen™ (poly(I)-poly(C12U), a synthetic RNA), Aptosyn™ (exisulind), Aredia™ (pamidronic acid), arglabin, L-asparaginase, atamestane (1-methyl-3,17-dione-androsta-1,4-diene), Avage™ (tazarotene), AVE-8062 (combretastatin derivative), BEC2 (mitumomab), cachectin or cachexin (tumor necrosis factor), Canvaxin™ (melanoma vaccine), CeaVac™ (cancer vaccine), Celeuk™ (celmoleukin), histamine including Ceplene™ (histamine dihydrochloride), Cervarix™ (AS04 adjuvant-adsorbed human papilloma virus (HPV) vaccine), CHOP (Cytoxan™ (cyclophosphamide)+Adriamycin™ (doxorubicin)+Oncovin™ (vincristine)+prednisone), combretastatin A4P, Cypat™ (cyproterone), DAB(389)EGF (catalytic and translocation domains of diphtheria toxin fused via a His-Ala linker to human epidermal growth factor), dacarbazine, dactinomycin, Dimericine™ (T4N5 liposome lotion), 5,6-dimethylxanthenone-4-acetic acid (DMXAA), discodermolide, DX-8951f (exatecan mesylate), eniluracil (ethynyluracil), squalamine including Evizon™ (squalamine lactate), enzastaurin, EPO-906 (epothilone B), Gardasil™ (quadrivalent human papilloma virus (Types 6, 11, 16, 18) recombinant vaccine), Gastrimmune™, Genasense™ (oblimersen), GMK (ganglioside conjugate vaccine), GVAX™ (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, Junovan™ and Mepact™ (mifamurtide), lonafarnib, 5,10-methylenetetrahydrofolate, miltefosine (hexadecylphosphocholine), Neovastat™ (AE-941), Neutrexin™ (trimetrexate glucuronate), Nipent™ (pentostatin), Onconase™ (ranpirnase, a ribonuclease enzyme), Oncophage™ (vitespen, melanoma vaccine treatment), OncoVAX™ (IL-2 vaccine), Orathecin™ (rubitecan), Osidem™ (antibody-based cell drug), Ovarex™ MAb (murine monoclonal antibody), paclitaxel albumin-stabilized nanoparticle, paclitaxel, Pandimex™ (aglycone saponins from ginseng comprising 20(S)-protopanaxadiol (aPPD) and 20(S)-protopanaxatriol (aPPT)), panitumumab, Panvac™-VF (investigational cancer vaccine), pegaspargase, peginterferon alfa (PEG interferon A), phenoxodiol, procarbazine, rebimastat, Removab™ (catumaxomab), Revlimid™ (lenalidomide), RSR13 (efaproxiral), Somatuline™ LA (lanreotide), Soriatane™ (acitretin), staurosporine (Streptomyces staurospores), talabostat (PT 100), Targretin™ (bexarotene), Taxoprexin™ (docosahexaenoic acid (DHA)+paclitaxel), Telcyta™ (canfosfamide, TLK-286), Temodar™ (temozolomide), tesmilifene, tetrandrine, thalidomide, Theratope™ (STn-KLH vaccine), Thymitaq™ (nolatrexed dihydrochloride), TNFerade™ (adenovector: DNA carrier containing the gene for tumor necrosis factor-α), Tracleer™ or Zavesca™ (bosentan), TransMID-107R™ (KSB-311, diphtheria toxins), tretinoin (retin-A), Trisenox™ (arsenic trioxide), Ukrain™ (derivative of alkaloids from the greater celandine plant), Virulizin™, Vitaxin™ (anti-αvβ3 antibody), Xcytrin™ (motexafin gadolinium), Xinlay™ (atrasentan), Xyotax™ (paclitaxel poliglumex), Yondelis™ (trabectedin), ZD-6126 (N-acetylcolchinol-O-phosphate), Zinecard™ (dexrazoxane), zoledronic acid, zorubicin and the like.

In one embodiment, a composition of the invention is administered in a therapeutically effective amount to a subject in need thereof to treat a disease during which is overexpressed one or more of antiapoptotic Bcl-2 protein, antiapoptotic Bcl-$X_L$ protein and antiapoptotic Bcl-w protein.

In another embodiment, a composition of the invention is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, a composition of the invention is administered in a therapeutically effective amount to a subject in need thereof to treat bladder cancer, brain cancer, breast cancer, bone marrow cancer, cervical cancer, chronic lymphocytic leukemia, acute lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

According to any of these embodiments, the composition is administered in monotherapy or in combination therapy with one or more additional therapeutic agents.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of (a) a composition of the invention and (b) one or more of etoposide, vincristine, CHOP, rituximab, rapamycin, R-CHOP, RCVP, DA-EPOCH-R or bortezomib.

In particular embodiments, a composition of the invention is administered in a therapeutically effective amount to a subject in need thereof in combination therapy with etoposide, vincristine, CHOP, rituximab, rapamycin, R-CHOP, RCVP, DA-EPOCH-R or bortezomib in a therapeutically effective amount, for treatment of a lymphoid malignancy such as B-cell lymphoma or non-Hodgkin's lymphoma.

In other particular embodiments, a composition of the invention is administered in a therapeutically effective amount to a subject in need thereof in monotherapy or in combination therapy with etoposide, vincristine, CHOP, rituximab, rapamycin, R-CHOP, RCVP, DA-EPOCH-R or bortezomib in a therapeutically effective amount, for treatment of chronic lymphocytic leukemia or acute lymphocytic leukemia.

The present invention also provides a method for maintaining in bloodstream of a human cancer patient a therapeutically effective plasma concentration of a compound of Formula I and/or one or more metabolites thereof, comprising administering to the subject a solid dispersion of the compound or a pharmaceutically acceptable salt thereof in essentially non-crystalline form in a matrix that comprises a pharmaceutically acceptable water-soluble polymeric carrier and a pharmaceutically acceptable surfactant, in a parentcompound-equivalent dosage amount of about 50 to about 500 mg per day, at an average dosage interval of about 3 hours to about 7 days.

What constitutes a therapeutically effective plasma concentration depends inter alia on the particular compound of Formula I, the particular cancer present in the patient, the stage, severity and aggressiveness of the cancer, and the outcome sought (e.g., stabilization, reduction in tumor growth, tumor shrinkage, reduced risk of metastasis, etc.). It is strongly preferred that, while the plasma concentration is sufficient to provide benefit in terms of treating the cancer, it should not be sufficient to provoke an adverse side-effect to an unacceptable or intolerable degree.

In another embodiment, a composition of the invention is administered in a therapeutically effective amount to a subject in need thereof to treat an immune or autoimmune disorder. Such disorders include acquired immunodeficiency disease syndrome (AIDS), autoimmune lymphoproliferative syndrome, hemolytic anemia, inflammatory diseases, thrombocytopenia, acute and chronic immune diseases associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis-associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anemia, autoimmune hepatitis, type-1 autoimmune hepatitis (classical autoimmune or lupoid hepatitis), autoimmune mediated hypoglycemia, autoimmune neutropenia, autoimmune thrombocytopenia, autoimmune thyroid disease, B-cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy-associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinemia), conjunctivitis, connective tissue disease-associated interstitial lung disease, contact dermatitis, Coombs-positive hemolytic anemia, cor pulmonale, Creutzfeldt-Jakob disease, cryptogenic autoimmune hepatitis, cryptogenic fibrosing alveolitis, culture-negative sepsis, cystic fibrosis, cytokine therapy-associated disorders, Crohn's disease, dementia pugilistica, demyelinating diseases, dengue hemorrhagic fever, dermatitis, dermatitis scleroderma, dermatologic conditions, dermatomyositis/polymyositis-associated lung disease, diabetes, diabetic arteriosclerotic disease, diabetes mellitus, diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine receptors, drug sensitivity, eczema, encephalomyelitis, endocarditis, endocrinopathy, enteropathic synovitis, epiglottitis, Epstein-Barr virus infection, crythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram-negative sepsis, gram-positive sepsis, granulomas due to intracellular organisms, group B streptococci (GBS) infection, Graves' disease, hemosiderosis-associated lung disease, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpura, hepatitis A, hepatitis B, hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopenia, idiopathic pulmonary fibrosis, idiopathic thrombocytopenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease-associated lung disease, monoclonal gammopathy, multiple myeloma, multiple systems degenerations (Mencel, Dejerine-Thomas, Shy-Drager and Machado-Joseph), myalgic encephalitis/Royal Free Disease, myasthenia gravis, microscopic vasculitis of the kidneys, *Mycobacterium avium* intracellulare, *Mycobacterium tuberculosis*, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, non-alcoholic steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *Pneumocystis carinii* pneumonia, pneumonia, POEMS syndrome (polyneuropathy, organomegaly, endocrinopathy, monoclonal gammopathy, and skin changes syndrome), post-perfusion syndrome, post-pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, progressive supranuclear palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis-associated interstitial lung disease, rheumatoid spondylitis, sarcoidosis, Schmidt's syndrome, scleroderma, senile chorea, senile dementia of Lewy body type, sepsis syndrome, septic shock, seronegative arthropathies, shock, sickle cell anemia, Sjögren's disease-associated lung disease, Sjögren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic polyglandular deficiency type I, sporadic polyglandular deficiency type II, Still's disease, streptococcal myositis, stroke, structural lesions of the cerebellum, subacute sclerosing panencephalitis, sympathetic ophthalmia, syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, lupus nephritis, systemic sclerosis, systemic sclerosis-associated interstitial lung disease, T-cell or FAB ALL, Takayasu's disease/arteritis, telangiectasia, Th2-type and Th1-type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

EXAMPLES

The following examples are merely illustrative, and do not limit this disclosure in any way. For example, it will be appreciate that lab-scale compositions or formulations, or extrusion blends, referenced herein may in general be scaled up in view of the details provided without departing from the intended scope of the present application.

Trademarked ingredients used in the examples, which can be substituted with comparable ingredients from other suppliers, include Tween™ 80 of Uniqema (polysorbate 80 surfactant), and Soluplus™ of BASF (graft copolymer of polyethylene glycol, polyvinyl caprolactam and polyvinyl acetate).

In the examples, "API" (active pharmaceutical ingredient) can be any compound of Formula I, added in essentially anhydrous parent-compound (i.e., not salt) form. The following compounds are more specifically contemplated for formulation according to the examples:

4-(4-{[2-(4-chlorophenyl)-4,4-dimethylcyclohex-1-en-1-yl]methyl}piperazin-1-yl)-2-(1H-indol-5-yloxy)-N-({3-nitro-4-[(1-tetrahydro-2H-pyran-4-ylpiperidin-4-yl)amino]phenyl}-sulfonyl)benzamide—Compound 89;

4-(4-{[2-(4-chlorophenyl)-4,4-dimethylcyclohex-1-en-1-yl]methyl}piperazin-1-yl)-2-(1H-indol-5-yloxy)-N-({4-[(4-methylpiperazin-1-yl)amino]-3-nitrophenyl}sulfonyl)-benzamide—Compound 91;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide—Compound 5;

trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-(1H-pyrrolo[2,3-b]pyridin-5-yloxy)benzamide—Compound 9;

cis-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide—Compound 29;

trans-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]-2-(1H-pyrrolo[2,3-b]pyridin-5-yloxy)benzamide—Compound 34;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-(1H-pyrrolo[2,3-b]pyridin-5-yloxy)benzamide—Compound 37;

N-[(5-chloro-6-{[4-fluoro-1-(oxetan-3-yl)piperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 277;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-(1H-pyrrolo[2,3-b]pyridin-5-yloxy)benzamide—Compound 61;

4-(4-{[2-(4-chlorophenyl)-5-methoxy-5-methylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide—Compound 378;

4-{[2-(4-chlorophenyl)-4,4-dimethylcyclohex-1-en-1-yl]methyl}piperazin-1-yl)-N-[(4-{[(3R)-1-(methylsulfonyl)pyrrolidin-3-yl]amino}-3-nitrophenyl)sulfonyl]-2-(1H-pyrrolo[2,3-b]pyridin-5-yloxy)benzamide—Compound 149;

4-(4-{[2-(4-chlorophenyl)-4,4-dimethylcyclohex-1-en-1-yl]methyl}piperazin-1-yl)-N-[(4-{[(trans-4-hydroxy-4- methylcyclohexyl)methyl]amino}-3-nitrophenyl)sulfo-
nyl]-2-(1H-pyrrolo[2,3-b]pyridin-5-yloxy)benzamide—
Compound 337;

4-(4-{[2-(4-chlorophenyl)-4,4-dimethylcyclohex-1-en-1-yl]
methyl}piperazin-1-yl)-N-[(4-{[(cis-4-hydroxy-4-meth-
ylcyclohexyl)methyl]amino}-3-nitrophenyl)sulfonyl]-2-
(1H-pyrrolo[2,3-b]pyridin-5-yloxy)benzamide—
Compound 338;

4-(4-{[2-(4-chlorophenyl)-4,4-dimethylcyclohex-1-en-1-yl]
methyl}piperazin-1-yl)-N-{[4-({3-[cyclopropyl(oxetan-
3-yl)amino]propyl}amino)-3-nitrophenyl]sulfonyl}-2-
(1H-pyrrolo[2,3-b]pyridin-5-yloxy)benzamide—
Compound 311;

4-(4-{[2-(4-chlorophenyl)-4,4-dimethylcyclohex-1-en-1-yl]
methyl}piperazin-1-yl)-N-{[3-nitro-4-({[(3R)-1-tetra-
hydro-2H-pyran-4-ylpyrrolidin-3-yl]methyl}amino)phe-
nyl]-sulfonyl}-2-(1H-pyrrolo[2,3-b]pyridin-5-yloxy)
benzamide—Compound 118;

4-(4-{[2-(4-chlorophenyl)-4,4-dimethylcyclohex-1-en-1-yl]
methyl}piperazin-1-yl)-N-[(4-{[(4-methylmorpholin-2-
yl)methyl]amino}-3-nitrophenyl)sulfonyl]-2-(1H-pyrrolo
[2,3-b]pyridin-5-yloxy)benzamide—Compound 134;

N-[(5-chloro-6-{[1-(cyanomethyl)piperidin-4-yl]
methoxy}pyridin-3-yl)sulfonyl]-4-(4-{[2-(4-chlorophe-
nyl)-4,4-dimethylcyclohex-1-en-1-yl]methyl}piperazin-
1-yl)-2-(1H-pyrrolo[2,3-b]pyridin-5-yloxy)benzamide—
Compound 253;

N-[(4-{[(4-aminotetrahydro-2H-pyran-4-yl)methyl]amino}-
3-nitrophenyl)sulfonyl]-4-(4-{[2-(4-chlorophenyl)-4,4-
dimethylcyclohex-1-en-1-yl]methyl}piperazin-1-yl)-2-
(1H-pyrrolo[2,3-b]pyridin-5-yloxy)benzamide—
Compound 108; and 4-(4-{[2-(4-chlorophenyl)-4,4-dimethylcyclohex-1-en-1-yl]
methyl}piperazin-1-yl)-N-({4-[(4-methoxytetrahydro-
2H-pyran-4-yl)methoxy]-3-nitrophenyl}sulfonyl)-2-(1H-
pyrrolo[2,3-b]pyridin-5-yloxy)benzamide—Compound
234.

Example 1: Melt Extrusion

Referring now to FIG. 1, an embodiment of a process including melt extrusion useful to form a solid dispersion product is shown at 100. A granulation step 105 includes combining one or more pharmaceutically acceptable polymers, one or more surfactants, and one or more other optional ingredients and transforming these components into a granular form. For example, a pharmaceutically acceptable polymer may be provided in a stock form, such as pellets, which are then ground and mixed with a surfactant. Other ingredients, such as an anti-caking agent or emulsifier, can be included in the granulation step 105.

The granulated polymer(s), surfactant(s), and optional ingredient(s) are then blended/sieved at 115 with the addition of the API 120. For example, once the API is suitably blended with the granulated polymer(s), surfactant(s), and optional ingredient(s) to form an essentially uniform mixture, the mixture can be further sieved to select a uniform size.

At this point, the blended and sieved mixture can be processed by an extrusion and calendering step 125 where the mixture is subjected to pressure and/or heat suitable to melt at least a portion of the mixture. For example, a screw-type extruder can be used in this step. Suitable screw-type extruders include a Leistritz Micro 18 or Micro 27 twin-screw extruder.

Following extrusion, the mixture or extrudate can be subjected to calendering by pressing with a roller or a series of rollers. That is, as shown at 125, the mixture from the blending/sieving step 115 is first extruded and then calendered. Calendering can include subjecting the extrudate to a roller having one or more cavities that press the extrudate into a lentil form or other shape. Optionally, the extrudate is not calendered at 125 (not shown) but can continue through the remainder of the illustrated process in FIG. 1.

The extruded and calendered material is cooled and allowed to return to a substantially solid phase prior to being milled, as shown at 130, where the solid is ground, pulverized or broken down into smaller particles. The milled material is then blended and/or sieved 135 following addition of one or more optional ingredients 140.

A compression step 145 forces the blended and/or sieved material into the desired final form, such as a tablet providing a particular dosage of the API. Finally, a coating may be applied to the compressed material as shown at 150. The coating, such as a polymer coating, can make the compressed material smoother and easier to swallow, can control the release rate of the API, can make the material more resistant to the environment (extending shelf life), and/or can enhance the tablet's appearance.

In an alternative embodiment, rather than introducing the surfactant into the composition as part of the granulation step 105, a liquid dosing system (not shown) may be used to dose a liquid surfactant (e.g., Tween80) into the composition at a different point in the process. For example, in one alternative embodiment a liquid surfactant may be dosed using a liquid dosing system into the composition during the extrusion step, 125.

Example 2: Tablets Formed by a Process Including Melt-Extrusion

The following components (in weight %) are combined and melt-extruded to form an extrudate:
12% API;
80% copovidone 60/40;
7% Tween™ 80; and
1% colloidal silicon dioxide.

In particular, these components can be processed as shown in FIG. 1 by granulation 105, blending and/or sieving 115, extrusion and calendering 125. The copovidone, Tween™ 80 and colloidal silicon dioxide can be provided at 110 into the granulation step 105 and the API can be provided at 120 into the blending/sieving step 115.

The extrusion/calendering step 125 is performed using a screw-type extruder where the extrusion process parameters include:

| Temperature: | heating block 1 | 95° C. |
|---|---|---|
| | heating blocks 2-5 | 155° C. |
| | heating block 6 (die) | 140° C. |
| Screw speed: | | 150 rpm |
| Feed rate: | | 1.5 kg/h |
| Vacuum: | | 200 mbar |

The resulting extrudate can then be processed as shown in FIG. 1 by milling 130, blending/sieving 135, compression 145, and coating 150. The extrudate is further combined with the following ingredients (provided at 140 as per FIG. 1) to provide the following tablet formulation:

| extrudate | 78.5% |
|---|---|
| dicalcium phosphate | 20.0% |

-continued

| | |
|---|---|
| sodium stearyl fumarate | 0.5% |
| colloidal silicon dioxide | 1.0% |

Example 3: Solid Dispersion Prepared by Melt-Extrusion

The following components (in weight %) are combined and melt-extruded to form an extrudate, by a process as described in Example 2:
10% API;
82% copovidone 60/40;
7% TPGS;
1% colloidal silicon dioxide.
The resulting extrudate can then be processed as described in Example 2.

Example 4: Solid Dispersion Prepared by Melt-Extrusion

The following components (in weight %) are combined and melt-extruded to form an extrudate, by a process as described in Example 2:
12% API;
78% copovidone 60/40;
7% TPGS;
2% propylene glycol laurate; and
1% colloidal silicon dioxide.
The resulting extrudate can then be processed as described in Example 2.

Example 5: Solid Dispersion Prepared by Melt-Extrusion

The following components (in weight %) are combined and melt-extruded to form an extrudate, by a process as described in Example 2:
12% API;
80% Soluplus™;
7% poloxamer; and
1% colloidal silicon dioxide.
The resulting extrudate can then be processed as described in Example 2.

Example 6. Melt Extrusion Feasibility Study

Feasibility experiments were performed to evaluate the influence of different excipients on extrudates with embedded amorphous drug. In these experiments, the formulations included copovidone (Kollidon VA 64; vinylpyrrolidone-vinyl acetate copolymer) as the matrix polymer, compound 5 as the active pharmaceutical ingredient (API), and a variety of surfactants/plasticizers.

Batches in the sizes of 10 g to 30 g were prepared. Surfactant/plasticizer and matrix polymer were pre-blended using a lab-mill (e.g. a IKA lab-mill A10 basic or Rotor GT95). The pre-blended mixture was left standing for 4-48 hours before blending compound 5 into the pre-blended mixture. The entire blend was extruded with a small-scale single screw extruder (e.g., a MicroCompounder Haake MiniLab extruder). The following Table 1 displays the appearance of the extrudate as a function of the extrusion temperature and the surfactant/plasticizer.

It was observed, from the single screw extrusions, that appearance is a function of temperature, as well as the concentration of the various components present in the mixture/blend. For example, in some cases, extrusion temperatures as low as 135° C. did not lead to uniformly clear extrudates, while extrusion temperature up to 160° C. led to an observable improvement. Notably, however, the extrudates were free of crystals.

TABLE 1

Feasibility Formulations and Extrudate Appearance

| Batch | Drug Load [%] | Kollidon VA64 [%] | Surfactant [%] | Temperature [° C.] | Appearance |
|---|---|---|---|---|---|
| 9P01-01 | 5% | 85% | 10% Vitamin E TPGS | 130° C. | almost clear |
| 9P01-02 | 5% | 85% | 10% Vitamin E TPGS | 135° C. | almost clear |
| 9P01-03 | 5% | 85% | 10% Vitamin E TPGS | 140° C. | almost clear |
| 9P01-04 | 5% | 85% | 10% Vitamin E TPGS | 145° C. | almost clear |
| 9P01-05 | 5% | 85% | 10% Vitamin E TPGS | 150° C. | almost clear |
| 9P02-01 | 10% | 80% | 10% Vitamin E TPGS | 150° C. | almost clear |
| 9P02-02 | 10% | 80% | 10% Vitamin E TPGS | 160° C. | clear |
| 9P03-01 | 12% | 78% | 10% Vitamin E TPGS | 155° C. | clear |
| 9P03-02 | 12% | 78% | 10% Vitamin E TPGS | 135° C. | clear |
| 9P04-01 | 5% | 85% | 10% Span20 | 140° C. | clear |
| 9P04-02 | 5% | 85% | 10% Span20 | 150° C. | clear |
| 9P05-01 | 5% | 85% | 10% Tween20 | 140° C. | clear |
| 9P05-02 | 5% | 85% | 10% Tween20 | 150° C. | clear |
| 9P06-01 | 5% | 85% | 10% Span20 | 140° C. | clear |
| 9P06-02 | 5% | 85% | 10% Span20 | 150° C. | clear |
| 9P07-01 | 5% | 85% | 7% Lauroglycol FCC 3% Vitamin E TPGS | 150° C. | cloudy |
| 9P07-02 | 5% | 85% | 7% Lauroglycol FCC 3% Vitamin E TPGS | 155° C. | cloudy |
| 9P08-01 | 5% | 95% | 0 | 140° C. | almost clear |
| 9P08-02 | 5% | 95% | 0 | 150° C. | clear |
| 9P09-01 | 10% | 80% | 5% SDS 5% PEG400 | 140° C. | clear |

Dispersibility of selected extrudates from the feasibility study above were tested by dispensing capsules (containing 500 mg milled extrudate and 250 mg Mannitol/Aerosil (99:1)) in 250 mL 0.1 N HCl at 37° C. After predetermined time points samples were taken and analyzed by HPLC (HPLC Conditions: Agilent 1100 Series; Column: Agilent Zorbax XDB C18, 150×4.6 mm, 3.5 µm; flow: 1.0 mL/min; injection volume: 25 µL; oven temperature: 30° C.; detection wavelength: 314 nm; solvent A: 0.1% TFA (trifluoroacetic acid) in water; solvent B: ACN (acetonitrile): Methanol (50:50); method used a gradient: 0 min=60% B; 7 min=95% B; 7.1 min=60% B; 10 min=60% B). Several formulations (e.g. 9P01-05) were able to release a satisfactory amount of compound 5, but not all of the dispersions were stable over a long period of time. Vitamin E-TPGS and Tween20 appeared from the feasibility and dispersibility studies to be more suitable candidates for surfactant.

Example 7. Extrusion Trials Series I

Further studies were performed to evaluate the effect of drug load, surfactant level, and extrusion temperature on the appearance of the extrudate. Compound 5 and Aerosil (1%) were used in each batch as drug and glidant, respectively. The extrudates were free of residual crystal. The results are summarized in Table 2. These results indicate that a more suitable extrusion temperature is 150° C.

Dispersibility of selected extrudates was tested by dispensing 5 mg compound 5 equivalent of unmilled extrudate in 75 mL 0.1 N HCl at 37° C. After predetermined time points samples were taken and analyzed by HPLC (200 µL of the dispersion was diluted with 800 µL acetonitrile to obtain a clear solution) (HPLC Conditions: Agilent 1100 Series; Column: Phenomenex Gemini-NX3µ C18 110 A; flow: 0.3 mL/min; injection volume: 5 µL; oven temperature: 30° C.; detection wavelength: 220 nm; solvent A: 0.1% TFA (trifluoroacetic acid) in water; solvent B: ACN (acetonitrile); method was isocratic solvent A 45%, solvent B 55%; peak elutes between 2.5 and 3.5 mins). Several formulations were able to release a satisfying amount of compound 5. As a general tendency, it was observed that the lower the drug load the better the drug release, and 20% drug load resulted in poor dispersibility. HPLC analysis of the extrudates showed that the content of the extrudates was inhomogeneous and correlates with the content found in dispersibility testing. This was believed to be the result of inhomogeneous blending of the API and other components prior to the extrusion process.

Example 8. Extrusion Trials Series II

To determine whether a drug loading of 12% was achievable, the appearance of extrusion blends containing 10-12% of compound 5 were recorded at 150° C. (Table 3). The blends showed inhomogeneity and were therefore neither extruded nor tested for dispersibility.

TABLE 2

Extrusion Trials Series I

| Batch | Drug Load [%] | Polymer [%] | Surfactant [%] | Temperature [° C.] | Appearance |
|---|---|---|---|---|---|
| 0P01-01 | 5% | 87.5% Copovidone | 6.6% Vitamin E TPGS | 130° C. | cloudy |
| 0P01-02 | 5% | 87.5% Copovidone | 6.6% Vitamin E TPGS | 140° C. | cloudy |
| 0P01-03 | 5% | 87.5% Copovidone | 6.6% Vitamin E TPGS | 150° C. | cloudy |
| 0P02-01 | 10% | 82.8% Copovidone | 6.2% Vitamin E TPGS | 140° C. | cloudy |
| 0P02-02 | 10% | 82.8% Copovidone | 6.2% Vitamin E TPGS | 150° C. | clear |
| 0P03-01 | 15% | 78.1% Copovidone | 5.9% Vitamin E TPGS | 140° C. | cloudy |
| 0P03-02 | 15% | 78.1% Copovidone | 5.9% Vitamin E TPGS | 150° C. | clear |
| 0P04-01 | 20% | 73.5% Copovidone | 5.5% Vitamin E TPGS | 140° C. | cloudy |
| 0P04-02 | 20% | 73.5% Copovidone | 5.5% Vitamin E TPGS | 150° C. | clear |
| 0P05-01 | 10% | 82.8% Copovidone | 6.2% Tween 80 | 140° C. | cloudy |
| 0P05-02 | 10% | 82.8% Copovidone 6 | 6.2% Tween 80 | 150° C. | clear |
| 0P06-01 | 15% | 78.1% Copovidone 5 | 5.9% Tween 80 | 140° C. | cloudy |
| 0P06-02 | 15% | 78.1% Copovidone | 5.9% Tween 80 | 150° C. | clear |
| 0P07-01 | 5% | 82.8% copovidone | 6.2% Tween 20 | 140° C. | cloudy |
| 0P07-02 | 5% | 82.8% Copovidonc | 6.2% Tween 20 | 150° C. | clear |
| 0P08-01 | 15% | 78.1% Copovidone | 5.9% Tween 20 | 140° C. | cloudy |
| 0P08-02 | 15% | 78.1% Copovidone | 5.9% Tween 20 | 150° C. | clear |
| 0P09-01 | 10% | 82.8% Copovidone | 6.2% Sucroester WP15 | 140° C. | cloudy |
| 0P09-02 | 10% | 82.8% Copovidone | 6.2% Sucroester WP15 | 150° C. | clear |
| 0P10-01 | 15% | 78.1% Copovidone | 5.9% Sucroester WP15 | 140° C. | cloudy |
| 0P10-02 | 15% | 78.1% Copovidone | 5.9% Sucroester WP15 | 150° C. | clear |
| 0P11-01 | 5% | 94% Soluplus | 0% | 140° C. | cloudy |
| 0P11-02 | 5% | 94% Soluplus | 0% | 150° C. | nearly clear |
| 0P12-01 | 10 | 89% Soluplus | 0% | 140° C. | cloudy |
| 0P12-02 | 10 | 89% Soluplus | 0% | 150° C. | nearly clear |
| 0P13-01 | 15% | 84% Soluplus | 0% | 140° C. | cloudy |
| 0P13-02 | 15% | 84% Soluplus | 0% | 150° C. | nearly clear |
| 0P14-01 | 10% | 82.8% Copovidone | 6.2% Span 20 | 140° C. | cloudy |
| 0P14-02 | 10% | 82.8% Copovidone | 6.2% Span 20 | 150° C. | clear |
| 0P15-01 | 20% | 79% Soluplus | 0% | 145° C. | cloudy |
| 0P15-02 | 20% | 79% Soluplus | 0% | 155° C. | nearly clear |

TABLE 3

Extrusion Trials Series II—Extrusion Blend with 10-12% Drug Load

| Batch | Drug Load [%] | Polymer [%] | Surfactant [%] | Glidant [%] | Appearance |
|---|---|---|---|---|---|
| 0P16-01 | 12% | 80% Kollidon VA64 | 7% Vitamin E TPGS | 1% Aerosil | clear |
| 0P17-01 | 12% | 82% Kollidon VA64 | 5% Vitamin E TPGS | 1% Aerosil | clear |
| 0P18-01 | 12% | 84% Kollidon VA64 | 3% Vitamin E TPGS | 1% Aerosil | cloudy |
| 0P19-01 | 12% | 78% Kollidon VA64 | 7% Vitamin E TPGS 2% Lauroglycol | 1% Aerosil | n.n. |
| 0P20-01 | 12% | 80% Kollidon VA64 | 7% Tween 20 | 1% Aerosil | clear |
| 0P21-01 | 12% | 80% Kollidon VA64 | 7% Tween 80 | 1% Aerosil | clear |
| 0P22-01 | 12% | 88% Soluplus | 0% | 0% | almost clear |
| 0P23-01 | 12% | 80% Soluplus | 7% Poloxamer F68NF | 1% Aerosil | clear |
| 0P24-01 | 12% | 84% Soluplus | 3% Poloxamer F68NF | 1% Aerosil | clear |
| 0P25-01 | 10% | 89% HMPC-E5 | 0% | 0% | — |
| 0P26-01 | 10% | 82% HMPC-E5 | 7% Sucroester WP15 | 1% Aerosil | — | n.n.: not noted

Example 9. Blending Experiments to Improve Blend Homogeneity

To improve the homogeneity of extrusion blends and therefore the quality of the extrudates, the results from using a blender with fast rotating knives (IKA mill, Rotor Swiss) and from manual blending (accomplished by using a bowl with either a plastic mortar or the gloves-protected hands) were compared. In order to check blend uniformity, five random samples were taken and the content of compound 5 (API) (extrusion blend: 12% Compound 5; 80% Kollidon VA64; 7% Tween 80; and, 1% Aerosil) in each determined by HPLC (Table 5) (HPLC Conditions: Agilent 1100 Series; Column: Phenomenex Gemini-NX3μ C18 110 A; flow: 0.3 mL/min; injection volume: 5 μL; oven temperature: 30° C.; detection wavelength: 220 nm; solvent A: 0.1% TFA (trifluoroacetic acid) in water; solvent B: ACN (acetonitrile); method was isocratic solvent A 45%, solvent B 55%; peak elutes between 2.5 and 3.5 mins). These results indicated that manual blending resulted in a homogeneous blend.

TABLE 5

Uniformity of Blends from Machine and Manual Blending

| Blending Type | Content [%]: Random Sample 1 | Content [%]: Random Sample 2 | Content [%]: Random Sample 3 | Content [%]: Random Sample 4 | Content [%]: Random Sample 5 | Mean [%] |
|---|---|---|---|---|---|---|
| manual blending by hand | 101.9 | 110.5 | 103.5 | 102.7 | 111.1 | 105.9 |
| IKA without API | 89.4 | 101.3 | 91.5 | 88.4 | 98.3 | 93.8 |
| IKA with API | 87.4 | 99.9 | 91.6 | 92.8 | 91.8 | 93.1 |
| manual blending with plastic mortar | 98.9 | 100.2 | 98.8 | 100.9 | 99.4 | 99.6 |

Example 10. Extrusion Trials Series III

In this series, formulations with 10% drug load (compound 5 as API) were compared to formulations with 12% drug load (1% Aerosil as glidant, 150° C.) (Table 6).

TABLE 6

Extrusion of Formulations with Compound 5 at 10% vs. 12% Drug Load

| Batch | Drug Load [%] | Polymer [%] | Surfactant [%] | Appearance |
|---|---|---|---|---|
| 0P27-02 | 10% | 82% Kollidon VA64 | 7% Vitamin E TPGS | clear |
| 0P28-01 | 12% | 80% Kollidon VA64 | 7% Vitamin E TPGS | n.n. |
| 0P29-01 | 10% | 82% Kollidon VA64 | 7% Vitamin E TPGS 2% Lauroglykol | cloudy |
| 0P30-01 | 12% | 80% Kollidon VA64 | 7% Vitamin E TPGS 2% Lauroglykol | cloudy |
| 0P31-01 | 10% | 82% Kollidon VA64 | 7% Tween 20 | clear |
| 0P32-01 | 12% | 80% Kollidon VA64 | 7% Tween 20 | clear |
| 0P33-01 | 10% | 82% Kollidon VA64 | 7% Tween 80 | n.n. |

TABLE 6-continued

Extrusion of Formulations with Compound 5 at 10% vs. 12% Drug Load

| Batch | Drug Load [%] | Polymer [%] | Surfactant [%] | Appearance |
|---|---|---|---|---|
| 0P21-01 | 12% | 80% Kollidon VA64 | 7% Tween 80 | clear |
| 0P35-01 | 10% | 82% Kollidon VA64 | 7% Poloxamer F68NF | almost clear |
| 0P36-01 | 12% | 80% Kollidon VA64 | 7% Poloxamer F68NF | almost clear | n.n.: not noted

Dispersibility of the selected extrudates was tested by dispensing a 25 mg-compound 5 equivalent of unmilled extrudate in 75 mL 0.1 N HCl at 37° C. After predetermined time points, samples were taken and analyzed by HPLC (HPLC Conditions: Agilent 1100 Series; Column: Phenomenex Gemini-NX3µ C18 110 A; flow: 0.3 mL/min; injection volume: 5 µL; oven temperature: 30° C.; detection wavelength: 220 nm; solvent A: 0.1% TFA (trifluoroacetic acid) in water; solvent B: ACN (acetonitrile); method was isocratic solvent A 45%, solvent B 55%; peak elutes between 2.5 and 3.5 mins). In general, most of the formulations in this study released substantially all (90-100%) of the API within 240 minutes. Both Tween 20 formulations (0P31-01 and 0P32-01) showed slow release rate and released more than about 60% API. While formulations with 7% Vitamin E TPGS and a 10% drug load (0P27-02) released substantially all API, formulations with the same surfactant and a 12% drug load (0P28-01) released only about 60% API. Both Tween 80 formulations (0P33-01 and 0P21-01) released API in a similar manner (about 100% within 240 minutes).

Example 11. Extrusion Trials Series IV—Tween 80 Formulations

In this series, Tween 80 formulations were studied to find the proper temperature and surfactant levels for the manufacture of extrudates containing 12% (Table 7), 13% (Table 8), 14% (Table 9), and 15% (Table 10) compound 5 as API. All batches have 1% Aerosil as glidant.

TABLE 7

Evaluation of Surfactant Level, Extrusion Temperature at 12% Drug Load

| Batch | Polymer [%] | Surfactant [%] | Temperature [° C.] | Appearance |
|---|---|---|---|---|
| 0P65-01 | 78% Kollidon VA64 | 9% Tween 80 | 120° C. | turbid |
| 0P65-02 | | | 130° C. | turbid |
| 0P65-03 | | | 140° C. | almost clear |
| 0P65-04 | | | 150° C. | almost clear |
| 0P65-05 | | | 160° C. | almost clear |
| 0P66-01 | 80% Kollidon VA64 | 7% Tween 80 | 120° C. | — |
| 0P66-02 | | | 130° C. | — |
| 0P66-03 | | | 140° C. | almost clear |
| 0P66-04 | | | 150° C. | clear |
| 0P66-05 | | | 160° C. | clear |
| 0P66-06 | | | 170° C. | clear |
| 0P67-01 | 82% Kollidon VA64 | 5% Tween 80 | 130° C. | — |
| 0P67-02 | | | 140° C. | almost clear |
| 0P67-03 | | | 150° C. | almost clear |
| 0P67-04 | | | 160° C. | clear |
| 0P67-05 | | | 170° C. | clear |

TABLE 7-continued

Evaluation of Surfactant Level, Extrusion Temperature at 12% Drug Load

| Batch | Polymer [%] | Surfactant [%] | Temperature [° C.] | Appearance |
|---|---|---|---|---|
| 0P68-01 | 84% Kollidon VA64 | 3% Tween 80 | 130° C. | — |
| 0P68-02 | | | 140° C. | turbid |
| 0P68-03 | | | 150° C. | almost clear |
| 0P68-04 | | | 160° C. | clear |
| 0P68-05 | | | 170° C. | clear |

TABLE 8

Evaluation of Surfactant Level, Extrusion Temperature at 13% Drug Load

| Batch | Polymer [%] | Surfactant [%] | Temperature [° C.] | Appearance |
|---|---|---|---|---|
| 0P69-01 | 77% Kollidon VA64 | 9% Tween 80 | 130° C. | — |
| 0P69-02 | | | 140° C. | — |
| 0P69-03 | | | 150° C. | — |
| 0P70-01 | 79% Kollidon VA64 | 7% Tween 80 | — | — |
| 0P71-01 | 81% Kollidon VA64 | 5% Tween 80 | 130° C. | turbid |
| 0P71-02 | | | 140° C. | turbid |
| 0P71-03 | | | 150° C. | almost clear |
| 0P71-04 | | | 160° C. | clear |
| 0P71-05 | | | 170° C. | clear |
| 0P72-01 | 83% Kollidon VA64 | 3% Tween 80 | 130° C. | — |
| 0P72-02 | | | 140° C. | turbid |
| 0P72-03 | | | 150° C. | turbid |
| 0P72-04 | | | 160° C. | clear |
| 0P72-05 | | | 170° C. | clear |

TABLE 9

Evaluation of Surfactant Level, Extrusion Temperature at 14% Drug Load

| Batch | Polymer [%] | Surfactant [%] | Temperature [° C.] | Appearance |
|---|---|---|---|---|
| 0P73-01 | 76% Kollidon VA64 | 9% Tween 80 | — | — |
| 0P74-01 | 78% Kollidon VA64 | 7% Tween 80 | — | — |
| 0P75-01 | 80% Kollidon VA64 | 5% Tween 80 | 130° C. | — |
| 0P75-02 | | | 140° C. | turbid |
| 0P75-03 | | | 150° C. | almost clear |
| 0P75-04 | | | 160° C. | clear |
| 0P75-05 | | | 170° C. | clear |
| 0P76-01 | 82% Kollidon VA64 | 3% Tween 80 | 130° C. | — |
| 0P76-02 | | | 140° C. | turbid |
| 0P76-03 | | | 150° C. | almost clear |
| 0P76-04 | | | 160° C. | clear |
| 0P76-05 | | | 170° C. | clear |

TABLE 10

Evaluation of Surfactant Level, Extrusion Temperature at 15% Drug Load

| Batch | Polymer [%] | Surfactant [%] | Temperature [° C.] | Appearance |
|---|---|---|---|---|
| 0P77-01 | 75% Kollidon VA64 | 9% Tween 80 | — | — |
| 0P78-01 | 77% Kollidon VA64 | 7% Tween 80 | — | — |
| 0P79-02 | 79% Kollidon VA64 | 5% Tween 80 | 140° C. | turbid |
| 0P79-03 | | | 150° C. | almost clear |
| 0P79-04 | | | 160° C. | clear |
| 0P79-05 | | | 170° C. | clear |

TABLE 10-continued

Evaluation of Surfactant Level, Extrusion Temperature at 15% Drug Load

| Batch | Polymer [%] | Surfactant [%] | Temperature [° C.] | Appearance |
|---|---|---|---|---|
| 0P80-02 | 81% Kollidon VA64 | 3% Tween 80 | 140° C. | turbid |
| 0P80-03 | | | 150° C. | almost clear |
| 0P80-04 | | | 160° C. | clear |
| 0P80-05 | | | 170° C. | clear |

Dispersibility of selected extrudates was tested by dispensing 25 mg compound 5 equivalent of unmilled extrudate in 75 mL 0.1 N HCl at 37° C. After predetermined time points samples were taken and analyzed by HPLC (HPLC Conditions: Agilent 1100 Series; Column: Phenomenex Gemini-NX3μ C18 110 A; flow: 0.3 mL/min; injection volume: 5 μL; oven temperature: 30° C.; detection wavelength: 220 nm; solvent A: 0.1% TFA (trifluoroacetic acid) in water; solvent B: ACN (acetonitrile); method was isocratic solvent A 45%, solvent B 55%; peak elutes between 2.5 and 3.5 mins). The results indicated that at least extrudates manufactured at 160° C. released 80-100% of API within 240 minutes. In general, formulations with higher drug load showed slower release rate, and higher surfactant level led to faster release rate.

Example 12. Pharmacokinetic Profile of Extrudates

Based on the results of dispersibility testing, a pharmacokinetic study in dogs was performed for extrudates of three formulations:
  Formulation 1 (batch 0P21-02): 12% compound 5, 80% copovidone, 7% Tween80, 1% Aerosil
  Formulation 2 (batch 0P27-01): 10% compound 5, 82% copovidone, 7% Vitamin E TPGS, 1% Aerosil
  Formulation 3 (batch 0P38-01): 12% compound 5, 78% copovidone, 7% Tween 80, 2% Lauroglykol, 1% Aerosil Capsules of 50 mg dosage strength were made using Aerosil/Mannitol as filler. Two capsules (100 mg) were orally administered to each of four Beagle dogs (two male and two female). The animals were fasted overnight and received food 30 min prior to dosing and throughout the duration of the study. Plasma samples were collected at 0.25, 0.5, 1, 2, 4, 6, 8, 24 and 48 hours post-dose administration. Compound 5 levels in plasma samples were analyzed by LC-MS/MS (Table 11). The following primary pharmacokinetic parameters were determined:

| | |
|---|---|
| $AUC_{(0-Inf)}$ | Area under the concentration versus time curve from time 0 to infinity calculated as $AUC(0-\infty) = AUC_{last} + (C_{last}/K_{el})$, where $C_{last}$ is the last quantifiable concentration |
| Dose-normalized $AUC_{(0-Inf)}$ | Dose-normalized area under the concentration versus time curve from time 0 to infinity ($AUC_{(0-\infty)}$.) $AUC_{(0-Inf)\,norm} = AUC_{(0-Inf)} * \frac{\text{normalized dose}}{\text{actual dose}}$ |
| $C_{max}$ | Maximum observed plasma concentration |
| Dose-normalized $C_{max}$ | Dose-normalized maximum observed plasma concentration $C_{max\,norm} = C_{max} * \frac{\text{normalized dose}}{\text{actual dose}}$ |
| Point Estimate | $C_{max}$ or AUC for an experimental formulation is divided by the $C_{max}$ from the reference formulation for each dog separately. The log of this ratio is calculated and then the mean of the log transformed values for all dogs is calculated for each formulation. The point estimate for the $C_{max}$ or AUC is then determined by calculating the anti-log. |
| $T_{max}$ | Time of maximum plasma concentration |

TABLE 11

Pharmacokinetic Parameters of Extrudate Capsules (Mean (n = 4) ± SEM)

| | $t_{1/2}$ (h) | $C_{max}$ (μg/mL) | $T_{max}$ (h) | $AUC_{(0-\infty)}$ (μg · h/mL) | Point Estimate $C_{max}$ | Point Estimate $AUC_{(0-\infty)}$ |
|---|---|---|---|---|---|---|
| Formulation 1 | 11.2 | 7.9 ± 1.1 | 6.0 ± 1.2 | 205.7 ± 18.1 | 1.55 | 1.64 |
| Formulation 2 | 10.5 | 5.7 ± 1.2 | 9.3 ± 5.1 | 134.6 ± 26.4 | 1.07 | 1.02 |
| Formulation 3 | 9.6 | 5.6 ± 1.2 | 3.5 ± 1.7 | 104.0 ± 20.4 | 1.06 | 0.78 |
| lipid reference | 10.4 | 5.2 ± 0.9 | 6.5 ± 1.0 | 127.6 ± 17.2 | — | — |

AUC and $C_{max}$ were normalized to a dose of 10 mg/kg.
Point estimates were calculated with non-normalized data.

The results indicate that all four formulations showed satisfying pharmacokinetic profile. The results from Formulations 2 and 3 were comparable to a reference lipid formulation. Formulation 1 showed exceptionally higher pharmacokinetic rate than the reference.

Example 13. Phase Separation Studies on Compound 5 Extrudates

To investigate phase separation potentials, differential scanning calorimetry (DSC) cycle tests were performed on extrudate of Formulation 1 in Example 13. The extrudate was milled using a standard laboratory ball mill, weighted into closed DSC crucibles and placed into the instrument (Mettler Toledo DSC 1/700/183). The samples were heated from −60° C. to 100° C. following a cooling to −60° C. (1 Cycle). This procedure was repeated up to 5 times (5 Cycles). The results indicated that extrudate of Formulation 1 was a monophasic system after manufacture and phase separation was not likely to happen when the formulation was stored at long term and accelerated conditions below or even close to its glass transition temperature.

Example 14. Scale-Up Extrusion Formulation and Conditions

Due to its results in the dog PK study, Formulation 1 (12% compound 5, 80% copovidon, 7% Tween 80, 1% Aerosil)

was chosen for larger scale production. The extruder, type Micro 18, was equipped with a gravimetric feeder system and a calender to realize a continuous process from blend to extrudate lentils, as an intermediate product. Experiments were conducted to evaluate the influence of feed rate, screw speed and temperature on product quality. The screw design (Micro 18-24) was chosen due to the good mixing properties. Samples were taken periodically every 30 min during the process and analyzed with respect to crystallinity, assay, and water content. The process parameters were stable over the whole run and the product did not show any significant deviation. Analytical results on the samples confirmed the stability of the process. The extruder conditions for batch production were as follows:

| Block No. | Set | Range |
| --- | --- | --- |
| Block 1 | 100° C. | 90-110° C. |
| Block 2-5 | 155° C. | 145-165° C. |
| Block 6 (die) | 140° C. | 135-145° C. |
| feed rate | 1.50 kg/h | 1.25-1.75 kg/h |
| screw speed | 150 rpm | 140-160 rpm |

In view of the results obtained here, it was determined that further scale up was possible, using these or appropriately modified process conditions for a larger extruder (e.g., a Micro 27 extruder).

Example 15. Extrudate Milling

Active extrudates of compound 5 of Formulation 1 (glass transition temperature (Tg) at approximately 78° C.) in batch sizes of a few hundred grams were milled using Quadro U5 Comil and Conidure (C type) screens with 813, 610 or 406 micron aperture sizes. Screens with larger aperture size resulted in an increase in milled extrudate particle size. There was no difference in particle size distribution in the beginning of the run compared to the end. Variation in milling batch size (from 127 g to 500 g) resulted in negligible change in particle size distribution. The particle size distribution of milled compound 5 and placebo extrudates were measured by laser diffraction using a Malvern Mastersizer 2000, and the results are summarized in Table 12.

TABLE 12

Particle Size Data for Milled Extrudates

| Batch Size (g) | Conidur Screen used (μm) | Impeller speed (rpm) | Sampling | Particle size (in micron) | | |
| --- | --- | --- | --- | --- | --- | --- |
| | | | | $d_{10}$ | $d_{50}$ | $d_{90}$ |
| 150 | 813 | 3500 | Composite | 119 | 407 | 802 |
| 153 | 610 | 3500 | Composite | 82 | 350 | 663 |
| 127 | 406 | 3500 | Composite | 32 | 156 | 360 |
| 500 | 406 | 3500 | Initial sample | 45 | 184 | 381 |
| 500 | 406 | 3500 | Final sample | 33 | 182 | 391 |

During the milling process, both the screen and product temperature reached a plateau, with the screen temperature maximized at about 43° C. and the product temperature below 30° C. Under this condition, the risk of screen clogging due to extrudate melting was minimal. Scanning electronic microphotographs (SEM) indicated that all samples were composed of irregular shaped particles with a mixture of smooth surfaces, surfaces with adherent smaller particles and fines, and areas with conchodial fractures. The sample obtained from 813 micron screen had the fewest fines.

Example 16. Tablet Production by Compression

The Presster (Metropolitan Computing Corporation) was used to perform tablet compression testing. Compression was executed using a 10 mm diameter flat-faced tooling, with a target tablet weight between 360 mg to 370 mg, and a dwell time of 6 ms. Alternatively, tablets may be compressed manually on using Carver Laboratory press Model C (Fred S. Carver Inc, asset #LC013794). Tooling used to compress the 50 mg and 100 mg tablets were P29628-10B and A-2238, respectively. Different compound 5 formulations were evaluated using the Presster (Table 13). Data generated from compressing these formulations on the MCC Presster tablet press simulator were gathered regarding 1) compressibility (solid fraction as a function of compaction pressure); 2) compactability (tensile strength as a function of solid fraction); and 3) tabletability (tensile strength as a function of compaction pressure).

TABLE 13

Compositions of Compound 5 Blends Used for Presster Evaluation

| Ingredients | No Filler Formula | 5% SCC Formula | 15% DCP Formula | 20% DCP Formula |
| --- | --- | --- | --- | --- |
| Extrudate* | 98.5 | 93.5 | 83.5 | 78.5 |
| Croscarmellose Sodium | 0 | 5 | 0 | 0 |
| Dicalcium Phosphate | 0 | 0 | 15 | 20 |
| Sodium Stearyl Fumarate | 0.5 | 0.5 | 0.5 | 0.5 |
| Aerosil (Colloidal Silicon Dioxide) | 1 | 1 | 1 | 1 |
| Total | 100 | 100 | 100 | 100 |

*API extrudate: 12% Compound 5, 7% Tween-80, 80% copovidone, and 1% of Aerosil
Placebo extrudate: 7% Tween-80, 92% copovidone, and 1% of Aerosil The clarity of the extrudates was found to have an effect on tabletability of formulations made with either the 20% DCP Formula or the No Filler Formula. Compound 5 formulations prepared using clear extrudates generally resulted in higher tensile strength over a compaction pressure range (e.g. 50 to 400 MPa) than those prepared using cloudy extrudates. At 7% Tween 80, placebo extrudates remained cloudy even when extrusion temperature was increased to 180° C. Comparison of tabletability between clear and cloudy placebo extrudates was therefore not performed. Further, blends prepared with cloudy placebo extrudates milled under the same condition as that of clear compound 5 extrudates were assessed for tabletability using the Presster. However, the placebo blends did not compress into strong enough tablets with either the 20% DCP Formula or the No Filler Formula.

Addition of 5% croscarmellose sodium (SCC) to the milled, slightly cloudy compound 5 extrudate showed no improvement on tabletability. However, addition of 15% of dicalcium phosphate (DCP) to the same milled extrudate resulted in improvement on tabletability. Further, it was shown that adding 20% DCP to the extragranular blend of milled extrudates (using both 406 and 610 μm C-screen) of compound 5 improved tabletability. Extrudates milled through Comil screens with apperture sizes larger than 406 micron all demonstrated poor tabletability, with tensile strength less than 1 MPa at a compaction pressure of 200 MPa, even with addition of 20% DCP. In contrast, the fine material milled through a 406 micron C-screen can compress to yield relatively strong tablets (approximately 1.5 MPa tensile strength at 200 MPa compaction pressure).

Based on the results above, a composition of tablet ingredients was determined for clinical studies (Table 14). The average hardness of the 50 mg compound 5 tablets was 13 kp, the average table weight was 532 mg, and the table thickness was about 5.2 mm. X-ray tomography showed no internal cracks or fissures in the 50 mg tablets.

TABLE 14

Composition of 50 mg tablets of Compound 5

| Process | Component | Quality Standard | Function | % (w/w) | mg/tablet |
|---|---|---|---|---|---|
| Extrudate | Compound 5, free base | In-house standard | Drug Substance | 9.420 | 50.0 |
| | Copovidone | USP-NF/Ph. Eur. | Carrier polymer | 62.800 | 333.3 |
| | Polysorbate 80 | USP-NF | Surfactant/Plasticizer | 5.495 | 29.2 |
| | Colloidal Silicon Dioxide | USP-NF/Ph. Eur./JP | Glidant | 0.785 | 4.2 |
| Post Extrusion | Dicalcium Phosphate | USP, Ph. Eur. | Filler | 20.000 | 106.2 |
| | Sodium Stearyl Fumarate | USP-NF/Ph. Eur. | Lubricant | 0.500 | 2.7 |
| | Colloidal Silicon Dioxide | USP-NF/Ph. Eur./JP | Glidant | 1.000 | 5.3 |
| Total | | | | 100.000 | 530.9 |

Example 17. Dissolution Profile of Compound 5 Tablets

Dissolution tests on Compound 5 tablets (50 mg) were performed using USP apparatus 2 method in 900 ml dissolution medium (0.05M sodium phosphate buffer, pH 6.8, with 0.2% SDS). A paddle speed of 75 rpm was used for 180 minutes, after which it was increased to 150 rpm. Samples are collected at predetermined time points, and the concentration of compound 5 was analyzed by HPLC. Substantially all compound 5 (about 90-100%) was released from tablets within 6 to 8 hours. The use of different dissolution medium (e.g. 0.05M sodium phosphate buffer, pH 6.8, with 0.5% CTAB, or 0.01 N HCl with 0.5% CTAB) resulted in similar dissolution profiles. The dissolution profile was independent of particle size of the milled extrudate, and addition of 20% DCP as a post-extrusion filler slightly decreased the drug release rate from the tablet. Further, the dissolution profile remained unchanged after exposure to 25° C./60% RH open dish condition for 2 weeks and a significant increase in moisture content (>9%) in the tablets. These results indicate that the compound 5 tablets erode rather than disintegrate during dissolution, and drug release is controlled by erosion mechanism.

Example 18. Dog Pharmacokinetic Profiles of Compound 5 Tablets

Dog studies were performed in groups of 6 fed dogs. The dogs received a single 100 mg oral dose of a lipid formulation (10 mg/mL in Cremophor EL:PEG-400:Oleic acid, 10:10:80 by weight; dosed in 10 mL/dog) in Period 1, No Filler Formulation (Example 17) in Period 2, and 20% DCP Formulation (Example 17) in Period 3. A washout period of one week separated the adjacent dosing periods. The dogs were fasted overnight and food was returned to the animals about 30 minutes prior to dosing (fed dogs). Plasma concentrations of compound 5 were determined by HPLC-MS/MS at the completion of the dosing periods (Table 15). Compared with the reference lipid formulation, the plasma concentration profiles obtained from the two tablets were similar, with an initial $T_{max}$ in 7-10 hours after dosing followed by a second peak in 12-24 hours. Peak concentrations obtained from 20% DCP Formulation tablet were slightly higher than those obtained from the No Filler formulation tablet. The difference in AUC between the two formulations was not significant. Point estimates for comparison of Formulation C to the lipid reference averaged 1.1 for Cmax and 0.73 for AUC. These results confirmed good bioavailability of API in these tablets, and showed that the addition of 20% DCP as extragranular tablet excipient did not change the bioavailability of API in dogs.

TABLE 15

| | | | | | | AUC/D (μg · hr/mL per |
|---|---|---|---|---|---|---|
| Period | Formulation | $t_{1/2}$ (hr) | $C_{max}$(μg/mL) | $T_{max}$ (hr) | AUC (μg · hr/mL) | mg/kg) |
| 1 | reference lipid formulation | 14.6 | 8.16 (1.24) | 9.3 (1.6) | 273 (48) | 22.5 (2.9) |
| 2 | 100 mg tablet, No Filler Formulation | 18.2 | 8.04 (1.60) | 7.3 (3.7) | 183 (36) | 14.9 (2.3) |
| 3 | 100 mg tablet, 20% DCP Formulation | 14.4 | 9.34 (1.35) | 9.8 (4.5) | 195 (31) | 16.2 (2.0) |

Pharmacokinetic Parameters in Dogs (Mean ± SEM, n = 6)

Example 19. Pharmacokinetic Profiles in Human—Phase 1 Study of Compound 5

A first-in-human Phase 1 open-label study was conducted to determine the safety, PK, MTD, and preliminary efficacy profile of compound 5 in human subjects with relapsed or refractory chronic lymphocytic leukemia (CLL; Arm A) or Non-Hodgkin's Lymphoma (NHL; Arm B). Three subjects were enrolled in the first cohort of CLL arm. All subjects had tumor lysis syndrome (TLS) after the first dose of compound 5 (in 50 mg tablet form).

Subject 1: bulky disease, initial dose=200 mg
Subject 2: non-bulky disease, initial dose=200 mg
Subject 3: bulky disease, initial dose=100 mg The dosing scheme for CLL arm was as follows: single dose on Week 1 Day −3; QD dose started on Week 1 Day 1. PK sampling was done on Week 1 Day −3 and Week 3 Day 1.

From the dose-normalized mean plasma concentration-time profiles of compound 5 in these three human subjects, preliminary PK results were obtained as summarized in Table 16.

TABLE 16

Preliminary Pharmacokinetic Parameters in Human

| Week/ Day | ID | Dose (mg) | $T_{max}$(h) | $C_{max}$ (μg/mL) | $C_{max}$/ Dose (μg/mL)/ mg) | $t_{1/2}^{\$}$ (h) | AUC* (μg · h/ mL) | AUC/Dose (μg · h/mL)/ mg | CL/F (L/h) |
|---|---|---|---|---|---|---|---|---|---|
| Week 1 Day-3 | Subject 1 | 200 | 6 | 0.73 | 0.0037 | 30.6 | 23.3 | 0.12 | 8.6 |
| | Subject 2 | 200 | 8 | 1.57 | 0.0079 | 50.9 | 76 | 0.38 | 2.6 |
| | Subject 3 | 100 | 8 | 1.19 | 0.0119 | 22.1 | 36.3 | 0.36 | 2.8 |
| | N | | 3 | 3 | 3 | 3 | 3 | 3 | 3 |
| | Mean | | 7.3 | — | 0.008 | 30.7 | — | 0.29 | 4.7 |
| | SD | | 1.2 | — | 0.004 | 12.6 | — | 0.15 | 3.4 |
| | CV % | | 15.7 | — | 52.8 | 42.9 | — | 51.5 | 73.2 |
| Week 3 Day 1 | 101 | 150 | 8 | 1.34 | 0.0089 | — | 21.1 | 0.14 | 7.1 |

*AUC = $AUC_{INF}$ on Week 1 Day-3 and $AUC_{ss,24}$ on Week 3 Day 1
$\$$Harmonic Mean and Pseudo Standard Deviation As indicated by these data, compound 5 reached $C_{max}$ around 7 hours. The terminal elimination half-life of compound 5 was 31 hrs (which was observed to be longer than a predicted value of 15 hrs). The observed average AUC normalized to 200 mg dose (58 μg·h/mL) was about 2-fold higher than the predicted AUC (30 μg·h/mL). Compound 5 clearance was 4.7 L/h (which was smaller than the predicted value of 10 L/h).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying FIGURES shall be interpreted as illustrative and not in a limiting sense.

What is claimed is:

1. An orally deliverable pharmaceutical tablet comprising
   9.42% by weight of a parent compound 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide,
   62.8% by weight of copovidone,
   5.495% by weight of polysorbate 80, and
   0.785% by weight of colloidal silicon dioxide.

2. The orally deliverable pharmaceutical tablet of claim 1, further comprising 20% by weight of dicalcium phosphate, 0.5% by weight of sodium stearyl fumarate, and 1% by weight of colloidal silicon dioxide.

3. The orally deliverable pharmaceutical tablet of claim 2, wherein the tablet comprises about 50 mg of the parent compound.

4. The orally deliverable pharmaceutical tablet of claim 2, wherein the tablet comprises about 100 mg of the parent compound.

5. An orally deliverable pharmaceutical tablet comprising a solid dispersion, the solid dispersion comprising:
   (a) 5% by weight to 20% by weight of a parent compound, wherein the parent compound is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, and wherein the parent compound is in essentially non-crystalline or amorphous form; and
   (b) 70% by weight to 95% by weight of at least one pharmaceutically acceptable water-soluble polymeric carrier.

6. The orally deliverable pharmaceutical tablet of claim 5, wherein the solid dispersion comprises about 5% by weight to about 15% by weight of the parent compound.

7. The orally deliverable pharmaceutical tablet of claim 5, wherein the solid dispersion comprises about 75% by weight to about 85% by weight of the at least one pharmaceutically acceptable water-soluble polymeric carrier.

8. The orally deliverable pharmaceutical tablet of claim 5, wherein the at least one pharmaceutically acceptable water-soluble polymeric carrier is selected from the group consisting of homopolymers and copolymers of N-vinyl lactams, cellulose esters, cellulose ethers, polyalkylene oxides, polyacrylates, polymethacrylates, polyacrylamides, vinyl acetate polymers, graft copolymers of polyethylene glycol, polyvinyl caprolactam and polyvinyl acetate, oligo- and polysaccharides and mixtures thereof.

9. The orally deliverable pharmaceutical tablet of claim 5, wherein the at least one pharmaceutically acceptable water-soluble polymeric carrier is selected from the group consisting of povidones, copovidones, hydroxypropyl methylcelluloses (HPMCs), graft copolymers of polyethylene glycol/polyvinyl caprolactam/polyvinyl acetate, and mixtures thereof.

10. The orally deliverable pharmaceutical tablet of claim 5, wherein the solid dispersion further comprises at least one pharmaceutically acceptable surfactant, wherein the pharmaceutically acceptable surfactant is non-ionic.

11. The orally deliverable pharmaceutical tablet of claim 10, wherein the pharmaceutically acceptable surfactant is selected from the group consisting of polyoxyethylene glycerides, fatty acid monoesters of sorbitan, polysorbates, a-tocopheryl polyethylene glycol succinate (TPGS) and mixtures thereof.

12. The orally deliverable pharmaceutical tablet of claim 5, wherein the solid dispersion further comprises at least one glidant.

13. The orally deliverable pharmaceutical tablet of claim 12, wherein the at least one glidant comprises colloidal silicon dioxide.

14. The orally deliverable pharmaceutical tablet of claim 5, wherein the solid dispersion comprises about 5% by weight to about 15% by weight of the parent compound, and about 75% by weight to about 85% by weight of the at least one pharmaceutically acceptable water-soluble polymeric carrier.

15. The orally deliverable pharmaceutical tablet of claim 14, wherein the at least one pharmaceutically acceptable water-soluble polymeric carrier is copovidone.

16. The orally deliverable pharmaceutical tablet of claim 15, wherein the solid dispersion further comprises at least one pharmaceutically acceptable surfactant, wherein the pharmaceutically acceptable surfactant is a polysorbate.

17. The orally deliverable pharmaceutical tablet of claim 16, wherein the solid dispersion further comprises at least one glidant.

18. The orally deliverable pharmaceutical tablet of claim 17, wherein the at least one glidant comprises colloidal silicon dioxide.

19. The orally deliverable pharmaceutical tablet of claim 5, wherein the solid dispersion comprises:
   between about 5% by weight and about 12% by weight of the parent compound; and
   between about 75% by weight and about 85% by weight of the at least one pharmaceutically acceptable water-soluble polymeric carrier.

20. The orally deliverable pharmaceutical tablet of claim 19, wherein the solid dispersion comprises:
   between about 5% by weight and about 12% by weight of the parent compound; and
   between about 75% by weight and about 84% by weight of the at least one pharmaceutically acceptable water-soluble polymeric carrier.

21. The orally deliverable pharmaceutical tablet of claim 20, wherein the at least one pharmaceutically acceptable water-soluble polymeric carrier is copovidone.

22. The orally deliverable pharmaceutical tablet of claim 19, wherein the solid dispersion comprises:
   12% by weight of the parent compound;
   80% by weight of copovidone 60/40;
   7% by weight of polysorbate 80; and,
   1% by weight of colloidal silicon dioxide.

23. The orally deliverable pharmaceutical tablet of claim 22, wherein the tablet comprises 78.5% by weight of the solid dispersion, and wherein the orally deliverable pharmaceutical tablet further comprises 20.0% by weight of dicalcium phosphate, 0.5% by weight of sodium stearyl fumarate, and 1.0% by weight of colloidal silicon dioxide.

24. The orally deliverable pharmaceutical tablet of claim 5, wherein the solid dispersion comprises at least one pharmaceutically acceptable surfactant.

25. The orally deliverable pharmaceutical tablet of claim 19, wherein the solid dispersion further comprises:
   between about 5% by weight and about 15% by weight of a pharmaceutically acceptable surfactant; and
   between about 0.1% by weight and about 2% by weight of a glidant.

26. The orally deliverable pharmaceutical tablet of claim 20, wherein the solid dispersion further comprises:
   between about 5% by weight and about 12% by weight of a pharmaceutically acceptable surfactant; and
   between about 0.5% by weight and about 1.5% by weight of a glidant.

27. The orally deliverable pharmaceutical tablet of claim 26, wherein the glidant is colloidal silicon dioxide.

28. The orally deliverable pharmaceutical tablet of claim 5, wherein the orally deliverable pharmaceutical tablet comprises 9.42% by weight of the parent compound, 62.8% by weight of copovidone, 5.495% by weight of polysorbate 80, and 0.785% by weight of colloidal silicon dioxide.

29. The orally deliverable pharmaceutical tablet of claim 28, wherein the orally deliverable pharmaceutical tablet further comprises 20% by weight of dicalcium phosphate, 0.5% by weight of sodium stearyl fumarate, and 1% by weight of colloidal silicon dioxide.

30. The orally deliverable pharmaceutical tablet of claim 5, wherein the orally deliverable pharmaceutical tablet comprises about 50 mg of the parent compound.

31. The orally deliverable pharmaceutical tablet of claim 5, wherein the orally deliverable pharmaceutical tablet comprises about 100 mg of the parent compound.

32. An orally deliverable solid dosage form comprising a solid dispersion, the solid dispersion comprising:
(a) 5% by weight to 20% by weight of a parent compound, wherein the parent compound is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, and wherein the parent compound is in essentially non-crystalline or amorphous form; and
(b) 70% by weight to 95% by weight of at least one pharmaceutically acceptable water-soluble polymeric carrier.

33. The orally deliverable solid dosage form of claim 32, wherein the solid dispersion comprises about 5% by weight to about 15% by weight of the parent compound, and about 75% by weight to about 85% by weight of the at least one pharmaceutically acceptable water-soluble polymeric carrier.

34. The orally deliverable solid dosage form of claim 32, wherein the solid dispersion further comprises at least one pharmaceutically acceptable surfactant, wherein the pharmaceutically acceptable surfactant is a polysorbate.

35. The orally deliverable solid dosage form of claim 32, wherein the solid dispersion comprises:
between about 5% by weight and about 12% by weight of the parent compound; and
between about 75% by weight and about 84% by weight of the at least one pharmaceutically acceptable water-soluble polymeric carrier.

36. The orally deliverable solid dosage form of claim 32, wherein the solid dispersion comprises:
12% by weight of the parent compound;
80% by weight of copovidone 60/40;
7% by weight of polysorbate 80; and,
1% by weight of colloidal silicon dioxide.

37. The orally deliverable pharmaceutical tablet of claim 7, wherein the solid dispersion further comprises at least one pharmaceutically acceptable surfactant, and between about 5% by weight and about 12% by weight of the parent compound.

38. The orally deliverable pharmaceutical tablet of claim 37, wherein the solid dispersion further comprises between about 5% by weight and about 15% by weight of a pharmaceutically acceptable surfactant.

39. The orally deliverable pharmaceutical tablet of claim 38, wherein the pharmaceutically acceptable surfactant is polysorbate 80.

40. The orally deliverable pharmaceutical tablet of claim 39, wherein the at least one pharmaceutically acceptable water-soluble polymeric carrier is copovidone.

41. The orally deliverable pharmaceutical tablet of claim 40, wherein the solid dispersion further comprises at least one glidant.

42. The orally deliverable pharmaceutical tablet of claim 40, wherein the solid dispersion further comprises between about 0.1% by weight and about 2% by weight of a glidant.

43. The orally deliverable pharmaceutical tablet of claim 42, wherein the at least one glidant comprises colloidal silicon dioxide.

44. The orally deliverable pharmaceutical tablet of claim 38, wherein the tablet comprises about 50 mg of the parent compound.

45. The orally deliverable pharmaceutical tablet of claim 38, wherein the tablet comprises about 100 mg of the parent compound.

46. The orally deliverable pharmaceutical tablet of claim 7, wherein the solid dispersion further comprises at least one pharmaceutically acceptable surfactant, and between about 5% by weight and about 12% by weight of the parent compound.

47. The orally deliverable pharmaceutical tablet of claim 46, wherein the solid dispersion further comprises between about 5% by weight and about 15% by weight of a pharmaceutically acceptable surfactant.

48. The orally deliverable pharmaceutical tablet of claim 47, wherein the pharmaceutically acceptable surfactant is polysorbate 80.

49. The orally deliverable pharmaceutical tablet of claim 48, wherein the at least one pharmaceutically acceptable water-soluble polymeric carrier is copovidone.

50. The orally deliverable pharmaceutical tablet of claim 49, wherein the solid dispersion further comprises at least one glidant.

51. The orally deliverable pharmaceutical tablet of claim 49, wherein the solid dispersion further comprises between about 0.1% by weight and about 2% by weight of a glidant.

52. The orally deliverable pharmaceutical tablet of claim 51, wherein the at least one glidant comprises colloidal silicon dioxide.

53. The orally deliverable pharmaceutical tablet of claim 47, wherein the tablet comprises about 50 mg of the parent compound.

54. The orally deliverable pharmaceutical tablet of claim 47, wherein the tablet comprises about 100 mg of the parent compound.

* * * * *

UNITED STATES PATENT AND TRADEMARK OFFICE
CERTIFICATE OF CORRECTION

PATENT NO. : 11,369,599 B2
APPLICATION NO. : 14/340435
DATED : June 28, 2022
INVENTOR(S) : Birtalan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this
Third Day of December, 2024

Katherine Kelly Vidal
*Director of the United States Patent and Trademark Office*